(12) United States Patent
Kaneko et al.

(10) Patent No.: US 8,932,990 B2
(45) Date of Patent: Jan. 13, 2015

(54) DETECTION OF DIGESTIVE ORGAN CANCER, GASTRIC CANCER, COLORECTAL CANCER, PANCREATIC CANCER, AND BILIARY TRACT CANCER BY GENE EXPRESSION PROFILING

(75) Inventors: Shuichi Kaneko, Kanazawa (JP); Masao Honda, Kanazawa (JP); Yoshio Sakai, Kanazawa (JP); Taro Yamashita, Kanazawa (JP)

(73) Assignee: National University Corporation Kanazawa University, Ishikawa (JP)

( * ) Notice: Subject to any disclaimer, the term of this patent is extended or adjusted under 35 U.S.C. 154(b) by 13 days.

(21) Appl. No.: 13/391,858

(22) PCT Filed: Aug. 3, 2010

(86) PCT No.: PCT/JP2010/063122

§ 371 (c)(1),
(2), (4) Date: Feb. 23, 2012

(87) PCT Pub. No.: WO2011/024618

PCT Pub. Date: Mar. 3, 2011

(65) Prior Publication Data

US 2012/0157341 A1 Jun. 21, 2012

(30) Foreign Application Priority Data

Aug. 24, 2009 (JP) .................. 2009-193702

(51) Int. Cl.
C40B 30/04 (2006.01)
*C12Q 1/68* (2006.01)
C40B 40/06 (2006.01)

(52) U.S. Cl.
CPC ........ *C12Q 1/6886* (2013.01); *C12Q 2600/158* (2013.01)
USPC .......................................................... 506/9

(58) Field of Classification Search
USPC ........................................................ 506/9, 16
See application file for complete search history.

(56) References Cited

U.S. PATENT DOCUMENTS

2005/0260572 A1 11/2005 Kato et al.
2006/0269921 A1* 11/2006 Segara et al. .............. 435/6

(Continued)

FOREIGN PATENT DOCUMENTS

JP 2005-304497 A 11/2005
JP 2007-074916 A 3/2007

(Continued)

OTHER PUBLICATIONS

Malati, T. Indian Journal of Clinical Biochemistry, 2007, 22(2), pp. 17-31.*

(Continued)

*Primary Examiner* — Larry Riggs
*Assistant Examiner* — Karla Dines
(74) *Attorney, Agent, or Firm* — Lucas & Mercanti, LLP

(57) ABSTRACT

The present invention provides a method and a reagent for detecting a digestive organ cancer, gastric cancer, colorectal cancer, pancreatic cancer, or biliary tract cancer patient by analyzing genes with expression levels (in peripheral blood) that vary in association with digestive organ cancer, gastric cancer, colorectal cancer, pancreatic cancer, or biliary tract cancer cases, compared with normal healthy subjects. Specifically, the method for detecting a digestive organ cancer, gastric cancer, colorectal cancer, pancreatic cancer, or biliary tract cancer patient based on expression profiles comprises obtaining the expression profile of at least one gene selected from the group consisting of probes corresponding to genes with expression levels (in peripheral blood) that vary in digestive organ cancer, gastric cancer, colorectal cancer, pancreatic cancer, and biliary tract cancer cases, compared with normal healthy subjects. The reagent for detecting digestive organ cancer, gastric cancer, colorectal cancer, pancreatic cancer, or biliary tract cancer contains nucleotides or partial sequences thereof consisting of the nucleotide sequence of at least one gene selected from the group consisting of probes with expression levels that vary in digestive organ cancer, gastric cancer, colorectal cancer, pancreatic cancer, or biliary tract cancer, or nucleotides containing sequences complementary thereto.

6 Claims, 220 Drawing Sheets

(56) References Cited

U.S. PATENT DOCUMENTS

| | | | |
|---|---|---|---|
| 2007/0065844 A1* | 3/2007 | Golub et al. .................... 435/6 |
| 2010/0086537 A1 | 4/2010 | Sooknanan et al. |
| 2012/0036101 A1* | 2/2012 | Rosenberg et al. ............. 706/52 |
| 2012/0040849 A1* | 2/2012 | Simon Valles et al. ........... 506/9 |

FOREIGN PATENT DOCUMENTS

| | | | |
|---|---|---|---|
| JP | 2007-236253 A | 9/2007 |
| NL | WO 2009/002175 A1 * | 12/2008 |
| WO | 2007/081740 A2 | 7/2007 |
| WO | 2007/147265 A1 | 12/2007 |
| WO | WO2008/147205 A1 * | 12/2008 |
| WO | 2009/126271 A1 | 10/2009 |

OTHER PUBLICATIONS

Marshall et al., International Journal of Cancer, 126, Mar. 1, 2010, pp. 1177-1186.*

Masao Honda, et al., "Shokaki Gan to Idenshi Ijo", Biotherapy, 2007, vol. 21, pp. 153 to 159.

Hansel, D.E., et al., "Identification of novel cellular targets in biliary tract cancers using global gene expression technology", Am. J. Pathol., 2003, vol. 163, pp. 217-229.

Karamitopoulou, E., et al., "Clinical significance of cell cycle- and apoptosisrelated markers in biliary tract cancer: a tissue microarray-based approach revealing a distinctive immunophenotype for intrahepatic and extrahepatic cholangiocarcinomas", Am. J. Clin. Pathol., 2008, vol. 130, pp. 780-786.

Hiroshi Yokozaki, "Shokudo Gan, I Gan no Akuseido o Kitei suru Bunshi Joho no Haaku to sore o Oyo shita Seiken Shindanho no Kakuritsu", Ministry of Health, Labour and Welfare Gan Kenkyu Joseikin ni yoru Kenkyu Hokokushu, Heisei 17 Nendo (2005), pp. 607 to 610.

Wataru Yasui, "I Gan no Bunshi Byorigakuteki Shindan", Japanese Journal of Cancer and Chemotherapy, 2005, vol. 32, pp. 427 to 431.

Kawaguchi, K., et al., "Differential gene alteration among hepatoma cell lines demonstrated by cDNA microarray-based comparative genomic hybridization", Biochem. Biophys. Res. Commun., 2005, vol. 329, pp. 370 to 380.

Jun, Lu, et al: "Micro RNA expression profiles classify human cancers", Nature: International Weekly Journal of Science, Nature Publishing Group, United Kingdom, vol. 435. No. 7043, Jun. 9, 2005. pp. 834-838, the whole document.

Extended European Search Report dated Mar. 1, 2013 issued in the corresponding European Application No. 10811669.0.

* cited by examiner

Fig. 1-1

| No | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P100292 | ZNF598 | TGAATCTTTTATGAGAGAAGCTGAATCTGGGATCTGAAATTGCCTGCTGACGTTTTATAA | SEQ ID NO: 1 | Homo sapiens mRNA for FLJ00086 protein, partial cds. [AK024487] |
| 2 | A_23_P100954 | ZBTB4 | GTATTTGAGCTGGGGAATTTGAATATTGTGAGTTTCAGATGTTGGAAATTTGGGATTTTG | SEQ ID NO: 2 | Homo sapiens zinc finger and BTB domain containing 4 (ZBTB4), mRNA [NM_020899] |
| 3 | A_23_P100779 | UBTF | CAGGACGTGCAGCATATAAAGAGTACATCTCAATAAACGTAAGAGCATGACCAAGCTG | SEQ ID NO: 3 | Homo sapiens upstream binding transcription factor, RNA polymerase I (UBTF), transcript variant 1, mRNA [NM_014233] |
| 4 | A_23_P101308 | ENST00000221462 | TAGTTCCTTTTTCCGGTGGGTCTGCGATAGAGTGAGGGCAGAGCCATGAGAATCTGTC | SEQ ID NO: 4 | Homo sapiens hypothetical protein LOC284352, mRNA (cDNA clone IMAGE:4779950), with apparent retained intron. [BC039061] |
| 5 | A_23_P101332 | FLJ12949 | ACAGGTCTGGCACCCACAAGTACTATCTGGTGCAGAGATCGTGTCATCTGTGGCGAGGCA | SEQ ID NO: 5 | Homo sapiens hypothetical protein FLJ12949 (FLJ12949), transcript variant 1, mRNA [NM_023008] |
| 6 | A_23_P101551 | BCAT2 | TCCGTACCAAATGACTCACCTGAAGTGCAATACGAAATAAAAGGCCAGCGGCGGCCTGTG | SEQ ID NO: 6 | Homo sapiens branched chain aminotransferase 2, mitochondrial (BCAT2), mRNA [NM_001190] |
| 7 | A_23_P102404 | CCT7 | GGGGTAGATAGTGGTATGGAGTAGACATGAACAACGAGGACATTGCTGACAACTTTGAAGCTT | SEQ ID NO: 7 | Homo sapiens chaperonin containing TCP1, subunit 7 (eta) (CCT7), transcript variant 1, mRNA [NM_006429] |
| 8 | A_23_P102508 | SLC5A6 | TTTTTCTCGTGGCTTGCCAATCTGTTTTTAAAGGATCAGGGTCGTAGGGAGGAAGGATCA | SEQ ID NO: 8 | Homo sapiens solute carrier family 5 (sodium-dependent vitamin transporter), member 6 (SLC5A6), mRNA [NM_021095] |
| 9 | A_23_P102973 | DGCR14 | TGGGCTCATAGAGCGTCACAGAGCCTGCAGGGCAGCGTGTACACCCAGCAGAGGACTCGA | SEQ ID NO: 9 | Homo sapiens DiGeorge syndrome critical region gene 14 (DGCR14), mRNA [NM_022719] |
| 10 | A_23_P102994 | PIK4CA | AAGATGGAGGCCAGACGCACACCCTTCAAGTGGTTCATGGAGATGTGTCCGAGGCTACGTGGCT | SEQ ID NO: 10 | Homo sapiens phosphatidylinositol 4-kinase, catalytic, alpha polypeptide (PIK4CA), transcript variant 1, mRNA [NM_002650] |
| 11 | A_23_P103104 | MFNG | CCAATTGTGATGATCCATTTCTGCCATTCCCAGCGCTTTCTTGTTAGGGCTACCAC | SEQ ID NO: 11 | Homo sapiens MFNG O-fucosylpeptide 3-beta-N-acetylglucosaminyltransferase (MFNG), mRNA [NM_002405] |
| 12 | A_23_P103942 | DNAJC11 | CTGTAACATTCATCTGCATTTTTAAAAAGGTTTCTCTGACGGCGCCACGGCCGGAGCC | SEQ ID NO: 12 | Homo sapiens DnaJ (Hsp40) homolog, subfamily C, member 11 (DNAJC11), mRNA [NM_018198] |
| 13 | A_23_P103968 | AKR7A3 | ACAGCCTGTGGCCGGTCTCTTTGGGAATAGGTGGGCAGAGAGATGTACAGGAATCGCTACTG | SEQ ID NO: 13 | Homo sapiens aldo-keto reductase family 7, member A3 (aflatoxin aldehyde reductase) (AKR7A3), mRNA [NM_012067] |
| 14 | A_23_P104641 | C11orf2 | ACTGCCACTTTGTGCAGCTCTACCTGTGCGCGTTTTGTGGGCGACGAAGAACTCGTGCACT | SEQ ID NO: 14 | Homo sapiens chromosome 11 open reading frame2 (C11orf2), mRNA [NM_013265] |
| 15 | A_23_P106532 | CHST14 | AAGGCGTTTGAGGTTGTGAGTGTGGCTGGTATATCGTGGCATGGCCATTTTTCTGATGCATTT | SEQ ID NO: 15 | Homo sapiens dermatan 4 sulfotransferase 1 (D4ST1), mRNA [NM_130468] |
| 16 | A_23_P106575 | GOT2 | CTATTGAGAGATTTCATCCAATTCTACTGCTGCTTGATTGACGATGAAGTCCATCCTATCGAG | SEQ ID NO: 16 | Homo sapiens glutamic-oxaloacetic transaminase 2, mitochondrial (aspartate aminotransferase 2) (GOT2), nuclear gene encoding mitochondrial protein, mRNA [NM_002080] |

Fig. 1-2

| No. | Probe ID No. | Symbols of genes | Sequence | SEQ ID NO: | Descriptions of genes (letters and numbers within [ ] indicate GenBank accession No.) |
|---|---|---|---|---|---|
| 17 | A_23_P106887 | FUS | TATTGACTGCTTGATGGTAAAGAATTCTCCGGAAATCCTATCAAGGTCCATTTGCTAC | SEQ ID NO: 17 | Homo sapiens fusion (involved in t(12:16) in malignant liposarcoma) (FUS), mRNA [NM_004960] |
| 18 | A_23_P106973 | SEPT9 | AGGGCTGTGTTCCTCAATGGGCTTTGCTACGTGCGTCCGGAGAAATTTGTCTTTTGTAT | SEQ ID NO: 18 | Homo sapiens septin 9 (SEPT9), mRNA [NM_006640] |
| 19 | A_23_P1072 | ATP1A1 | TGCCCTGGAATGGGTGTTGGTCTTAGGATGTATCCCCTCAAACGTACCTGGTGGTTCTGT | SEQ ID NO: 19 | Homo sapiens ATPase, Na+/K+ transporting, alpha 1 polypeptide (ATP1A1), transcript variant 1, mRNA [NM_000701] |
| 20 | A_23_P108376 | THADA | CTGTGTGGAAGAGCATGACATCAGGTGGAAGAAGACTACGCTGTTGAAAAGCAGAAGTCAA | SEQ ID NO: 20 | Homo sapiens thyroid adenoma associated (THADA), transcript variant 1, mRNA [NM_022065] |
| 21 | A_23_P109001 | KIAA0406 | TGATGGAACGCGTGCATCCACTTGTTGTCAGATAAAAATCTGCAAATCCGGCTGAAGGTGT | SEQ ID NO: 21 | Homo sapiens KIAA0406 (KIAA0406), mRNA [NM_014657] |
| 22 | A_23_P110062 | EIF2B5 | CATTGAGGAGTTCTTCCTAGAGCATGAAAGTCTTGGTATTTCCATGGGCAAGGTACTGAT | SEQ ID NO: 22 | Homo sapiens eukaryotic translation initiation factor 2B, subunit 5 epsilon, 82kDa (EIF2B5), mRNA [NM_003907] |
| 23 | A_23_P111745 | ZMIZ2 | TGGGTGGGCTCTCAGATTCAGCCTCTGTGTAAAGATTCTCTGAGGGGCTGGGCTCCCAAGT | SEQ ID NO: 23 | Homo sapiens zinc finger, MIZ-type containing 2 (ZMIZ2), transcript variant 1, mRNA [NM_031449] |
| 24 | A_23_P112406 | GTF3C5 | AGCTGACCGTAGCACTGGGTGTGCAACATGCTGCTTGGTGGTGCCTCTGGTCCTGAGGGGGTT | SEQ ID NO: 24 | Homo sapiens general transcription factor IIIC, polypeptide 5, 63kDa (GTF3C5), mRNA [NM_012087] |
| 25 | A_23_P113026 | PARN | GAGTGTGGGCTGTGTGGAAATCGCAAAAGAGGTGAGATAGTCGCCTGTTTTCCTGTGATCATGAATT | SEQ ID NO: 25 | Homo sapiens poly(A)-specific ribonuclease (deadenylation nuclease) (PARN), mRNA [NM_002582] |
| 26 | A_23_P113184 | FTO | TTGGGGCATGACCCAGGCCTATGGTTGGCATACTCGCCTCTTTTCTGCGTTTTTTCATTA | SEQ ID NO: 26 | Homo sapiens fatso (FTO), mRNA [NM_001080432] |
| 27 | A_23_P116840 | C12orf44 | CTGGGGCAGATGTCCTTGGAGTTCTACCAGAAGAAGAGTCTCGCTGGCCATTCTCAGAC | SEQ ID NO: 27 | Homo sapiens chromosome 12 open reading frame 44 (C12orf44), mRNA [NM_021834] |
| 28 | A_23_P119095 | PPP1R13L | AGTCACTGCTGACACATCCTCCAAGCAGTCTTGGGTGTCTGGCTGGGAAAGATTGGTCT | SEQ ID NO: 28 | Homo sapiens protein phosphatase 1, regulatory (inhibitor) subunit 13 like (PPP1R13L), mRNA [NM_006663] |
| 29 | A_23_P119907 | ANKZF1 | GACAAATCAACAGGTAATGAGTTCCGAAGGTTCATGGAGAAGAATCCAGATGCCTACGAT | SEQ ID NO: 29 | Homo sapiens ankyrin repeat and zinc finger domain containing 1 (ANKZF1), transcript variant 1, mRNA [NM_018089] |
| 30 | A_23_P120146 | TGFBRAP1 | AAATGGCTTTTGTGAGGCCTGTGTTTGTTAGATACCCAAATGGTGGTCTGTGCACACCA | SEQ ID NO: 30 | Homo sapiens transforming growth factor, beta receptor associated protein 1 (TGFBRAP1), mRNA [NM_004257] |
| 31 | A_23_P120915 | ANKRD54 | ACCTTGTATGGCCAAAGGGGCTTTGGCAGATGTAATGAAGTTAAGGATGTTTCGGCAGGAA | SEQ ID NO: 31 | Homo sapiens ankyrin repeat domain 54 (ANKRD54), mRNA [NM_138797] |
| 32 | A_23_P120821 | ANKRD54 | TTTTCTCCGAGTCATTGAAAGACCAAAACTATTATACCGGGAGGGTGTAATAGTTTTGCT | SEQ ID NO: 32 | Homo sapiens ankyrin repeat domain 54 (ANKRD54), mRNA [NM_138797] |
| 33 | A_23_P120942 | XRCC6 | TTTATGTTTTGAGGCTTTCTGTTGCCATGGTGATGGTGTAGCCCTGCCACTTTGCTGTT | SEQ ID NO: 33 | Homo sapiens X-ray repair complementing defective repair in Chinese hamster cells 6 (Ku autoantigen, 70kDa) (XRCC6), mRNA [NM_001469] |

Fig. 1-3

| No | Probe ID No. | Symbols of genes | Sequence | SEQ ID NO: | Descriptions of genes (letters and numbers within [ ] indicates GenBank accession No.) |
|---|---|---|---|---|---|
| 34 | A_23_P120947 | XRCC6 | GCAAGAATGAAGGCTATCGTTGAGAAGGCTTGGCTTCACATACAGAAGTGACAGCTTTGAGA | SEQ ID NO: 34 | Homo sapiens X-ray repair complementing defective repair in Chinese hamster cells 6 (Ku autoantigen, 70kDa) (XRCC6), mRNA [NM_001469] |
| 35 | A_23_P121499 | WFS1 | CTGACCTTTCTGAGTGACATGGGTGTGCCAGGCTAGAGTAGGAGGTTCCGGTGTGTGGAA | SEQ ID NO: 35 | Homo sapiens Wolfram syndrome 1 (wolframin) (WFS1), mRNA [NM_006005] |
| 36 | A_23_P122116 | DDX41 | GGGGCGCTGAGGAAACACAGGACATCGGCACTACGTTCATCAACAAAGCGTGTGATGAGTGA | SEQ ID NO: 36 | Homo sapiens DEAD (Asp-Glu-Ala-Asp) box polypeptide 41 (DDX41), mRNA [NM_016222] |
| 37 | A_23_P122679 | DAXX | CAGAGGAGCCCTTCACCACTGTCTTAGAGAATGGAGGAGGCATGGTCTCTTCTACTTCCT | SEQ ID NO: 37 | Homo sapiens death-associated protein 6 (DAXX), mRNA [NM_001350] |
| 38 | A_23_P122650 | LOC649233 | CCACGCCCTGGTGGAAAGATGGTGAGGAGCTTCAATCTTGGTGATGCGCTGAGACAGCAGTAA | SEQ ID NO: 38 | PREDICTED: Homo sapiens similar to Keratin, type I cytoskeletal 18 (Cytokeratin-18) (CK-18) (Keratin-18) (K18) (LOC649233), mRNA [XR_018843] |
| 39 | A_23_P122876 | TAF6 | TTGCTTCGTTCATGTGTCACTTTCTTTTAGATATTGTACAAGCAGTTTGTGAGAATAAAAG | SEQ ID NO: 39 | Homo sapiens TAF6 RNA polymerase II, TATA box binding protein (TBP)-associated factor, 80kDa (TAF6), transcript variant 1, mRNA [NM_005641] |
| 40 | A_23_P124044 | DEAF1 | GGAAGGTAAAGAAACTTGCCTGGACAAGTCAATTAACACACACTTTAAGCGAATGGTGCCCTGG | SEQ ID NO: 40 | Homo sapiens deformed epidermal autoregulatory factor 1 (Drosophila) (DEAF1), mRNA [NM_021008] |
| 41 | A_23_P124522 | DCAKD | TAGGCGAAACTTGCCTGGTTTCTACTAGACTGTAAGCCGTGTAGGGACAGGGACAGT | SEQ ID NO: 41 | Homo sapiens dephospho-CoA kinase domain containing (DCAKD), mRNA [NM_024819] |
| 42 | A_23_P126689 | USP21 | AGAAGCCGGAGCTCCTGTATACCAGCTGTATGCCGTTTGCAACCAGTCAGGAGGGTCC | SEQ ID NO: 42 | Homo sapiens ubiquitin specific peptidase 21 (USP21), transcript variant 1, mRNA [NM_012475] |
| 43 | A_23_P126790 | SARS | CAGGACTGCAAGAACTGATGCCCTTTGTGAAGCCTGCGGCCATTGAGCAGGAGCCATCAA | SEQ ID NO: 43 | Homo sapiens seryl-tRNA synthetase (SARS), mRNA [NM_006513] |
| 44 | A_23_P127079 | PPRC1 | ACCGGGAAGACTTGACCCAGCACCTGTAAAGAGCAAATTTGATTCTGTTGAAGTTTGACA | SEQ ID NO: 44 | Homo sapiens peroxisome proliferator-activated receptor gamma, coactivator-related 1 (PPRC1), mRNA [NM_015062] |
| 45 | A_23_P127394 | CRY2 | AGATGGTTGCAGGGCAAAATGCACGTTGGCGATTATAGAGATTTCTGTATTGTGGGAAGGTGTGTTTC | SEQ ID NO: 45 | Homo sapiens cryptochrome 2 (photolyase-like) (CRY2), mRNA [NM_021117] |
| 46 | A_23_P127525 | ETS1 | CCTGCTGAGACCTTCCAAGAGACACCCGTGTTGGTTGGACTCTGAATTTTGAATTGTTATT | SEQ ID NO: 46 | Homo sapiens v-ets erythroblastosis virus E26 oncogene homolog 1 (avian) (ETS1), mRNA [NM_005238] |
| 47 | A_23_P127793 | EML3 | TGCAAGCAGCTGAAGAATCGGTATGAGAGCCGAGAGACCGGGAAATGGGGTACCTACACCGTGT | SEQ ID NO: 47 | Homo sapiens echinoderm microtubule associated protein like 3 (EML3), mRNA [NM_153265] |
| 48 | A_23_P129678 | SETD1A | GCTGACGAGATGCGGTCATCGAATACGTGGGTCAGAACATCCGTCAGATGGTGCGGACATG | SEQ ID NO: 48 | Homo sapiens SET domain containing 1A (SETD1A), mRNA [NM_014712] |
| 49 | A_23_P130149 | ENO3 | CTCGGAGGCGTCTGGCCAAATACAACGAAGTCATGATGAGGATGGAGGAGGCTGTTGGGGACAA | SEQ ID NO: 49 | Homo sapiens enolase 3 (beta, muscle) (ENO3), transcript variant 1, mRNA [NM_001976] |
| 50 | A_23_P13033 | RBM4 | TTACGGGCATGAGAGTGAGGATGTTGTCCGAAGTTCAGCAGGAGATGAGGAGAATTCTCTGTACGA | SEQ ID NO: 50 | Homo sapiens RNA binding motif protein 4 (RBM4), mRNA [NM_002896] |
| 51 | A_23_P130455 | MZF1 | GTGTGGGAAGGCTTCCGGCAGGGGCCCACGCTCACGAGGATGTGCGGCACCGACGACG | SEQ ID NO: 51 | Homo sapiens myeloid zinc finger 1 (MZF1), transcript variant 2, mRNA [NM_198055] |

Fig. 1-4

| No. | Probe ID No. | Symbols of genes | Sequence | SEQ ID NO: | Descriptions of genes (letters and numbers within [ ] indicate GenBank accession No.) |
|---|---|---|---|---|---|
| 52 | A_23_P130753 | DBP | CACGAGAACGTTTGACCCTCGAAGAGCATCGCTTCTCAGAAGAGGAA CTTAAGCGCCAGCCA | SEQ ID NO: 52 | Homo sapiens D site of albumin promoter (albumin D-box) binding protein (DBP), mRNA [NM_001352] |
| 53 | A_23_P131626 | ASCC3L1 | CTTTTGGGTAAAGGAGGAGTTGAGCGTGAATTAGGAATGTGTACAT TGTAGGAATCCTGGT | SEQ ID NO: 53 | Homo sapiens activating signal cointegrator 1 complex subunit 3-like 1 (ASCC3L1), mRNA [NM_014014] |
| 54 | A_23_P13338 | INTS5 | TAAAGCCACCCAAGTTTGTCCAGTCACGAAATCAGCAGGAAGTGA TCTATAACACCCAGA | SEQ ID NO: 54 | Homo sapiens integrator complex subunit 5 (INTS5), mRNA [NM_030628] |
| 55 | A_23_P135104 | MRPS2 | TTCTCAATCTAAATGCCTTTGAGGTGGGCGGGTTCCTTGGCTACG TGGTTCCAGGGGGCT | SEQ ID NO: 55 | Homo sapiens mitochondrial ribosomal protein S2 (MRPS2), nuclear gene encoding mitochondrial protein, mRNA [NM_016034] |
| 56 | A_23_P135634 | MAGED1 | TTGAGTGAGATGTTGGATATTGTGCTATATCGCAGTAGTCTTTCC CCTGCTGTGACCTGAA | SEQ ID NO: 56 | Homo sapiens NRAGE mRNA, complete cds. [AF217963] |
| 57 | A_23_P135914 | SF3B3 | TTAATTGGTTTCTTGTAAATACAGTTTTGTACAATGTTATCTGT GTGGGAGGAAGGAGG | SEQ ID NO: 57 | Homo sapiens splicing factor 3b, subunit 3, 130kDa (SF3B3), mRNA [NM_012426] |
| 58 | A_23_P135977 | CKAP5 | AAGTCCTACATAGTTTAAAATGGCCTCAGGAGGCCTAGTGTATACA AACTGGTTGTATGTA | SEQ ID NO: 58 | Homo sapiens cytoskeleton associated protein 5 (CKAP5), transcript variant 1, mRNA [NM_001008938] |
| 59 | A_23_P137073 | ZMYM3 | GGGTTCTGTGACCCATCCCGCACATAGGTAGAGCTCTGTTGTTGAGG CATGACCTAGGGAAA | SEQ ID NO: 59 | Homo sapiens zinc finger, MYM-type 3 (ZMYM3), transcript variant 1, mRNA [NM_005096] |
| 60 | A_23_P137423 | IGSF8 | TACCATCACTTCCTCCTTCGTCATGAAGAGGCTTGAAAACGGTGATC CCTTACTCCCCAGGT | SEQ ID NO: 60 | Homo sapiens immunoglobulin superfamily, member 8 (IGSF8), mRNA [NM_052866] |
| 61 | A_23_P137715 | POGK | GGGAGGTTAAAGATTTTACACAGACCTAATTTTGGGTTCCTTCCT TGAGCCATAGTTAC | SEQ ID NO: 61 | Homo sapiens pogo transposable element with KRAB domain (POGK), mRNA [NM_017542] |
| 62 | A_23_P138058 | NOC2L | TTCAGTCGGCGAAGTGTTTGAAAATTTGGTTCCTTTCGTTTGAAGT CACATTTCTTTTAA | SEQ ID NO: 62 | Homo sapiens nucleolar complex associated 2 homolog (S. cerevisiae) (NOC2L), mRNA [NM_015658] |
| 63 | A_23_P13885 | ATN1 | CTCGCCCGTTGGTGTGATTATTTCATCTGTTAGATGTTGGCTGTTT TGGGTAGCATGGTGT | SEQ ID NO: 63 | Homo sapiens atrophin 1 (ATN1), transcript variant 1, mRNA [NM_001007026] |
| 64 | A_23_P141180 | TOM1L2 | GCTACTGAAAAGAGGAAATGTGTTGAATGTCGCGTTTGGTGTCGAC TCGTCGTAGAAGTTT | SEQ ID NO: 64 | Homo sapiens target of myb1-like 2 (chicken) (TOM1L2), transcript variant 3, mRNA [NM_001082968] |
| 65 | A_23_P144484 | C17orf63 | ATTCTGTAGTGATGATCTGAAGCAATGTGACTGAAGACCAGTTTTAAG TTATGTGTTGGCAAG | SEQ ID NO: 65 | Homo sapiens chromosome 17 open reading frame 63 (C17orf63), transcript variant 2, mRNA [NM_018182] |
| 66 | A_23_P141779 | CXXC1 | GTGCTACGGCAAGTATGAGAGCCAGAGTGCTTGGGTCCATGTA CCCACACGCATTGA | SEQ ID NO: 66 | Homo sapiens CXXC finger 1 (PHD domain) (CXXC1), mRNA [NM_014593] |
| 67 | A_23_P142018 | PRPF31 | TCAAGGGCAGAAGAGTGGCCTTATGTCCAGCTGAATGACTGGGT GTGTGCAAGGTGGCT | SEQ ID NO: 67 | Homo sapiens PRP31 pre-mRNA processing factor 31 homolog (S. cerevisiae) (PRPF31), mRNA [NM_015629] |
| 68 | A_23_P142272 | PAF1 | AAAATTGCTCGGGAGTACAACTGGAACGTGAAGAACAAAGCTAGCA AGGGCTATGAGGAAA | SEQ ID NO: 68 | Homo sapiens Paf1, RNA polymerase II associated factor, homolog (S. cerevisiae) (PAF1), mRNA [NM_019088] |
| 69 | A_23_P143580 | KLHL22 | ACAACAATGTCCAAGGATTTCGAGCAGAGATCCCGGATCGTGGAGGT ATGAGCCAGGGCACA | SEQ ID NO: 69 | Homo sapiens kelch-like 22 (Drosophila) (KLHL22), mRNA [NM_032775] |

Fig. 1-5

| No. | Probe ID No. | Symbols of genes | Sequence | SEQ ID NO: | Descriptions of genes (letters and numbers within [ ] indicates GenBank accession No.) |
|---|---|---|---|---|---|
| 70 | A_23_P144202 | EEFSEC | GTTGATGTTGTTCAGTCCTGGTCCAAGATAACTTTGACCAGGAGCCTATACTGGAACTCTTT | SEQ ID NO: 70 | Homo sapiens eukaryotic elongation factor, selenocysteine-tRNA-specific (EEFSEC), mRNA [NM_021937] |
| 71 | A_23_P145289 | GNL1 | AACACCCCTGGTGTGCCTGGGACATCTGTGAAGCCTGGGCAGGAGAAACGTTGTTACAAGA | SEQ ID NO: 71 | Homo sapiens guanine nucleotide binding protein-like 1 (GNL1), mRNA [NM_005275] |
| 72 | A_23_P145935 | EPHB6 | GAGGACAACTTCTCCAAGTTTGGCCTGTACGTTCAGTGATGTGGGTCAGCTCAGGCTA | SEQ ID NO: 72 | Homo sapiens EPH receptor B6 (EPHB6), mRNA [NM_004445] |
| 73 | A_23_P146637 | OPRS1 | ATTTGAAGAATGCTTGAAGTCAGGGTGTTGCATTCCAGAAAGACCCCCATTCTCCTTTG | SEQ ID NO: 73 | Homo sapiens opioid receptor, sigma 1 (OPRS1), transcript variant 1, mRNA [NM_005866] |
| 74 | A_23_P147641 | TCEA2 | ATCGAGGAATGCATCTTCCGGGAGCGTTGGAAACACAGAACATGAAAGTATAAGAACCATGTA | SEQ ID NO: 74 | Homo sapiens transcription elongation factor A (SII), 2 (TCEA2), transcript variant 1, mRNA [NM_003195] |
| 75 | A_23_P148473 | IL2RG | CTTTCCTGTTTGGCATTGGAAGCCGGTGGTTATCTCTGTTGGCTCCATGGGATTGATTATCA | SEQ ID NO: 75 | Homo sapiens interleukin 2 receptor, gamma (severe combined immunodeficiency) (IL2RG), mRNA [NM_000206] |
| 76 | A_23_P150255 | RBM14 | GATGGTGAGGGGCACAGTCCCACTTCCCCATCTGCCCAAGTAGGTGGTGTTAGAAAACCT | SEQ ID NO: 76 | Homo sapiens RNA binding motif protein 14 (RBM14), mRNA [NM_006328] |
| 77 | A_23_P150403 | VPS11 | ACGAGATCTCATGATGAATTCGAGCATCAGCTCAAGTGCTCGAATGACAGCTTTCTGT | SEQ ID NO: 77 | Homo sapiens vacuolar protein sorting 11 homolog (S. cerevisiae) (VPS11), mRNA [NM_021729] |
| 78 | A_23_P150852 | FAM62A | GCCTTTGGCTGACCAAAGAAGAAAGACCGTATGTTCCGTTTACTGCAGGGCCTTTATCCT | SEQ ID NO: 78 | Homo sapiens family with sequence similarity 62 (C2 domain containing), member A (FAM62A), mRNA [NM_015292] |
| 79 | A_23_P150931 | LMBR1L | AGAGTTTGGGACCAGGAGCCTCCTGCCTTTTCCATACTTAACTGTGGCCTCAGCATGGGTA | SEQ ID NO: 79 | Homo sapiens limb region 1 homolog (mouse)-like (LMBR1L), mRNA [NM_018113] |
| 80 | A_23_P151426 | FOXO1 | GAAGGTTAGTGAGCAGGTTACAGTTAAAAGTAGTTCAGATTGTGTGACACGAGGAACTGA | SEQ ID NO: 80 | Homo sapiens forkhead box O1A (FOXO1A), mRNA [NM_002015] |
| 81 | A_23_P15247 | C16orf5 | GTGAATGATCAGACCCTGGTAGGTAAGGAAGTTGTCCCTTTGAGTCAGTGTGCAGAAC | SEQ ID NO: 81 | Homo sapiens chromosome 16 open reading frame 5 (C16orf5), mRNA [NM_013399] |
| 82 | A_23_P152818 | MYST2 | CAAAGTAATGTCCACTTTTCGCCTTTCATGCTGCATATAAGTGGTTAATTATACTGCAGA | SEQ ID NO: 82 | Homo sapiens MYST histone acetyltransferase 2 (MYST2), mRNA [NM_007067] |
| 83 | A_23_P152992 | AK125872 | GGCAACAAAGCAAGACGCCTGGTCTCCACCAAAAATAAGTAATTAATTTTTAAAGGAGA | SEQ ID NO: 83 | Homo sapiens cDNA FLJ43694 fis, clone TBAES2001492. [AK125872] |
| 84 | A_23_P153892 | XRCC1 | CGATACGTCACAGCCTTCAATGGGGAGCTCGAGGACTATATGAGTGACCGGGTTCAGTTT | SEQ ID NO: 84 | Homo sapiens X-ray repair complementing defective repair in Chinese hamster cells 1 (XRCC1), mRNA [NM_006297] |
| 85 | A_23_P154962 | KIAA1666 | TTGCTGATAACGTATGGCAGGTATACGGAGGAGAAGCGGCGTTTTTCTGTGGCCAATGTGTGTTT | SEQ ID NO: 85 | Homo sapiens KIAA1666 protein, mRNA (cDNA clone IMAGE:4827837), complete cds. [BC035246] |
| 86 | A_23_P155027 | MORC2 | GGCACCTTGGTTTGACTTACACGGGGACATTTGTGTTTTTGGAGGAAAAGATACGCCTGATTC | SEQ ID NO: 86 | Homo sapiens MORC family CW-type zinc finger 2 (MORC2), mRNA [NM_014941] |
| 87 | A_23_P155257 | FOXP1 | CAACCACAGTCCAGATTTTGACCACAGAGAGATTACGGAAGAATGAACCAGTAAACGAGGA | SEQ ID NO: 87 | Homo sapiens forkhead box P1 (FOXP1), transcript variant 1, mRNA [NM_032682] |

Fig. 1-6

| No. | Probe ID No. | Symbols of genes | Sequence | SEQ ID NO: | Descriptions of genes (letters and numbers within [ ] indicates GenBank accession No.) |
|---|---|---|---|---|---|
| 88 | A_23_P15603 | MRM1 | CGAGCCCAGGGAGGGACCCGTTCCTCGTTGAACCAGTCATTGCGTGTGG CAAATGTGTGTATGA | SEQ ID NO: 88 | Homo sapiens mitochondrial rRNA methyltransferase 1 homolog (S. cerevisiae) (MRM1), mRNA [NM_024864] |
| 89 | A_23_P158897 | BE531123 | TAGGAAGATGAATACCTTACAAGCTGAAAGCTGAAAGCTGGAAGTTCCCG AAAGGGTTTGGGTAT | SEQ ID NO: 89 | BE531123 601278493F1 NIH_MGC_39 Homo sapiens cDNA clone IMAGE:3610487 5', mRNA sequence [BE531123] |
| 90 | A_23_P1594 | VEGFB | TGTCTCAGTTTCTGAACCACTCTGTGTGCAAGTAAGCATCTTTACAGT GGCTCTCTCGCCT | SEQ ID NO: 90 | Homo sapiens vascular endothelial growth factor B (VEGFB), mRNA [NM_003377] |
| 91 | A_23_P161257 | PDCD11 | CAGCACAGACCCAAGCTAGTTGTTGAAGCCAGTTCTTTTTTGTCT GGTCATGAGGGAATT | SEQ ID NO: 91 | RRP5 protein homolog (Programmed cell death protein 11). [Source:Uniprot/SWISSPROT:Acc:O14690] [ENST00000369797] |
| 92 | A_23_P16143 | GTF2F1 | ACCTGACACGGAAGGCGATGACCACTAAGGACCTGCTGAAAAAGT TCCAACCAAGAAGA | SEQ ID NO: 92 | Homo sapiens general transcription factor IIF, polypeptide 1, 74kDa (GTF2F1), mRNA [NM_002096] |
| 93 | A_23_P161562 | ZNF289 | TGTGATGAATTCCTTGCAAGGATGGCTAGGGTTCCTACTGATCCGA GCTCTGTGACTCAGG | SEQ ID NO: 93 | Homo sapiens zinc finger protein 289, ID1 regulated (ZNF289), mRNA [NM_032389] |
| 94 | A_23_P161918 | CCDC86 | AAATACABACAATAGACGAAAGTCCCTGCCGTCGAGGAGGCTTTCA TTCTGATGGAGAGAA | SEQ ID NO: 94 | Homo sapiens coiled-coil domain containing 86 (CCDC86), mRNA [NM_024098] |
| 95 | A_23_P162120 | NUMA1 | AGAAGAAAGGAGGTCCAGGTTCTGTACTAAACAGAAAATTGATGATCGTGACTC AGTCGATGGCCTTCA | SEQ ID NO: 95 | Homo sapiens nuclear mitotic apparatus protein 1 (NUMA1), mRNA [NM_006185] |
| 96 | A_23_P162374 | DDX54 | CTATCAGAAGTGGAAACAGAAACAGGAAGGTCAGAGAAAGAAGAGGGC | SEQ ID NO: 96 | Homo sapiens DEAD (Asp-Glu-Ala-Asp) box polypeptide 54 (DDX54), mRNA [NM_024072] |
| 97 | A_23_P162525 | UTP20 | GTAGGCAATTGGATCGTTGGGATAGACAAGGTAAAGGCGTATCTCCAA ATGATCATAGGTCCT | SEQ ID NO: 97 | Homo sapiens UTP20, small subunit (SSU) processome component, homolog (yeast) (UTP20), mRNA [NM_014503] |
| 98 | A_23_P163258 | PARP6 | GACGGCAAGATACGAAGAGGAAATCATGCGTGTGATGGAAGTCAG GTTTACACAAACTGA | SEQ ID NO: 98 | Homo sapiens poly (ADP-ribose) polymerase family, member 6 (PARP6), mRNA [NM_020214] |
| 99 | A_23_P164718 | SNRPA | TCACCAACCTGCCAGGAGACCAACGAGGTCATGCTGTCCATGC TTTTCAATCAGTTCC | SEQ ID NO: 99 | Homo sapiens small nuclear ribonucleoprotein polypeptide A (SNRPA), mRNA [NM_004596] |
| 100 | A_23_P166280 | THC2614148 | CTCAGGGGAGTTCTCAGCTTGGACCCTTATCTCCCAGAATCCTG GAAGCTGGTCCTCT | SEQ ID NO: 100 | Q59G86_HUMAN (Q59G86) Androgen-regulated short-chain dehydrogenase/reductase 1 variant (Fragment), partial (7%) [THC2614148] |
| 101 | A_23_P166491 | RUTBC3 | ATTCCCGGTCTGGTCGTCTGTCTCTATAAGACGTCAGGTTGGATGAAGATG CCAAAGTCCTGACCG | SEQ ID NO: 101 | Homo sapiens RUN and TBC1 domain containing 3 (RUTBC3), mRNA [NM_015705] |
| 102 | A_23_P166609 | DHX30 | CGTACGATATAGGACAAATCAGGCAACATCCTGCTGCACAAGTC GACGATTAACAGGGA | SEQ ID NO: 102 | Homo sapiens DEAH (Asp-Glu-Ala-His) box polypeptide 30 (DHX30), transcript variant 2, mRNA [NM_014966] |
| 103 | A_23_P168826 | DCP1A | CATTCTTCACGTGATAATGGAGGTTTCAGTGTGAAGCATCACCAGCA GATCCTTGTTTTGAC | SEQ ID NO: 103 | Homo sapiens DCP1 decapping enzyme homolog A (S. cerevisiae) (DCP1A), mRNA [NM_018403] |
| 104 | A_23_P167093 | IDUA | ACATACGAGCATCCAGTTGTCTTCAGGACGGTAAGGCGGTACACCCGG GTCAGGAGGAAGCCA | SEQ ID NO: 104 | Homo sapiens iduronidase, alpha-L- (IDUA), mRNA [NM_000203] |
| 105 | A_23_P168541 | C7orf26 | TGGAGGGAAGAGTCCAGCCTGTGCCGAGAGCCTGCTGCGTGCATT TTTAAAGATGCCGA | SEQ ID NO: 105 | Homo sapiens chromosome 7 open reading frame 26 (C7orf26), mRNA [NM_024067] |
| 106 | A_23_P171336 | USP11 | ACTTTGATGACAACAGCGTCTCGCCTGTCAATGAGAATCAGAATCG AGTCCAAGGCAGGCT | SEQ ID NO: 106 | Homo sapiens ubiquitin specific peptidase 11 (USP11), mRNA [NM_004651] |

Fig. 1-7

| No. | Probe ID No. | Symbols of genes | Sequence | SEQ ID NO: | Descriptions of genes (letters and numbers within [ ] indicates GenBank accession No.) |
|---|---|---|---|---|---|
| 107 | A_23_P18205 | RAD54L2 | GAGGTTGGGTTCAGCTCCAATGATGATGAGGATAAAGACGATGATGTGATAGAGGTCACT | SEQ ID NO: 107 | Homo sapiens RAD54-like 2 (S. cerevisiae) (RAD54L2), mRNA [NM_015106] |
| 108 | A_23_P20489 | TMEM63A | CTCCTGGGGATTCTGGGGAATGGAACTGAACTTAAGAGCTTCTGCCTGAGAAGCCTCCTCC | SEQ ID NO: 108 | Homo sapiens transmembrane protein 63A (TMEM63A), mRNA [NM_014698] |
| 109 | A_23_P202156 | NFKB2 | GGCCACACGCGCTCTTGAGCTCACTTGAGCGACGCAAGGTGAAGACCTTGCTGGTAAATGCT | SEQ ID NO: 109 | Homo sapiens nuclear factor of kappa light polypeptide gene enhancer in B-cells 2 (p49/p100) (NFKB2), transcript variant 2, mRNA [NM_002502] |
| 110 | A_23_P202708 | MADD | GTGTCCTTGAGACATTTGTGTTGTGGTTCCTTGTCCTGTCCCTGGGGTTATAACTGTCC | SEQ ID NO: 110 | Homo sapiens MAP-kinase activating death domain (MADD), transcript variant 4, mRNA [NM_003682] |
| 111 | A_23_P203406 | GANAB | CCTTTGAGGGGCAGTTAAGATGGAGAAATCAGTTGTGGTTTCAGTGAATCATCGGTCACCT | SEQ ID NO: 111 | Homo sapiens glucosidase, alpha; neutral AB (GANAB), transcript variant 2, mRNA [NM_198334] |
| 112 | A_23_P203488 | SMPD1 | GTGTACCAAATAGATGGAAAACTAGTCCGGGAGGTCTCACGTGGTCCTGACCATGAGACC | SEQ ID NO: 112 | Homo sapiens sphingomyelin phosphodiesterase 1, acid lysosomal (acid sphingomyelinase) (SMPD1), transcript variant 1, mRNA [NM_000543] |
| 113 | A_23_P203737 | INTS4 | ACCATTCGGTTCAGCAAGCCTGTAAAACTAGTCCGGGAGGTTTATATAATGGGCAAACCTGACCACGGCGCTAA | SEQ ID NO: 113 | Homo sapiens integrator complex subunit 4 (INTS4), mRNA [NM_033547] |
| 114 | A_23_P203819 | GOLGA3 | TCTCACAGGAATCCGGAGGGAAAATGTGTTAGAGGGGTCTGGAAAATTCAGTGCTTTTGAGTT | SEQ ID NO: 114 | Homo sapiens golgi autoantigen, golgin subfamily a, 3 (GOLGA3), mRNA [NM_005895] |
| 115 | A_23_P20427 | RHOBTB2 | AGGAGGTATGAATCCCAGTCCCCAGGAACCTAGGTCTGTTAAACTCTGGGAGTCGGATTC | SEQ ID NO: 115 | Homo sapiens Rho-related BTB domain containing 2 (RHOBTB2), mRNA [NM_015178] |
| 116 | A_23_P204364 | NCL1 | GGCAAGACTGAGAATTGTCCACTGTGTCAGTTCTGTCGACAAAGACCGAAGCTTCCTCCAGCTT | SEQ ID NO: 116 | Homo sapiens nucleolar protein 1, 120kDa (NOL1), transcript variant 1, mRNA [NM_006170] |
| 117 | A_23_P205841 | MYO9A | TGAAGGCAAAAGCCTTTGGGGTTTATTTTGGGATAGTTAGGACCTAGGGTAGAATATAATT | SEQ ID NO: 117 | Homo sapiens myosin IXA (MYO9A), mRNA [NM_006901] |
| 118 | A_23_P20722 | SNAPC4 | ATGCTCTTCCCCAAGTGCACACTGAACACTTGGAGGAATAAAGTTCTGTTTTAATTG | SEQ ID NO: 118 | Homo sapiens small nuclear RNA activating complex, polypeptide 4, 190kDa (SNAPC4), mRNA [NM_003086] |
| 119 | A_23_P207319 | MAP3K14 | CAGGAGCTCACGTAGCCATTAAATCAGCTGTGAATCGTCAGGAGGGTGTCTGCTAGCCTGAAC | SEQ ID NO: 119 | Homo sapiens mitogen-activated protein kinase kinase kinase 14 (MAP3K14), mRNA [NM_003954] |
| 120 | A_23_P207736 | AK023077 | TTCGTTAATTCTTGGGGACTGGGACCAGGTGGTGAAGCACGAAGATGACTTCTGAGCGTTTATCACTGTT | SEQ ID NO: 120 | Homo sapiens cDNA FLJ13015 fis, clone NT2RP3000622. [AK023077] |
| 121 | A_23_P20793 | A_23_P20793 | TGCCCTTCCATAAGGTCGGGGTTTGTAGGGGTCTTGTGGTTGCTTCTGGTCTCTCCAAGGTT | SEQ ID NO: 121 | |
| 122 | A_23_P208358 | RPL28 | CACCATCGAACAAGAATAAGTGCTCGGCGCCACGGCTCAAGCAGCATCAAGACATCATGATCCGCCAAGAA | SEQ ID NO: 122 | Homo sapiens ribosomal protein L28 (RPL28), mRNA [NM_000991] |
| 123 | A_23_P208551 | LPHN1 | TCGGGTATCTGGGGAGCAGATTTGGGTCTGGATCCGGTGGGGAGTGGGTCCTGGGCTT | SEQ ID NO: 123 | Homo sapiens latrophilin 1 (LPHN1), transcript variant 1, mRNA [NM_001008701] |
| 124 | A_23_P208582 | A_23_P208582 | GTATTCATGTCGCCTGGGAGTTCCTGCGTCATCATAGTACCCAGTGAGCCCAGAAGATCCTAC | SEQ ID NO: 124 | |
| 125 | A_23_P208961 | MUM1 | CATTGTGGGTTCCTGAGAGTAGGACACATTGGGGATGGCATGGTTTTGTGGGAATCACGGCGCCCT | SEQ ID NO: 125 | Homo sapiens melanoma associated antigen (mutated) 1 (MUM1), mRNA [NM_032853] |
| 126 | A_23_P210319 | DTNB | CAGAGGGACATTCCTCTCCATCTTTCCACGGCACACGTGGACCAGGCTTGACGGCTGCCA | SEQ ID NO: 126 | Homo sapiens dystrobrevin, beta (DTNB), transcript variant 4, mRNA [NM_183360] |

Fig. 1-8

| No. | Probe ID No. | Symbols of genes | Sequence | SEQ ID NO: | Descriptions of genes (letters and numbers within [ ] indicates GenBank accession No.) |
|---|---|---|---|---|---|
| 127 | A_23_P210343 | THIL | ATGGTTCACCTGCTGGTGAAGGTCAAGGTTATGTACTGCTGTTGTCAGTTACATCCGAAAGTGT | SEQ ID NO: 127 | Homo sapiens THI-like (Drosophila) (THIL), transcript variant 1, mRNA [NM_198976] |
| 128 | A_23_P211878 | FLNB | GCCCCAAGCCAACTTCATGGGTCACTTCATTTTCGTGGAAAATAATGATCTGTACAGACAGGAGA | SEQ ID NO: 128 | Homo sapiens filamin B, beta (actin binding protein 278) (FLNB), mRNA [NM_001457] |
| 129 | A_23_P214687 | TRIM26 | ATTATGTCTAGAATTGGTCGTTGTGAGGGGGAGTTTAAGAATCGAGAACTGTCTCTTG | SEQ ID NO: 129 | Homo sapiens tripartite motif-containing 26 (TRIM26), mRNA [NM_003449] |
| 130 | A_23_P214638 | EHMT2 | GGTCTTCATGCTGCACCAAGAACCTGCGATTTGCACGCATCGGCTTCTTCAGTTCCCCGAGA | SEQ ID NO: 130 | Homo sapiens euchromatic histone-lysine N-methyltransferase 2 (EHMT2), transcript variant NG36/09a, mRNA [NM_006709] |
| 131 | A_23_P21495 | FCGBP | TCAGTCATCCACCAGGAACGAAGGATTTCCTGAAGAAGACCTGGTCCCTCTGGAGGTTGCG | SEQ ID NO: 131 | Homo sapiens Fc fragment of IgG binding protein (FCGBP), mRNA [NM_003890] |
| 132 | A_23_P215175 | ABCF2 | GAGGGTGGGTATGATGTCGTCAGCCATGACTCAGACTCATTCAGCAGGTTGCACAGGAA | SEQ ID NO: 132 | Homo sapiens ATP-binding cassette, sub-family F (GCN20), member 2 (ABCF2), nuclear gene encoding mitochondrial protein, transcript variant 2, mRNA [NM_005692] |
| 133 | A_23_P215449 | BAZ1B | CAGGTCCTAGAACATGAGAATCAAGCCTCTTAATTTAAACTGCGGAATGTGGCCTCTGC | SEQ ID NO: 133 | Homo sapiens bromodomain adjacent to zinc finger domain, 1B (BAZ1B), mRNA [NM_032408] |
| 134 | A_23_P21640 | CHD3 | GTCCAATGGGCGACGGAGGAGAAAGAGAGAGAACCCCCGGTCATGTTCAATATCGCCGA | SEQ ID NO: 134 | Homo sapiens chromodomain helicase DNA binding protein 3 (CHD3), transcript variant 1, mRNA [NM_001005273] |
| 135 | A_23_P217028 | USP20 | GGGAAGGGGCTGTGGGACCAGGACCCCCCACAGTACTGCGTCTTTG TTTCTATGAGTCTT | SEQ ID NO: 135 | Homo sapiens ubiquitin specific peptidase 20 (USP20), transcript variant 1, mRNA [NM_001008563] |
| 136 | A_23_P218086 | TPCN1 | TCCTAGAAAACCCATTGTGTCTGTCTGGATCTGTAGCACGATTACTACGAAGAGCCTCTGGTTT | SEQ ID NO: 136 | Homo sapiens mRNA for KIAA1169 protein, partial cds. [AB032995] |
| 137 | A_23_P218215 | AA601902 | AACCCTTACTATCCAACAGATTCTGTGTTGCAAATCTATCTACTCGCTAAAATATATCTG | SEQ ID NO: 137 | AA601902_np02b01.s1 NCI_CGAP_Pr2 Homo sapiens cDNA clone IMAGE:1115113 similar to contains Alu repetitive element; mRNA sequence [AA601902] |
| 138 | A_23_P23854 | ZGPAT | GTCCCATCTGGACACTTACTTGCCCACCTGCGAGTGTGTGGGACATTTCCTTGGCAAGGA | SEQ ID NO: 138 | Homo sapiens zinc finger, CCCH-type with G patch domain (ZGPAT), transcript variant 1, mRNA [NM_032527] |
| 139 | A_23_P218751 | GNB1L | GGAGTCCCGCTGTCTCTCAATGAGGTTGGTATTTCCTTTTGTGGAGTGCCTCATCACAGGA | SEQ ID NO: 139 | Homo sapiens guanine nucleotide binding protein (G protein), beta polypeptide 1-like (GNB1L), mRNA [NM_053004] |
| 140 | A_23_P23411 | PRCC | GCAAGAGGAAGCCAGGGAGGGAAGAAGAAATCAACTTGTGGAGATCAAAGGTGATGACCAGC | SEQ ID NO: 140 | Homo sapiens papillary renal cell carcinoma (translocation-associated) (PRCC), transcript variant 1, mRNA [NM_005973] |
| 141 | A_23_P23894 | RIPK5 | AGGGCCAAGCTATCCGTTTAGCAAAAAGTGTCTCAGATGTGTAAAAGCCTAGGGAATGTG | SEQ ID NO: 141 | Homo sapiens receptor interacting protein kinase 5 (RIPK5), transcript variant 1, mRNA [NM_015375] |
| 142 | A_23_P24068 | BMS1 | TCATGAAGAAAGATCGTTGCACTCGTGCGATGCTGAGTACGGTGCATAGTCAGAAGAT | SEQ ID NO: 142 | Homo sapiens BMS1 homolog, ribosome assembly protein (yeast) (BMS1), mRNA [NM_014753] |
| 143 | A_23_P251259 | GTF2H4 | TCTGGGCAAGGATTAGTCTGTGGAAGGTATGAGTGATTCTCTGTTGAACTTCCTGCAACA | SEQ ID NO: 143 | Homo sapiens general transcription factor IIH, polypeptide 4, 52kDa (GTF2H4), mRNA [NM_001517] |

Fig. 1-9

| No. | Probe ID No. | Symbols of genes | Sequence | SEQ ID NO: | Descriptions of genes [letters and numbers within [ ] indicates GenBank accession No.] |
|---|---|---|---|---|---|
| 144 | A_23_P251860 | ABCF1 | CCCACTCTGATTGCATCGATTCTCTGAAAGACTGTTGTTCTGCTTCTCTGATATAA | SEQ ID NO: 144 | Homo sapiens ATP-binding cassette, sub-family F (GCN20), member 1 (ABCF1), transcript variant 2, mRNA [NM_001090] |
| 145 | A_23_P252642 | BBS5 | GAAAAGATTGAGGAATCGGATGGTTGCCGTGTCTGTGTGTAGAAAGAAGTAGACATGGGAGA | SEQ ID NO: 145 | Homo sapiens Bardet-Biedl syndrome 5 (BBS5), mRNA [NM_152384] |
| 146 | A_23_P25348 | ACAD10 | CAGGAGGAGGACAGTGCTTGCTATGTCATAAACGGTCACAAATGGTGGATGACAGGCATCGT | SEQ ID NO: 146 | Homo sapiens acyl-Coenzyme A dehydrogenase family, member 10 (ACAD10), mRNA [NM_025247] |
| 147 | A_23_P255669 | DUS1L | AAAGTGTGACCAGTGTGTGGAAACCCAAAGGCAACAGATGTGTGTTCAGGGTGTGCGGCGG | SEQ ID NO: 147 | Homo sapiens dihydrouridine synthase 1-like (S. cerevisiae) (DUS1L), mRNA [NM_022156] |
| 148 | A_23_P256021 | LAS1L | AGACAACCTGGGAGCAGGCCTGGATCAGCAGCCAATCAACTCAACTTGTCAACGAGGGGAA | SEQ ID NO: 148 | Homo sapiens LAS1-like (S. cerevisiae) (LAS1L), mRNA [NM_031206] |
| 149 | A_23_P257155 | ATXN7 | TTGGTGAAGAGCAGGTGATTCTAGTGTCTTCTCTTGGGCCATTCATCACCAGTCCAATGAAC | SEQ ID NO: 149 | Homo sapiens ataxin 7 (ATXN7), mRNA [NM_000333] |
| 150 | A_23_P258124 | ZNF346 | AAGCTGGGGATCTGCTTTATGTGTGAGAGAACTGTTCTGGGTGTTATGTAAAGGAGTGCA | SEQ ID NO: 150 | Homo sapiens zinc finger protein 346 (ZNF346), mRNA [NM_012279] |
| 151 | A_23_P258190 | AKR1B1 | GTGATCCCAAGTCGTGTGACACCAGAACAGCATTGCTGAGAAGTTAAGGTCTTTGACTTT | SEQ ID NO: 151 | Homo sapiens aldo-keto reductase family 1, member B1 (aldose reductase) (AKR1B1), mRNA [NM_001628] |
| 152 | A_23_P26375 | ACD | GCAAAGAAGGCATCGTGATGATTTCTGCCTTCCAGTATGAGTATGAGCGACCCTGCACGTCC | SEQ ID NO: 152 | Homo sapiens adrenocortical dysplasia homolog (mouse) (ACD), transcript variant 2, mRNA [NM_022814] |
| 153 | A_23_P26810 | TP53 | CTGTGAGGGATGATTTGGGAGATGTAAGAAATGTTCTTGCAGTTAAGGGTTAGTTTAGAAT | SEQ ID NO: 153 | Homo sapiens tumor protein p53 (Li-Fraumeni syndrome) (TP53), mRNA [NM_000546] |
| 154 | A_23_P27894 | SAFB2 | CAGGGTTCCAAGTTGGGAGGATGTTTTAAAAGCAAAGTAAATCGTGCCACCATGTT | SEQ ID NO: 154 | Homo sapiens scaffold attachment factor B2 (SAFB2), mRNA [NM_014649] |
| 155 | A_23_P28857 | SIRPG | TCCGATCCATGGCCTTGAGACTGACGGTAAACCACAGACAGCGCTCTCCAGGTTCTGAAGAGT | SEQ ID NO: 155 | Homo sapiens signal-regulatory protein gamma (SIRPG), transcript variant 2, mRNA [NM_080816] |
| 156 | A_23_P300150 | NFATC1 | AGCCTTTCTCAGGGGACGTGTCATTGAAAAGGAAAGGTTTGATGTCTGTGTCAGGTGTCTT | SEQ ID NO: 156 | Homo sapiens nuclear factor of activated T-cells, cytoplasmic, calcineurin-dependent 1 (NFATC1), transcript variant 3, mRNA [NM_172387] |
| 157 | A_23_P300714 | SORBS3 | ACGCAGGACGCTTCTTAGGGATGTAGGGCTGGCAAGAGGCTGTGGCCCCAAGGCCTCGTCTT | SEQ ID NO: 157 | Homo sapiens sorbin and SH3 domain containing 3 (SORBS3), transcript variant 1, mRNA [NM_005775] |
| 158 | A_23_P300826 | C6orf136 | TACAAGGGTGACAAAGACGAGGATTACCGGACCCTATGATGGCTACTCCACTTCTACGCTG | SEQ ID NO: 158 | Homo sapiens chromosome 6 open reading frame 136 (C6orf136), mRNA [NM_145029] |
| 159 | A_23_P309803 | ZNF777 | TGTAGGGCCCATCTAGTTGGGGATAGAAGCTTTATAATTAGGTTTTGGATACTGTGTTCT | SEQ ID NO: 159 | Homo sapiens zinc finger protein 777 (ZNF777), mRNA [NM_015694] |
| 160 | A_23_P309850 | RPUSD2 | GCTTCTAAAGAGACCTTGCTCATACTTGCTACGTCCTCCAGTGGGAATTTGGGAGCTTT | SEQ ID NO: 160 | Homo sapiens RNA pseudouridylate synthase domain containing 2 (RPUSD2), mRNA [NM_152260] |
| 161 | A_23_P310331 | RANBP3 | CCGCCATGTGTTTTGGAACATTTATGTAAGATTGTCATATGAAATGTATTTGGGAACTAC | SEQ ID NO: 161 | Homo sapiens RAN binding protein 3 (RANBP3), transcript variant RANBP3-a, mRNA [NM_003624] |
| 162 | A_23_P311740 | PARC | CTGCCCTGTCATAGGAGGAGGGGAATTCCCAGGCTGCTGTGAGTGCTTCCTGTTTCCTGAATA | SEQ ID NO: 162 | Homo sapiens p53-associated parkin-like cytoplasmic protein (PARC), mRNA [NM_015089] |

Fig. 1-10

| No. | Probe ID No. | Symbols of genes | Sequence | SEQ ID NO: | Descriptions of genes [letters and numbers within [ ] indicate GenBank accession No.] |
|---|---|---|---|---|---|
| 163 | A_23_P312179 | ALMS1 | GAGATTGTGAAGCAGTGCCAAAAAAGACACTCGAGATGTTGGGATAAGTTTCGCAACTCCA | SEQ ID NO: 163 | Homo sapiens Alstrom syndrome 1 (ALMS1), mRNA [NM_015120] |
| 164 | A_23_P3128 | YLPM1 | AAGAGAAGAAGATGCAGATAGGAAAAGGGCCATAGGTTTGTGGTCGGACAGAGTGATT | SEQ ID NO: 164 | Homo sapiens YLP motif containing 1, mRNA (cDNA clone IMAGE:3835908), complete cds. [BC023570] |
| 165 | A_23_P31477 | NUDCD3 | AAGTGATGCAGTGGTGTGAGATGCGTACACCTGTTATTTGGGAGACTTTGAGAGTCAT | SEQ ID NO: 165 | Homo sapiens NudC domain containing 3 (NUDCD3), mRNA [NM_015332] |
| 166 | A_23_P31489 | URG4 | GAGGAAGTGACGTCACAGACCAGCTCAGAGATGTTACCAAGAATATCACAGCCCACCAGGG | SEQ ID NO: 166 | Homo sapiens up-regulated gene 4 (URG4), transcript variant 1, mRNA [NM_017920] |
| 167 | A_23_P315252 | AK097322 | CATGGGTGGGTGAATAGTACTTGCGGCAGTAGTGCTTAAAAGTAGGCGGCTATGGTATAAT | SEQ ID NO: 167 | Homo sapiens cDNA FLJ40003 fis, clone STOMA2003716. [AK097322] |
| 168 | A_23_P315378 | ATG16L1 | GTGTTGTTTCAGTTTATAGTCTTTGTCCAAAAGTCAGTTTCAAAATAATTTGCAATGGGAC | SEQ ID NO: 168 | Homo sapiens cDNA FLJ10035 fis, clone HEMBA1000919. [AK000897] |
| 169 | A_23_P315843 | NCOA5 | GCCCCGCATGGGATGTTACCAGAGGGCATTACTGAAGGTAAATCTTTCAACTCTCCCCAGTC | SEQ ID NO: 169 | Homo sapiens nuclear receptor coactivator 5 (NCOA5), mRNA [NM_020967] |
| 170 | A_23_P316472 | DNHD1 | TAAGCTGCAGAGCGAGGAACATCGTGATGCATCGTGCCTTTAGCCACCAAAGCTCAGCCCCAA | SEQ ID NO: 170 | Homo sapiens dynein heavy chain domain 1 (DNHD1), mRNA [NM_144666] |
| 171 | A_23_P319270 | AZI1 | GATGCCGCACAGGCTAAGGACGTGTGGGTGCATTTTAACAGTAAGGAGGGCGTTGTTTCA | SEQ ID NO: 171 | Homo sapiens 5-azacytidine induced 1 (AZI1), transcript variant 1, mRNA [NM_014984] |
| 172 | A_23_P320304 | AFAR3 | AGGGTGCCCAAGGCTTTTCGTCAACTCGTTTTGCTCTCGCGCGCTTTGTCTAATTTAGAA | SEQ ID NO: 172 | Homo sapiens aflatoxin B1 aldehyde reductase 3 (AFAR3), mRNA [NM_201252] |
| 173 | A_23_P320837 | DKFZP434A0131 | GCCTCTGAGTCCCATCATCATCTGTTGGGAAAGTCGTTGAAGGTGAACGTCACGGGTGAAACGGGGGCAGAGT | SEQ ID NO: 173 | Homo sapiens mRNA; cDNA DKFZp434A0131 (from clone DKFZp434A0131). [AL137492] |
| 174 | A_23_P32125 | PMPCA | CCCGTTCCGGTGCGTGTTAGTTTGGACACGAAGATTTAGTGTCTAAAAGGTGTCTGGTTGTAT | SEQ ID NO: 174 | Homo sapiens peptidase (mitochondrial processing) alpha (PMPCA), nuclear gene encoding mitochondrial protein, mRNA [NM_015160] |
| 175 | A_23_P321361 | DHX30 | ACCGGTTACACACGGTTACGGAGGCGGATGGCTGAGCTCTATTTCATGGCAGTCAAGTCCAAT | SEQ ID NO: 175 | Homo sapiens DEAH (Asp-Glu-Ala-His) box polypeptide 30 (DHX30), transcript variant 3, mRNA [NM_138614] |
| 176 | A_23_P325093 | GGTL3 | TGGGCGCGAGCTTAGGGATGTGCTTGGCAAACCCTTCTCAAGGGTCTCACAACCCCAACAT | SEQ ID NO: 176 | Homo sapiens gamma-glutamyltransferase-like 3 (GGTL3), mRNA [NM_178026] |
| 177 | A_23_P326142 | NAG8 | CTGTTGGGATTAGGAGTGGAATGAGGAATAGTTTAGGACCACAAGAGATTTGGCGCTGCTT | SEQ ID NO: 177 | Homo sapiens nesopharyngeal carcinoma associated gene protein-8 (NAG8), mRNA [NM_014411] |
| 178 | A_23_P328133 | GOT2 | TCAACTCGATCGGATCGGATCGGAGAATCGGATTATTTAAGAATGAAGAACATAATTTTCGTCGTGATGCCG | SEQ ID NO: 178 | Human mitochondrial aspartate aminotransferase mRNA, complete cds. [M22632] |
| 179 | A_23_P329212 | ETS1 | GTCAACCCAGCCTATCCAGAATCCGGCTATACCTCGGATTACTTCGATTAGCTATGGTATT | SEQ ID NO: 179 | Homo sapiens v-ets erythroblastosis virus E26 oncogene homolog 1 (avian) (ETS1), mRNA [NM_005238] |
| 180 | A_23_P332042 | RECQL5 | CTTTCTGCTTGCAAAGCCTCTTGCAAAGCCTATAGACCCTTCTCAGAGCGGGTCGTCATGGGCTGGGTTTTCTG | SEQ ID NO: 180 | Homo sapiens RecQ protein-like 5 (RECQL5), transcript variant 1, mRNA [NM_004259] |
| 181 | A_23_P336015 | NOC2L | GGAATTTAAAGACCTCTTTGACCTGAACAGGTCTGAAGAGGACGAACACTGAGGGATTCTC | SEQ ID NO: 181 | Homo sapiens nucleolar complex associated 2 homolog (S. cerevisiae) (NOC2L), mRNA [NM_015658] |

Fig. 1-11

| No. | Probe ID No. | Symbols of genes | Sequence | SEQ ID NO: | Descriptions of genes (letters and numbers within [ ] indicates GenBank accession No.) |
|---|---|---|---|---|---|
| 182 | A_23_P336218 | MGC27345 | TGAGTGACTGCTTTGTTGAATCAGATAGTAACAAAACATTTATTTGTAGTCTGGTTGTGTC | SEQ ID NO: 182 | Homo sapiens hypothetical protein MGC27345, mRNA (cDNA clone MGC:27345 IMAGE:4670552), complete cds. [BC024231] |
| 183 | A_23_P336513 | GEMIN5 | AGACCTTGGCAGAAGATGATCGGACAACACCAAAAGAGTCAACTCTGTAAATCCACAGGAA | SEQ ID NO: 183 | Homo sapiens gem (nuclear organelle) associated protein 5 (GEMIN5), mRNA [NM_015465] |
| 184 | A_23_P339095 | SPTBN1 | AGTGGGATAGTTGAAAAGGAGAAGAAGTTTCCCAAAAGGGTTTGCCAGCTGAACAGGGAT | SEQ ID NO: 184 | Homo sapiens spectrin, beta, non-erythrocytic 1 (SPTBN1), transcript variant 2, mRNA [NM_178313] |
| 185 | A_23_P42131 | CYBASC3 | GCTGACCGACTCTGAGGTGTTCGTGTTTCGTATTGCTGCTGTGTGTCTGCATGTATTGTGAC | SEQ ID NO: 185 | Homo sapiens cytochrome b, ascorbate dependent 3 (CYBASC3), mRNA [NM_153611] |
| 186 | A_23_P4496 | TMEM39B | CCTGATCCTCTTCAGCAACTACTACTAGCCTCTTCAAGCTGGTCCGGGACCGGCTTGGTATT | SEQ ID NO: 186 | Homo sapiens transmembrane protein 39B (TMEM39B), mRNA [NM_018056] |
| 187 | A_23_P349310 | TNRC6A | CGTGGGGTGTCTACTATGCCTTGATGTTGGCTACCTTATTGTGGTATGGTGGAGTTTTAA | SEQ ID NO: 187 | Homo sapiens trinucleotide repeat containing 6A (TNRC6A), mRNA [NM_014494] |
| 188 | A_23_P3502 | NHN1 | AGTTGACAGTGTTGAATAAGGCGGCTGATAAAGGAAGGAAGAAGCGCTATGAACCATCAG | SEQ ID NO: 188 | Homo sapiens conserved nuclear protein NHN1 (NHN1), mRNA [NM_144604] |
| 189 | A_23_P356565 | KIAA0409 | TGAGGACAAAGTGTGATAAAACCTGTGGCTCAGACTTGCTCTACTGAAGGCTTCTTGGTT | SEQ ID NO: 189 | Homo sapiens KIAA0409 (KIAA0409), mRNA [NM_015324] |
| 190 | A_23_P359174 | BC069659 | CCAGGCGGTGCATACTAGGGCTGAATAAAGAAAATTTTGTAATAGGAACAGTGGTTTGGGATTTT | SEQ ID NO: 190 | Homo sapiens cDNA clone IMAGE:7262526, with apparent retained intron. [BC069659] |
| 191 | A_23_P36076 | SSRP1 | AATGCAGGATGCCAAATCTCATCTTAGTTTGCCGACCTTAAGGATGTAGCTGCTGCTTGT | SEQ ID NO: 191 | Homo sapiens structure specific recognition protein 1 (SSRP1), mRNA [NM_003146] |
| 192 | A_23_P36140 | B3GAT3 | AGAGAGTCTTCTGAGCCACCTTGTGGATCCCAAGGACCTGGAGCCACGGGCTGCCAACT | SEQ ID NO: 192 | Homo sapiens beta-1,3-glucuronyltransferase 3 (glucuronosyltransferase I) (B3GAT3), mRNA [NM_012200] |
| 193 | A_23_P36157 | WDR74 | TAGAGACACCTATGCAGAGTACCCAGTAACAGCCATGACCCTGACTCGCGGGAGGCAACT | SEQ ID NO: 193 | Homo sapiens WD repeat domain 74 (WDR74), mRNA [NM_018093] |
| 194 | A_23_P364637 | DDX51 | CCTCGTTCCAGAGCAGTGCGTGATCACTGGATCGTGTATGTGAGGAAAGGAATCCCCCAGT | SEQ ID NO: 194 | Homo sapiens DEAD (Asp-Glu-Ala-Asp) box polypeptide 51 (DDX51), mRNA [NM_175066] |
| 195 | A_23_P367676 | SIN3A | CGTGGAACTGTTTTGTATCTGGCTCTTTACTAGTCTACGTTAGTGCCATGCCACGCAGCTT | SEQ ID NO: 195 | Homo sapiens SIN3 homolog A, transcription regulator (yeast) (SIN3A), mRNA [NM_015477] |
| 196 | A_23_P368996 | LRRC56 | CAAACCAACATTTCCAGCTCTCAGGTGTACAGAAATGCGGTTTACTTTGTAGGCACAGTT | SEQ ID NO: 196 | Homo sapiens leucine rich repeat containing 56 (LRRC56), mRNA [NM_198075] |
| 197 | A_23_P371765 | C21orf56 | GAACATCCCCGAGAAGATCGGACAGAGACCTCCAGCAAGTCTGTGGACGGCTCCGTGGACGA | SEQ ID NO: 197 | Homo sapiens chromosome 21 open reading frame 56 (C21orf56), mRNA [NM_032261] |
| 198 | A_23_P37205 | NDRG2 | CGTTTGGCTGCAGTAAGTTTGGTAGCTCAGTGTGCATCTCAGAGTGGGACTGGGAGGGAG | SEQ ID NO: 198 | Homo sapiens NDRG family member 2 (NDRG2), transcript variant 1, mRNA [NM_201535] |
| 199 | A_23_P372255 | ITPKB | TCAGTTGTATTTAGCTTTGAGTTTCTGTGGATCGTCAGCCCATGTGTATATAACCAG | SEQ ID NO: 199 | Homo sapiens inositol 1,4,5-trisphosphate 3-kinase B (ITPKB), mRNA [NM_002221] |
| 200 | A_23_P38219 | PRPF8 | CCAGAACAGAAGGACAAGGGCAACGACGCCAAGGGCTAGCTGCCTTCACAGTATGAGAGGGT | SEQ ID NO: 200 | Homo sapiens PRP8 pre-mRNA processing factor 8 homolog (S. cerevisiae) (PRPF8), mRNA [NM_006445] |

Fig. 1-12

| No. | Probe ID No. | Symbols of genes | Sequence | SEQ ID NO: | Descriptions of genes (letters and numbers within [ ] indicates GenBank accession No.) |
|---|---|---|---|---|---|
| 201 | A_23_P383060 | SLC5A6 | GAAATAGGGATGGAAGTGCATCCTCTGGGAAAAGATAATAGCTTCTGATTCAACATAGC | SEQ ID NO: 201 | Homo sapiens solute carrier family 5 (sodium-dependent vitamin transporter), member 6 (SLC5A6), mRNA [NM_021095] |
| 202 | A_23_P384698 | LOC442075 | CACCTCAGTTGACAAGGAGATGAGAACTATCAGTTCATAGACAGCATCGATAGGGAAG | SEQ ID NO: 202 | Homo sapiens cDNA FLJ35033 fis, clone OCBBF2016590, weakly similar to CELL SURFACE ANTIGEN 114/A10 PRECURSOR. [AK092352] |
| 203 | A_23_P3949 | TRAP1 | ACTCATCAGGAAACTCGGGGACGGTTTTACAGGAGAGGGCTGATCAAATGTTCATTGACCA | SEQ ID NO: 203 | Homo sapiens TNF receptor-associated protein 1 (TRAP1), mRNA [NM_016292] |
| 204 | A_23_P38876 | LIPE | GGGGGACGGGCACACACAGCGGTCACGGAAGCGGCTGGACCTGACCA CGGCACCGGCTGCCTT | SEQ ID NO: 204 | Homo sapiens lipase, hormone-sensitive (LIPE), mRNA [NM_005357] |
| 205 | A_23_P388780 | DMAP1 | GATACCAGTATTTGATGGTGGGCACGAACGACGCGGGAAGGAACAGGTTGAGCGTCTCTA | SEQ ID NO: 205 | Homo sapiens DNA methyltransferase 1 associated protein 1 (DMAP1), transcript variant 1, mRNA [NM_019100] |
| 206 | A_23_P388914 | CCDC101 | CAACAAGTATGAGGTAGATGACATCGATGAAGAAGGCAAAGAGAG ACACACCCTGAGCCG | SEQ ID NO: 206 | Homo sapiens coiled-coil domain containing 101 (CCDC101), mRNA [NM_138414] |
| 207 | A_23_P389907 | ATXN2 | TTTCAGAGTGCCGGCAGGTCGGCCAGGTCTGTTGCCGAAACTGGAAGTTATTATTTT | SEQ ID NO: 207 | Homo sapiens ataxin 2 (ATXN2), mRNA [NM_002973] |
| 208 | A_23_P39034 | SMARCA4 | CTGGCATCAGTAGCATCGTGTAACAGCATTAACTGTCTTAAAGAGAGAGAAGAGAATTCC | SEQ ID NO: 208 | Homo sapiens SWI/SNF related, matrix associated, actin dependent regulator of chromatin, subfamily a, member 4 (SMARCA4), mRNA [NM_003072] |
| 209 | A_23_P39040 | SMARCA4 | AAGGAGCGCATTCGGCAAGCACAGAAGTACCGCAGGCTCAACGACCTAGAGAAGGACGTCATG | SEQ ID NO: 209 | Homo sapiens SWI/SNF related, matrix associated, actin dependent regulator of chromatin, subfamily a, member 4 (SMARCA4), mRNA [NM_003072] |
| 210 | A_23_P391275 | DSCR1L2 | TAAATTATGATTTACTCTGTGCTGTTTCCAAATTGGGACCAGGAGAGAAATATGAACTTC | SEQ ID NO: 210 | Homo sapiens Down syndrome critical region gene 1-like 2 (DSCR1L2), mRNA [NM_013441] |
| 211 | A_23_P3921 | FLJ11710 | CCTGATTCATGATTGAAGTACGATTAAATAATGCTATACATCCATGCATTGGATGTTTA | SEQ ID NO: 211 | Homo sapiens cDNA FLJ11710 fis, clone HEMBA1005149 [AK021772] |
| 212 | A_23_P292501 | TNRC6C | GGTTGTGACTGGTTTTGGGGGAGCCTGGGGTTTGGGCTCCAGCTGTTTACAGACGCTTT | SEQ ID NO: 212 | Homo sapiens cDNA FLJ31859 fis, clone NT2RP7001231 [AK056421] |
| 213 | A_23_P393401 | LOC339047 | CAATGACTTTTCTTTACCCCGCTAGGTGTCGGCAGTAGTCAGTGGAAGGGTGATATTATGA | SEQ ID NO: 213 | Homo sapiens hypothetical protein LOC339047 (cDNA clone IMAGE:4184431), complete cds. [BC068178] |
| 214 | A_23_P394917 | SRCAP | TGGTGGCTGTAATTCAGGATGACGTGGACTTAGCAGAATAGCGGGGCCAGGCGGGTTGGAAT | SEQ ID NO: 214 | Homo sapiens Snf2-related CBP activator protein (SRCAP), mRNA [NM_006662] |
| 215 | A_23_P39844 | MMT | GGCTTGGTGAGGGCAATCAAAATAATGTTTGTGATGCTACTAGTGTTGATTTTGGCGTCG | SEQ ID NO: 215 | Homo sapiens inner membrane protein, mitochondrial (mitofilin) (IMMT), mRNA [NM_006839] |
| 216 | A_23_P40049 | CAD | CCTGACACTGATGTGCTCTACAGATGACTCGAATCCAGAAGGAACGATTTTGGCTCTACCCAG | SEQ ID NO: 216 | Homo sapiens carbamoyl-phosphate synthetase 2, aspartate transcarbamylase, and dihydroorotase (CAD), mRNA [NM_004341] |
| 217 | A_23_P401084 | ZNF575 | CTTTGGGAGATCTCAAACCATGGACATTGGAGCGTGTGTTTGGTTTGACAGCCGCTGGCTCTGCTT | SEQ ID NO: 217 | Homo sapiens zinc finger protein 575 (ZNF575), mRNA [NM_174945] |

Fig. 1-13

| No | Probe ID No. | Symbols of genes | Sequence | SEQ ID NO: | Descriptions of genes (letters and numbers within [ ] indicates GenBank accession No.) |
|---|---|---|---|---|---|
| 218 | A_23_P40194 | DDX27 | CATGTCTGTCAATCTCCGTCTTGTCGATTAGGTTTCATATGACTATATTAAATGGAAGT | SEQ ID NO: 218 | Homo sapiens DEAD (Asp-Glu-Ala-Asp) box polypeptide 27 (DDX27), mRNA [NM_017895] |
| 219 | A_23_P406105 | GCN1L1 | TCTGGGAGGGGTATAGGTTTGAAAGGTGTTTGAAAGAGGAATGTTTAATAAAGGCTT | SEQ ID NO: 219 | Homo sapiens GCN1 general control of amino-acid synthesis 1-like 1 (yeast) (GCN1L1), mRNA [NM_006836] |
| 220 | A_23_P407601 | C8orf6 | GTCTCCTAGGTTAGTGTAGGAGAGATTCTATTCTCAGATAAGACTTCGGTGTCGGCTGAA | SEQ ID NO: 220 | Homo sapiens mRNA for hypothetical protein (C8orf6 gene), [AJ307469] |
| 221 | A_23_P407684 | ZNF598 | TGTCTGCACACACGGACTTCTGCAACGCGCAGAAGGCCTCTGAGCACCAAGTCCAAGAAGA | SEQ ID NO: 221 | Homo sapiens zinc finger protein 598 (ZNF598), mRNA [NM_178167] |
| 222 | A_23_P40989 | USP13 | TGAGATGGAGAATAATGGCAATGCAAACATTATTTGTGAGGCAAGCCCGAAGAGACCTAG | SEQ ID NO: 222 | Homo sapiens ubiquitin specific peptidase 13 (isopeptidase T-3) (USP13), mRNA [NM_003940] |
| 223 | A_23_P41021 | NISCH | TAATTGACTGTCCTCGGCAGAGAATGTGACATGTGTGTGTTGTGTTAATTCTTTCTG | SEQ ID NO: 223 | Homo sapiens nischarin (NISCH), mRNA [NM_007184] |
| 224 | A_23_P410653 | MLLT6 | AAACACAGAGACTGTTGTCTACCAGATGATGCAGGAGATCGAAGGAGAAACGGGAAGGTGCAGC | SEQ ID NO: 224 | Homo sapiens myeloid/lymphoid or mixed-lineage leukemia (trithorax homolog, Drosophila); translocated to, 6 (MLLT6), mRNA [NM_005937] |
| 225 | A_23_P411246 | TMC8 | GTCCTGACGGTGTGGTCTGCAGACCAGGCAATGCAGGGCCATCCACAGGCTCCGG | SEQ ID NO: 225 | Homo sapiens transmembrane channel-like 8 (TMC8), mRNA [NM_152468] |
| 226 | A_23_P41755 | PURA | CAACTCCATCACCGATGCCGTTACAAGGTGTGGGCCAAGTTCGGACACACGTCTCGCAAGTA | SEQ ID NO: 226 | Homo sapiens purine-rich element binding protein A (PURA), mRNA [NM_005859] |
| 227 | A_23_P422305 | SFXN4 | GATTTAACCGTCAAGGCCAATTGATAGTGAGAGGTTAAGGGCACAGAGTTGATCA | SEQ ID NO: 227 | Homo sapiens cDNA FLJ37976 fis, clone CTONG2010148, [AK095295] |
| 228 | A_23_P423457 | SERINC5 | TTTTGGTTCTTTAAACTTCTGCTGTTGGGGGCCATGTGCTCAGGAGCTTTCTTCATTCCA | SEQ ID NO: 228 | Homo sapiens serine incorporator 5 (SERINC5), mRNA [NM_178276] |
| 229 | A_23_P425932 | VTI1A | TACCTCAAAAATAGAACAAGACACTCCATGCGTGCGGATGACTGTCAAGGTCACTGA | SEQ ID NO: 229 | Vesicle transport through interaction with t-SNAREs homolog 1A (Vesicle transport v-SNARE protein Vti1-like 2) (Vti1-rp2). [Source:Uniprot/SWISSPROT;Acc:Q96AJ9] [ENST00000369309] |
| 230 | A_23_P431418 | U2AF2 | TGAAGACGATGGGCAGAGAGTGAGAGCGCCAGACACACAGAGCCGGCAGCAACTGGAA | SEQ ID NO: 230 | Homo sapiens U2 small nuclear RNA auxiliary factor 2 (U2AF2), transcript variant 1, mRNA [NM_007279] |
| 231 | A_23_P45108 | QRICH1 | GAAAGGGCTTGGACTGTGAAAAGAAATGTGGCCCTTTCCATCTTCAAGAGAGATGGAAT | SEQ ID NO: 231 | Homo sapiens glutamine-rich 1 (QRICH1), transcript variant 1, mRNA [NM_017730] |
| 232 | A_23_P48964 | VPS33B | CCTCACAGCCGTGGAGAGATAAAGTGAGGCAAGCTGGTGACGGACAAGGCTGCAGGAAAGAT | SEQ ID NO: 232 | Homo sapiens vacuolar protein sorting 33 homolog B (yeast) (VPS33B), mRNA [NM_018668] |
| 233 | A_23_P4922 | LOC374920 | GAGAGTGTCCAGCAGGGGAGGGGGAATTGTTTGGACTATTGTTCTCAGGATTGGAATAAA | SEQ ID NO: 233 | Homo sapiens hypothetical protein LOC374920 (LOC374920), mRNA [NM_199341] |
| 234 | A_23_P49327 | ZNF174 | AATCACAAAACTGTGTGACTTACAAGGAAAGGACGAGGCCTTGAGGAATGATGATGCA | SEQ ID NO: 234 | Homo sapiens zinc finger protein 174 (ZNF174), transcript variant 1, mRNA [NM_003450] |
| 235 | A_23_P4944 | CALM3 | CTCAGTGCCCAGGTCGATCAAGTGGCTTCCTGGGACCTGCCCAGCTTTGAGAATCTCT | SEQ ID NO: 235 | Homo sapiens calmodulin 3 (phosphorylase kinase, delta) (CALM3), mRNA [NM_005184] |

Fig. 1-14

| No. | Probe ID No. | Symbols of genes | Sequence | SEQ ID NO: | Descriptions of genes (letters and numbers within [ ] indicate GenBank accession No.) |
|---|---|---|---|---|---|
| 236 | A_23_P49900 | PELP1 | TGAGTCTCGCCCAAAGGTCAGCCAGACCCGAACCCGAACCCGG GCTGGTTTTGGAAGT | SEQ ID NO: 236 | Homo sapiens proline, glutamic acid and leucine rich protein 1 (PELP1), mRNA [NM_014389] |
| 237 | A_23_P50020 | COG1 | GCATGAAGACGACTCGAAAGGCTAAATCAACCAGAAACATCGAAA CAAAAGCTCAAGCTTG | SEQ ID NO: 237 | Homo sapiens component of oligomeric golgi complex 1 (COG1), mRNA [NM_018714] |
| 238 | A_23_P501795 | SURF5 | CCATCATTCGGAGTCATCATCGTCGTGTTTGCTGCGTTCCTCGGCCAG CCAGGTGGAAGAAAG | SEQ ID NO: 238 | Homo sapiens surfeit 5 (SURF5), transcript variant b, mRNA [NM_133640] |
| 239 | A_23_P501887 | DHPS | GCTGATGCCCATTCTGGACCAAGATGGTGATGGAGCAGAACACAGA GGGTGTAAAGTGGAC | SEQ ID NO: 239 | Homo sapiens deoxyhypusine synthase (DHPS), transcript variant 3, mRNA [NM_013407] |
| 240 | A_23_P502196 | IDH3B | CATGTGAAGTGACTTCCTGGGTATATGACTCGGCACGAACAATGTA GACCTGGTGATCATT | SEQ ID NO: 240 | Homo sapiens isocitrate dehydrogenase 3 (NAD+) beta (IDH3B), nuclear gene encoding mitochondrial protein, transcript variant 2, mRNA [NM_174855] |
| 241 | A_23_P50472 | ALDH16A1 | CTGTGGCTGCCTATGGCGGACTGATGCGTGAGGCGCACCCTACTGC ATTTTGGACACCTCA | SEQ ID NO: 241 | Homo sapiens aldehyde dehydrogenase 16 family, member A1 (ALDH16A1), mRNA [NM_153329] |
| 242 | A_23_P51639 | KIAA0467 | GGTTCCAATCCGAGGTCTGCCTTTGAAGGACTGTGGCGACCCTG AAGTCCGTTGCTCT | SEQ ID NO: 242 | Homo sapiens KIAA0467 (KIAA0467), mRNA [NM_015284] |
| 243 | A_23_P53015 | TUT1 | CATATAGAAGCAGCAACCAAGAGAACGCGGTCAGGAAGGAGGTGGA ACTGGGGAGTCGTCT | SEQ ID NO: 243 | Homo sapiens terminal uridylyl transferase 1, U6 snRNA-specific (TUT1), mRNA [NM_022830] |
| 244 | A_23_P33641 | CHD4 | TGCTGAGTGACATGAAAGGCTGATGTGACTCGAGTCAAGGAGAGGTCCAGGTACCA TTGGCGGAATTCCCC | SEQ ID NO: 244 | Homo sapiens chromodomain helicase DNA binding protein 4 (CHD4), mRNA [NM_001273] |
| 245 | A_23_P56091 | FTSJ3 | GAGTCAGAGGTCATTTCAAGGTGGTGGACTCCAAGGATGAAGAAGG ACCAAAGAGCACAGC | SEQ ID NO: 245 | Homo sapiens FtsJ homolog 3 (E. coli) (FTSJ3), mRNA [NM_017647] |
| 246 | A_23_P553 | TARS2 | GTCCCAAATGCGGAAGAAATTTTCTGAGCTTCTGTACATAGATGA GGCAAAAACGTGGCA | SEQ ID NO: 246 | Homo sapiens threonyl-tRNA synthetase 2, mitochondrial (putative) (TARS2), mRNA [NM_025150] |
| 247 | A_23_P56948 | PRR12 | TGTCTCTTGCTCTTTCTTGGGCTTCTGTACAAGTCAAGCTGTATA CACTGTGTACACACA | SEQ ID NO: 247 | Homo sapiens mRNA for KIAA1205 protein, partial cds. [AB033031] |
| 248 | A_23_P56127 | C19orf61 | GTCAACTTATTCGTGCGTACCGTTCATGACGAGATCGAAGCAGAGAGT GAAACCCGACCAAGA | SEQ ID NO: 248 | Homo sapiens hypothetical protein FLJ12886 (FLJ12886), mRNA [NM_019108] |
| 249 | A_23_P57236 | GGTL3 | CGAAGGACGAACAACTCATCATCGGTCGTTAAGGACCGCTCGGAGC CCAGATGCAGCTGGA | SEQ ID NO: 249 | Homo sapiens gamma-glutamyltransferase-like 3 (GGTL3), mRNA [NM_178026] |
| 250 | A_23_P67819 | TATDN2 | TAGTTTTCTGTGTAGGATTTAGATTATCATTTATGTGCTGTTGGA CAGTGAAACCCTCACC | SEQ ID NO: 250 | Homo sapiens TatD DNase domain containing 2 (TATDN2), mRNA [NM_014760] |
| 251 | A_23_P586 | DMAP1 | CTCTGCTGAGCCGGCAGTGACTGACGAACCGGACTTGGTCCTGACCGC CAAGGACGACATCAT | SEQ ID NO: 251 | Homo sapiens DNA methyltransferase 1 associated protein 1 (DMAP1), transcript variant 1, mRNA [NM_019100] |
| 252 | A_23_P60180 | ABL1 | AGGGCCCTAGGTTTACGGCTCATCACCTAAAGCTTGTACTTTATTTTT CTGATAGAAATGGTT | SEQ ID NO: 252 | Homo sapiens v-abl Abelson murine leukemia viral oncogene homolog 1 (ABL1), transcript variant a, mRNA [NM_005157] |
| 253 | A_23_P60657 | KIAA0460 | TTATAACAAAGGGGCTCCTCTTCCAAAGTAAGAAATCACATACGGT TACGGTTTTACTATTC | SEQ ID NO: 253 | Homo sapiens KIAA0460 (KIAA0460), mRNA [NM_015203] |
| 254 | A_23_P61268 | C8orf30A | TGAAGGAGCTTAGGTTGTCTTCTTGGCAATTCAGAATGGGTCACT CCACACCCTAAACT | SEQ ID NO: 254 | Homo sapiens chromosome 8 open reading frame 30A (C8orf30A), mRNA [NM_016458] |

Fig. 1-15

| No | Probe ID No. | Symbols of genes | Sequence | SEQ ID NO: | Descriptions of genes (letters and numbers within [ ] indicates GenBank accession No.) |
|---|---|---|---|---|---|
| 255 | A_23_P6223 | SFRS15 | AAATGACCGGGAACGGTATGGGAACCGTAATGATGATAGAGATAATAGTAACGGTGACAG | SEQ ID NO: 255 | Homo sapiens splicing factor, arginine/serine-rich 15 (SFRS15), mRNA [NM_020706] |
| 256 | A_23_P62868 | EXOSC10 | TGGGAAACAAAAGCATGTGCTTCGAACTGGAAAGTCAGACAGAGAGCTTCAGGTACAACT | SEQ ID NO: 256 | Homo sapiens exosome component 10 (EXOSC10), transcript variant 1, mRNA [NM_001001998] |
| 257 | A_23_P63128 | OBSCN | CCTCGCTTCAGCGCGGCGGGATTCTTCGCGCTGCATTTGTTGCATTGTTTGCATTAATATGAAT | SEQ ID NO: 257 | Homo sapiens cDNA FLJ14124 fis, clone MAMMA1002498. [AK024186] |
| 258 | A_23_P63281 | MGC10334 | GAACCAGGGTGAAGGTCACAGGTCCCAGGGTGTGGAGGGCTCCATCCTTTCTCGTTTCTGCC | SEQ ID NO: 258 | Homo sapiens hypothetical protein MGC10334 (MGC10334), mRNA [NM_001029985] |
| 259 | A_23_P64770 | DDX23 | AGTGGAATCTTAGTGTCATCATCGGAGAGAGCTGTTTCCTGTTGGATGGTAAAGGAAGTTGA | SEQ ID NO: 259 | Homo sapiens DEAD (Asp-Glu-Ala-Asp) box polypeptide 23 (DDX23), mRNA [NM_004818] |
| 260 | A_23_P65797 | KLHL25 | GACGTGCCATGGTGCTTTCCGCAAAAGTTGTGTTGCTTTTATCAGTTTTCTAACTTAATA | SEQ ID NO: 260 | Homo sapiens kelch-like 25 (Drosophila) (KLHL25), mRNA [NM_022480] |
| 261 | A_23_P65890 | CIB2 | TGTGGCCTCGAAGCTCCCCAGGAAGAAAGCACGTGGGCAGCCTGTGGGGTTTACACACAAATAT | SEQ ID NO: 261 | Homo sapiens calcium and integrin binding family member 2 (CIB2), mRNA [NM_006383] |
| 262 | A_23_P66867 | GEMIN4 | AAAGAAAATAGTTTCTTGGGTATTTGTAACGTACAAAACTACATAAAAATTCTCTGTTT | SEQ ID NO: 262 | Homo sapiens gem (nuclear organelle) associated protein 4 (GEMIN4), mRNA [NM_015721] |
| 263 | A_23_P6602 | RRP9 | CCGATGGTGGAGAATCAAAGAGAGGCTGGAATTCTGTCTGCATGATCCCACTCCGCAGGGT | SEQ ID NO: 263 | Homo sapiens RRP9, small subunit (SSU) processome component, homolog (yeast) (RRP9), mRNA [NM_004704] |
| 264 | A_23_P68087 | ATIC | GCAGAAGAAAGGAATGGGTTGAGAAACTGACTGAAGTTCTATCAGCTCTGATGCGTTC | SEQ ID NO: 264 | Homo sapiens 5-aminoimidazole-4-carboxamide ribonucleotide formyltransferase/IMP cyclohydrolase (ATIC), mRNA [NM_004044] |
| 265 | A_23_P71146 | POLD2 | CTTCCGTGAGAGACGCAGGGAAGTTCTGGTGGAGGACTATTGCTTTGCTGACGTTGCTCC | SEQ ID NO: 265 | Homo sapiens polymerase (DNA directed), delta 2, regulatory subunit 50kDa (POLD2), mRNA [NM_006230] |
| 266 | A_23_P71889 | ODF2 | AAGATCCTTAAAGATGAGATGAACAAAAGAGATTGAAGGCGGCACGAAGCAGTTCCAGTGT | SEQ ID NO: 266 | Homo sapiens outer dense fiber of sperm tails 2 (ODF2), transcript variant 2, mRNA [NM_153437] |
| 267 | A_23_P73160 | ENST00000354261 | TGGTTGTTCATTAGACTCCTGGATATTCTTAAAATACAGATTCACATTCAGTAGAG | SEQ ID NO: 267 | Leucine-rich repeat and calponin homology domain-containing protein 3 precursor. [Source:Uniprot/SWISSPROT;Acc:Q961I8] [ENST00000354261] |
| 268 | A_23_P73604 | CXorf34 | ACTGCATTACAGAGGTGATTCAAGCCATTCGAAAGTTCAGGGCCATCCACAGGCTAGTTTT | SEQ ID NO: 268 | Homo sapiens chromosome X open reading frame 34 (CXorf34), mRNA [NM_024917] |
| 269 | A_23_P74269 | SRM | TCGTATTACCAGCTCATGATGAAGACAGCCCTCAAGGAAGATGGTGTCCTCTGTGCCAGGGC | SEQ ID NO: 269 | Homo sapiens spermidine synthase (SRM), mRNA [NM_003132] |
| 270 | A_23_P74653 | NUDC | GGCAGGCAGCAGATCATTGATGGGGAGCCTCTACAATGAAGTGAAGGTGGAAGGAGGGTCGT | SEQ ID NO: 270 | Homo sapiens nuclear distribution gene C homolog (A. nidulans) (NUDC), mRNA [NM_006600] |
| 271 | A_23_P75609 | CEP164 | CTGGGACAGCTTGGTGTATATTGGGCATTGTTTCCATCGTCTTTTGTACCTGTGCA | SEQ ID NO: 271 | Homo sapiens centrosomal protein 164kDa (CEP164), mRNA [NM_014956] |
| 272 | A_23_P77437 | PRMT7 | AGAAAATCTTCAAGGCTAAGCACACTTGGAAGATAAAATTAACATCATAGAAAACGGCCG | SEQ ID NO: 272 | Homo sapiens protein arginine methyltransferase 7 (PRMT7), mRNA [NM_019023] |

Fig. 1-16

| No. | Probe ID No. | Symbols of genes | Sequence | SEQ ID NO: | Descriptions of genes (letters and numbers within [ ] indicates GenBank accession no.) |
|---|---|---|---|---|---|
| 273 | A_23_P77440 | NFATC3 | GTGTCAGTTACAACGTTATTAGACATATGGTCGTTCACATTCAGGGGTCTGGCTACAACAGCTTC | SEQ ID NO: 273 | Homo sapiens nuclear factor of activated T-cells, cytoplasmic, calcineurin-dependent 3 (NFATC3), transcript variant 4, mRNA [NM_173164] |
| 274 | A_23_P77502 | PKD1 | CCTGCACCGTCTCACTGTGTCTGTGTCGTGTCAGTAATTTATATGGTGTTAAAATGTGTATA | SEQ ID NO: 274 | Homo sapiens polycystic kidney disease 1 (autosomal dominant) (PKD1), transcript variant 1, mRNA [NM_001009944] |
| 275 | A_23_P78170 | MYBBP1A | CTGGCACGGGAAAAAGGCAAGGCTGTGTTTGGTCATCAGGAGTGCCAGCCTGCTCAGAGT | SEQ ID NO: 275 | Homo sapiens MYB binding protein (P160) 1a (MYBBP1A), mRNA [NM_014520] |
| 276 | A_23_P78191 | C17orf68 | TGCCTACTTGTTCTGTGATTGAACCAAGGAGTCCAGATTCACAAACTGGTACTCCAGTAT | SEQ ID NO: 276 | Homo sapiens chromosome 17 open reading frame 68 (C17orf68), mRNA [NM_025099] |
| 277 | A_23_P78685 | FARSA | CCTGGAGCGCCCAACGATGATCAAATATGGCATGACAATATCCGGGAGCTGGTGGGCCA | SEQ ID NO: 277 | Homo sapiens phenylalanyl-tRNA synthetase, alpha subunit (FARSA), mRNA [NM_004461] |
| 278 | A_23_P79927 | NOL5A | GCCACATACTGCCGTCTTGCCCAGTTTATTGGAAAACCGAAGGGAACTGAATGAGGACAAG | SEQ ID NO: 278 | Homo sapiens nucleolar protein 5A (56kDa with KKE/D repeat) (NOL5A), mRNA [NM_006392] |
| 279 | A_23_P80129 | RRP1 | CTCCGCCTGTGGCTGTGATGACCTTGGGGCCAAGAAGGTCAAAGTCCGAAGAGTGAAAGTCT | SEQ ID NO: 279 | Homo sapiens DNA segment on chromosome 21 (unique) 2056 expressed sequence (D21S2056E), mRNA [NM_003683] |
| 280 | A_23_P80136 | RRP1 | TGAATGAACTGGACACAGGATGAGGAGGTGGCGTCGGACAGTGATGAGTCCTGAGG | SEQ ID NO: 280 | Homo sapiens DNA segment on chromosome 21 (unique) 2056 expressed sequence (D21S2056E), mRNA [NM_003683] |
| 281 | A_23_P84782 | THAP4 | CACAGCCAATGACTCAGGCATCTCACGTCACCTACAGAGAGGTGACCCCGGTAAACCTAGA | SEQ ID NO: 281 | Homo sapiens THAP domain containing 4 (THAP4), mRNA [NM_015963] |
| 282 | A_23_P8848 | RC74 | CCAGCCTTTGGTTTCGTTACTTGCCTACAGTGCTGTAGGCAATAAGATGATGCCAA | SEQ ID NO: 282 | Homo sapiens integrator complex subunit 9 (RC74), mRNA [NM_018250] |
| 283 | A_23_P89835 | THC2619205 | AGCTATACATTCTTCTTCTGGTCGCATCTTAAACGTCTCTGTTGTGGTGCACGCCAAGA | SEQ ID NO: 283 | MARE2_HUMAN (Q15555) Microtubule-associated protein RP/EB family member 2 (APC-binding protein EB2) (End-binding protein 2) (EB2), partial (87%) [THC2619205] |
| 284 | A_23_P89884 | TRIM28 | AGTTTGCCGAGGATGATGGGCCGGACGATGTTCAAGGAATTCAACAAGTTAACTGAGGACAAGG | SEQ ID NO: 284 | Homo sapiens tripartite motif-containing 28 (TRIM28), mRNA [NM_005762] |
| 285 | A_23_P90089 | GCDH | GAATGGGATTTCTGCAGAGTATCACGTGATCCGGCAGGCGATGAACCTGGAGGGCGGTGAA | SEQ ID NO: 285 | Homo sapiens glutaryl-Coenzyme A dehydrogenase (GCDH), nuclear gene encoding mitochondrial protein, transcript variant 2, mRNA [NM_013976] |
| 286 | A_23_P91328 | NOL5A | GAGGTTCCTCAGGAGAATGGAAGACCGGATCTATCTCTTTCTCCAAACCAAGAAA | SEQ ID NO: 286 | Homo sapiens nucleolar protein 5A (56kDa with KKE/D repeat) (NOL5A), mRNA [NM_006392] |
| 287 | A_23_P93818 | DKFZP434A0131 | TTTGAATGAGAGTCTCATCTTGGCTAGGACGATGGGCGAACAACTGGGGAGGTGGAGGT | SEQ ID NO: 287 | Homo sapiens mRNA; cDNA DKFZp434A0131 (from clone DKFZp434A0131). [AL137492] |
| 288 | A_23_P9415 | ACO1 | AATTATACCAGTCTTAAGTGACATAGAAGATAAGAAGTTTGCACACTTCAAATCAGAGCAGTG | SEQ ID NO: 288 | Homo sapiens aconitase 1, soluble (ACO1), mRNA [NM_002197] |
| 289 | A_23_P9416 | ACO1 | TACCGTCGTTATTGTTCCTCTTACGGCTCTGCCTCAATGAAAACTTCCTCTTGAGGGTCATTT | SEQ ID NO: 289 | Homo sapiens aconitase 1, soluble (ACO1), mRNA [NM_002197] |

Fig. 1-17

| No. | Probe ID No. | Symbols of genes | Sequence | SEQ ID NO: | Descriptions of genes (letters and numbers within ( ) indicate GenBank accession No.) |
|---|---|---|---|---|---|
| 290 | A_23_P9426 | GOLGA2 | CCTTGTCAGTCAAGCGCTTACGCTTACAGTAGGAAGCATAGACCGCGTGTCAACGGGGGT | SEQ ID NO: 290 | Homo sapiens golgi autoantigen, golgin subfamily a, 2 (GOLGA2), mRNA [NM_004486] |
| 291 | A_23_P98863 | FAF1 | GCGTTTGCTGGCGAGCAACAAGGCTCAGAATGTCGTTTGATTTTGTAGGTTGCAAAGGATT | SEQ ID NO: 291 | Homo sapiens Fas (TNFRSF6) associated factor 1 (FAF1), mRNA [NM_007051] |
| 292 | A_23_P97274 | SCAMP3 | TGCCAGGCTTTCAGAAGGGCCAAGGCCAAGAATTTGCTGCGTGGTGTCTTCTCAAGCCTGCGGT | SEQ ID NO: 292 | Homo sapiens secretory carrier membrane protein 3 (SCAMP3), transcript variant 2, mRNA [NM_052837] |
| 293 | A_23_P97736 | NCDN | GGTTGGTTGAAGGGACGGAGAGTCTTTGGGCCCAGATCTTTAAACCTTTGTCTGTGTTG | SEQ ID NO: 293 | Homo sapiens neurochondrin (NCDN), transcript variant 3, mRNA [NM_014284] |
| 294 | A_23_P9823 | MLXIP | TCTTGTTGTTGTATGAGGTTTCTTGTTTGGAATGTGTGCCTGATGAATCCAGGCCAGGACCAAGG | SEQ ID NO: 294 | Homo sapiens MLX interacting protein (MLXIP), mRNA [NM_014938] |
| 295 | A_23_P98252 | ARL2 | TGCCGGGCATCGACTGGCTGCTGGATGACATTTCCAGCCGCATTTTCAGAGGTGACTGAA | SEQ ID NO: 295 | Homo sapiens ADP-ribosylation factor-like 2 (ARL2), mRNA [NM_001667] |
| 296 | A_23_P98645 | DCHS1 | GTTGCTCACTGACCTGTGACCAGGTCCAATGTGGGGACAAATATGAAGGAGGTAGGAGCC | SEQ ID NO: 296 | Homo sapiens dachsous 1 (Drosophila) (DCHS1), mRNA [NM_003737] |
| 297 | A_24_P100234 | MORC2 | TGAATTCAGATGAGCTAATATCTTTTCGTCTGAAGGAGTACTTCAAGGAATATGAAGTAG | SEQ ID NO: 297 | Homo sapiens MORC family CW-type zinc finger 2 (MORC2), mRNA [NM_014941] |
| 298 | A_24_P101402 | NOL5A | GGCTGGCAAGACAGCTCCAAGAAGAAGACTAAAAGTTCCAATAAAGCATGCCAGGAGATTA | SEQ ID NO: 298 | Homo sapiens nucleolar protein 5A (56kDa with KKE/D repeat) (NOL5A), mRNA [NM_006392] |
| 299 | A_24_P101426 | A_24_P101426 | GTTTATGAGTCGGACCAAACAGCCACCTGTCTGCCTTTGCCAGATGATCCGATGATGAA | SEQ ID NO: 299 | |
| 300 | A_24_P102512 | CABIN1 | CTCCTGTGGGTGATATTTCTGGGGGAGATAAATCCAAGAAAGGGGTAAAACGAAGAAGA | SEQ ID NO: 300 | Homo sapiens calcineurin binding protein 1 (CABIN1), mRNA [NM_012295] |
| 301 | A_24_P105633 | VIPR1 | TCTGATAGGAATGTGAAAGCACGGACTCTTAGTGCTAAGTTTTGTGTATCGTAACCAGCC | SEQ ID NO: 301 | Homo sapiens vasoactive intestinal peptide receptor 1 (VIPR1), mRNA [NM_004624] |
| 302 | A_24_P110719 | ZNF236 | AGTTCTCAGAGACTGCTGCTGTTTTAAGCGGCCACACTTTTCAGAGTTACCTCTTCAA | SEQ ID NO: 302 | Homo sapiens zinc finger protein 236 (ZNF236), mRNA [NM_007345] |
| 303 | A_24_P119337 | AK054562 | GCAGTTGCAGTTAGGACCACACTAAAAGGTTAATGTCCACGCGTGTTGACCAAGCCCT | SEQ ID NO: 303 | Homo sapiens mRNA for FLJ00054 protein, partial cds. [AK054562] |
| 304 | A_24_P127701 | LOC441616 | CCAGGTGATGGATAGTCAGACGGACATGGTGCAGCAGAGATCCGGGCTCTAGAGCAACAAT | SEQ ID NO: 304 | PREDICTED: Homo sapiens similar to Protein C11orf2 (Another new gene 2 protein) (LOC441616), mRNA [XM_001129707] |
| 305 | A_24_P128001 | ZNF395 | GAATTCTTTGCTTTCTAAACTGTTCCAGAAAGGACTGTGAGCAAGATGAATTTACTTTTG | SEQ ID NO: 305 | Homo sapiens zinc finger protein 395 (ZNF395), mRNA [NM_018660] |
| 306 | A_24_P128057 | MBNL1 | AGAATATTGCTGCAACACTATCTGTGATTGGTTATCTCTCTATCATGGATTGCTTGACAA | SEQ ID NO: 306 | Homo sapiens muscleblind-like (Drosophila) (MBNL1), mRNA (cDNA clone IMAGE:3935812), partial cds. [BC005296] |
| 307 | A_24_P142289 | HIRIP3 | GAGAGGAAGAACCGCTCTTCCAAGAAGAGCTCAGGAAAGCAGGACACGAAGGCTCCTCT | SEQ ID NO: 307 | Homo sapiens HIRA interacting protein 3 (HIRIP3), mRNA [NM_003609] |
| 308 | A_24_P142963 | PIK4CA | TGACTCTCATGTTGGACAGGGGCCTGCCCGTGTTTTCGGCGGCCAGACAATCAAGGCTCTTGA | SEQ ID NO: 308 | Homo sapiens phosphatidylinositol 4-kinase, catalytic, alpha polypeptide (PIK4CA), transcript variant 1, mRNA [NM_002650] |

Fig. 1-18

| No | Probe ID No. | Symbols of genes | Sequence | SEQ ID NO: | Descriptions of genes (letters and numbers within [ ] indicates GenBank accession No.) |
|---|---|---|---|---|---|
| 309 | A_24_P144601 | POU5F1 | AACAATGAAAATCTTCAGGAGATATGCAAAGCAGAAAGCCTGGTGGAGGCCGAAAGAGA | SEQ ID NO: 309 | Homo sapiens POU domain, class 5, transcription factor 1 (POU5F1), transcript variant 1, mRNA [NM_002701] |
| 310 | A_24_P145047 | ZNF609 | AGTATTTAAACGTGCCTGCGTGGGAGTTAGGACGGATGGTTTCCGATGAAAGTTAGGAATGACGGGAAAAGTACC | SEQ ID NO: 310 | Homo sapiens zinc finger protein 609 (ZNF609), mRNA [NM_015042] |
| 311 | A_24_P147910 | SEPT9 | GTCCATCACGGCAGGATATTGAGGAGAAAAGGGTCCGAGATGAAAGCTGACAGTGATTGACAC | SEQ ID NO: 311 | Homo sapiens septin 9 (SEPT9), mRNA [NM_006640] |
| 312 | A_24_P158567 | CRY2 | CACCACGACGTCGTGCCAGTGACAGGCACAGCTGACACCCAGGCAGGGAAACCATCTAGTCTTT | SEQ ID NO: 312 | Homo sapiens cryptochrome 2 (photolyase-like) (CRY2), mRNA [NM_021117] |
| 313 | A_24_P165042 | IMPDH2 | TTGGACTCTTCCCAGGGAAATTCCATCTTCCAGATCAATATGATCAAGTACATCAAAGAC | SEQ ID NO: 313 | Homo sapiens IMP (inosine monophosphate) dehydrogenase 2 (IMPDH2), mRNA [NM_000884] |
| 314 | A_24_P166645 | REPIN1 | CCCGTGCGTAGGCACCCAGACTTGGAGAGACCCGTCTGCTGTTAATACTTGCATCCTCTT | SEQ ID NO: 314 | Homo sapiens replication initiator 1 (REPIN1), transcript variant 2, mRNA [NM_014374] |
| 315 | A_24_P169645 |  | AAGTTGTGGTGAAGAGGTTATTTATGAGTTGCACCAAATGGCCATCTCTGTCTCTTTCCT | SEQ ID NO: 315 |  |
| 316 | A_24_P171345 | PUM1 | GAGCACAGGTCGTCCTGAGGATAAAAGCAAAATTGTAGCAGAAATCCGAGGCAATGTACTT | SEQ ID NO: 316 | Homo sapiens pumilio homolog 1 (Drosophila) (PUM1), transcript variant 2, mRNA [NM_014676] |
| 317 | A_24_P181108 | WDR74 | TGGGTTGCAGTCGCACCCTTCAAAGCCTACAGTAGCCTCCTGTGGCTTGGACAGAGTCTT | SEQ ID NO: 317 | Homo sapiens WD repeat domain 74 (WDR74), mRNA [NM_018093] |
| 318 | A_24_P185158 | FAM134C | GCCGGTAGTAGCAAATCATGTGTAGTGTTGAGAGAGAAACCTAAACATGGTACTTGATTGTAAAC | SEQ ID NO: 318 | Homo sapiens hypothetical protein LOC162427 (LOC162427), mRNA [NM_178126] |
| 319 | A_24_P191067 | CLSTN1 | ACCGACATAGGACTTTGCTCTTGGTTACATGTAAAATTTTAGATTTCTAAAACAGGTGGG | SEQ ID NO: 319 | Homo sapiens calsyntenin 1 (CLSTN1), transcript variant 1, mRNA [NM_001009566] |
| 320 | A_24_P193570 | CNOT1 | AGAGTTCGTTGTGATTACCATTATGGGTCTGTGATGTGATCCCACCTAATTGTATGCA | SEQ ID NO: 320 | Homo sapiens CCR4-NOT transcription complex, subunit 1 (CNOT1), transcript variant 1, mRNA [NM_016284] |
| 321 | A_24_P196298 | MLL | GCACTTTGAACATCCTCAGCACTCTCTCCAATGGCAATAGTTGTAAGCAAAAATTCCAG | SEQ ID NO: 321 | Homo sapiens myeloid/lymphoid or mixed-lineage leukemia (trithorax homolog, Drosophila) (MLL), mRNA [NM_005933] |
| 322 | A_24_P200694 | RING1 | GAAATTCTGGAAGGTGTCCGCGGCCACTGGAGGCTGTGTATGCTCCCACCAAGGATGCAAA | SEQ ID NO: 322 | Homo sapiens ring finger protein 1 (RING1), mRNA [NM_002931] |
| 323 | A_24_P2093 | XAB2 | ACGTGAGGAAGGACTTTGAGGTCCGGGATGGGCAATGAGGACGACATCAAGGAAATGCTGGGT | SEQ ID NO: 323 | Homo sapiens XPA binding protein 2 (XAB2), mRNA [NM_020196] |
| 324 | A_24_P212764 | A_24_P212764 | GTCGCGACTTGTGGGCAGAGGAGTTCTAGACCAGGTTGTCTCCTGGGAGCATTGACAC | SEQ ID NO: 324 |  |
| 325 | A_24_P213175 | A_24_P213175 | TTTCGCCTGAGAGCTGACAGTAGCAATGTTGTTTCAGAGAGCCCATTTGCACAGGTTTCA | SEQ ID NO: 325 |  |
| 326 | A_24_P214841 | POU5F1 | AATCTTCAGGAGATATGCAAAGCAGAAACCCTCGTGCAGAGGCCGAAAGAGAAAGCGAACC | SEQ ID NO: 326 | Homo sapiens POU domain, class 5, transcription factor 1 (POU5F1), transcript variant 1, mRNA [NM_002701] |

Fig. 1-19

| No. | Probe ID No. | Symbols of genes | Sequence | SEQ ID NO: | Descriptions of genes (letters and numbers within [ ] indicates GenBank accession No.) |
|---|---|---|---|---|---|
| 327 | A_24_P216087 | PAF1 | GACGATGCGCACTCTGATGATGAGGACAAGAGGACAAGGCCAAGGTGGGCAGTGAGAATGAT | SEQ ID NO: 327 | Homo sapiens Paf1, RNA polymerase II associated factor, homolog (S. cerevisiae) (PAF1), mRNA [NM_019088] |
| 328 | A_24_P221668 | AW172689 | GGAGGTCTGGGATGTCTGATTATATCTGATTTCTGAGCTCTGGGCATGGAGGTCTGTCTG | SEQ ID NO: 328 | xj79h10.x1 Soares_NFL_T_GBC_S1 Homo sapiens cDNA clone IMAGE:2663491 3' similar to TR:O13116 Q13116 MEMBRANE PROTEIN-LIKE PROTEIN ;, mRNA sequence [AW172689] |
| 329 | A_24_P224926 | MFNG | AGAACAATCATCCACAGACGTATTCCGTCGAAGCATCGTGGTTCTGTAGAAAAATTAAATGCTTA | SEQ ID NO: 329 | Homo sapiens MFNG O-fucosylpeptide 3-beta-N-acetylglucosaminyltransferase (MFNG), mRNA [NM_002405] |
| 330 | A_24_P231132 | ACVR2B | CTGTCACCAATGTGGACCTGCCCGTAAAGAGTCAAGCATCTAAGCCGAGGACATGAGTG | SEQ ID NO: 330 | Homo sapiens activin A receptor, type IIB (ACVR2B), mRNA [NM_001106] |
| 331 | A_24_P231173 | PERQ1 | CCCTACTTGGGTTCGTCTCCGGCCACATTTTGGGTTTTGTAACAGTTTTGTCTTTTGGGTTT | SEQ ID NO: 331 | Homo sapiens PERQ amino acid rich, with GYF domain 1 (PERQ1), mRNA [NM_022574] |
| 332 | A_24_P235131 | TRIAD3 | TCCAGTATCCCCCATGTGAAGGTCACTTCCCTTCCTTCATGGAGTCAGGTGAAGCATCAGCTC | SEQ ID NO: 332 | Homo sapiens TRIAD3 protein (TRIAD3), transcript variant 1, mRNA [NM_207111] |
| 333 | A_24_P238215 | DKFZP566P0123 | TTGAAAACACAGATTCCCCATCTGGAATTTTGAACAGCAGTCAAGCCTATCAAAAGAGG | SEQ ID NO: 333 | Homo sapiens hypothetical protein (DKFZP566P0123), mRNA [NM_015531] |
| 334 | A_24_P241862 | RANBP3 | TGCTCAGACTCAATGACATGGCGTCCACCGATGACGGCAGACTACAGTCCGAGTCAGTGA | SEQ ID NO: 334 | Homo sapiens RAN binding protein 3 (RANBP3), transcript variant RANBP3-b, mRNA [NM_007320] |
| 335 | A_24_P244575 | TPCN1 | CCCTTTGAGAAAGACAACACATTATTGAGACTCACTGTGTGATTCCCGCGGGAGTCAGACTGG | SEQ ID NO: 335 | Homo sapiens mRNA for KIAA1169 protein, partial cds. [AB032995] |
| 336 | A_24_P245246 | PIP5K2B | TTTGAGACCGTGTTACTGTTGAAAATGCATGCATGGTTACGATGAATCGAACCTGAGG | SEQ ID NO: 336 | Homo sapiens phosphatidylinositol-4-phosphate 5-kinase, type II, beta (PIP5K2B), mRNA [NM_003559] |
| 337 | A_24_P248053 | TOP1MT | GCAGGAGAAGACTTTGAATCTAACGACGAGCGGTGTTGAAAGTTGTTTGTATGTGTGT | SEQ ID NO: 337 | Homo sapiens topoisomerase (DNA) I, mitochondrial (TOP1MT), nuclear gene encoding mitochondrial protein, mRNA [NM_052963] |
| 338 | A_24_P250333 | SNRPA | CAGCTCGCGATGCCCTGCAGGGCTTTAAGATCACGCAGAGAAGACAGCCATGAAGATCTCCT | SEQ ID NO: 338 | Homo sapiens small nuclear ribonucleoprotein polypeptide A (SNRPA), mRNA [NM_004596] |
| 339 | A_24_P251688 | ABCF3 | TTGGGGACAGGCTTATTCCCAAATGTCTCTATCCTTTTGACTGGAGGCATCTCTGCACAA | SEQ ID NO: 339 | Homo sapiens ATP-binding cassette, sub-family F (GCN20), member 3 (ABCF3), mRNA [NM_018358] |
| 340 | A_24_P252130 | PPARD | GGTGAGGATACAGCTCTTCTCAGTGTGTGAACAATCCAAAATTGAAATGTATATTTT | SEQ ID NO: 340 | Homo sapiens peroxisome proliferator-activated receptor delta (PPARD), mRNA [NM_006238] |
| 341 | A_24_P254437 | THC2663227 | GGGAGGGCACTGTCTCTTTTTCTCTCATTTTTAAAATGAAGTGTTGTTGGCTTTGTAT | SEQ ID NO: 341 | CA312433 UI-CF-FNO-afk-i-18-0-UI.s1 UI-CF-FNO Homo sapiens cDNA clone UI-CF-FNO-afk-i-18-0-UI 3', mRNA sequence [CA312433] |
| 342 | A_24_P256063 | LOC442249 | CTCAGGACCATTCCAAGATCCAAGATCATGGCAGAGACATCCAGGCCCAATATAACGAAGCTCTCTCGGA | SEQ ID NO: 342 | PREDICTED: Homo sapiens hypothetical LOC442249 (LOC442249), mRNA [XR_019231] |
| 343 | A_24_P258846 | NFATC1 | CTCTCGGTCGTTGAGATCCGGCCATTTCGGAATCAGGAGGATAACCAGCCCCCGGTTCACGTCA | SEQ ID NO: 343 | Homo sapiens nuclear factor of activated T-cells, cytoplasmic, calcineurin-dependent 1 (NFATC1), transcript variant 1, mRNA [NM_172390] |

Fig. 1-20

| No. | Probe ID No. | Symbols of genes | Sequence | SEQ ID NO: | Descriptions of genes (letters and numbers within [ ] indicates GenBank accession No.) |
|---|---|---|---|---|---|
| 344 | A_24_P28170 | VPRBP | GGAGACTGACAGCTCTGAAGAAGTGTGATTTGGAAGATGAGATGAT CTTATCTCTGAATGA | SEQ ID NO: 344 | Homo sapiens Vpr (HIV-1) binding protein (VPRBP), mRNA [NM_014703] |
| 345 | A_24_P266728 | SF1 | GGTTCGTTTTATGTTTGTTTTAATCGCAAATGTCTGAATGTTTT GGCAGTGTGTAGGGGT | SEQ ID NO: 345 | Homo sapiens splicing factor 1 (SF1), transcript variant 1, mRNA [NM_004630] |
| 346 | A_24_P267452 | CD3EAP | ACAGTGAAGCAGGAACAGATTAAGACTGAGACGTCTAGAAGACAGA GTCGTGTCCCGGACC | SEQ ID NO: 346 | Homo sapiens CD3e molecule, epsilon associated protein (CD3EAP), mRNA [NM_012099] |
| 347 | A_24_P272594 | MAPKBP1 | GGGGTGTTTTAAGGTGGGCGTTTGTAGTGATGTATGAAGTTGTG AATAAACAGCAATTGT | SEQ ID NO: 347 | Homo sapiens mitogen activated protein kinase binding protein 1 (MAPKBP1), mRNA [NM_014994] |
| 348 | A_24_P273823 | NPAT | TGGCATTAGCCGGCATAGGACGCATAAGAGAAACTGAATGAGAAAA GAAAGTTTCTCCAAG | SEQ ID NO: 348 | Homo sapiens nuclear protein, ataxia-telangiectasia locus (NPAT), mRNA [NM_002519] |
| 349 | A_24_P294931 | PPP2R5D | TCACAGACATGGAAGGGAGGACGACCCTGGGGCTGACTGCTTTCTGT GGTGTTGGTTCCAA | SEQ ID NO: 349 | Homo sapiens protein phosphatase 2, regulatory subunit B', delta isoform (PPP2R5D), transcript variant 2, mRNA [NM_180876] |
| 350 | A_24_P29641 | NSUN5C | CAATAAAGACCAGTCACTTGGCTGCTCTTCTGAAAGAACCAAGGGA AGATCTTTGCCTTTG | SEQ ID NO: 350 | Homo sapiens NOL1/NOP2/Sun domain family, member 5C (NSUN5C), transcript variant 2, mRNA [NM_148936] |
| 351 | A_24_P298360 | LTBP3 | CTGCTGTTGGGGAAGCCCCCAAGAGATGAGGAGCAGTTCAGAGGGAG GATTCAGGAGAGTGT | SEQ ID NO: 351 | Homo sapiens latent transforming growth factor beta binding protein 3 (LTBP3), mRNA [NM_021070] |
| 352 | A_24_P307103 | tcag7.1017 | ATGTTTGGAATGCATGTGATGAGGCAGAAGAAGGATGGGCCC TGAGCCTGAGGAGAC | SEQ ID NO: 352 | Homo sapiens similar to Williams Beuren syndrome chromosome region 19 (MGC57359), mRNA [NM_001004351] |
| 353 | A_24_P312325 | C8orf15 | CTTGTTGAATGTGACTACTTTTAGTTGCGTGTCGAATATGAAGTAG AAAGCAGATTCTG | SEQ ID NO: 353 | Homo sapiens chromosome 8 open reading frame 15 (C8orf15), mRNA [NM_001033692] |
| 354 | A_24_P315564 | LOC646253 | AGCAAGATCAGGGCTCTACAGAGCAACATGCAAACCCTGGTCTATG AGAACTACAATAAGT | SEQ ID NO: 354 | PREDICTED: Homo sapiens similar to Protein C11orf2 (Another new gene 2 protein) (LOC646253), mRNA [XM_001130995] |
| 355 | A_24_P316414 | BC014346 | TAACGTTGGGGTCTTGGGAGTGGGGAGGATTCGTTAGCTTGAATAATTTA AGGGCTTGGCTGTA | SEQ ID NO: 355 | Homo sapiens, clone IMAGE:4042868, mRNA, partial cds. [BC014346] |
| 356 | A_24_P317927 | C9orf127 | AGCCTTCCGAAGACATGGATTCCTTCCCAGGGAGACAAAGCCCTG TCAGGAGCAGCAGCAT | SEQ ID NO: 356 | Homo sapiens chromosome 9 open reading frame 127 (C9orf127), transcript variant 1, mRNA [NM_001042590] |
| 357 | A_24_P321093 | SPOCK2 | CTGGAAGAAGCTTAAGCATGTGTTCAAAGAACGGTTTCTTGCTTG CTTGGTCCTGGGAACT | SEQ ID NO: 357 | Homo sapiens sparc/osteonectin, cwcv and kazal-like domains proteoglycan (testican) 2 (SPOCK2), mRNA [NM_014767] |
| 358 | A_24_P322847 | POLR3H | ACATGCCTGGGTCCCTGGGCTGCTGATGACTGATTAGTCTCTTCTGTCAC AGGGGTGCCTGGAGA | SEQ ID NO: 358 | Homo sapiens polymerase (RNA) III (DNA directed) polypeptide H (22.9kD) (POLR3H), transcript variant 4, mRNA [NM_001018051] |
| 359 | A_24_P32295 | C19orf36 | TTAAGGTGTCTGGAGGCCCCACACTTGGCCAACCTGACCTTGGAA GATGCTGCTGAGTGT | SEQ ID NO: 359 | Homo sapiens chromosome 19 open reading frame 36 (C19orf36), transcript variant 3, mRNA [NM_001039846] |
| 360 | A_24_P323628 | FLJ45655 | ATTGAGGAAGACGGCACGGAAAGCGAAGGAAGCTGGTGCTGCGTCC TAAAGGGGAAGCCAA | SEQ ID NO: 360 | Homo sapiens hypothetical protein LOC644128, mRNA (cDNA clone IMAGE:6158500), [BC064938] |

Fig. 1-21

| No. | Probe ID No. | Symbols of genes | Sequence | SEQ ID NO: | Descriptions of genes (letters and numbers within [ ] indicates GenBank accession No.) |
|---|---|---|---|---|---|
| 361 | A_24_P32646 | LOC648644 | AGATCGTGATCGCTCTGCAAGAGCAAGGCTGCTGGATCCTGCCCACTGTGTACCATGGCA | SEQ ID NO: 361 | PREDICTED: Homo sapiens similar to Aflatoxin B1 aldehyde reductase member 2 (AFB1-AR 1) (Aldoketoreductase 7) (LOC648644), mRNA [XR_018390] |
| 362 | A_24_P327815 | STIP1 | CACCAAACTGCTGGAGTTCCAGCTGGGACTCAAGGACTGTGAGGAATGTATGCAGCTGGA | SEQ ID NO: 362 | Homo sapiens stress-induced-phosphoprotein 1 (Hsp70/Hsp90-organizing protein) (STIP1), mRNA [NM_006819] |
| 363 | A_24_P329839 | VPS11 | CGTCATCAGGGACTACCTGGTCCAAAAACTACAGAAACAGAGCCAGGAGATTGCACAGGA | SEQ ID NO: 363 | Homo sapiens vacuolar protein sorting 11 homolog (S. cerevisiae) (VPS11), mRNA [NM_021729] |
| 364 | A_24_P335358 | PUS1 | CCTGGAGTTTGCGGTGATCAGGTGAAGGGCCAGAGCTTCATGATGGATCAGATCCGGAA | SEQ ID NO: 364 | Homo sapiens pseudouridylate synthase 1 (PUS1), transcript variant 1, mRNA [NM_025215] |
| 365 | A_24_P338892 | EDC3 | TTGGCCAAAATGTGAGGAGCAGTCTAGGTTACAGGGCTTTTTGGTAGGTAGGTTCTGGCTG | SEQ ID NO: 365 | Homo sapiens enhancer of mRNA decapping 3 homolog (S. cerevisiae) (EDC3), mRNA [NM_025083] |
| 366 | A_24_P340881 | LOC402149 | CTACGTGCGGACCATCATCAAGAAGAAGGCTGGAGCCAAAGTCAGCAGCATCAGATACAT | SEQ ID NO: 366 | PREDICTED: Homo sapiens similar to ribosomal protein L28 (LOC402149), mRNA [XR_019242] |
| 367 | A_24_P349002 | POM121 | AGGTAAATTAATGAACCATATATTTTAAAATCCTATTTTTCCCAAACAGGGCCCTCTGCAG | SEQ ID NO: 367 | Homo sapiens POM121 membrane glycoprotein (rat) (POM121), mRNA [NM_172020] |
| 368 | A_24_P350644 | ENST00000320547 | CATGTAGACACAGATATTTGAAAGGGCAGACGATGGCTAGAGGTGTAATGTGCAGCTTGTT | SEQ ID NO: 368 | Uncharacterized protein KIAA0515 [Source:Uniprot/SWISSPROT;Acc:Q5JSZ5] [ENST00000320547] |
| 369 | A_24_P356 | AAK1 | GCGGCTTATGTTCTGAATTTGTTTATGAGACTGATCATTAGTGAGACTGGCCACGTAT | SEQ ID NO: 369 | AP2-associated protein kinase 1 (EC 2.7.11.1) (Adaptor-associated kinase 1). [Source:Uniprot/SWISSPROT;Acc:Q2M2I8] [ENST00000360555] |
| 370 | A_24_P364970 | DHX33 | ATTTAATTCAGAAGGCAAGTAATCTTTCCCCAGATAATATTTGCCCGTAGAAGAGACCG | SEQ ID NO: 370 | Homo sapiens DEAH (Asp-Glu-Ala-His) box polypeptide 33 (DHX33), mRNA [NM_020162] |
| 371 | A_24_P369263 | MMS19L | TTCTACTGGAAGGCACCCCAAGTCATGAGTCTTCACGTGGACACCGTCGTCACGCAAGTTTG | SEQ ID NO: 371 | Homo sapiens MMS19-like (MET18 homolog, S. cerevisiae) (MMS19L), mRNA [NM_022362] |
| 372 | A_24_P371670 | HNRPA0 | AGTTCTGCGCAGTTTGGCACGGTGGACAAGAGGCCGAGATTATCGCGACAAGCAGTCCGGCA | SEQ ID NO: 372 | Homo sapiens heterogeneous nuclear ribonucleoprotein A0 (HNRPA0), mRNA [NM_006805] |
| 373 | A_24_P372613 | APBB1 | AAACCTGTTGGGGTAGATGTGATTAATGAGGCCCTCGAGTCAGTCGTGTCCTCCAGCAGC | SEQ ID NO: 373 | Homo sapiens amyloid beta (A4) precursor protein-binding, family B, member 1 (Fe65) (APBB1), transcript variant 1, mRNA [NM_001164] |
| 374 | A_24_P373312 | NFATC3 | GAACCAGAAGATCGGAGGAGGGTAACTTGGAACCATTGGTCTGCGAGGACATGACTTTAGAT | SEQ ID NO: 374 | Homo sapiens nuclear factor of activated T-cells, cytoplasmic, calcineurin-dependent 3 (NFATC3), transcript variant 4, mRNA [NM_173164] |
| 375 | A_24_P375592 | PHF20 | GGAGCCCAGGATTGAAAACAAAATGTTAAAATGCCAACATTTGTGTTAATTCTAGCTAC | SEQ ID NO: 375 | Homo sapiens cDNA FLJ33479 fis, clone BRAMY2002739. [AK090798] |
| 376 | A_24_P376422 | BC035371 | GAGGCAAGTTTGCATTTTGACACGGCATCTCACACTCCTGTGACGTCTCAACTTGGAGG | SEQ ID NO: 376 | Homo sapiens HSPC047 protein, mRNA (cDNA clone MGC:34368 IMAGE:5178752), complete cds. [BC035371] |

Fig. 1-22

| No. | Probe ID No. | Symbols of genes | Sequence | SEQ ID NO: | Descriptions of genes (letters and numbers within [ ] indicate GenBank accession No.) |
|---|---|---|---|---|---|
| 377 | A_24_P392765 | NHP2L1 | TACGTGTTCAAGTGATCAAGGGGTTTCATTTCGTCTTGGGGGATT AGGTATCATTGGGG | SEQ ID NO: 377 | Homo sapiens NHP2 non-histone chromosome protein 2-like 1 (S. cerevisiae) (NHP2L1), transcript variant 1, mRNA [NM_005008] |
| 378 | A_24_P384779 | PRKAG2 | CCATAAATGACAGCCAGGTGAGGGCAGAAATGGTGAGGGCAGAATAGGA AATGGAAATACACAA | SEQ ID NO: 378 | Homo sapiens cDNA FLJ90194 fis, clone MAMMA1001284. [AK074675] |
| 379 | A_24_P399038 | WDR46 | TAGAGCACCAGGTGAAGATCTTTGACTTGCGAGGGACGTACCAGC CTCTGAGCACTCGGA | SEQ ID NO: 379 | Homo sapiens WD repeat domain 46 (WDR46), mRNA [NM_005452] |
| 380 | A_24_P38844 | CCDC86 | TTCTCCCAGATCGTTCAGGACAAGCGCGTGCGCACATGGTGGCAG CGGAAGATGAAGGAA | SEQ ID NO: 380 | Homo sapiens coiled-coil domain containing 86 (CCDC86), mRNA [NM_024098] |
| 381 | A_24_P391526 | MAGED1 | GCTGAGATTCATTGCAGAGGTTCAGAAAGAGACCCTGGTGACTG GACTGCACAGTTCAT | SEQ ID NO: 381 | Homo sapiens melanoma antigen family D, 1 (MAGED1), transcript variant 1, mRNA [NM_001005333] |
| 382 | A_24_P396197 | PRKCSH | AGCCGGTCGGTGAAGGACGATGGAGGAGGTCCATCAGGAACGTGGAGC AAGAGATTCTTTG | SEQ ID NO: 382 | Homo sapiens protein kinase C substrate 80K-H (PRKCSH), transcript variant 1, mRNA [NM_002743] |
| 383 | A_24_P399065 | NUDT16L1 | GCCAGGTCGTCGTTTGCCCTCAAGGTGCTCAACATGATGCCCGGAGG AGAAGGCTGGTTGAGG | SEQ ID NO: 383 | Homo sapiens nudix (nucleoside diphosphate linked moiety X)-type motif 16-like 1 (NUDT16L1), mRNA [NM_032349] |
| 384 | A_24_P40010 | RPS28 | GCGGCGGCCATGATGGACCAGGCCGTGTGCAGCCGTATCGAAGCTGG CCAGGGTCACGAAGG | SEQ ID NO: 384 | Homo sapiens ribosomal protein S28 (RPS28), mRNA [NM_001031] |
| 385 | A_24_P401521 | A_24_P401521 | CAAGTTAAGTATCTCCTGGCTATGGTCAAGCGTATTTTAGGCGGGGC CAGACCCTTCCCTG | SEQ ID NO: 385 | |
| 386 | A_24_P401637 | AK095727 | CGGGGGGGCTTCCTCCCTTCTTAGAAGTCAGGTCATGCATATATTTG ATCTGGCGTTGCCAG | SEQ ID NO: 386 | Homo sapiens cDNA FLJ38408 fis, clone FEBRA2009029. [AK095727] |
| 387 | A_24_P465621 | NISCH | TGAAGTCCAGTGCAGGTGGCAGGTGTTGTCCCCAGTGCTGAGAGCAGAGA GAAGCTCATCTCGCT | SEQ ID NO: 387 | Homo sapiens nischarin (NISCH), mRNA [NM_007184] |
| 388 | A_24_P409881 | LOC338756 | CAGGAGGTTCCTCAGGAGAGAAACAGAAGACCCATGCTATCTCTTTC TGCAAACCCAAGAAA | SEQ ID NO: 388 | PREDICTED: Homo sapiens similar to nucleolar protein 5A (LOC338756), mRNA [XM_291989] |
| 389 | A_24_P412976 | TMEM143 | TTATTGGTCTATCAATTTCTGCCGTCTGGTGTCCCAAAGTAATAA ATCATGTTTAATAAG | SEQ ID NO: 389 | Homo sapiens transmembrane protein 143 (TMEM143), mRNA [NM_018273] |
| 390 | A_24_P416289 | KIAA0195 | GGGCTAAAGCAGACCCATTTCTGAACAGGGGAGTTTGTATCATG AATGTTTCCAGGTTT | SEQ ID NO: 390 | Homo sapiens KIAA0195 (KIAA0195), mRNA [NM_014738] |
| 391 | A_24_P42136 | KRT18 | GCTCACAGAGCTGAGACAGCATACAGTCCAGTCTTGGAGATCGACCT GGACTCCTTGAGAA | SEQ ID NO: 391 | Homo sapiens keratin 18 (KRT18), transcript variant 1, mRNA [NM_000224] |
| 392 | A_24_P42569 | BC030138 | AGCTTGCTTGCTGATGAACACTTCCACAGTCGTTTTGAGCTAAGTA GTTTTTGTAATTAGT | SEQ ID NO: 392 | Homo sapiens cDNA clone IMAGE:4335164, partial cds. [BC030138] |
| 393 | A_24_P44514 | CIB1 | CCATTATGCGTTCCGCATGTTTGACTTTGATGATGACGGGAACCTT GAACAGAAGACACCT | SEQ ID NO: 393 | Homo sapiens calcium and integrin binding 1 (calmyrin) (CIB1), mRNA [NM_006384] |
| 394 | A_24_P44891 | TNPO2 | GATGGTCCTCAACAACCTGGTGGAAATCATTAACGGACGGACGAGAC ACCCAAGAACACTGGT | SEQ ID NO: 394 | Homo sapiens transportin 2 (importin 3, karyopherin beta 2b) (TNPO2), mRNA [NM_013433] |
| 395 | A_24_P460763 | AK022443 | GTGAGTAGGACAGGGTACTTAAGATGCCTAGTGGGTGTAAATGTGAA ATGCTATTGGCAGAT | SEQ ID NO: 395 | Homo sapiens cDNA FLJ12381 fis, clone MAMMA1002566. [AK022443] |

Fig. 1-23

| No | Probe ID No. | Symbols of genes | Sequence | SEQ ID NO: | Descriptions of genes (letters and numbers within [ ] indicates Gen-Bank accession No.) |
|---|---|---|---|---|---|
| 396 | A_24_P477127 | PKD1 | CCAGATACGGAAGAACATCACGGAGACTCTGGTGTCCCCTGAGGGTCCACACGTGGATGA | SEQ ID NO: 396 | Homo sapiens polycystic kidney disease 1 (autosomal dominant) (PKD1), transcript variant 2, mRNA [NM_000296] |
| 397 | A_24_P481783 | LOC390595 | GCATCTAGGCCCAATGCCAGACGTGGCAAGCCATCCTAAGTGTATTATTAAAACGAAGTA | SEQ ID NO: 397 | Homo sapiens cDNA FLJ13740 fis, clone PLACE3000199. [AK023802] |
| 398 | A_24_P51350 | LARS | GAAAAGAGAAAATAGAGCGTGTATGGTTGCCCCCCTGATTTCAGATGAAGAAGGAAGA | SEQ ID NO: 398 | Homo sapiens leucyl-tRNA synthetase (LARS), mRNA [NM_020117] |
| 399 | A_24_P529786 | AK091744 | GATACATAACAGGACAATACAAATATTATCACATACGGTCAATTTATTTGTGAATATTGAA | SEQ ID NO: 399 | Homo sapiens cDNA FLJ34425 fis, clone IHDPC2008297. [AK091744] |
| 400 | A_24_P648264 | AL512741 | AAGAATTGAGTTAGAACTGCCGTATAATGTAATGCAGAATATTTCGCAATAATGCGTAGG | SEQ ID NO: 400 | Homo sapiens mRNA; cDNA DKFZp667N064 (from clone DKFZp667N064). [AL512741] |
| 401 | A_24_P55719 | SURF5 | GTCAAGCGTTTGCGAAGCTAATGACCTGGCTCTGTGCGAAGGTTACGGGAGGCTGGACGT | SEQ ID NO: 401 | Homo sapiens surfeit 5 (SURF5), transcript variant b, mRNA [NM_133640] |
| 402 | A_24_P55971 | VEGFB | CACTGGGGACACCAAGAAGTCCGGATGCAGATGCAGATCCGGTACCCGAAGCAGTCAGGT | SEQ ID NO: 402 | Homo sapiens vascular endothelial growth factor B (VEGFB), mRNA [NM_003377] |
| 403 | A_24_P5743 | ALDH16A1 | CTTGCACCAAGAGCTCAGGTCAGATCCTGATGGTATTTCGGATCAGACCAGGGTTCCCAGTTTGT | SEQ ID NO: 403 | Homo sapiens aldehyde dehydrogenase 16 family, member A1 (ALDH16A1), mRNA [NM_153329] |
| 404 | A_24_P583330 | THC2657163 | GTAAGCAGTCATTATAATTTGTTGATGATAGTTTAAGTATATGGGGTATGCCCATTAGCC | SEQ ID NO: 404 | |
| 405 | A_24_P562421 | AL050185 | TTTTTTCTATACCCGTTTCATAGGACAGCTAATGAGACTGGATATGATTAAAAGCGTGA | SEQ ID NO: 405 | Homo sapiens mRNA; cDNA DKFZp586A0423 (from clone DKFZp586A0423). [AL050185] |
| 406 | A_24_P598516 | AK021595 | CTGAGTTCCTGATGATGTTCCTGGAGTTATCCTTTTCCTTATGATTTAAAAGTGTTTAGC | SEQ ID NO: 406 | Homo sapiens cDNA FLJ11533 fis, clone HEMBA1002678. [AK021595] |
| 407 | A_24_P611114 | hCG_1739474 | CTTTTGTTTATCAGGTACAGTAGCATGTTCATGGGCTAAGCATAGACATTAGTACCCAAAT | SEQ ID NO: 407 | Homo sapiens cDNA FLJ10133 fis, clone HEMBA1003067. [AK000995] |
| 408 | A_24_P63608 | NOLA2 | ATTGAGGTATACTGGCATCTCCCAGTCACTGTGTGAGGACGCGAAATTTGCCGTATGTCTAT | SEQ ID NO: 408 | Homo sapiens nucleolar protein family A, member 2 (H/ACA small nucleolar RNPs) (NOLA2), transcript variant 1, mRNA [NM_017838] |
| 409 | A_24_P636318 | LOC130074 | GGAAACTGCATGTTTCAGAAAGTTTGTCTCTTTTTCCTACTCATTATTTGAAGAAGACAG | SEQ ID NO: 409 | Homo sapiens p20 (LOC130074), mRNA [NM_001009993] |
| 410 | A_24_P636390 | AF009267 | TTGGGATATCACTGTGTGTGTACCGTGGAAGTCCTGGAGTGTGTTGGGTCCTCATCAGCAG | SEQ ID NO: 410 | Homo sapiens clone FBA1 Cri-du-chat region mRNA. [AF009267] |
| 411 | A_24_P6381 | SERINC5 | GGTCATTTTATGACGAGAAGAAAGGCACCGTCTACATCTACTGCTACTGCTACTGCTACTGTACTTCGCAGCTTCGTGTT | SEQ ID NO: 411 | Homo sapiens serine incorporator 5 (SERINC5), mRNA [NM_178276] |
| 412 | A_24_P55941 | C21orf96 | ATTGGGACTTCTCCCAGGATGTACTGAATTCAAGGAAGCTTCTCTAGGTTAGCAGAAA | SEQ ID NO: 412 | Homo sapiens cDNA: FLJ20856 fis, clone ADKA01509. [AK024509] |
| 413 | A_24_P662427 | AK022109 | GAAGCCCTTAAGGCATGTTTCCATAAGTGACATCTGATGCAGACGTCATCTTTCTGATATC | SEQ ID NO: 413 | Homo sapiens cDNA FLJ12047 fis, clone HEMBB1001983. [AK022109] |
| 414 | A_24_P864995 | AK055641 | TAAGCATTTATCTGTTTCCATAACTGACATCTGATGCAGACGTCATTCTCTCCCCGTCTT | SEQ ID NO: 414 | Homo sapiens cDNA FLJ31079 fis, clone HSYRA2001595. [AK055641] |
| 415 | A_24_P37784 | KIAA1666 | GGAACTCCAAGAGACTCCCACTGTGGACTCCAAAGACTGAAGACTGATGATAGCAGCTCTGAGACTATG | SEQ ID NO: 415 | Homo sapiens KIAA1666 protein, mRNA (cDNA clone IMAGE:4827837), complete cds. [BC035246] |

Fig. 1-24

| No. | Probe ID No. | Symbols of genes | Sequence | SEQ ID NO: | Descriptions of genes (letters and numbers within [ ] indicate GenBank accession No.) |
|---|---|---|---|---|---|
| 416 | A_24_P677890 | BC016364 | CCTTTGTAGCAGTTCCCAGGTTTTTCAGAAGAGTGGTGAATCCATGCCTTGGCAATCCT | SEQ ID NO: 416 | Homo sapiens, clone IMAGE:4703872, mRNA. [BC016364] |
| 417 | A_24_P690273 | AK024900 | TACCTGTGTGAGATAGTAGTATTGATGGTGAGACGTGAATAGTAAAATATCTTGAGGTA | SEQ ID NO: 417 | Homo sapiens cDNA: FLJ21247 fis, clone COL01205. [AK024900] |
| 418 | A_24_P69784 | PACS1 | AAGTTCCGTGATGAAGACTCCTATCAGAAGTTTATTCCCTTGATTGGCGTGGTGAAGGTG | SEQ ID NO: 418 | Homo sapiens phosphofurin acidic cluster sorting protein 1 (PACS1), mRNA [NM_018026] |
| 419 | A_24_P700170 | A_24_P700170 | ACGGCTGAACATCATCTCTAACCTGGACGTGTGTGAACGAGGGTGATTGGCATCCGGTCAGC | SEQ ID NO: 419 | |
| 420 | A_24_P706901 | BF895757 | TCTGGGCTCTGGAGAGTGACAAGACAAGCAGCCTTTGGCTTTGTAAGAAGTTGATCTAC | SEQ ID NO: 420 | BF895757 RC3-HT0162-221100-012-H03 HT0162 Homo sapiens cDNA, mRNA sequence [BF895757] |
| 421 | A_24_P713185 | THC2595309 | AATATGACTAGGTTACACAGAATAGGTCAGATAGTACAGATAGTCTTTACGGAGGTCCACTTA | SEQ ID NO: 421 | HMITCSEQ Hylobates lar complete mitochondrial DNA sequence, partial (3%) [THC2595309] |
| 422 | A_24_P713312 | THC2639056 | TTTATATGGTCGGATGCTCCATGTAGGATTAAGGGGTAATTAATAGTAATGTATGTGGA | SEQ ID NO: 422 | ALU8_HUMAN (P39195) Alu subfamily SX sequence contamination warning entry, partial (10%) [THC2639056] |
| 423 | A_24_P728115 | AK024937 | ACTGCATAGTCACTACTTTTAGTGAGTATGTGTTTAGGAGAGGCTATGTAAGTACCA | SEQ ID NO: 423 | Homo sapiens cDNA: FLJ21284 fis, clone COL01911. [AK024937] |
| 424 | A_24_P782337 | AK026477 | AGTCAAAGACCTTGCTGGTGAGAATGTAAGTTGTTAGGATTCTCTGAATCGGGAAGTTATA | SEQ ID NO: 424 | Homo sapiens cDNA: FLJ22824 fis, clone KAIA3991. [AK026477] |
| 425 | A_24_P801451 | EHMT2 | AAATCGGGACATCCGCACCGAGGAGAATCATTCTGCCGAGACCGTGGCTCGGGGCTATGA | SEQ ID NO: 425 | Homo sapiens euchromatic histone-lysine N-methyltransferase 2 (EHMT2), transcript variant NG36/69a, mRNA [NM_006709] |
| 426 | A_24_P83183 | WHSC2 | GACACTTTTTGGAGTCAAGCTCAACGTTACATTTTTGAATGTAGTAGTAAGTAATTAACCAAAAAGT | SEQ ID NO: 426 | Homo sapiens Wolf-Hirschhorn syndrome candidate 2 (WHSC2), mRNA [NM_005663] |
| 427 | A_24_P84984 | TTC3 | TGCGCGGTTCAAGGCCAGTCGTCCAAAAAGGCGTTCAATAGTATTATTGAACCACCTGTCAGT | SEQ ID NO: 427 | Homo sapiens tetratricopeptide repeat domain 3 (TTC3), transcript variant 1, mRNA [NM_003316] |
| 428 | A_24_P85283 | POLR3A | AAGATGAACCTTTGGAGTTTAAAAGGGGTCTGACAACATCAAAGCAGTCTTCCCGTGTG | SEQ ID NO: 428 | Homo sapiens polymerase (RNA) III (DNA directed) polypeptide A, 155kDa (POLR3A), mRNA [NM_007055] |
| 429 | A_24_P87763 | EEF2 | CATGTTTGTGGTCAAGGCCTACTCGCCGTCAACGAGTCGTTTGGCTTCACCGGCTGACCT | SEQ ID NO: 429 | Homo sapiens eukaryotic translation elongation factor 2 (EEF2), mRNA [NM_001961] |
| 430 | A_24_P87824 | ZMYND8 | GACGGTCAGCTCAGGAAAGCAAGGAGAGTGGCTCGACCCGCTTGACCTTTCTGGGTCCAGAGA | SEQ ID NO: 430 | Homo sapiens zinc finger, MYND-type containing 8 (ZMYND8), transcript variant 2, mRNA [NM_012408] |
| 431 | A_24_P883109 | AL833452 | GGGCAACTAGTCATCTACTAGTTAGCTTAGTAAGGTAAGGATTAAATCTAAGAAATAGCA | SEQ ID NO: 431 | Homo sapiens mRNA; cDNA DKFZp686E08116 (from clone DKFZp686E08116). [AL833452] |
| 432 | A_24_P898583 | TRIM26 | TTGACCACCATTGTCTCAGAGCGCTGCCCACTTTGTGTGTGTGCACATGCTGCCTGAGTGACA | SEQ ID NO: 432 | Homo sapiens tripartite motif-containing 26 (TRIM26), mRNA [NM_003449] |
| 433 | A_24_P910490 | BX099367 | AGGGACCCAGAGTTGCAGACCACCTTGGGCTACAGAGGTGACAGGCTGTGTGATAGAAAACTA | SEQ ID NO: 433 | BX099367 Soares_fetal_liver_spleen_1NFLS_S1 Homo sapiens cDNA clone IMAGp998C05977, mRNA sequence [BX099367] |
| 434 | A_24_P914102 | A_24_P914102 | TTAGTAGACCCTAGATTTTGTGTACAAATGTAAAATGTTATTTTTACTGTTGAAAATCAG | SEQ ID NO: 434 | |

Fig. 1-25

| No. | Probe ID No. | Symbols of genes | Sequence | SEQ ID NO: | Descriptions of genes (letters and numbers within [ ] indicates GenBank accession No.) |
|---|---|---|---|---|---|
| 435 | A_24_P916006 | AA435826 | GGAAATGGTCTTCGGGTGGACGGATCAAGGAAAGCAGTCCCTGAC CTTGCAGAAAGTGGT | SEQ ID NO: 435 | AA435826 zt80a02.s1 Soares_testis_NHT Homo sapiens cDNA clone IMAGE:728618 3' similar to TR:G790819 G790819 POLYCYSTIC KIDNEY DISEASE-ASSOCIATED PROTEIN. ;, mRNA sequence [AA435826] |
| 436 | A_24_P921402 | THC2484646 | AGTGTTGGGCATCCACTTCAGTAGAATTCAGCTGACAATATGAT GAATCATTCCAGAGA | SEQ ID NO: 436 | |
| 437 | A_24_P923684 | SIRT3 | GGAATTGGTGACCTAGGAAAACTGTTGAATTCTAAAAAGAATGAA GTTAGTTCTAACCC | SEQ ID NO: 437 | Homo sapiens sirtuin (silent mating type information regulation 2 homolog) 3 (S. cerevisiae) (SIRT3), transcript variant 1, mRNA [NM_012239] |
| 438 | A_24_P924462 | PRKCZ | GCATAGAGATGAAAGATGATATTTTAATTCTATCATTGAGGCATAG TCTTCCAAGACACC | SEQ ID NO: 438 | Homo sapiens mRNA, chromosome 1 specific transcript KIAA0505. [AB007974] |
| 439 | A_24_P92852 | ARID1A | ATCACCGTTGATGAACTCATTGGTTCACAAGTCATTTGTGATGT ACTGTTTTGATTGG | SEQ ID NO: 439 | Homo sapiens AT rich interactive domain 1A (SWI-like) (ARID1A), transcript variant 1, mRNA [NM_006015] |
| 440 | A_24_P93062 | CXXC5 | GCGCTTTCCCATGAACCCAAGGCTGTTCATTATGACCCCGGCAG GTGTGTTCCTGGCCG | SEQ ID NO: 440 | Homo sapiens CXXC finger 5 (CXXC5), mRNA [NM_016463] |
| 441 | A_24_P930337 | THC2503773 | AGCAAGTGGAACCGACGACCAAAATATGACTTGAAGAATGTAATT TAAAATGTAGCATAG | SEQ ID NO: 441 | |
| 442 | A_24_P930391 | AK022351 | AAGTGGGTTTAATTTCGTTTCATGAAAAGGAAAGATTAGGTTTCA TGGAAACAGTTGGTC | SEQ ID NO: 442 | Homo sapiens cDNA FLJ12289 fis, clone MAMMA1001788. [AK022351] |
| 443 | A_24_P930707 | THC2653001 | ATGTTAGTTACGTCGGCTTGCCATGTGTCAGTGTGGACACAGGCTGGTTTCC ACAGTTTAAAAGAA | SEQ ID NO: 443 | BX098637 BX098637 Soares fetal liver spleen 1NFLS Homo sapiens cDNA clone IMAGp998F16386 ; IMAGE:200847, mRNA sequence [BX098637] |
| 444 | A_24_P92418 | AP2A2 | CGGCGCTGCAGAGAGGGGCCTCAGTGTGCAGTCCTGCGTCAAAGAA AATAAAGGGTAGAA | SEQ ID NO: 444 | Homo sapiens adaptor-related protein complex 2, alpha 2 subunit (AP2A2), mRNA [NM_012305] |
| 445 | A_24_P933514 | AK094334 | CGTAGTCCCACTGTAGAATTTCCTTAGGTGGCCATATATATAC TACGTGAACTGTGGC | SEQ ID NO: 445 | Homo sapiens cDNA FLJ37015 fis, clone BRACE2010208. [AK094334] |
| 446 | A_24_P934861 | A_24_P934861 | GGAGGTATCAAGCAGGAAAGTTCTGGGAAATAGTGGACC AGATCGTCTCGATGG | SEQ ID NO: 446 | |
| 447 | A_24_P935682 | AY358248 | AGTCAGTAATCAGCATTCAATCAATATGAGGTCTAACATGATGCT TGACAGTATGCAAC | SEQ ID NO: 447 | Homo sapiens clone DNA166629 MRSS6228 (UNQ6228) mRNA, complete cds. [AY358248] |
| 448 | A_24_P93703 | LOC440104 | GGGATGGCACTAATTTCGTCGTTAACCAGAAGTTGTTCCAGCGAC TGAGCGCATTCTAAGT | SEQ ID NO: 448 | Homo sapiens cDNA FLJ36942 fis, clone BRACE2005518. [AK094261] |
| 449 | A_24_P940310 | ENST00000270201 | AGGTTGACCTCCCATCCAGCGGCTGTATGTGAGTGTAGTTCATTTT ATATCGATAGCGAA | SEQ ID NO: 449 | Nucleolar preribosomal-associated protein 1 (Fragment). [Source:Uniprot/SWISSPROT:Acc:O60287] [ENST00000270201] |
| 450 | A_24_P940551 | FLJ38723 | TTGGCAGGTTACCCGCTTTACCCTTTACAGTAGGAAAATAAGACCCCT ATCTAGTGAGGGAGA | SEQ ID NO: 450 | Homo sapiens hypothetical protein FLJ38723 (FLJ38723), mRNA [NM_173805] |
| 451 | A_24_P942604 | SMC1A | GGGGGTGACAAGATAAGGCCAGGCTCTAGAGCGTGCTTTGGATCATGA ACCATTTCAAGTTT | SEQ ID NO: 451 | Homo sapiens structural maintenance of chromosomes 1A (SMC1A), mRNA [NM_006306] |

Fig. 1-26

| No. | Probe ID No. | Symbols of genes | Sequence | SEQ ID NO: | Descriptions of genes (letters and numbers within [ ] indicates GenBank accession No.) |
|---|---|---|---|---|---|
| 452 | A_24_P942893 | TEX261 | GATGCAGTGGCTCTCCATTGCCACTCTGATTCCTGCGTTCTTTTG GTCACAGAGAAAGGG | SEQ ID NO: 452 | Homo sapiens testis expressed 261 (TEX261), mRNA [NM_144582] |
| 453 | A_24_P945262 | AK097139 | ACAGTCTGTGTATACGGTGGTCAGAGTGTGGCTGAGACACATG AGATGGTAAAGAATT | SEQ ID NO: 453 | Homo sapiens cDNA FLJ39820 fis, clone SPLEN2010625. [AK097139] |
| 454 | A_24_P96234 | QTRT1 | TGCCGAAGGACAAGGCCCGATATGTGATGGCGGGTTGGCTATGCCA CTGATCTGTAGTCT | SEQ ID NO: 454 | Homo sapiens queuine tRNA-ribosyltransferase 1 (tRNA-guanine transglyosylase) (QTRT1), mRNA [NM_031209] |
| 455 | A_24_P96325 | ZGPAT | CCAGCTCTCGGAATGTGTTTGACTTCCTCAATGAAAAGCTGCAA GGTCAGGGTCGTGGG | SEQ ID NO: 455 | Homo sapiens zinc finger, CCCH-type with G patch domain (ZGPAT), transcript variant 1, mRNA [NM_032527] |
| 456 | A_32_P10633 | BC022417 | GTTGATGTTTAAACAGGAAGCTCCACGGAGTTCAGCCCTGTGTG CATTCCTCATGTAT | SEQ ID NO: 456 | Homo sapiens cDNA clone IMAGE:4243782, partial cds. [BC022417] |
| 457 | A_32_P111394 | THC2643957 | GAATACAGTGTTGCTTTTTCATCCCATATTTGAGTGAACCTAAGAC ACATCAATTATAAGG | SEQ ID NO: 457 | |
| 458 | A_32_P112546 | LOC649344 | AGGGAGGTCAGTATGACAGGTAGGACTGGGAACAGGAGCAGCCACC TGAGGCTCAGCCCTA | SEQ ID NO: 458 | PREDICTED: Homo sapiens similar to Keratin, type II cytoskeletal 8 (Cytokeratin-8) (CK-8) (Keratin-8) (K8) (LOC649344), mRNA [XR_018597] |
| 459 | A_32_P116997 | THC2719256 | AAACATTAGGTAGGCAGCTTGTGAGAGGATAGTATTTAGGGTCATGAT GTCCTTCTTGTTGGC | SEQ ID NO: 459 | BE147120 PM2-HT0224-221099-001-b10 HT0224 Homo sapiens cDNA, mRNA sequence [BE147120] |
| 460 | A_32_P118220 | AK091308 | GAATGTAACACACTTCGTCGGGGTTTGGGAGGTGGATATAATATCAT TATGGCGTTCTCAG | SEQ ID NO: 460 | Homo sapiens cDNA FLJ33989 fis, clone DFNES2006944. [AK091308] |
| 461 | A_32_P11899 | C12orf65 | AAGGAGTACCGTGCAGTGCTGCTTCCTTGGATGGAGAATGAAGTCGAA GAGCAGTTGTGAAA | SEQ ID NO: 461 | Homo sapiens chromosome 12 open reading frame 65 (C12orf65), mRNA [NM_152269] |
| 462 | A_32_P120454 | THC2642550 | ACAGAATCAGATGACTGGAGTGGTTCATCTGTTGTTTATTGGCAAGCT CAGGACAGGGTATGA | SEQ ID NO: 462 | |
| 463 | A_32_P121755 | THC2672892 | AAACCCTCGTGCTCCAGAGTGGTTCCGGGCGTGGCATTTGTTGAGGTGG GATTCCGAGGCCAGA | SEQ ID NO: 463 | Q2TXF9_ASPOR (Q2TXF9) Predicted protein, partial (5%) [THC2672892] |
| 464 | A_32_P124493 | LOC642826 | AAGAAAAGAGGGTTACAGATCATTGGCACATGGAGAAATATTCCC ABCAGTAACGACTTC | SEQ ID NO: 464 | Homo sapiens cDNA FLJ39589 fis, clone SKMUS2008607. [AK096908] |
| 465 | A_32_P124538 | THC2758091 | AGTAGGGTTGGTCTTCTTGATTCCGGGAGAGCCTCATGTAAGCAG GTCGTTAAACCAGAC | SEQ ID NO: 465 | |
| 466 | A_32_P125589 | THC2649341 | CGGCTCTATCGCTTGCTTTGCTTTTGAATGAAAGTGAGATGTCT CATCAGCTCAGATAG | SEQ ID NO: 466 | |
| 467 | A_32_P12703 | THC2697162 | TTGAAGGAAAAGAGTATAGGGGGGAAGTGCCAGACTAAACGAATC CTAAGTAAATAGGGT | SEQ ID NO: 467 | |
| 468 | A_32_P127583 | THC2650423 | AGAGAGGCCCTTCTATGTACATGAGTGTTCTGTCCCTTAGGTAGAT TAGTTCATCCAACTG | SEQ ID NO: 468 | |
| 469 | A_32_P131294 | BM854107 | AGTAGGGAAAAAGGTTTGTTGTTCGTTAATAAGGGTAGTGTCGGGAAA TGCTAGCACTTGTGC | SEQ ID NO: 469 | K-EST0136406 S22SNU16nT Homo sapiens cDNA clone S22SNU16n1-145-F11 5', mRNA sequence [BM854107] |
| 470 | A_32_P136538 | BF928446 | CTGCCGAAATGGTGAGAAATAAAAGGAAGCATTCTGGCGTTCTCAG GTTTTTCAAACTCAC | SEQ ID NO: 470 | BF928446 IL2-NT0200-061200-260-F07 NT0200 Homo sapiens cDNA, mRNA sequence [BF928446] |

Fig. 1-27

| No. | Probe ID No. | Symbols of genes | Sequence | SEQ ID NO: | Descriptions of genes (taken and numbers within [ ] indicates GenBank accession No.) |
|---|---|---|---|---|---|
| 471 | A_32_P138178 | BE835321 | AGATTGGCCTTAATCCCAGAGACAGTATGAGATACAATTCTGGGACTTTGTCTTCGTAACC | SEQ ID NO: 471 | BE835321 RC5-FN0022-300600-022-G12 FN0022 Homo sapiens cDNA, mRNA sequence [BE835321] |
| 472 | A_32_P145385 | AK001118 | CGGCAATTAACACTCGAGGAAGCTTAAATTTCAAGCTTTTTGATTCTCAGGAAATGAGAT | SEQ ID NO: 472 | Homo sapiens cDNA FLJ10256 fis, clone HEMBB1000870. [AK001118] |
| 473 | A_32_P146844 | THC2539689 |  GCTGTGGGCTGTATTCCAGACTGAGAGTTGAAGTTTGTGTGCATCATCATGTGCATTAA | SEQ ID NO: 473 | |
| 474 | A_32_P151244 | AK022268 | GTAGTCAGATGTGAGAGAGTTATTTCATGTGTAAGCTTTGAAGTGTTGATGTGTT | SEQ ID NO: 474 | Homo sapiens cDNA FLJ12206 fis, clone MAMMA1000941. [AK022268] |
| 475 | A_32_P151544 | KRT18 | GAGGACTTCATCCTTGGTGATGCCTTGGACAGCAGCAAGCTCCATGCAAAACCATCGAAAAG | SEQ ID NO: 475 | Homo sapiens keratin 18 (KRT18), transcript variant 1, mRNA [NM_000224] |
| 476 | A_32_P155091 | ATXN2L | GAGTGACCTGTGTGAGACAGATGCCCATGAGGATGGCTGGACAAGAAGCTTTTA | SEQ ID NO: 476 | Homo sapiens ataxin 2-like (ATXN2L), transcript variant B, mRNA [NM_145714] |
| 477 | A_32_P155416 | PRNPIP | TAGATCCAAACGTCAAGTCAATTTTGTCACGTGCTGGGAGACTGGGAGTGTTGATGTGC | SEQ ID NO: 477 | Homo sapiens prion protein interacting protein (PRNPIP), mRNA [NM_024066] |
| 478 | A_32_P155841 | AL079294 | CCTTCCTGTTTATATACCTGCAGTTACCAGTTGTTGTTGTTAAGGAAGAATGGCAAATGCAAA | SEQ ID NO: 478 | Homo sapiens mRNA full length insert cDNA clone EUROIMAGE 362780. [AL079294] |
| 479 | A_32_P158171 | THC2634329 | TCCTATGTGGACTCTGATTTAAGGGGTATAAGGCTGTCTGTCTTCCGTACCGAATAGAAGGTT | SEQ ID NO: 479 | |
| 480 | A_32_P159176 | THC2744561 | CAGAAGAAGATAGAAGCAGCATCTCACCAAAGACAAGCAAGTTGACCCTAAGTCTTAAATCAT | SEQ ID NO: 480 | |
| 481 | A_32_P162095 | THC2673084 | AAGGTGCTTTATTTGTGGGCCAAATAGTAGGAGGTATTAGATACGTTGGTGGGCCAAGAA | SEQ ID NO: 481 | |
| 482 | A_32_P163458 | tcag7.1017 | AGATGTGGATTTTCAGGAGGACGTTATTCCAATGCTAATGGCAGACATCAGGAAGGAGG | SEQ ID NO: 482 | Homo sapiens similar to Williams Beuren syndrome chromosome region 19 (MGC57359), mRNA [NM_001004351] |
| 483 | A_32_P164573 | THC2611661 | AGGTGTTTCTATTAACACTCGAAGTACTCTGAGAGCTTGGAAATTTCAAGTGCAAAATC | SEQ ID NO: 483 | RR12_SPINX (P42344) Chloroplast 30S ribosomal protein S12, partial (11%) [THC2611661] |
| 484 | A_32_P16462 | THC2567672 | GGCAGAAGAATGGGAGGACAGTGATGAGGAATAATTTTCAGTCTTTATCATTTTATAT | SEQ ID NO: 484 | W18193 IMAGE:20064 Soares infant brain 1NIB Homo sapiens cDNA clone IMAGE:20064, mRNA sequence [W18193] |
| 485 | A_32_P165990 | AK094623 | TGTGGGGACACAGACAGACTCGTCGCATGGGTGATTTAATTTTGGGCCTCAGTT | SEQ ID NO: 485 | Homo sapiens cDNA FLJ37304 fis, clone BRAMY2016070. [AK094623] |
| 486 | A_32_P165356 | THC2685727 | GTGTCTGATTTTAGCCACCAGTGAAAAACAAGGGTGAATTGCTTAATGCCTGCAATGCTG | SEQ ID NO: 486 | |
| 487 | A_32_P167883 | THC2697442 | AGGTAATTGGGGGTATGACTTCAGTCAGTTTGAAATATTGGGAACTAAATCTCTCATT | SEQ ID NO: 487 | |
| 488 | A_32_P169316 | A_32_P169316 | AGGAAGTGGAAGCATACTACTTGTTAGCCACGAGCTAGATGGCAAAGCAGCTGTTTGAATATAAC | SEQ ID NO: 488 | |
| 489 | A_32_P170811 | KIAA1509 | CAGTGTGAGGAGAAAGAGCAGTTCATTGAAAGAATCAAACAGCTGGACATTGAGACCCAG | SEQ ID NO: 489 | Homo sapiens KIAA1509 (KIAA1509), mRNA [NM_001080414] |
| 490 | A_32_P176609 | ZNF609 | ATGATGGCTCTGATGATGGACCCTCAGTCATGATGGATGAAAACAAGGCAATGATGCCTTTGATT | SEQ ID NO: 490 | Homo sapiens zinc finger protein 609 (ZNF609), mRNA [NM_015042] |

Fig. 1-28

| No. | Probe ID No. | Symbols of genes | Sequence | SEQ ID NO: | Descriptions of genes (letters and numbers within [ ] indicates GenBank accession No.) |
|---|---|---|---|---|---|
| 491 | A_32_P179526 | ZBTB20 | TTGAAGTTGGAAATCAAGGGGAATCTAAAACCGACGATGTTTCTGCTGCTGGGAAAGG | SEQ ID NO: 491 | Homo sapiens zinc finger and BTB domain containing 20, mRNA (cDNA clone IMAGE:4291354), partial cds. [BC010934] |
| 492 | A_32_P181564 | THC2606490 | TTATAAGTGCCGTTAATATCTCCAGTATCTCCACAGAGAATTTTGTCTTCAAGGCTTGGC | SEQ ID NO: 492 | |
| 493 | A_32_P184039 | A_32_P184039 | ATCATTGTTAGTCTTGGGCCAAAATAGTTGTTATGTATCATGCGTAATAACTGACGAGC | SEQ ID NO: 493 | |
| 494 | A_32_P185361 | AL109784 | GGAAGGCTGTTTGCTGAATAAGACAAAGATACAGAGCATGCAAAGTAAAGGATGTGGGCGT | SEQ ID NO: 494 | Homo sapiens mRNA full length insert cDNA clone EUROIMAGE 122871. [AL109784] |
| 495 | A_32_P187304 | A_32_P187304 | ATAAATGAGAAGAACATTCACATAGAACAAAGGTGTGGTGGAAGGCTCTGACCAGCTTAACC | SEQ ID NO: 495 | |
| 496 | A_32_P192545 | TCEAL6 | ATTTGGGAGGCCGAATGCTTAACCTTAAGCTAGGCTGATATTTTGGTTTAGATGTCAATCTGG | SEQ ID NO: 496 | Homo sapiens transcription elongation factor A (SII)-like 6 (TCEAL6), mRNA [NM_001006938] |
| 497 | A_32_P194072 | DKFZP434B0335 | ATGGGGCTCAGGGCCTCTTTACCATGTGCAGTGACGATGCAGTGAACATTCTCAGAGCAGGACTTGCAAA | SEQ ID NO: 497 | Homo sapiens DKFZp434B0335 protein (DKFZP434B0335), mRNA [NM_015395] |
| 498 | A_32_P196297 | THC2652466 | CCTTTCAGAAAGACTGTAAGGCTTACGCAAGAGCATTAATTTTGCTGCATAGGCGGCCTGTT | SEQ ID NO: 498 | Q9BHM3_PARIE (Q9BHM3) Cytophilin-RNA interacting protein, partial (4%) [THC2652466] |
| 499 | A_32_P198845 | THC2651047 | GCGAACCAATCAACAACTGTCTTCAGTGAGTGACAGTGCTTCTATAGCTAACAATTAACC | SEQ ID NO: 499 | |
| 500 | A_32_P19917 | BM684461 | ATATGATCTTAAGAGTGTAAACATTCAAGAGACGAGGGCAAGAAAGCGAGTCACATGTAG | SEQ ID NO: 500 | Ui-E-EJO-aip-c-14-0-UI.si Ui-E-EJO Homo sapiens cDNA clone Ui-E-EJO-aip-c-14-0-UI 3', mRNA sequence [BM684461] |
| 501 | A_32_P200429 | A_32_P200429 | GGAGGAGAGTTCACATCTGGACCATTGAGAACAGGAAGCGACTCATTAAAGATGTTA | SEQ ID NO: 501 | |
| 502 | A_32_P203515 | SPECC1L | GATTCCTTTTGCCTCGTCTGATAATGGATGCTTAGGACACTGTGGGCTTTAGGAATGACTA | SEQ ID NO: 502 | Homo sapiens SPECC1-like (SPECC1L), mRNA [NM_015330] |
| 503 | A_32_P204565 | A_32_P204565 | CAGGATCAGAATGATACACCGGGATGTGTTTCAGTGTGATGGAAAGATTGTTTCCAGTGA | SEQ ID NO: 503 | |
| 504 | A_32_P205323 | tcag7.1017 | TCATCTAGAAGAACCTGGACCATTCTTGGACAGAGCTGAATACAGTGATCACGTTGTCCTC | SEQ ID NO: 504 | Homo sapiens similar to Williams Beuren syndrome chromosome region 19 (MGC57359), mRNA [NM_001004351] |
| 505 | A_32_P208039 | AL049390 | TTTCATGTTGAGCATTCAGATTGGGCTTTATTTCTCAAGGCATGTGGCAAAGCTCACAA | SEQ ID NO: 505 | Homo sapiens mRNA; cDNA DKFZp586O1318 (from clone DKFZp586O1318) [AL049390] |
| 506 | A_32_P209562 | THC2663167 | CAATGTAAAGCCAGAATATGAACGTCGTTTTGTCAAGATTTTCAAACGTATTTGGCTGAT | SEQ ID NO: 506 | ALU1_HUMAN (P39188) Alu subfamily J sequence contamination warning entry, partial (5%) [THC2663167] |
| 507 | A_32_P211048 | A_32_P211048 | GTTCACAAAAACACCTAGTAGGTATTCAGTTCATATTGGGAATGAATGAGAAAATGAGCAG | SEQ ID NO: 507 | |
| 508 | A_32_P213509 | THC2663555 | GATTTGTTCCAGTGTTGGAGCGCGTTTTTAATGAAAAATCTCAACACCTACACTCGGAAAA | SEQ ID NO: 508 | |
| 509 | A_32_P214054 | THC2755661 | GGCTTATCTCCTTTGTTTAACAGTTGGGGGTTGGCTTCGCATAGCAATGATTTGCAAAT | SEQ ID NO: 509 | |

Fig. 1-29

| No. | Probe ID No. | Symbols of genes | Sequence | SEQ ID NO: | Descriptions of genes (letters and numbers within [ ] indicates GenBank accession No.) |
|---|---|---|---|---|---|
| 510 | A_32_P216122 | AK130891 | TTCTTCCTCTATATGTTTGGGAGGGCATTCATGAAGAATTGAGTAG AGATATATGGGTC | SEQ ID NO: 510 | Homo sapiens cDNA FLJ27381 fis, clone UBA07680. [AK130891] |
| 511 | A_32_P220567 | A_32_P220567 | GGAAAGTGAAAAATAGTTCCTATGGTGGAAGGTGGGGGTGAGAC ATACCTCCTCTGAAA | SEQ ID NO: 511 | |
| 512 | A_32_P220580 | AK124352 | ACCGAGGAGAATCAGGACTACTATCTTTTGGGAAATAAGCTGGGTCC TTATGATGGAGTCGG | SEQ ID NO: 512 | Homo sapiens cDNA FLJ42361 fis, clone UTERU2025366. [AK124352] |
| 513 | A_32_P224522 | SLC25A23 | CTTACATTCTGCACTCATAGTTGGATTCTGAGGTAGGATCATG TGGAGACCCGATGGA | SEQ ID NO: 513 | Homo sapiens solute carrier family 25 (mitochondrial carrier; phosphate carrier), member 23 (SLC25A23), mRNA [NM_024103] |
| 514 | A_32_P225625 | AA971667 | GCCAAATGCTGCTCCTTTTCCAAGAGATAGAAAAGCATCTTTTAA ATCATCCTCCATTTT | SEQ ID NO: 514 | AA971667 opB5c06.s1 Soares_NFL_T_GBC_S1 Homo sapiens cDNA clone IMAGE:1583626 3', mRNA sequence [AA971667] |
| 515 | A_32_P227110 | THC2512148 | TAAACAAATCCTTTTGATTCAGGCGACTGTGTATTGATAATGGCT TATTTATTACAATCA | SEQ ID NO: 515 | |
| 516 | A_32_P227657 | BX114900 | GTCGAGACCTGAACAGAAGCTTCCTGAGACTTAGTCAGGGCCGTG TTTCACGGTAAGGAC | SEQ ID NO: 516 | BX114900 Soares_fetal_liver_spleen_1NFLS_S1 Homo sapiens cDNA clone IMAGp998L191010, mRNA sequence [BX114900] |
| 517 | A_32_P232651 | THC2645586 | CTTTGAAAAGGATATCCTTCAACATTCGTTTTCGAGAAAATGAGG TCACGTGACTTATTTC | SEQ ID NO: 517 | Q9P3E1_NEUCR (Q9P3E1) Related to rna-binding protein fus/tls, partial (5%) [THC2645586] |
| 518 | A_32_P234661 | THC2650029 | AACCAAGATAAGCTAAGTAAGTCAGGCTTTGATTTGTCGTTGCCA GGAAAAAGACTTAGG | SEQ ID NO: 518 | Q88PH0_PSEPK (Q88PH0) Dipeptide ABC transporter, permease protein, partial (5%) [THC2650029] |
| 519 | A_32_P29442 | AI911989 | ATAGTTTACATGTGCGACATGAGCTAGTGTTGTTGTACATGTGACAG ACCTTGTTTCTGGAT | SEQ ID NO: 519 | AI911989 wd78e07.x1 NCI_CGAP_Lu24 Homo sapiens cDNA clone IMAGE:2337732 3', mRNA sequence [AI911989] |
| 520 | A_32_P3342 | THC2676548 | TATAGCATTTTGTGAAAGATACATGTTGTAGCTCGTTCTCGTTCGTCTAGA TGATTTGGTCAACAG | SEQ ID NO: 520 | ALU7_HUMAN (P39194) Alu subfamily SQ sequence contamination warning entry, partial (19%) [THC2676548] |
| 521 | A_32_P38782 | BX113029 | CATGCTGAGTGTGAGAAGTGCAGTGCCGTTTCTCTACCCACAGCC ACTCAGACGACCCAG | SEQ ID NO: 521 | BX113029 Soares_fetal_liver_spleen_1NFLS_S1 Homo sapiens cDNA clone IMAGp998E061010, mRNA sequence [BX113029] |
| 522 | A_32_P402521 | PRPF8 | GTGCTCGTCAGTGGAACTACAACTTCATGGGTGTTCGGCATGACCGCAA CATGAAATATGAGCT | SEQ ID NO: 522 | Homo sapiens PRP8 pre-mRNA processing factor 8 homolog (S. cerevisiae) (PRPF8), mRNA [NM_006445] |
| 523 | A_32_P40673 | A_32_P40673 | CATCACACTTGATATATAGGACAGCCTACCTACTTGTTTGAGTGTC ACAGCGTGATATGTA | SEQ ID NO: 523 | |
| 524 | A_32_P430359 | DDX54 | CCTGAGTGCCTCAGGGTTTGGGAATGGAATTTTTAATGTAATAAA TCTTTATTGAGCACT | SEQ ID NO: 524 | Homo sapiens DEAD (Asp-Glu-Ala-Asp) box polypeptide 54 (DDX54), mRNA [NM_024072] |
| 525 | A_32_P43878 | DB111455 | ATGTGAGAAAGGTTCTTTAAGGTTTAATGACGAAGTTCCATGTG AGGTCTTAGTTGGGA | SEQ ID NO: 525 | DB111455 THYMU2 Homo sapiens cDNA clone THYMU2015028 5', mRNA sequence [DB111455] |
| 526 | A_32_P46404 | AK092468 | CTGCATGCCGAACGTCTTTTGCATAAATACTTATGGATTCAGCC AAGAGGAAAAGCACT | SEQ ID NO: 526 | Homo sapiens cDNA FLJ35149 fis, clone PLACE6010485. [AK092468] |
| 527 | A_32_P514790 | UNK | AGGACGAAAAGGGCGTTCAATGAATTAAGTGAAAACTTTTTGTTT TTTACAAAATGCAA | SEQ ID NO: 527 | Homo sapiens unkempt homolog (Drosophila) (UNK), mRNA [NM_001080419] |

Fig. 1-30

| No. | Probe ID No. | Symbols of genes | Sequence | SEQ ID NO: | Descriptions of genes (letters and numbers within [ ] indicates GenBank accession No.) |
|---|---|---|---|---|---|
| 528 | A_32_P52206 | TYW1 | GAGGAAGCATCCATTGATTTCGATTTGGCAAAACTTACGTGAAG GGTATGAGAGATGGG | SEQ ID NO: 528 | Homo sapiens tRNA-yW synthesizing protein 1 homolog (S. cerevisiae) (TYW1), mRNA [NM_018264] |
| 529 | A_32_P55161 | CENTG2 | AAAGAGGGTTACAGATGATTGCACAGATGCAAAATATTCCCAGCAGT AAACACTTCCATTA | SEQ ID NO: 529 | Homo sapiens centaurin, gamma 2 (CENTG2), transcript variant 1, mRNA [NM_001037131] |
| 530 | A_32_P5542 | AF131782 | GAGGCTGTTACGATGTAACTTCGACTGAGTAACGTGGGAAGAAATGTCTT ATAAATAAACAACAG | SEQ ID NO: 530 | Homo sapiens clone 24941 mRNA sequence. [AF131782] |
| 531 | A_32_P55427 | THC2701763 | CAGTTTTATCCCTTATCTGTAAAAGAAACTACAAATTGAGAGAGTA CATTCGATAGGCTGG | SEQ ID NO: 531 | Q9F6M7_CARHY (Q9F6M7) DTDP-glucose 4,6-dehydratase (Fragment), partial (11%) [THC2701763] |
| 532 | A_32_P55987 | THC2639487 | GAAAAGAAGCCCAGTCGTGTAACGGAAGTCTAATAGCTGCTCAGTA CATAGTAAATGCTAT | SEQ ID NO: 532 | Q70GE4_ANOGA (Q70GE4) ENSANGP00000015281 (Fragment), partial (6%) [THC2639487] |
| 533 | A_32_P6740 | JMJD1C | GAGTGGGTTAAAGTTTATGAAGATTTTCAACTTTCGTTGGTGGAA TACCACTTAATGTGG | SEQ ID NO: 533 | Homo sapiens jumonji domain containing 1C (JMJD1C), transcript variant 1, mRNA [NM_032776] |
| 534 | A_32_P6415 | TNRC6B | GCATAAGGTTTAATCAAACTCCCATATGTTGAAATTGGTCTCTGA TATTACTGGTTTTAC | SEQ ID NO: 534 | Homo sapiens trinucleotide repeat containing 6B (TNRC6B), transcript variant 1, mRNA [NM_015088] |
| 535 | A_32_P65067 | THC2618074 | CCCCAAAGTGAATTTAAACTTGACTTATTTATGCCGTTCTCAT AGCAACAGGAAAAGT | SEQ ID NO: 535 | |
| 536 | A_32_P6972 | THC2621771 | AGGGCTGATTGTGGAAATGATGGTTAGAGTCAGAGAAGAAAGTGAGAG TGATGAAGGCAGAAT | SEQ ID NO: 536 | |
| 537 | A_32_P70875 | CD239706 | CTTTGTTTGAGAAGTTCCTAATGCAGTAGGAGAGGAAGAAGTGACAG TTTTGTTTATTTACTG | SEQ ID NO: 537 | FNPXFO3 FNP Homo sapiens cDNA, mRNA sequence [CD239706] |
| 538 | A_32_P71171 | A_32_P71171 | TCTAGATAGTAATAGGAAACCAAGAATCCAGGTGGTGATGGGTG GAGGGAGTGATTGAA | SEQ ID NO: 538 | |
| 539 | A_32_P718498 | MLLT6 | CCACAGCTATTCCCGAGCTATAGAGTGGGCAATTCTCACCTTCA AAGAGTCCCGCACCTG | SEQ ID NO: 539 | Homo sapiens myeloid/lymphoid or mixed-lineage leukemia (trithorax homolog, Drosophila); translocated to, 6 (MLLT6), mRNA [NM_005937] |
| 540 | A_32_P749354 | MGC11102 | GTTTTGTGTTTTCGGCTGTCGTCCTGTCTATTGGATGTGATATGTTAT GGATGTGATGTGTTA | SEQ ID NO: 540 | Homo sapiens hypothetical protein MGC11102 (MGC11102), mRNA [NM_032325] |
| 541 | A_32_P79103 | BM932034 | GTGCTACAGAATGAAAATAGACATTTTAGGAAGGTTGAGTCAGAGG TGGAGTGGGGCATA | SEQ ID NO: 541 | UI-E-EJ1-aji-k-24-0-UI.r1 UI-E-EJ1 Homo sapiens cDNA clone UI-E-EJ1-aji-k-24-0-UI 5', mRNA sequence [BM932034] |
| 542 | A_32_P81357 | FAHD2A | CAACACCAAGCAAGCAGATGGTATTCAAGACAGAGGAGCTGATAGCCTG GGTGTCCCAGTTTGT | SEQ ID NO: 542 | Homo sapiens fumarylacetoacetate hydrolase domain containing 2A (FAHD2A), mRNA [NM_016044] |
| 543 | A_32_P8251 | KIAA1542 | TCGAGTTCGTCGTCGCTGACACGTCGTCGTGCACGTGTGTTGCTCA CAGTTGAAAACTGGA | SEQ ID NO: 543 | Homo sapiens CTD-binding SR-like protein rA9 (KIAA1542), mRNA [NM_020901] |
| 544 | A_32_P83453 | LOC647768 | TTTTCTTGGATGTCCCCGTTTTGTTGTTGATTGACAACTGTAT TGCATTGAAGAAAGT | SEQ ID NO: 544 | PREDICTED: Homo sapiens similar to tetratricopeptide repeat protein 3 (TPR repeat protein 3) (TPR repeat protein D) (LOC647768), mRNA [XR_018202] |
| 545 | A_32_P84289 | C1orf93 | ACAGTGGAACGTGTCTGCGAAGGAGCGGCCAGGTTCTGCAGCGACCC CAGTAGCCTGTGGGT | SEQ ID NO: 545 | Homo sapiens chromosome 1 open reading frame 93 (C1orf93), mRNA [NM_152371] |
| 546 | A_32_P86 | LOC728411 | TCGTCGAGGAGGTCTGGGATGTCTGGTTATATCGTGATTTCTGACC TCTGGGCATGGAGGT | SEQ ID NO: 546 | Homo sapiens, clone IMAGE:4590099, mRNA. [BC048193] |

Fig. 1-31

| No. | Probe ID No. | Symbols of genes | Sequence | SEQ ID NO: | Descriptions of genes (letters and numbers within [ ] indicates GenBank accession No.) |
|---|---|---|---|---|---|
| 547 | A_32_P88626 | PHACTR4 | TGAAGGCTGAGAGGAAGGCTCAGGATGTGACATGTCTTCCTTTTCGTCACAAGTCATCAT | SEQ ID NO: 547 | Homo sapiens phosphatase and actin regulator 4 (PHACTR4), transcript variant 2, mRNA [NM_023923] |
| 548 | A_32_P88987 | AK022346 | ATGGGAAGTTAGTACGCAGGCTTACCAAAAGGTCAGGTTTATATAAAGTGGCGTTCCTTT | SEQ ID NO: 548 | Homo sapiens cDNA FLJ12284 fis, clone MAMMA1001757. [AK022346] |
| 549 | A_32_P90468 | A_32_P90468 | AAGGCAGGAATAATTTTCTATCTCATGGTAAGCTAACTGCTGGAAGTTATGATGAGACCCT | SEQ ID NO: 549 | |
| 550 | A_32_P91328 | THC2641595 | GTTAGGCGAATAATGTCATTGAAGTCTTAAGCTCTAGGCTGACTCTAACGGCAGGGTTCA | SEQ ID NO: 550 | |
| 551 | A_32_P92783 | STIP1 | CCAGGCACTCAGGGAACAGTTAAAGAATCCGTAATCGCAAAGAAGATCCAGAAGCTGAT | SEQ ID NO: 551 | Homo sapiens stress-induced-phosphoprotein 1 (Hsp70/Hsp90-organizing protein) (STIP1), mRNA [NM_006819] |
| 552 | A_32_P97305 | THC2681839 | AATATGGACACACAAAACTAAAGAAAGGATGTCAGTTGAGCACACAGGTTCGTGCCGCCT | SEQ ID NO: 552 | |
| 553 | A_32_P98847 | POLRMT | AGGCAGAAGAACGGCTTGCCGCCCAACTTCATGCAGTCGCTGGACTCCTCACACATGATGC | SEQ ID NO: 553 | Homo sapiens polymerase (RNA) mitochondrial (DNA directed) (POLRMT), nuclear gene encoding mitochondrial protein, mRNA [NM_005035] |
| 554 | A_32_P98940 | THC2745859 | AAGGTATTCCCAAGATAGCAAAGGTGTGTTGTTTTAGGCAGGTGTATTTCAGCTAGTTA | SEQ ID NO: 554 | |
| 555 | A_32_P99097 | TNPO1 | AAATTGGAGGCATTTCTCTGACCAGTTTGCGTCTCCCTTAAAAAGAGCGTCTTGCAGGTG | SEQ ID NO: 555 | Homo sapiens transportin 1 (TNPO1), transcript variant 1, mRNA [NM_002270] |
| 556 | A_23_P102235 | SNRPG | ACAACAGAACAATATTGGAATGGTAATAGGAGGAAATAGTATCATCATGTTAGAAGC | SEQ ID NO: 556 | Homo sapiens small nuclear ribonucleoprotein polypeptide G (SNRPG), mRNA [NM_003096] |
| 557 | A_23_P108835 | YPEL5 | AAAGTGACTTCTGAGTGACATTAAGTTCGTCCTCTATTTGGCACTGGGCTGTTGGTTAGAAG | SEQ ID NO: 557 | Homo sapiens yippee-like 5 (Drosophila) (YPEL5), mRNA [NM_016061] |
| 558 | A_23_P110704 | SLU7 | CCTCTTTCCTTGGACAGTAGGACAACTAGTCAGAAGAAGACCATCCAAGATAGAATGCAGGTGATA | SEQ ID NO: 558 | Homo sapiens SLU7 splicing factor homolog (S. cerevisiae) (SLU7), mRNA [NM_006425] |
| 559 | A_23_P111583 | CD36 | CTTTGGCTTAATGAGACATGGGACCATTGGTGATGAGAAGGAGCAAACATGTCAGAAGTCAA | SEQ ID NO: 559 | Homo sapiens CD36 molecule (thrombospondin receptor) (CD36), transcript variant 2, mRNA [NM_001001547] |
| 560 | A_23_P115872 | CEP55 | GTAAACGAAAAACTTTTAAATTTCTTCAGGTTTTGTAACATGCTTACCACTGGGCTACTG | SEQ ID NO: 560 | Homo sapiens centrosomal protein 55kDa (CEP55), mRNA [NM_018131] |
| 561 | A_23_P117852 | KIAA0101 | TACTGCTGCCATTTTTATTGGTGTTGATTATTGATTTGGAATGGTGCCATATTGTCAGTCGTTC | SEQ ID NO: 561 | Homo sapiens KIAA0101 (KIAA0101), transcript variant 1, mRNA [NM_014736] |
| 562 | A_23_P118061 | CKLF | GCACAAGGCCCTGAACCATATATTGTTATCACTGGATTTGAAGTCACCGTTATCTTATTT | SEQ ID NO: 562 | Homo sapiens chemokine-like factor (CKLF), transcript variant 4, mRNA [NM_181641] |
| 563 | A_23_P118150 | ARL6IP1 | TTCAGATTTTCAGCTGACATTAGCTATAGTATACAGTAGGTTAAGACTCATGTGTATGAG | SEQ ID NO: 563 | Homo sapiens ADP-ribosylation factor-like 6 interacting protein 1 (ARL6IP1), mRNA [NM_015161] |
| 564 | A_23_P119992 | VRK2 | TTTAAGTTTCCAGCTGTTCACCGAAATGTGTATTCTTATTTCAGTGTTTCCTTCCAGAG | SEQ ID NO: 564 | Homo sapiens vaccinia related kinase 2 (VRK2), mRNA [NM_006296] |

Fig. 1-32

| No. | Probe ID No. | Symbols of genes | Sequence | SEQ ID NO: | Descriptions of genes (letters and numbers within [ ] indicates GenBank accession No.) |
|---|---|---|---|---|---|
| 565 | A_23_P120316 | MTHFD2 | AGGATATTCCTTGGTATTAGTACTCATTTTATGTATGTTACCCTTCAGTAAGTTCTCCC | SEQ ID NO: 565 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 566 | A_23_P120644 | A_23_P120644 | GGCTTTGTTGTAGGAGGACCAATGACTGTTGTTATATCATGTATCGAGAATTCTGGGCAAAAC | SEQ ID NO: 566 | |
| 567 | A_23_P121253 | TNFSF10 | GGAAGAATCCATCTCTCAAGTAGTGTATGCAACAGTAGTAGCCTGAAGGTTTCCTTAAGGGA | SEQ ID NO: 567 | Homo sapiens tumor necrosis factor (ligand) superfamily, member 10 (TNFSF10), mRNA [NM_003810] |
| 568 | A_23_P121622 | SULT1B1 | GAAATAGAGATTGTGTGTAGTTGATTGAAAGGAGGGCAGTTATGAATTGATTTGGGGAAT | SEQ ID NO: 568 | Homo sapiens mRNA for SULT1B2, complete cds. [D89479] |
| 569 | A_23_P122007 | C5orf30 | ATCAGATTTCTCGTTGGGCTGGAAATGTTCGGCTGTTGTATATTTAAAGTAAATTGCAC | SEQ ID NO: 569 | Homo sapiens chromosome 5 open reading frame 30 (C5orf30), mRNA [NM_033211] |
| 570 | A_23_P123608 | JAK2 | GGATAACATGGCTGGATGAAAGAAATGACCTTCATTCTGAGACCAAAGTAGATTTACAGA | SEQ ID NO: 570 | Homo sapiens Janus kinase 2 (a protein tyrosine kinase) (JAK2), mRNA [NM_004972] |
| 571 | A_23_P124823 | THC2510119 | GGAAGAGAGATTCCTATAAGTTCACCGAGTCTTGAAGATTCGAAAATTTGTTGTTTAT | SEQ ID NO: 571 | BC000359 SPC18 protein [Homo sapiens] [exp=-1; wgp=0; cg=0], partial (77%) [THC2510119] |
| 572 | A_23_P126057 | SCP2 | ACATTGGCAAATAGCGTGGGATAGATTGTTGTTAATGGGTGTGACCAATCCGTGTTTT | SEQ ID NO: 572 | Homo sapiens sterol carrier protein 2 (SCP2), transcript variant 1, mRNA [NM_002979] |
| 573 | A_23_P127195 | PRPF18 | TGAGTTCTACCTGACTGATGTAACTCTTGATTGGTTTTAAGAACTTTGTTGGCCTTCATTCAT | SEQ ID NO: 573 | Homo sapiens PRPF18 pre-mRNA processing factor 18 homolog (S. cerevisiae) (PRPF18), mRNA [NM_003675] |
| 574 | A_23_P128192 | PFDN5 | CACGTCCATTGCTCAGCTCAAAGTGGTACAGAGACCAAGTATGTGGAAGCCAAGGACTGTCT | SEQ ID NO: 574 | Homo sapiens prefoldin subunit 5 (PFDN5), transcript variant 1, mRNA [NM_002624] |
| 575 | A_23_P128384 | VPS29 | CAAGCTAATTGGAGGATGATGTGAAAGTAGAAGGAATGAATACAAAAAACGTTAAAGCCAA | SEQ ID NO: 575 | Homo sapiens vacuolar protein sorting 29 homolog (S. cerevisiae) (VPS29), transcript variant 2, mRNA [NM_057180] |
| 576 | A_23_P128447 | LRRK2 | GGAGAAAGAGATACAATCCTTGCTTGAGCGTTTGGGACATCAATCTTCCACATGAAGTGCA | SEQ ID NO: 576 | Homo sapiens leucine-rich repeat kinase 2 (LRRK2), mRNA [NM_198578] |
| 577 | A_23_P130089 | IFT20 | TGGCCAGTTTCAGAAAATAGTTGGTGGTTTAATTGAGCTTGTTGACGAACATGCAAAACAGA | SEQ ID NO: 577 | Homo sapiens intraflagellar transport 20 homolog (Chlamydomonas) (IFT20), mRNA [NM_174887] |
| 578 | A_23_P130293 | ANKRD12 | TCAAGCATTTTACGAAAATCGAAGGAGTTTATGTTCGCGTTGTTGATGTTACGAGGGACTTTG | SEQ ID NO: 578 | Homo sapiens ankyrin repeat domain 12 (ANKRD12), mRNA [NM_015208] |
| 579 | A_23_P130444 | ZNF701 | CTCCTTGCAGAATACATCAATAACGTTCATTTTGAGGTAATAGTTACAAATGGCGGTGAGGAC | SEQ ID NO: 579 | Homo sapiens zinc finger protein 701 (ZNF701), mRNA [NM_018260] |
| 580 | A_23_P13065 | ZDHHC13 | CATACAATCTTGGATTCGATGGAGAAGCCTGGCAGAGATTTCTTTCAGTGTGGCTGCTTTGGCT | SEQ ID NO: 580 | Homo sapiens zinc finger, DHHC-type containing 13 (ZDHHC13), transcript variant 1, mRNA [NM_019028] |
| 581 | A_23_P132863 | ENST00000306024 | AGCTAAATGGTATTTTGATTTTCTGAAGGTCTCCAATAAATATGACCACCAAGAGATGCAAG | SEQ ID NO: 581 | U6 snRNA-associated Sm-like protein LSm3. [Source:Uniprot/SWISSPROT:Acc:P62310] [ENST00000306024] |
| 582 | A_23_P132935 | SPCS3 | GAATGTCAGTTTGACCCTGTCTTGGAACGTCGTACCAAATGCTGGAATTCTACCTCTTGT | SEQ ID NO: 582 | Homo sapiens signal peptidase complex subunit 3 homolog (S. cerevisiae) (SPCS3), mRNA [NM_021928] |

Fig. 1-33

| No. | Probe ID No. | Symbols of genes | Sequence | SEQ ID NO: | Descriptions of genes (letters and numbers within [ ] indicates GenBank accession No.) |
|---|---|---|---|---|---|
| 583 | A_23_P133438 | FAM105A | TGAGCATGGAAGGAATTAGGAGAGCTTTCTTCAGGATTACAGGTACAGTGGATGCAGGCAT | SEQ ID NO: 583 | Homo sapiens family with sequence similarity 105, member A (FAM105A), mRNA [NM_019018] |
| 584 | A_23_P133648 | FAM8A1 | AGTTCGGCGGGAATTAGAAATGAGTGTTTTAGATCAAGTGACGGTAAAGGATTTGTT | SEQ ID NO: 584 | Homo sapiens family with sequence similarity 8, member A1 (FAM8A1), mRNA [NM_016255] |
| 585 | A_23_P134247 | RHEB | GTGGATGTTTTTCGAAGGATAATAATTTGGAGGAGAAAAATGGACGGGGGCAGCTTCACAA | SEQ ID NO: 585 | Homo sapiens Ras homolog enriched in brain (RHEB), mRNA [NM_005614] |
| 586 | A_23_P13701 | TMBIM4 | TGCAGATCGGAATGGGCTTTCTGAGAAAAGTGTACAAGGATTCTTCTCTGCAGGTGTCT | SEQ ID NO: 586 | Homo sapiens transmembrane BAX inhibitor motif containing 4 (TMBIM4), mRNA [NM_016056] |
| 587 | A_23_P137016 | SAT1 | GAAATAATAGAATTGAGGACAGCCATTCCAAAGGTTTATTACCAGTGGCGTTGTTGGATGTTT | SEQ ID NO: 587 | Homo sapiens spermidine/spermine N1-acetyltransferase 1 (SAT1), mRNA [NM_002970] |
| 588 | A_23_P138308 | CD58 | AACCTGTATCCGAAGGCAGGGGTCATTCAAGACACAGATATGGACTTATACCATACCATT | SEQ ID NO: 588 | Homo sapiens CD58 molecule (CD58), mRNA [NM_001779] |
| 589 | A_23_P138507 | CDC2 | CCCATGTCAAAAACTTGGATGAAAATGGGCTTGGATTTGCTCTCGAAAAATGTTAATCTATG | SEQ ID NO: 589 | Homo sapiens cell division cycle 2, G1 to S and G2 to M (CDC2), transcript variant 1, mRNA [NM_001786] |
| 590 | A_23_P140301 | PSMA3 | TGAACTAGAACTCAGCTGGGTTGGGTGAATTAACTAATGGAAGACATGAAATTGTTCGAAA | SEQ ID NO: 590 | Homo sapiens proteasome (prosome, macropain) subunit, alpha type, 3 (PSMA3), transcript variant 1, mRNA [NM_002788] |
| 591 | A_23_P140423 | NDUFB1 | GGATGTTATTTAGACAGAAGAGTGATGATGAAGGCTAAGTGCCTCCGGAACAGAGTATG | SEQ ID NO: 591 | Homo sapiens NADH dehydrogenase (ubiquinone) 1 beta subcomplex, 1, 7kDa (NDUFB1), mRNA [NM_004545] |
| 592 | A_23_P142560 | ZEB2 | CTTTTAATCTGTGTTCTGCAAGTGCGCATGGTGCATGTGTACAGTGTTAAGAGGGTAACATGGGT | SEQ ID NO: 592 | Homo sapiens zinc finger E-box binding homeobox 2 (ZEB2), mRNA [NM_014795] |
| 593 | A_23_P144145 | DCUN1D1 | TCTTTAGTGAAATATCATCGTGCATATCTCGTGTAAGTTCAATTGTGTTTCTTACAGTCCCTG | SEQ ID NO: 593 | Homo sapiens RP42 protein mRNA, complete cds. [AF292100] |
| 594 | A_23_P144224 | TLOC1 | ATGGGATTGTGAAGAGGATGGAGATGGAAAATGATGGAGAAACACGTAAATCTTCAC | SEQ ID NO: 594 | Homo sapiens translocation protein 1 (TLOC1), mRNA [NM_003262] |
| 595 | A_23_P14564 | GPR65 | AACAAGTTAAATTGTTGTTGCTGATCGAATCTGTACTGTTTTGTAACGGAAACAGGAAG | SEQ ID NO: 595 | Homo sapiens G protein-coupled receptor 65 (GPR65), mRNA [NM_003608] |
| 596 | A_23_P145777 | NDUFA4 | ACGGCTGCTTTAGAATGAAGGTCTTCCAGAAGCCACATCCGCACAATTTTCCACTTAACCA | SEQ ID NO: 596 | Homo sapiens NADH dehydrogenase (ubiquinone) 1 alpha subcomplex, 4, 9kDa (NDUFA4), nuclear gene encoding mitochondrial protein, mRNA [NM_002489] |
| 597 | A_23_P14734 | RPS27L | TACAAGATGACCACAGGGTTTCAGGCATGGTCACAGAGACAGTGGTTCTTTGTGTAGGTTGTTCA | SEQ ID NO: 597 | Homo sapiens ribosomal protein S27-like (RPS27L), mRNA [NM_015920] |
| 598 | A_23_P147404 | A_23_P147404 | TGGGGTGAACATGAAATTGATTACATTTGTTGGAGATGGTGAGCAGCGTCCTCAGTGTG | SEQ ID NO: 598 | |
| 599 | A_23_P148273 | RP11-217H1.1 | GGTCCCAAGATATAAGACACTTGGAGTACTGGAAATTGAAAACGAAAATCGTGTGT | SEQ ID NO: 599 | Homo sapiens implantation-associated protein (DKFZp564K142), mRNA [NM_032121] |
| 600 | A_23_P148297 | SH3BGRL | ATAAAACAGGTTGGCGATCATTTCCAAGATTGGTTTCCCTTGAGTTTTGCTAAAAGAA | SEQ ID NO: 600 | Homo sapiens SH3 domain binding glutamic acid-rich protein like (SH3BGRL), mRNA [NM_003022] |
| 601 | A_23_P149892 | GALNACT-2 | CATGGTGATTCAGAATAGAATGAGGCATAGGATGGTGGTTTGTTGTTTGCTTCAATTTTC | SEQ ID NO: 601 | Homo sapiens chondroitin sulfate GalNAcT-2 (GALNACT-2), mRNA [NM_018590] |

Fig. 1-34

| No. | Probe ID No. | Symbols of genes | Sequence | SEQ ID NO: | Descriptions of genes (letters and numbers within [ ] indicates GenBank accession No.) |
|---|---|---|---|---|---|
| 602 | A_23_P152002 | BCL2A1 | TGTAACCCATATTTGCATTTGAAGGTATTCTGATCAAAGAAACTTCTACGAACAGCAAATTGC | SEQ ID NO: 602 | Homo sapiens BCL2-related protein A1 (BCL2A1), mRNA [NM_004049] |
| 603 | A_23_P154235 | NMI | CCATGTTTCTGAATCTCTTCTTTGTTTGAAATGGTGGTGCATGTTTTGAACTACGAATAAGTG | SEQ ID NO: 603 | Homo sapiens N-myc (and STAT) interactor (NMI), mRNA [NM_004688] |
| 604 | A_23_P154832 | ATP5J | TACAAATCTAAGCGACGACATCTGGAGGACGTGTTGATGCTAGTTCAGAGTATCAGGAA | SEQ ID NO: 604 | Homo sapiens ATP synthase, H+ transporting, mitochondrial F0 complex, subunit F6 (ATP5J), nuclear gene encoding mitochondrial protein, transcript variant 1, mRNA [NM_001003703] |
| 605 | A_23_P15564 | AMZ2 | AAACCCGTGGAAGGCTTTAAGGAATGAAAGAGAGTGGATATAAAATGCCTGGCTGTTCTC | SEQ ID NO: 605 | Homo sapiens archaemetzincins-2 (AMZ2), transcript variant 1, mRNA [NM_016627] |
| 606 | A_23_P155677 | HIP2 | GATTTTGGGGTCTATAGAGATTGGTTTATTGGATAGTTCAAGTCATTCTTGCTTGCACTT | SEQ ID NO: 606 | Homo sapiens huntingtin interacting protein 2 (HIP2), mRNA [NM_005339] |
| 607 | A_23_P165765 | HMGB2 | TAAAAATGGAGGTTGTAGGCTTTTTTGATGGGCTACTCATACAGTTACATTTTACAGCTC | SEQ ID NO: 307 | Homo sapiens high-mobility group box 2 (HMGB2), mRNA [NM_002129] |
| 608 | A_23_P155815 | NCAPG | AAGTTAGGAAAGACGATGGAGGTGGAATCCTTTAAGAATTATGCCAGTATTTGCTTTAA | SEQ ID NO: 608 | Homo sapiens non-SMC condensin I complex, subunit G (NCAPG), mRNA [NM_022346] |
| 609 | A_23_P157452 | POLR2K | GGAATGTCTTCACTTATACTTGGATTTGCTCTCTTCCCATTTGTGATGTTGTATAGGCTT | SEQ ID NO: 609 | Homo sapiens polymerase (RNA) II (DNA directed) polypeptide K, 7.0kDa (POLR2K), mRNA [NM_005034] |
| 610 | A_23_P159839 | C1GALT1C1 | TCCAAATCAGATCATGATGATGATGTATGGGGTATACCGCCTTAGGGGCATTTGGGCATAT | SEQ ID NO: 610 | Homo sapiens C1GALT1-specific chaperone 1 (C1GALT1C1), transcript variant 1, mRNA [NM_152692] |
| 611 | A_23_P163216 | ATP8B4 | ATCAGTGTATTTTCCATAAAGTGATTGGGGCATATTTGTGTGAAAAGGTCAGTTGTGTCA | SEQ ID NO: 611 | Homo sapiens ATPase, Class I, type 8B, member 4 (ATP8B4), mRNA [NM_024837] |
| 612 | A_23_P165402 | SF3B14 | CATGTGATCACGTATCGGGATTCAATGTTTGTAACAGATACCTTGTGGTTTGTACTATCA | SEQ ID NO: 612 | Homo sapiens splicing factor 3B, 14 kDa subunit (SF3B14), mRNA [NM_016047] |
| 613 | A_23_P165819 | A_23_P165819 | AGGATGTTGTTGTTGAAGTGTGGAGTTGTAACTCGTCGGTGGACTATGGACAGCACACAAT | SEQ ID NO: 613 | |
| 614 | A_23_P168592 | CCDC126 | GGGCAGTATCAGATAGCAGTTGAAAATCACGTTGTGCTGCTCCATCCACTGTGGATTATA | SEQ ID NO: 614 | Homo sapiens coiled-coil domain containing 126 (CCDC126), mRNA [NM_138771] |
| 615 | A_23_P169576 | EXOC6 | ATGCTGAATCTTCCCTTTGCCTTTCAGGATTTAGGCGTGTAAGAAACTATGCGTGATTC | SEQ ID NO: 615 | Homo sapiens exocyst complex component 6 (EXOC6), transcript variant 2, mRNA [NM_001013848] |
| 616 | A_23_P170233 | CSTA | AACTGGCTACTGAGTCATGATGATCCTTGCTGATAAATATAAGCATCAATAAAGAAGCATTCT | SEQ ID NO: 616 | Homo sapiens cystatin A (stefin A) (CSTA), mRNA [NM_005213] |
| 617 | A_23_P17287 | IAH1 | TGGGAGGATGGAGACCAATTAGCCAATGACAGGAGAGCCCAAATCTGCTTGTTATCTACAGAA | SEQ ID NO: 617 | Homo sapiens isoamyl acetate-hydrolyzing esterase 1 homolog (S. cerevisiae) (IAH1), mRNA [NM_001039613] |
| 618 | A_23_P18325 | PDCD10 | CCAACCGACTAATTCATCAAACCAACTTAATACTTCAGACCTTCAAACTGTGGCCTGAA | SEQ ID NO: 618 | Homo sapiens programmed cell death 10 (PDCD10), transcript variant 1, mRNA [NM_007217] |
| 619 | A_23_P200507 | CNIH4 | TGGTTGAAGTCAGGCTACGACAGTGCACAGTTGACGGAGGCAGAGAGTCGTTAAATCAT | SEQ ID NO: 619 | Homo sapiens cornichon homolog 4 (Drosophila) (CNIH4), mRNA [NM_014184] |

Fig. 1-35

| No. | Probe ID No. | Symbols of genes | Sequence | SEQ ID NO: | Descriptions of genes (letters and numbers within [ ] indicates GenBank accession No.) |
|---|---|---|---|---|---|
| 620 | A_23_P201758 | CD46 | GTCATGAGTGGAACGTGTGGCTTAGCTAATATTGCAATGTGGCTTGAATGTAGGTAGGCATC | SEQ ID NO: 620 | Homo sapiens CD46 molecule, complement regulatory protein (CD46), transcript variant a, mRNA [NM_002389] |
| 621 | A_23_P201918 | ABCB10 | CATGGATGAGGTAGACGCTAGAAGAAGTAATTAAGTCAATGTAAATCAAATGGAAGTTTTC | SEQ ID NO: 621 | Homo sapiens ATP-binding cassette, sub-family B (MDR/TAP), member 10 (ABCB10), nuclear gene encoding mitochondrial protein, mRNA [NM_012089] |
| 622 | A_23_P202750 | C11orf54 | TGCAAGGTTTCTGTATGCATTGGTCAACCAAAAGAGAGACGCATTCGATTGGGGGAGAATTA | SEQ ID NO: 622 | Homo sapiens chromosome 11 open reading frame 54 (C11orf54), mRNA [NM_014039] |
| 623 | A_23_P202978 | CASP1 | CTGTTCGTGTGATGTGGAGGAAAATTTTCCGGCAAGGTTCGATTTTCATTTGAGGAGCCAGA | SEQ ID NO: 623 | Homo sapiens caspase 1, apoptosis-related cysteine peptidase (interleukin 1, beta, convertase) (CASP1), transcript variant alpha, mRNA [NM_033292] |
| 624 | A_23_P203M | LSM1 | TGAGTGAAAGTGACATCCTGGGCACGTCACGCATTTGATCAGAGACTGTAGAGTTTTGAA | SEQ ID NO: 624 | Homo sapiens LSM1 homolog, U6 small nuclear RNA associated (S. cerevisiae) (LSM1), mRNA [NM_014462] |
| 625 | A_23_P204550 | SCYL2 | TGTGACTTCCCTGACTACGTTCGATATTTGATTTCAAATTGAAACTTCTGAAGGTTGCA | SEQ ID NO: 625 | Homo sapiens SCY1-like 2 (S. cerevisiae) (SCYL2), mRNA [NM_017988] |
| 626 | A_23_P205281 | C14orf2 | TGATAAAAGAAGTAAGGCTTTGAAAGGTTCAGGCGCTGCTCCTGGTCATCACTAACCAGA | SEQ ID NO: 626 | Homo sapiens chromosome 14 open reading frame 2 (C14orf2), mRNA [NM_004894] |
| 627 | A_23_P205768 | ARPP-19 | GGGCAATATTTGCCCATTCGTCTGGTGTAACTATGTGACTCAGTGCTTAACAGCTGCGATT | SEQ ID NO: 627 | Homo sapiens cyclic AMP phosphoprotein, 19 kD (ARPP-19), mRNA [NM_006628] |
| 628 | A_23_P206396 | CKLF | ATTATCAACTCACTCGGTAACAACAGTATTCATGCTCATGCTATCTGTGTTGGCACTGATA | SEQ ID NO: 628 | Homo sapiens chemokine-like factor (CKLF), transcript variant 1, mRNA [NM_016951] |
| 629 | A_23_P207445 | MAP2K6 | ACAGCATCAATAGAAAGATCATCTTTGAGATAATTTAACCCTGCCTCTCAGAGGGTTTTCT | SEQ ID NO: 629 | Homo sapiens mitogen-activated protein kinase kinase 6 (MAP2K6), mRNA [NM_002758] |
| 630 | A_23_P20882 | ATP6V1G1 | AGGTCCTTCGACTTTTTGGAGAGTAGGCAATGTAGCCTTTTTTGTACAGACTTAGAAATTA | SEQ ID NO: 630 | Homo sapiens ATPase, H+ transporting, lysosomal 13kDa, V1 subunit G1 (ATP6V1G1), mRNA [NM_004888] |
| 631 | A_23_P208866 | GMFG | GTCCAAGAAAAGTTGTCTTCTTTCGTTGATCTCTGGGCTGGGGACTGAATTCCTGATGT | SEQ ID NO: 631 | Homo sapiens glia maturation factor, gamma (GMFG), mRNA [NM_004877] |
| 632 | A_23_P210274 | PREI3 | GGATCAGTATGCGGTAGGATTTAGAGAATATTTCACATGCTTATTTCATCATCGGCAG | SEQ ID NO: 632 | Homo sapiens preimplantation protein 3 (PREI3), transcript variant 1, mRNA [NM_015387] |
| 633 | A_23_P211840 | UBE1C | GCCACCCTAGAGGGGAAAAAATAGAACACTTACTTACAGTCGGTAACCTCTATTGAAGAA | SEQ ID NO: 633 | Homo sapiens ubiquitin-activating enzyme E1C (UBA3 homolog, yeast) (UBE1C), transcript variant 1, mRNA [NM_003968] |
| 634 | A_23_P212706 | ATG3 | AAGACATCAGTCAGGATCATGTGAAGAAAACAGTGACCATTGAAAATCACCCTCATCTGC | SEQ ID NO: 634 | Homo sapiens ATG3 autophagy related 3 homolog (S. cerevisiae) (ATG3), mRNA [NM_022488] |
| 635 | A_23_P213247 | FBXL5 | ATGAAGGTGATTGGTTCTCTTTACACATTAACACTGTACCAAGCTTGGAGATCTTTTCG | SEQ ID NO: 635 | Homo sapiens F-box and leucine-rich repeat protein 5 (FBXL5), transcript variant 2, mRNA [NM_033535] |
| 636 | A_23_P213638 | PANK3 | TGTATATAGCCAGTGTTAAATCCTTAAATGGAATACAGAGCCTCGATTATTGAGCTGCTC | SEQ ID NO: 636 | Homo sapiens pantothenate kinase 3 (PANK3), mRNA [NM_024594] |
| 637 | A_23_P217236 | HMGB3 | GACCTGTTGACTCTGCAGGGGGCATCCATTTAGCTTCAGGTTGTCTTGTTTCTGTATATA | SEQ ID NO: 637 | Homo sapiens high-mobility group box 3 (HMGB3), mRNA [NM_005342] |

Fig. 1-36

| No. | Probe ID No. | Symbols of genes | Sequence | SEQ ID NO: | Descriptions of genes (Notes and numbers within [ ] indicates GenBank accession No.) |
|---|---|---|---|---|---|
| 638 | A_23_P22571 | SYBL1 | CAAACGGAATACGGTCAGCAGTCAACTCGAGGGTTTGGGCTTGAT TCCTGTTGAATAATA | SEQ ID NO: 638 | Homo sapiens synaptobrevin-like 1 (SYBL1), mRNA [NM_005638] |
| 639 | A_23_P24515 | ACAT1 | CAGGATTGTTGGTCATTGACTCATGGCTTGAAGCAAGGAGAATA CGGTCTTGCCAGTAT | SEQ ID NO: 639 | Homo sapiens acetyl-Coenzyme A acetyltransferase 1 (acetoacetyl Coenzyme A thiolase) (ACAT1), nuclear gene encoding mitochondrial protein, mRNA [NM_000019] |
| 640 | A_23_P250042 | SELT | GCAAGATAGTGTTTCAGTGGTGGCGATATTTTGGAATTCTGCACAT TCATGGAGTGCAATA | SEQ ID NO: 640 | Homo sapiens selenoprotein T (SELT), mRNA [NM_016275] |
| 641 | A_23_P250904 | UBQLN1 | CTTTGACAAACATCTCCAGGACAAAAGTGCCGGTTAGTCAGGTTTG TTGAAAATACAGTAG | SEQ ID NO: 641 | Homo sapiens ubiquilin 1 (UBQLN1), transcript variant 1, mRNA [NM_013438] |
| 642 | A_23_P251421 | CDCA7 | ATTTACTTGCATATGTAAACCATTGCTGTGCCATTCAATGTTTGA TGCATAATTGGACCT | SEQ ID NO: 642 | Homo sapiens cell division cycle associated 7 (CDCA7), transcript variant 1, mRNA [NM_031942] |
| 643 | A_23_P251945 | DCTN4 | ACACGTTGACATAGACTACAGACATGTCATGCCTTATGCAGGT AGCTGGTATTTATTC | SEQ ID NO: 643 | Homo sapiens dynactin 4 (p62) (DCTN4), mRNA [NM_016221] |
| 644 | A_23_P252145 | C1GALT1 | ATATGTGTATATATATGAGGAACTTGTGTTTTTTAAATGGTGGCC AGGTAGAGGAACTAG | SEQ ID NO: 644 | Homo sapiens core 1 synthase, glycoprotein-N-acetylgalactosamine 3-beta-galactosyltransferase, 1 (C1GALT1), mRNA [NM_020156] |
| 645 | A_23_P252371 | RBBP8 | GGCAAGGAGCAGAAGAGACATAGACGTTGAAACAGAAACAGAAGGAT GAAGGACAGTTTTT | SEQ ID NO: 645 | Homo sapiens retinoblastoma binding protein 8 (RBBP8), transcript variant 1, mRNA [NM_002894] |
| 646 | A_23_P253524 | CENPE | CTGAGTGCAAAACTCAGTAGACTGGTCTTGTGTCTTGTCACTTCTGTGGAG ATCAGCATTCCTA | SEQ ID NO: 646 | Homo sapiens centromere protein E, 312kDa (CENPE), mRNA [NM_001813] |
| 647 | A_23_P253223 | VBP1 | TGAACTCAGGCATGTTGGAAAAGAATTATGGACTGCCAGAAA GAATCTTGATTCCCT | SEQ ID NO: 647 | Homo sapiens von Hippel-Lindau binding protein 1 (VBP1), mRNA [NM_003372] |
| 648 | A_23_P256231 | FBXO30 | GCCTTTTAAAGTTTTGCTGGAGAATGTGTCTGTGGTTAGGATAGC AGAAGCATTAAGCTT | SEQ ID NO: 648 | Homo sapiens F-box protein 30 (FBXO30), mRNA [NM_032145] |
| 649 | A_23_P253866 | DCP2 | CCGTGGCATGCTAATGGACATTGGACAAGTTGCCCTTTTCATCCAGAG CGTTTTTGAGTTCA | SEQ ID NO: 649 | Homo sapiens DCP2 decapping enzyme homolog (S. cerevisiae) (DCP2), mRNA [NM_152624] |
| 650 | A_23_P25735 | PSMA6 | TAGGAGAGAGGACTAAACATTGCGTTAGTTTAGGAGATCCGTG ATGCCAGTTACGTGT | SEQ ID NO: 650 | Homo sapiens proteasome (prosome, macropain) subunit, alpha type, 6 (PSMA6), mRNA [NM_002791] |
| 651 | A_23_P258814 | ENST00000328644 | GGAAGGTGTGGCAATGTGTCCAGGCTGCTCTCTCATTATAAAAGT GATTTATGACAAGA | SEQ ID NO: 651 | DPH3 homolog B (CSL-type zinc finger-containing protein 1). [Source:Uniprot/SWISSPROT;Acc:Q9H4G8] [ENST00000328644] |
| 652 | A_23_P259272 | WSB2 | AACGTTACGATGAGTCGTTGGAGAAAAGTTGAGGAATTTGCTGTACCA CGTTGTTGCTGAA | SEQ ID NO: 652 | Homo sapiens WD repeat and SOCS box-containing 2 (WSB2), mRNA [NM_018639] |
| 653 | A_23_P259521 | WDR41 | TTCGGCAGTTTAAGATTATTTCAAAAATTAGAGGAGAATGGTGAC TTATACGTTGGTGTG | SEQ ID NO: 653 | Homo sapiens WD repeat domain 41 (WDR41), mRNA [NM_018268] |
| 654 | A_23_P2705 | P2RY5 | TCTGTATTGCTGTTTCCAACTGTTGTTTGACCGTATAGTTTACT ACTTTACTCGGACA | SEQ ID NO: 654 | Homo sapiens purinergic receptor P2Y, G-protein coupled, 5 (P2RY5), mRNA [NM_005767] |
| 655 | A_23_P28664 | KIAA1212 | GGGACTTCTCTATGATAGACGGACAACTAAGGCTGAGTTTTTGAGAC CTGGTCGTCGAAAAA | SEQ ID NO: 655 | Homo sapiens KIAA1212 (KIAA1212), mRNA [NM_018084] |
| 656 | A_23_P29005 | SAMSN1 | CTCTGGTTGCTATATCTCATCAGGAAATTCAGATAATGGCAAAGA GGATCTGGAGTCTGA | SEQ ID NO: 656 | Homo sapiens SAM domain, SH3 domain and nuclear localization signals 1 (SAMSN1), mRNA [NM_022136] |

Fig. 1-37

| No. | Probe ID No. | Symbols of genes | Sequence | SEQ ID NO: | Descriptions of genes (letters and numbers within [ ] indicates GenBank accession No.) |
|---|---|---|---|---|---|
| 657 | A_23_P30069 | FLJ31033 | AGATTTGTTTAAGTGCGCTACACTTTCTTATTTCTAAATGATCAAGAGTACAGTTCCTGG | SEQ ID NO: 657 | Homo sapiens cDNA FLJ13681 fis, clone PLACE2000014, weakly similar to HYPOTHETICAL HELICASE C28H8.3 IN CHROMOSOME III. [AK023743] |
| 658 | A_23_P30338 | CCNH | AGGTCTCAAAGAAATCAAAACATGAGGAGGAAGAATGGACTGATGAGGACGTGGTAGAAT | SEQ ID NO: 658 | Homo sapiens cyclin H (CCNH), mRNA [NM_001239] |
| 659 | A_23_P304287 | PSMC2 | GATCCAGCAGCTGATGAGGCCAGGGACAGATGGATAGAAAAATTGAATTTAGCTTGCGCGAT | SEQ ID NO: 659 | Homo sapiens proteasome (prosome, macropain) 26S subunit, ATPase, 2 (PSMC2), mRNA [NM_002803] |
| 660 | A_23_P305759 | ABHD3 | AGTCCTAGACGTGAAGTCAGTAGGAATTCCAGTATTGTGTCTAAATTCTGTGGATGATGTT | SEQ ID NO: 660 | Homo sapiens abhydrolase domain containing 3 (ABHD3), mRNA [NM_138340] |
| 661 | A_23_P307940 | CAPZA2 | CTACAAGATTGGCAAAGAGATGCAGAATGGATAAGATGAACATTGGATGACCGGATGATT | SEQ ID NO: 661 | Homo sapiens capping protein (actin filament) muscle Z-line, alpha 2 (CAPZA2), mRNA [NM_006136] |
| 662 | A_23_P31097 | OSTM1 | ACTGAAAATGTGCTGGGGTTTGTTCTGGTCGTCACTGTTTATGCTGCTGGAAGTTAGCACT | SEQ ID NO: 662 | Homo sapiens osteopetrosis associated transmembrane protein 1 (OSTM1), mRNA [NM_014028] |
| 663 | A_23_P31315 | CBX3 | GCGTTGGAAGAGTTGTTGGGGGTTTTTGCATCCATAGCACTGGTTAGTTTGAACAAATA | SEQ ID NO: 663 | Homo sapiens chromobox homolog 3 (HP1 gamma homolog, Drosophila) (CBX3), transcript variant 2, mRNA [NM_016587] |
| 664 | A_23_P314202 | PAPD4 | TCTGTGTAGAAGAAAGCTTTTGATGGAACAAATACAGCGCAGAGCAGTGCACGAAAAGCAGA | SEQ ID NO: 664 | Homo sapiens PAP associated domain containing 4 (PAPD4), mRNA [NM_173797] |
| 665 | A_23_P316601 | RIT1 | TGGTTGCTTGCTCTTTCAGTTCAGTTAACTGATAAGAGAGCAGATGCCTACTAGGAGTTTTTTAAGTGA | SEQ ID NO: 665 | Homo sapiens Ras-like without CAAX 1 (RIT1), mRNA [NM_006912] |
| 666 | A_23_P31671 | UQCRB | AAGCCATAAGAAGAGCTTCCTGAGAACCTTTATAATGACGAGGATGTTTCGCATTAAGAGGG | SEQ ID NO: 666 | Homo sapiens ubiquinol-cytochrome c reductase binding protein (UQCRB), mRNA [NM_006294] |
| 667 | A_23_P324633 | C9orf72 | TTTGTGGATTTAGTCCGTGGGGATTCCAGTCGTGTAGAAATGTCTAATAGTCTCTATAGTCC | SEQ ID NO: 667 | Homo sapiens chromosome 9 open reading frame 72 (C9orf72), transcript variant 1, mRNA [NM_018325] |
| 668 | A_23_P32577 | DACH1 | AATATTAATGTCTAGTTGTTCTATATATTATAACCACATTTGCGCTCTATGCAAGCCCTGG | SEQ ID NO: 668 | Homo sapiens dachshund homolog 1 (Drosophila) (DACH1), transcript variant 1, mRNA [NM_080759] |
| 669 | A_23_P326170 | CALM2 | TAAACTTTGTTTAGGCACTTAAAATCTGCTTATGGACAATTTGGCTCAAAATGCATTCC | SEQ ID NO: 669 | Homo sapiens calmodulin 2 (phosphorylase kinase, delta) (CALM2), mRNA [NM_001743] |
| 670 | A_23_P328511 | HSBP1 | TTTCTTGAAGATGGTATCTTCAGATGTTGGACCTTGGTCAGTTGTGCTATTCATTATTAA | SEQ ID NO: 670 | Homo sapiens heat shock factor binding protein 1 (HSBP1), mRNA [NM_001537] |
| 671 | A_23_P329198 | OBFC2A | ACATGTCATAAGTGCTGTACCGACTTTCCCGTTTTTACTGTCAGGGTGGATAACTCTTAGGATT | SEQ ID NO: 671 | Homo sapiens oligonucleotide/oligosaccharide-binding fold containing 2A (OBFC2A), mRNA [NM_001031716] |
| 672 | A_23_P339480 | HAT1 | AACATGAAGAGCTGGAAGAGAGTTTCAGGAAGTAGTGGAAGATTACCGGCGGTGTTATTG | SEQ ID NO: 672 | Homo sapiens histone acetyltransferase 1 (HAT1), transcript variant 1, mRNA [NM_003642] |
| 673 | A_23_P339557 | MLSTD2 | GGGGCAATGTAAATCTAACCTCAGAATCATCATGTTTTATATCATTACTGGATTGCTGTAAGCC | SEQ ID NO: 673 | Homo sapiens male sterility domain containing 2 (MLSTD2), mRNA [NM_032228] |
| 674 | A_23_P344973 | MYL6 | CCTATGAGGATTATGTCGAAGGAACTTCGGGTGTTGACAAGGAAGGAAATGGCAGGGTCA | SEQ ID NO: 674 | Homo sapiens myosin, light chain 6, alkali, smooth muscle and non-muscle (MYL6), transcript variant 2, mRNA [NM_079423] |
| 675 | A_23_P345591 | PSMA2 | GCCTGGAAAAGCTACAGCAATGGGAAAGAAGTATGTGAATGGGAAGACTTTCCTTGAGAAA | SEQ ID NO: 675 | Homo sapiens proteasome (prosome, macropain) subunit, alpha type, 2 (PSMA2), mRNA [NM_002787] |

Fig. 1-38

| No. | Probe ID No. | Symbols of genes | Sequence | SEQ ID NO: | Descriptions of genes [letters and numbers within ] indicates GenBank accession No.) |
|---|---|---|---|---|---|
| 676 | A_23_P340006 | CCPG1 | TATGGTGGACTAATGGAAGACAAATGGGAAATCTTGAAATAGAATTGGGGCAATTACCT | SEQ ID NO: 676 | Homo sapiens cell cycle progression 1 (CCPG1), transcript variant 2, mRNA [NM_020739] |
| 677 | A_23_P34628 | GTF2B | TGTTACAATCAGACAGTCCTATAGACTGATCTATCCTCGAGCCCCAGATCTGTTTCCTAC | SEQ ID NO: 677 | Homo sapiens general transcription factor IIB (GTF2B), mRNA [NM_001514] |
| 678 | A_23_P351903 | TMEM167 | AAACTGGATTGTTGGGTATATTTTGGAAGTGTGCCAAGAATTGGGTGAACGGAAGAGTCCTT | SEQ ID NO: 678 | Homo sapiens transmembrane protein 167 (TMEM167), mRNA [NM_174909] |
| 679 | A_23_P355067 | TMCO1 | AACTCAAGAACTCTTTATTTCTATCATTCTTCTGAGACACACAACATCAGACTGGCAA | SEQ ID NO: 679 | Homo sapiens transmembrane and coiled-coil domains 1 (TMCO1), mRNA [NM_019026] |
| 680 | A_23_P355244 | SAMD9 | TCACTGGAGGAAGAATTTTCCCTTGGTGTGCATAAAATTTTAACTCCATAACTTATAAGC | SEQ ID NO: 680 | Homo sapiens sterile alpha motif domain containing 9 (SAMD9), mRNA [NM_017654] |
| 681 | A_23_P357995 | ZBTB8OS | ATCAATTGGGTGGGGAGAAGAATTTTCATTGTGCAAGGACGCTCAGGGAACAGAAGTCAA | SEQ ID NO: 681 | Homo sapiens zinc finger and BTB domain containing 8 opposite strand (ZBTB8OS), mRNA [NM_178547] |
| 682 | A_23_P371266 | DNM3 | ACTGTCTTCTTGGGCACTTTCAGGGATTTCTTAATGCTGATATATGGACTCTTAGAATGGAA | SEQ ID NO: 682 | Homo sapiens dynamin 3 (DNM3), mRNA [NM_015569] |
| 683 | A_23_P37441 | B2M | TTGTCTTCAGCAGGAGTGGTCTTCTTCGTGTCGTCGTCGTAGTACAGTGAATTCACCCCACT | SEQ ID NO: 683 | Homo sapiens beta-2-microglobulin (B2M), mRNA [NM_004048] |
| 684 | A_23_P37535 | RAB8B | AGCCTTTCCCTATTTCAGGACGAATCTAGACTCATATTTGGCACAGTTTGTGTCGTGAAG | SEQ ID NO: 684 | Homo sapiens RAB8B, member RAS oncogene family (RAB8B), mRNA [NM_016530] |
| 685 | A_23_P378722 | SAT1 | GCATGTACTATTTACCTATGACCCGTGGATTGGCAAGTTATTGTATCTTGAGGACTTCT | SEQ ID NO: 685 | Homo sapiens spermidine/spermine N1-acetyltransferase 1 (SAT1), mRNA [NM_002970] |
| 686 | A_23_P380848 | TXNL5 | CTGGTGGAAATGTGTCTCTGAAGTTAAGATTAGGATGGAATCATGTGTTGATGT | SEQ ID NO: 686 | Homo sapiens thioredoxin-like 5 (TXNL5), mRNA [NM_032731] |
| 687 | A_23_P389118 | TMEM16F | TATGTTTGAGAGGGGTAAAATGTATGAGCAGCTTAACTGAAGTAGAAGTATTCATGATGC | SEQ ID NO: 687 | Homo sapiens transmembrane protein 16F (TMEM16F), mRNA [NM_001025356] |
| 688 | A_23_P406355 | FAM76B | AAACTGTGGAACAACTTCAGGCAAAACAGAGAACTACTCAAACAGGTCGAGCATTAT | SEQ ID NO: 688 | Homo sapiens family with sequence similarity 76, member B (FAM76B), mRNA [NM_144664] |
| 689 | A_23_P41114 | CSTA | AAACAAATGAGACTTATGGAAATTGGAAGGTGTGCAGTATAAAACTCAAGTTGTTGCTG | SEQ ID NO: 689 | Homo sapiens cystatin A (stefin A) (CSTA), mRNA [NM_005213] |
| 690 | A_23_P412392 | SEC22B | GTTTTGATGGCTTTTAAACAAGACTCCAGTATGTGAAGGTTAATTGCTGTCGTCGACA | SEQ ID NO: 690 | Homo sapiens SEC22 vesicle trafficking protein homolog B (S. cerevisiae) (SEC22B), mRNA [NM_004892] |
| 691 | A_23_P412980 | SNX13 | CCCATCTCAAGCAAGAATGGCGTTGGTTTCTCTGCATTTCAAACTAATCAGCATTCTCCA | SEQ ID NO: 691 | Homo sapiens sorting nexin 13 (SNX13), mRNA [NM_015132] |
| 692 | A_23_P41645 | ELL2 | TGTCTTTTCAAAGTGCTGCCAGTTGAAAGTGAAAGGGAAGCATTATGTTTACAAATCTGTTTGA | SEQ ID NO: 692 | Homo sapiens elongation factor, RNA polymerase II, 2 (ELL2), mRNA [NM_012081] |
| 693 | A_23_P419239 | ETNK1 | GGGCTTGGGACTGAAGTTAGTGAGTGCGTAAAAGCGGGAGGTAGAAATACTCTTCATTCAAGTCAATCA | SEQ ID NO: 693 | Homo sapiens ethanolamine kinase 1 (ETNK1), transcript variant 1, mRNA [NM_018638] |
| 694 | A_23_P422794 | NSMCE2 | CATTGTTCGATGATGAGTCGAAGGTCCAGGCAAAAGCGGGAAAGAAAAAGGCCTATGCCCTCAAAT | SEQ ID NO: 694 | Homo sapiens non-SMC element 2, MMS21 homolog (S. cerevisiae) (NSMCE2), mRNA [NM_173685] |
| 695 | A_23_P424080 | YIPF4 | AAAGCATTGTGTTTTTAAGATTGTCGATATTCACCTAAAAACTTGTGCCAAAAGCACG | SEQ ID NO: 695 | Homo sapiens Yip1 domain family, member 4 (YIPF4), mRNA [NM_032312] |

Fig. 1-39

| No. | Probe ID No. | Symbols of genes | Sequence | SEQ ID NO: | Descriptions of genes (letters and numbers within [ ] indicates GenBank accession No.) |
|---|---|---|---|---|---|
| 696 | A_23_P42514 | C6orf62 | TCGTTTGGAGTAAAAGTAGTGCTTACCCAGTTTCGAATGTATTTAGCTTCTGGTTGGAAT | SEQ ID NO: 696 | Uncharacterized protein C6orf62 (HBV X-transactivated gene 12 protein). [Source:Uniprot/SWISSPROT;Acc:Q9GZU0] [ENST00000378119] |
| 697 | A_23_P42491 | FLJ25416 | GCTTGGTCACCTGAATTGTTTTCATAAAAGTCACCTGAACGCAATTCCTGAACTTTTAA | SEQ ID NO: 697 | Homo sapiens hypothetical protein FLJ25416 (FLJ25416), mRNA [NM_145018] |
| 698 | A_23_P42975 | PRKAR2B | GCCACATTTTAGAAGACGTGTTTAACATTTTTGCAAAACCTTCTTGTAGGAAAAGAGAGC | SEQ ID NO: 698 | Homo sapiens protein kinase, cAMP-dependent, regulatory, type II, beta (PRKAR2B), mRNA [NM_002736] |
| 699 | A_23_P43049 | DCTN6 | AAATACATTTGAAGTCATCCCTGAGAATACGAGGTGATCTATGGTGCAGACTGCCTTCGTCG | SEQ ID NO: 699 | Homo sapiens dynactin 6 (DCTN6), mRNA [NM_006571] |
| 700 | A_23_P434768 | NUP50 | TATATCTCAGCTTGTATTAGTTTTTGAATGCTCCCATCGAGGAAGTGTAAGAATCCATG | SEQ ID NO: 700 | Homo sapiens nucleoporin 50kDa (NUP50), transcript variant 2, mRNA [NM_007172] |
| 701 | A_23_P434809 | S100A8 | AAAGCCATGAAGAAAGGCACAAAGAGATAGGTGAGTTACTGGGGCCAGAGGCTGGGCCCT | SEQ ID NO: 701 | Homo sapiens S100 calcium binding protein A8 (S100A8), mRNA [NM_002964] |
| 702 | A_23_P43846 | CIP29 | AAAGAGCAGAGCGCTTTGGGAATTGCCTGATGAAAAGTTCCTGATACTTCTGTTCTCAAG | SEQ ID NO: 702 | Homo sapiens cytokine induced protein 29 kDa (CIP29), mRNA [NM_030821] |
| 703 | A_23_P44768 | TBK1 | TCTACTCTGAGTGGGGCTAAATAAGTTATTTCTGTGACGGCTACTGGAAATATTTTA | SEQ ID NO: 703 | Homo sapiens TANK-binding kinase 1 (TBK1), mRNA [NM_013254] |
| 704 | A_23_P48887 | CCPG1 | AAGTCAGAAGAGCTCATATATATAATTCTAATGTCCCACCTATGTCCATTCCATATACCA | SEQ ID NO: 704 | Homo sapiens cell cycle progression restoration 8 protein (CPR8) mRNA, complete cds. [AF011794] |
| 705 | A_23_P500381 | HTR7 | TAACTCCCATTGACATTGTTCTTACGACAGAGATAGGGAGAAAAGTACCTTTCCTGAAAGGG | SEQ ID NO: 705 | Homo sapiens 5-hydroxytryptamine (serotonin) receptor 7 (adenylate cyclase-coupled) (HTR7), transcript variant d, mRNA [NM_019859] |
| 706 | A_23_P50108 | NDC80 | AAAGTGGGAAATAAGCTTGAAGGTCTCTTAGAGATGGTTGCTACACATGTTGGGTCTGTA | SEQ ID NO: 706 | Homo sapiens NDC80 homolog, kinetochore complex component (S. cerevisiae) (NDC80), mRNA [NM_006101] |
| 707 | A_23_P51009 | NDUFB3 | CCGGAATGAAGCTTGGAGATACATGGGTGGCTTGGAAAAGAGTGTTTCCTTTTCTGATGT | SEQ ID NO: 707 | Homo sapiens NADH dehydrogenase (ubiquinone) 1 beta subcomplex, 3, 12kDa (NDUFB3), mRNA [NM_002491] |
| 708 | A_23_P51487 | GBP3 | AATCCTAAAGACATAAGTAGTCTTTTCCTGATTGTTAAAGGTCATACTTGAAATCCTGCC | SEQ ID NO: 708 | Homo sapiens guanylate binding protein 3 (GBP3), mRNA [NM_018284] |
| 709 | A_23_P51572 | TSNAX | GAATGGGGACATTGATACCCCTTTGAAGTGAGGCAGTTTTACGTCAGGTTTATGATGG | SEQ ID NO: 709 | Homo sapiens translin-associated factor X (TSNAX), mRNA [NM_005999] |
| 710 | A_23_P5389 | LOC84661 | TACCTGATCAGACAGTTGTGCTATGTATTACAGGGACTTGCTGTGGTTGCAAAGGAA | SEQ ID NO: 710 | Homo sapiens dpy-30-like protein (LOC84661), mRNA [NM_032574] |
| 711 | A_23_P58390 | C4orf32 | TAATACTAAGTATTTAGTATACTGTCCAGTACTGTACATGTGACACTGGTGTTAATAGGG | SEQ ID NO: 711 | Homo sapiens chromosome 4 open reading frame 32 (C4orf32), mRNA [NM_152400] |
| 712 | A_23_P58396 | PDGFC | CATGGATATTTTATGTACAGAAGTAGTGTCTGTCTTAACCAGTTCACTTATTGTACTGGC | SEQ ID NO: 712 | Homo sapiens platelet derived growth factor C (PDGFC), mRNA [NM_016205] |
| 713 | A_23_P59921 | SUB1 | CAGATTGGGAAATGAGGTACGTTAGTGTTGTTCGCGATTTTAAAGGCAAAGTGCTAATTGAT | SEQ ID NO: 713 | Homo sapiens SUB1 homolog (S. cerevisiae) (SUB1), mRNA [NM_006713] |

Fig. 1-40

| No. | Probe ID No. | Symbols of genes | Sequence | SEQ ID NO: | Descriptions of genes (letters and numbers within [ ] indicates GenBank accession No.) |
|---|---|---|---|---|---|
| 714 | A_23_P60248 | TXN | GGACAAAAGGTGGGTGAATTTCTGGAGCCAATAAGAAAAGCTT GAAGCCACCATTAAT | SEQ ID NO: 714 | Homo sapiens thioredoxin (TXN), mRNA [NM_003329] |
| 715 | A_23_P63655 | ATP5C1 | AGAGAGGTGAAACCAGCTCGAATATATGGATTCGATCTTTAGCT CTGTATGAAAAAGCT | SEQ ID NO: 715 | Homo sapiens ATP synthase, H+ transporting, mitochondrial F1 complex, gamma polypeptide 1 (ATP5C1), nuclear gene encoding mitochondrial protein, transcript variant 2, mRNA [NM_005174] |
| 716 | A_23_P63896 | FAS | ATGTCTATCCACAGGCTAACCCCAGTCTATGAATCAATAGAAGAA GCTATGAACGTTTGC | SEQ ID NO: 716 | Homo sapiens Fas (TNF receptor superfamily, member 6) (FAS), transcript variant 1, mRNA [NM_000043] |
| 717 | A_23_P64129 | HTATIP2 | AAAGTCAGCATGTTTTAACTTGTTGTTTACTATCCTCAGGCAT CCATTCCAATCAACA | SEQ ID NO: 717 | Homo sapiens HIV-1 Tat interactive protein 2, 30kDa (HTATIP2), mRNA [NM_006410] |
| 718 | A_23_P65262 | RP11-298P3.3 | AGCCAAGACTTAAGAAGACTTAAGGCGTTCCCTTGAGGTACCA TTATGCAAGGGTT | SEQ ID NO: 718 | Human BRCA2 region, mRNA sequence CG016. [U50629] |
| 719 | A_23_P69188 | DPH3 | TGCTGTTCTGTAAGAGTGTGGATTCTTCGTATCGAAGTGCTGATAT CATCTCAGGAAGCA | SEQ ID NO: 719 | Homo sapiens DPH3, KTI11 homolog (S. cerevisiae) (DPH3), transcript variant 1, mRNA [NM_206831] |
| 720 | A_23_P69908 | GLRX | CTGATAAAACTTACAGCCCGCTACAGCAAGAGTGTATCGTGAAA GAGGTCCTACAGTTT | SEQ ID NO: 720 | Homo sapiens glutaredoxin (thioltransferase) (GLRX), mRNA [NM_002064] |
| 721 | A_23_P69958 | AP3S1 | GATCACAAGGTGCAGCATTCCTTAATTCCTTCTGGTATATGTCACA CAGTTGTTATTTGGA | SEQ ID NO: 721 | Homo sapiens adaptor-related protein complex 3, sigma 1 subunit (AP3S1), mRNA [NM_001284] |
| 722 | A_23_P70290 | TMEM30A | ATCTTCTGCTCAACTGTCAAACCACATGTAAGTGCTTAATGGAGA CTGTTTTCATTCTTG | SEQ ID NO: 722 | Homo sapiens transmembrane protein 30A (TMEM30A), mRNA [NM_018247] |
| 723 | A_23_P71117 | SLC25A40 | AGCCAAAGAAGATGGAGACTCTTAGGCAAGACTCTTGTTTTCACCAT TATTCTCACAATG | SEQ ID NO: 723 | Homo sapiens solute carrier family 25, member 40 (SLC25A40), mRNA [NM_018843] |
| 724 | A_23_P74799 | SLC25A24 | GATTCTGTATCTTTTGGAAAAAAGGCCAGAGAGTTGAAGATAGTATA TTTCTGGTAGTACTG | SEQ ID NO: 724 | Homo sapiens solute carrier family 25 (mitochondrial carrier; phosphate carrier), member 24 (SLC25A24), transcript variant 2, mRNA [NM_213651] |
| 725 | A_23_P75028 | REEP3 | AGAAACGAGCACACAAGTGTATTTTAGTCATCTACACGTCAAATAT CCCAAGACAGAATAT | SEQ ID NO: 725 | Homo sapiens receptor accessory protein 3 (REEP3), mRNA [NM_001001330] |
| 726 | A_23_P76480 | BF213738 | AAATCGAAACAGGACAACAATGGGTAGATGGAGCTACATTACCAAATC GTTTGGCATGACACGG | SEQ ID NO: 726 | BF213738 601847628F1 NIH_MGC_55 Homo sapiens cDNA clone IMAGE:4078519 5', mRNA sequence [BF213738] |
| 727 | A_23_P76799 | BAZ1A | TACACAGAATGAATGAATCCAATCTTATAAGCTTGAAGTGCTGTACCA GTGCTGGCTGCAGGT | SEQ ID NO: 727 | Homo sapiens bromodomain adjacent to zinc finger domain, 1A (BAZ1A), transcript variant 1, mRNA [NM_013448] |
| 728 | A_23_P77073 | SPPL2A | ATGTTCAGACTGGTTCTTCTTACAGTATACTATGTTTCGTCTACAG TTGCCTATGCTATTG | SEQ ID NO: 728 | Homo sapiens signal peptide peptidase-like 2A (SPPL2A), mRNA [NM_032802] |
| 729 | A_23_P77145 | RAB11A | TATAGAATATAGTCCAGTTAAATCTTTGGTTTCAGTATGTCAGTGTCGAA GAGTACAGTGAGAGG | SEQ ID NO: 729 | Homo sapiens RAB11A, member RAS oncogene family (RAB11A), mRNA [NM_004663] |
| 730 | A_23_P78092 | EVI2A | GGTGAATCAGACAGCTTGGAAAAAGAACAAAACAGGCTCACAGGACCC AACCTAGTGATGCAA | SEQ ID NO: 730 | Homo sapiens ecotropic viral integration site 2A (EVI2A), transcript variant 1, mRNA [NM_001003927] |

Fig. 1-41

| No. | Probe ID No. | Symbols of genes | Sequence | SEQ ID NO: | Descriptions of genes (letters and numbers within [ ] indicates GenBank accession No.) |
|---|---|---|---|---|---|
| 731 | A_23_P79199 | DBI | TGGTCAGGATAGGGGTCTAACAGATTAGGGGGGTAAACGATTACTGAGTTGGTTGAGTA | SEQ ID NO: 731 | Homo sapiens diazepam binding inhibitor (GABA receptor modulator, acyl-Coenzyme A binding protein) (DBI), transcript variant 1, mRNA [NM_020548] |
| 732 | A_23_P81212 | MRPS18C | ATGGGGTTTATGCCAGTTACATACAAGGATCCTGCATATCTCAAGGACCCTAAAGTTTGT | SEQ ID NO: 732 | Homo sapiens mitochondrial ribosomal protein S18C (MRPS18C), nuclear gene encoding mitochondrial protein, mRNA [NM_016067] |
| 733 | A_23_P81612 | SRP19 | AGGAAAGAAAAGAAGTAACCTAGTATACAGCATGAAGTATGTGGTACTACTGTAAGAGAC | SEQ ID NO: 733 | Homo sapiens signal recognition particle 19kDa (SRP19), mRNA [NM_003135] |
| 734 | A_23_P81690 | COX7A2 | AGCTCTCTATGGACCCAGTAATCTGATAAATAACCGAGGTCTTCTTTGGGGATCAATATT | SEQ ID NO: 734 | Homo sapiens cytochrome c oxidase subunit VIIa polypeptide 2 (liver) (COX7A2), mRNA [NM_001865] |
| 735 | A_23_P82674 | GBAS | TTACAAGTGTAGCCAATAACTGAAAATGTTTTAAGTCACTCTCATTGTAAGCAGTCCAC | SEQ ID NO: 735 | Homo sapiens glioblastoma amplified sequence (GBAS), mRNA [NM_001483] |
| 736 | A_23_P82748 | ENY2 | CATTCCTTGCTCAGCATGCCAGCCTTTAAGATGAATTAGATTGTGTTGTCTGTCGTTTTA | SEQ ID NO: 736 | Homo sapiens enhancer of yellow 2 homolog (Drosophila) (ENY2), mRNA [NM_020189] |
| 737 | A_23_P83073 | HIATL1 | AAACAACTCAAGCATTCTGGTGGCAACATAGAGATTGTAGGCTGCTTCTAAGAAAGTTAT | SEQ ID NO: 737 | Homo sapiens hippocampus abundant transcript-like 1 (HIATL1), mRNA [NM_032558] |
| 738 | A_23_P83175 | PTPLAD2 | CATCGTTTTTGTGGTCGATGACCAGTCAGGAAGTCCAAGAGAAATATGTTGGTGTGTGT | SEQ ID NO: 738 | Homo sapiens protein tyrosine phosphatase-like A domain containing 2 (PTPLAD2), mRNA [NM_001109015] |
| 739 | A_23_P83278 | CHMP5 | CATTGCTCTTTTATTTTTCCATTAAGAGACTCATTGGTCTGGGAAATGCTTCTTGTAC | SEQ ID NO: 739 | Homo sapiens chromatin modifying protein 5 (CHMP5), mRNA [NM_016410] |
| 740 | A_23_P83414 | PPP1CB | AAATAGCACATTGTCCAATCGAGTGATTTTAATCATACAGTTGACTGGGCAAGTTTA | SEQ ID NO: 740 | Homo sapiens protein phosphatase 1, catalytic subunit, beta isoform (PPP1CB), transcript variant 1, mRNA [NM_002709] |
| 741 | A_23_P86403 | KIF5B | AACAGAACTAGAGTGCAACATGGAATTTTGGCATCGTTAGGGAGGAAAAAGGACAGTTACAACTGTG | SEQ ID NO: 741 | Homo sapiens kinesin family member 5B (KIF5B), mRNA [NM_004521] |
| 742 | A_23_P86653 | SRGN | AGGGACTTGGGTCAACATGGATTAGAAGAGGATTTATGTTATAAAGAGGATATTTCCCAC | SEQ ID NO: 742 | Homo sapiens serglycin (SRGN), mRNA [NM_002727] |
| 743 | A_23_P92842 | SAR1B | TAATCTGACATCACCCACCCCAGCGCCATTTGTAAGAGCAACTTTCCAGCAGTACATTTGAAG | SEQ ID NO: 743 | Homo sapiens SAR1 gene homolog B (S. cerevisiae) (SAR1B), transcript variant 2, mRNA [NM_016103] |
| 744 | A_23_P94230 | LY96 | TGAAGGTATTTCTGGGAGGCCCAGAAGGAAAATGCTCTTTTGCTTGGAGTTGTTCATCGTACA | SEQ ID NO: 744 | Homo sapiens lymphocyte antigen 96 (LY96), mRNA [NM_015364] |
| 745 | A_23_P94533 | CTSL1 | AAGACATGGATCATGGTGTGTGCTGGTGTAAAGTGATTCGTATAGTCTCGCACAGAATCAGATA | SEQ ID NO: 745 | Homo sapiens cathepsin L1 (CTSL1), transcript variant 1, mRNA [NM_001912] |
| 746 | A_23_P94932 | C2orf25 | TCTGTTGATGACCTTGGATGCTGTGTAAAGTGATTCGTATAGTCTCTGGGGGTACCCATGTA | SEQ ID NO: 746 | Homo sapiens chromosome 2 open reading frame 25 (C2orf25), mRNA [NM_015702] |
| 747 | A_23_P95130 | SLC37A3 | TTGAGGAGTACGCTAATTCGATTCGATTCGGTTAGGGGATATTTTTCAACCTCTTGCTTTATACT | SEQ ID NO: 747 | Homo sapiens solute carrier family 37 (glycerol-3-phosphate transporter), member 3 (SLC37A3), transcript variant 1, mRNA [NM_207113] |
| 748 | A_23_P98382 | TIMM8B | TTGTTACTAAGGAGATTTAAGGGTCAGTGGGGGAAGGCTATCAACCCATTGTCAGATCAG | SEQ ID NO: 748 | Homo sapiens translocase of inner mitochondrial membrane 8 homolog B (yeast) (TIMM8B), mRNA [NM_012459] |

Fig. 1-42

| No. | Probe ID No. | Symbols of genes | Sequence | SEQ ID NO: | Descriptions of genes (letters and numbers within [ ] indicates GenBank accession No.) |
|---|---|---|---|---|---|
| 749 | A_24_P101959 | LOC392221 | GCTTCAGTCGAGGAAGTAATGGTGAGCCTGCAAAAGTTGACATCACTTACCAGCAGGATC | SEQ ID NO: 749 | PREDICTED: Homo sapiens similar to Coiled-coil-helix-coiled-helix domain-containing protein 2 (HCV NS2 trans-regulated protein) (NS2TP) (LOC392221), mRNA [XM_373252] |
| 750 | A_24_P103386 | ID1 | GTCTCGTCCTTCAAAACAGTCTTAATTAACTTTCATATATTAGGAGATTAAACTAGCAGAG | SEQ ID NO: 750 | Homo sapiens isopentenyl-diphosphate delta isomerase 1 (IDI1), mRNA [NM_004508] |
| 751 | A_24_P105164 | RP11-217H1.1 | GGAATAATGTGTGTGGCTGGTATTGGACTTGTTGTATTATTCTCAGTGGATGCTCTCT | SEQ ID NO: 751 | Homo sapiens implantation-associated protein (DKFZp564K142), mRNA [NM_032121] |
| 752 | A_24_P105648 | BX111927 | TTATAGAGATGCTTCAGTTCAAATAACAGTGCAGTAATTACCGTATATCTAAAAGACTGCC | SEQ ID NO: 752 | BX111927 Soares_multiple_sclerosis_2NbHMSP Homo sapiens cDNA clone IMAGp998G05619, mRNA sequence [BX111927] |
| 753 | A_24_P11045 | THC2785765 | CCACCAGAAAACGTACACCTGATTTCATGACAAATACGGTAGGCAACACAGTCGGAATAG | SEQ ID NO: 753 | COX7B_HUMAN (P24311) Cytochrome c oxidase polypeptide VIIb, mitochondrial precursor partial (78%) [THC2785765] |
| 754 | A_24_P110591 | A_24_P110591 | TGATGGAACTATAACAACAGAATCAGGAACTGTAATGAGGTCTCTTGGGCAGAATCCCAC | SEQ ID NO: 754 | |
| 755 | A_24_P111737 | ATP11B | GGTCGTCGTTCAAGTGGTTCTGTGGTTGGTTGCCATAATCCTGATGGTTGTTACATGTCTATT | SEQ ID NO: 755 | Homo sapiens ATPase, Class VI, type 11B (ATP11B), mRNA [NM_014616] |
| 756 | A_24_P114249 | GALNT3 | ATTTCAAATGCAGAATACTTGACTCATTTAAAGCTAAATTTGTTACTGATTCAATTATA | SEQ ID NO: 756 | Homo sapiens UDP-N-acetyl-alpha-D-galactosamine:polypeptide N-acetylgalactosaminyltransferase 3 (GalNAc-T3) (GALNT3), mRNA [NM_004482] |
| 757 | A_24_P114617 | CHMP2B | GCCTAATTGAAATATGTACTCTATTTTAGACACGCCTCTGTTAAAACAGACCAAGGTTT | SEQ ID NO: 757 | Homo sapiens chromatin modifying protein 2B (CHMP2B), mRNA [NM_014043] |
| 758 | A_24_P115774 | BIRC2 | GATACCATTTTGGTTAAAGGAAATGCGGCGGCCAACATGTCAAAAAGTGTCTAAAAGAA | SEQ ID NO: 758 | Homo sapiens baculoviral IAP repeat-containing 2 (BIRC2), mRNA [NM_001166] |
| 759 | A_24_P119141 | PROS1 | AGCAGCAGAGGAATCTTACTCTTGGCAGGTCAGTCTGTCAAGAATGAAGATCAGATTA | SEQ ID NO: 759 | Homo sapiens protein S (alpha) (PROS1), mRNA [NM_000313] |
| 760 | A_24_P12149 | CLINT1 | TTAACTTGGCAAGGCTTCGTTCGAGTGTTTATCCTGTAGGCATCATTTAAGTCAGGAACA | SEQ ID NO: 760 | Homo sapiens clathrin interactor 1 (CLINT1), mRNA [NM_014666] |
| 761 | A_24_P123052 | RAP2B | GGAATAAGTTCCTGCATTATAAGTATAAAGGGAACCGAGATTTAATTGAGAGCATCAC | SEQ ID NO: 761 | Homo sapiens RAP2B, member of RAS oncogene family (RAP2B), mRNA [NM_002886] |
| 762 | A_24_P124992 | PSMA4 | AAACGTCCCTTTGGTGTTTCATTGCTGTACATTGGCTGGGATAAGCACTATGGCTTTCAG | SEQ ID NO: 762 | Homo sapiens proteasome (prosome, macropain) subunit, alpha type, 4 (PSMA4), mRNA [NM_002789] |
| 763 | A_24_P125741 | ENST00000309178 | AGCCTCCAACCACACTAACAACAGAATTCAAGATTACTTGCAACAGCTGACAGGAGCAGAAT | SEQ ID NO: 763 | |
| 764 | A_24_P131392 | FAM82A | GTATGCCCTGGTTATTCTAATCCCAATTAGATGTAGTAGCAAAGTGTTATACTGATCTT | SEQ ID NO: 764 | Homo sapiens family with sequence similarity 82, member A (FAM82A), mRNA [NM_144713] |
| 765 | A_24_P137372 | ATP2C1 | TCCGGTTCAGAAGGTTTTCAGAGACTGAGAGCCTAAGGACATACTGGATCTGTTGTTTCTTTT | SEQ ID NO: 765 | Homo sapiens ATPase, Ca++ transporting, type 2C, member 1 (ATP2C1), transcript variant 2, mRNA [NM_001001487] |

Fig. 1-43

| No. | Probe ID No. | Symbols of genes | Sequence | SEQ ID NO: | Descriptions of genes (letters and numbers within [ ] indicates GenBank accession No.) |
|---|---|---|---|---|---|
| 766 | A_24_P140827 | PCMT1 | GGATGAATTGCTAAAAGCAACATCAGGTTGACCAGTATAAAATTAGAGTGGATTGCTCATC | SEQ ID NO: 766 | Homo sapiens protein-L-isoaspartate (D-aspartate) O-methyltransferase (PCMT1), mRNA [NM_005389] |
| 767 | A_24_P148670 | SLK | TGTTGGTTGCTGGTGTGTGTAATTATTAATGAAATGTTCAGTCCTAGTCCCTTATGAGGCT | SEQ ID NO: 767 | Homo sapiens STE20-like kinase (yeast) (SLK), mRNA [NM_014720] |
| 768 | A_24_P152385 | THC2736233 | CAAACAGGTCACACTGCAAGGAAGGTGTGTTGAATGTTTCAGAGGTCACTGGGGTGTGGAT | SEQ ID NO: 768 | ATP5L_PONPY (Q5RFH0) ATP synthase subunit g, mitochondrial (ATPase subunit g), partial (91%) [THC2736233] |
| 769 | A_24_P157415 | ATP11B | CTGTACTGTAACACAGGTGTAAAGTTAGGCATATAAATGCAAGGGTATATCATATATAC | SEQ ID NO: 769 | Homo sapiens ATPase, Class VI, type 11B (ATP11B), mRNA [NM_014616] |
| 770 | A_24_P169976 | LOC652912 | TTGTGTTCTGTTCTGAGTATCAGCCCAAAAACCAAGAGAAGAATCCTGTCAGTCCACTA | SEQ ID NO: 770 | PREDICTED: Homo sapiens similar to High mobility group protein B1 (High mobility group protein 1) (HMG-1) (Amphoterin) (Heparin-binding protein p30) (LOC652912), mRNA [XR_019552] |
| 771 | A_24_P175187 | SAMD9 | CAACCAGGCATAGTGTCTGAGTAATCAAAATGTAATTTTCGCCTAATAAATTATGGATATGGGCAAG | SEQ ID NO: 771 | Homo sapiens sterile alpha motif domain containing 9 (SAMD9), mRNA [NM_017654] |
| 772 | A_24_P175188 | SAMD9 | TGGCAATGTACTGGACAGATTAACATACAACCTATGTTGTTTGAACAAAACACCAAGGGATA | SEQ ID NO: 772 | Homo sapiens sterile alpha motif domain containing 9 (SAMD9), mRNA [NM_017654] |
| 773 | A_24_P175519 | TXN | AAGTAGATGTGGATGAGACTGTGCAGTATGTTGCTTCAGAGTGTGAAGTCAAATGCACGGCCAA | SEQ ID NO: 773 | Homo sapiens thioredoxin (TXN), mRNA [NM_003329] |
| 774 | A_24_P175989 | VPS29 | GAGAGGAGACTTCGGATGAGAATCTGAATTATCCAGACAGAAAAGTTGTGACTGTTGGACA | SEQ ID NO: 774 | Homo sapiens vacuolar protein sorting 29 homolog (S. cerevisiae) (VPS29), transcript variant 2, mRNA [NM_057180] |
| 775 | A_24_P177634 | A_24_P177634 | CATTCATTCAGGTCTCTGTATGGACCAGAACATCTGATAAATGAGTTCTTCTTTGGGGATCAA | SEQ ID NO: 775 | |
| 776 | A_24_P180424 | TMEM30A | CAATGTGTATGCAACATTCTGTTTAGTTAAGGCACCAATTGTTTTGGTTGGTTTTCGTAAG | SEQ ID NO: 776 | Homo sapiens transmembrane protein 30A (TMEM30A), mRNA [NM_018247] |
| 777 | A_24_P186862 | CHMP5 | TGAGAATTTACAAGACACCAGCTAGTGGACATGATGGAAGATGCAAATGAAATCCAAGAAGC | SEQ ID NO: 777 | Homo sapiens chromatin modifying protein 5 (CHMP5), mRNA [NM_016410] |
| 778 | A_24_P195327 | LOC391040 | ACAGCTTAACAATCCTTAAGAAGTTAGGTGAACAGTTCCATGGCAAGTCTTGGAGAGTA | SEQ ID NO: 778 | PREDICTED: Homo sapiens similar to basic transcription factor 3-like 4 (LOC391040), mRNA [XR_019253] |
| 779 | A_24_P200162 | HIGD1A | TATTCAGTGTATCGGGAATTCTGGGCAAAAACCTAAGGCTTAGAAGAAGATGCTGTGTT | SEQ ID NO: 779 | Homo sapiens HIG1 domain family, member 1A (HIGD1A), mRNA [NM_014056] |
| 780 | A_24_P201120 | KIAA1212 | TTGGACAATGAAAATGCCTTAAAAGGAATGCATATGGATAAAGTTGCACTTATAACACCC | SEQ ID NO: 780 | Homo sapiens KIAA1212 (KIAA1212), mRNA [NM_018084] |
| 781 | A_24_P201702 | CLEC2B | ATTGGAATTCAAGTAAATACAACTGTCCAGTCAACATGCCGACCTAACTATAATTGACA | SEQ ID NO: 781 | Homo sapiens C-type lectin domain family 2, member B (CLEC2B), mRNA [NM_005127] |
| 782 | A_24_P209204 | C6orf62 | GGTTGCATACTTTATTGGAGTAAATCTGAATGATCCTAGTCCTTTGGAGTAAGACTAGT | SEQ ID NO: 782 | Homo sapiens chromosome 6 open reading frame 62 (C6orf62), mRNA [NM_030939] |
| 783 | A_24_P211351 | ENST00000370395 | GTTGTGGATTCGTTCGATCAACTGCTGATTTCATCTTCAGGAAGCAAGTCCATAACATGA | SEQ ID NO: 783 | DPH3 homolog B (CSL-type zinc finger-containing protein 1). [Source:Uniprot/SWISSPROT;Acc:Q9H4G8] [ENST00000370395] |

Fig. 1-44

| No. | Probe ID No. | Symbols of genes | Sequence | SEQ ID NO: | Descriptions of genes (letters and numbers within [ ] indicates GenBank accession No.) |
|---|---|---|---|---|---|
| 784 | A_24_P216654 | SOAT1 | CGCAGTAATGTTCTGCACAACAGTATTGTAATTGTAATGGAATCATAACCTGCTAACTAG | SEQ ID NO: 784 | Homo sapiens sterol O-acyltransferase (acyl-Coenzyme A: cholesterol acyltransferase) 1 (SOAT1), transcript variant 1, mRNA [NM_003101] |
| 785 | A_24_P223124 | FNDC3B | CTCACTGTTGGACATACATTCCAAGGCTTTCAACTCTAGGAGAAAAAGAAAATCATGTTT | SEQ ID NO: 785 | Homo sapiens fibronectin type III domain containing 3B (FNDC3B), mRNA [NM_022763] |
| 786 | A_24_P23245 | NDUFA6 | TTCTGGTCATTTAAGGGAAAGATCGAACTGGAAGAAAACAATTAAAGTATGGAAGCAGGGGA | SEQ ID NO: 786 | Homo sapiens NADH dehydrogenase (ubiquinone) 1 alpha subcomplex, 6, 14kDa (NDUFA6), nuclear gene encoding mitochondrial protein, mRNA [NM_002490] |
| 787 | A_24_P234214 | HNRPLL | AGAGCTGTCACACACGTTAATAATGTCAAATTATTTGGGAAAAGACTTAATGTTTGCGTG | SEQ ID NO: 787 | Homo sapiens heterogeneous nuclear ribonucleoprotein L-like (HNRPLL), mRNA [NM_138394] |
| 788 | A_24_P240065 | VPS24 | CACCATGAGGGAGTTGTCCAAAGAAATGATGAAGGCTGGGATCATAGAGGAGAATGTTAGA | SEQ ID NO: 788 | Homo sapiens vacuolar protein sorting 24 homolog (S. cerevisiae) (VPS24), transcript variant 1, mRNA [NM_016079] |
| 789 | A_24_P247608 | PCMT1 | GTATGGTTGGATGTACTGGAAAATGCATAGGAATTGATCACATTAAAGAGCTAGTAGATG | SEQ ID NO: 789 | Homo sapiens protein-L-isoaspartate (D-aspartate) O-methyltransferase (PCMT1), mRNA [NM_005389] |
| 790 | A_24_P255314 | SRP14P1 | TATCGATGGGAAAAAGAAGAAGATGAGACTGTGTGAACTCCAAGGAAGTGAGTAAGTTTCA | SEQ ID NO: 790 | Homo sapiens signal recognition particle 14kDa (homologous Alu RNA binding protein) pseudogene 1 (SRP14P1) on chromosome 12 [NR_003273] |
| 791 | A_24_P263524 | TXNDC9 | TGAGTTCACCACAGAAAACTTTAGAATGGGGGCTCAGTGTTCTGTACATTCTTAATTACAG | SEQ ID NO: 791 | Homo sapiens thioredoxin domain containing 9 (TXNDC9), mRNA [NM_005783] |
| 792 | A_24_P278460 | MLSTD2 | ACCCATGGAAGCAATATGGTTAGGAATTACAGAGGAAGCAGTCCTTAGTTACACTTCTTGTCTG | SEQ ID NO: 792 | Homo sapiens male sterility domain containing 2 (MLSTD2), mRNA [NM_032228] |
| 793 | A_24_P283320 | PCMT1 | CAAAATGTAAGCCATACATGGATTGTCCACAATCAATAGGTTTCCAAGCAACAATCAGTG | SEQ ID NO: 793 | Homo sapiens protein-L-isoaspartate (D-aspartate) O-methyltransferase (PCMT1), mRNA [NM_005389] |
| 794 | A_24_P320284 | DHFR | CTCTCTGATGTCCAGGAGGAGAGGAAAGGGCATTAAGTACAAATTGAAGTATATGAGAGAAT | SEQ ID NO: 794 | Homo sapiens dihydrofolate reductase (DHFR), mRNA [NM_000791] |
| 795 | A_24_P320328 | SUB1 | CAGAAAAACGTGTAAAGAAAAACAAAAGACAGGTGAGACTTGGAGACTTCTCTA | SEQ ID NO: 795 | Homo sapiens SUB1 homolog (S. cerevisiae) (SUB1), mRNA [NM_006713] |
| 796 | A_24_P322353 | PSTPIP2 | AGAATCTTTCCCTTGCTCAGACCCCAGAATTTAAATGCATCCGTCTTACACTTTCACAAA | SEQ ID NO: 796 | Homo sapiens proline-serine-threonine phosphatase interacting protein 2 (PSTPIP2), mRNA [NM_024430] |
| 797 | A_24_P324506 | A_24_P324506 | GCAATATAAGGCAGCTAATTGCAAATACAAGTATGGCTATTCCTGTGGACATGCTGTGT | SEQ ID NO: 797 | |
| 798 | A_24_P324886 | DOCK4 | ATTTGCCTCTTTTGTTGGGAAGGTCATTTAGTTAACCATGTTTGTTTGTTGGTAGC | SEQ ID NO: 798 | Homo sapiens dedicator of cytokinesis 4 (DOCK4), mRNA [NM_014705] |
| 799 | A_24_P325176 | KIAA1109 | TTGATCGAGTAGGTGTTGATTATATTCTTGAAAAATTGGGGCTTTGATCATGCTAGGAGTA | SEQ ID NO: 799 | Homo sapiens KIAA1109, mRNA (cDNA clone IMAGE:3924668), complete cds, [BC108274] |
| 800 | A_24_P32766 | LOC730556 | ACAGCAGCAGCAGCCTTGCTTCTTCATGAGCAGTGTGCTGGAGTGTGCCGAGAACCAGGGTGA | SEQ ID NO: 800 | PREDICTED: Homo sapiens similar to Coiled-coil helix-coiled-coil-helix domain-containing protein 2 (HCV NS2 trans-regulated protein) (NS2TP) (LOC730556), mRNA [XR_015322] |

Fig. 1-45

| No. | Probe ID No. | Symbols of genes | Sequence | SEQ ID NO: | Descriptions of genes (letters and numbers within [ ] indicates GenBank accession No.) |
|---|---|---|---|---|---|
| 801 | A_24_P351451 | OPA1 | TTTTTGGGTATACAGGCGCATGCTTGGTATCACCGGCAAATACTTTAAGGCAACAAGTTACA | SEQ ID NO: 801 | Homo sapiens optic atrophy 1 (autosomal dominant) (OPA1), nuclear gene encoding mitochondrial protein, transcript variant 8, mRNA [NM_130837] |
| 802 | A_24_P355601 | HEXIM1 | GATGAACCCATGAAATTATTGTAGAGTTGTATGTACATTTTCTGGGGAGAAGGTTGA | SEQ ID NO: 802 | Homo sapiens hexamethylene bis-acetamide inducible 1 (HEXIM1), mRNA [NM_006460] |
| 803 | A_24_P362540 | DDEF2 | TGGTGCTATTGTGCAGTAACTAATAGTAGTACTTACCAGAGGAGAAATTATATTAACGACC | SEQ ID NO: 803 | Homo sapiens development and differentiation enhancing factor 2 (DDEF2), mRNA [NM_003887] |
| 804 | A_24_P362646 | TXNDC9 | CTCCAGATTCAGGTGTAAAATAGTAGACAGACATCTGGCAATATTGTCGAAGAAACACCT | SEQ ID NO: 804 | Homo sapiens thioredoxin domain containing 9 (TXNDC9), mRNA [NM_005783] |
| 805 | A_24_P379379 | CAP2A1 | ACCAGTTTCAGGCTAAAAACTTGTGGAATGGTCGTTGGAGATACAGAGTGAAGTTCACCA | SEQ ID NO: 805 | Homo sapiens capping protein (actin filament) muscle Z-line, alpha 1 (CAPZA1), mRNA [NM_006135] |
| 806 | A_24_P388810 | SRP19 | GTTGTATGCAGCAGAAATGATACCTAAACTAAAACAAGGACAAAAACAGGAGGTGC | SEQ ID NO: 806 | Homo sapiens signal recognition particle 19kDa (SRP19), mRNA [NM_003135] |
| 807 | A_24_P39378 | CCPG1 | TACTTTTTGTGGGTGGGAAGGAAGTTGATCAGTTGATCAATAAGTTTTTCCTAAACGGTGT | SEQ ID NO: 807 | Homo sapiens cell cycle progression 1 (CCPG1), transcript variant 1, mRNA [NM_004748] |
| 808 | A_24_P400760 | LOC643454 | TCCATGTAGACAAGGTCACAGTATTCTTGCAGAAATAATGGGGGAATGGTATTGGAGA | SEQ ID NO: 808 | PREDICTED: Homo sapiens similar to AP-3 complex subunit sigma-1 (Adapter-related protein complex 3 sigma-1 subunit) (Sigma-adaptin 3a) (AP-3 complex sigma-3A subunit) (Sigma-3A-adaptin) (LOC643454), mRNA [XR_016772] |
| 809 | A_24_P405298 | PPP1CB | GTATTAGGTTAGGTCACAAAGGTTTTATCTGAGGTGATTAAATAACTTCCTGATTGGAG | SEQ ID NO: 809 | Homo sapiens protein phosphatase 1, catalytic subunit, beta isoform (PPP1CB), transcript variant 1, mRNA [NM_002709] |
| 810 | A_24_P409410 |  | ACCAGGTAATATATGGATGCTTGGCTCTGGAGAAAAAGCTGGTATCAAGGTGCC | SEQ ID NO: 810 |  |
| 811 | A_24_P414256 | CCDC72 | TCTTTGGTCGTTGTTCTCAGGGTAAACTTGTATCACCGTGAATTAAGCCAAGTCATTTGA | SEQ ID NO: 811 | Homo sapiens HSPC330 mRNA, partial cds. [AF161448] |
| 812 | A_24_P417281 | TXNDC10 | ATGATGAGTGATTCTTGGGAAGGATAAATGTTAATGTTGCCAATAGTCAAGCTGTTGTTTGC | SEQ ID NO: 812 | Homo sapiens thioredoxin domain containing 10 (TXNDC10), mRNA [NM_019022] |
| 813 | A_24_P50753 | NUDT4 | AACAGAAAATAAGTAGTTTTTGTGAATGACTTGCAGACAAAGTAGAAACTGTGCTGCATG | SEQ ID NO: 813 | Homo sapiens nudix (nucleoside diphosphate linked moiety X)-type motif 4 (NUDT4), transcript variant 2, mRNA [NM_199040] |
| 814 | A_24_P53080 | ETFA | TGCTGTTGATGCTGGCTTTGTTCCCAATGACATGCAAGTTGGACAGACGGGAAAAATAGT | SEQ ID NO: 814 | Homo sapiens electron-transfer-flavoprotein, alpha polypeptide (glutaric aciduria II) (ETFA), nuclear gene encoding mitochondrial protein, mRNA [NM_000126] |
| 815 | A_24_P548415 | BC092452 | TATTTGTATGGTAAATCCTTGCAAACATGGAAACAATGCATTTGGCCCAGTGCTTTGTGG | SEQ ID NO: 815 | Homo sapiens cDNA clone IMAGE:30325817. [BC092452] |
| 816 | A_24_P561223 | THC2697551 | TTATGCCCAGTTACATACAAGGATCGTGCCATATTTCAGGGACCCTAAAGTTTATTAAGAT | SEQ ID NO: 816 | ALU1_HUMAN (P39188) Alu subfamily J sequence contamination warning entry, partial (8%) [THC2697551] |

Fig. 1-46

| No. | Probe ID No. | Symbols of genes | Sequence | SEQ ID NO: | Descriptions of genes (letters and numbers within [ ] indicate GenBank accession No.) |
|---|---|---|---|---|---|
| 817 | A_24_P56130 | MYL6 | CCAAGAGAGTGATGAGATGAATGTGAAGGTGGTGCTTTGAGGACTTTCTGCCCATGCTGC | SEQ ID NO: 817 | Homo sapiens myosin, light chain 6, alkali, smooth muscle and non-muscle (MYL6), transcript variant 2, mRNA [NM_079423] |
| 818 | A_24_P587882 |  | CTGGAAATGGTGTGTATTAGCACTGAGAAGACAGAAATCCATTCTGTATGATGAAGCA | SEQ ID NO: 818 |  |
| 819 | A_24_P675386 | BX109843 | ACGTGAAATGCACTTTAAATGTTTGCCTTATATCCAAGTGTTACTTGATATCCATGACG | SEQ ID NO: 819 | BX109843 Soares placenta Nb2HP Homo sapiens cDNA clone IMAGp998I14208, mRNA sequence [BX109843] |
| 820 | A_24_P684186 | U52054 | GCTTGACTAACCCCAGAATTATCTTCAAGACTTAATCTGATCTTGTGTCTTAGAGAAGC | SEQ ID NO: 820 | Human S6 H-8 mRNA expressed in chromosome 6-suppressed melanoma cells. [U52054] |
| 821 | A_24_P703614 |  | AAGAACATTACCGGAATGGAGTCTGCACTGTAAGTCATCAGTAGCAGCTTTGTGTGTG | SEQ ID NO: 821 |  |
| 822 | A_24_P724640 | SNRPB2 | ATCCTCAGGTCCTCGATTACCCTCCAAACTATATTTATTCTTAATAACTTACGACAGAAG | SEQ ID NO: 822 | Homo sapiens small nuclear ribonucleoprotein polypeptide B" (SNRPB2), transcript variant 1, mRNA [NM_003092] |
| 823 | A_24_P745670 |  | GGTAAAACAGAGACATGAATACATTTCCAACTCAAATTTGAAGATCCCAAATCTGAAGTC | SEQ ID NO: 823 |  |
| 824 | A_24_P787947 | YPEL2 | AAGGTAAAGCCTAGAACATGAAAACTATCATGAAAGCTATTCTCATGTTACCAAATTCTATCTGGGC | SEQ ID NO: 824 | Homo sapiens yippee-like 2 (Drosophila) (YPEL2), mRNA [NM_001005404] |
| 825 | A_24_P79413 | SEC11A | GTTTTCGTTACTGGATGTTTGGAGTAGATACTGGTCTGTGATTGGTGGAATGGAGAGAC | SEQ ID NO: 825 | Homo sapiens SEC11 homolog A (S. cerevisiae) (SEC11A), mRNA [NM_014300] |
| 826 | A_24_P81965 | RAP2A | TTCTTTTGATGTTGCAACTTTTGGGTTCTTTTAAACGTGTGATAGTGATGGTAACGTAGC | SEQ ID NO: 826 | Homo sapiens RAP2A, member of RAS oncogene family (RAP2A), mRNA [NM_021033] |
| 827 | A_24_P859859 | THC2553238 | TTTAACGAGACGTCTGCACCTTTTCTGCCTGATATACTGAGGACACTCGGTCTCTAGGCAAT | SEQ ID NO: 827 | 13D5349A cystic fibrosis antigen. [Homo sapiens] (exp=-1; wgp=0; cg=0), partial (65%) [THC2553238] |
| 828 | A_24_P879563 | LOC220906 | TGTAGTTGCAAGGAAAAAATTCCCAGAGTTTTCTGCATTCGGTGCTGGGTCATCTGAAAT | SEQ ID NO: 828 | Homo sapiens hypothetical protein LOC220906, mRNA (cDNA clone IMAGE:4837455). [BC045818] |
| 829 | A_24_P920181 | YIPF6 | AAGTCTTAAAAGTCAACCGTTAATCATTAAGTCTTTGCCTCTCAAAGTCTTTGCCTCTG | SEQ ID NO: 829 | Protein YIPF6 (YIP1 family member 6). [Source:Uniprot/SWISSPROT:Acc:Q86EC3] [ENST00000374643] |
| 830 | A_24_P941699 | PCGF5 | TGGTATATTCAACTACAGACTTCTAAGGATAGGACTACTTTCATGTCTAGTAATACACTG | SEQ ID NO: 830 | Homo sapiens polycomb group ring finger 5 (PCGF5), mRNA [NM_032373] |
| 831 | A_24_P95029 | TAX1BP1 | TGGTTGATTCGAGCTTTGATGTTCACAAGAAGTGTCGCCCTCTGTGAGTTAATGTTTCCT | SEQ ID NO: 831 | Homo sapiens Tax1 (human T-cell leukemia virus type I) binding protein 1 (TAX1BP1), transcript variant 1, mRNA [NM_006024] |
| 832 | A_24_P100338 | THC2586959 | AATTAGAGAAACATTCTGTGTGTTTGATAAGGATGGAATGGGTATATTAGTGGTGTAGA | SEQ ID NO: 832 | 1PK0_D Chain D, Crystal Structure Of The Ef3-Gam Complexed With Pmeapp. [Homo sapiens] (exp=-0; cg=0), partial (70%) [THC2586959] |
| 833 | A_32_P10100 | A_32_P10100 | TATGAGGAAATAGTATCATGATTAGAAGCGTTGGAATGAGTATAAATAATGGCTGGTC | SEQ ID NO: 833 |  |
| 834 | A_32_P10424 | AX721252 | AAATTTGTCAGGAAGGAAGGAATGGGAACGTCTAGATGTGCACAACTGATACCAGGGCTCAACAA | SEQ ID NO: 834 | Sequence 212 from Patent WO0220754. [AX721252] |

Fig. 1-47

| No. | Probe ID No. | Symbols of genes | Sequence | SEQ ID NO: | Descriptions of genes (letters and numbers within [ ] indicates GenBank accession No.) |
|---|---|---|---|---|---|
| 835 | A_32_P131377 | REEP5 | CATCACTAAAGCAAGAAGGGAAGAAAAGCTACGGTGAATTTACTGGGTGAAGAAAGAAGAGCAG | SEQ ID NO: 835 | Homo sapiens receptor accessory protein 5 (REEP5), mRNA [NM_005669] |
| 836 | A_32_P135402 | THOC7 | AGCTGGAATTGAGACGGAAACAGTTCATGTCTTCTTAGTACCATCCATGAACTCAGC | SEQ ID NO: 836 | Homo sapiens THO complex 7 homolog (Drosophila) (THOC7), mRNA [NM_025075] |
| 837 | A_32_P143323 | CR613267 | AGAGAGCTCAAACAATGGGGTTTATGCCAGTTACATACAAGGATCGTGCATATTTCAGGG | SEQ ID NO: 837 | full-length cDNA clone CS0DL011YP14 of B cells (Ramos cell line) Cot 25-normalized of Homo sapiens (human) [CR613267] |
| 838 | A_32_P147603 | THC2499508 | GCGTTGACTCGGACGGAGAAAATATCTAAAAATTCCGACGGGTCGGCGGTAGGGGTCCTGTGGTTT | SEQ ID NO: 838 | |
| 839 | A_32_P147747 | THC2575761 | TTGATACCCTCTGATTCTGATGACAAACGCCAATTTGGGTTCTGCAGGTACATAGAAGTTG | SEQ ID NO: 839 | HUMRPL7Y ribosomal protein L7 [Homo sapiens] (exp=-1; wgp=0; cg=0), partial (40%) [THC2575761] |
| 840 | A_32_P154830 | OSTM1 | GTTGGTAAATGTTACTTATATTGGGACTAGTAGTATTTTGTAAATGTTCTGGGATATGCTCCC | SEQ ID NO: 840 | Homo sapiens osteopetrosis associated transmembrane protein 1 (OSTM1), mRNA [NM_014028] |
| 841 | A_32_P159651 | PCAF | GAGTGGTGTCTAGATTTGTAATGAAGAATCATGATACAGTTTGGATTAAGTATCTTGGAC | SEQ ID NO: 841 | Homo sapiens p300/CBP-associated factor (PCAF), mRNA [NM_003884] |
| 842 | A_32_P161432 | CBWD2 | GAAAGAGAAACGTGATGGCCTTATCAATGAAGCTACTAGAACAAGTTGGCTTGGCAGATGCC | SEQ ID NO: 842 | Homo sapiens COBW domain containing 2 (CBWD2), mRNA [NM_172003] |
| 843 | A_32_P162250 | ARHGAP18 | AAGTCCTGAATAAGTCTACTGGAAGAATTATTCTTCGGGTGAAAAAGCTTTTTGTTGTG | SEQ ID NO: 843 | Homo sapiens Rho GTPase activating protein 18 (ARHGAP18), mRNA [NM_033515] |
| 844 | A_32_P162416 | BE218351 | GTCTATTTCAAATTCAGGTGTCCACTAGGTCAGGTTTAGAGGAGATGGTCTTTTAACAT | SEQ ID NO: 844 | hv37e08.x1 NCI_CGAP_Lu24 Homo sapiens cDNA clone IMAGE:3175622 3', mRNA sequence [BE218351] |
| 845 | A_32_P165713 | CIP29 | AAAGCAAGATCTTATCACAGACTCCAGGCATATCTGAAGAACATGCTGAAGAGGAGGC | SEQ ID NO: 845 | Homo sapiens cytokine induced protein 29 kDa (CIP29), mRNA [NM_033082] |
| 846 | A_32_P17163 | ENST00000368149 | TCGTTAGTGAGTTTTAAATCTCAAGCTAGAATTTTTATTGTTTTCTGTGTGTGTATGAG | SEQ ID NO: 846 | Rho GTPase-activating protein 18 (MacGAP). [Source:Uniprot/SWISSPROT;Acc:Q8N392] [ENST00000368149] |
| 847 | A_32_P17504 | THC2698882 | ATGTCTATGCTGTTTCAGTATGCTGCAAATATTCCCAGCTTTTCCCCTGATGCCCAAA | SEQ ID NO: 847 | |
| 848 | A_32_P195387 | DKFZP779L1068 | ATATAACCTTGGAATTCATTCTAATTATGTTGTTCTGGCTGCTTGTAGTATCAGTTCGC | SEQ ID NO: 848 | Homo sapiens cDNA clone IMAGE:5555490. [BC110326] |
| 849 | A_32_P200724 | FAM19A2 | AGAACAAAGTAATTTCTGAAGGAAGCTGAGAATATGGAAAACATATATTGGAGCTAC | SEQ ID NO: 849 | Homo sapiens mRNA; cDNA DKFZp781P0552 (from clone DKFZp781P0552). [CR749367] |
| 850 | A_32_P205550 | RPL26L1 | AGGTAGTTCGAGGACACATACAAAAGGTCAGGAAATTGGAAAGGTAATCCAGGTGTACAGAA | SEQ ID NO: 850 | Homo sapiens ribosomal protein L26-like 1 (RPL26L1), mRNA [NM_016093] |
| 851 | A_32_P205553 | RPL26L1 | TTCGGAATGTCTGGAACATTTGATTTCCTGTTTGTTACCTGTGGCTCTGTAAATGTACT | SEQ ID NO: 851 | Homo sapiens ribosomal protein L26-like 1 (RPL26L1), mRNA [NM_016093] |
| 852 | A_32_P206541 | LOC642123 | TTAAGAAGGCCCCATACCTGGTAGAGGCATGTACCATCTTACATGCTTAAATAACTCCAC | SEQ ID NO: 852 | Homo sapiens cDNA FLJ46881 fis, clone UTERU3015647, moderately similar to Embigin precursor. [AK128714] |
| 853 | A_32_P207231 | AI630435 | TTCTTCAGCTTTTCTTAAGGGTTTCTGGAACAGAGAGGAACCTCCTTCTTCTTCTTCT | SEQ ID NO: 853 | AI630435 ad10b05.y1 Hembase: Erythroid Progenitor Cells (LCB:ad library) Homo sapiens cDNA clone ad10b05 random, mRNA sequence [AI630435] |

Fig. 1-48

| No. | Probe ID No. | Symbols of genes | Sequence | SEQ ID NO: | Descriptions of genes (letters and numbers within [ ] indicates GenBank accession No.) |
|---|---|---|---|---|---|
| 854 | A_32_P223189 | SUMO1P3 | GAATGGAGGAAGAAGATGTGATTGAGGTTTATCAGGAACAAATCGGAGGTCATTCAACAG | SEQ ID NO: 854 | Homo sapiens SUMO1 pseudogene 3 (SUMO1P3) on chromosome 1 [NR_002190] |
| 855 | A_32_P224666 | CAPZA2 | AATGTGTTTTGAGATTCTGAAATTAAATGAAAATAGTTATTTCACAAATGCATTTAATG | SEQ ID NO: 855 | Homo sapiens capping protein (actin filament) muscle Z-line, alpha 2 (CAPZA2), mRNA [NM_006136] |
| 856 | A_32_P2333 | SUB1 | AGGAAGAAAAGGTATTTCTTTAAATCGAGAACAATGGAGCCAGCTGACAGAACAGATTTC | SEQ ID NO: 856 | Homo sapiens SUB1 homolog (S. cerevisiae) (SUB1), mRNA [NM_006713] |
| 857 | A_32_P26895 | KIAA1600 | AATTCTTGGTCCCTCCGTCGGTGGAGAAACTCTTCAGATGGTCATTGTGTACGTACTCTCTT | SEQ ID NO: 857 | KIAA1600 (KIAA1600), mRNA [Source:RefSeq_dna;Acc:NM_020940] [ENST00000369248] |
| 858 | A_32_P30004 | AF086044 | ATTTCTCTTTCTAAAGGGGAGTAAGTTTTTAAAGGCTTCCTGATTTTAGCCTGGCAATGT | SEQ ID NO: 858 | Homo sapiens full length insert cDNA clone YX74DC5. [AF086044] |
| 859 | A_32_P32250 | C10orf84 | CAAAAAGGAGGTTGAAAATTCACAGGCTGCCCGAAAAAAGAAGAAACTTGCATGGGGGTT | SEQ ID NO: 859 | Homo sapiens chromosome 10 open reading frame 84 (C10orf84), mRNA [NM_022063] |
| 860 | A_32_P32315 | A_32_P32315 | AAAGTGGGAAGATACGATTCAAGTCCTGGATTCTCGTCTTTGGAAAAAGGTCAGTCCTCA | SEQ ID NO: 860 | |
| 861 | A_32_P43217 | PSMA6 | TTGTTGTTAGTTTACCAGATCCGTGATGCCACTTACGTCTGTGTTTGGGTAACAAGAAACA | SEQ ID NO: 861 | Homo sapiens proteasome (prosome, macropain) subunit, alpha type, 6 (PSMA6), mRNA [NM_002791] |
| 862 | A_32_P44394 | AIM2 | GAAGAGATAAGGTTCGACTTACATTCTTCAGACTGTCAAAAATGGAGAAAAAGTTACAG | SEQ ID NO: 862 | Homo sapiens absent in melanoma 2 (AIM2), mRNA [NM_004833] |
| 863 | A_32_P62342 | GLT8D3 | TGTGATGTAACTGATGTAACCATTGAGAATCTATATGTGCGTTTATACATTCATCTCTG | SEQ ID NO: 863 | Homo sapiens glycosyltransferase 8 domain containing 3, mRNA (cDNA clone MGC:21651 IMAGE:4508300), complete cds. [BC039145] |
| 864 | A_32_P73222 | AA631847 | TTTCTTGTTTTGGACAATCTCATAAGAACTTTAGGTCTTACAGCACGAACCCGTCGAAG | SEQ ID NO: 864 | np6ib02.s1 NCI_CGAP_Br2 Homo sapiens cDNA clone IMAGE:1130763 3' similar to TR:G971838 G971838 60S RIBOSOMAL PROTEIN L34 ;, mRNA sequence [AA631847] |
| 865 | A_32_P81768 | TMEM167 | CCTCAGTACTGTCACTCACAATATTACATTCTGGAAATGTTATTCTGTTGTATCAGATACG | SEQ ID NO: 865 | Homo sapiens transmembrane protein 167 (TMEM167), mRNA [NM_174909] |
| 866 | A_32_P82424 | LOC647252 | ATTGGATGCTGAGCTAGTGAACTATAAGGACCAGATCAAGATGAGAGGGGGTCCTACAAA | SEQ ID NO: 866 | PREDICTED: Homo sapiens similar to Charged multivesicular body protein 5 (Chromatin-modifying protein 5) (Vacuolar protein sorting 60) (Vps60) (hVps60) (SNF7 domain-containing protein 2) (LOC647252), mRNA [XR_019210] |
| 867 | A_32_P89730 | THC2544977 | GGAGAATAAGTCATTCTGGTCTCTGTTTCCCGTTTTCCAGATAAAAGTATATTTGTCTTG | SEQ ID NO: 867 | |
| 868 | A_32_P95397 | ITGB1 | GTCTTACTTTGAGTTAGTTAGTGCCATAACAGAGACCACTGTATGTGTTTACTTCTGACCATTTGAGT | SEQ ID NO: 868 | Homo sapiens integrin, beta 1 (fibronectin receptor, beta polypeptide, antigen CD29 includes MDF2, MSK12) (ITGB1), transcript variant 1A, mRNA [NM_002211] |

Fig. 2

| No. | Probe ID No. | Symbols of genes | Sequence | SEQ ID NO: | Descriptions of genes (letters and numbers within [ ] indicate GenBank accession No.) |
|---|---|---|---|---|---|
| 1 | A_23_P407601 | C8orf6 | GTGTCCTAGGTTAGTGTAGGCAGAGATTCTATTGTGAGATAAGACTTCCGTGTCGGCTGAA | SEQ ID NO: 220 | Homo sapiens mRNA for hypothetical protein (C8orf6 gene), [AJ3074691] |
| 2 | A_32_P209582 | THC2663167 | CAATGTAAAGGCAGAATATGAAGGTCCTTTGTCAAGATTTTGAAACCTATTTGGCTGAT | SEQ ID NO: 506 | ALU1_HUMAN (P39188) Alu subfamily J sequence contamination warning entry, partial (5%) [THC2663167] |
| 3 | A_32_P213509 | THC2663555 | GATTTGTTCCAGTGTTGGAGGCGTTTTAATGAAAATTCTCAACACCTACACTGGAAAAA | SEQ ID NO: 508 | |
| 4 | A_32_P40673 | A_32_P40673 | CATCACAGTTGATATTAGGACAGGCTAGCTACTGTTGAGTGTCACAGGCTGATATGTA | SEQ ID NO: 523 | |
| 5 | A_32_P71171 | A_32_P71171 | TCTAGATAGTAATAGGAAACAAGAATCCAGCCTGGTGATGGCTGGAGGGAAGTGATTGAA | SEQ ID NO: 538 | |
| 6 | A_32_P98940 | THC2745859 | AAGAGTATTCCGAAGATAGGAAAGGTGTGTGTTGTTTTAGGAGGTGTATTTCAGCTAGTTA | SEQ ID NO: 554 | |
| 7 | A_23_P123608 | JAK2 | GGATAACGATGGCTGGATGAAAGAATGACCTTCATTCTGAGACCAAAGTAGATTTTACAGA | SEQ ID NO: 570 | Homo sapiens Janus kinase 2 (a protein tyrosine kinase) (JAK2), mRNA [NM_004972] |
| 8 | A_23_P138507 | CDC2 | CCCATGTCAAAAACTTGGATGAAAATGGGTTGGATTTGGTCTCGAAAATGTTAATGTATG | SEQ ID NO: 589 | Homo sapiens cell division cycle 2, G1 to S and G2 to M (CDC2), transcript variant 1, mRNA [NM_001786] |
| 9 | A_23_P14734 | RPS27L | TACAAGATCACCACGGTTTTCAGCGATGGTCAGACAGTGGTCTTTGTGTAGGTGTTCA | SEQ ID NO: 597 | Homo sapiens ribosomal protein S27-like (RPS27L), mRNA [NM_015920] |
| 10 | A_23_P152002 | BCL2A1 | GTTAACCATATTTTGGCATTTGAAGGTTATTCATCAAGAAAACTTCTACGACAGCAAATTGC | SEQ ID NO: 602 | Homo sapiens BCL2-related protein A1 (BCL2A1), mRNA [NM_004049] |
| 11 | A_23_P18325 | PDCD10 | CCAACCCACTAATTCATCAAAGCAAGCTAATACTTCAGACCTTCAAAACTGTGGCCTGA | SEQ ID NO: 618 | Homo sapiens programmed cell death 10 (PDCD10), transcript variant 1, mRNA [NM_007217] |
| 12 | A_23_P2705 | P2RY5 | TCTGTATTGCTGTTTCAACTGTTGTTTTGACCCTATAGTTACTAGTTTACATGGAGCA | SEQ ID NO: 654 | Homo sapiens purinergic receptor P2Y, G-protein coupled, 5 (P2RY5), mRNA [NM_005767] |
| 13 | A_23_P41114 | CSTA | AAAGATGAGATTATGGAAAATTGGAAGGTGTGCAGTAGTATAAACTCAAGTTGTTGCTG | SEQ ID NO: 689 | Homo sapiens cystatin A (stefin A) (CSTA), mRNA [NM_005213] |
| 14 | A_23_P424809 | S100A8 | AAAGGCATGAAGAAAGGACAATGGGTAGATGGAGCTAGCATTTACCAAATCAGAGGCTGGGCCCT | SEQ ID NO: 701 | Homo sapiens S100 calcium binding protein A8 (S100A8), mRNA [NM_002964] |
| 15 | A_23_P76480 | BF213738 | AATCAACAGGAGACGAATGGGTAGATGGAGCTACGATTTACCAAATCGTTGGCATGACAGG | SEQ ID NO: 726 | BF213738 601847628F1 NIH_MGC_55 Homo sapiens cDNA clone IMAGE:4078519 5', mRNA sequence [BF213738] |
| 16 | A_23_P94230 | LY96 | TGAAGTATATTCTGGGAGCCCAGAAGAAAATGCTCTTTGTTGGAGTTTGTCATCCTACA | SEQ ID NO: 744 | Homo sapiens lymphocyte antigen 96 (LY96), mRNA [NM_015364] |
| 17 | A_24_P124992 | PSMA4 | AAACGTCCCTTTGGTGTTTCATTGCTGTACATTGGCTGGGATAAGCACTATGGCTTTCAG | SEQ ID NO: 762 | Homo sapiens proteasome (prosome, macropain) subunit, alpha type, 4 (PSMA4), mRNA [NM_002789] |
| 18 | A_24_P126741 | ENST00000309178 | AGCCTCCAACCACGACTAACAAGATTCAAGATTAGTTGCAACAGGTCACAGAGCGAGAAT | SEQ ID NO: 763 | |
| 19 | A_24_P201702 | CLEC2B | ATTGGAATTCAAGTAAATAAATGTCACTCAACATGCCACTGCGACCTAACTATAATTGACA | SEQ ID NO: 781 | Homo sapiens C-type lectin domain family 2, member B (CLEC2B), mRNA [NM_005127] |
| 20 | A_24_P320328 | SUB1 | CAGAAAAACCTGTAAAGAACAAAAGACAGGTGAGACTTCGAGAGCCCTGTCATCTTCTA | SEQ ID NO: 795 | Homo sapiens SUB1 homolog (S. cerevisiae) (SUB1), mRNA [NM_006713] |
| 21 | A_32_P200724 | FAM9A2 | AGAACAAAGTAATTTTCTGAAGGGAAGCTGCAGAATATGGAAAACATATATTGGAGGTAC | SEQ ID NO: 849 | Homo sapiens mRNA; cDNA DKFZp781P0552 (from clone DKFZp781P0552), [CR749367] |

Fig. 3-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P12343 | GSTM3 | AGCTTGTTTTGTTTCATCCTCTCCGTAAGGGGTCAGCGCTGTTGG TTTGCTCTTTTCAAT | SEQ ID NO: 869 | Homo sapiens glutathione S-transferase M3 (brain) (GSTM3), mRNA [NM_000849] |
| 2 | A_23_P143247 | TSHZ2 | CCCACAAGACGGTATGCAAATCTCTAAGTTTACGGGACTCTCAAT GACCACTACAGTCA | SEQ ID NO: 870 | Homo sapiens teashirt family zinc finger 2 (TSHZ2), mRNA [NM_173485] |
| 3 | A_23_P146325 | DDEF1IT1 | TGGAAAGTGAAGTGAAGGATTTTGTCATACAGCCAGTAAGTGCC AGAACTGACTTGAAC | SEQ ID NO: 871 | Homo sapiens DDEF1 intronic transcript 1 (DDEF1IT1) on chromosome 8 [NR_002765] |
| 4 | A_23_P14853 | LTK | AGCTTTGATCTTGGGGCCAGAGGCGGCCTTACACACACCCCAGG TGTGCATGGGGAGCA | SEQ ID NO: 872 | Homo sapiens leukocyte tyrosine kinase (LTK), transcript variant 1, mRNA [NM_002344] |
| 5 | A_23_P20666 | TPM2 | GGAGTATTCCACCAAAGAAGAATAAATATGAAGAGGAAGATGAAACT GTTGGAGGAGAAGCT | SEQ ID NO: 873 | Homo sapiens tropomyosin 2 (beta) (TPM2), transcript variant 2, mRNA [NM_213674] |
| 6 | A_23_P315378 | ATG16L1 | CTGTGTTTCCAGTTTATACTCTTTGTCCAAAACTCAGTTTCAAAA TATTTGCAATGGGAC | SEQ ID NO: 874 | Homo sapiens cDNA FLJ10035 fis, clone HEMBA1000919. [AK000997] |
| 7 | A_23_P339095 | SPTBN1 | AGTAGGGATACTTCAAAAGGACAACAGTTTCCAAAACGGTTTGC CAGCTGAACAGGGAT | SEQ ID NO: 875 | Homo sapiens spectrin, beta, non-erythrocytic 1 (SPTBN1), transcript variant 2, mRNA [NM_178313] |
| 8 | A_23_P344531 | SYNPO | TCCTGCTGCTGTGAAGATGAGAAGGTGCTCTTACTCAGTTAATGA TGAGTGACTATATTT | SEQ ID NO: 876 | Synaptopodin. [Source:Uniprot/SWISSPROT;Acc:Q8N3V7] [ENST00000307662] |
| 9 | A_23_P359174 | BC069659 | CCAGGGGTGCATACTACTAGGGTAAAGAACAAAATTTTGTAATAGCAAACA GTGGTTTGGGATTTT | SEQ ID NO: 877 | Homo sapiens cDNA clone IMAGE:7262526, with apparent retained intron. [BC069659] |
| 10 | A_23_P359870 | C8orf6 | CTGAGGTTATAATTTTCAGTTAACATTGTCGAGTTGGCATTTTGG TTTTAGTGAATGGT | SEQ ID NO: 878 | Homo sapiens mRNA for hypothetical protein (C8ORF16). [AJ312026] |
| 11 | A_23_P379147 | KRT74 | ATGTCTGCTGAGAATGCATGCTGTGTGAGGATCTCTGTCATCAGC AGTAGGAGGTACAGC | SEQ ID NO: 879 | Homo sapiens keratin 74 (KRT74), mRNA [NM_175053] |
| 12 | A_23_P3921 | FLJ11710 | CCTGATTCATGATTGAAGTACCATTAGGCTATACCATAAATGCC ATGCATTGGATGTTA | SEQ ID NO: 880 | Homo sapiens cDNA FLJ11710 fis, clone HEMBA1005149. [AK021772] |
| 13 | A_23_P407601 | C8orf6 | GTCTCGTAGGTTAGGTGTAGGAGAGATTCTATTCTCAGATAAGACT TCCGTGTCGGCTGAA | SEQ ID NO: 881 | Homo sapiens mRNA for hypothetical protein (C8orf6 gene). [AJ307469] |
| 14 | A_23_P88222 | PLD4 | TGAAAGTCTTCATCGTGCCGTGGGGAACCATTCCAACATCCCAT TCAGGAGGTGAAGC | SEQ ID NO: 882 | Homo sapiens phospholipase D family, member 4 (PLD4), mRNA [NM_138790] |
| 15 | A_24_P126057 | MBNL1 | AGAATATTGCTGCAACACTACTCTGTGATTGGTTATCTCTCATCA TGGATTGCTCACAA | SEQ ID NO: 883 | Homo sapiens muscleblind-like (Drosophila), mRNA (cDNA clone IMAGE:3935812), partial cds. [BC052961] |
| 16 | A_24_P312325 | C8orf15 | GTTGTTCAATGTGACTACTTGACTTTAGTTGGCTGTCGAATATGAAGTAG AAAACAGATTTCTG | SEQ ID NO: 884 | Homo sapiens chromosome 8 open reading frame 15 (C8orf15), mRNA [NM_001033662] |
| 17 | A_24_P350136 | LOC652370 | CCAGCTACCACCACCCTGCTGAAGATGAGGACTTCAATCTTAGGG ATGCCGTGGACAGCA | SEQ ID NO: 885 | PREDICTED: Homo sapiens similar to Keratin, type I cytoskeletal 18 (Cytokeratin-18) (CK-18) (Keratin-18) (K18) (LOC652370), mRNA [XR_019330] |
| 18 | A_24_P360499 | DDEF1IT1 | TGTTCCTTTTAATGTAGGGCAGGCTACTCGTATAGTTCAGATTTAACTT TGAAATGTAGGATAG | SEQ ID NO: 886 | Homo sapiens DDEF1 intronic transcript 1 (DDEF1IT1) on chromosome 8 [NR_002765] |
| 19 | A_24_P460763 | AK022443 | GTGAGTAGGAGGCTACTTAAGATGCCTAGTGGGTCTAAATGTCAA ATGCTATTGGCAGAT | SEQ ID NO: 887 | Homo sapiens cDNA FLJ12381 fis, clone MAMMA1002566. [AK022443] |
| 20 | A_24_P491923 | THC2491622 | CTTCTGTTGTTTCTCAATAAAGTAGACAAGTCCATCTGATGGGTG TTTAGTAGGGTATGA | SEQ ID NO: 888 | |

Fig. 3-2

| No. | Probe ID No. | Symbols of genes | Sequence | SEQ ID NO: | Descriptions of genes (letters and numbers within [ ] indicates GenBank accession No.) |
|---|---|---|---|---|---|
| 21 | A_24_P648264 | AL512741 | AAGAATTGAGTTAGAACTGCCCTATAATGTAATGCAGAATATTTGCCAATAATGCCTAGG | SEQ ID NO: 889 | Homo sapiens mRNA; cDNA DKFZp667N064 (from clone DKFZp667N064) [AL512741] |
| 22 | A_24_P558141 | A_24_P558141 | AACCCTGTCCTGCTGGCATAACCTCTCTACATTTTCCCATGAGCTGTGCTGATCAAACTAA | SEQ ID NO: 890 | |
| 23 | A_24_P642771 | AK024956 | ATTCTCCATATATTTTAGTGTGTCTATTGGGCTAGAAAGACAAAGAAGGGGAATGTGG | SEQ ID NO: 891 | Homo sapiens cDNA: FLJ21303 fis, clone COLO2107. [AK024956] |
| 24 | A_24_P693321 | AK123481 | ATCACAACTATGCCAAATAATCAATGCTACAAATGTCCAAAATTTTACTTTAAAACTGGAA | SEQ ID NO: 892 | Homo sapiens cDNA FLJ41487 fis, clone BRTHA2004350. [AK123481] |
| 25 | A_24_P69784 | PACS1 | AAGTTCCCTGATGAAGAGTCGTATCGAAGTTTATTCCGTTCATTGGCGTGGTGAAGGTG | SEQ ID NO: 893 | Homo sapiens phosphofurin acidic cluster sorting protein 1 (PACS1), mRNA [NM_018026] |
| 26 | A_24_P713312 | THC2639056 | TTTATATGGTCGGATGCTCCATGTTAGGATTAAGGGGTAATTAATAGTAATGTATGTGGA | SEQ ID NO: 894 | ALU8_HUMAN (P39195) Alu subfamily SX sequence contamination warning entry, partial (10%) [THC2639056] |
| 27 | A_24_P728115 | AK024937 | ACTGCATAGTCACTACTTTTAGTGAGTTTGAAATCTGTTGGAGAGGTATGTAAGTACGCA | SEQ ID NO: 895 | Homo sapiens cDNA: FLJ21284 fis, clone COLO1911. [AK024937] |
| 28 | A_24_P792389 | THC2671169 | ATGCTAAGGGTGGAGACTAAGGCATAGAAGTATGACTAGAATTGGCAGCTACACATTAGA | SEQ ID NO: 896 | |
| 29 | A_24_P79855 | ENST00000390643 | AAAGATTGGTCCCGTTTTACCCACGGAAGAGCTACCAAGAAGCGAACCTGATAGGAGATGG | SEQ ID NO: 897 | Homo sapiens hypothetical protein DKFZp566H0824, mRNA (cDNA clone MGC:129790 IMAGE:40021976), complete cds. [BC104430] |
| 30 | A_24_P883109 | AL833452 | GGGCAACTAGTCATCTACTAGTTAGCTTAGTAAGCTAAGGATTAAATCTAAGAGAATAGCA | SEQ ID NO: 898 | Homo sapiens mRNA; cDNA DKFZp686E08116 (from clone DKFZp686E08116). [AL833452] |
| 31 | A_24_P898619 | THC2635386 | AATGTAGCATGAGTGTTCCCGGTTAAAAGCCGTGTTTGAGTACTCTAAAGTACTTTTCT | SEQ ID NO: 899 | |
| 32 | A_24_P914102 | A_24_P914102 | TTAGTAGACGCTAGATTTCTCTACAAATGTAAAATGTTATTTTACTGTTGAAAATCAG | SEQ ID NO: 900 | |
| 33 | A_24_P626025 | DKFZp547E087 | TGTTATGAACATAGTCATGTTAAGTCTCCATTTAAATACAACGTGAAATACCAAAGTTA | SEQ ID NO: 901 | Homo sapiens cDNA FLJ30147 fis, clone BRACE2000266. [AK054709] |
| 34 | A_24_P930337 | THC2503773 | AGCAAGTGGAACCGACAACCCAAAATGACTTGAAGAATGTAATTTAAAATGTAGCATAG | SEQ ID NO: 902 | |
| 35 | A_24_P930391 | AK022351 | AAGTGGGTTTAATTTCCTTTCATGAAAGGAAAGATTAGCTTCATGCAACACTTGGTC | SEQ ID NO: 903 | Homo sapiens cDNA FLJ12289 fis, clone MAMMA1001788. [AK022351] |
| 36 | A_24_P931364 | AK022062 | TCCCGATCTGGAGTATGGTTGGAAGTCATTGTTGTTGTAAGGCATTATTTTCTGGT | SEQ ID NO: 904 | Homo sapiens cDNA FLJ12000 fis, clone HEMBB1001531. [AK022062] |
| 37 | A_24_P933514 | AK094334 | CGTAGTCCCACTGTGAGAATTTCCTTAGGTGGCATATATATACTACGTGAACTCTGGC | SEQ ID NO: 905 | Homo sapiens cDNA FLJ37015 fis, clone BRACE2010208. [AK094334] |
| 38 | A_24_P933548 | A_24_P933548 | CACGTCCACGTTTATATGCTTTATACCTGCAGAACTATAACCTAAGGGAAGGAATG | SEQ ID NO: 906 | |
| 39 | A_24_P934861 | A_24_P934861 | GGAAGTATCAAGCAGCAACAAATTCCAGTTTCTGGGAAATAGTGGACCAGATCGTCGCATGG | SEQ ID NO: 907 | |
| 40 | A_24_P935682 | AY358248 | AGTCAGTAATCAGGCATTCAAGCAATCAATATGAGGCTCTAACAATGCTTGAACAGTTATGCAAC | SEQ ID NO: 908 | Homo sapiens clone DNA166629 MRSS6228 (UNQ6228) mRNA, complete cds. [AY358248] |

Fig. 3-3

| No. | Probe ID No. | Symbols of genes | Sequence | SEQ ID NO: | Descriptions of genes (letters and numbers within [ ] indicates GenBank accession No.) |
|---|---|---|---|---|---|
| 41 | A_32_P105940 | A_32_P105940 | GTGCCAAGGTAAGCTAAGCTACCACACTTTTGGTTTTATTTCAAGGCACAAG ATGAAATAAGCATTG | SEQ ID NO: 909 | |
| 42 | A_32_P116997 | THC2719256 | AAACATTAGGTAGCAGCTTGTAGAGGATATATTTAGGGTCATGAT GTCCTTCTTGTTGGC | SEQ ID NO: 910 | BE147120 PM2-HT0224-221099-001-b10 HT0224 Homo sapiens cDNA, mRNA sequence [BE147120] |
| 43 | A_32_P120454 | THC2842550 | ACAGAATGAGATGACTGGACTGGTTCATCGTGTTTATTGGGAAGCT CAGGACAGGGTATGA | SEQ ID NO: 911 | |
| 44 | A_32_P121978 | A_32_P121978 | CAGATTAGACCACCTCATAATGAGTTGTTGATTGCACTTCAGATT GTCTTGATGGGGCAC | SEQ ID NO: 912 | |
| 45 | A_32_P12703 | THC2697162 | TTGAAAGGAAAGATATAGGGGCGAAGTGCCAGACTAAACGAATC CTAAGTAAATAGGGT | SEQ ID NO: 913 | |
| 46 | A_32_P131294 | BM854107 | AGTAGGGAAAAAGGTTTGTTCCTTAATTAGAAGTAGTCTGCTGGAAA TGCTAGCCACTCGTGC | SEQ ID NO: 914 | K-EST0138406 S22SNU16n1 Homo sapiens cDNA clone S22SNU16n1-145-F11 5', mRNA sequence [BM854107] |
| 47 | A_32_P132936 | THC2673888 | AAATGGAAGTATTGACGAGATTAAAGAGTGGTTAAGTCATGGCCA TGAATGAATTACCA | SEQ ID NO: 915 | QG5549 9ALPH (Q65549) Glycoprotein C, partial (4%) [THC2673888] |
| 48 | A_32_P145385 | AK001118 | CCGCAATTAAGACTCGAAGGAAGCTTAAATTCCAGCTTTTTGATT GTCAGGAAATGAGAT | SEQ ID NO: 916 | Homo sapiens cDNA FLJ10256 fis, clone HEMBB1000870. [AK001118] |
| 49 | A_32_P146844 | THC2639689 | CCTGTGGGGTGATTCCAGACTGAAGGCAAGGAAGACTGTCAGAAGAC ATCATGTGGCATTAA | SEQ ID NO: 917 | |
| 50 | A_32_P147969 | AL080232 | TAATGAGGCTCTTTCGGCATGAAGGGAAGGAAGACTGTCAGAAGAC GTCTGGAGAATTCTT | SEQ ID NO: 918 | Homo sapiens mRNA; cDNA DKFZp586A061 (from clone DKFZp586A061) [AL080232] |
| 51 | A_32_P151244 | AK022268 | GTAGTCAGATGTCACAGAGACAGTTATTTCATGTGTAAGCTTTTGA ACTGTTGATGTTGTT | SEQ ID NO: 919 | Homo sapiens cDNA FLJ12206 fis, clone MAMMA1000941. [AK022268] |
| 52 | A_32_P164573 | THC2611661 | AGGTGTTTTTCTATTAAGACTGAAGTAGTCTGAGAGCTTGGAAATT TTCAGTGCAAAATC | SEQ ID NO: 920 | RR12 SP1MX (P42344) Chloroplast 30S ribosomal protein S12, partial (11%) [THC2611661] |
| 53 | A_32_P167883 | THC2697442 | AGGTAATTGGGGGTATGACTTCAGTCACTCTTGAAATATTGGGAA CTAAATTGTGTCATT | SEQ ID NO: 921 | |
| 54 | A_32_P184039 | A_32_P184039 | ATCATTGTTAGTCTTGGCCGAAAATAGTTGTTATGTATCATGGC TAATAACTGACCAGC | SEQ ID NO: 922 | |
| 55 | A_32_P184330 | AK130741 | TGTGACCGTTTGTGACGAGTTATCTCAGTCCTCACATGAGTTCTT ACATGAGTCGGTCTA | SEQ ID NO: 923 | Homo sapiens cDNA FLJ27231 fis, clone SYNO6240. [AK130741] |
| 56 | A_32_P194372 | AK129547 | AGACCAGAGAAACATAGACCCATGATATTTGGACCAAGCATAGGT TAAAAGTAGGGGAGG | SEQ ID NO: 924 | Homo sapiens cDNA FLJ26636 fis, clone PRS00145. [AK129547] |
| 57 | A_32_P204565 | A_32_P204565 | CAGGACAGAATGATACACACGGGATGTGTTTCAGTGTGATGGAAA GATTGTTTCAGTGA | SEQ ID NO: 925 | |
| 58 | A_32_P208039 | AL049390 | TTTCATGTTTGAGGATTCAGATTGGGCTTATTCTCAAGGCATG TGGCAAACCTCACAA | SEQ ID NO: 926 | Homo sapiens mRNA; cDNA DKFZp58601318 (from clone DKFZp58601318) [AL049390] |
| 59 | A_32_P209552 | THC2663167 | CAATGTAAAGCCAGAATACAACGTCCTTTGTGAAGATTTTGAA ACCTATTTCGGTGAT | SEQ ID NO: 927 | ALU1_HUMAN (P39188) Alu subfamily J sequence contamination warning entry, partial (5%) [THC2663167] |
| 60 | A_32_P211048 | A_32_P211048 | GTTCAGAAAAACACCTAGTAGGTATTCAGTTCATATTGGAATGAA TGAGAAAATGAGCAG | SEQ ID NO: 928 | |
| 61 | A_32_P213509 | THC2663555 | GATTTGTTCCAGTGTTGGAGCCCTTTTTAATGAAAATTCTGAACA CCTACACTGGAAAAA | SEQ ID NO: 929 | |

Fig. 3-4

| No. | Probe ID No. | Symbols of genes | Sequence | SEQ ID NO: | Descriptors of genes (letters and numbers within [ ] indicates GenBank accession No.) |
|---|---|---|---|---|---|
| 62 | A_32_P216122 | AK130891 | TTGTTGGTGTATATGTTGGGAGGCATTGAAGAATTGAGTAC ACATATATATGGGTC | SEQ ID NO: 930 | Homo sapiens cDNA FLJ27381 fis, clone UBA07680. [AK130891] |
| 63 | A_32_P224638 | THC2731042 | ACACCAGTCTAACTGCTAGCTTAATGAGCATGGAAACAAAATAGC TCAATCTCTTCTAAC | SEQ ID NO: 931 | Q4SSA7_TETNG (Q4SSA7) Chromosome 11 SCAF14479, whole genome shotgun sequence. (Fragment), partial (5%) [THC2731042] |
| 64 | A_32_P227110 | THC2512148 | TAAAAGAAATCCTTTTGATTCAGCCACTGTGTATTGATAATGGCT TATTATTACAATCA | SEQ ID NO: 932 | |
| 65 | A_32_P232851 | THC2645886 | CTTTGAAAGGATATCCTTGACATTCGTTTTCGAGAAAATTGAGG TGACTGACTTATTC | SEQ ID NO: 933 | Q9P3E1_NEUCR (Q9P3E1) Related to rna-binding protein fus/tis, partial (5%) [THC2645886] |
| 66 | A_32_P25243 | THC2656826 | GGGCTCTGGGCACCATTGGAAGACTGGAGATATAAATGACAAGTGA TTTATTTGTTTTCA | SEQ ID NO: 934 | |
| 67 | A_32_P33304 | ANK3 | TGTTGGAATACGGGCGGGTGATCTCTCTTTTATAAAGTCACCTGAT TTAAAGGAAAGATGA | SEQ ID NO: 935 | Homo sapiens cDNA FLJ44903 fis, clone BRAMY3005184, highly similar to Mus musculus ankyrin 3, epithelial (Ank3). [AK126811] |
| 68 | A_32_P3342 | THC2676548 | TATAGCATTTTCTGAAGATCATGTTGTACTCTTCTTCGTCTAGA TGATTTGGTCAACAG | SEQ ID NO: 936 | ALU7_HUMAN (P39194) Alu subfamily SQ sequence contamination warning entry, partial (19%) [THC2676548] |
| 69 | A_32_P40673 | A_32_P40673 | CATGACAGTTGATATTAGGAACAGGCTACCTACTCGTTGAGTGTG ACAGCCTGATATGTA | SEQ ID NO: 937 | |
| 70 | A_32_P41099 | THC2658419 | AGGGCGAGAAATATTTGGGTTCGTCGGTTATTAGTAAAGTGTCT TTGAGTATTGTGTC | SEQ ID NO: 938 | |
| 71 | A_32_P42976 | THC2713078 | CTTATCCTTTCCTTTCTGTGGTGTCAACCTGCCAACATTGTGGGCT CATTCTTTCTGGCTA | SEQ ID NO: 939 | |
| 72 | A_32_P43878 | DB111455 | ATGTGAGAAAGGTTCTTTAAGGTTTAATGACCAAGTTCCATGTG AGCTCTTACTTGGGA | SEQ ID NO: 940 | DB111455 THYMU2 Homo sapiens cDNA clone THYMU2015028 5', mRNA sequence [DB111455] |
| 73 | A_32_P542 | AF131782 | GAGGCTCTTACGGATCTAACTTCACTTAAGCTGGGAGGAAAATGTCTT ATAAATAACAACAG | SEQ ID NO: 941 | Homo sapiens clone 24941 mRNA sequence. [AF131782] |
| 74 | A_32_P60551 | BU567588 | GCAGAGTACAAGGCTTTGATGGGTGTCATCTATTGATCTATTCCTAGT ACATAAAATTTAGCC | SEQ ID NO: 942 | AGENCOURT_10399418 NIH_MGC_82 Homo sapiens cDNA clone IMAGE:6614194 5', mRNA sequence [BU567586] |
| 75 | A_32_P65067 | THC2618074 | CCGCAAAGTGAATTTAAACTTGACTTATTTATGCCGTTCTGCAT AGCAACAGGAAAAGT | SEQ ID NO: 943 | |
| 76 | A_32_P67209 | BU726026 | CTGACTTATATTTATTCTCGCACCTACGCTGCACGTGACACTGC TATTCTTTCAGAGAAG | SEQ ID NO: 944 | UI-E-C10-aac-g-02-0-UI.s1 UI-E-C10 Homo sapiens cDNA clone UI-E-C10-aac-g-02-0-UI 3', mRNA sequence [BU726029] |
| 77 | A_32_P70875 | CD239706 | CTTTGTTTGTTGAGAAGTTCCTAATGACGTAGGAGAACAAAGTGACAG TTTCGTTATTTACTG | SEQ ID NO: 945 | FMPBXF03 FMP Homo sapiens cDNA, mRNA sequence [CD239706] |
| 78 | A_32_P71171 | A_32_P71171 | TCTAGATAGTAATAGGAACCAAGAATCCAGCCTGGTGATGGCGTG GAGGGACTGATTGAA | SEQ ID NO: 946 | |
| 79 | A_32_P79103 | BM932034 | GTGCTACAGAATGAAAATAGCATTTAGGAAGGTTGAGTCAAGAGG TGCAAGTGGGCCATA | SEQ ID NO: 947 | UI-E-EJi-aji-k-24-0-UI.r1 UI-E-EJI Homo sapiens cDNA clone UI-E-EJi-aji-k-24-0-UI 5', mRNA sequence [BM932034] |
| 80 | A_32_P88987 | AK022346 | ATGGAAGTTAGTACCCAGGGCTTACCAAAAGGTCAGGTTTATATA AAGTTGGCGTTCCTTT | SEQ ID NO: 948 | Homo sapiens cDNA FLJ12284 fis, clone MAMMA1001767. [AK022346] |

Fig. 3-5

| No. | Probe ID No. | Symbols of genes | Sequence | SEQ ID NO: | Descriptions of genes (letters and numbers within [ ] indicates GenBank accession No.) |
|---|---|---|---|---|---|
| 81 | A_32_P89097 | AL134462 | TTCATGGAGCTTCTAGTCAAGCGAGACCGCACTAAACAGTAAAGGGACAAATAGGATTACT | SEQ ID NO: 948 | DKFZp547J085_r1 547 (synonym: hfbr1) Homo sapiens cDNA clone DKFZp547J085 5', mRNA sequence [AL134462] |
| 82 | A_32_P90468 | A_32_P90468 | AAGCCAGGAATAATTTTCTATCTGCATGTACCTAACCTCCTGGAAGTTATCATGAGACCCT | SEQ ID NO: 949 | |
| 83 | A_32_P91328 | THC2641695 | GTTAGCGCAATAATGTCATTGAAGTCTTTAAGTCTGTAGCCTGACTCTAAGGCCAGGGTTCA | SEQ ID NO: 950 | |
| 84 | A_32_P98940 | THC2745859 | AAGAGTATTCCCAAGATAGCAAAGGTGTGTTGTTTTTAGGAGTGTATTTCAGGTAGTTA | SEQ ID NO: 951 | |
| 85 | A_23_P102060 | SSFA2 | GTATCATCCAAATAATGGGGGCTATGACTGAATGAATAGAAATGAATAAGGTGGTGTTT | SEQ ID NO: 952 | Homo sapiens sperm specific antigen 2 (SSFA2), mRNA [NM_006751] |
| 86 | A_23_P102235 | SNRPG | ACAACAGAAGAATATTGGAATGGTGGTAATACAGAGAAATAGTATCATCATGTTAGAAGC | SEQ ID NO: 953 | Homo sapiens small nuclear ribonucleoprotein polypeptide G (SNRPG), mRNA [NM_003096] |
| 87 | A_23_P104054 | C1orf9 | TAAATTTCTTCCTGTCTGCACAATTAGCTATTCAGAGGAAGAGGGCCTGATTTATAGA | SEQ ID NO: 954 | Homo sapiens chromosome 1 open reading frame 9 (C1orf9), transcript variant 2, mRNA [NM_016227] |
| 88 | A_23_P106131 | KTN1 | ATGTTTTCACCCTTCTACTTTGTCAGAAAACTGAACAGAGTTTTGTCTTTTCTAATCC | SEQ ID NO: 955 | Homo sapiens kinectin 1 (kinesin receptor) (KTN1), transcript variant 1, mRNA [NM_182926] |
| 89 | A_23_P106145 | ERO1L | ATTGTGTTGGTTGTTTAAATGTCGTCTGTGGGGAAAAGGTTCAGACTCAGGGGTTGGGCA | SEQ ID NO: 956 | Homo sapiens ERO1-like (S. cerevisiae) (ERO1L), mRNA [NM_014584] |
| 90 | A_23_P108835 | YPEL5 | AAAGTGACTGTCGTGATACAGTTAAGTTGGTCGTCCTATTTGGCCAGTGGGCTGGTTGGAAAG | SEQ ID NO: 957 | Homo sapiens yippee-like 5 (Drosophila) (YPEL5), mRNA [NM_016061] |
| 91 | A_23_P109774 | ZBTB11 | GCCTCTCCCAGTTTACTTTAAAAATGGCTTTAAGGATAAAGAATAAATGATAGGCTGTG | SEQ ID NO: 958 | Homo sapiens zinc finger and BTB domain containing 11 (ZBTB11), mRNA [NM_014415] |
| 92 | A_23_P110352 | MAP2K1IP1 | ACTGAGACAAGTTGTGGAAGTTTCTAATCTGCACAGTGGTTTCAGTGTGTACGTTATCTT | SEQ ID NO: 959 | Homo sapiens mitogen-activated protein kinase kinase 1 interacting protein 1 (MAP2K1IP1), mRNA [NM_021970] |
| 93 | A_23_P110611 | ZH2C2 | CTCTTGAAAAGGACAGAGACTTTCAGTCGTTGTTGGACTCTTCAAACACAGGTTCTTGAATACGTTAA | SEQ ID NO: 960 | Homo sapiens zinc finger, H2C2 domain containing (Zh2C2), mRNA [NM_017676] |
| 94 | A_23_P110704 | SLU7 | CCTCTTTCCTTGGACAGTAGCAACTAGTCAGAAGACCATCGAAGATAGATGCAGCTGATA | SEQ ID NO: 961 | Homo sapiens SLU7 splicing factor homolog (S. cerevisiae) (SLU7), mRNA [NM_006425] |
| 95 | A_23_P110811 | COX7C | AGCCTCTGGAAGTGGAATCACAAACTAGAACTCATATCGATAGATATGTTTGTCAATAA | SEQ ID NO: 962 | Homo sapiens cytochrome c oxidase subunit VIIc (COX7C), nuclear gene encoding mitochondrial protein, mRNA [NM_001867] |
| 96 | A_23_P114616 | ANKRD13C | GTCTCAAGAATGCATCTGTCAAGTTTTTAGACTGACCAGTAGCTTAAACGTTTTTTCAGG | SEQ ID NO: 963 | Homo sapiens mRNA; cDNA DKFZp566D1346 (from clone DKFZp566D1346), [AL136717] |
| 97 | A_23_P11652 | USP1 | TTGGGCATGGACTAATTTTGTATCTGTTAAGTCATCATATTCTGCACGATCGTATATAGTAC | SEQ ID NO: 964 | Homo sapiens ubiquitin specific peptidase 1 (USP1), transcript variant 1, mRNA [NM_003368] |
| 98 | A_23_P11685 | PLA2G4A | GAAATGGCAGCAGTTTCTGATGCTGAGGCAGTTTGCAATCCATGACAACTGGATTTAAA | SEQ ID NO: 965 | Homo sapiens phospholipase A2, group IVA (cytosolic, calcium-dependent) (PLA2G4A), mRNA [NM_024420] |

Fig. 3-6

| No. | Probe ID No. | Symbols of genes | Sequence | SEQ ID NO: | Descriptions of genes (letters and numbers within [ ] indicates GenBank accession No.) |
|---|---|---|---|---|---|
| 99 | A_23_P117163 | RCBTB1 | AAGTGAAGGACCACTTCTCATATTAGATTACTAAGTCATTTGTATGAAATATGTGGCAG | SEQ ID NO: 967 | Homo sapiens regulator of chromosome condensation (RCC1) and BTB (POZ) domain containing protein 1 (RCBTB1), mRNA [NM_018191] |
| 100 | A_23_P117721 | RPS17 | AATTATGTTCCTGAGGTCTGAGCCTTGGATCAGGAGAATTATTGAAGTAGATCCTGAACACT | SEQ ID NO: 968 | Homo sapiens ribosomal protein S17 (RPS17), mRNA [NM_001021] |
| 101 | A_23_P117852 | KIAA0101 | TACTGCTGCCATTTTATTGGTCTTTGATTATTGGAATGGTGCCATATTGTCAGTCGTTC | SEQ ID NO: 969 | Homo sapiens KIAA0101 (KIAA0101), transcript variant 1, mRNA [NM_014736] |
| 102 | A_23_P118516 | FAM18B | TATTCTGTAGATTGTTTTCAGGAGAAAGTTTTGGTTCTATGGTAAGAAGTGAGCACTTTG | SEQ ID NO: 970 | Homo sapiens family with sequence similarity 18, member B (FAM18B), mRNA [NM_016078] |
| 103 | A_23_P120048 | BAZ2B | TATTTCGTCTGAAGGTAATGATAAGCTATACAGTCTGTACAGTAATTATCGTCTACGAAG | SEQ ID NO: 971 | Homo sapiens bromodomain adjacent to zinc finger domain, 2B (BAZ2B), mRNA [NM_013450] |
| 104 | A_23_P120316 | MTHFD2 | AGGATTATTCCTTGGTATTAGTACTCATTTTATGTATGTTACCCTTCAGTAAGTTCTCCC | SEQ ID NO: 972 | Homo sapiens methylenetetrahydrofolate dehydrogenase (NAD+ dependent) 2, methenyltetrahydrofolate cyclohydrolase (MTHFD2), nuclear gene encoding mitochondrial protein, transcript variant 1, mRNA [NM_006636] |
| 105 | A_23_P1206 | RPS24 | TTTTGGATTCAGAAGTCATTTGGTGGTGGCAAGACAACTGGCTTTGGCATAGTTTATGAT | SEQ ID NO: 973 | Homo sapiens ribosomal protein S24 (RPS24), transcript variant 2, mRNA [NM_001026] |
| 106 | A_23_P121366 | IFT57 | TGGAACACACTACTCGCAATCAAAAGCTGAAGGAAGAAGTCCAACATGACTAGGAACATGC | SEQ ID NO: 974 | Homo sapiens intraflagellar transport 57 homolog (Chlamydomonas) (IFT57), mRNA [NM_018010] |
| 107 | A_23_P121622 | SULT1B1 | GAAATAGAGATTGTCTGTAGTTGATTGAAACGAGGGCAGTTATGAATTGATTTGGGGAAT | SEQ ID NO: 975 | Homo sapiens mRNA for ST1B2, complete cds. [D89479] |
| 108 | A_23_P121825 | FLJ13611 | CATGTGTTACTGTTACAAAAGTTTCCTCTCCATGTAATCACACTTAGTTATGAGGAAAG | SEQ ID NO: 976 | Homo sapiens hypothetical protein FLJ13611 (FLJ13611), mRNA [NM_024941] |
| 109 | A_23_P121875 | C5orf28 | TTAAAACATGTTGGGCTACACAGTAGGACACTTTACTGAAGTAGTATTTTTGGTATGTCTAGGC | SEQ ID NO: 977 | Homo sapiens chromosome 5 open reading frame 28 (C5orf28), mRNA [NM_022483] |
| 110 | A_23_P122007 | C5orf30 | ATCAGATTCTCGTTCGATTGGGCTGGAAATGTTTCGCTGTGTATATTTTAAAGTAAATTGCAC | SEQ ID NO: 978 | Homo sapiens chromosome 5 open reading frame 30 (C5orf30), mRNA [NM_033211] |
| 111 | A_23_P122174 | XRCC4 | AAACCAACTGATCTCTCTCTGGTTTGGGAGGGGGGTCAGCTTCAGCTGCTGTAAGTAAAGATGATTCCATTAT | SEQ ID NO: 979 | Homo sapiens X-ray repair complementing defective repair in Chinese hamster cells 4 (XRCC4), transcript variant 3, mRNA [NM_022550] |
| 112 | A_23_P123315 | BC067244 | CTTCCAAATCACTGGTTTGGACGTGGATACATGCTCATTTCTGTACATGATGCAT | SEQ ID NO: 980 | Homo sapiens cDNA clone IMAGE:4807381, partial cds. [BC067244] |
| 113 | A_23_P123343 | NUDCD1 | TTGGCGCTCTTTGTACTGGTGAAAATGGAAATATTCAGTGGTACCTGGAGGTCTGGACAGTTATACTG | SEQ ID NO: 981 | Homo sapiens NudC domain containing 1 (NUDCD1), mRNA [NM_032869] |
| 114 | A_23_P123608 | JAK2 | GGATAACATGGCTGGCTGGATGAAAGAAATGACCTTCATTGTTGAGAGACCAAGTAGATTTACAGA | SEQ ID NO: 982 | Homo sapiens Janus kinase 2 (a protein tyrosine kinase) (JAK2), mRNA [NM_004972] |
| 115 | A_23_P127579 | PTS | GTGGTTTATAAAGGAGGAATAGCTATTGGGGGTTAGCATTTACCCTTGCTGGCCCAGTTGTTTCT | SEQ ID NO: 983 | Homo sapiens 6-pyruvoyltetrahydropterin synthase (PTS), mRNA [NM_000317] |
| 116 | A_23_P128060 | ZNF26 | ATCCGTTCGCACTAGGTACAGGTGAGCTCAAAGTGGTACAGAGGCATTTTACCCTGTTGGATAATGGTAATCTCTTT | SEQ ID NO: 984 | Homo sapiens zinc finger protein 26 (ZNF26), mRNA [NM_019591] |
| 117 | A_23_P128192 | PFDN5 | CAGGTCCATTGGTCAGCTCAAAGTTGGTACAGAGGCAAGTATGTGGAAGCCAAGGACTGTCT | SEQ ID NO: 985 | Homo sapiens prefoldin subunit 5 (PFDN5), transcript variant 1, mRNA [NM_002624] |

Fig. 3-7

| No. | Probe ID No. | Symbols of genes | Sequence | SEQ ID NO: | Descriptions of genes (letters and numbers within [ ] indicates GenBank accession No.) |
|---|---|---|---|---|---|
| 118 | A_23_P128930 | PSMC6 | GAACAAGCAAGATTAGACATACTGAAAATCGATGCAGGTCCGATTACAAAGCATGGTGAA | SEQ ID NO: 986 | Homo sapiens proteasome (prosome, macropain) 26S subunit, ATPase, 6 (PSMC6), mRNA [NM_002806] |
| 119 | A_23_P130444 | ZNF701 | CTCCTTGGCAGAATATCATAACGTTCATTTTTGAGGTAATAGTTACAATGCGGTGAGCAC | SEQ ID NO: 987 | Homo sapiens zinc finger protein 701 (ZNF701), mRNA [NM_018260] |
| 120 | A_23_P133375 | SLC25A46 | CAGTGCTAGCAACGTTAATTCTCATACATTTATAGAGTTTGGTTTGCTTTGCTAGTTGTG | SEQ ID NO: 988 | Homo sapiens solute carrier family 25, member 46 (SLC25A46), mRNA [NM_138773] |
| 121 | A_23_P133648 | FAM8A1 | ACTTCGCCGAATTAGAAATGAGTGTTTTTAGATTCAAGTGACGGTAAAAGGATTTGTT | SEQ ID NO: 989 | Homo sapiens family with sequence similarity 8, member A1 (FAM8A1), mRNA [NM_016255] |
| 122 | A_23_P134786 | PHF20L1 | AGTTGTATGTGCCCCCAGTGCTACATACGCAGGTATGCGTAAGTGTGTATGCTTGTTTTA | SEQ ID NO: 990 | Homo sapiens PHD finger protein 20-like 1 (PHF20L1), transcript variant 1, mRNA [NM_016018] |
| 123 | A_23_P135494 | CLIC4 | CTCGTCAAGCCGTAAGTGTTGAACGAATTGGAGTATTTGTTTATAATTTCTTGAACAGG | SEQ ID NO: 991 | Homo sapiens chloride intracellular channel 4 (CLIC4), mRNA [NM_013943] |
| 124 | A_23_P135499 | CLIC4 | CTTCCCTTTTTGATGTAGATGCAGATATTCTATACAGATCTGATTGTCTTTTACTAGGAC | SEQ ID NO: 992 | Homo sapiens chloride intracellular channel 4 (CLIC4), mRNA [NM_013943] |
| 125 | A_23_P13822 | STYK1 | ACGGCTTAGTAGCTCAGTCTTAACAAGAGGTAGAAAAGAATGTAATCTGATATGGAAGGA | SEQ ID NO: 993 | Homo sapiens serine/threonine/tyrosine kinase 1 (STYK1), mRNA [NM_018423] |
| 126 | A_23_P138308 | CD58 | AACCTGTATCCAAGCAAGCGGTCATTAATTCTTAAAGGGCTCTTTTCAGTTATACCCATACCATT | SEQ ID NO: 994 | Homo sapiens CD58 molecule (CD58), mRNA [NM_001779] |
| 127 | A_23_P140069 | FBXL3 | TAACCCGCAGTGGAATAGATTATTCTTAAAGGGCTCTTTTCAGTAGTGTGACTTTTAGA | SEQ ID NO: 995 | Homo sapiens F-box and leucine-rich repeat protein 3 (FBXL3), mRNA [NM_012158] |
| 128 | A_23_P140301 | PSMA3 | TGAAGTAGAAGTCAGGTCGGGTTGGTCAATTAACTAATGGAAGACATGAAATGTTCCAAA | SEQ ID NO: 996 | Homo sapiens proteasome (prosome, macropain) subunit, alpha type, 3 (PSMA3), transcript variant 1, mRNA [NM_002788] |
| 129 | A_23_P141549 | RPS7 | GTCAAAGTAGATGGCAGCCGGCTCATAAAGGTTCATTGGACAAAGCAAGGAGAACAAT | SEQ ID NO: 997 | Homo sapiens ribosomal protein S7 (RPS7), mRNA [NM_001011] |
| 130 | A_23_P143958 | RPL22L1 | ATTGGCTTCGAGTGCTGGTTGGATGTGACGAGGAGACCTACGAACTTCGTTACTTCCAGATTA | SEQ ID NO: 998 | Homo sapiens ribosomal protein L22-like 1 (cDNA clone IMAGE:4865966), [BC049823] |
| 131 | A_23_P144224 | TLOC1 | ATGGGGATTGGTGAAGAGGAGGATGAGGAAAATGATGAGAAACACCTAAATGTTCAC | SEQ ID NO: 999 | Homo sapiens translocation protein 1 (TLOC1), mRNA [NM_003262] |
| 132 | A_23_P144497 | RPS3A | CCAAATCGGGAAGAAGAATGATGGAAATGATGACCCGAGAGGTGCAGACAAATGACTTGAA | SEQ ID NO: 1000 | Homo sapiens ribosomal protein S3A (RPS3A), mRNA [NM_001006] |
| 133 | A_23_P144684 | ANKRD32 | AAACTTCTACAAAACTCTAGTATGGGCTTCTGACTTTTTCCAGGGTGTAGAATTTGACTC | SEQ ID NO: 1001 | Homo sapiens ankyrin repeat domain 32 (ANKRD32), mRNA [NM_032290] |
| 134 | A_23_P145397 | CCNC | TAGTAGACCAGTTGGAAATAAAACATTGGACAGATTTCAGTAATGTCTTCAGTTGGAACAC | SEQ ID NO: 1002 | Homo sapiens cyclin C (CCNC), transcript variant 1, mRNA [NM_005190] |
| 135 | A_23_P14564 | GPR65 | AACAAGTTAAATTGTTGTTGGCTGCAGTTCTGTAGTGTTTGTAACGCAAAGAGGAAG | SEQ ID NO: 1003 | Homo sapiens G protein-coupled receptor 65 (GPR65), mRNA [NM_003608] |
| 136 | A_23_P145777 | NDUFA4 | ACGGCTGCTTAGAATGAATGAAGGTCTTGCAGAAGCCACATCCCGCACAATTTTCCACTTAACCA | SEQ ID NO: 1004 | Homo sapiens NADH dehydrogenase (ubiquinone) 1 alpha subcomplex, 4, 9kDa (NDUFA4), nuclear gene encoding mitochondrial protein, mRNA [NM_002489] |
| 137 | A_23_P148347 | FAM29A | TTGGACACGAAAGGTCAAGGAATGGGAAGCCATTTTGATTCTTGAGTAATCTTGTAAGC | SEQ ID NO: 1005 | Homo sapiens family with sequence similarity 29, member A (FAM29A), mRNA [NM_017645] |

Fig. 3-8

| No. | Probe ID No. | Symbols of genes | Sequence | SEQ ID NO: | Descriptions of genes (letters and numbers within [ ] indicates GenBank accession No.) |
|---|---|---|---|---|---|
| 138 | A_23_P14708 | SUHW4 | TCTTTGTACCTCCATAAGTGTTAGCCTGCCAGGGCTGTAAGCTTACCTTAATTAAACTT | SEQ ID NO: 1006 | Homo sapiens suppressor of hairy wing homolog 4 (Drosophila) (SUHW4), transcript variant 1, mRNA [NM_017661] |
| 139 | A_23_P14734 | RPS27L | TACAAGATCACCACAGGTTTTCAGGCATGGTCAGACAGTGGTTCTTTGTGTAGGTGTTCA | SEQ ID NO: 1007 | Homo sapiens ribosomal protein S27-like (RPS27L), mRNA [NM_015920] |
| 140 | A_23_P147404 | A_23_P147404 | TGGGGTGAACATGAAATTGATTACATATTTTGTTGGATGGTGAGCAGCGTCGCTCTCATGTG | SEQ ID NO: 1008 | |
| 141 | A_23_P149775 | ARHGAP12 | TGTATATAAAAGACAGGGTTTGGAAGGTTTTGTTACAGGGAGCATGGTCTGTTGAAGAT | SEQ ID NO: 1009 | Homo sapiens Rho GTPase activating protein 12 (ARHGAP12), mRNA [NM_018287] |
| 142 | A_23_P149892 | GALNACT-2 | CATGGTGGTCAGAATAGATGAGGATGAGCATAGCAGTGTTTGTTTGTTTTGCTTTGAATTTC | SEQ ID NO: 1010 | Homo sapiens chondroitin sulfate GalNAcT-2 (GALNACT-2), mRNA [NM_018590] |
| 143 | A_23_P150129 | SAPS3 | TTACCTTGTTAACAAGCATCACGAATGAACATTTCAAGAGCAATCTGGATATTTAACAGAC | SEQ ID NO: 1011 | Homo sapiens SAPS domain family, member 3 (SAPS3), mRNA [NM_018312] |
| 144 | A_23_P151018 | LEMD3 | CCCCATCTTGTAACCTGTTGGAAGAGTGAATGTAAAAATAGTTGTGGGATTTTAAAAGG | SEQ ID NO: 1012 | Homo sapiens LEM domain containing 3 (LEMD3), mRNA [NM_014319] |
| 145 | A_23_P152002 | BCL2A1 | TGTAACCATATTTGAAGGTATTGTCATCAAGAAAGTTCTACGACAGCAAATTGG | SEQ ID NO: 1013 | Homo sapiens BCL2-related protein A1 (BCL2A1), mRNA [NM_004049] |
| 146 | A_23_P154330 | TXNDC9 | CTCAGTTCTTAAATTATCTGGGAAGGGCTGGATTCTCTGTATTTTGAGATTGACTTATC | SEQ ID NO: 1014 | Homo sapiens thioredoxin domain containing 9 (TXNDC9), mRNA [NM_057783] |
| 147 | A_23_P154387 | STK17B | TACCCAATGCCGCATGAACTGTTCAGATTGGTCTGTGTTAGGACATTTTCTTTGACTCA | SEQ ID NO: 1015 | Homo sapiens serine/threonine kinase 17b (STK17B), mRNA [NM_004226] |
| 148 | A_23_P155765 | HMGB2 | TAAAAATGCAGGTTGTAGCTTTTGATGGGCTAGTCACAGTTAGATTTACAGGTTC | SEQ ID NO: 1016 | Homo sapiens high-mobility group box 2 (HMGB2), mRNA [NM_002129] |
| 149 | A_23_P155815 | NCAPG | AAGTTAGGAAAGACGAATGGAGGTGGAATCCTTTAAGAATTATGTCAGTTATTGGTTTAA | SEQ ID NO: 1017 | Homo sapiens non-SMC condensin I complex, subunit G (NCAPG), mRNA [NM_022346] |
| 150 | A_23_P156356 | TMEM161B | AGGTTTGGACCTGGCATATTTTATTCTGTGATCCTAACTAGTTCCTTTAATAGG | SEQ ID NO: 1018 | Homo sapiens transmembrane protein 161B (TMEM161B), mRNA [NM_153354] |
| 151 | A_23_P156842 | EEF1E1 | AAGAAAAAGCAATGCTTCAGCAGTGGTTAGAATACAGGGTCACTCAAGTAGATGGGCACT | SEQ ID NO: 1019 | Homo sapiens eukaryotic translation elongation factor 1 epsilon 1 (EEF1E1), mRNA [NM_004280] |
| 152 | A_23_P157449 | POLR2K | GGTCTCTGTTGCTGTTCAAAATATCTCTTGTACAGTACTGCACCATTTTAGATGTGGTTGAC | SEQ ID NO: 1020 | Homo sapiens polymerase (RNA) II (DNA directed) polypeptide K, 7.0kDa (POLR2K), mRNA [NM_005034] |
| 153 | A_23_P157452 | POLR2K | GGAATGTCTTCAGTTATACTTGGATTTGGTCTTCTCCCATTCTGATTGTTGTATAGCTT | SEQ ID NO: 1021 | Homo sapiens polymerase (RNA) II (DNA directed) polypeptide K, 7.0kDa (POLR2K), mRNA [NM_005034] |
| 154 | A_23_P159650 | COX7B | CAAATACGGTAATGCTGTATTAGCTAGTAGTGGAGCCACTTTCTGTATTGTTACATGGACATA | SEQ ID NO: 1022 | Homo sapiens cytochrome c oxidase subunit VIIb (COX7B), nuclear gene encoding mitochondrial protein, mRNA [NM_001866] |
| 155 | A_23_P159839 | C1GALT1C1 | TCCAAATCAGATGCATGGATGATGATGTATACCGACCGCTTAGGGGCATTTGGGCATAT | SEQ ID NO: 1023 | Homo sapiens C1GALT1-specific chaperone 1 (C1GALT1C1), transcript variant 1, mRNA [NM_152692] |
| 156 | A_23_P160466 | SLC19A2 | CTTGTATGTGGCCATATTTATAGAATGCTGAACTCAATGTGCAAGTTGTACTGTATGGA | SEQ ID NO: 1024 | Homo sapiens solute carrier family 19 (thiamine transporter), member 2 (SLC19A2), mRNA [NM_006996] |

Fig. 3-9

| No. | Probe ID No. | Symbols of genes | Sequence | SEQ ID NO: | Descriptors of genes (letters and numbers within [ ] indicates GenBank accession No.) |
|---|---|---|---|---|---|
| 157 | A_23_P161091 | ZMYM1 | GAGGTATTTTCCTAAGTGGTATTGTGACGGTGTATACTGTTCTTG AGGTTGTCTTCTCTG | SEQ ID NO: 1025 | Homo sapiens zinc finger, MYM-type 1 (ZMYM1), mRNA [NM_024772] |
| 158 | A_23_P162279 | CCDC91 | AGTACAGGCATATATGAAATCTTTCCCAGTATTTCAGAATGTACT TAATGACAGGGAGG | SEQ ID NO: 1026 | Homo sapiens coiled-coil domain containing 91 (CCDC91), mRNA [NM_018318] |
| 159 | A_23_P162596 | ACTR6 | TTAACGGCTTCACTGGACGTTTTCCTTAGAAGGTAGTTTTGTGT GACTGTGACTAAACT | SEQ ID NO: 1027 | Homo sapiens ARP6 actin-related protein 6 homolog (yeast) (ACTR6), mRNA [NM_022496] |
| 160 | A_23_P162866 | HSP90AA1 | CTGGGTATTGTGATGAAGATGACCCTACTGCTGATGATACCAGTGCT GCTGTAACTGAAGAA | SEQ ID NO: 1028 | Homo sapiens heat shock protein 90kDa alpha (cytosolic), class A member 1 (HSP90AA1), transcript variant 2, mRNA [NM_005348] |
| 161 | A_23_P163113 | PRPF39 | TAGTAATAGGGGGAAAATGTCAATTAGTAGCTTACCACAGATACT GTTTCCTAGGATTTA | SEQ ID NO: 1029 | Homo sapiens PRP39 pre-mRNA processing factor 39 homolog (S. cerevisiae) (PRPF39), mRNA [NM_017922] |
| 162 | A_23_P163216 | ATP8B4 | ATCAGTGTATTTTCGATAAAGTGATTGGGGGATATTTGTGTGAAA ACCTGAGTTCTGTCA | SEQ ID NO: 1030 | Homo sapiens ATPase, Class I, type 8B, member 4 (ATP8B4), mRNA [NM_024837] |
| 163 | A_23_P167828 | RWDD1 | GAGGATGCTGGAAACAACATCGTGGAGGTAGAGAAGTCTTTGTTCGAA GAAATGGATGACTG | SEQ ID NO: 1031 | Homo sapiens RWD domain containing 1 (RWDD1), transcript variant 2, mRNA [NM_016104] |
| 164 | A_23_P16817 | CLK1 | ATGGAAAGGATTCTTGGACCTCTACCAAACATATGATACAGAAAA ACCAGGAAAACGTAAA | SEQ ID NO: 1032 | Homo sapiens CDC-like kinase 1 (CLK1), transcript variant 1, mRNA [NM_004071] |
| 165 | A_23_P168656 | GTPBP10 | AATTGTGGATTTCTGATAGAATGTCTTCTACTGAGGCACCATCA AAGCACTGTGTTACT | SEQ ID NO: 1033 | Homo sapiens GTP-binding protein 10 (putative) (GTPBP10), transcript variant 2, mRNA [NM_033107] |
| 166 | A_23_P168974 | SDCBP | GGAAACGACAAGTTCATCTTGAGAATTTATACAGACTGGTCGAG AACAACCATCCTCAG | SEQ ID NO: 1034 | Homo sapiens cDNA FLJ46804 fis, clone TRACH3032570, highly similar to Homo sapiens syndecan binding protein (syntenin) (SDCBP), [AK128645] |
| 167 | A_23_P169050 | MRPS28 | GAGCACAACAGATACAACTGTACTAGAGGGTAATGCAGTTCTGT TGGGAATGCAGGAGA | SEQ ID NO: 1035 | Homo sapiens mitochondrial ribosomal protein S28 (MRPS28), nuclear gene encoding mitochondrial protein, mRNA [NM_014018] |
| 168 | A_23_P169576 | EXOC6 | ATGTGAAATCTTCCCTTTGCCTTTTCAGGATTTAGGCCTGTAAGA AACTATGCGTGATTC | SEQ ID NO: 1036 | Homo sapiens exocyst complex component 6 (EXOC6), transcript variant 2, mRNA [NM_001013848] |
| 169 | A_23_P17021 | SCRN3 | GTCAAAGTTAGTTCTTAGTGATCATCATGGTCAAGCTAATATTAGTT CTTAGTGATCAGTGG | SEQ ID NO: 1037 | Homo sapiens secernin 3 (SCRN3), mRNA [NM_024583] |
| 170 | A_23_P170233 | CSTA | AACTGGCTACTGAGTCAGTCATCAGTCCTTGCTGATAAATATAACCATCA ATAAGAAGCATCT | SEQ ID NO: 1038 | Homo sapiens cystatin A (stefin A) (CSTA), mRNA [NM_005213] |
| 171 | A_23_P18325 | PDCD10 | CCAACCGACTAATTCATCAAACCAACTTAATACTTCAGACCTTCA AAACTGTGGCCTGAA | SEQ ID NO: 1039 | Homo sapiens programmed cell death 10 (PDCD10), transcript variant 1, mRNA [NM_007217] |
| 172 | A_23_P18422 | MRPL3 | CAGTACAAAACCATATGGGGACTATAGTGCAACCTATTTGGGTAA AGAAAACCATTTGGTA | SEQ ID NO: 1040 | Homo sapiens mitochondrial ribosomal protein L3 (MRPL3), nuclear gene encoding mitochondrial protein, mRNA [NM_007208] |
| 173 | A_23_P18598 | PI4K2B | AGGCTTAAAACCAATGTAACTAGAAGTAACTTGTGACAACCTCAGTTG TGGTCTAGGCCTTT | SEQ ID NO: 1041 | Homo sapiens phosphatidylinositol 4-kinase type 2 beta (PI4K2B), mRNA [NM_018323] |
| 174 | A_23_P200030 | FPGT | TAAAAATTGGTAAACTAGAAGTAACTGTCACAACCCTCAGTTA TGATACGTTATGTGCG | SEQ ID NO: 1042 | Homo sapiens fucose-1-phosphate guanylyltransferase (FPGT), mRNA [NM_003838] |

Fig. 3-10

| No. | Probe ID No. | Symbols of genes | Sequence | SEQ ID NO: | Descriptions of genes (letters and numbers within [ ] indicates GenBank accession No.) |
|---|---|---|---|---|---|
| 175 | A_23_P200298 | AGL | TAGATTTTAACAGGTGTCATTTGAGTAAACGTTTCGGTAGAATGCTTCATAGCTTGAGTG | SEQ ID NO:1043 | Homo sapiens amylo-1, 6-glucosidase, 4-alpha-glucanotransferase (glycogen debranching enzyme, glycogen storage disease type III) (AGL), transcript variant 4, mRNA [NM_000028] |
| 176 | A_23_P200493 | LBR | GAGCCCATTTATCAATACAGTGCTGCAATTCTCTGGATATGAGCTACAGTTGTTTTAAGT | SEQ ID NO:1044 | Homo sapiens lamin B receptor (LBR), transcript variant 1, mRNA [NM_002296] |
| 177 | A_23_P200507 | CNIH4 | TGGATTGAAGTCAGGCAGCACACTGGACAGTTGAGGAGCCAGAGACTGTTAAATCAT | SEQ ID NO:1045 | Homo sapiens cornichon homolog 4 (Drosophila) (CNIH4), mRNA [NM_014184] |
| 178 | A_23_P200955 | A_23_P200955 | AGAGCATGATTGAAGCTGAGATTGATGTCAAGACTACCGATGGTTATTGTTTCATCTAC | SEQ ID NO:1046 | |
| 179 | A_23_P201519 | NEK7 | TGAAGGCAAAGAAGTCACTGTTAAAGGACTGTGTGGCATCGTACAACCTGGATGAA | SEQ ID NO:1047 | Serine/threonine-protein kinase Nek7 (EC 2.7.11.1) (NimA-related protein kinase 7). [Source:Uniprot/SWISSPROT:Acc:Q8TDX7] [ENST00000367385] |
| 180 | A_23_P201918 | ABCB10 | CATGCATGAGGCTAGACCCTAAGAGAAGTAATTAAGTCAATGTAAATCAAATGGAAGTTTTC | SEQ ID NO:1048 | Homo sapiens ATP-binding cassette, sub-family B (MDR/TAP), member 10 (ABCB10), nuclear gene encoding mitochondrial protein, mRNA [NM_012089] |
| 181 | A_23_P201951 | ARID4B | ATGTTTACAGGTTTGAATTAGGCTAAAAGGTCTTGCAGTGGCTTTTCATGGGCCTTCAAA | SEQ ID NO:1049 | Homo sapiens AT rich interactive domain 4B (RBP1-like) (ARID4B), transcript variant 1, mRNA [NM_016374] |
| 182 | A_23_P20225 | RRM2B | TGCTCCTTTGTAAAAGATTTGAAAGAGAATCTCATATCCCGAGGCATTAGGA | SEQ ID NO:1050 | Homo sapiens ribonucleotide reductase M2 B (TP53 inducible) (RRM2B), mRNA [NM_015713] |
| 183 | A_23_P202496 | NOC3L | ACAGCTTGCACTATTCTAGGAGTGGCTAAGAAATGCGTGTTCAGTGACTAGATAT | SEQ ID NO:1051 | Homo sapiens nucleolar complex associated 3 homolog (S. cerevisiae) (NOC3L), mRNA [NM_022451] |
| 184 | A_23_P202637 | SAPS3 | TGATTATTCCTACAAGTGGAAACAGTAGACTATTTGGAGTGTATATGGCTGTGTTTTGGG | SEQ ID NO:1052 | Homo sapiens SAPS domain family, member 3 (SAPS3), mRNA [NM_018312] |
| 185 | A_23_P203498 | TRIM22 | GTAGATAAGAATCTATCACTAAGTAATGTATGTCTTCAGAATGTGTTGGTTTACCAGTGAC | SEQ ID NO:1053 | Homo sapiens tripartite motif-containing 22 (TRIM22), mRNA [NM_006074] |
| 186 | A_23_P203645 | CREBZF | TCTGTTGAGATATTTTCTTCCTTACGTCAATACTTTCCTGCATTATTTGAAATTGTGGG | SEQ ID NO:1054 | Homo sapiens CREB/ATF bZIP transcription factor (CREBZF), mRNA [NM_001039618] |
| 187 | A_23_P204187 | FLJ22028 | CTATAAGCTTGCTACTGCTGTGGGAAAATACAATGCACAGAGCGCTTAGGTTCAGATCATGAATT | SEQ ID NO:1055 | Homo sapiens hypothetical protein FLJ22028 (FLJ22028), mRNA [NM_024854] |
| 188 | A_23_P204269 | USP15 | GACCAGGATAAATGAGGTATGTTGATCATGAGGTTTGGTTTTATATCTTGATATTAAAGCTG | SEQ ID NO:1056 | Homo sapiens ubiquitin specific peptidase 15 (USP15), mRNA [NM_006313] |
| 189 | A_23_P204564 | PPP1R12A | GTATAAGATGTTAGATCTGTGTAATCTCACATTCATTTTAGCAGGTACTGAGTGATGCTG | SEQ ID NO:1057 | Homo sapiens protein phosphatase 1, regulatory (inhibitor) subunit 12A (PPP1R12A), mRNA [NM_002480] |
| 190 | A_23_P205027 | ABHD13 | ATTTGTGCAGAATGATAAGAATGTTCCTTTTAGAAGTGTGTTATGTCGTACCTGTCTG | SEQ ID NO:1058 | Homo sapiens abhydrolase domain containing 13 (ABHD13), mRNA [NM_032859] |
| 191 | A_23_P205336 | C14orf129 | CAATTCATTGCCAGACTTCATTGGAATGCTTTGTTTGATGATGTATGTTCATTCTCAGCT | SEQ ID NO:1059 | Homo sapiens chromosome 14 open reading frame 129 (C14orf129), mRNA [NM_016472] |

Fig. 3-11

| No. | Probe ID No. | Symbols of genes | Sequence | SEQ ID NO: | Descriptions of genes (letters and numbers within [ ] indicate GenBank accession No.) |
|---|---|---|---|---|---|
| 192 | A_23_P205645 | MAP4K5 | GTAATGCTAGCAGGGGGAAGTATTTAATTGCCCATGATATGTATTT TACTTATACTATGCC | SEQ ID NO: 1060 | Homo sapiens mitogen-activated protein kinase kinase kinase kinase 5 (MAP4K5), transcript variant 2, mRNA [NM_198794] |
| 193 | A_23_P20606 | NIPSNAP3A | GTAAGTACGACTTCAAAAAATAGTTCTGTTTACTTCTGTTTGCATGGT ATTTCAGTGTGTGTC | SEQ ID NO: 1061 | Homo sapiens nipsnap homolog 3A (C. elegans) (NIPSNAP3A), mRNA [NM_015469] |
| 194 | A_23_P207288 | LOC51136 | CCAAAACAGCAATTTGAAATTAGAACTAGTGGTTTTAGAGAAGTC AGGTATTCTTCCTG | SEQ ID NO: 1062 | Homo sapiens PTD016 protein (LOC51136), mRNA [NM_016125] |
| 195 | A_23_P207999 | PMAIP1 | TTAGAGAATCGTTCTAGTGTTTTTGCCGAAGATTACCGCTGGCT ACTGTGAAGGGAGAT | SEQ ID NO: 1063 | Homo sapiens phorbol-12-myristate-13-acetate-induced protein 1 (PMAIP1), mRNA [NM_021127] |
| 196 | A_23_P208238 | ZNF137 | CCATACTGGACATAAAATCTTAAGTGTCTTAAGTGTGGCAAGGT CTTCAGTGTGTGGGC | SEQ ID NO: 1064 | Homo sapiens zinc finger protein 137 (ZNF137), mRNA [NM_003438] |
| 197 | A_23_P209032 | ZNF302 | TCAGAAAAATGTATCTGGGGAAAAGTTGTATGAAGGTGGTGAAC ATGGAGAGCTTTAG | SEQ ID NO: 1065 | Homo sapiens zinc finger protein 302 (ZNF302), transcript variant 1, mRNA [NM_018443] |
| 198 | A_23_P209879 | ATF2 | TCATGTAAACGGTTAACAAGCTTACCAAGGTTAGCAAAACTTCA TTGTAAATCAGTCTG | SEQ ID NO: 1066 | Homo sapiens cDNA FLJ46899 fis, clone UTERU3022588, highly similar to Cyclic-AMP-dependent transcription factor ATF-2. [AK128731] |
| 199 | A_23_P210274 | PREI3 | GGATCAGTATGCCGTAGGATTTAGAGAATAATATTTCAACATGCTAT TTCATCACTCGGCAG | SEQ ID NO: 1067 | Homo sapiens preimplantation protein 3 (PREI3), transcript variant 1, mRNA [NM_015387] |
| 200 | A_23_P210829 | PCMTD2 | TCCTGCGGCACCTTATACCAGAATTCAGTATATAATACACTACTTCT GTTTCAAACAGATA | SEQ ID NO: 1068 | Homo sapiens protein-L-isoaspartate (D-aspartate) O-methyltransferase domain containing 2 (PCMTD2), mRNA [NM_018257] |
| 201 | A_23_P211840 | UBE1C | GCCACACCCTAGAGCGAAAAAATAGAACACACTTACTTACGATCGGTA ACCTCTATTGAAGAA | SEQ ID NO: 1069 | Homo sapiens ubiquitin-activating enzyme E1C (UBA3 homolog, yeast) (UBE1C), transcript variant 1, mRNA [NM_003968] |
| 202 | A_23_P212728 | TBC1D23 | TGTACCCTGTTAACGACCAGTCATTCATTTTGATTTAGTTATGGAAATC AAGTGAATAAAAGGC | SEQ ID NO: 1070 | Homo sapiens TBC1 domain family, member 23, mRNA (cDNA clone MGC:8800 IMAGE:3847561), complete cds. [BC020955] |
| 203 | A_23_P2129 | TMEM126B | CATATGCATCATTGGCTGCACACTTCGATTTTTGTGTAGTGTTGTTA CTGCAAAGCTTTTG | SEQ ID NO: 1071 | Homo sapiens transmembrane protein 126B (TMEM126B), mRNA [NM_018480] |
| 204 | A_23_P213661 | HISPPD1 | GTATGTAAGTTTCTGTTTGTGAAAATGTAGTAATGTACTGACT GTGGAGGTCATAAGG | SEQ ID NO: 1072 | Homo sapiens histidine acid phosphatase domain containing 1 (HISPPD1), mRNA [NM_015216] |
| 205 | A_23_P215751 | NDUFA5 | TAAAAGTGGAGTCACTAAATAGTTTGCAGTACGTTTCTATATAA GTGTAGGTGGGTATC | SEQ ID NO: 1073 | Homo sapiens NADH dehydrogenase (ubiquinone) 1 alpha subcomplex, 5, 13kDa (NDUFA5), nuclear gene encoding mitochondrial protein, mRNA [NM_005000] |
| 206 | A_23_P21734 | TAF9 | CATGGTTGTGATTTCTTCCGTGAACGCGTGGTTTCATATAGTTTT GTGCTGAGAACAGAT | SEQ ID NO: 1074 | Homo sapiens TAF9 RNA polymerase II, TATA box binding protein (TBP)-associated factor, 32kDa (TAF9), transcript variant 3, mRNA [NM_001015891] |
| 207 | A_23_P217384 | AP1S2 | AAACGTTGCTCTCTCTTCACAGTATTATGTGTAAAAGTCATTGTTT AAAGCACGAATGTTC | SEQ ID NO: 1075 | Homo sapiens adaptor-related protein complex 1, sigma 2 subunit (AP1S2), mRNA [NM_003916] |
| 208 | A_23_P217564 | ACSL4 | GTTATAGGTCGTTAGAAACACATAATTAACACTTAAGGTTGGGT CGTGCTAATTGTTTG | SEQ ID NO: 1076 | Homo sapiens acyl-CoA synthetase long-chain family member 4 (ACSL4), transcript variant 1, mRNA [NM_004458] |

Fig. 3-12

| No. | Probe ID No. | Symbols of genes | Sequence | SEQ ID NO: | Descriptions of genes (letters and numbers within [ ] indicates GenBank accession No.) |
|---|---|---|---|---|---|
| 209 | A_23_P218928 | C4orf18 | CAGATGAGTTCATTTGCTTCTCTAGATGTGTTTTCAAGAGCTAGGTACAGACGAATGTTTG | SEQ ID NO: 1077 | Homo sapiens chromosome 4 open reading frame 18 (C4orf18), transcript variant 2, mRNA [NM_016613] |
| 210 | A_23_P219072 | SAMD9 | AACCTACGCTCCAAGATTAGTAAAGCCAGTTGAAAAACTAAAAGATCAGCCTCGGAGAAGTCT | SEQ ID NO: 1078 | Homo sapiens sterile alpha motif domain containing 9 (SAMD9), mRNA [NM_017654] |
| 211 | A_23_P22671 | SYBL1 | CAAACGGAATACGGTCAGCAGTGCAAACTCGAAGGGTTTGGGCTTGATTCCTGTTGAATAATA | SEQ ID NO: 1079 | Homo sapiens synaptobrevin-like 1 (SYBL1), mRNA [NM_005638] |
| 212 | A_23_P23765 | ITGB3BP | AGTATACAGGCTTGGAGGGCAGTAGAGAGCTTGAAAATCTCATTGGAATCTCCGTGTGCA | SEQ ID NO: 1080 | Homo sapiens integrin beta 3 binding protein (beta3-endonexin) (ITGB3BP), mRNA [NM_014288] |
| 213 | A_23_P23960 | BLOC1S2 | GAGTAAAGTGGAGGACTGTGGGTATTCCTGAACCTTCTTTGAGAGAGAATCCCTCAGAAT | SEQ ID NO: 1081 | Homo sapiens biogenesis of lysosome-related organelles complex-1, subunit 2 (BLOC1S2), transcript variant 2, mRNA [NM_001001342] |
| 214 | A_23_P24365 | ANKRD49 | GGGCACTGGTTGTATAGTCTCTCAAGTTCAGAGGAAATGTTGATTTTCTAAGGTCCTCAT | SEQ ID NO: 1082 | Homo sapiens ankyrin repeat domain 49 (ANKRD49), mRNA [NM_017704] |
| 215 | A_23_P250002 | HACE1 | TAAGCAGTCATTGTGTTTGCCAGTAATGTTTGAGAGACATGTAAGTTGAAAGTTTTGCTA | SEQ ID NO: 1083 | Homo sapiens HECT domain and ankyrin repeat containing, E3 ubiquitin protein ligase 1 (HACE1), mRNA [NM_020771] |
| 216 | A_23_P250800 | ST3GAL6 | ATGTCACGAAGTTCACCTAGCTGGTTTTAAATACAACTTTTCTGACCTCAAGAGTCCTT | SEQ ID NO: 1084 | Homo sapiens ST3 beta-galactoside alpha-2,3-sialyltransferase 6 (ST3GAL6), mRNA [NM_006100] |
| 217 | A_23_P250930 | CRBN | TGATGTATTGAGGAATTCAGGCTGCTTAAAATTGGCAGTGCTGCTATCCAGCGAGTTGGCTGTGA | SEQ ID NO: 1085 | Homo sapiens cereblon (CRBN), mRNA [NM_016302] |
| 218 | A_23_P250994 | ANAPC10 | GATTCATTGTCCTTACGTAACATGACAATGCATAAGAAGCCAACTCGTAGATTCCATATACAGAT | SEQ ID NO: 1086 | Homo sapiens anaphase promoting complex subunit 10 (ANAPC10), mRNA [NM_014885] |
| 219 | A_23_P251421 | CDCA7 | ATTTACTTGCATATGTAAACCATTGGTGTGCCATTGAATGTTGATGGAATAATTGGAACCT | SEQ ID NO: 1087 | Homo sapiens cell division cycle associated 7 (CDCA7), transcript variant 1, mRNA [NM_031942] |
| 220 | A_23_P251937 | CPEB4 | GTATGTCAGTTAATTGTACTACTTGGCTGAATTTCCATATAGTTTTACTGTGTATGGGG | SEQ ID NO: 1088 | Homo sapiens cytoplasmic polyadenylation element binding protein 4 (CPEB4), mRNA [NM_030627] |
| 221 | A_23_P252145 | C1GALT1 | ATATGTCTATATATATGAGGGAACTTGTGTTTTTAAATGGTGGCCAGGTAGAGGAACTAG | SEQ ID NO: 1089 | Homo sapiens core 1 synthase, glycoprotein-N-acetylgalactosamine 3-beta-galactosyltransferase, 1 (C1GALT1), mRNA [NM_020156] |
| 222 | A_23_P252201 | EAF2 | CAGGATTCCTGATATAGATGCCAGTCATAATAGATTTCGGAGACAACAGTGGCCTTCTGAT | SEQ ID NO: 1090 | Homo sapiens ELL associated factor 2 (EAF2), mRNA [NM_016456] |
| 223 | A_23_P252371 | RBBP8 | GGGAAGGGAGGAGAGAAGACATAGACGTTGAAACAGAAACAGAAGGATGAAGGACAGTTTTT | SEQ ID NO: 1091 | Homo sapiens retinoblastoma binding protein 8 (RBBP8), transcript variant 1, mRNA [NM_002894] |
| 224 | A_23_P253412 | MRPL50 | GAAAAGTTTTGAGAGGGACTGTCAACTTGGGTTAAGACAGAGGACATTGCAAGTTGA | SEQ ID NO: 1092 | Homo sapiens mitochondrial ribosomal protein L50 (MRPL50), nuclear gene encoding mitochondrial protein, mRNA [NM_019051] |
| 225 | A_23_P254472 | C6orf211 | TTCATTCAATAGGTTGTTTCATTTGACACGCCTTGTATTTGATTGAACTTGTAGAATGG | SEQ ID NO: 1093 | Homo sapiens chromosome 6 open reading frame 211 (C6orf211), mRNA [NM_024573] |
| 226 | A_23_P254702 | DEK | TTTTTTATTAACTGCTTTTTGCCATATAACATGCTGATATTTAGTGGAAACCTAGCCAGC | SEQ ID NO: 1094 | Homo sapiens DEK oncogene (DNA binding) (DEK), mRNA [NM_003472] |
| 227 | A_23_P254733 | MLF1IP | GCTGTTACCTTCTGAAACGTACCTTTATAAATCAATTGTTTTGCAAAGAAGTTATGGGC | SEQ ID NO: 1095 | Homo sapiens MLF1 interacting protein (MLF1IP), mRNA [NM_024629] |

Fig. 3-13

| No. | Probe ID No. | Symbols of genes | Sequence | SEQ ID NO: | Descriptions of genes (letters and numbers within [ ] indicates GenBank accession No.) |
|---|---|---|---|---|---|
| 228 | A_23_P264756 | CD164 | TTAGTTTTAGTGAGTGCTGTAGGATTAATTCGAAAATAGGGAGAATTCGAATGGTCCCA | SEQ ID NO: 1096 | Homo sapiens CD164 molecule, sialomucin (CD164), mRNA [NM_006016] |
| 229 | A_23_P25503 | FNDC3A | ATACTGCCATTTGAGCCTCACTGCAAAATTAGTGCAGAGGAGAAAACGAATTTTAATGT | SEQ ID NO: 1097 | Homo sapiens fibronectin type III domain containing 3A (FNDC3A), transcript variant 2, mRNA [NM_014923] |
| 230 | A_23_P255663 | MANEA | AAAGAGTCGTACATCTTCAGAGTTTCAGTCGGGAATTTCTTGGCCATGGATGTAGAACC | SEQ ID NO: 1098 | Homo sapiens mannosidase, endo-alpha (MANEA), mRNA [NM_024641] |
| 231 | A_23_P256231 | FBXO30 | GGCTTTTAAAGTTTTGCTGAAGAATGTGTCGTGGTTAGGATAGCACAAGAATAACTT | SEQ ID NO: 1099 | Homo sapiens F-box protein 30 (FBXO30), mRNA [NM_032145] |
| 232 | A_23_P256342 | SNX13 | ATTAGGCAGGTGATGATCCTTGAAACATCTTCAGGTGTCGAGAAAGAGAAGAATG | SEQ ID NO: 1100 | Homo sapiens sorting nexin 13 (SNX13), mRNA [NM_015132] |
| 233 | A_23_P25638 | C13orf7 | CTTGCATTCCAGGGGAGTTTCTTTGAGTAGTATGTTCTTGTTTGCATGTCCTGTTG | SEQ ID NO: 1101 | Homo sapiens chromosome 13 open reading frame 7 (C13orf7), mRNA [NM_024546] |
| 234 | A_23_P25735 | PSMA6 | TAGCAGAGAGAGACTAAACATTGTCGTTAGTTACCAGATCGGTGATGCAACTTACCTGT | SEQ ID NO: 1102 | Homo sapiens proteasome (prosome, macropain) subunit, alpha type, 6 (PSMA6), mRNA [NM_002791] |
| 235 | A_23_P257911 | USP16 | GTACTTTGTGTTTAATATCTGGGTGATGGATCACAACATGAATAAACTGACTTACC | SEQ ID NO: 1103 | Homo sapiens ubiquitin specific peptidase 16 (USP16), transcript variant 1, mRNA [NM_006447] |
| 236 | A_23_P258108 | LOC731224 | GTGAGCCCAGGTGTTGCTTGTTGAATATGCCAAGCCAGAAAGATGAGTCATCGTAAA | SEQ ID NO: 1104 | PREDICTED: Homo sapiens similar to 60S ribosomal protein L9 (LOC731224), mRNA [XR_015767] |
| 237 | A_23_P259054 | SNX14 | CATCAGACTCGTGTTTGATCGGCTTACAGACAGCAGCTACTCAACGAGCAGGCTGACTTATGT | SEQ ID NO: 1105 | Homo sapiens sorting nexin 14 (SNX14), transcript variant 1, mRNA [NM_153816] |
| 238 | A_23_P259594 | AKAP7 | GAAGATAAGCTCCAGGTCTTATCGTATCCCTTGCCATCTGAACTTGTTTGCACTGCTCT | SEQ ID NO: 1106 | Homo sapiens A kinase (PRKA) anchor protein 7 (AKAP7), transcript variant gamma, mRNA [NM_016377] |
| 239 | A_23_P26021 | COPS2 | TGCTTTTTGATCAAGCTGGTTTGTGTTTGCTGCTGCATTATCCCAAGAAAAACAGCTT | SEQ ID NO: 1107 | Homo sapiens COP9 constitutive photomorphogenic homolog subunit 2 (Arabidopsis) (COPS2), mRNA [NM_004236] |
| 240 | A_23_P2705 | P2RY5 | TCTGTGTATTGCTGTTCCAAGCTGTTGTTTTGACCCTATAGTTTACTACTTTACATCGGACA | SEQ ID NO: 1108 | Homo sapiens purinergic receptor P2Y, G-protein coupled, 5 (P2RY5), mRNA [NM_005767] |
| 241 | A_23_P28169 | ARL6IP6 | GGAAAGGAAATAATAGCCTACTACTGCCACTTTATAGAAGCTACTTTAAATCAGAATAT | SEQ ID NO: 1109 | Homo sapiens ADP-ribosylation-like factor 6 interacting protein 6 (ARL6IP6), mRNA [NM_152522] |
| 242 | A_23_P29005 | SAMSN1 | CTCTTGGTTGCTATATCTCATCAGGAAAATTCAGATAATGGCAAAGAGGATCTGAGTCTGA | SEQ ID NO: 1110 | Homo sapiens SAM domain, SH3 domain and nuclear localization signals 1 (SAMSN1), mRNA [NM_022136] |
| 243 | A_23_P302550 | RGS18 | GAGTCTAAGGCCCTAGGCATTTGGGCATCTGCCAACATTGGTTCATATTCAGAAAGTGTTA | SEQ ID NO: 1111 | Homo sapiens regulator of G-protein signalling 18 (RGS18), mRNA [NM_130782] |
| 244 | A_23_P30307 | CRSP9 | CAATTGTACTGGACAGAATGAACATCAAAGAGAAAATTCAGGTCATAGGAGAGATCAGAT | SEQ ID NO: 1112 | Homo sapiens cofactor required for Sp1 transcriptional activation, subunit 9, 33kDa (CRSP9), mRNA [NM_004270] |
| 245 | A_23_P303260 | STX7 | GTCTGATGTTTACGGGGACGAGTGTAGTTACTAACATGTTTAACATAATTTGGAAGAAG | SEQ ID NO: 1113 | Homo sapiens syntaxin 7 (STX7), mRNA [NM_003569] |
| 246 | A_23_P305060 | PBEF1 | TGCCTGTGGCTCTATATGCACCTCAAGATTTAAGGAGATAATGTTTTTAAGAGAATT | SEQ ID NO: 1114 | Homo sapiens pre-B-cell colony enhancing factor 1 (PBEF1), mRNA [NM_005746] |

Fig. 3-14

| No. | Probe ID No. | Symbols of genes | Sequence | SEQ ID NO: | Descriptions of genes (letters and numbers within [ ] indicates GenBank accession No.) |
|---|---|---|---|---|---|
| 247 | A_23_P305723 | MIER1 | TGATGTATTTTCAAATACAGTTCAGGATCTGAGAATTCAGTTGAAC ACAAGTTTGTTGAGC | SEQ ID NO: 1115 | Homo sapiens mesoderm induction early response 1 homolog (Xenopus laevis) (MIER1), transcript variant 1, mRNA [NM_020948] |
| 248 | A_23_P306890 | POLI | TCAATAACGGAGTAAACTGTTCAGATAAAGCAAGAATAGTTGCA ACAAGTAAATCTCGG | SEQ ID NO: 1116 | Homo sapiens polymerase (DNA directed) iota (POLI), mRNA [NM_007195] |
| 249 | A_23_P307940 | CAPZA2 | CTACAAGATTGGCAAGAAGAGATGCAAGAATGCATAAGATGAACATTG CATGACCGGATCATT | SEQ ID NO: 1117 | Homo sapiens capping protein (actin filament) muscle Z-line, alpha 2 (CAPZA2), mRNA [NM_006136] |
| 250 | A_23_P308600 | GLS | CGGAAGAAGATAAGAATACTGCGGAATAGCGCCTCAAAGTTAAAA AAGAAAAAACTTTGC | SEQ ID NO: 1118 | Homo sapiens glutaminase C mRNA, complete cds. [AF158555] |
| 251 | A_23_P30956 | KIAA0776 | TTTTTCATTTGTCAAATGCTCTTTTGTTGCCACAGTAAAGAA CAGTTTTTATTGTTT | SEQ ID NO: 1119 | Homo sapiens KIAA0776 (KIAA0776), mRNA [NM_015293] |
| 252 | A_23_P31097 | OSTM1 | ACTGAAAATGTGCTGGGGTTTGTTGCTGTCACTGTTTATGGTG CTGGAACTTAGCACT | SEQ ID NO: 1120 | Homo sapiens osteopetrosis associated transmembrane protein 1 (OSTM1), mRNA [NM_014028] |
| 253 | A_23_P312246 | CCDC82 | GGCTTTATAACGATGACTGTCAAGTGAATGAAGTGTTGATATCC TGTCAGTTTAGTCAA | SEQ ID NO: 1121 | Homo sapiens coiled-coil domain containing 82 (CCDC82), mRNA [NM_024725] |
| 254 | A_23_P314191 | ZDHHC17 | TGGACTCTTTAGCAAATAAGGAACTAATTCTCAGCACTGAACAT GAATTACTTCCTTGG | SEQ ID NO: 1122 | Homo sapiens zinc finger, DHHC-type containing 17 (ZDHHC17), mRNA [NM_015336] |
| 255 | A_23_P314591 | NFYB | GGAGGCATTTACTAAGCAGTTACCAGCTGGGCTTAATAACCACAGA CGGTCAACAACAAAA | SEQ ID NO: 1123 | Homo sapiens nuclear transcription factor Y, beta (NFYB), mRNA [NM_006166] |
| 256 | A_23_P31671 | UQCRB | AAGCCATAAGAGAGACTTCCTGAGAACGTTTATAATGACAGAGATGT TTCGGCATTAAGAGGG | SEQ ID NO: 1124 | Homo sapiens ubiquinol-cytochrome c reductase binding protein (UQCRB), mRNA [NM_006294] |
| 257 | A_23_P31702 | PXMP3 | CTTCTCTGGCATGGTTTTGGTGAATTTCTGATTTTTCTCTTACCA CTTATCAATGTCCAG | SEQ ID NO: 1125 | Homo sapiens peroxisomal membrane protein 3, 35kDa (Zellweger syndrome) (PXMP3), transcript variant 1, mRNA [NM_000318] |
| 258 | A_23_P317347 | ESCO1 | GCTAATTTTTAAAAGGCCTGAACTATAGTTTGAAGAAAGCGGCTAT AGAAAAGGAAAGCTC | SEQ ID NO: 1126 | Homo sapiens establishment of cohesion 1 homolog 1 (S. cerevisiae) (ESCO1), mRNA [NM_052911] |
| 259 | A_23_P3204 | MAPK6 | AACGTGCTCACTGTGTATAGGAATTGTATTTGGAGGTGCTTGA TGTATGTACAAAGAA | SEQ ID NO: 1127 | Homo sapiens mitogen-activated protein kinase 6 (MAPK6), mRNA [NM_002748] |
| 260 | A_23_P324633 | C9orf72 | TTTGTTGGATTTAGTCCCTGGGATTCAGTCTGTGTAGAAATGTCTAAT AGTTCTCTATAGTCG | SEQ ID NO: 1128 | Homo sapiens chromosome 9 open reading frame 72 (C9orf72), transcript variant 1, mRNA [NM_018325] |
| 261 | A_23_P325501 | MORC3 | CATGCATAAAATACTATATGCTTATTGGTCCCATGTTTTGTGCAA TTTTAAAGAGATGGC | SEQ ID NO: 1129 | Homo sapiens MORC family CW-type zinc finger 3 (MORC3), mRNA [NM_015358] |
| 262 | A_23_P327022 | MDFIC | TTATGATTCTTAATGTAAATGTTTTTGAAGTATAGGCTAT CATGACTAAGTGCTA | SEQ ID NO: 1130 | Homo sapiens MyoD family inhibitor domain containing (MDFIC), mRNA [NM_199072] |
| 263 | A_23_P329198 | OBFC2A | ACATGTCATAAGTGTACGGCACTTCCCCTTTTTACTGTAGGGTGG ATAAGTCTTAGGATT | SEQ ID NO: 1131 | Homo sapiens oligonucleotide/oligosaccharide-binding fold containing 2A (OBFC2A), mRNA [NM_001031716] |
| 264 | A_23_P33045 | RPL26 | TACAAAGGTCAGCAAATTGGCAAAGTAGTAGTCAAGGTTTTACAGAAG AAATATGTTATCTAC | SEQ ID NO: 1132 | Homo sapiens ribosomal protein L26 (RPL26), mRNA [NM_000987] |
| 265 | A_23_P332439 | NUPL1 | ATTGAAATCTTGAATGTATTGAATCTGTCAAGGTACACAGCGGGTG CCTTTGTAAATGTTC | SEQ ID NO: 1133 | Homo sapiens KIAA0410 mRNA, partial cds. [AB007870] |
| 266 | A_23_P339480 | HAT1 | AACATGAACAGCTGGAAGAGAGTTTCAGGAACTAGTGAAGATT ACCGGCGGTGTTATTG | SEQ ID NO: 1134 | Homo sapiens histone acetyltransferase 1 (HAT1), transcript variant 1, mRNA [NM_003642] |

Fig. 3-15

| No. | Probe ID No. | Symbols of genes | Sequence | SEQ ID NO: | Descriptions of genes (letters and numbers within [ ] indicates GenBank accession No.) |
|---|---|---|---|---|---|
| 267 | A_23_P34307 | PIGK | ATTCATTTCAGAGTCTTCTATTGTTGGACCAGTTACATTGTACCA AATGTTTTCCTTTGG | SEQ ID NO: 1135 | Homo sapiens phosphatidylinositol glycan anchor biosynthesis, class K (PIGK), mRNA [NM_005482] |
| 268 | A_23_P247059 | MOBKL1A | CTAGAAGGGGAAAAATCATGTAAGTTATGAAATCAACATAGGCG CTATATTAGAAACTG | SEQ ID NO: 1136 | Homo sapiens MOB1, Mps One Binder kinase activator-like 1A (yeast) (MOBKL1A), mRNA [NM_173468] |
| 269 | A_23_P247198 | SP3 | GACCACGTCAAATTTAAAGGGTAGGTTATTGTACGTTAAAGTGT ATTATAACAGTGTGG | SEQ ID NO: 1137 | Homo sapiens Sp3 transcription factor (SP3), transcript variant 1, mRNA [NM_003111] |
| 270 | A_23_P249083 | FCHO2 | GTGAAATGGTTAAACTTGTGCACTTTGTGTAGTTACCACAGTGTTC ATACCAAGTATTGGG | SEQ ID NO: 1138 | Homo sapiens FCH domain only 2 (FCHO2), mRNA [NM_138782] |
| 271 | A_23_P251467 | CMAH | GCTTACATTTGTGGATCACTACACATAGCCAGAATCAAAAATATTTT AGTTGTTCGATCGAC | SEQ ID NO: 1139 | Homo sapiens cytidine monophosphate-N-acetylneuraminic acid hydroxylase (CMP-N-acetylneuraminate monooxygenase) (CMAH) on chromosome 6 [NR_002174] |
| 272 | A_23_P253704 | RP5-1022P6.2 | TGTCTCTCACTACGTATTACACACTGTGTTGGTTGTGGGTTTGTTT TGTATGTCGGTGTGT | SEQ ID NO: 1140 | Homo sapiens hypothetical protein KIAA1434 (KIAA1434), mRNA [NM_019593] |
| 273 | A_23_P254094 | ZNF567 | ACCTAAGAGTTACCACCTCGGTAGGCTATAACATCAAAAGTAGT TTTTGCATGTTTCA | SEQ ID NO: 1141 | Homo sapiens zinc finger protein 567 (ZNF567), mRNA [NM_152603] |
| 274 | A_23_P255067 | TMCO1 | AACTCAAGAACTCTTTATTTCTATCATTGTTCTCAGAGACACAC ACATCAGACTTGGCAA | SEQ ID NO: 1142 | Homo sapiens transmembrane and coiled-coil domains 1 (TMCO1), mRNA [NM_019026] |
| 275 | A_23_P255244 | SAMD9 | TCAGTGGAGGAAGATTTTCCCTTGCTTCTGCATAAAATTTTAACT CCATAACTTATAAGC | SEQ ID NO: 1143 | Homo sapiens sterile alpha motif domain containing 9 (SAMD9), mRNA [NM_017654] |
| 276 | A_23_P256122 | ZNF451 | TTTTACCTGCTTAGATCCTTTTAATTACTGCTGTGTATATTTGTTGATTTTGGAGTTA AAAGGGAATGGTGTC | SEQ ID NO: 1144 | Homo sapiens zinc finger protein 451 (ZNF451), transcript variant 2, mRNA [NM_015555] |
| 277 | A_23_P256125 | KIAA1468 | GCACTGCTTTAATTACTGGTGTATATTTGTTGATTTTGGAGTTA CAACTGTGGTGATAG | SEQ ID NO: 1145 | Homo sapiens KIAA1468 (KIAA1468), mRNA [NM_020854] |
| 278 | A_23_P257811 | MBNL1 | ATCGTTTCAAACCTGCATGACTGACTGAACAAAAACTCGATGGGAGCCAAA TCTGCCTGAAGATCA | SEQ ID NO: 1146 | Homo sapiens muscleblind-like (Drosophila) (MBNL1), transcript variant 1, mRNA [NM_021038] |
| 279 | A_23_P258470 | CCDC111 | ATGACCCTGTATGTAAGGACAGAAGAAAACTTCAAATCTGACTGTTCC CATTACCTGCTGAAG | SEQ ID NO: 1147 | Homo sapiens coiled-coil domain containing 111 (CCDC111), mRNA [NM_152683] |
| 280 | A_23_P264107 | C14orf106 | AGGAGAGAGTGTTGTATTTGTATTTTCAACTGGGAGTACATGTATTTTCTT TGTAAAGTAGGTTGC | SEQ ID NO: 1148 | Homo sapiens chromosome 14 open reading frame 106 (C14orf106), mRNA [NM_018353] |
| 281 | A_23_P36776 | PUS7L | GGGGCTTCAGTTTCAGATCTGTTCAAACATCGTGTAAAATGGGCATGTTAACATTGCC TACGTCATAGGATTA | SEQ ID NO: 1149 | Homo sapiens pseudouridylate synthase 7 homolog (S. cerevisiae)-like (PUS7L), mRNA [NM_031292] |
| 282 | A_23_P371266 | DNM3 | ACTGTCTTCTTGGCACTTCAGGATTTCTTAATGCTGATATATGG ACTCTTAGAATGGAA | SEQ ID NO: 1150 | Homo sapiens dynamin 3 (DNM3), mRNA [NM_015569] |
| 283 | A_23_P37275 | CGRRF1 | GAGGAAGATAAAGACAAACGAAGACTGTCTTGAAGACATCGTAAG ACTGAAAAGTAGACT | SEQ ID NO: 1151 | Homo sapiens cell growth regulator with ring finger domain 1 (CGRRF1), mRNA [NM_006568] |
| 284 | A_23_P37441 | B2M | TTGTCTTTCAGCAAGGACTGGTCTTCTATCGTGTTAGTACAGT GAATTCACGCCCGACT | SEQ ID NO: 1152 | Homo sapiens beta-2-microglobulin (B2M), mRNA [NM_004048] |
| 285 | A_23_P37636 | FAM96A | CTTGAACGTGACTGATAGGTCTGTTTTAAGAGCCACTGCCCTGTAAT TGTTTGATATATTG | SEQ ID NO: 1153 | Homo sapiens family with sequence similarity 96, member A (FAM96A), transcript variant 1, mRNA [NM_032231] |

Fig. 3-16

| No. | Probe ID No. | Symbols of genes | Sequence | SEQ ID NO: | Descriptions of genes (letters and numbers within [ ] indicates GenBank accession No.) |
|---|---|---|---|---|---|
| 286 | A_23_P38275 | THC2504576 | TCTCGGCAAAATGAAGTTTAATCCCTTGTGACTTCGGAGCGAAG CAAGAATCGGCAAAAG | SEQ ID NO: 1154 | RL26_BOVIN (P61257) 60S ribosomal protein L26, complete [THC2504576] |
| 287 | A_23_P384056 | CCDC14 | TAGCTCAGTATGATCATCTCCCTTCATGTAAGGACGACGTTTAACTC TTAGGAAGCTGAATG | SEQ ID NO: 1155 | Homo sapiens coiled-coil domain containing 14 (CCDC14), mRNA [NM_022757] |
| 288 | A_23_P390734 | FGFR1OP2 | CCAACGAGATACAGAAATGTGCTTTAACATCAGTTGAAAACCTAAAT TTTCTTATGTTGTGG | SEQ ID NO: 1156 | Homo sapiens FGFR1 oncogene partner 2 (FGFR1OP2), mRNA [NM_015633] |
| 289 | A_23_P394276 | RWDD4A | TTGTTCAGGCTTATTATGGCTCATAGATTACAGAGAATGATGCTA GTTACATGCCAATGA | SEQ ID NO: 1157 | Homo sapiens RWD domain containing 4A (RWDD4A), mRNA [NM_152682] |
| 290 | A_23_P394605 | SEC24A | GATTATTCTTCTAATCAAAGATGCATAACAGCTATTATCTAGG GGACCACCAAATGTG | SEQ ID NO: 1158 | Homo sapiens SEC24 related gene family, member A (S. cerevisiae) (SEC24A), mRNA [NM_021982] |
| 291 | A_23_P396353 | NIN | ATCTTCAGGTCTAGTATTTAATAATGACAGTATTAGCCAGGGGCA GATATTATGAGAAAC | SEQ ID NO: 1159 | Homo sapiens ninein (GSK3B interacting protein) (NIN), transcript variant 2, mRNA [NM_020921] |
| 292 | A_23_P399073 | PPM1B | GGTTCAGTAACTTTTCATTTTATACAATTGGGCACGGTACAGAGT GATTGTCAGATAAGG | SEQ ID NO: 1160 | Homo sapiens protein phosphatase 1B (formerly 2C), magnesium-dependent, beta isoform (PPM1B), transcript variant 2, mRNA [NM_177968] |
| 293 | A_23_P40059 | PMS1 | GATCCTCGTCTTACAGCGGAATGGTTCAAGATAAAATTGATACCA GGAGTTTCAATTACT | SEQ ID NO: 1161 | Homo sapiens PMS1 postmeiotic segregation increased 1 (S. cerevisiae) (PMS1), mRNA [NM_000534] |
| 294 | A_23_P405873 | C9orf72 | GAGGAATGGAAGATCAAGGTCAAGATATTATTCCAATGGTTACTGG AGAAGTGATTCCTGT | SEQ ID NO: 1162 | Homo sapiens chromosome 9 open reading frame 72 (C9orf72), transcript variant 2, mRNA [NM_145005] |
| 295 | A_23_P408455 | SLC25A36 | CCATTAACCTACAGACACTGATTTTTATGCTACTCCTTGTAGAAACA AAATTCTGGTTGAC | SEQ ID NO: 1163 | Homo sapiens mRNA; cDNA DKFZp564C053 (from clone DKFZp564C053). [AL049246] |
| 296 | A_23_P41114 | CSTA | AAACAAATGAGACGTTATGGAAGGTGTGCAGTATAAAA CTCAAGTGTTGCTC | SEQ ID NO: 1164 | Homo sapiens cystatin A (stefin A) (CSTA), mRNA [NM_005213] |
| 297 | A_23_P413796 | CCDC5 | GGATGGATGGCTTCTGTTCTGTCTCATCAGTCGCTTAGTAGGCACTACTACAG AGAAACTGGAAGAT | SEQ ID NO: 1165 | Homo sapiens coiled-coil domain containing 5 (spindle associated) (CCDC5), mRNA [NM_138443] |
| 298 | A_23_P41470 | FLJ20035 | TGTCGCTTAATGCTATAGCACTGATTTCTACAACATGGTTCCT TGATAGGATTAGTCC | SEQ ID NO: 1166 | Homo sapiens hypothetical protein FLJ20035 (FLJ20035), mRNA [NM_017631] |
| 299 | A_23_P41512 | C4orf15 | TAAGGCTGTTAGTCTTGAAGATTGAAGATTACTGAAAACTGAATC TTTATTACGTGTCCT | SEQ ID NO: 1167 | Homo sapiens chromosome 4 open reading frame 15 (C4orf15), mRNA [NM_024511] |
| 300 | A_23_P41645 | ELL2 | TGTCTTTTGAAAGTGCTGCCAGTTGAAAAGGGAAGCATTATGTTT ACAAATCTGTTTTGA | SEQ ID NO: 1168 | Homo sapiens elongation factor, RNA polymerase II, 2 (ELL2), mRNA [NM_012081] |
| 301 | A_23_P41664 | ENST00000334994 | TGGCTTGGAGCAGATTCGAGTTCATAACAAATTGTTCCTGAAAA TGAGGCACAGGTCAT | SEQ ID NO: 1169 | Synleurin (CGLQ1891). [Source:Uniprot/SPTREMBL;Acc:Q72Q07] [ENST00000334994] |
| 302 | A_23_P421583 | LSM3 | CATAAGAGAACCGTCCATACATTTTGATATTAAGAAATAATTCCC GGGATTCTTCGACTG | SEQ ID NO: 1170 | Homo sapiens LSM3 homolog, U6 small nuclear RNA associated (S. cerevisiae) (LSM3), mRNA [NM_014463] |
| 303 | A_23_P422083 | TMEM55A | AAATTTATGGAATCAGCTCGTCGGCACTGCCACTGCTTTGCAGTTTTG AAAAAGAAATTGGTT | SEQ ID NO: 1171 | Homo sapiens transmembrane protein 55A (TMEM55A), mRNA [NM_018710] |
| 304 | A_23_P422794 | NSMCE2 | CATTGTTCGGATGATTGAGTCCAAGGTCAAGGCAAAAGCGGAAGAAAAAGGC CTATTGCCCTCAAAT | SEQ ID NO: 1172 | Homo sapiens non-SMC element 2, MMS21 homolog (S. cerevisiae) (NSMCE2), mRNA [NM_173685] |

Fig. 3-17

| No. | Probe ID No. | Symbols of genes | Sequence | SEQ ID NO: | Descriptions of genes (letters and numbers within [ ] indicates GenBank accession No.) |
|---|---|---|---|---|---|
| 305 | A_23_P428468 | ENST00000369577 | AAACTACCGTCAGTCTGAAAAAACTTGAAGTACATTCAAATGATCCAGATATGTCTGTT | SEQ ID NO: 1173 | Zinc finger protein 292. [Source:Uniprot/SWISSPROT;Acc:O60281] [ENST00000369577] |
| 306 | A_23_P429491 | FLJ25416 | GGTTGGTCACCTGACATTGTTTTTCATAAAAAGTGACGTGAAGCCAATTCCTGAACTTTTAA | SEQ ID NO: 1174 | Homo sapiens hypothetical protein FLJ25416 (FLJ25416), mRNA [NM_145018] |
| 307 | A_23_P42975 | PRKAR2B | GCCACATTTTTAGAAGACACTGTTTAACATTTTTGCAAAAACCTTCTTGTAGGAAAAGAGAGC | SEQ ID NO: 1175 | Homo sapiens protein kinase, cAMP-dependent, regulatory, type II, beta (PRKAR2B), mRNA [NM_002736] |
| 308 | A_23_P430161 | EXOC8 | AACTACAGGATTTCTTCAGCTAAAATCTGTGTGTTCCAATTACAGTTGTAGCTGAAGGA | SEQ ID NO: 1176 | Homo sapiens exocyst complex component 8 (EXOC8), mRNA [NM_175876] |
| 309 | A_23_P434809 | S100A8 | AAAGGCATGAAGAAAGGCCACAAAGAGATAGGTGAGTTACTGGTGGGCCCAGAGGCTAGGCGCCT | SEQ ID NO: 1177 | Homo sapiens S100 calcium binding protein A8 (S100A8), mRNA [NM_002964] |
| 310 | A_23_P43946 | CIP29 | AAAGAGCAGAGCGGTTGGGATTGGCTGATGAAAAGTTCCTGATACTTTCTGTCTCCAG | SEQ ID NO: 1178 | Homo sapiens cytokine induced protein 29 kDa (CIP29), mRNA [NM_033082] |
| 311 | A_23_P44257 | COMMD8 | AACATTTTACTTCTGCGGCTTCTATGTTGGGAAGACATGCTCTGATAAAAATAGGTGTC | SEQ ID NO: 1179 | Homo sapiens COMM domain containing 8 (COMMD8), mRNA [NM_017845] |
| 312 | A_23_P4462 | A_23_P4462 | GGTCTGAAAAGACAGGAATAACCTATTTTCGTCTGACCGGCTATTAAGGTCTTCTATA | SEQ ID NO: 1180 | |
| 313 | A_23_P44768 | TBK1 | TGTAGTCTGAGTGGGGCTAAAATAAGTTATTTCTCTGACCGGCTACTGAAATATTTTA | SEQ ID NO: 1181 | Homo sapiens TANK-binding kinase 1 (TBK1), mRNA [NM_013254] |
| 314 | A_23_P44974 | MRPL13 | ATGGAGTAAAACAACTGCTACAGTTCAGCACCTGTTTTATGTGCCGAATCACTGTGGGGA | SEQ ID NO: 1182 | Homo sapiens mitochondrial ribosomal protein L13 (MRPL13), nuclear gene encoding mitochondrial protein, mRNA [NM_014078] |
| 315 | A_23_P46396 | PTBP2 | AACCAGGTGGGACCAAAGTTTATGTGCCTTAGTGTTAATTTACCTTGCATTGTAATATT | SEQ ID NO: 1183 | Homo sapiens polypyrimidine tract binding protein 2 (PTBP2), mRNA [NM_021190] |
| 316 | A_23_P48166 | TWF1 | TGGAGCAGACCAATAGGTGAAGGTGTTATTTTCAGTCAGGAGAGTACCTGTCATGAAGGT | SEQ ID NO: 1184 | Homo sapiens twinfilin, actin-binding protein, homolog 1 (Drosophila) (TWF1), mRNA [NM_002822] |
| 317 | A_23_P48897 | CCPG1 | AAGTCAGAGAGCTCATATATAATCTAATGTCCGACGTATGTCCATTCCATGTACCA | SEQ ID NO: 1185 | Homo sapiens cell cycle progression restoration 8 protein (CPR8) mRNA, complete cds. [AF011794] |
| 318 | A_23_P501080 | ZNF92 | GAATATTAAGTGCTACTTGAGGTACGACATTGAGACTACGATTACATTCTTTTGCAGTATAGTGAG | SEQ ID NO: 1186 | Homo sapiens zinc finger protein 92 (ZNF92), transcript variant 1, mRNA [NM_007139] |
| 319 | A_23_P50195 | A_23_P50195 | CCTGCACAAGTGTGATGATTGCTGGGCAAGGTTACTTCATGTTCACACCGTCTTAGACATC | SEQ ID NO: 1187 | |
| 320 | A_23_P502425 | MRPL47 | GTTTCCACAGTCTTGCTGAAGCCCAAAAGTCAAGTCTTCTTGTCTAAGATGTCTGAACTATTAA | SEQ ID NO: 1188 | Homo sapiens mitochondrial ribosomal protein L47 (MRPL47), nuclear gene encoding mitochondrial protein, transcript variant 1, mRNA [NM_020409] |
| 321 | A_23_P502797 | WDFY1 | GTAACAGTTTAGTGGTTGTTCCATTCCTGAATATGCAGGCTAATTTGTACAGATAGGGAT | SEQ ID NO: 1189 | Homo sapiens WD repeat and FYVE domain containing 1 (WDFY1), mRNA [NM_020830] |
| 322 | A_23_P52832 | RBM12 | CTGGGAGTTCTATAGTAGTCAGAGACTTTAGAAAACGAAACAGAAGATGGCTTGTTGCC | SEQ ID NO: 1190 | Homo sapiens RNA binding motif protein 12 (RBM12), transcript variant 1, mRNA [NM_006047] |
| 323 | A_23_P50907 | ITGAV | AAAGAGGTGATTAAGTGAGGTTATTTACCCCTAAATGGTCCATTCTGCATTGTATTTGAGG | SEQ ID NO: 1191 | Homo sapiens integrin, alpha V (vitronectin receptor, alpha polypeptide, antigen CD51) (ITGAV), mRNA [NM_002210] |

Fig. 3-18

| No. | Probe ID No. | Symbols of genes | Sequence | SEQ ID NO: | Description of genes (letters and numbers within [ ] indicates GenBank accession No.) |
|---|---|---|---|---|---|
| 324 | A_23_P51009 | NDUFB3 | CCGGAATGAAGCTTGGAGATACAATGGGTGGGCTTGCAAAGAGTGTTTCCTTTTGTGATGT | SEQ ID NO: 1192 | Homo sapiens NADH dehydrogenase (ubiquinone) 1 beta subcomplex, 3, 12kDa (NDUFB3), mRNA [NM_002491] |
| 325 | A_23_P51317 | CCDC76 | GCCTTGTTATAAGTTTTATGTCAAGTAAGGTAGTTGTTTAAGTTAGTTACCCATGTCCC | SEQ ID NO: 1193 | Homo sapiens coiled-coil domain containing 76 (CCDC76), mRNA [NM_019083] |
| 326 | A_23_P51487 | GBP3 | AATCCTAAAGCATAAGTTAGTCTTTCCTGATTCTAAAGGTCATACTTGAAATCCTGCC | SEQ ID NO: 1194 | Homo sapiens guanylate binding protein 3 (GBP3), mRNA [NM_018284] |
| 327 | A_23_P53658 | NFYB | TGGGCTCATATTGTGCATACCATTTGTAACGTGGTTTTTCACTTAACAATATATTCGG | SEQ ID NO: 1195 | Homo sapiens nuclear transcription factor Y, beta (NFYB), mRNA [NM_006166] |
| 328 | A_23_P53957 | C14orf112 | TTATACTTCCCAGCTATTCCATCTGTGGATGAAAGTAAGAATGTTGGGCAGTATATTT | SEQ ID NO: 1196 | Homo sapiens chromosome 14 open reading frame 112 (C14orf112), mRNA [NM_016468] |
| 329 | A_23_P5611 | RIF1 | ATGTATTCTTGGCTGCTATGCGTGGTTTTTCAGGAAATTTAATATCTTACTGAGATGTG | SEQ ID NO: 1197 | Homo sapiens RAP1 interacting factor homolog (yeast) (RIF1), mRNA [NM_018471] |
| 330 | A_23_P56330 | ZC3H15 | GTCACCCAAGTAAGAAGTGTATCGTCCTTTGCGTTCCATGTTTGTTTTCATTTGGGCATGTG | SEQ ID NO: 1198 | Homo sapiens zinc finger CCCH-type containing 15 (ZC3H15), mRNA [NM_018471] |
| 331 | A_23_P56734 | HNMT | GCTTTGTCCACCATGGATATATCTGAGTGGTTTATTGATGGTAATGAAATGGAGACCT | SEQ ID NO: 1199 | Homo sapiens histamine N-methyltransferase (HNMT), transcript variant 1, mRNA [NM_006895] |
| 332 | A_23_P56739 | KRCC1 | GATATCCGTGTTCATACACTTTCTTATGTGAATAGGTTCTTTAACTTCTAACAAAGGC | SEQ ID NO: 1200 | Homo sapiens lysine-rich coiled-coil 1 (KRCC1), mRNA [NM_016618] |
| 333 | A_23_P58877 | GOPC | AAGGTTCATGTGATTCATGTGTAAGATGCAGATATTGAACATCCTGATTATGTAATCC | SEQ ID NO: 1201 | Homo sapiens golgi associated PDZ and coiled-coil motif containing (GOPC), transcript variant 1, mRNA [NM_020399] |
| 334 | A_23_P58898 | CASP8AP2 | ATGTATATTGTTATTACTCAGTGACTCTCTAATTCAGCATGCAGATGTGTG | SEQ ID NO: 1202 | Homo sapiens CASP8 associated protein 2 (CASP8AP2), mRNA [NM_012115] |
| 335 | A_23_P58912 | SLC35A1 | ATGATCAGTGCGGTTATGTGGAAAGACAACAAAGAACAAAACGAAGCTATCGAGTGAACTGC | SEQ ID NO: 1203 | Homo sapiens solute carrier family 35 (CMP-sialic acid transporter), member A1 (SLC35A1), mRNA [NM_006416] |
| 336 | A_23_P59637 | DOCK4 | TTTGGCAGTGAGCGCTGGAGGTTGAATTTATCTTGAATTTATCATGTGTGTGTATTTCTGAAGCAG | SEQ ID NO: 1204 | Homo sapiens dedicator of cytokinesis 4 (DOCK4), mRNA [NM_014705] |
| 337 | A_23_P59921 | SUB1 | CAGATTGGGAAAATGAGGTAGGTTGTTCGGGATTTTAAAGGCAAAGTGCTAATTGAT | SEQ ID NO: 1205 | Homo sapiens SUB1 homolog (S. cerevisiae) (SUB1), mRNA [NM_006713] |
| 338 | A_23_P60565 | ZNF354A | AAACCAAAGCTCATCGAAGAATACATCCTTGAGAGAGATGTAATAAATGTAATGGATGTG | SEQ ID NO: 1206 | Homo sapiens zinc finger protein 354A (ZNF354A), mRNA [NM_005649] |
| 339 | A_23_P61674 | CLK4 | GAAAGGCATGCAGTTTGTCCATTGTGACAGATTTGTTTAATAAAACCACATACACACTTTA | SEQ ID NO: 1207 | Homo sapiens CDC-like kinase 4 (CLK4), mRNA [NM_020666] |
| 340 | A_23_P62890 | GBP1 | CAAAGATGCATTTACCTGTGTATCAAGTCAGGAAATCTCATAAGCTGGTACCACTCAGGA | SEQ ID NO: 1208 | Homo sapiens guanylate binding protein 1, interferon-inducible, 67kDa (GBP1), mRNA [NM_002053] |
| 341 | A_23_P63190 | NRAS | ATGAATGTCTGAGATACGTCTGTGACTTATCTACGGATTCTGAAGGAAAGGTATATGTATTTG | SEQ ID NO: 1209 | Homo sapiens neuroblastoma RAS viral (v-ras) oncogene homolog (NRAS), mRNA [NM_002524] |
| 342 | A_23_P63205 | DR1 | TCCCAACTAGATGGCCTAGAGTCCAAACATTACCTTTTGAGATGACATTATTGTCTCCATA | SEQ ID NO: 1210 | Homo sapiens down-regulator of transcription 1, TBP-binding (negative cofactor 2) (DR1), mRNA [NM_001939] |

Fig. 3-19

| No. | Probe ID No. | Symbols of genes | Sequence | SEQ ID NO: | Descriptions of genes (letters and numbers within [ ] indicate GenBank accession No.) |
|---|---|---|---|---|---|
| 343 | A_23_P63343 | UTS2 | AGAATCTGGAAACCATACAAGAAACGTGAGACTCCTGATTGCTTCTGGAAATACTGTGTG | SEQ ID NO: 1211 | Homo sapiens urotensin 2 (UTS2), transcript variant 1, mRNA [NM_021995] |
| 344 | A_23_P63655 | ATP5C1 | AGAGAGCTGAAACCAGCCTGGAATATATGGATTGGGATCTTTAGGTCTGTATGAAAAAGCT | SEQ ID NO: 1212 | Homo sapiens ATP synthase, H+ transporting, mitochondrial F1 complex, gamma polypeptide 1 (ATP5C1), nuclear gene encoding mitochondrial protein, transcript variant 2, mRNA [NM_005174] |
| 345 | A_23_P63769 | ZWINT | TCAAAGATTCAGAGAATTGGGCTTTTGTCATCCACTATTGTATGTTTGTTTCATTGACCTC | SEQ ID NO: 1213 | Homo sapiens ZW10 interactor (ZWINT), transcript variant 4, mRNA [NM_001005414] |
| 346 | A_23_P63896 | FAS | ATGTGTATCCACAGCGTAAGCCAGTCTATGAATAGAATAGAAGAAGGTAGACCTTTTCC | SEQ ID NO: 1214 | Homo sapiens Fas (TNF receptor superfamily, member 6) (FAS), transcript variant 1, mRNA [NM_000043] |
| 347 | A_23_P65262 | RP11-208P3.3 | AGCGAAGACTTAACAAGCAGTGACTACGGTTCCCTTGAGCTAGGATATCACAAGGGTTT | SEQ ID NO: 1215 | Human BRCA2 region, mRNA sequence CG016. [U50529] |
| 348 | A_23_P65768 | C15orf15 | TCCTGCATTGGCATCTACATATAATACAGATATTAGGGATGGTTAGATTGCATCTCAGTGTT | SEQ ID NO: 1216 | Homo sapiens chromosome 15 open reading frame 15 (C15orf15), mRNA [NM_016304] |
| 349 | A_23_P66260 | ZNF267 | TGTGATGAATGTGGTAAAGCGTTCAGCTATAGGTCAGATAGCTACTACAGATCGGAGAAGT | SEQ ID NO: 1217 | Homo sapiens zinc finger protein 267 (ZNF267), transcript variant 498723, mRNA [NM_003414] |
| 350 | A_23_P67992 | C1D | AATGAATAATGACGTTATGAAGTATGCTATCGTAGGCTAGAATTATAGGTACATCGTTT | SEQ ID NO: 1218 | Homo sapiens nuclear DNA-binding protein (C1D), transcript variant 1, mRNA [NM_006333] |
| 351 | A_23_P68472 | DPM1 | CTATTGGCGAGGTTCCAATATCATTGTTGGATCGTGTTTATGGTGAATCCAAGTTGGGAG | SEQ ID NO: 1219 | Homo sapiens dolichyl-phosphate mannosyltransferase polypeptide 1, catalytic subunit (DPM1), mRNA [NM_003859] |
| 352 | A_23_P69791 | C4orf16 | GGCTCCATTGATATTTATTAAGGCTTGCTTCACCTTGTAGTAGAAGAGTGCTTAATGGGAT | SEQ ID NO: 1220 | Homo sapiens chromosome 4 open reading frame 16 (C4orf16), mRNA [NM_018569] |
| 353 | A_23_P69908 | GLRX | CTGATAAAACTTACAGCCCCGCTACAGCAAGAGTATCGTGTGAAAGAGCTCCTACACTTT | SEQ ID NO: 1221 | Homo sapiens glutaredoxin (thioltransferase) (GLRX), mRNA [NM_002064] |
| 354 | A_23_P70047 | MATR3 | GCAACAGACAGAAGTAGTTCTGTAGAGATTGACTTCCTAAGGCTACTTAAGACAACTTGCAC | SEQ ID NO: 1222 | Homo sapiens matrin 3 (MATR3), transcript variant 1, mRNA [NM_199189] |
| 355 | A_23_P70318 | ENPP4 | TGTTTTGGGTGTCGTCCTTCGTTGGTGCCCATATCTGATAAGCTTATGGATTATTGCATTT | SEQ ID NO: 1223 | Homo sapiens ectonucleotide pyrophosphatase/phosphodiesterase 4 (putative function) (ENPP4), mRNA [NM_014936] |
| 356 | A_23_P70328 | CENPQ | CAATGCTTACAGTTTCTCTGTCTGTCTGGTCATGTGGAACTTGAAAAATCCTCAAATGCGTTGAG | SEQ ID NO: 1224 | Homo sapiens centromere protein Q (CENPQ), mRNA [NM_018132] |
| 357 | A_23_P7086 | RPL9 | GGTCTCTTGTTGAAATCCGAAATTTGTTGGGGTGAAAATATATCCGCAGGGTTCGCATGA | SEQ ID NO: 1225 | Homo sapiens ribosomal protein L9 (RPL9), transcript variant 1, mRNA [NM_000661] |
| 358 | A_23_P70838 | STARD3NL | GCATTATGTGTATAGGCGTGAAGTGTTGGACTTGGAAAAGGGGAAGAAAGGAATTGCGAAT | SEQ ID NO: 1226 | Homo sapiens STARD3 N-terminal like (STARD3NL), mRNA [NM_032016] |
| 359 | A_23_P71433 | UBE2W | CATGAGCCCTACTGCCTAAACACTATTTCATTTATTTATGTTTGGAAACCCGTAAACAT | SEQ ID NO: 1227 | Homo sapiens ubiquitin-conjugating enzyme E2W (putative) (UBE2W), transcript variant 1, mRNA [NM_001001481] |
| 360 | A_23_P71727 | CKS2 | GATAAAAGTTCCAGTCAGTTTTCTCTTAAGTGCCTGTTTGAGTTTACTGAAACAGT | SEQ ID NO: 1228 | Homo sapiens CDC28 protein kinase regulatory subunit 2 (CKS2), mRNA [NM_001827] |

Fig. 3-20

| No. | Probe ID No. | Symbols of genes | Sequence | SEQ ID NO: | Descriptions of genes (letters and numbers within [ ] indicates GenBank accession No.) |
|---|---|---|---|---|---|
| 361 | A_23_P72503 | KLHL2 | TTTTTGATATTTAACAATGCTTAAGACTTTAAATGCCACTTCTGAGGAAATGGAACCTGGTG | SEQ ID NO: 1229 | Homo sapiens kelch-like 2, Mayven (Drosophila) (KLHL2), mRNA [NM_007246] |
| 362 | A_23_P72568 | SNX4 | AACCTGAGTAATGAGGCTAAATTTACTCTGGTTGGCTCTCTACACGATGGCATTTCAGGGT | SEQ ID NO: 1230 | Homo sapiens sorting nexin 4 (SNX4), mRNA [NM_003794] |
| 363 | A_23_P7282 | ELMOD2 | TTCAAGTAGCTTTCTCTGGGGGAAAAAGTACCACTTGGACACTTAAGGAATGGGATTT | SEQ ID NO: 1231 | ELMO domain-containing protein 2. [Source:Uniprot/SWISSPROT;Acc:Q8IZ81] [ENST00000323570] |
| 364 | A_23_P3114 | PROS1 | CCAGAACAAATTTTAACAAAAGGAACAACCAGAGGGATATAGTGAATATCGTATCATTG | SEQ ID NO: 1232 | Homo sapiens protein S (alpha) (PROS1), mRNA [NM_000313] |
| 365 | A_23_P3577 | DYNLT3 | TGTTTCTTTATGGTGCTGGGCTTTTGTGCCCTGGAAGATCATAATAGTGACCAAAATATAC | SEQ ID NO: 1233 | Dynein light chain Tctex-type 3 (T-complex-associated testis-expressed 1-like) (Protein 91/23). [Source:Uniprot/SWISSPROT;Acc:P51808] [ENST00000378878] |
| 366 | A_23_P73835 | MOSPD1 | TATGTGGAGATGATTTTTCACGTTTAAACTGTAAGCCAAGTGTAAGAAACTCTTGATAGC | SEQ ID NO: 1234 | Homo sapiens motile sperm domain containing 1 (MOSPD1), mRNA [NM_019556] |
| 367 | A_23_P74001 | S100A12 | TGAAGGCTTTTTACCCAGGAACATGTCCTCAATGAGGGTCTTTTCTTTCCCTCAGCAAAACC | SEQ ID NO: 1235 | Homo sapiens S100 calcium binding protein A12 (S100A12), mRNA [NM_005621] |
| 368 | A_23_P74799 | SLC25A24 | GATTCTGTATCTTTTGGAAAAAAGCCGAGAGTTGAAGATAGTATATTTCTGGTAGTAGTG | SEQ ID NO: 1236 | Homo sapiens solute carrier family 25 (mitochondrial carrier; phosphate carrier), member 24 (SLC25A24), transcript variant 2, mRNA [NM_213651] |
| 369 | A_23_P7543 | ZFYVE16 | TCTGCCTCAGCATTATCTAAATGATCTTGATAGTGCTCTGATACCTGTGATCCATGGTGG | SEQ ID NO: 1237 | Homo sapiens zinc finger, FYVE domain containing 16 (ZFYVE16), mRNA [NM_014733] |
| 370 | A_23_P76159 | EEA1 | TATTGTGTTTACTACTTGTGATCATGTAGTTGTGTCCTTACTTTGTGAGAAAGTTAGGTC | SEQ ID NO: 1238 | Homo sapiens early endosome antigen 1 (EEA1), mRNA [NM_003566] |
| 371 | A_23_P76480 | BF213738 | AAATCGAACAGGACGAATGGGTAGATGGGAGCTACATTTACGAAATCGTTTGGGATGACAGG | SEQ ID NO: 1239 | BF213738 601847628F1 NIH_MGC_55 Homo sapiens cDNA clone IMAGE:4078519 5', mRNA sequence [BF213738] |
| 372 | A_23_P76658 | EFHA1 | AAAGTACTTGAGACCAAGGCCAGCATCAATTCCAGACACATCTTCATGTTCCTAATAGGCTA | SEQ ID NO: 1240 | Homo sapiens EF-hand domain family, member A1 (EFHA1), mRNA [NM_152726] |
| 373 | A_23_P76799 | BAZ1A | TACACATGAATGAATCCAATCTTATAACCTTGAAGTGGTGTACCAGTGCTGGCTGCAGGT | SEQ ID NO: 1241 | Homo sapiens bromodomain adjacent to zinc finger domain, 1A (BAZ1A), transcript variant 1, mRNA [NM_013448] |
| 374 | A_23_P76951 | TXNDC1 | ATTTCTGTAATGTCCCCTTCGTTCAGGGCTCTGTTGCTGTGTGAATCCATTAGATTTACA | SEQ ID NO: 1242 | Homo sapiens thioredoxin domain containing 1 (TXNDC1), mRNA [NM_030755] |
| 375 | A_23_P78018 | ABCA5 | ACTGGAGAAGCAAGAACGCACTTGAAATTTTTCTAAGGTCCTTAATTGAAAATGCTGTGGT | SEQ ID NO: 1243 | Homo sapiens ATP-binding cassette, sub-family A (ABC1), member 5 (ABCA5), transcript variant 1, mRNA [NM_018672] |
| 376 | A_23_P78092 | EVI2A | GCTGAATGAGAGACACTTGGAAAAGAACAAAACAGCTCAGAGGACCGAACCTAGTGATGCAA | SEQ ID NO: 1244 | Homo sapiens ecotropic viral integration site 2A (EVI2A), transcript variant 1, mRNA [NM_001003927] |

Fig. 3-21

| No. | Probe ID No. | Symbols of genes | Sequence | SEQ ID NO: | Descriptions of genes (letters and numbers within [ ] indicates GenBank accession No.) |
|---|---|---|---|---|---|
| 377 | A_23_P79199 | DBI | TGCTCACGATACGGCTCTAACAGATTAGGGGCTAAAACGATTACTGACTTCCTTGAGTA | SEQ ID NO: 1245 | Homo sapiens diazepam binding inhibitor (GABA receptor modulator, acyl-Coenzyme A binding protein) (DBI), transcript variant 1, mRNA [NM_020548] |
| 378 | A_23_P81212 | MRPS18C | ATGGGGTTTATGGCAGTTACATACGAAGGATCCTGCATATGTCAAGGACCGTAAAGTTGT | SEQ ID NO: 1246 | Homo sapiens mitochondrial ribosomal protein S18C (MRPS18C), nuclear gene encoding mitochondrial protein, mRNA [NM_016067] |
| 379 | A_23_P81248 | TAF7 | TGCTAGTTTGGATATGTTTCCTATGCAATAGTAGTTGTTTTCCAGTTATTGAAAACAGGTT | SEQ ID NO: 1247 | Homo sapiens TAF7 RNA polymerase II, TATA box binding protein (TBP)-associated factor, 55kDa (TAF7), mRNA [NM_005642] |
| 380 | A_23_P82047 | BU507302 | TCTGTTTCGTTAATGTCAGGTGCCTGAACATTCAGGAGTTTATAAATTGCTTAATTTGTG | SEQ ID NO: 1248 | AGENCOURT_10309688 NIH_MGC_71 Homo sapiens cDNA clone IMAGE:6501220 5', mRNA sequence [BU507302] |
| 381 | A_23_P8241 | FBXO5 | GATACGAACAGAAAATATCAACTTCTGGAGTCTATTAAATGTGTTGTCACCTTTCTAAAGC | SEQ ID NO: 1249 | Homo sapiens F-box protein 5 (FBXO5), mRNA [NM_012177] |
| 382 | A_23_P83175 | PTPLAD2 | CATCCTTTTTGTGGTGATGATCACGAGTCAAGAGGAAGTCAAGAGAAATATGTGGTGTGT | SEQ ID NO: 1250 | Homo sapiens protein tyrosine phosphatase-like A domain containing 2 (PTPLAD2), mRNA [NM_0010109151] |
| 383 | A_23_P83278 | CHMP5 | CATTGGTCTTTATTTTTTCCATTAAGAACTCATTGCTTGGGAAATGCTTCTTGGTAG | SEQ ID NO: 1251 | Homo sapiens chromatin modifying protein 5 (CHMP5), mRNA [NM_016410] |
| 384 | A_23_P84070 | LARP7 | TGATTTGCTAGAAGGGGATACAGAATGCCATGCTAGAATTAAGACTCCTGAGGATGCTCA | SEQ ID NO: 1252 | Homo sapiens La ribonucleoprotein domain family, member 7 (LARP7), transcript variant 1, mRNA [NM_016648] |
| 385 | A_23_P86653 | SRGN | AGGACTTGGGTCAACATGGATTAGAAGAGGATTTTATGTTATAAAAGAGGATTTCGCAC | SEQ ID NO: 1253 | Homo sapiens serglycin (SRGN), mRNA [NM_002727] |
| 386 | A_23_P87769 | C12orf48 | GTAAGAAATATGGTCAGTTCGGTCCTAATGCATATTGTGACTGTTTGCATATACTCTGTT | SEQ ID NO: 1254 | Homo sapiens chromosome 12 open reading frame 48 (C12orf48), mRNA [NM_017915] |
| 387 | A_23_P87879 | CD69 | TGTGCAATATATGTGATGTGGCAAATCTGTATTAGGAAATATTCTGTAATGTTCAGACCTAG | SEQ ID NO: 1255 | Homo sapiens CD69 molecule (CD69), mRNA [NM_001781] |
| 388 | A_23_P89145 | ZNF83 | GTATAATGAATGTAGCAAGAGCCTTTAGTTTTTTGTTCAAGGCTTAATAACGGTTAGCTAGA | SEQ ID NO: 1256 | Homo sapiens zinc finger protein 83 (ZNF83), mRNA [NM_018300] |
| 389 | A_23_P89755 | RNF138 | TGTGACCGTGATATAGTGCAGAAAGATCCTACCAACCACTGTTTCACTACTTTTTAGTTAA | SEQ ID NO: 1257 | Homo sapiens ring finger protein 138 (RNF138), transcript variant 1, mRNA [NM_016271] |
| 390 | A_23_P89921 | ZNF180 | AGTTGCATCATTTACTACATGATCTTCCAATTAGATAGCTGTAATCTGTTTACAAGC | SEQ ID NO: 1258 | Homo sapiens zinc finger protein 180 (ZNF180), mRNA [NM_013256] |
| 391 | A_23_P9056 | RB1CC1 | TTCATTTTCAAAGGGCATACCTTGTGCATTGTGGCTTATGATGAGCCATATTAATTGC | SEQ ID NO: 1259 | Homo sapiens RB1-inducible coiled-coil 1 (RB1CC1), mRNA [NM_014781] |
| 392 | A_23_P91346 | BC006667 | GGGCTTAGGAGTGAGAGTTCTGCTGTACAAGAAATGATGATGCTCATGAATTTTGACATT | SEQ ID NO: 1260 | Homo sapiens cDNA clone MGC:17708 IMAGE:3868595, complete cds. [BC006667] |
| 393 | A_23_P92410 | CASP3 | TGCACGAAGTCTCACTGGCTGTCAGTATGATGACATTTCACGGGAGATTCTTGTTGCTCAAA | SEQ ID NO: 1261 | Homo sapiens caspase 3, apoptosis-related cysteine peptidase (CASP3), transcript variant alpha, mRNA [NM_004346] |
| 394 | A_23_P92441 | MAD2L1 | TGTACCTGAAAAATGGGAAGAGTCGGACCACAGTTTATTACCAATTCTGAGGAAGTCCG | SEQ ID NO: 1262 | Homo sapiens MAD2 mitotic arrest deficient-like 1 (yeast) (MAD2L1), mRNA [NM_002358] |

Fig. 3-22

| No. | Probe ID No. | Symbols of genes | Sequence | SEQ ID NO: | Descriptions of genes (letters and numbers within [ ] indicates GenBank accession No.) |
|---|---|---|---|---|---|
| 395 | A_23_P92842 | SAR1B | TAATCTGAGATCACCCGAGCGCCATTTGTAAAGAGCAACTTTCCAGCAGTACATTTGAAG | SEQ ID NO: 1263 | Homo sapiens SAR1 gene homolog B (S. cerevisiae) (SAR1B), transcript variant 2, mRNA [NM_016103] |
| 396 | A_23_P933 | RWDD3 | GGAATCTTTTAGTAGTAAAATAGCAGTGTTTTTTGTTGTTTTGGATTGGATTTGGGGAGTGG | SEQ ID NO: 1264 | Homo sapiens RWD domain containing 3 (RWDD3), mRNA [NM_015485] |
| 397 | A_23_P94230 | LY96 | TGAAGGTATTTCTGGGAGCCCAGAAGACAAGAAATGCTCTTTTGCTTGGAGTTTGTGATCCTACGA | SEQ ID NO: 1265 | Homo sapiens lymphocyte antigen 96 (LY96), mRNA [NM_015364] |
| 398 | A_23_P94601 | ANXA1 | GGCTCTTTGTCGAGGAAAACTAAACATTCCCATTGATCTCTCAAGCTATGATCAGAAGACT | SEQ ID NO: 1266 | Homo sapiens annexin A1 (ANXA1), mRNA [NM_000700] |
| 399 | A_23_P94546 | GKAP1 | TACCAGGGTGGCAGAAAAGGGAAAAGAAACTCTGAATCCGACCAGTGTAGGTGATTACAT | SEQ ID NO: 1267 | Homo sapiens G kinase anchoring protein 1 (GKAP1), mRNA [NM_025211] |
| 400 | A_23_P95130 | SLC37A3 | TTGAGGGATACCTAATTTGCATTCGGTTAGGGGGATATTTTCAACCTCTTGCTTTATACT | SEQ ID NO: 1268 | Homo sapiens solute carrier family 37 (glycerol-3-phosphate transporter), member 3 (SLC37A3), transcript variant 1, mRNA [NM_207113] |
| 401 | A_23_P95594 | NAT1 | TGCTTGGAGAGAAAGGTTGTGCCGAAACATGGTGATAGATTTTTTACTATTTAGAATAAG | SEQ ID NO: 1269 | Homo sapiens N-acetyltransferase 1 (arylamine N-acetyltransferase) (NAT1), mRNA [NM_000662] |
| 402 | A_23_P9574 | ECT2 | TAATAGTTAACTGACTATAGATTGTTTTCTATGCATGTATGTGCCACTTCTGAGAGTAG | SEQ ID NO: 1270 | Homo sapiens epithelial cell transforming sequence 2 oncogene (ECT2), mRNA [NM_018098] |
| 403 | A_23_P98382 | TIMM8B | TGTTAGTAAGCAGATTTAAGGTCAGTGGGGGAAGGCTATCAACCCATTGTCAGATCAG | SEQ ID NO: 1271 | Homo sapiens translocase of inner mitochondrial membrane 8 homolog B (yeast) (TIMM8B), mRNA [NM_012459] |
| 404 | A_23_P98446 | SC5DL | TGTGAACACCAGGACTTTAATCTTATGCTTAAAATGCCAGATGTTGTTCGGGGGACAACT | SEQ ID NO: 1272 | Homo sapiens sterol-C5-desaturase (ERG3 delta-5-desaturase homolog, S. cerevisiae)-like (SC5DL), transcript variant 2, mRNA [NM_001024956] |
| 405 | A_23_P99405 | ZMYM2 | GCTGGGTATTACCATGTAAAAAACGCTAGAGTTAGTCTCTTTTGAAGTTGCCATTATTCTATGTAGTGGT | SEQ ID NO: 1273 | Homo sapiens zinc finger, MYM-type 2 (ZMYM2), mRNA [NM_003453] |
| 406 | A_23_P99693 | ZBTB1 | TATTAGAGTCTAAAAAAACCCACTTCATTGGACATGTTGGAATAGCAAAGGAGGTATAGAGA | SEQ ID NO: 1274 | Homo sapiens zinc finger and BTB domain containing 1 (ZBTB1), mRNA [NM_014950] |
| 407 | A_23_P99853 | KIAA1370 | CTTTTGTACTGTTGAAACCACTTCAATTGGACATGTTGGAATAGCAAAAGGGCAGTTAG | SEQ ID NO: 1275 | Homo sapiens KIAA1370 (KIAA1370), mRNA [NM_019600] |
| 408 | A_23_P99980 | HMGB1 | GGATTCTTTCCATTTGCATTTGTTTTATGTAATTTCAGGAGGAAATACTGAACATCTGAGTC | SEQ ID NO: 1276 | Homo sapiens high-mobility group box 1 (HMGB1), mRNA [NM_002128] |
| 409 | A_23_P99985 | HMGB1 | TGGGCCAGGTTTTCAAACAAAGATGCCACATTCAAAATAGGGTATATTTTCCTATATTAC | SEQ ID NO: 1277 | Homo sapiens high-mobility group box 1 (HMGB1), mRNA [NM_002128] |
| 410 | A_23_P100387 | GK | TAAAAGGTTCTGTTTTTGTTTTGGAATCAATAACAGTGCAGTAATTCACCTATGTCTGATGTCTG | SEQ ID NO: 1278 | Homo sapiens glycerol kinase (GK), transcript variant 1, mRNA [NM_203391] |
| 411 | A_24_P105648 | BX111927 | TTATGAGATGGTTCAGTTCAAATAACAGTGCAGTAATTCACCTATATCTAAAAGACTGGC | SEQ ID NO: 1279 | BX111927 Soares_multiple_sclerosis_2NbHMSP Homo sapiens cDNA clone IMAGp998G05619, mRNA sequence [BX111927] |
| 412 | A_24_P105913 | THC2606573 | GTGTGGCTCTAGGAAATGCAGCAATACCAAAGGTCAATGTGGAAATATGGGCATGTTTGCC | SEQ ID NO: 1280 | AY151386 NAP1 [Homo sapiens] (exp=-1; wgp=0; cg=0), partial (35%) [THC2606573] |
| 413 | A_24_P108308 | RPL26L1 | TGGCAAGGTAGTGCAGGTGTACAGAAAGAAATATGCATGTACATCGACCGGGTGCAGCG | SEQ ID NO: 1281 | Homo sapiens ribosomal protein L26-like 1 (RPL26L1), mRNA [NM_016093] |

Fig. 3-23

| No. | Probe ID No. | Symbols of genes | Sequence | SEQ ID NO: | Descriptions of genes (letters and numbers within [ ] indicates GenBank accession No.) |
|---|---|---|---|---|---|
| 414 | A_24_P107257 | LIN7C | TATTAGTGTGGGACTGTGACTGAGGTCTTAAAGACTGAAAGAGTTGGGGTTCATTTTCTG | SEQ ID NO: 1282 | Homo sapiens lin-7 homolog C (C. elegans) (LIN7C), mRNA [NM_018362] |
| 415 | A_24_P11045 | THC2785765 | CCGACGAGAAACGTACACCTGATTTTCAATGACAAATACGGTAGGAACAGAAGTCAGAATAG | SEQ ID NO: 1283 | COX7B_HUMAN (P24311) Cytochrome c oxidase polypeptide VIIb, mitochondrial precursor partial (78%) mRNA [THC2785765] |
| 416 | A_24_P114249 | GALNT3 | ATTTCAAATGCAGAATACTTGAGTCATTTAAAGGTAAATTTTGTTACTGATTCAATTATA | SEQ ID NO: 1284 | Homo sapiens UDP-N-acetyl-alpha-D-galactosamine:polypeptide N-acetylgalactosaminyltransferase 3 (GalNAc-T3) (GALNT3), mRNA [NM_004482] |
| 417 | A_24_P115774 | BIRC2 | GATACGATTTTGGTTAAAGGAAAATGCTGGGGCGCAACATCTTCAAAAGTGTCTAAAAGAA | SEQ ID NO: 1285 | Homo sapiens baculoviral IAP repeat-containing 2 (BIRC2), mRNA [NM_001166] |
| 418 | A_24_P116766 | ZNF207 | TTTCTGAGACGACGTATACGAGTGAAATTAGCTTCTGAGTAAATTTCTAATTATGCCC | SEQ ID NO: 1286 | Homo sapiens mRNA; cDNA DKFZp761N202 (from clone DKFZp761N202), [AL834501] |
| 419 | A_24_P123521 | CLK4 | CGGACACTGAAAAACGACAGATATCAAAGTTGTTGACTTTGGAAGTGCAACGTATGATGAT | SEQ ID NO: 1287 | Homo sapiens CDC-like kinase 4 (CLK4), mRNA [NM_020666] |
| 420 | A_24_P124325 | IKZF5 | GCTACAACTTCTTGAACTTCAAGTTAAGGGTAGAGCATTTACTTTGAAAAATCCACTGG | SEQ ID NO: 1288 | Homo sapiens mRNA; cDNA DKFZp781B0249 (from clone DKFZp781B0249), [CR749800] |
| 421 | A_24_P124992 | PSMA4 | AAACGTCCCTTTGGTGTTGTTCATTGCTACATTGCTGGGATAAGCACTATGGCTTTCAG | SEQ ID NO: 1289 | Homo sapiens proteasome (prosome, macropain) subunit, alpha type, 4 (PSMA4), mRNA [NM_002789] |
| 422 | A_24_P126741 | ENST00000309178 | AGGCTCCAACAGCACACGTAAGAAGATTCAAGATTACTTGGCAACAGCTCACAGGAGCGGAGAAT | SEQ ID NO: 1290 | |
| 423 | A_24_P127181 | LOC442237 | AACTGAAATCTTCCAGAAAATCCAAGTCCAGCTAGTAGAATTGGAGAAAAAGTTCAGTG | SEQ ID NO: 1291 | PREDICTED: Homo sapiens similar to 40S ribosomal protein S7 (S8) (LOC442237), mRNA [XR_018963] |
| 424 | A_24_P127621 | A_24_P127621 | TCGAAAGCAAGTACCACACAAAAGGCATTTCAATGCACTTTCCCACATTCTCAGAAATATTAG | SEQ ID NO: 1292 | |
| 425 | A_24_P129232 | SERINC1 | CAGGTCAGAGAATGATGGAATGTTTTAGAATAAAGTCCTGCTTATAGTATACTACACAG | SEQ ID NO: 1293 | Homo sapiens serine incorporator 1 (SERINC1), mRNA [NM_020755] |
| 426 | A_24_P132787 | RAB18 | TAAAACCTCACATTCTACTTGATTTACACTTCCTAGTCTACATTACATGTGGTTGAAGG | SEQ ID NO: 1294 | Homo sapiens RAB18, member RAS oncogene family (RAB18), mRNA [NM_021252] |
| 427 | A_24_P133991 | ANKRD12 | TTTGGAATGGAGTATATGCCTGAAAAGGTTTTGGATTCAGAAAGAAAAAGGATGGTTAGT | SEQ ID NO: 1295 | Homo sapiens ankyrin repeat domain 12 (ANKRD12), mRNA [NM_015208] |
| 428 | A_24_P134352 | STCH | TGAGTAACTTATTTGTATCAGGAATGTTTTGGTACTGTGTTTCACTCAAAACACTGAC | SEQ ID NO: 1296 | Homo sapiens stress 70 protein chaperone, microsome-associated, 60kDa (STCH), mRNA [NM_006948] |
| 429 | A_24_P135242 | A_24_P135242 | GATGGCAAGAAAAGGTGGCAAGCTACTTGTACGTGGGAACCGAAACTGGGCATTTGTCAT | SEQ ID NO: 1297 | |
| 430 | A_24_P135551 | LOC130865 | TAACAGCATAGCTGTCCCTGTGGGCATTCAGCCAAAAGGTGGTTATGACTAGACTAAAAGT | SEQ ID NO: 1298 | PREDICTED: Homo sapiens similar to 60S ribosomal protein L26 (Silica-induced gene 20 protein) (Sig-20) (LOC130865), mRNA [XR_019454] |
| 431 | A_24_P139208 | USP25 | GAATATACAGCAAGGTGATTATTCAAGAGAATCCGAAAGTACTTGAATAAGGGCTATTG | SEQ ID NO: 1299 | Homo sapiens ubiquitin specific peptidase 25 (USP25), mRNA [NM_013396] |
| 432 | A_24_P144383 | A_24_P144383 | GTGCGTTGAGGCCAAAAGTGCTGGCTAAAAGATGCAAGCATTTTGAACT | SEQ ID NO: 1300 | |

Fig. 3-24

| No. | Probe ID No. | Symbols of genes | Sequence | SEQ ID NO: | Descriptions of genes [letters and numbers within [ ] indicate GenBank accession No.] |
|---|---|---|---|---|---|
| 433 | A_24_P144666 | LOC401975 | TGTCGATGTCAAGACTAATGATGGCTAGTTCTTTAATCTGTTCTGTGTTGGTTTTACTGA | SEQ ID NO: 1301 | PREDICTED: Homo sapiens similar to ribosomal protein S3a (LOC401975), mRNA [XR_017247] |
| 434 | A_24_P148151 | TSNAX | AAAGTTGAGTTATATACTTCTACATACAATGGAAATGCTTTTTAGTAATGATTATTTAGCA | SEQ ID NO: 1302 | Homo sapiens translin-associated factor X (TSNAX), mRNA [NM_005999] |
| 435 | A_24_P152753 | LOC285260 | TGTCTCATACCGAATCCGTGTGCGATTATCAGAAAGGATGAAGATTCACCAAATAAGCT | SEQ ID NO: 1303 | PREDICTED: Homo sapiens similar to ribosomal protein L31 (LOC285260), mRNA [XR_019376] |
| 436 | A_24_P153324 | LOC390413 | GAAGCTAACAAGGTTCAATTAACATGCTGGGGATTGTAGAACCATATATTGCAGGGTA | SEQ ID NO: 1304 | PREDICTED: Homo sapiens similar to 60S ribosomal protein L7 (LOC390413), mRNA [XR_018341] |
| 437 | A_24_P153511 | OSBPL8 | CCTTGTGCCATATACAACACAAAATTTGTGGAAGGCAGTTTTAACTTTCTGAAGATATC | SEQ ID NO: 1305 | Homo sapiens oxysterol binding protein-like 8 (OSBPL8), transcript variant 1, mRNA [NM_020841] |
| 438 | A_24_P15765 | AK098605 | TCCAAGTCTGGCTAGTACGTGAATTGGAGAAAAAGTTGGGAAGCATGTTGTCTTTATTG | SEQ ID NO: 1306 | Homo sapiens cDNA FLJ25739 fis, clone TST05834, [AK098605] |
| 439 | A_24_P161914 | LOC130728 | CTATACTGTTGGAAAACACTTCAAAGAAAAATAACTTCCTGCGGCCATTCAAATTACTTC | SEQ ID NO: 1307 | PREDICTED: Homo sapiens similar to 60S ribosomal protein L7 (LOC130728), mRNA [XR_019248] |
| 440 | A_24_P165816 | AK023645 | AAGATTGAATGGCTAGGAGTAATTCTTGTTCTCGTATAGGGAACTTAACTTCACTGTGGAA | SEQ ID NO: 1308 | Homo sapiens cDNA FLJ13583 fis, clone PLACE1009050, [AK023645] |
| 441 | A_24_P167063 | ZNF518 | AAAGAAAGCCATACATAGAATGCTTCAAGCTATGTCTGCTATGCACATTATACTGTAGTG | SEQ ID NO: 1309 | Homo sapiens zinc finger protein 518 (ZNF518), mRNA [NM_014803] |
| 442 | A_24_P169378 | RPS7 | AACTGAAATCTTTGGAGAAAATCCAAATCGGCTAGTAAGTAAGTTGGAGAAAAAGTTCA | SEQ ID NO: 1310 | Homo sapiens ribosomal protein S7 (RPS7), mRNA [NM_001011] |
| 443 | A_24_P170025 | A_24_P170025 | TCCATGCTATTGTTGTGTCAGAGGGAGTACCTGTTATTAAAGTGGCCATTGATAATGCTC | SEQ ID NO: 1311 | |
| 444 | A_24_P171873 | FBXO4 | GATTCCACAGATTCAAAAGTGTGTGAAGTGTAGATGGGTTCATCTATGTTGCAAATGC | SEQ ID NO: 1312 | Homo sapiens F-box protein 4 (FBXO4), transcript variant 1, mRNA [NM_012176] |
| 445 | A_24_P172481 | TRIM22 | TGCCCCTTAAAGATTGAAGAAGAGAAACTTGTCAACTCATATCCACGTTATCTAGGCAA | SEQ ID NO: 1313 | Homo sapiens tripartite motif-containing 22 (TRIM22), mRNA [NM_006074] |
| 446 | A_24_P175059 | ATG5 | TTGCACAAGAGGCTGGTCTGAATATGATTGTTCACATTAAGAGTGTTTATCGTCGGTTC | SEQ ID NO: 1314 | Homo sapiens ATG5 autophagy related 5 homolog (S. cerevisiae) (ATG5), mRNA [NM_004849] |
| 447 | A_24_P175176 | PHTF2 | AGATTGAGGTTAACTTAAGTTGGGAGTTGATTTATTAAGTACAGTATACCTCTCAACAG | SEQ ID NO: 1315 | Homo sapiens putative homeodomain transcription factor 2 (PHTF2), mRNA [NM_020432] |
| 448 | A_24_P175187 | SAMD9 | CAACCAGGGATACGTAATGAAACAGTAATTTTCCCCTAATAAATATGGATATATGGGCAG | SEQ ID NO: 1316 | Homo sapiens sterile alpha motif domain containing 9 (SAMD9), mRNA [NM_017654] |
| 449 | A_24_P175188 | SAMD9 | TGCCAATGTACTGGCAGATTAACATAACGTATGTTTTGAACAAAACAACCAGGGATA | SEQ ID NO: 1317 | Homo sapiens sterile alpha motif domain containing 9 (SAMD9), mRNA [NM_017654] |
| 450 | A_24_P178351 | TPT1 | GAAAGAGACAGAAAAGAGATAAAACGTTTATGACAGGGGCTGCAGAACAAATCAAGCAC | SEQ ID NO: 1318 | Homo sapiens tumor protein, translationally-controlled 1 (TPT1), mRNA [NM_003295] |
| 451 | A_24_P180424 | TMEM30A | CAATGTGTATCGACATCTCTCTTTAGTTAAGGACGCAATTGTTTTGGTTGGTTTTCCTAAG | SEQ ID NO: 1319 | Homo sapiens transmembrane protein 30A (TMEM30A), mRNA [NM_018247] |
| 452 | A_24_P183864 | IMPA1 | TCAGCCTTATCCCTTGGCACGTAACACAGACTACTAGACTTATTGTAGGTTCGTTTGAGCT | SEQ ID NO: 1320 | Homo sapiens inositol(myo)-1(or 4)-monophosphatase 1 (IMPA1), mRNA [NM_005536] |
| 453 | A_24_P183944 | LOC389404 | AGGAACCCTGCGGAGGGAACTTCAATCACATGTAGAACTGACTCAGTGTTCTGGAAAGAAAAA | SEQ ID NO: 1321 | PREDICTED: Homo sapiens similar to 60S ribosomal protein L9 (LOC389404), mRNA [XR_018133] |

Fig. 3-25

| No. | Probe ID No. | Symbols of genes | Sequence | SEQ ID NO: | Descriptions of genes (letters and numbers within [ ] indicates GenBank accession No.) |
|---|---|---|---|---|---|
| 454 | A_24_P191417 | NAB1 | AAGTTTCCTTAACTATCTTATGTTCTTAGTCTTGTTCAAGCTTAGTG ATAAGGTGAAGCAC | SEQ ID NO: 1322 | Homo sapiens NGFI-A binding protein 1 (EGR1 binding protein 1) (NAB1), mRNA [NM_005966] |
| 455 | A_24_P191833 | SFRS12 | AAGGACTTACGAGTATATGGGAAGGTTATGGTTTTATGTTTAAGG ATACGTTTACTTGAG | SEQ ID NO: 1323 | Homo sapiens splicing factor, arginine/serine-rich 12 (SFRS12), transcript variant 2, mRNA [NM_139168] |
| 456 | A_24_P192555 | DNAJA1 | TATAGGAAGGTGTTCTTTAGGTATGTTACAGGATTACTTTAAACC ATTTGACTTTCGCTC | SEQ ID NO: 1324 | DnaJ homolog subfamily A member 1 (Heat shock 40 kDa protein 4) (DnaJ protein homolog 2) (HSJ-2) (HSDJ). [Source:Uniprot/SWISSPROT;Acc:P31689] [ENST00000330899] |
| 457 | A_24_P194313 | C21orf66 | ATTTAAATTAAGCCTCTCAGTTAATTGTCCCGCTGTAAACGATGTG TGCAGTGTAAATTGT | SEQ ID NO: 1325 | Homo sapiens chromosome 21 open reading frame 66 (C21orf66), transcript variant 1, mRNA [NM_016631] |
| 458 | A_24_P199500 | RNF2 | AAACTGCTTAGATTTTGTTGATGACATTAGATTAGTTAGTTCATT AAATAACTAAATTCC | SEQ ID NO: 1326 | Homo sapiens ring finger protein 2 (RNF2), mRNA [NM_007212] |
| 459 | A_24_P201702 | CLEC2B | ATTGGAATTCAAGTAAATACAAGTGTTCCACTCAACATGCCGACC TAACTATATATTGACA | SEQ ID NO: 1327 | Homo sapiens C-type lectin domain family 2, member B (CLEC2B), mRNA [NM_005127] |
| 460 | A_24_P203909 | RPL34 | GAGGGGTTCGTCGTGTAAGACTTAAAGTTCTTATGAAATTGTCCA AAGAAACAAACATG | SEQ ID NO: 1328 | Homo sapiens ribosomal protein L34 (RPL34), transcript variant 2, mRNA [NM_033625] |
| 461 | A_24_P208045 | EDEM3 | TTTAGAGGGGGGTAGAATTTAGTAAATATTCCAGCCAGGTGTTTTT ATGCACAAGGCTCA | SEQ ID NO: 1329 | Homo sapiens ER degradation enhancer, mannosidase alpha-like 3 (EDEM3), mRNA [NM_025191] |
| 462 | A_24_P20996 | BC043173 | AAGGAAAATGTTCATATATGTATATGAATCTCTCTTTATGCTG AAGGGCTCTGATTGG | SEQ ID NO: 1330 | Homo sapiens cDNA clone IMAGE:5287121. [BC043173] |
| 463 | A_24_P212864 | LOC645161 | ACAGAAGTACAACGTTGCGATCCATGATCCGAAAGAATGAATGAAGT TAGGCTGTATGAGG | SEQ ID NO: 1331 | PREDICTED: Homo sapiens similar to 60S ribosomal protein L26 (LOC646161), mRNA [XR_018048] |
| 464 | A_24_P213375 | A_24_P213375 | AAATGTTGTTCCATGATCAAAAATGGGAGACAATGATTCTTCATC TGTTCTGTGTTGGTT | SEQ ID NO: 1332 | |
| 465 | A_24_P213783 | RPL31 | CTTTGGTTACCTATGTACGTGTTTACGACTTTCAAAAATCTACAGA CAGTCAATGATGATG | SEQ ID NO: 1333 | Homo sapiens ribosomal protein L31 (RPL31), mRNA [NM_000993] |
| 466 | A_24_P221375 | A_24_P221375 | TACTTTGGTTACCCATGATCACCACTACCACTTTCAAAAATCTACAGAG AGTCAATGTGGAGGA | SEQ ID NO: 1334 | |
| 467 | A_24_P222911 | SFRS7 | CAGAAAATGTCAATGAGAGTAAAGTGGTTTTGTAAATGTCAGCTAT ATTTAGCAACACTCC | SEQ ID NO: 1335 | Homo sapiens splicing factor, arginine/serine-rich 7, 35kDa (SFRS7), mRNA [NM_001031684] |
| 468 | A_24_P225308 | ARID4B | GTTGAAAATGGTTTCGAAGTTATTCAAAGTTTCAAGGACTGTAAA GATTTGTTCACAGCA | SEQ ID NO: 1336 | Homo sapiens AT rich interactive domain 4B (RBP1-like) (ARID4B), transcript variant 1, mRNA [NM_016374] |
| 469 | A_24_P225468 | ANP32E | TCATCTTAGTGTGCATCGAAAATTAGAGTACTTTGGTTTGAAAAC AACACTTAGAGCCTC | SEQ ID NO: 1337 | Homo sapiens acidic (leucine-rich) nuclear phosphoprotein 32 family, member E (ANP32E), mRNA [NM_030920] |
| 470 | A_24_P225719 | PREI3 | GACTATTTTCTTAGTGAATATTTATACTAAGGTAGTGACTGAGAT TTGGTGATCGTGGTG | SEQ ID NO: 1338 | Homo sapiens preimplantation protein 3 (PREI3), transcript variant 1, mRNA [NM_015387] OTTHUMP00000016694. [Source:Uniprot/SPTREMBL;Acc:Q9NU98] |
| 471 | A_24_P229066 | ENST00000078131 | AAGAAGCTCCAGAACAAGAGACGAGGTTATGTCACCGATCTGATG AACCAGATTCAAGAGA | SEQ ID NO: 1339 | [ENST00000078131] |

Fig. 3-26

| No. | Probe ID No. | Symbols of genes | Sequence | SEQ ID NO: | Descriptions of genes (letters and numbers within [ ] indicate GenBank accession No.) |
|---|---|---|---|---|---|
| 472 | A_24_P232856 | RPL9 | GAACCCTGCGGAGGGACTTCAATCACATCAATGTAGAAACTCAGCCTTCTTGGAAAGAAAA | SEQ ID NO: 1340 | Homo sapiens ribosomal protein L9 (RPL9), transcript variant 1, mRNA [NM_000661] |
| 473 | A_24_P234792 | CSNK1G3 | GGGTTTTTGGATTGTACAGTGTTTATATGATCTGAACTCGTTATACATAAGAAGGTGTG | SEQ ID NO: 1341 | Homo sapiens casein kinase 1, gamma 3 (CSNK1G3), transcript variant 1, mRNA [NM_004384] |
| 474 | A_24_P235429 | ABCA1 | CCAAAGAGCCATGTGTGTCATGTAATACTGAACCACTTGATATTGAGAGATTAATTTGTAC | SEQ ID NO: 1342 | Homo sapiens ATP-binding cassette, sub-family A (ABC1), member 1 (ABCA1), mRNA [NM_005502] |
| 475 | A_24_P236008 | SCYL2 | ATAGAGTATGTACTTGTCTGGTTTTGTTTTGTTTTATTTTGGAATGCTTATAAGCTCC | SEQ ID NO: 1343 | Homo sapiens mRNA for KIAA1360 protein, partial cds. [AB037781] |
| 476 | A_24_P242299 | ZRANB2 | GACTTTTTGAAAGTCTACCTTCTAAATTGCCCCGAGGATCTAGATTGTAGATGTTACCAT | SEQ ID NO: 1344 | Homo sapiens zinc finger, RAN-binding domain containing 2 (ZRANB2), transcript variant 2, mRNA [NM_005455] |
| 477 | A_24_P243749 | PDK4 | ATTTGACATTTGTGTGTGTAATTTCATGGTGGCTGGCCTAGTGTTGTGGTGCTTCTGGTAATGGTA | SEQ ID NO: 1345 | Homo sapiens pyruvate dehydrogenase kinase, isozyme 4 (PDK4), mRNA [NM_002612] |
| 478 | A_24_P250922 | PTGS2 | TGAGATATTTAAGGTTGAATGTTTGTCCTTAGGATAGGCCTATGTGCTAGGCCACAAAGA | SEQ ID NO: 1346 | Homo sapiens prostaglandin-endoperoxide synthase 2 (prostaglandin G/H synthase and cyclooxygenase) (PTGS2), mRNA [NM_000963] |
| 479 | A_24_P25328 | ZMYM6 | AGCACTATTTAAATCAGTGTCTGTAACTCAGTTTTGGATAAAATGCAAAGACAAGTTACCC | SEQ ID NO: 1347 | Homo sapiens zinc finger, MYM-type 6 (ZMYM6), mRNA [NM_007167] |
| 480 | A_24_P255252 | A_24_P255252 | TGGAGTACTGGAAGGATGGTGTGACTCCAATGTGATTGTTCTTTGAGGATGATTTAGAAA | SEQ ID NO: 1348 | |
| 481 | A_24_P257151 | CLK1 | TATGGAAGTCTGTGAATTTTTGCACAGTAATAAGTTGACTCACACAGACTAAAGCCTG | SEQ ID NO: 1349 | Homo sapiens CDC-like kinase 1 (CLK1), transcript variant 1, mRNA [NM_004071] |
| 482 | A_24_P263524 | TXNDC9 | TGACTTCAGCACAGAAAAGTTTAGAATGGGGGCTCAGTTGTTCTGACATTCTTAATTACAG | SEQ ID NO: 1350 | Homo sapiens thioredoxin domain containing 9 (TXNDC9), mRNA [NM_005783] |
| 483 | A_24_P265856 | SENP7 | TTGTGTGTGTTGGGGGGTAGTTTAAAGGTGAGTATTGTTTTGTACATCTAATTTTGGGA | SEQ ID NO: 1351 | Homo sapiens SUMO1/sentrin specific peptidase 7 (SENP7), transcript variant 1, mRNA [NM_020654] |
| 484 | A_24_P268786 | MYNN | TGGAGAGGATCATACTTTGAGTGAACAGGAATTCCATACAAAAAAGTCCTTTATCAGAAAC | SEQ ID NO: 1352 | Homo sapiens myoneurin (MYNN), mRNA [NM_018657] |
| 485 | A_24_P268917 | RAB33B | CCCAGAATCTAATGTAGTTCGGCTATTAATAACAATGGATTATTGAAAGTATATTTGAAAT | SEQ ID NO: 1353 | Homo sapiens RAB33B, member RAS oncogene family (RAB33B), mRNA [NM_031296] |
| 486 | A_24_P276583 | TMCC1 | CCTTCATTTTCTGTGTATATTCTCTGTACTATGTCGATCGACAGAACATTCAGAAGATTC | SEQ ID NO: 1354 | Homo sapiens transmembrane and coiled-coil domains 1 (TMCC1), mRNA [NM_019026] |
| 487 | A_24_P278008 | DCTN6 | CTATGAAAAGGAAGCTGAACTCCAACTTCCAAGTAAAGAACTAAGAAGACAGTGTAAAGCATGAAGATAAC | SEQ ID NO: 1355 | Homo sapiens dynactin 6 (DCTN6), mRNA [NM_006571] |
| 488 | A_24_P278460 | MLSTD2 | ACCCATGGAACAATATGCTTAGGATTACAAGGAAGCAGTCGTTAGTTACAGTTCTTGTCTG | SEQ ID NO: 1356 | Homo sapiens male sterility domain containing 2 (MLSTD2), mRNA [NM_032228] |
| 489 | A_24_P280897 | LOC388532 | AGCACTCTGAGAGCTGGGATAGGCTTCCTGAAATACATGAAGGAAAATGATCAGAAAAAGA | SEQ ID NO: 1357 | PREDICTED: Homo sapiens similar to ribosomal protein L21 (LOC388532), mRNA [XM_001127035] |
| 490 | A_24_P285179 | THC2649313 | AGTGGGAATTTTGAAATGGCATGTCCTATATATTGTGGCATATTTGTTGGCACAGATTTGCA | SEQ ID NO: 1358 | |

Fig. 3-27

| No. | Probe ID No. | Symbols of genes | Sequence | SEQ ID NO: | Descriptions of genes (letters and numbers within [ ] indicates GenBank accession No.) |
|---|---|---|---|---|---|
| 491 | A_24_P286054 | ZFYVE16 | GTGTATGTATTCTGCCATGTAAGTAATTGAACAGTCTTAAAATAACCAAATGGTAGAGGG | SEQ ID NO: 1359 | Zinc finger FYVE domain-containing protein 16 (Endofin) (Endosome- associated FYVE domain protein). [Source:Uniprot/SWISSPROT;Acc:Q7Z3T8] [ENST00000380248] |
| 492 | A_24_P287756 | NUDT21 | CCCATACTTACTTCACTTGTTATACATCACTGATTATTTGGGTTAAACTGGACTCATTTC | SEQ ID NO: 1360 | Homo sapiens nudix (nucleoside diphosphate linked moiety X)-type motif 21 (NUDT21), mRNA [NM_007006] |
| 493 | A_24_P288754 | PIGA | CTTTCTGGATACCTTAATTGTAACTGTCAGTTTGCACTGGTCGGTATATGGAAACACATT | SEQ ID NO: 1361 | Homo sapiens phosphatidylinositol glycan anchor biosynthesis, class A (paroxysmal nocturnal hemoglobinuria) (PIGA), transcript variant 1, mRNA [NM_002641] |
| 494 | A_24_P290257 | A_24_P290257 | CCAATTCATTCAACATAGAACAAGCCAATTATACCATCCAGTCATTGAAGGACACACAAGA | SEQ ID NO: 1362 | |
| 495 | A_24_P295643 | BLOC1S2 | GTTTATTTTCTATGTGAGTCAACATTGACATGCGATCCAGTTTGGGAAATGTGATGAAAACA | SEQ ID NO: 1363 | Homo sapiens biogenesis of lysosome-related organelles complex-1, subunit 2 (BLOC1S2), transcript variant 2, mRNA [NM_001001342] |
| 496 | A_24_P298238 | A_24_P298238 | ATGCTTGAAGGAAATGACATTGAGCTTGTTTGAATTCAGCAAGCCACAACAGTTAAAAAC | SEQ ID NO: 1364 | |
| 497 | A_24_P298604 | LOC731599 | GATGGAAATCATGACCAGAGGTGCGGCAAATGACTTGAAAGAATTGGTCAATAAAATGAT | SEQ ID NO: 1365 | PREDICTED: Homo sapiens hypothetical protein LOC731599 (LOC731599), mRNA [XR_015536] |
| 498 | A_24_P306527 | ENST00000308989 | ACCGACATCCGTGCGTGGTTATCCAGAAAATGTAATGAGGATGAAGATTCACCAAATAAGT | SEQ ID NO: 1366 | PREDICTED: Homo sapiens similar to ribosomal protein L3i (LOC729005), mRNA [XM_001133428] |
| 499 | A_24_P306726 | TPT1 | GACCAGAAACAAGTAAAACCTTTTATGACAGGAGCTGCAAAACAATCAAGGAGATCCTTG | SEQ ID NO: 1367 | Homo sapiens tumor protein, translationally-controlled 1 (TPT1), mRNA [NM_003295] |
| 500 | A_24_P309415 | TMEM123 | GTTTCCTCTGCATTGGGTTTGAAGTAGTTTAGTTATGTCTTTTCTCTATGTAAGTAG | SEQ ID NO: 1368 | Homo sapiens transmembrane protein 123 (TMEM123), mRNA [NM_052932] |
| 501 | A_24_P310894 | CAPZA1 | TGTATTATTTGTCCTTCATACTATCCATCGATACCACACTATCTTCTGTATCAGGTAGTC | SEQ ID NO: 1369 | Homo sapiens capping protein (actin filament) muscle Z-line, alpha 1 (CAPZA1), mRNA [NM_006135] |
| 502 | A_24_P312417 | ZBTB26 | AGAGGAGGAAGATTTTAAAAACCTTTATCATTCAGCATTTGTATTTTATGGATCCCCAGG | SEQ ID NO: 1370 | Zinc finger and BTB domain-containing protein 26 (Zinc finger protein 481) (Zinc finger protein Bioref). [Source:Uniprot/SWISSPROT;Acc:Q9HCK0] [ENST00000373656] |
| 503 | A_24_P315326 | LOC341412 | AAGCTCTATATGTTGGTTACCAATGTAGCCGTTACGGGTTCAAAAATCACAGGGCAATG | SEQ ID NO: 1371 | AGENCOURT_10640955 NIH_MGC_126 Homo sapiens cDNA clone IMAGE:6723568 5', mRNA sequence [CA452253] |
| 504 | A_24_P316074 | LOC730902 | TATCAATGGTGTGAGCCCAAAGGTCAAAGGTCGTTGCAGCTTCTTCCCTTCGTCAAATCTT | SEQ ID NO: 1372 | PREDICTED: Homo sapiens similar to 60S ribosomal protein L7 (LOC730902), mRNA [XR_015600] |
| 505 | A_24_P320328 | SUB1 | CAGAAAACCTGTAAAGAAACAAAAGACAGGTGAGACTTCGAGAGCCCTGTCATCTTCTA | SEQ ID NO: 1373 | Homo sapiens SUB1 homolog (S. cerevisiae) (SUB1), mRNA [NM_006713] |
| 506 | A_24_P321511 | GOLT1B | TTAGAGCAAGAATAGTATCTGCTAATGTAAGGAGACATCGTATTTAACTCCTTTGTAGAC | SEQ ID NO: 1374 | Homo sapiens golgi transport 1 homolog B (S. cerevisiae) (GOLT1B), mRNA [NM_016072] |
| 507 | A_24_P324224 | A_24_P324224 | AAAGCTGTCTGGCCAAAGGAATTCCTATAGGCCATGTGCGGTTGTCCAGAAAA | SEQ ID NO: 1375 | |

Fig. 3-28

| No. | Probe ID No. | Symbols of genes | Sequence | SEQ ID NO: | Descriptions of genes (letters and numbers within [ ] indicates GenBank accession No.) |
|---|---|---|---|---|---|
| 508 | A_24_P324506 | A_24_P324506 | GGAATATAAGGCAGCTAATTGCAAATACAAGTATGGCTATTTCCTGTGGACATGCTGTGT | SEQ ID NO: 1376 | |
| 509 | A_24_P324581 | KIAA1466 | ATAATAGCTCATAGAATGAATTGCTGTACCAACCAAGGCTAAAAGAATTAAGTAGCCC | SEQ ID NO: 1377 | Homo sapiens mRNA for KIAA1466 protein, partial cds. [AB040899] |
| 510 | A_24_P330397 | STRN3 | ATGGTGTAACTAAAGATTTTGTTTGTGTAATGCATGATGATTAAGACAATAAAGTATTTTTC | SEQ ID NO: 1378 | Homo sapiens striatin, calmodulin binding protein 3 (STRN3), mRNA [NM_014574] |
| 511 | A_24_P33213 | A_24_P33213 | GACCATATATTACATGGGGGTACCCAAATCTGAAGTCAGTAAATGAACTTATGTAGAAGG | SEQ ID NO: 1379 | |
| 512 | A_24_P333112 | A_24_P333112 | GGTCATCAGAATCAGAGGTATCAAGGTGTGAGCCCACAGGACCAAAAGGTATTGCAACTT | SEQ ID NO: 1380 | |
| 513 | A_24_P334361 | FLJ20035 | GTGAAAATGAAGACGAACAACGTTGTCTTAGCCTTTGAACAACTGAGTAAGACTTTTTGGG | SEQ ID NO: 1381 | Homo sapiens hypothetical protein FLJ20035 (FLJ20035), mRNA [NM_017631] |
| 514 | A_24_P33607 | LOC652558 | TAAGAAAATAATTGCTTTGACACAGAACAACGCGTTTGATTGCTGCATCTGTTGGTAAATATGG | SEQ ID NO: 1382 | PREDICTED: Homo sapiens similar to 60S ribosomal protein L7 (LOC652558), mRNA [XR_019386] |
| 515 | A_24_P349636 | LOC388401 | AGTTGCTTCGACAGATAACACTTTGATTGCTGCGATCTGTCTTGGTAAATATAGCATCAACTG | SEQ ID NO: 1383 | PREDICTED: Homo sapiens similar to 60S ribosomal protein L7 (LOC388401), mRNA [XR_016879] |
| 516 | A_24_P351435 | CRBN | GAAAGTGAAAGCAATTGGAAGACAAATGGTTCAAAGTCCTTGGTAAAAGAACAGTCAGA | SEQ ID NO: 1384 | Homo sapiens cereblon (CRBN), mRNA [NM_016302] |
| 517 | A_24_P352645 | MRPL42 | TTTTTAGTGCATGACAATCACAATGACAACAAAGGGTGGTTTTCTTTTCACCGAAGAATGTGCTTTCG | SEQ ID NO: 1385 | Homo sapiens mitochondrial ribosomal protein L42 (MRPL42), nuclear gene encoding mitochondrial protein, transcript variant 3, mRNA [NM_172178] |
| 518 | A_24_P354257 | AK025305 | GAAAAACAGATGTTTTTCTTAAGTGAAAGCAGCTTTAATTGCTCTAACGGTACATCGTG | SEQ ID NO: 1386 | Homo sapiens cDNA: FLJ21652 fis, clone COL08582. [AK025305] |
| 519 | A_24_P354412 | AK091335 | TGTAGACTGAAGGAGTCTTTCAAAACACCCCAGCATTAAATCTCACTCTGGGCTGCTCT | SEQ ID NO: 1387 | Homo sapiens cDNA FLJ34016 fis, clone FCBBF2002541. [AK091335] |
| 520 | A_24_P354954 | CCDC126 | AATGGAACCTCTGAGGAGCTTTAGCCAGGTGTATATAATAAAGGTACTTTGTCTGCTGATT | SEQ ID NO: 1388 | Homo sapiens coiled-coil domain containing 126 (CCDC126), mRNA [NM_138771] |
| 521 | A_24_P357576 | KIAA1370 | TGCTGCATATGAACTCAAATCTTACACTGAATCACCACAAAGGGTCAGTTTTCACCAAG | SEQ ID NO: 1389 | Homo sapiens KIAA1370 (KIAA1370), mRNA [NM_019600] |
| 522 | A_24_P362646 | TXNDC9 | CTCGACATTGAGGTGTAAAATAGTAGACAGACATCCTGGCAATATTGTCCAAGAAACACGT | SEQ ID NO: 1390 | Homo sapiens thioredoxin domain containing 9 (TXNDC9), mRNA [NM_005783] |
| 523 | A_24_P364807 | AYTL1 | TGTAACTCTTGTTCTAGGTAATCGTTCTGTCTGCAAGAAAAGTTCTCAGGGCGTCTGTGTAA | SEQ ID NO: 1391 | Homo sapiens mRNA; cDNA DKFZp686H22112 (from clone DKFZp686H22112). [BX641069] |
| 524 | A_24_P365048 | C17orf42 | CGGACTGAGTGGAAAAGACGCTAGTGAAGCAGTTTCTCTTCGATTCTATACTGAAGGGAT | SEQ ID NO: 1392 | Homo sapiens chromosome 17 open reading frame 42 (C17orf42), mRNA [NM_024633] |
| 525 | A_24_P366105 | LOC391126 | ACTTCGAACGAAATCAAAAATAGGCAAAAGGCATTTCAATGAATGCGTTCCACATTGCAGG | SEQ ID NO: 1393 | PREDICTED: Homo sapiens similar to 60S ribosomal protein L26 (Silica-induced gene 20 protein) (SIG-20) (LOC391126), mRNA [XR_019504] |
| 526 | A_24_P366546 | RPL31P10 | CGGCTGTCCAGAAAACGTAATGAGGATGAAGATTCAAATAAGGTCTATACTTTGGTTACC | SEQ ID NO: 1394 | PREDICTED: Homo sapiens similar to ribosomal protein L31 (LOC390283), mRNA [XR_018695] |
| 527 | A_24_P367139 | A_24_P367139 | ACACCATGAAACTGCTCAGGCCATGAAGGGCTATACATAAAAGCAAAGAAGTATCTGAAGG | SEQ ID NO: 1395 | |

Fig. 3-29

| No. | Probe ID No. | Symbols of genes | Sequence | SEQ ID NO: | Descriptions of genes (letters and numbers within [ ] indicate GenBank accession No.) |
|---|---|---|---|---|---|
| 528 | A_24_P367191 | LOC652890 | AGTTAACATGCTGAGGACTGTAAAGCCAATATATTGGCTGTGGGTACCCAAATGTGAAGTC | SEQ ID NO: 1395 | PREDICTED: Homo sapiens similar to 60S ribosomal protein L7 (LOC652890), mRNA [XR_019544] |
| 529 | A_24_P367199 | A_24_P367199 | TCTTATGGTCAGCACCACCAAGACGTGACCAAATCAAGAAGAAGGTGTAATGATGACCTGAGA | SEQ ID NO: 1397 | |
| 530 | A_24_P367369 | A_24_P367369 | ATTTAAAGGTTTCGATGTAGATTCTGTCGGTCGGAGGATATCGAAGTGAACAAAGGACTCTAA | SEQ ID NO: 1398 | |
| 531 | A_24_P371303 | C3orf63 | GTCAGTCTCAAGAAAATGAGAATTAGTTCTTATCTGCTTATACTGAAAGCTTGGATAGAG | SEQ ID NO: 1399 | Homo sapiens chromosome 3 open reading frame 63 (C3orf63), mRNA [NM_015224] |
| 532 | A_24_P374319 | RAP2C | ATTGTGTGTGATGTTGAAATAAAGTGGTATCTACATTCATGTGATTTATGGGTCAGGATG | SEQ ID NO: 1400 | Homo sapiens RAP2C, member of RAS oncogene family (RAP2C), mRNA [NM_021183] |
| 533 | A_24_P37519 | LZTFL1 | GCTAGGTAGAATTTGTACTTGTTTTCTTGGTAGGAGTTTGAAATATTCTATACAGTACG | SEQ ID NO: 1401 | Homo sapiens leucine zipper transcription factor-like 1 (LZTFL1), mRNA [NM_020347] |
| 534 | A_24_P375599 | LOC731681 | TGTATGCTCACTTCCCCGATCAAGTCGTTATCCAGAATGGGTCTCTTGTTGAAATCCGAA | SEQ ID NO: 1402 | PREDICTED: Homo sapiens similar to 60S ribosomal protein L9 (LOC731681), mRNA [XR_016944] |
| 535 | A_24_P375849 | ENST00000359659 | AAGAAGCTCTGCAACAAGACATAGACAGGCTATGTCACACATCTGATGAAGCGGATTCAGAGA | SEQ ID NO: 1403 | Q8BT90_MOUSE (Q8BT90) 10, 11 days embryo whole body cDNA, RIKEN full-length enriched library, clone:2810021H19 product:ribosomal protein S17, full insert sequence, (Fragment), partial (98%) [THC2555910] |
| 536 | A_24_P381625 | PSMC6 | ATGAAAGCAGTCAGAAAAGTGGCTGATTCTGTAAGAAGCTGGAGTCTAAATTGGACTACAAA | SEQ ID NO: 1404 | Homo sapiens proteasome (prosome, macropain) 26S subunit, ATPase, 6 (PSMC6), mRNA [NM_002806] |
| 537 | A_24_P383999 | RPS3A | TGGTTTTACTAAAAAACGGCAACAATCAGATACAGAAGACCTCTTATGCCCAGGACCAACG | SEQ ID NO: 1405 | Homo sapiens ribosomal protein S3A (RPS3A), mRNA [NM_001006] |
| 538 | A_24_P384411 | A_24_P384411 | ATGGGAAAATCAATAAGAGTCAAGAGTTTGACAGATATTGTTGACAGGTCGATCTCTTG | SEQ ID NO: 1406 | |
| 539 | A_24_P384539 | LOC730452 | CAAGAAAAGCTGGGAACTTCTATGTACCCACAAAACCGAAATTGGCATTTGTCATCAGGA | SEQ ID NO: 1407 | PREDICTED: Homo sapiens similar to 60S ribosomal protein L7 (LOC730452), mRNA [XM_001128595] |
| 540 | A_24_P387869 | PKN2 | TTGTCAGAGATCATTTATATTACGTTCGAAATTGTTTATTAGCCAAGATGCTTTGGGAG | SEQ ID NO: 1408 | Homo sapiens protein kinase N2 (PKN2), mRNA [NM_006256] |
| 541 | A_24_P389612 | ARL5B | ATTAATGCATTCACATGATCACTTCTTGAAAATGGTTCAAACGATGTTTCCTGATGGTG | SEQ ID NO: 1409 | ADP-ribosylation factor-like protein 5B (ADP-ribosylation factor-like protein 8). [Source:Uniprot/SWISSPROT;Acc:Q96KC2] [ENST00000377275] |
| 542 | A_24_P392231 | LOC641784 | CCATCAATATTCACAAGTGCATCCATGGAGTGGGCAAGAAGCGTGCCCGCTCGGGAACTCA | SEQ ID NO: 1410 | xr55h07.x1 NCI_CGAP_Ov26 Homo sapiens cDNA clone IMAGE:2764093 3' similar to gb:X69181 60S RIBOSOMAL PROTEIN L31 (HUMAN) ;, mRNA sequence [AW302767] |
| 543 | A_24_P39378 | CCPG1 | TACTTTTTGTCGGTGGAACGAACTTGATCAGTTCATCAATAAGTTTTTCCTAAACGGTGT | SEQ ID NO: 1411 | Homo sapiens cell cycle progression 1 (CCPG1), transcript variant 1, mRNA [NM_004748] |
| 544 | A_24_P393811 | TMCO1 | AGATGAGCACAGACTGTGCTTCATTTTCCTGTATATTCTGTACTATGTCGATTCG | SEQ ID NO: 1412 | Homo sapiens transmembrane and coiled-coil domains 1 (TMCO1), mRNA [NM_019026] |

Fig. 3-30

| No. | Probe ID No. | Symbols of genes | Sequence | SEQ ID NO: | Descriptions of genes (letters and numbers within [ ] indicates GenBank accession No.) |
|---|---|---|---|---|---|
| 545 | A_24_P396720 | PPP1CB | TTTCTCAACCACTACCTTCTACATTGGTTGACTTAGACCGTAAG GTTTTTAAGTTTCTC | SEQ ID NO: 1413 | Homo sapiens protein phosphatase 1, catalytic subunit, beta isoform (PPP1CB), transcript variant 1, mRNA [NM_002709] |
| 546 | A_24_P399942 | ATP11C | TGAGGATGTTAGCTAGTAGAACTGAAAAGTCATTCATTCCATATCTAC TTACAGATACACCAG | SEQ ID NO: 1414 | Homo sapiens ATPase, Class VI, type 11C (ATP11C), transcript variant 1, mRNA [NM_173694] |
| 547 | A_24_P40417 | FMR1 | TTTGTGAGTTTGTTTGTTTGAATTTTCATTTTACAGTTACTTTTGC TTGCATACAAAGAAG | SEQ ID NO: 1415 | Homo sapiens fragile X mental retardation 1 (FMR1), mRNA [NM_002024] |
| 548 | A_24_P405002 | PDIK1L | TGGTGCTAAGGATACTTTGTCATTATGATGAAGTAAGTGTTAAG TGTCAGATAAATAGC | SEQ ID NO: 1416 | Homo sapiens PDLIM1 interacting kinase 1 like (PDIK1L), mRNA [NM_152835] |
| 549 | A_24_P405298 | PPP1CB | GTATTAGGTTAGGTCACAAAGGTTTTATCTGAGGTGATTAAATA ACTTCCTGATTGGAG | SEQ ID NO: 1417 | Homo sapiens protein phosphatase 1, catalytic subunit, beta isoform (PPP1CB), transcript variant 1, mRNA [NM_002709] |
| 550 | A_24_P405430 | TIA1 | GGATTTTCTCGTTGTTTAAATCACAAAAATGATAGTCCCGAATGG TTCTTTATAGGAGG | SEQ ID NO: 1418 | Homo sapiens cDNA FLJ36425 fis, clone THYMU2011482. [AK093744] |
| 551 | A_24_P408034 | SLC35A1 | ATGTACAAGTATATTGTCCTAGCAGGATAAAGACCTAGCTCTTTC TTACAAGAGGGCAGAA | SEQ ID NO: 1419 | Homo sapiens solute carrier family 35 (CMP-sialic acid transporter), member A1 (SLC35A1), mRNA [NM_006416] |
| 552 | A_24_P409681 |  | ACATGAGCTGTCCCTGCCGCGGATTGAGATGATTCTTGAAAAGGAAC AGATGTTCATAAAC | SEQ ID NO: 1420 |  |
| 553 | A_24_P414556 | TTC33 | TACTGAACATTTGGTATATTGTTTGAGTAATGACATGGATGTTTGTTT TGTGTAATTTGTGA | SEQ ID NO: 1421 | Homo sapiens tetratricopeptide repeat domain 33 (TTC33), mRNA [NM_012382] |
| 554 | A_24_P414952 | TMEM168 | TTTTTCTACTGAAGGTCAGAGGATAGGAAACAGATATTTCTGTTCT GGTATACATTAATG | SEQ ID NO: 1422 | Homo sapiens transmembrane protein 168 (TMEM168), mRNA [NM_022484] |
| 555 | A_24_P41551 | LOC641790 | AACGAGCTGGGAACTCTCTCTGATGTGCGCATTGATATGAGGCAGAAG AAAGTACTCTGGAAA | SEQ ID NO: 1423 | PREDICTED: Homo sapiens similar to ribosomal protein L31 (LOC641790), mRNA [XR_018025] |
| 556 | A_24_P417281 | TXNDC10 | ATGATGAGTGATTCTTGGGAAGATAAATGTTAAGTGTTCCGAATAG TCAAGCTTGTTTTGC | SEQ ID NO: 1424 | Homo sapiens thioredoxin domain containing 10 (TXNDC10), mRNA [NM_019022] |
| 557 | A_24_P418418 | RPS17 | GATGAACTTCAAAATGCCTCGGCGGACCTGTTTGAATTTTTCTGC AGTGCTGTATATTTT | SEQ ID NO: 1425 | Homo sapiens ribosomal protein S17 (RPS17), mRNA [NM_001021] |
| 558 | A_24_P418712 | A_24_P418712 | AGGGTCAACAAAGCTGTCTGGGCCAAAGAATAAGGAATATATCGAT ACCATATCTGTGTTA | SEQ ID NO: 1426 |  |
| 559 | A_24_P450172 | AK095151 | TATGCACTGAATAAAGCTACTTAAACCAGAGTAATTTTGGATA TTAATCCTAAGGCTAC | SEQ ID NO: 1427 | Homo sapiens cDNA FLJ37832 fis, clone BRSSN2009630. [AK095151] |
| 560 | A_24_P487736 | CXorf23 | TGGATACCTACTATGTGTAAGAGCAAATGGATGGATTTTAAAT GAAATTTTTAGGGCGC | SEQ ID NO: 1428 | Homo sapiens chromosome X open reading frame 23 (CXorf23), mRNA [NM_198279] |
| 561 | A_24_P497226 | RPS6KB1 | TAACATTATAGCACAAGTATATCTCAGTGGATTATCCGGAATAA CATCTGAAAGATGGG | SEQ ID NO: 1429 | Homo sapiens ribosomal protein S6 kinase, 70kDa, polypeptide 1 (RPS6KB1), mRNA [NM_003161] |
| 562 | A_24_P50437 | BC065737 | TGCAGAAGAATGAAGTTGCATTTAGAAAATTCCTGATTACTGAAG ATGTTCAGGGCAAAA | SEQ ID NO: 1430 | Homo sapiens cDNA clone IMAGE:30404477, partial cds. [BC065737] |
| 563 | A_24_P50472 | LOC649839 | TAAAACTAGAAACAAGATTGTGCTGGGCGCTTGAGTGGCATTCAGCC CAACTGCAGATCCAA | SEQ ID NO: 1431 | PREDICTED: Homo sapiens similar to large subunit ribosomal protein L36a (LOC649839), mRNA [XM_001129410] |

Fig. 3-31

| No. | Probe ID No. | Symbols of genes | Sequence | SEQ ID NO. | Descriptions of genes (letters and numbers within [ ] indicates GenBank accession No.) |
|---|---|---|---|---|---|
| 564 | A_24_P50554 | LOC391655 | TGAAGGGTTTAGATGTAGATTGTGTCATTGAGTATAACCAGTAAACAAAGCACCTA | SEQ ID NO: 1432 | PREDICTED: Homo sapiens similar to 60S ribosomal protein L17 (L23) (LOC391655), mRNA [XR_018405] |
| 565 | A_24_P50567 | A_24_P50567 | CCTTGCTAATTTCAAAAAGTACGAGAACGATGAATGCAAGATGGCATGGTTGCTCTGGAGTA | SEQ ID NO: 1433 | |
| 566 | A_24_P538403 | ROCK1 | TTAGAGGTTTGTTGGACTTTGGACTTGATAAATTGAGTACAATCTTTGGATCAAACTACGTGCTAC | SEQ ID NO: 1434 | Homo sapiens Rho-associated, coiled-coil containing protein kinase 1 (ROCK1), mRNA [NM_006406] |
| 567 | A_24_P54178 | TMED5 | GCTCTGATATGCATTGGATGATTAATGTTATGCTGTTGTTCATGTGAATGTCAAGACA | SEQ ID NO: 1435 | Homo sapiens transmembrane emp24 protein transport domain containing 5 (TMED5), mRNA [NM_016040] |
| 568 | A_24_P551028 | LOC339745 | TCGAGTTGAACAAATATTGAGTGCCTATCATATGGAAGACTAACTCCTTAGTAGGAATGA | SEQ ID NO: 1436 | Homo sapiens hypothetical protein LOC339745 (LOC339745), mRNA [NM_001001664] |
| 569 | A_24_P561223 | THC2697551 | TTATGCCAGTTACATACAAGGATCGTCGCCATATTTCAGGGACCCTAAAGTTTATAACAT | SEQ ID NO: 1437 | ALU1_HUMAN (P39188) Alu subfamily J sequence contamination warning entry, partial (8%) [THC2697551] |
| 570 | A_24_P56240 | CPNE8 | TACAACTATGTGACTTAGTGCACAACACATTTGTGAAAATAACCTACTCCTATATACTGAC | SEQ ID NO: 1438 | Homo sapiens copine VIII (CPNE8), mRNA [NM_153634] |
| 571 | A_24_P56252 | AF086032 | GTATCTAAAACTGAACAGCTACTGTGCTATATTGATTTATTGGTAGTATTGAAGCAAGACC | SEQ ID NO: 1439 | Homo sapiens full length insert cDNA clone YW25G09. [AF086032] |
| 572 | A_24_P57837 | THC2567891 | AGAAATCCGGAAGAGCTCTTATGCTCAGTCAGCCAAATCGGGAAGAAGATGATGGAA | SEQ ID NO: 1440 | Q6NXR8_HUMAN (Q6NXR8) Ribosomal protein S3a, partial (91%) [THC2567891] |
| 573 | A_24_P587938 | A_24_P587938 | CTTCAAAGAAGCAAAAGCCTAATGCGGGTGAACAGGGAGGACCAGATTAACAGTCTTAT | SEQ ID NO: 1441 | |
| 574 | A_24_P606663 | LOC392030 | TGTCCGGTTGCCCAGAAGCGAAAAAGTTAATGCGGGTGAAGATTCACGAAATAAGCTCCATACTT | SEQ ID NO: 1442 | PREDICTED: Homo sapiens hypothetical LOC392030 (LOC392030), mRNA [XR_018063] |
| 575 | A_24_P62659 | TSPAN2 | CCCTTTTGGAGATAAGCTTTCCAAAATATGGTATGAGTATAAATTAGAGAATTCACCAC | SEQ ID NO: 1443 | Homo sapiens tetraspanin 2 (TSPAN2), mRNA [NM_005725] |
| 576 | A_24_P62860 | STAM2 | GTCTATATGGTACTTGATCTACATTTAAGTAGAAAAATTAGGCAGTATTTGAAAGCTCAGT | SEQ ID NO: 1444 | Homo sapiens signal transducing adaptor molecule (SH3 domain and ITAM motif) 2 (STAM2), mRNA [NM_005843] |
| 577 | A_24_P630039 | AL049321 | AACATGAGACATACAAAGTTAGATATTTGGACCATATTAAAACTGCAAGAAGACAGGGG | SEQ ID NO: 1445 | Homo sapiens mRNA; cDNA DKFZp564D156 (from clone DKFZp564D156). [AL049321] |
| 578 | A_24_P66125 | STAG2 | TAATCATTCCATGCCTTAATATGCTTGGCAATACAAGAATATGTTCAGATGGGTGAATACC | SEQ ID NO: 1446 | Homo sapiens stromal antigen 2 (STAG2), transcript variant 4, mRNA [NM_006603] |
| 579 | A_24_P675947 | ENST00000388400 | CTTCATGGCGAAGGTAGCAGTTCTGGAAAAGCTACTGGAGAAGAGACAGGTTGTAAAGTT | SEQ ID NO: 1447 | similar to 40S ribosomal protein S3a (V-fos transformation effector protein) (LOC391706), mRNA [Source:RefSeq_dna;Acc:XR_017186] [ENST00000388400] |
| 580 | A_24_P685729 | A_24_P685729 | TTGAAGTTATGTTGATGTCAAGACTATCAGTGATTATATTTGCTTTGTCTGTTTTGTGTGG | SEQ ID NO: 1448 | |
| 581 | A_24_P688133 | AK124299 | TAGGATATCGTGCAGGAAAATATCTGTTGTTAGTGATATGCCCAATAGTGATTGATTTC | SEQ ID NO: 1449 | Homo sapiens cDNA FLJ42306 fis, clone TRACH2001646. [AK124299] |

Fig. 3-32

| No. | Probe ID No. | Symbols of genes | Sequence | SEQ ID NO: | Descriptions of genes (letters and numbers within [ ] indicates GenBank accession No.) |
|---|---|---|---|---|---|
| 582 | A_24_P6975 | LOC342994 | GGAAGAGCTTCGAGGGGTTCGTGCTGTAAGAGCCTAAAGTTCTTATGAAATGTCAAAAAGA | SEQ ID NO: 1450 | PREDICTED: Homo sapiens similar to ribosomal protein L34 (LOC342994), mRNA [XM_938484] |
| 583 | A_24_P703614 | A_24_P703614 | AAGAACATTACCCGAATGGAGTCTGCAGTGTAAGTCATCAGTAGCAGCTTTGTGTGTG | SEQ ID NO: 1451 | |
| 584 | A_24_P712350 | CHML | GTGTAGAAGACTATAAAAAGGGCTTTATAAGTGATCTTTGACATAGTCACTTTGAGTGC | SEQ ID NO: 1452 | Homo sapiens choroideremia-like (Rab escort protein 2) (CHML), mRNA [NM_001821] |
| 585 | A_24_P7181 | A_24_P7181 | TCATGGTGGATTAACTCACACGTGATCTCTCCGTGCCACTCGAAATGATCTTTAGTGA | SEQ ID NO: 1453 | |
| 586 | A_24_P75158 | PTAR1 | CGATTAGATTTGTTCTTATGTGAGCATGTACCAAGCCAGCTATAAAGTATTGTATTCTG | SEQ ID NO: 1454 | Homo sapiens mRNA; cDNA DKFZp313P0917 (from clone DKFZp313P0917). [AL832683] |
| 587 | A_24_P755505 | A_24_P755505 | ATACAGAAGACCTCTTATGCTCAGGAGCAGCAACAGAGAAAAGTAAAATGCTGAAGAAGGCCAA | SEQ ID NO: 1455 | |
| 588 | A_24_P76358 | LOC643981 | TTACTGAAGATGTTCAGGGGAAAAACTGCCTAACTTCCGGCATGGATCTTATTCGTGACA | SEQ ID NO: 1456 | PREDICTED: Homo sapiens similar to 40S ribosomal protein S3a (V-fos transformation effector protein) (LOC643981), mRNA [XR_018444] |
| 589 | A_24_P77681 | PAIP1 | AGCTGATCCAGATTACCAAGAGAGAAAACTGGCTAACGAATTACTTGAAAGAGAGGAACTTTTTCC | SEQ ID NO: 1457 | Homo sapiens poly(A) binding protein interacting protein 1 (PAIP1), transcript variant 1, mRNA [NM_006451] |
| 590 | A_24_P781846 | AK024092 | ACTTTTTATAGATACAAATGTATCGTGGTAGTACAAGGACTTTGTTACTTGGCGTGG | SEQ ID NO: 1458 | Homo sapiens cDNA FLJ14030 fis, clone HEMBA1004086. [AK024092] |
| 591 | A_24_P792734 | PSMC6 | AGAACGTTAACGGAGTTACTGAATCAAATGATGGATTTGATACTCTGCATAGAGTTAAA | SEQ ID NO: 1459 | Homo sapiens proteasome (prosome, macropain) 26S subunit, ATPase, 6 (PSMC6), mRNA [NM_002806] |
| 592 | A_24_P795230 | AK027541 | ACAAGTTCTAGGAGTTTGAACTTTGGGTCAAGATGTTGATTCGTTTTAATGTGCGAGGGT | SEQ ID NO: 1460 | Homo sapiens cDNA FLJ14635 fis, clone NT2RP2001196. [AK027541] |
| 593 | A_24_P80915 | BCLAF1 | AACTGTGTGCAATGATGGTAATGAGACAAAACTTGTACATTTAATTAAGGTACCAGTTG | SEQ ID NO: 1461 | Homo sapiens BCL2-associated transcription factor 1 (BCLAF1), transcript variant 1, mRNA [NM_014739] |
| 594 | A_24_P81865 | RAP2A | TTCTTTGATGTTGCAACTTGGGTTGCTTTAAACGTGATAGTGATGGTAACTGATGC | SEQ ID NO: 1462 | Homo sapiens RAP2A, member of RAS oncogene family (RAP2A), mRNA [NM_021033] |
| 595 | A_24_P82630 | SMCHD1 | TGTTTAATATGTAACACGTAAGAACAATTGAAATTTCTTCTAAGATTTAATTACTAGTGT | SEQ ID NO: 1463 | Homo sapiens mRNA for KIAA0650 protein, partial cds. [AB014550] |
| 596 | A_24_P83968 | LOC730887 | ACAAAGCCAGCAGAACAACGTGGAACACAGAGAAACTTTTCTGGTGTCTGTAAGAAGC | SEQ ID NO: 1464 | PREDICTED: Homo sapiens similar to 40S ribosomal protein S7 (S8) (LOC730887), mRNA [XR_015607] |
| 597 | A_24_P84408 | AK027541 | AAGGTAGATCCAGGAGGTGGTCATTGACAAGTCATACAGAGAGAAAAGATGGCGTGTTTCTT | SEQ ID NO: 1465 | |
| 598 | A_24_P84808 | LOC729449 | GAATTGCTTTGAGACGATAAGGCTTTGGATGTCTTGGGAAAATATGGCATATCGTATGG | SEQ ID NO: 1466 | PREDICTED: Homo sapiens similar to 60S ribosomal protein L7 (LOC729449), mRNA [XR_015548] |
| 599 | A_24_P850187 | A_24_P850187 | TAAATGAACTAATCTACAAGCGTGCTTATGGCAAAATCAATTGACTTGCACTTTCGTAC | SEQ ID NO: 1467 | |
| 600 | A_24_P859859 | THC2553238 | TTTAACCAGACAGTCTGCACCCTTTTTCCTGATACTGTGAGGACACTCGGTCTCTAGCAAT | SEQ ID NO: 1468 | 1305349A cystic fibrosis antigen. [Homo sapiens] (exp=-1; wgp=0; cg=0), partial (65%) [THC2553238] |
| 601 | A_24_P867201 | AK022997 | GTGACATGTGATAAATATTTCAGTGACTTTTCAGAGATTTATTTCTTGTTAGCCGCTGTGTC | SEQ ID NO: 1469 | Homo sapiens cDNA FLJ12935 fis, clone NT2RP2004982. [AK022997] |

Fig. 3-33

| No. | Probe ID No. | Symbols of genes | Sequence | SEQ ID NO: | Descriptions of genes (letters and numbers within [ ] indicates GenBank accession No.) |
|---|---|---|---|---|---|
| 602 | A_24_P886040 | DCP2 | CATTTGGAAGAAGGTTTCATTCTGTTTCTAGATTTATGTGTTGTAGTTGAAGAACGAAGTG | SEQ ID NO: 1470 | Homo sapiens DCP2 decapping enzyme homolog (S. cerevisiae) (DCP2), mRNA [NM_152624] |
| 603 | A_24_P880636 | CR627148 | AATTGCCTTCCTTGTAACCCTAAGTATGCTGAAGACAGAATTGAATTCTACAAAGTCTTTC | SEQ ID NO: 1471 | Homo sapiens mRNA; cDNA DKFZp779F2127 (from clone DKFZp779F2127). [CR627148] |
| 604 | A_24_P91852 | DYNLT3 | ATACATATAGAGAGAGGAACCATAACTCATTGAATTTGGAGAGGAATAAGCTTAGCGTT | SEQ ID NO: 1472 | Homo sapiens dynein, light chain, Tctex-type 3 (DYNLT3), mRNA [NM_006520] |
| 605 | A_24_P91916 | NXT2 | AAGGATGCTTTCTTCTGTAGTACTGATTGAAACTTACACGTTTTATTCTACTCATAGTGAGC | SEQ ID NO: 1473 | Homo sapiens nuclear transport factor 2-like export factor 2 (NXT2), mRNA [NM_018698] |
| 606 | A_24_P931282 | THC2726401 | GGAAATATTTCTCCTCTCAAATGCATGAAATCATGATTGAGGTAATCTTACTGGAGATTACAC | SEQ ID NO: 1474 | Q26195 PLAV1 (Q26195) Pval protein, partial (14%) [THC2726401] |
| 607 | A_24_P935886 | BCAT1 | ATGTCTTGAAGGTTTTCTAGAAGCAGAATTAAACATCATAAATGACTTTGTTACACCAGA | SEQ ID NO: 1475 | Homo sapiens branched chain aminotransferase 1, cytosolic (BCAT1), mRNA [NM_005504] |
| 608 | A_24_P937095 | SLC30A1 | TTTGATGTAGGTCTACGGATACGTATGTGGTAATGCTATTTTGTTTTACTAACAAGGTCTG | SEQ ID NO: 1476 | Zinc transporter 1 (ZnT-1) (Solute carrier family 30 member 1). [Source:Uniprot/SWISSPROT;Acc:Q9Y6M5] [ENST00000367100] |
| 609 | A_24_P940426 | QKI | AAGCTGTTGAATGAGTCTTATAAAATTATACTACTGTTAAGTGGACCAAGTTTGGTGAAGC | SEQ ID NO: 1477 | Homo sapiens quaking homolog, KH domain RNA binding (mouse) (QKI), transcript variant 4, mRNA [NM_206855] |
| 610 | A_24_P940725 | C6orf111 | AATTATGATTAGTGAGTGGTCTAACAGTTAAGGGCATTGATAAGTTACAAGTAGAGTGGG | SEQ ID NO: 1478 | Splicing factor, arginine/serine-rich 130 (Serine-arginine-rich- splicing regulatory protein 130) (SRrp130) (SR-rich protein) (SR-related protein). [Source:Uniprot/SWISSPROT;Acc:O8TF01] [ENST00000369239] |
| 611 | A_24_P940776 | BDP1 | TCGGAGGCGGAAAATTGTCTATAAGTAGGCATTTATTCATGATTGATATGTCAAGAAATC | SEQ ID NO: 1479 | Homo sapiens B double prime 1, subunit of RNA polymerase III transcription initiation factor IIIB (BDP1), mRNA [NM_018429] |
| 612 | A_24_P941643 | PLCB1 | ATGATCTGCAGTTTTGTGCCTTTATGTATTGGGTTGTTCTTTGTCGAATGTGTGAAATT | SEQ ID NO: 1480 | Homo sapiens phospholipase C, beta 1 (phosphoinositide-specific) (PLCB1), transcript variant 2, mRNA [NM_182734] |
| 613 | A_24_P941699 | PCGF5 | TGGTATATTGAAGTACACAGCTTTCTAAGGATGGACTACTTTCATGTCTAGTAATACAGTG | SEQ ID NO: 1481 | Homo sapiens polycomb group ring finger 5 (PCGF5), mRNA [NM_032373] |
| 614 | A_24_P944458 | INSIG2 | ATGTATTCGTGTATCCATTAGTGAATAGTTCAAGTCTGTTAAGAGTGTATTGAGATGGC | SEQ ID NO: 1482 | Homo sapiens insulin induced gene 2 (INSIG2), mRNA [NM_016133] |
| 615 | A_24_P95029 | TAX1BP1 | TGCTTTGATTCCAGCTTTGATGTTCACAGAAGAAGTGCCCCTCGTGAGTTAATGTTTCCT | SEQ ID NO: 1483 | Homo sapiens Tax1 (human T-cell leukemia virus type I) binding protein 1 (TAX1BP1), transcript variant 1, mRNA [NM_006024] |
| 616 | A_24_P99046 | STK38L | GCTATCTGTCTTTTGCTGATCTACAAATAAATGAATTGAGAATTTAGTGCATAGAGGTCG | SEQ ID NO: 1484 | Homo sapiens serine/threonine kinase 38 like (STK38L), mRNA [NM_015000] |
| 617 | A_32_P10100 | A_32_P10100 | TATGAGGAAATAGTATCATCATGTTAGAAGCCTTGGAATGAGTATAAATAATGGCTGGTC | SEQ ID NO: 1485 | |

Fig. 3-34

| No. | Probe ID No. | Symbols of genes | Sequence | SEQ ID NO: | Descriptions of genes (letters and numbers within [ ] indicates GenBank accession No.) |
|---|---|---|---|---|---|
| 618 | A_32_P10424 | AX721252 | AAATTGTCAGGAAGGAGATGGGAACTCTAGATGTGCAAAGTGATACCAGGCTGAACAA | SEQ ID NO: 1486 | Sequence 212 from Patent WO0220754. [AX721252] |
| 619 | A_32_P105397 | THC2642694 | TAAAATGCTACTACAGTATTCTAGGATGGAGGCTGAATGTATATTACAGTAATTCTCTGG | SEQ ID NO: 1487 | Q6TDT1_HUMAN (Q6TDT1) Protein transactivated by hepatitis B virus E antigen, partial (11%) [THC2642694] |
| 620 | A_32_P106732 | FANCM | AATGAAGCTGCTCAAGATGGGGTTTCAAAGACCTCACACATATTAAATGCAGTTCAT | SEQ ID NO: 1488 | Homo sapiens Fanconi anemia, complementation group M (FANCM), mRNA [NM_020937] |
| 621 | A_32_P107372 | GBP1 | GGTACTGAGCAGCAAGTCTTAGGTAAAAGTCTTGGGAAATATTTGGGCATTGGTCTGGCCAA | SEQ ID NO: 1489 | Homo sapiens guanylate binding protein 1, interferon-inducible, 67kDa (GBP1), mRNA [NM_002053] |
| 622 | A_32_P109522 | C6orf113 | TAGAGGGTGGTCTTTCTCTAGAAGGAGAAACTTGGCAGGAGGACAAAGCTTGTCAAGTCTTTA | SEQ ID NO: 1490 | Homo sapiens chromosome 6 open reading frame 113 (C6orf113), mRNA [NM_145062] |
| 623 | A_32_P113154 | LOC730861 | ACCACGAGTCCAAGAATCTGTTTAAAGTTCAGAGTTAAAAGAGTACCAAATAAAAGTCC | SEQ ID NO: 1491 | PREDICTED: Homo sapiens similar to 40S ribosomal protein S3a (V-fos transformation effector protein) (LOC730861), mRNA [XR_015591] |
| 624 | A_32_P113584 | ZNF292 | GGGCCTTTTGGGTTTTATTGAATAGTTCATTTCACGTGTTAAGACTTACTACCAATAAG | SEQ ID NO: 1492 | Zinc finger protein 292. [Source:Uniprot/SWISSPROT;Acc:O60281] [ENST00000339907] |
| 625 | A_32_P114215 | COMMD6 | AATTGGTATCATTCTAAAGTCATGAGTTGAGTTTGGGGAACAAAACTAAATAAGGATGG | SEQ ID NO: 1493 | Homo sapiens COMM domain containing 6 (COMMD6), transcript variant 2, mRNA [NM_203495] |
| 626 | A_32_P1144 | AK091357 | GGGACTTAATATTTACATGTTACTACGTGTCATAGGTTTTAAGTGCTTTAATGGGG | SEQ ID NO: 1494 | Homo sapiens cDNA FLJ34038 fis, clone FCBBF2005645. [AK091357] |
| 627 | A_32_P11451 | NMD3 | CAGTTTAGGGCAGTAGCTGCTTTTGTCATAAATATCTTCCTACCAGATCAAAATGCTGG | SEQ ID NO: 1495 | Homo sapiens NMD3 homolog (S. cerevisiae) (NMD3), mRNA [NM_016938] |
| 628 | A_32_P115505 | ZNF294 | TGTGGTCAGAGGATTATAGTTGAAGAGTGAAGTACTATGTGTGAGTTATAGATCTCTGGAA | SEQ ID NO: 1496 | Homo sapiens zinc finger protein 294 (ZNF294), mRNA [NM_015565] |
| 629 | A_32_P11931 | LOC441073 | GTGTGATCCATGCCCATCGGAAAGGAAGGATGATGAAGTTCAGGTTGTACGTGAACATATAAA | SEQ ID NO: 1497 | PREDICTED: Homo sapiens similar to 60S ribosomal protein L26 (Silica-induced gene 20 protein) (SIG-20) (LOC441073), mRNA [XR_016376] |
| 630 | A_32_P12430 | SPG20 | TCAGGGTAAAGAATATGAAAACCTTAGACGTAATCCATGGTGGATAGGCATTATGGTTTC | SEQ ID NO: 1498 | Homo sapiens spastic paraplegia 20, spartin (Troyer syndrome) (SPG20), mRNA [NM_015087] |
| 631 | A_32_P124580 | THC2610143 | ATTAGCTGGGACTAAAACGGCAGATGTTTGTTTTGTGAATTGTACCTAAATGTCTCTA | SEQ ID NO: 1499 | AA490192 aa43f10.r1 Soares_NhHMPu_S1 Homo sapiens cDNA clone IMAGE:823723 5', mRNA sequence [AA490192] |
| 632 | A_32_P125549 | RPL31P4 | TCTACAGACAGTCAACATGTGGATGGAGAACTAATCCCTGATCGTCAGATACTGAAATAAAG | SEQ ID NO: 1500 | PREDICTED: Homo sapiens ribosomal protein L31 pseudogene 4 (RPL31P4), mRNA [XR_018222] |
| 633 | A_32_P125917 | THC2753798 | GCTTATAAAGTGTAAGTGGAGAGCGCTAAATTGTGAGTACAAAGTTTCTTTTCACAAGAG | SEQ ID NO: 1501 | BF238843 601904455F1 NIH_MGC_54 Homo sapiens cDNA clone IMAGE:4132429 5', mRNA sequence [BF238843] |
| 634 | A_32_P128781 | A_32_P128781 | CATATATTGCATGGGGTACCCCAATCTGAAGTCAGTAAATGAACTAATCTACAAGAGTG | SEQ ID NO: 1502 | |
| 635 | A_32_P128980 | BC062780 | AGATGGGAGGACAGAGGAAGTAGTGACAAGGAGTAGAAGCACTGTAGACGTTTTCATATCAT | SEQ ID NO: 1503 | Homo sapiens cDNA clone IMAGE:4700531, partial cds. [BC062780] |

Fig. 3-35

| No. | Probe ID No. | Symbols of genes | Sequence | SEQ ID NO: | Descriptions of genes (letters and numbers within [ ] indicates GenBank accession No.) |
|---|---|---|---|---|---|
| 636 | A_32_P135818 | RPS3A | CTTGCTTCATCTGTTCTGTATTGGTTTTAATAAAAACGGAACAATCAGATATGGAAGAC | SEQ ID NO: 1504 | Homo sapiens ribosomal protein S3A (RPS3A), mRNA [NM_001006] |
| 637 | A_32_P136319 | RPL36A | AAGTGATCCAGTTCTAAGTGTCATCTTTTATCATGAAGACAACAAAATCTTGAGTTTATG | SEQ ID NO: 1505 | Homo sapiens ribosomal protein L36a (RPL36A), mRNA [NM_021029] |
| 638 | A_32_P137266 | KIAA1799 | AAGTGGGACCCAAATCTACAAGTCTTTGTCAACATGTAATGGCTTTGAATGAACGACAAG | SEQ ID NO: 1506 | Homo sapiens KIAA1799 protein (KIAA1799), mRNA [NM_032437] |
| 639 | A_32_P143323 | CR613267 | AGAGAGCTCAAACAATGAGGGTTTATGGCAGTTACATACAAGGATCCTGCATATTTCAGGG | SEQ ID NO: 1507 | full-length cDNA clone CS0DL011YP14 of B cells (Ramos cell line) Cot 25-normalized of Homo sapiens (human) [CR613267] |
| 640 | A_32_P145153 | RPL31 | ATCCGTGTCTGGAGCTGTCCAAGAAAACGTAATGAGGATGAAGAATTCACCAAATAAGCACATAT | SEQ ID NO: 1508 | Homo sapiens ribosomal protein L31 (RPL31), mRNA [NM_000993] |
| 641 | A_32_P145159 | A_32_P145159 | CATACATTGGCGTGTGTACATAAACGTTTGTGGAAAAACTTAGTGTGTGATTATTCTCTTTG | SEQ ID NO: 1509 | |
| 642 | A_32_P147747 | THC2575761 | TTGATACCTGTCTGATTCTGATGACAAAGCGCAATTTGGGGTCTGGCAGGTACATAGAAGTTG | SEQ ID NO: 1510 | HUMRPL7Y ribosomal protein L7 [Homo sapiens] (exp=-1; wgp=0; cg=0), partial (40%) [THC2575761] |
| 643 | A_32_P148824 | C1orf27 | GAAAAACAGATGTATCCTCAGCACAGAAATTCAGTAAAGAGACTACAAAAGGATGATCTTC | SEQ ID NO: 1511 | Homo sapiens chromosome 1 open reading frame 27 (C1orf27), mRNA [NM_017847] |
| 644 | A_32_P1516 | AA714537 | CTGAGGATAAAGAGGGTCTTCCGTATCTGATTTTTTAGTAAAAAGCAACACAGAA | SEQ ID NO: 1512 | nw20g12.s1 NCI_CGAP_GCB0 Homo sapiens cDNA clone IMAGE:1241062 3' similar to gb:M84711 40S RIBOSOMAL PROTEIN S3A (HUMAN); mRNA sequence [AA714537] |
| 645 | A_32_P153726 | KIAA1033 | TTTTTAAAAGATGGCAAGTTTGTTACGTCACGTCACTGAGTGGGGTTTTCGTTTTCGGGCAAT | SEQ ID NO: 1513 | Homo sapiens KIAA1033 (KIAA1033), mRNA [NM_015275] |
| 646 | A_32_P155364 | RPL7 | TCAACAGGGCTTATTAGAAAATGAACCAAGGTGTCTACCATGATAATTTTCTAAGGTGG | SEQ ID NO: 1514 | Homo sapiens ribosomal protein L7 (RPL7), mRNA [NM_000971] |
| 647 | A_32_P156811 | CD2AP | AAAGGATGGTTCTCTCTCAAAAAGAAAATTAAAGGATTTTATTGCCAGTCGTGTCAGTC | SEQ ID NO: 1515 | Homo sapiens CD2-associated protein (CD2AP), mRNA [NM_012120] |
| 648 | A_32_P158746 | RPL17 | TTTTGCTGCACATGCTAAAAATGCAGAGAGTAATGGTGAACTTAAGGGTTTAGATGTAG | SEQ ID NO: 1516 | Homo sapiens ribosomal protein L17 (RPL17), transcript variant 1, mRNA [NM_000985] |
| 649 | A_32_P159651 | PCAF | GAGTGGTGTCTAGATTTCTAATGAAGAATCATGATACAGTTTGGATTAAGTATCTTGGAC | SEQ ID NO: 1517 | Homo sapiens p300/CBP-associated factor (PCAF), mRNA [NM_003884] |
| 650 | A_32_P162150 | MAP3K7IP3 | AGGGATAGAAGAATTGTCCTCTAAAAATATCAATGATGTATCCTGGAATGTGAAGATGTC | SEQ ID NO: 1518 | Homo sapiens mitogen-activated protein kinase kinase kinase 7 interacting protein 3 (MAP3K7IP3), mRNA [NM_152787] |
| 651 | A_32_P164203 | THC2683448 | TTGATGGTCATTGTACGAGCTATTGTATGGATTACTGGTGGAGTGCTGTTTAGCACATGAT | SEQ ID NO: 1519 | Q7WZG3_PASP1 (Q7WZG3) Ferric uptake regulator, partial (8%) [THC2683448] |
| 652 | A_32_P167122 | RCOR3 | GTATCTGAGGGATGTGCTGTAATCTGATTTAGATGCATTAGAGCACACAGTAGAAAAACT | SEQ ID NO: 1520 | Homo sapiens REST corepressor 3 (RCOR3), mRNA [NM_018254] |
| 653 | A_32_P170444 | SUB1 | TAGGTATCTCTCCTGAAATTCTTTGCAGTTCATTTTTATGGCAGTTAATGCAGTGAAAC | SEQ ID NO: 1521 | Activated RNA polymerase II transcriptional coactivator p15 (SUB1 homolog) (Positive cofactor 4) (PC4) (p14). [Source:Uniprot/SWISSPROT;Acc:P53999] [ENST00000265073] |

Fig. 3-36

| No. | Probe ID No. | Symbols of genes | Sequence | SEQ ID NO: | Descriptions of genes (letters and numbers within [ ] indicates GenBank accession No.) |
|---|---|---|---|---|---|
| 654 | A_32_P170736 | AK098422 | AGGTCATAATTGTTGAGGGCAAGGCTTGATTGTTGATAGTGCAAAGTGTCGCTGTTGTGAT | SEQ ID NO:1522 | Homo sapiens cDNA FLJ25556 fis, clone JTH02629. [AK098422] |
| 655 | A_32_P172578 | THC2661509 | ACTTAATGAATGTCTCAAAGATTTCTAGGGATTCTCCATCTCATGCATTCCTTGTGTTCC | SEQ ID NO:1523 | |
| 656 | A_32_P173385 | ENST00000334683 | AAATGCAGAGAGTGATGCTGAACTTAAGGGTGTCAGATGTAGAATTCTCTGGTCATTGAGCA | SEQ ID NO:1524 | PREDICTED: Homo sapiens similar to 60S ribosomal protein L17 (L23) (LOC650948), mRNA [XR_019013] |
| 657 | A_32_P176819 | CMAH | GATTATATATGGTAGGTGTGATTCTGAAGATACAAGAATTCAATGGTGGAATTTGTCTCC | SEQ ID NO:1525 | Homo sapiens cytidine monophosphate-N-acetylneuraminic acid hydroxylase (CMP-N-acetylneuraminate monooxygenase) (CMAH) on chromosome 6 [NR_002174] |
| 658 | A_32_P177040 | WBSCR19 | AATCTTTGTATGTATTATTACACGTCGTTGCTGAAGGGAGCATGGTTTTATCTGTGATAC | SEQ ID NO:1526 | Homo sapiens Williams Beuren syndrome chromosome region 19 (WBSCR19), mRNA [NM_175064] |
| 659 | A_32_P177953 | GCLM | ATTTATTGTATGTTGGCTAGCAGTTCATCCTCTGCAAAATATGCATTCAGAGAAATGTG | SEQ ID NO:1527 | Glutamate—cysteine ligase regulatory subunit (EC 6.3.2.2) (Gamma-glutamylcysteine synthetase) (Gamma-ECS) (GCS light chain) (Glutamate—cysteine ligase modifier subunit). [Source:Uniprot/SWISSPROT;Acc:P48507] [ENST00000370238] |
| 660 | A_32_P179966 | ENST00000379426 | GTAATATACAGGGTGAACTCTTACTGATACACACAAGAACAAGTGTTAAAAAGTGAATCG | SEQ ID NO:1528 | Novel protein. [Source:Uniprot/SPTREMBL;Acc:Q5T4T1] [ENST00000379426] |
| 661 | A_32_P180435 | WBSCR19 | CTTTGAATGTTGTATCATATTATTACACGGTGCTGCTGCTGAAGGGAGGATGTTTTATCTATG | SEQ ID NO:1529 | Homo sapiens Williams Beuren syndrome chromosome region 19 (WBSCR19), mRNA [NM_175064] |
| 662 | A_32_P186981 | RPL17 | CATTGAGATGATCCTTACGGGAAAAGGAACAGATTGTTCCTAAACGAGAAGGAAGGTTGC | SEQ ID NO:1530 | Homo sapiens ribosomal protein L17 (RPL17), transcript variant 1, mRNA [NM_000985] |
| 663 | A_32_P190488 | hCG_26523 | CCCAGGCAAGGTGGTTACACTAGGCTAAAACTGGACAAAGACCGCAAAAGATCCTTGAA | SEQ ID NO:1531 | PREDICTED: Homo sapiens similar to 60S ribosomal protein L26 (LOC646161), mRNA [XR_018048] |
| 664 | A_32_P193322 | RICTOR | ACCACATGAGTTTGTTCTTTTATTTAGTAATAACGCTGCTACATATTTGGAGGTTCTGG | SEQ ID NO:1532 | Homo sapiens rapamycin-insensitive companion of mTOR (RICTOR), mRNA [NM_152756] |
| 665 | A_32_P195587 | DKFZP779L1068 | ATATAACCTTGGAATTCTATTCTAATTATGTTGTTCTGGCTGCTTGTAGTATCAGTTCGC | SEQ ID NO:1533 | Homo sapiens cDNA clone IMAGE:5555490. [BC110326] |
| 666 | A_32_P196483 | RPS3A | GGGGCAAGAAGAAGATGGTTGATCGATTTTTCTAAGGAAAGATTGGTATGATGTGAAAGCA | SEQ ID NO:1534 | Homo sapiens ribosomal protein S3A (RPS3A), mRNA [NM_001006] |
| 667 | A_32_P19752 | FAM76B | TTGTGCTTTTAGCGTGTTTCCAGTATTATTAATTAGCAGTAAGGGTCATTTTGACAAGAGA | SEQ ID NO:1535 | Homo sapiens family with sequence similarity 76, member B (FAM76B), mRNA [NM_144664] |
| 668 | A_32_P20240 | SP3 | CTTAGGCTCTTAATTGTTGTAGTTTAAATTCCAGTACTGCCTACTCAGACCCAAAAGTTTGT | SEQ ID NO:1536 | Homo sapiens mRNA; cDNA DKFZp686N17231 (from clone DKFZp686N17231). [BX648577] |
| 669 | A_32_P202488 | RPL21 | AAGAGGAGAGCCACCGATATATGTCTGTAGGCGTTTTTAAAAACATGGCAATGGGTAC | SEQ ID NO:1537 | Homo sapiens ribosomal protein L21, mRNA (cDNA clone IMAGE:6605332), complete cds. [BC104478] |
| 670 | A_32_P203320 | ROCK1 | AACGGCCATCACTATCAAGATCAGGCTCAGGAAGAGTAAAGAAAATATCAAATGAG | SEQ ID NO:1538 | Homo sapiens Rho-associated, coiled-coil containing protein kinase 1, mRNA (cDNA clone IMAGE:5269992), complete cds. [BC041849] |

Fig. 3-37

| No. | Probe ID No. | Symbols of genes | Sequence | SEQ ID NO: | Descriptions of genes (letters and numbers within [ ] indicates GenBank accession No.) |
|---|---|---|---|---|---|
| 671 | A_32_P20367 | RPS7 | ATCCTTGAGGACTTGGTCTTCACAAGGAAATTGTGGGGAAGAGAATCCGGCGTGAAACTA | SEQ ID NO: 1539 | Homo sapiens ribosomal protein S7 (RPS7), mRNA [NM_001011] |
| 672 | A_32_P204330 | AK093982 | AAACCGTGAAGCTTTTTGCTCGTCTTGGTAGCAGATATCTGTAAAACCTACCCAGAATTG | SEQ ID NO: 1540 | Homo sapiens cDNA FLJ36663 fis, clone UTERU2002826. [AK093982] |
| 673 | A_32_P205550 | RPL26L1 | AGGTAGTTCAGGACACTACAAAGGTCAGGAAATTGGCAAGGTAATCCAGGTGTACAAGA | SEQ ID NO: 1541 | Homo sapiens ribosomal protein L26-like 1 (RPL26L1), mRNA [NM_016093] |
| 674 | A_32_P205553 | RPL26L1 | TTCGGAATGTGTGGAACATTTCATTCGTGTTTGTTACCTGTGGCTCTGTAAATCTACT | SEQ ID NO: 1542 | Homo sapiens ribosomal protein L26-like 1 (RPL26L1), mRNA [NM_016093] |
| 675 | A_32_P207231 | AI630435 | TTCCTTCGCTTTTTTCTTAAGGGTTTCGTGGAACAGGAGGAAACCTCCTTCTTCTTCTTCT | SEQ ID NO: 1543 | AI630435 ad10b05.y1 Hembase; Erythroid Progenitor Cells (LCB:ad library) Homo sapiens cDNA clone ad10b05 random. mRNA sequence [AI630435] |
| 676 | A_32_P208178 | RPS3A | GGAAAAGACGTAGAAAAGGCTTGGCAATCGTATTTATCGTCTCGGATGATGTCTTCGTTAGA | SEQ ID NO: 1544 | Homo sapiens ribosomal protein S3A (RPS3A), mRNA [NM_001006] |
| 677 | A_32_P21384 | RPL17 | AGATGTCACTTTAGAGAAGAAACAGTGTGTACCATTCGGACATTACAACGGTGGGAGTTGGCAG | SEQ ID NO: 1545 | Homo sapiens ribosomal protein L17 (RPL17), transcript variant 1, mRNA [NM_000985] |
| 678 | A_32_P220127 | RPL34 | CAAAACTAGGCGTGTCCTGAACCCGTCCTGGTAATAGAATTGTTGACCTTTATACCAAGAGGT | SEQ ID NO: 1546 | Homo sapiens ribosomal protein L34 (RPL34), transcript variant 2, mRNA [NM_033625] |
| 679 | A_32_P223319 | ESCO1 | ATGCCGTCATTACTGGACTTGCATTTTGATACTGTCGTCTATCGTTCATAGTGCCGTCGTACTT | SEQ ID NO: 1547 | Homo sapiens establishment of cohesion 1 homolog 1 (S. cerevisiae) (ESCO1), mRNA [NM_052911] |
| 680 | A_32_P224666 | CAPZA2 | AATGCTGTTTTTGAGATTCTGAAATTAAATGAAAATACTTATTTGAGAAATGCATTTAATG | SEQ ID NO: 1548 | Homo sapiens capping protein (actin filament) muscle Z-line, alpha 2 (CAPZA2), mRNA [NM_006136] |
| 681 | A_32_P22539 | hCG_28523 | ACTACGAAGGTCAGCAAGTTGGCAAATGGTCCAGGTTTACAGGAAAGAAATATGTTATGT | SEQ ID NO: 1549 | PREDICTED: Homo sapiens similar to 60S ribosomal protein L26 (Silica-induced gene 20 protein) (SIG-20) (LOC400065), mRNA [XM_374987] |
| 682 | A_32_P226786 | BC045174 | TTATTGGTGCATGTAAGCAATTATGCTGTCTTAATGAACCGATTAATGCTGTTGATTGTT | SEQ ID NO: 1550 | Homo sapiens cDNA clone IMAGE:5273245. [BC045174] |
| 683 | A_32_P2333 | SUB1 | AGGAAGAAAAGGTATTTCTTAAATCAGAAGAAATGGAGGCGAGCTGACAGAACAGATTTC | SEQ ID NO: 1551 | Homo sapiens SUB1 homolog (S. cerevisiae) (SUB1), mRNA [NM_006713] |
| 684 | A_32_P233304 | LIN9 | AAAGCTTCCGTATTCTTTGTTGTATTGTGCCACTGCAGAACTTTAGTGCAGAGTTTAT | SEQ ID NO: 1552 | Homo sapiens lin-9 homolog (C. elegans) (LIN9), mRNA [NM_173083] |
| 685 | A_32_P233314 | EXOC8 | AGGATTGGGAATTTGGACATGACATGTACTATAAAAGTCAGTCTATGCATACTGCTT | SEQ ID NO: 1553 | Homo sapiens exocyst complex component 8 (EXOC8), mRNA [NM_175876] |
| 686 | A_32_P234738 | RPL21 | GTTCTAAACAAAGAAGTTAAGGGGAAGATTCTTGCAAGAGAATTAATGTGCGTATTGAG | SEQ ID NO: 1554 | Homo sapiens ribosomal protein L21 (RPL21), mRNA [NM_000982] |
| 687 | A_32_P26895 | KIAA1600 | AATTCTTGGTCCCTGCGTGGAGAAAACTCTCAGATGGTCATTGTGTACCTACTCTCTCTT | SEQ ID NO: 1555 | KIAA1600 (KIAA1600), mRNA [Source:RefSeq_dna;Acc:NM_020940] [ENST00000369248] |
| 688 | A_32_P30710 | RPL23 | ACGAAAGTCATACCGGTAGAAAAGATGGCGTGTTTCTTTATTTTGAAGATAATGCAGGAGT | SEQ ID NO: 1556 | Homo sapiens ribosomal protein L23 (RPL23), mRNA [NM_000978] |
| 689 | A_32_P31182 | RPL7 | GTAGAAGAGAAGAAGGTTCCTGCTGTGCAGAAACCCTTAAGAAAAGGAAGGAAT | SEQ ID NO: 1557 | Homo sapiens ribosomal protein L7 (RPL7), mRNA [NM_000971] |

Fig. 3-38

| No. | Probe ID No. | Symbols of genes | Sequence | SEQ ID NO: | Descriptions of genes (letters and numbers within [ ] indicates GenBank accession No.) |
|---|---|---|---|---|---|
| 690 | A_32_P3742 | RFX3 | CCTCTGAAAATTGGCAGGAGGCTAAATAATAGTTTGTGGGCGGATTTGTATTGTGTACTGTA | SEQ ID NO: 1558 | Transcription factor RFX3. [Source:Uniprot/SWISSPROT:Acc:P48380] [ENST00000382004] |
| 691 | A_32_P43217 | PSMA6 | TTGTTGTTAGTTACCAGATCCGTGATGCCACTTACCTGCTGTGTTTGGTAACAACAAACA | SEQ ID NO: 1559 | Homo sapiens proteasome (prosome, macropain) subunit, alpha type, 6 (PSMA6), mRNA [NM_002791] |
| 692 | A_32_P4532 | LOC643932 | GATTCCAGACAGCAGGATTGGAAAAGACATAGAAAAGGCTTGCCATCTATCGTCTCCATGAT | SEQ ID NO: 1560 | PREDICTED: Homo sapiens similar to 40S ribosomal protein S3a (V-fos transformation effector protein) (LOC643932), mRNA [XR_017289] |
| 693 | A_32_P46765 | C12orf29 | TTTAGAATAGCCAGTGATCAGTCAGCTAGCTAATTCTCATATCATGCCTTTTGTCCTGTTAC | SEQ ID NO: 1561 | Homo sapiens chromosome 12 open reading frame 29 (C12orf29), mRNA [NM_001009894] |
| 694 | A_32_P49164 | AV714556 | AAATGCAGACTTGTTATTTGCCAAAGAAGAATTCATCATGTTCCTTCCTTCTTTTTGCC | SEQ ID NO: 1562 | AV714556 AV714556 DCB Homo sapiens cDNA clone DCBADG06 5', mRNA sequence [AV714556] |
| 695 | A_32_P49392 | A_32_P49392 | AATTCTGCCAAATCTGGAAGAAGATGGAAAATCATGACCGAAGAGGTGGAGACAAATG | SEQ ID NO: 1563 | |
| 696 | A_32_P50417 | LOC649314 | AATCAGGCTGAATTTTCTAAATGCAACTTCATCATTCTGGAAATCAGCAAGACTCACTTC | SEQ ID NO: 1564 | Homo sapiens cDNA FLJ35212 fis, clone PROST1000136. [AK092531] |
| 697 | A_32_P54305 | LOC401397 | AGAATCTTAGGAAATCACCACGTCGGTATAATCACTGCCTCCTGAATCGTTGAGGAG | SEQ ID NO: 1565 | Homo sapiens hypothetical LOC401397, mRNA (cDNA clone IMAGE:4244115), complete cds. [BC107860] |
| 698 | A_32_P58074 | RPS3A | GTTGGTTTTACTAAAAAACGCAAAAATCAGATACGGAAGACCTCTTATGCTCAGCAGGAA | SEQ ID NO: 1566 | Homo sapiens ribosomal protein S3A (RPS3A), mRNA [NM_001006] |
| 699 | A_32_P61857 | KIAA1468 | TCAGTGTACAGTTCCACTGGAATTTGACAGTTGTCTCTACAGTCATGCAACTGGAAGTAG | SEQ ID NO: 1567 | Homo sapiens KIAA1468 (KIAA1468), mRNA [NM_020854] |
| 700 | A_32_P62342 | GLT8D3 | TGTGATGTAACTGATGTAACCATTGACAATGCTATGTGTGGCTTTATACATTTCATCTCTG | SEQ ID NO: 1568 | Homo sapiens glycosyltransferase 8 domain containing 3, mRNA (cDNA clone MGC:21651 IMAGE:4508300), complete cds. [BC039145] |
| 701 | A_32_P68586 | ARL1 | TTGGGTTACCTGCCTTGAAGGACGGAAAATGGCAGAATATTCAAAACGTCAGCAACGAAAG | SEQ ID NO: 1569 | Homo sapiens ADP-ribosylation factor-like 1 (ARL1), mRNA [NM_001177] |
| 702 | A_32_P7118 | PSMC6 | AGCAGACTGAGAATGTTTGTAGTGACAGCAGGTATGTCGGCAATTGGTGCTGATCATGA | SEQ ID NO: 1570 | Homo sapiens proteasome (prosome, macropain) 26S subunit, ATPase, 6 (PSMC6), mRNA [NM_002806] |
| 703 | A_32_P77571 | AK024584 | GTCATCCTCTTAATGAAGCATTATGCAGCTGTTAAAGATGATAGATCTAAAGGTTATGAG | SEQ ID NO: 1571 | Homo sapiens cDNA: FLJ20931 fis, clone ADSE01282. [AK024584] |
| 704 | A_32_P81768 | TMEM167 | CCTCAGTAGTGTCACTACAATATTACATTCTGAAATGTTATTCTGTTGTATCAGATACG | SEQ ID NO: 1572 | Homo sapiens transmembrane protein 167 (TMEM167), mRNA [NM_174909] |
| 705 | A_32_P83784 | CENTD1 | ACAGGCCCATACTTCAGTCAGTCAGTCAATCAGTCAATCATCAGAGTACAGATGATGTGGTGGTAGAT | SEQ ID NO: 1573 | Homo sapiens centaurin, delta 1 (CENTD1), transcript variant 1, mRNA [NM_015230] |
| 706 | A_32_P86400 | LYSMD3 | AAATGTTGCTCAGGTAATCAGTATTTTCTTCGACGTATGTGCATATTGCACTGTTAGATC | SEQ ID NO: 1574 | Homo sapiens LysM, putative peptidoglycan-binding, domain containing 3 (LYSMD3), mRNA [NM_198273] |
| 707 | A_32_P86494 | A_32_P86494 | TGAGCCTTCCCTGCCACATTGAGATGATGCCTTACTGAAAAGGAAACAGATTGTTCCTAAAC | SEQ ID NO: 1575 | |
| 708 | A_32_P8857 | A_32_P8857 | TAATGTCGGAATGGTACACACTGTTTGTGTAAAGTGACATCTTTCAGATAGTTCCTGGCT | SEQ ID NO: 1576 | |

Fig. 3-39

| No. | Probe ID No. | Symbols of genes | Sequence | SEQ ID NO: | Descriptions of genes (letters and numbers within [ ] indicates GenBank accession No.) |
|---|---|---|---|---|---|
| 709 | A_32_P89679 | THC2643265 | TTATAGGTCAGAAAAATGAGGTCCACACTAATTTTGCGTCTTCCACAGGGAGATAGATTC | SEQ ID NO: 1577 | ALU1_HUMAN (P39188) Alu subfamily J sequence contamination warning entry, partial (5%) [THC2643265] |
| 710 | A_32_P93782 | RPL26 | AGGTTGTACATGGACACTATAAAAGGTCAGCAAATTGGCAAAGTAGTCCAGGTTTACAGGA | SEQ ID NO: 1578 | Homo sapiens ribosomal protein L26 (RPL26), mRNA [NM_000987] |
| 711 | A_32_P9382 | RP11-11C5.2 | AACAAAGCAGGAAAATATATTGAGAAGGGATCGTGTTTACAGAGGACTTCTTTAAAGTGT | SEQ ID NO: 1579 | Homo sapiens similar to RIKEN cDNA 2410129H14 (LOC440145), mRNA [NM_001071775] |
| 712 | A_32_P96213 | TPT1 | GAAAGGACAAGTAATCACTGGTGTCGATGTTGTCATGAACCATCACCTGGAGGAAACAAGT | SEQ ID NO: 1580 | Homo sapiens tumor protein, translationally-controlled 1 (TPT1), mRNA [NM_003295] |
| 713 | A_32_P98313 | NDUFA4 | AGCCCTGGAAACAAACTGGGTCCCAATGATCAATACAAAGTTCTGCTCAGTGAATGTGGATT | SEQ ID NO: 1581 | Homo sapiens NADH dehydrogenase (ubiquinone) 1 alpha subcomplex, 4, 9kDa (NDUFA4), nuclear gene encoding mitochondrial protein, mRNA [NM_002489] |

Fig. 4-1

| No. | Probe ID No. | Symbols of genes | Sequence | SEQ ID NO. | Description of genes (letters and numbers within [ ] indicates GenBank accession No.) |
|---|---|---|---|---|---|
| 1 | A_32_P184330 | AK130741 | TGTGACCGTTTGTGACGAGTTATCTCAGTCGTCACATGAGTTCTTACATGAGTCGGTCTA | SEQ ID NO: 923 | Homo sapiens cDNA FLJ27231 fis, clone SYN06240. [AK130741] |
| 2 | A_32_P209582 | THC2663167 | CAATGTAAAGCCAGAATATCGAAGGTCGTTTGTCAAGATTTTCAAAGCTATTTGGCTGAT | SEQ ID NO: 927 | ALU1_HUMAN (P39188) Alu subfamily J sequence contamination warning entry, partial (5%) [THC2663167] |
| 3 | A_32_P213509 | THC2663555 | GATTTGTTCCAGTGTTGGAGCCCTTTTAATGAAAATCTCAAACACCTACACTGAAAAA | SEQ ID NO: 929 | |
| 4 | A_32_P227110 | THC2512148 | TAAACAAATCGTTTTGATTCAGCCACGTGTGTATTGATAATGGCTTATTTATTACAATCA | SEQ ID NO: 932 | |
| 5 | A_32_P71171 | A_32_P71171 | TCTAGATAGTAATAGGAAACCAAGAATCCAGCGTCGGTGATGGGTGGAGGGAGTGATTGAA | SEQ ID NO: 946 | |
| 6 | A_32_P88940 | THC2745859 | AAGAGTATCCCAAGATAGCAAAGGTGTGTTGTTTTTAGCAGGTGTATTTCAGGTAGTTA | SEQ ID NO: 952 | |
| 7 | A_23_P128930 | PSMC6 | GAACAAGGAAGAATTAGAGATAGTGAAAATCCAATGCAAGGTCCCATTACAAAGCATGGTGAA | SEQ ID NO: 986 | Homo sapiens proteasome (prosome, macropain) 26S subunit, ATPase, 6 (PSMC6), mRNA [NM_002806] |
| 8 | A_23_P143358 | RPL22L1 | ATTGGCTTGGAGTGTTGGCATCTGACAAGGAGAGACCTACGAACTTCGTTAGTTCCAGATTA | SEQ ID NO: 998 | Homo sapiens ribosomal protein L22-like 1, mRNA (cDNA clone IMAGE:4865966). [BC049823] |
| 9 | A_23_P144497 | RPS3A | CCAAATCCGGAAGAAGAATGAAAATGATGGAAAATCATGACCCGAGAGGTCGAAGACAAATGACTTGAA | SEQ ID NO: 1000 | Homo sapiens ribosomal protein S3A (RPS3A), mRNA [NM_001006] |
| 10 | A_23_P14708 | SUHW4 | TCTTTGTACCTCCATACAGTGTTAGGCTGCCAGGCTGTAAGCTTACCTTAATTAAACTT | SEQ ID NO: 1006 | Homo sapiens suppressor of hairy wing homolog 4 (Drosophila) (SUHW4), transcript variant 1, mRNA [NM_017661] |
| 11 | A_23_P14734 | RPS27L | TAGAAGATACCACGACGGTTTCAGCCATGCTCAGACAGTGGTTCTTTGTGTAGGTGTTCA | SEQ ID NO: 1007 | Homo sapiens ribosomal protein S27-like (RPS27L), mRNA [NM_015920] |
| 12 | A_23_P152002 | BCL2A1 | TGTAACCATATTTGCATTTGAAGGTATTCCATCAGAAAACTTCTAGGACAGAATTGC | SEQ ID NO: 1013 | Homo sapiens BCL2-related protein A1 (BCL2A1), mRNA [NM_004049] |
| 13 | A_23_P156842 | EEF1E1 | AAGAAAAGCAATCGTTCAGGCAGTGGTTAGAATACAGGGTCACTCAAGTAGAATGGGCACT | SEQ ID NO: 1019 | Homo sapiens eukaryotic translation elongation factor 1 epsilon 1 (EEF1E1), mRNA [NM_004280] |
| 14 | A_23_P157449 | POLR2K | GGTCTCTGTTGCTTGCAAATATGTTCTTGTACAGTAGTCACCATTTAGATGTGGTTGAC | SEQ ID NO: 1020 | Homo sapiens polymerase (RNA) II (DNA directed) polypeptide K, 7.0kDa (POLR2K), mRNA [NM_005034] |
| 15 | A_23_P159650 | COX7B | CAAATACGGTAATGCTGTATTAGCTAGTGGAGCCACTTTGTATTGTTACATGAGACATA | SEQ ID NO: 1022 | Homo sapiens cytochrome c oxidase subunit VIIb (COX7B), nuclear gene encoding mitochondrial protein, mRNA [NM_001866] |
| 16 | A_23_P162596 | ACTR6 | TTAACGGCTTCACTGGAGACAGAGTTTCTTAGAAGGTAGTTTGTGTGAGTGTGACTAAACT | SEQ ID NO: 1027 | Homo sapiens ARP6 actin-related protein 6 homolog (yeast) (ACTR6), mRNA [NM_022496] |
| 17 | A_23_P18325 | PDCD10 | CCAACCGACTAATTCATCAAACGAAGTTAATACTTCAGACGTTCAAAACTGTGGCCTGAA | SEQ ID NO: 1039 | Homo sapiens programmed cell death 10 (PDCD10), transcript variant 1, mRNA [NM_007217] |
| 18 | A_23_P200955 | A_23_P200955 | AGACCATGATTGAACCTCACATTGATGTCAAGACTACCGGATGGTTATTTGTTTCATGTAC | SEQ ID NO: 1046 | |

Fig. 4-2

| No. | Probe ID No. | Symbols of genes | Sequence | SEQ ID NO: | Descriptions of genes (letters and numbers within [ ] indicates GenBank accession No.) |
|---|---|---|---|---|---|
| 19 | A_23_P15751 | NDUFA5 | TAAAAGTGGAGTCACTAAATAGTTTGGCAGTACGTTTGTAATATAAGTGTAGGTGGGTATC | SEQ ID NO: 1073 | Homo sapiens NADH dehydrogenase (ubiquinone) 1 alpha subcomplex, 5, 13kDa (NDUFA5), nuclear gene encoding mitochondrial protein, mRNA [NM_005000] |
| 20 | A_23_P52201 | EAF2 | GAGGATTCCTGATATAGATGCCAGTGATCATAATAGATTTCGAGACAACAGTGGCCTTCTGAT | SEQ ID NO: 1090 | Homo sapiens ELL associated factor 2 (EAF2), mRNA [NM_018456] |
| 21 | A_23_P26021 | COPS2 | TGCTTTTTTGATCAACTGGTTGTGTTTTGCTGCTGCATTTATCCCAAGAAAACAGGTT | SEQ ID NO: 1107 | Homo sapiens COP9 constitutive photomorphogenic homolog subunit 2 (Arabidopsis) (COPS2), mRNA [NM_004236] |
| 22 | A_23_P2705 | P2RY5 | TCTGTATTGCTGTTTCCAACTGTTGTTTGTTTTGACCCTATAGTTTACTACTTTACATCGGACA | SEQ ID NO: 1108 | Homo sapiens purinergic receptor P2Y, G-protein coupled, 5 (P2RY5), mRNA [NM_005767] |
| 23 | A_23_P307940 | CAPZA2 | CTACAAGATTGGCAAAGAAGATGCAGAATGCATAAGATGAAGATTGCATGACCGGATCATT | SEQ ID NO: 1117 | Homo sapiens capping protein (actin filament) muscle Z-line, alpha 2 (CAPZA2), mRNA [NM_006136] |
| 24 | A_23_P312246 | CCDC82 | GGCTTTATAACAGATGACTGTCAAGTGAATGAGTAGCTGTTGATATCCTGTCAGTTTAGTCAA | SEQ ID NO: 1121 | Homo sapiens coiled-coil domain containing 82 (CCDC82), mRNA [NM_024725] |
| 25 | A_23_P33045 | RPL26 | TACAAAGGTCAGCAAATTGGCAAAAGTAGTCAGGTTTACAGGAAAGAAATATGTTATCTAC | SEQ ID NO: 1132 | Homo sapiens ribosomal protein L26 (RPL26), mRNA [NM_000987] |
| 26 | A_23_P339480 | HAT1 | AACATGAACACGTGGAAGAGAGATTTTCAAGGAAGTAGTGGAAGATTACCGGCGTGTTATTG | SEQ ID NO: 1134 | Homo sapiens histone acetyltransferase 1 (HAT1), transcript variant 1, mRNA [NM_003642] |
| 27 | A_23_P38275 | TH-C2504576 | TCTCGGCAAAATGAAGTTAATCCGTTTGTGAGTTCGGACGCGAAAGCAAGAATGGATTCCTGT | SEQ ID NO: 1154 | RL26_BOVIN (P61257) 60S ribosomal protein L26, complete [TH2504576] |
| 28 | A_23_P405873 | C9orf72 | GAGAATGGAAGATCAGGATCAGAGATTATTATTCCAATGCTTACTGGAGAAGTGATTCCTGT | SEQ ID NO: 1162 | Homo sapiens chromosome 9 open reading frame 72 (C9orf72), transcript variant 2, mRNA [NM_145005] |
| 29 | A_23_P44257 | COMMD8 | AACATTTACTTCTGCGCTCTGTCATGTTGGGAAAGATTGCTCTGATAAAAATAGCTGTC | SEQ ID NO: 1179 | Homo sapiens COMM domain containing 8 (COMMD8), mRNA [NM_017845] |
| 30 | A_23_P46395 | PTBP2 | AACCAGGTGGGACCAAAGTTTATGTGCCTTTAGTCTTAATTTACCTTGCATTGTAATATT | SEQ ID NO: 1183 | Homo sapiens polypyrimidine tract binding protein 2 (PTBP2), mRNA [NM_021190] |
| 31 | A_23_P50907 | ITGAV | AAAGAGTGATTAAGTGAGGTTATTTACCGCGTAAATGGTCCATTCTGCATTGTATTTCAGG | SEQ ID NO: 1191 | Homo sapiens integrin, alpha V (vitronectin receptor, alpha polypeptide, antigen CD51) (ITGAV), mRNA [NM_002210] |
| 32 | A_23_P59921 | SUB1 | CAGATTGGCAAAATGAGGTACGTTAGTGTCGTCGGCGATTTTAAAGGCAAAGTGCTAATTGAT | SEQ ID NO: 1205 | Homo sapiens SUB1 homolog (S. cerevisiae) (SUB1), mRNA [NM_006713] |
| 33 | A_23_P61674 | CLK4 | GAAAGGCGATGCAAGTTGTGTCCATTGTGACAAGTTTGTTTAATAAAACCACATACACACTTTA | SEQ ID NO: 1207 | Homo sapiens CDC-like kinase 4 (CLK4), mRNA [NM_020666] |
| 34 | A_23_P63343 | UTS2 | AGAATGTGGAAACGATACACAGAAAAGTGAGACTCGTGATTGCTTCTGGAAATACTGTGTC | SEQ ID NO: 1211 | Homo sapiens urotensin 2 (UTS2), transcript variant 1, mRNA [NM_021995] |
| 35 | A_23_P65768 | C15orf15 | TCCTTGCATTGGCATCTAGATATCAGATTATCGGATATTACGGATGTTAGATTGCATCCACTGTT | SEQ ID NO: 1216 | Homo sapiens chromosome 15 open reading frame 15 (C15orf15), mRNA [NM_016304] |
| 36 | A_23_P86280 | ZNF267 | TGTGATGAATGTGGTAAAGCCTTCAGCTATACTATAGCTGGTCATAGCTTCACTACACGAGAAGT | SEQ ID NO: 1217 | Homo sapiens zinc finger protein 267 (ZNF267), transcript variant 498723, mRNA [NM_003414] |
| 37 | A_23_P70328 | CENPQ | CAATTGGCTTACAGTTTCTGCTCGGTCATCTGGAACTTGAAAAATCGTGAAATGCCTTCAC | SEQ ID NO: 1224 | Homo sapiens centromere protein Q (CENPQ), mRNA [NM_018132] |

Fig. 4-3

| No. | Probe ID No. | Symbols of genes | Sequence | SEQ ID NO: | Descriptions of genes (letters and numbers within [ ] indicates GenBank accession No.) |
|---|---|---|---|---|---|
| 38 | A_23_P76480 | BF213738 | AAATCGAACAGGACAATGGGTAGGATGGAGCTAGACATTTACCAAATCGTTTGGCATGAACAGG | SEQ ID NO: 1239 | BF213738 601847628F1 NIH_MGC_55 Homo sapiens cDNA clone IMAGE:4078519 5', mRNA sequence [BF213738] |
| 39 | A_23_P78092 | EVI2A | GCTGAATCAGACACTTGGAAAAGAACGAAAACAGCTCAAGGACCCAACCTAGTGATGCAA | SEQ ID NO: 1244 | Homo sapiens ecotropic viral integration site 2A (EVI2A), transcript variant 1, mRNA [NM_001003927] |
| 40 | A_23_P83278 | CHMP5 | CATTGCTCTTTTATTTTTCGATTAAGAGACTCATTGCTTGGGAAATGCTTCTTGGTAC | SEQ ID NO: 1251 | Homo sapiens chromatin modifying protein 5 (CHMP5), mRNA [NM_016410] |
| 41 | A_23_P87769 | C12orf48 | GTAAGAAATATCGTCAGTCGTCCTAATGCATATGTGACTGTTTGCATATAGTTCTGTTT | SEQ ID NO: 1254 | Homo sapiens chromosome 12 open reading frame 48 (C12orf48), mRNA [NM_017915] |
| 42 | A_23_P87579 | CD69 | TGTCGAATATGTGATGTGGCAAATCTCTATTAGGAAATATTCTGTAATCTTCAGACGTAG | SEQ ID NO: 1255 | Homo sapiens CD69 molecule (CD69), mRNA [NM_001781] |
| 43 | A_24_P11045 | THC2785765 | GCACCAGAAACGTACACCTGATTTTCATGAGAAATACGGTAGGAACACAAGTCGGAATAG | SEQ ID NO: 1283 | COX7B_HUMAN (P24311) Cytochrome c oxidase polypeptide VIIb, mitochondrial precursor partial (78%) [THC2785765] |
| 44 | A_24_P115774 | BIRC2 | GATACCATTTGGTTAAAGGAAATGGTGCGGCCAACATCTTCAAAAGTGTGTAAAAGAA | SEQ ID NO: 1285 | Homo sapiens baculoviral IAP repeat-containing 2 (BIRC2), mRNA [NM_001166] |
| 45 | A_24_P144665 | LOC401975 | TGTCGATGTCAAGACTAATGATGGCTACTTCTTTAATGTGTTCTGTGTTGGTTTTACTGA | SEQ ID NO: 1301 | PREDICTED: Homo sapiens similar to ribosomal protein S3a (LOC401975), mRNA [XR_017247] |
| 46 | A_24_P153324 | LOC390413 | GAAGCTTAACAAGGTTCAATTAACATGGTGGGGATTGTAGAACCATATATTGCAGGGTA | SEQ ID NO: 1304 | PREDICTED: Homo sapiens similar to 60S ribosomal protein L7 (LOC390413), mRNA [XR_016341] |
| 47 | A_24_P175187 | SAMD9 | CAACCAGGGATACGTAATCAAAATGTAATTTCCCCTAATAAATTATGCAATATGGGCGAG | SEQ ID NO: 1316 | Homo sapiens sterile alpha motif domain containing 9 (SAMD9), mRNA [NM_017654] |
| 48 | A_24_P175188 | SAMD9 | TGGCAATGTACTGGCAGAATTAAGACATACAACCTATGTTTTGAACAAAACAACCAGGATA | SEQ ID NO: 1317 | Homo sapiens sterile alpha motif domain containing 9 (SAMD9), mRNA [NM_017654] |
| 49 | A_24_P201702 | CLEC2B | ATTGGAATTCAAGTAAATACAACTGTTCCACTCAACATGCCACCTAACTATAATTGACA | SEQ ID NO: 1327 | Homo sapiens C-type lectin domain family 2, member B (CLEC2B), mRNA [NM_005127] |
| 50 | A_24_P203909 | RPL34 | GAGGGGTTCGTGCTGTGAAGACTTAAAGTTCTTATGAAATTGTCCAAAACAAACAACATG | SEQ ID NO: 1328 | Homo sapiens ribosomal protein L34 (RPL34), transcript variant 2, mRNA [NM_033625] |
| 51 | A_24_P212864 | LOC646161 | ACAGAAGTACAACGTGCGATCGATCGAAAGAATGATGAAGTAGGCTTGTACCAGG | SEQ ID NO: 1331 | PREDICTED: Homo sapiens similar to 60S ribosomal protein L26 (LOC646161), mRNA [XR_018048] |
| 52 | A_24_P221375 | A_24_P221375 | TACTTTGGTTACCCATGTACCTACCACCTTTCAAAAATCTACAGAGAGTCAATGTGGAGGA | SEQ ID NO: 1332 | |
| 53 | A_24_P243749 | PDK4 | ATTTGACATTTGTGTGTAATTTCATGGGCCTAGTGTTGTGGTGCTTCTGTAATGGTA | SEQ ID NO: 1345 | Homo sapiens pyruvate dehydrogenase kinase, isozyme 4 (PDK4), mRNA [NM_002612] |
| 54 | A_24_P286054 | ZFYVE16 | GTGTATGTATTCTGCCATGTAGTAAGTAATTGAACAGTCTTAAATAACCAAATGGTAGAGGG | SEQ ID NO: 1359 | Zinc finger FYVE domain-containing protein 16 (Endofin) (Endosome-associated FYVE domain protein). [Source:Uniprot/SWISSPROT;Acc:Q7Z3T8] [ENST00000380248] |
| 55 | A_24_P298604 | LOC731599 | GATGGAAATCATGACCAGAGGGTGCGGCAAATGACTTGAAAGAATTGGTCAATAAAATGAT | SEQ ID NO: 1365 | PREDICTED: Homo sapiens hypothetical protein LOC731599 (LOC731599), mRNA [XR_015536] |
| 56 | A_24_P306527 | ENST00000308869 | ACCGCATCCGTGCGTGGTTATCCAGAAAATGTAATGAGGATGAAGATTCACCGAAATAAGT | SEQ ID NO: 1366 | PREDICTED: Homo sapiens similar to ribosomal protein L31 (LOC729005), mRNA [XM_001133428] |

Fig. 4-4

| No. | Probe ID No. | Symbols of genes | Sequence | SEQ ID NO: | Descriptions of genes (letters and numbers within [ ] indicates GenBank accession No.) |
|---|---|---|---|---|---|
| 57 | A_24_P316074 | LOC730902 | TATCAATGGTGTGAGCCCAAAGGTCAAAGGTGTTGCAGGTTCTTCCCTTCGTCAAAATCTT | SEQ ID NO: 1372 | PREDICTED: Homo sapiens similar to 60S ribosomal protein L7 (LOC730902), mRNA [XR_015600] |
| 58 | A_24_P320328 | SUB1 | CAGAAAAACCTGTAAAGAACAAAAGACAGGTGAGACTTCGAGAGCCCTGTCATCTTCTA | SEQ ID NO: 1373 | Homo sapiens SUB1 homolog (S. cerevisiae) (SUB1), mRNA [NM_006713] |
| 59 | A_24_P324224 | A_24_P324224 | AAAGGTGTCTGGGCCAAGAATAAGGAATTCCTATAGGCATGTGCGGTTGTCTGCAGAAAA | SEQ ID NO: 1375 | |
| 60 | A_24_P33213 | A_24_P33213 | GACCATATATTACATGGGGTACCCAAATCTGAAGTCAGTAAATGAACTTATCTACAAGG | SEQ ID NO: 1379 | |
| 61 | A_24_P333112 | A_24_P333112 | GGTCATCAGAATCAGAGAGTATCAATGTGTGAGCCCACAGAGGACCAAAAGTATTGCAAGTT | SEQ ID NO: 1380 | |
| 62 | A_24_P33607 | LOC652558 | TAAGAAATAATTGCTTTGACAGACAACCGTTTGATTGCTCCATCTCTTGGTAAGTATATGG | SEQ ID NO: 1382 | PREDICTED: Homo sapiens similar to 60S ribosomal protein L7 (LOC652558), mRNA [XR_019336] |
| 63 | A_24_P349636 | LOC388401 | AGTTGCTTGGACAGATAACACTTTGATTGCTCGATCTCTTGGTAAATATAGGATCAACTG | SEQ ID NO: 1383 | PREDICTED: Homo sapiens similar to 60S ribosomal protein L7 (LOC388401), mRNA [XR_016679] |
| 64 | A_24_P366165 | LOC391126 | ACTTCCAAGCAAATCAAAAATGCATTCAATGCACCTTCCCAGCATTCACAGG | SEQ ID NO: 1393 | PREDICTED: Homo sapiens similar to 60S ribosomal protein L26 (Silica-induced gene 20 protein) (SIG-20) (LOC391126), mRNA [XR_019504] |
| 65 | A_24_P366546 | RPL31P10 | CGGGTGTCCAGAAAACGTAATGAGGATGAAGATTCAAATAAGCTCTATACTTTGGTTACC | SEQ ID NO: 1394 | PREDICTED: Homo sapiens similar to ribosomal protein L31 (LOC390283), mRNA [XR_018695] |
| 66 | A_24_P367191 | LOC652890 | AGTTAACGATGCTGAGGACTGTAGAGCCTATATTGCCTGTGTGGTACCCAAATCTGAAGTC | SEQ ID NO: 1396 | PREDICTED: Homo sapiens similar to 60S ribosomal protein L7 (LOC652890), mRNA [XR_019644] |
| 67 | A_24_P367199 | A_24_P367199 | TCTTATGCTCAGCACCAACAGTCTGCCAAATCAGAGAAGAAGGTGTAATCATGACCTGAGA | SEQ ID NO: 1397 | |
| 68 | A_24_P381625 | PSMC6 | ATGAAAGCAGTCAGAAAGTGGCTGATTCTAAGAAGCTGGAGTCTAAATTTACTAAAA | SEQ ID NO: 1404 | Homo sapiens proteasome (prosome, macropain) 26S subunit, ATPase, 6 (PSMC6), mRNA [NM_002806] |
| 69 | A_24_P383999 | RPS3A | TGGTTTTACTAAAAAGGAACAACAATCAGATACAGAAGAGACCTACTTATGCCCAGCACCCACGG | SEQ ID NO: 1405 | Homo sapiens ribosomal protein S3A (RPS3A), mRNA [NM_001006] |
| 70 | A_24_P384411 | A_24_P384411 | ATGGCAAAATCAATAAGACTGAAGCTTTGAACAGATAATGCTTTGACAGGCTGATCTCTTG | SEQ ID NO: 1406 | |
| 71 | A_24_P384539 | LOC730452 | CAAGAAAAGCTGGCAAGCTTCTATGTACCCACGACAACCCAAATTGGCATTTGTCATCAGGA | SEQ ID NO: 1407 | PREDICTED: Homo sapiens similar to 60S ribosomal protein L7 (LOC730452), mRNA [XM_001125895] |
| 72 | A_24_P414656 | TTC33 | TACTCAACATTTGGTATATTGTTTGACTAATGGATGTTTGTTTTTGTGTTAATTTGTGA | SEQ ID NO: 1421 | Homo sapiens tetratricopeptide repeat domain 33 (TTC33), mRNA [NM_012382] |
| 73 | A_24_P41651 | LOC641790 | AAGGAGAATGGGAACTTCCTGATGTGGGCATTGATGAGGACACAACAAAGTAGTCTGGAAA | SEQ ID NO: 1423 | PREDICTED: Homo sapiens similar to ribosomal protein L31 (LOC641790), mRNA [XR_018025] |
| 74 | A_24_P418712 | A_24_P418712 | AGGGTCAACAAAGCTGTCTCGGCCAAAGAAGAATAAGGAATATCGATACCATATCTGTGTTA | SEQ ID NO: 1426 | |
| 75 | A_24_P50437 | BC065737 | TGCAGAATGATGAAGTTGCATTTAGAAAATTCCTGATTACTGAAGATGTTCAGGGCAAA | SEQ ID NO: 1430 | Homo sapiens cDNA clone IMAGE:30404477, partial cds. [BC065737] |
| 76 | A_24_P57837 | THC2567891 | AGAAATCCGGAAGACCTCTTATGCTCAGTACCAGCCAAATCCGGAAGAAGATGATGGAAA | SEQ ID NO: 1440 | Q6NXR8_HUMAN (Q6NXR8) Ribosomal protein S3a, partial (91%) [THC2567891] |

Fig. 4-5

| No. | Probe ID No. | Symbols of genes | Sequence | SEQ ID NO: | Descriptions of genes (letters and numbers within [ ] indicates GenBank accession No.) |
|---|---|---|---|---|---|
| 77 | A_24_P587938 | A_24_P587938 | CTTCAAAGAAGCAAAAGGTGGAGATGCTGGAACAGCGAGGAGGCAGATTAACAGTCTTAT | SEQ ID NO: 1441 | |
| 78 | A_24_P606663 | LOC392030 | TGTGCGGTTGCCCAGAAACGTAATGCGGGTGAAGATTCACCAAATAAGCTCCATACTTT | SEQ ID NO: 1442 | PREDICTED: Homo sapiens hypothetical LOC392030 (LOC392030), mRNA [XR_018063] |
| 79 | A_24_P685729 | A_24_P685729 | TTGAAGGTTATGTTGATGTCAAGAGTATCAGTGATTGATTTGCTTTGTCTGTTTTGTGTGG | SEQ ID NO: 1448 | |
| 80 | A_24_P6975 | LOC342994 | GGAAGAGTCGAGGGAGGTCGTGCTGTAAGACCTAAAGTTCTTATGAAATTGTCAAAAGA | SEQ ID NO: 1450 | PREDICTED: Homo sapiens similar to ribosomal protein L34 (LOC342994), mRNA [XM_938484] |
| 81 | A_24_P75158 | PTAR1 | CCATTAGATTTGTTCTTTATGTGACCATGTACCAAGCAGCACTATAAAGTATTGTATTTCTG | SEQ ID NO: 1454 | Homo sapiens mRNA; cDNA DKFZp313P0917 (from clone DKFZp313P0917). [AL832683] |
| 82 | A_24_P755505 | A_24_P755505 | ATACAGAAGACCTCTTATGCTCAGCACCAAGAGAAAAGTAAAAATGGTGAAGAAGCCCAA | SEQ ID NO: 1455 | |
| 83 | A_24_P76358 | LOC643981 | TTACTGAAGATGTTCAGGGCAAAAGTGCCTAACTTCCGGCGCATGGATCTTATTCGTGAGA | SEQ ID NO: 1458 | PREDICTED: Homo sapiens similar to 40S ribosomal protein S3a (V-fos transformation effector protein) (LOC643981), mRNA [XR_018444] |
| 84 | A_24_P792734 | PSMC6 | AGAAGGTTAACGGAGGTTACTGAATCAAATCAAATGGATTTGATACTCTGCATAGAGATTAAA | SEQ ID NO: 1459 | Homo sapiens proteasome (prosome, macropain) 26S subunit, ATPase, 6 (PSMC6), mRNA [NM_002806] |
| 85 | A_24_P84808 | LOC729449 | GAATTGCTTTGACAGATAACGCTTTGGATCTCTTGGAAAATATGGCATCATCTGTATGG | SEQ ID NO: 1465 | PREDICTED: Homo sapiens similar to 60S ribosomal protein L7 (LOC729449), mRNA [XR_015548] |
| 86 | A_24_P850187 | A_24_P850187 | TAAATGAAGTAATCTACAAGGCGTGCTTATGGCAAAATGAATTTGACTTGCACTTTCCTAC | SEQ ID NO: 1467 | |
| 87 | A_24_P113154 | LOC730861 | ACCACCAGTCAAGAATCTGTTTAAAGTTCAGACTTAAAACAGTACCAAATAAAAGTCC | SEQ ID NO: 1491 | PREDICTED: Homo sapiens similar to 40S ribosomal protein S3a (V-fos transformation effector protein) (LOC730861), mRNA [XR_015591] |
| 88 | A_24_P11931 | LOC441073 | GTGTGATCATGCCATCGGAAAGGATGAAGTTCAGGTTGTACGTGGAACACTATAAA | SEQ ID NO: 1497 | PREDICTED: Homo sapiens similar to 60S ribosomal protein L26 (Silica-induced gene 20 protein) (SIG-20) (LOC441073), mRNA [XR_016376] |
| 89 | A_32_P125549 | RPL31P4 | TCTACAGACAGTCAATGTGGGGGTACCCCAATCTGAAGTCAGTAAATGAACATACATCAAATAAAG | SEQ ID NO: 1500 | PREDICTED: Homo sapiens ribosomal protein L31 pseudogene 4 (RPL31P4), mRNA [XR_018222] |
| 90 | A_32_P128781 | A_32_P128781 | GATATATTGCATGGGGGTACCCACGAATCGAAGTCAGTAAATGAACTAATCTAGAAGAGTG | SEQ ID NO: 1502 | |
| 91 | A_32_P135818 | RPS3A | CTTGCTTCATCTGTCTGTGTTGTGTTTTAATAAAAACGCAACAATCAGATATGGAAGAC | SEQ ID NO: 1504 | Homo sapiens ribosomal protein S3A (RPS3A), mRNA [NM_001006] |
| 92 | A_32_P145153 | RPL31 | ATCGGTGTGCAGCTGTCCAGAAAACGTAATGAGGATGAAGATTCACCAAATAAGCCATAT | SEQ ID NO: 1508 | Homo sapiens ribosomal protein L31 (RPL31), mRNA [NM_000993] |
| 93 | A_32_P153725 | KIAA1033 | TTTTGTAAAAGATGGCAAGTTTGTTACCTCACTTGAGTGGGGTTTCCTTTTCCCCCAAT | SEQ ID NO: 1513 | Homo sapiens KIAA1033 (KIAA1033), mRNA [NM_015275] |
| 94 | A_32_P155364 | RPL7 | TCAACAGGGTTATTAGAAAATGAACCAAGGTGTCTACCAGATTATTTTCTAAGCTGG | SEQ ID NO: 1514 | Homo sapiens ribosomal protein L7 (RPL7), mRNA [NM_000971] |
| 95 | A_32_P164203 | THC2683448 | TTGATGGTCATTGTACGAGGTATTGTGATTAGTGTGAGTGCTGTTTAACCAGATGAT | SEQ ID NO: 1519 | Q7WZ63_PASPI (Q7WZ63) Ferric uptake regulator, partial (8%) [THC2683448] |

Fig. 4-6

| No. | Probe ID No. | Symbols of genes | Sequence | SEQ ID NO: | Descriptions of genes (letters and numbers within [ ] indicates GenBank accession No.) |
|---|---|---|---|---|---|
| 96 | A_32_P190468 | hCG_26523 | CCCAGGAAGGTGGTTATCACTAGGCTAAAACTGGAGAAAGACCGCAAAAGATCCTTGAA | SEQ ID NO: 1531 | PREDICTED: Homo sapiens similar to 60S ribosomal protein L26 (LOC646161), mRNA [XR_018048] |
| 97 | A_32_P196483 | RPS3A | GGGGCCAAGAAGAAAGTGGTTGATCCATTTCAAGAAAGATTGGTATGATGTGAAAGCA | SEQ ID NO: 1534 | Homo sapiens ribosomal protein S3A (RPS3A), mRNA [NM_001006] |
| 98 | A_32_P208178 | RPS3A | GGAAAAGACGTTAGAAAAGGCTTGCCAATCTATTTATCCTCTCCATCATGTCTTGGTTAGA | SEQ ID NO: 1544 | Homo sapiens ribosomal protein S3A (RPS3A), mRNA [NM_001006] |
| 99 | A_32_P220127 | RPL34 | CAAAACTAGGCTGTCCTGAACCCCTGCTAATAGAATTGTTCACCTTTATACCAAGAAGGT | SEQ ID NO: 1546 | Homo sapiens ribosomal protein L34 (RPL34), transcript variant 2, mRNA [NM_033625] |
| 100 | A_32_P22539 | hCG_26523 | ACTAGGAAGGTCAGCAAATTGGCAAAGTGGTCCAGGTTTACAGGAAGAAATATGTTATCT | SEQ ID NO: 1549 | PREDICTED: Homo sapiens similar to 60S ribosomal protein L26 (Silica-induced gene 20 protein) (SIG-20) (LOC400055), mRNA [XM_374987] |
| 101 | A_32_P2333 | SUB1 | AGGAAGAAAAGTATTTCTTTAAATCCAGAACAATGGAGCCAGCTGACAGAACAGATTC | SEQ ID NO: 1551 | Homo sapiens SUB1 homolog (S. cerevisiae) (SUB1), mRNA [NM_006713] |
| 102 | A_32_P4532 | LOC643932 | GATTCAGAGACAGCATTGGAAAAGACATAGAAGAAAGGGTTGCCAATCTATCCTCTCCATGAT | SEQ ID NO: 1560 | PREDICTED: Homo sapiens similar to 40S ribosomal protein S3a (V-fos transformation effector protein) (LOC643932), mRNA [XR_017289] |
| 103 | A_32_P49392 | A_32_P49392 | AATTCTGCCAAATCTGAAGAAGATGATGGAAATCATGACCGAAGAGGTGCAGACAAATG | SEQ ID NO: 1563 | |
| 104 | A_32_P58074 | RPS3A | GTTGGTTTACTAAAAAACGCAAAAATCAGATACGGAAGACCTCTTATGCTCAGCACCAA | SEQ ID NO: 1566 | Homo sapiens ribosomal protein S3A (RPS3A), mRNA [NM_001006] |
| 105 | A_32_P7118 | PSMC6 | AGGAGACCTGAGAAATGTTTGTACTGAAGCAGGTATGTTCGGAATTCGTGCTGATCATGA | SEQ ID NO: 1570 | Homo sapiens proteasome (prosome, macropain) 26S subunit, ATPase, 6 (PSMC6), mRNA [NM_002806] |
| 106 | A_32_P77571 | AK024584 | GTCATCTCTTAATGAAGCATTATGGAGCTGTTAAAGATGATAGATGTAAAGGTTATGAG | SEQ ID NO: 1571 | Homo sapiens cDNA: FLJ20931 fis, clone ADSE01282. [AK024584] |
| 107 | A_32_P93782 | RPL26 | AGGTTGTACATGGAACACTATAAAGGTCAGCAAATTGGCAAAGTAGTCCAGGTTTACAGGA | SEQ ID NO: 1578 | Homo sapiens ribosomal protein L26 (RPL26), mRNA [NM_000987] |

Fig. 5-1

| No. | Probe ID No. | Symbols of genes | Sequence | SEQ ID NO: | Descriptors of genes (letters and numbers within [ ] indicates GenBank accession No.) |
|---|---|---|---|---|---|
| 1 | A_23_P141415 | MYCBPAP | TGTGCAGGTGACTCTCGGGCCAAGACAACCTTCTGGAAAACGGGGTTAATAAATCAA | SEQ ID NO: 1582 | Homo sapiens MYCBP associated protein (MYCBPAP), mRNA [NM_032133] |
| 2 | A_23_P143247 | TSH22 | CCCAAGAAGACGGTATGCAAATCTGTAAGTTTACGGGACTCTCAATGACCACTATCAGTCA | SEQ ID NO: 1583 | Homo sapiens teashirt family zinc finger 2 (TSHZ2), mRNA [NM_173485] |
| 3 | A_23_P146325 | DDEF1IT1 | TGGAAAGTGAAGTGAAGGATTTTTGTCATACAGACCAGTAAGTGCCAGAAGTGACTCGAAC | SEQ ID NO: 1584 | Homo sapiens DDEF1 intronic transcript 1 (DDEF1IT1) on chromosome 8 [NR_002765] |
| 4 | A_23_P151426 | FOXO1 | TGGGGTTAGTGAGCAGGTTAGAGTTAAAAGTAGTTCAGATTGTCTGACACAAGGAAGTGA | SEQ ID NO: 1585 | Homo sapiens forkhead box O1A (FOXO1A), mRNA [NM_002015] |
| 5 | A_23_P151805 | FBLN5 | GGGAACCCTGGGAGTTAGGTAGTTTGCTTTTGGGTACACAGAGAAGGCTATGTAAACAGA | SEQ ID NO: 1586 | Homo sapiens fibulin 5 (FBLN5), mRNA [NM_006329] |
| 6 | A_23_P153516 | MADCAM1 | CTTTCTGGACGGAACCAGGTACTTTTACATACATTGATTCATGTCTCACGTGTCCGTAA | SEQ ID NO: 1587 | Homo sapiens mucosal vascular addressin cell adhesion molecule 1 (MADCAM1), transcript variant 1, mRNA [NM_130760] |
| 7 | A_23_P154627 | TSHZ2 | GTAATTGGGGTTCTGTAGGTTGTGTTAAAAATTGTGTGGTCGAATGCAAGGTTATTAGGCCA | SEQ ID NO: 1588 | Teashirt homolog 2 (Zinc finger protein 218) (Ovarian cancer-related protein 10-2) (OVC10-2). Source:Uniprot/SWISSPROT;Acc:Q9NRE2] [ENST00000371497] |
| 8 | A_23_P157299 | AEBP1 | ACAGTAGAGACCTAGACGTGAACTTTGGGGACTTCTGAGATCAGCGTCCTACCAAGACC | SEQ ID NO: 1589 | Homo sapiens AE binding protein 1 (AEBP1), mRNA [NM_001129] |
| 9 | A_23_P157333 | EPHA1 | TATGGGGAGATGAGCAATCAGGAGGTTATGAAGAGCATTGAGGATGACCAGTGGCTGCCC | SEQ ID NO: 1590 | Homo sapiens EPH receptor A1 (EPHA1), mRNA [NM_005232] |
| 10 | A_23_P163492 | BAIAP3 | GACCCATTTTTGGTAATCACAGAGGAGTGAAAAGGGTGCCACTGGCACCACTGGGTG | SEQ ID NO: 1591 | Homo sapiens BAI1-associated protein 3 (BAIAP3), mRNA [NM_003933] |
| 11 | A_23_P16496 | A_23_P16496 | GGAGATCTGGGGCTGGGAAGAATGTAAAGCAACCTAAACAGTAATTTAAGAATGGAGA | SEQ ID NO: 1592 | |
| 12 | A_23_P202520 | ABLIM1 | TCACTGCACTCGTTTGTCATATACTCGCATCGTCATACTCACAACTTCGTGAATAA | SEQ ID NO: 1593 | Homo sapiens actin binding LIM protein 1 (ABLIM1), transcript variant 3, mRNA [NM_001034081] |
| 13 | A_23_P209055 | CD22 | GCCTCAGGCACCACAGAAAATGTGGACTATGTGATCCTGAAACATTGACAGTGGATGGGCTG | SEQ ID NO: 1594 | Homo sapiens CD22 molecule (CD22), mRNA [NM_001771] |
| 14 | A_23_P214821 | EDN1 | AGGCGGCTGGGACATTCAGGGGACAGAAAACTCAAAGTCCAAGACAAGATTTTCTAAGGAAT | SEQ ID NO: 1595 | Homo sapiens endothelin 1 (EDN1), mRNA [NM_001955] |
| 15 | A_23_P250212 | DKFZp761P0423 | GAAGTGAATGCAGCCTGGAGACATGGCCTCAATACCTTGTTAGGATTTGTTCACCCTTTT | SEQ ID NO: 1596 | Tyrosine-protein kinase SgK223 (EC 2.7.10.2) (Sugen kinase 223). [Source:Uniprot/SWISSPROT;Acc:Q86YV5] [ENST00000330777] |
| 16 | A_23_P255896 | ENST00000335459 | GCAAGGGGCTCTACGCAGAGTAGCTGTCGAATGCTATTGCCGGAAACTGGGAGCGGAAGA | SEQ ID NO: 1597 | Homo sapiens hypothetical protein LOC129293, mRNA (cDNA clone IMAGE:5762496), partial cds. [BC051789] |
| 17 | A_23_P315378 | ATG16L1 | CTGTGTTTCCAGTTTATACTCTCTTTGTCCAAAACTCAGTTTCAAAATATTTGGAATGGGAC | SEQ ID NO: 1598 | Homo sapiens cDNA FLJ10035 fis, clone HEMBA1000919. [AK000897] |
| 18 | A_23_P315386 | RHPN1 | CGGGCTGGCCTGAAGGAGAGGGCGACTACATTGTGTCAGTGAATGGGCAGCCATGCAGGTGGT | SEQ ID NO: 1599 | Homo sapiens rhophilin, Rho GTPase binding protein 1 (RHPN1), mRNA [NM_052924] |

Fig. 5-2

| No. | Probe ID No. | Symbols of genes | Sequence | SEQ ID NO: | Descriptions of genes (letters and numbers within [ ] indicate GenBank accession No.) |
|---|---|---|---|---|---|
| 19 | A_23_P338919 | SPEG | GCAGGGGCCACTCTGTAGTGAGGGTGGAGAAATTTGGAAACACCTATTTCTTAACTCAAAT | SEQ ID NO: 1600 | Homo sapiens cDNA FLJ30825 fis, clone FEBRA2001706, highly similar to Human APEG-1 mRNA. [AK055387] |
| 20 | A_23_P341938 | NOG | GCCABCGGCTGGGGCTGGATTCCCATCCGAGTACCCCATCATTTCCGAGTGCAAGTGCTGGT | SEQ ID NO: 1601 | Homo sapiens noggin (NOG), mRNA [NM_005450] |
| 21 | A_23_P343398 | CCR7 | AAGAGAGCAACAATTTACCGACACACAGATAAAGTTTTCCCTTGAGGAAACAACAGCTTT | SEQ ID NO: 1602 | Homo sapiens chemokine (C-C motif) receptor 7 (CCR7), mRNA [NM_001838] |
| 22 | A_23_P344531 | SYNPO | TCGTGCTGCTGTGAAGATGAAGGTGCTCTTACTCAGTTAATGATGACTGACTATATTT | SEQ ID NO: 1603 | Synaptopodin. [Source:Uniprot/SWISSPROT:Acc:Q9N3X7] [ENST00000307862] |
| 23 | A_23_P357504 | AL834280 | CCCACAGGGCAATCAACACGCTTCTGTGAATAAATAAAAGTTTATCATTCCGTACAAAC | SEQ ID NO: 1604 | |
| 24 | A_23_P359870 | C8orf16 | CTGAGGTTATAATTTCACTTAACATTGTGCAAGTTGGCATTTTGGTTTTAGTCCAATGGT | SEQ ID NO: 1605 | Homo sapiens mRNA for hypothetical protein (C8ORF16). [AJ312926] |
| 25 | A_23_P391275 | DSCR1L2 | TAAATTATGATTTAGTGTGTGCTGTTTCCAAATTGGGAACGAGGAGAGAAATATGAACGTTC | SEQ ID NO: 1606 | Homo sapiens Down syndrome critical region gene 1-like 2 (DSCR1L2), mRNA [NM_013441] |
| 26 | A_23_P3921 | FLJ11710 | CGTGATTCATGATTGAAGTACGATTACCACACTTCTCTCCCCTTAGAGAATGCATGGATTA | SEQ ID NO: 1607 | Homo sapiens cDNA FLJ11710 fis, clone HEMBA1005149. [AK021772] |
| 27 | A_23_P420873 | NR1D1 | CCCTTCTGTACAAGATGGAAGTCTGCAACTCTCTCTCCTTAGAGAGAAAAGGAAAAGCA | SEQ ID NO: 1608 | Homo sapiens nuclear receptor subfamily 1, group D, member 1 (NR1D1), mRNA [NM_021724] |
| 28 | A_23_P48585 | SALL2 | CTAGTAAAATGTCAAGAAGACAGGAGATATTAGTGTCTTTCCCTGTATCATTAAAGGT | SEQ ID NO: 1609 | Homo sapiens sal-like 2 (Drosophila) (SALL2), mRNA [NM_005407] |
| 29 | A_23_P49638 | GRAP | CCAGGCAGACAGAAGAAGTTGGGCCAGACTAGGTTTTAGAGACTGTACAAGGACGCA | SEQ ID NO: 1610 | Homo sapiens GRB2-related adaptor protein (GRAP), mRNA [NM_006613] |
| 30 | A_23_P500130 | ANKRD15 | TTTACCGTGTCAGATTTACTTAGTCTGTCCTCTATGTATTAAATGTTTGAAGTGCCTTAGAC | SEQ ID NO: 1611 | Homo sapiens ankyrin repeat domain 15 (ANKRD15), transcript variant 2, mRNA [NM_153186] |
| 31 | A_23_P7582 | TCF7 | CCCAGAAAAACCTCCAGTAGTGGAACAACAGGTTTTCACCATAGCCCTACGTTAACCCATTTT | SEQ ID NO: 1612 | Homo sapiens transcription factor 7 (T-cell specific, HMG-box) (TCF7), transcript variant 1, mRNA [NM_003202] |
| 32 | A_23_P83388 | EPPK1 | GTTTTTTGGTGTGTTTTCTGGGTCGTCTATGTGTCATATGGTTTAGTTTCTCCCGGAA | SEQ ID NO: 1613 | Homo sapiens epiplakin 1 (EPPK1), mRNA [NM_031308] |
| 33 | A_23_P84399 | CNTNAP2 | CTTGAGGCAGATCCTTAAATATCAGACAAGAAGTTGGGGGAGCAGGGCAATGGAATATATG | SEQ ID NO: 1614 | Homo sapiens contactin associated protein-like 2 (CNTNAP2), mRNA [NM_014141] |
| 34 | A_24_P128057 | MBNL1 | AGAATATTGCTGCAAGACTATCTGTGATTGGTATCTCTGTATCATGGATTGCTTCACAA | SEQ ID NO: 1615 | Homo sapiens muscleblind-like (Drosophila), mRNA (cDNA clone IMAGE:3935812), partial cds. [BC005296] |
| 35 | A_24_P252945 | BLR1 | TTTTTTTTTAATAAAAGGCACCACCTATAAAACAGGTCAATACAGTACAGGCAGCACAGAG | SEQ ID NO: 1616 | Homo sapiens Burkitt lymphoma receptor 1, GTP binding protein (chemokine (C-X-C motif) receptor 5) (BLR1), transcript variant 2, mRNA [NM_032966] |
| 36 | A_24_P280751 | DTX1 | TCCAATTTTGAGAGCAGGGAAAGGCTGGGGCTCGACTTCAGGAGGCGAAAGGAGGAGGCCT | SEQ ID NO: 1617 | Homo sapiens deltex homolog 1 (Drosophila) (DTX1), mRNA [NM_004416] |
| 37 | A_24_P288360 | LTBP3 | CTCGTCGTGGGGGAAGCCCCAAGAGATGAGGACAGTTCAGAGGAGGATTCGACGAGTGT | SEQ ID NO: 1618 | Homo sapiens latent transforming growth factor beta binding protein 3 (LTBP3), mRNA [NM_021070] |

Fig. 5-3

| No. | Probe ID No. | Symbols of genes | Sequence | SEQ ID NO: | Descriptions of genes (letters and numbers within [ ] indicates GenBank accession No.) |
|---|---|---|---|---|---|
| 38 | A_24_P312325 | C8orf15 | CTTGTTCAATGTGACTAGTTTAGTTGCCTGTCCAATATGAAGTAGAAAAGCAGATTCTG | SEQ ID NO: 1619 | Homo sapiens chromosome 8 open reading frame 15 (C8orf15), mRNA [NM_001033662] |
| 39 | A_24_P316414 | BC014346 | TAACGTTGGGGTGTTGGGAGTAGAACTTTAGCTTTGAATAATTTAAGGGCTTGGCCTGTA | SEQ ID NO: 1620 | Homo sapiens, clone IMAGE:4042988, mRNA, partial cds. [BC014346] |
| 40 | A_24_P340112 | THC2683124 |  | TCCAATTTGTTAAGTGTTGAGTCCAACTGATGTAGAAGTTGTGACTTGTAAACCATTCATCC | SEQ ID NO: 1621 |  |
| 41 | A_24_P360499 | DDEF1IT1 | TGTTCGTTTTAATGTTAGGGCAGGTCCTATACTTCAGATTTAACTTTGAAATGTAGCATAG | SEQ ID NO: 1622 | Homo sapiens DDEF1 intronic transcript 1 (DDEF1IT1) on chromosome 8 [NR_002765] |
| 42 | A_24_P360722 | DIP2C | GGCTTTAGGTTGGCAAATAGCACTGTTTTCTTAGCTGCAAGAATTCATTGCACAATGTTT | SEQ ID NO: 1623 | Homo sapiens DIP2 disco-interacting protein 2 homolog C (Drosophila) (DIP2C), mRNA [NM_014974] |
| 43 | A_24_P37020 | THC2690931 | TGCTTCTACGTCCAAGTAAAAGAGAAAAGAGGGTGAAGGTCAGCCATGTTAGCTATGAGA | SEQ ID NO: 1624 | AF235005 suppression of tumorigenicity 16 protein [Homo sapiens] (expn=-1; wgp=0; cg=0), partial (13%) [THC2690931] |
| 44 | A_24_P413126 | TMEPAI | AAGAAACTGGTTGTTGTGTATCAGTAATCATTAGTGGGAATGATGACATTCTGAAAAGCT | SEQ ID NO: 1625 | Homo sapiens transmembrane, prostate androgen induced RNA (TMEPAI), transcript variant 1, mRNA [NM_020182] |
| 45 | A_24_P417352 | ENST00000390559 | TGACCAGCTATGACAGCGTGACCATCTCCTGGACCGGCAGAATGCGCAAGCTGTGAAAA | SEQ ID NO: 1626 | Immunoglobulin heavy chain C gene segment [Source:IMGT/GENE_DB:Acc:IGHM] [ENST00000390559] |
| 46 | A_24_P460763 | AK022443 | GTGAGTAGCAGGGTAGTTAAGATGCCTAGTGGGTCTAAATGTCAAATGCTATTGGGAGAT | SEQ ID NO: 1627 | Homo sapiens cDNA FLJ12381 fis, clone MAMMA1002566. [AK022443] |
| 47 | A_24_P491923 | THC2491622 | CTTCTGTTGTTTCTCAATAAAGTAGAACAAGTCGATCTGATGGGTGTTTAGTAGGGTATGA | SEQ ID NO: 1628 |  |
| 48 | A_24_P648264 | AL512741 | AAGAATTGAGTTAGAAGTGCCTATAATGTAATGCAGAATATTTCCGAATAATGCCTAGG | SEQ ID NO: 1629 | Homo sapiens mRNA; cDNA DKFZp667N064 (from clone DKFZp667N064) [AL512741] |
| 49 | A_24_P642771 | AK024956 | ATTCTCCATATATTTTAGTTGTTCTATTGGCTAGAAAGACAAAACAAGGGAATCTGG | SEQ ID NO: 1630 | Homo sapiens cDNA: FLJ21303 fis, clone COL02107. [AK024956] |
| 50 | A_24_P662177 | THC2666469 | GGGCAGGTAGGATTTGAATGGCATGTTACATAACCATCCTCTAAAGGGACAGAATGTACA | SEQ ID NO: 1631 |  |
| 51 | A_24_P713312 | THC2639056 | TTTATATGGTCGGATGGTCCATGTTAGGAATTAAGGGGTAATTAATAGTAATGTATGTGGA | SEQ ID NO: 1632 | ALU8_HUMAN (P39195) Alu subfamily SX sequence contamination warning entry, partial (10%) [THC2639056] |
| 52 | A_24_P728115 | AK024937 | ACTGGATAGTCACTACTTTTAGTGAGTTGAAATCTGTTTGGAGAGCTATGTAAGTACCA | SEQ ID NO: 1633 | Homo sapiens cDNA: FLJ21284 fis, clone COL01911. [AK024937] |
| 53 | A_24_P792389 | THC2671169 | ATGCTAACGGTGGAGAGTAAGGCATAAGAAGTATGACTAGAATTGCCAGCTACACATTAGA | SEQ ID NO: 1634 |  |
| 54 | A_24_P7974 | SLC26A6 | GTTGCTTTATGTAGGCAAATTCTCCGTTTGGAGCTTTTAAAATAGGATTATTTGCCAGAAC | SEQ ID NO: 1635 | Homo sapiens HSPC106 mRNA, partial cds. [AF161369] |
| 55 | A_24_P79855 | ENST00000390643 | AAACGATTGGTCCCTTTTACCCAGGAAGGACTCAAGAAGGCCGAACGTGATAGGAGATGG | SEQ ID NO: 1636 | Homo sapiens hypothetical protein DKFZp566H0824, mRNA (cDNA clone MGC:129790 IMAGE:40021976), complete cds. [BC104430] |
| 56 | A_24_P810490 | BX099367 | AGGCCCAGAGTTGCAGAGCACCTTGGGCTACAGAGTGACAGCCTGTCTGTACAAAACTA | SEQ ID NO: 1637 | BX099367 Soares_fetal_liver_spleen_1NFLS_S1 Homo sapiens cDNA clone IMAGp998G05977, mRNA sequence [BX099367] |

Fig. 5-4

| No. | Probe ID No. | Symbols of genes | Sequence | SEQ ID NO: | Descriptions of genes (letters and numbers within [ ] indicates GenBank accession No.) |
|---|---|---|---|---|---|
| 57 | A_24_P914102 | A_24_P914102 | TTAGTAGACCCTAGATTTCTCTACAAATGTAAAATGTTATTTTT ACTGTTGAAAATCAG | SEQ ID NO: 1638 | |
| 58 | A_24_P915361 | AF086536 | AGTCACTCGAGAAGGTGAGAGCTCTGGAACTGAGGGCCTGGGAGC TCTGTTACGAGAGGAA | SEQ ID NO: 1639 | Homo sapiens full length insert cDNA clone ZE08A03. [AF086536] |
| 59 | A_24_P928025 | DKFZp547E087 | TGTTATGAACATAGTTCATGTTAAGTCTCCATTTAATACAACCT GAAATACCAAAGTTA | SEQ ID NO: 1640 | Homo sapiens cDNA FLJ30147 fis, clone BRACE2000266. [AK054709] |
| 60 | A_24_P927090 | AF116678 | TGTTGGTTTCTCTTTAACAGATTCAGGGCGTCATCCTTTGACTCGG AACGAGGAAGGAATT | SEQ ID NO: 1641 | Homo sapiens PRO1995 mRNA, complete cds. [AF116678] |
| 61 | A_24_P930337 | THC2503773 | AGGAAGTGGAACCGACACCCAAAATATGACTTGAAGAATGTAATT TAAAATGTTAGCATAG | SEQ ID NO: 1642 | |
| 62 | A_24_P930391 | AK022351 | AAGTGGGTTTAATTCCTTTTGATGAAAGGAAGAATTAGGCTTTGA TGCAAACAGTTGCTC | SEQ ID NO: 1643 | Homo sapiens cDNA FLJ12289 fis, clone MAMMA1001788. [AK022351] |
| 63 | A_24_P930983 | LOC650392 | GCCCCATTTCAAGTATACAGGAGGGAAAATGGTGCTTGAAATA AGCATGCCACAAAGG | SEQ ID NO: 1644 | Homo sapiens cDNA clone IMAGE:5264670. [BC036550] |
| 64 | A_24_P933548 | A_24_P933548 | CACCTCGACCTTATATCTTATGTTTATACGTGCAGAAGTATAAC CTAAGGGAAGGAATG | SEQ ID NO: 1645 | |
| 65 | A_24_P934861 | AF116678 | GGAGGTATCAAGCAGGAAATTCCAGTTTCTGGGAAATAGTGGACC AGATCGTCTCGATGG | SEQ ID NO: 1646 | |
| 66 | A_24_P935682 | AY358248 | AGTCAGTAATCAGGATTCAATCAATATGAGGTCTAAGCATGATGCT TGACAGTTATGGAAC | SEQ ID NO: 1647 | Homo sapiens clone DNA166629 MRSS6228 (UNQ6228) mRNA, complete cds. [AY358248] |
| 67 | A_24_P945096 | CACNA1I | CTTAGAGAGTCGCTCTTTAGCCCAGATAGACATAGTCTCTTTTTGTC TTTGTGCAATAATCA | SEQ ID NO: 1648 | Homo sapiens calcium channel, voltage-dependent, T type, alpha 1I subunit (CACNA1I), transcript variant 1, mRNA. [NM_021096] |
| 68 | A_32_P101002 | CA433167 | CTGTGAACTTGTCAAACATCATGCACTGGACAGGAGGACCTA CTGAGGAGACATTTC | SEQ ID NO: 1649 | UI-H-C00-ark-e-04-0-UI_s1 NCI_CGAP_Sub9 Homo sapiens cDNA clone UI-H-C00-ark-e-04-0-UI 3', mRNA sequence [CA433167] |
| 69 | A_32_P105940 | A_32_P105940 | GTGCCAAGGTAAGGCTACGACTTTTGGTTTTTATTTCAAGCAGAAC ATGAAAGGCCCTA | SEQ ID NO: 1650 | |
| 70 | A_32_P111394 | THC2643957 | GAATACAGTGTTCCTTTTCATCGCATATTTGACTGAAGCTAAGAC ACATCAATTATAAGG | SEQ ID NO: 1651 | |
| 71 | A_32_P112546 | LOC649344 | AGGGAGGTCACTATGCGAGGGTAGGACTGGCAGCAGGAGGACCCACC TGAAGGCTGAGCCTA | SEQ ID NO: 1652 | PREDICTED: Homo sapiens similar to Keratin, type II cytoskeletal 8 (Cytokeratin-8) (CK-8) (Keratin-8) (K8) (LOC649344), mRNA [XR_018597] |
| 72 | A_32_P116997 | THC2719256 | AAACATTAGGTAGGAGCTTGTAGAGGATATATTTGAGTGCATGAT GTCCTTCTTCTTGGC | SEQ ID NO: 1653 | BE147120 PM2-HT0224-221099-001-b10 HT0224 Homo sapiens cDNA, mRNA sequence [BE147120] |
| 73 | A_32_P121978 | A_32_P121978 | CAGATTAGACCACCTCATAATGAGTTCTTGATTGCACTTCAGATT GTCTGATGGGGCAC | SEQ ID NO: 1654 | |
| 74 | A_32_P125589 | THC2649341 | CGGTCTATCCTTGCTTCTTAGCCTTTGAATGAAAGTGAAGTGTGT CATCAGGCTAGATAG | SEQ ID NO: 1655 | |
| 75 | A_32_P12703 | THC2697162 | TTGAAAGGAAAGAGTATAGGGGGGAAGTGCCAGAGTAAACGAATC CTAAGTAAATAGGGT | SEQ ID NO: 1656 | |
| 76 | A_32_P131294 | BM854107 | AGTAGGGAAAAAAGGTTTGTTCCTTAATTAGAGAGTAGTCTGGGAAA TGCTAGCACTTGTGC | SEQ ID NO: 1657 | K-EST0136406 S22SNU16n1 Homo sapiens cDNA clone S22SNU16n1-145-F11 5', mRNA sequence [BM854107] |

Fig. 5-5

| No. | Probe ID No. | Symbols of genes | Sequence | SEQ ID NO: | Descriptions of genes (letters and numbers within [ ] indicates GenBank accession No.) |
|---|---|---|---|---|---|
| 77 | A_32_P132936 | THC2673888 | AAATGGAAGTATTGAGGAGATTAAAGAGTGGTTAAGTCATGGCCATGAATGAATTTACCA | SEQ ID NO: 1658 | O65549_9ALPH (O65549) Glycoprotein C, partial (4%) [THC2673888] |
| 78 | A_32_P136033 | AK090477 | AGCCTCCGTCTAGAGTCTCATGTCCTTCTGTGTCAGCTGGTTGACTTGAATATTGATGAA | SEQ ID NO: 1659 | Homo sapiens mRNA for FLJ00399 protein. [AK090477] |
| 79 | A_32_P136597 | THC2714164 | CCCAGTGTTTTGCCGCAGAGAAATAGATGGAAGATTCTTCCCATATCTCCTACTA | SEQ ID NO: 1660 | |
| 80 | A_32_P146826 | THC2852700 | ACCGTGTACAGGAGAGTTGGAAAGTTGTGAAGGTTTGAATTGTCTGGAGGATGTGGTTC | SEQ ID NO: 1661 | |
| 81 | A_32_P146844 | THC2639689 | CCTGTGGGCTGATTCCAGAGTGAGAGTTGAAGTTTTGTGTGCATCATCATGTGCCATTAA | SEQ ID NO: 1662 | |
| 82 | A_32_P147969 | AL080232 | TAATGAGCTGTTTTCGGCATGAACAGAAGGCAAGGAAGTGTCCAGAGAGACCTCTGGAGAATTCTT | SEQ ID NO: 1663 | Homo sapiens mRNA: cDNA DKFZp586A061 (from clone DKFZp586A061) [AL080232] |
| 83 | A_32_P155841 | AL079294 | CCTTCCTGTTTATATACCTGCAGTTCCATGTTCTGTTAAGGAAGAATGGCAAATGCAAA | SEQ ID NO: 1664 | Homo sapiens mRNA full length insert cDNA clone EUROIMAGE 362780. [AL079294] |
| 84 | A_32_P156062 | THC2681718 | CTGGAGGTTGTTGGCATTGGTTCAGTCTCTCAGGAGGTCACGGCTCAGTTCACTGTTC | SEQ ID NO: 1665 | |
| 85 | A_32_P164573 | THC2611661 | AGCTGTTTTCTATTAACACTCAAGTCTCGAGAGCTTGGAAATTTTCAAGTGCAAATG | SEQ ID NO: 1666 | RR12_SPINX (P42344) Chloroplast 30S ribosomal protein S12, partial (11%) [THC2611661] |
| 86 | A_32_P165407 | AK024926 | AAAGGAAGGAGGATCCCTGGACCAGGGACTTCACAGGAACCAAACATGATTCATGAAAA | SEQ ID NO: 1667 | Homo sapiens cDNA: FLJ21273 fis, clone COL01778. [AK024926] |
| 87 | A_32_P171253 | THC2674306 | GGCTCAGACCTTAAGGAACTGATGGTCTTCTTTACTTCGACAAAGTCTAAGCAGT | SEQ ID NO: 1668 | Q9F8M7_CARHY (Q9F8M7) DTDP-glucose 4,6-dehydratase (Fragment), partial (11%) [THC2674306] |
| 88 | A_32_P179526 | ZBTB20 | TTGAAGTTGGAAATCGAAGGGGAATCTAAAACGGACCAGAGTTTCTGCTGCTGGAAAGG | SEQ ID NO: 1669 | Homo sapiens zinc finger and BTB domain containing 20, mRNA (cDNA clone IMAGE:4291354), partial cds. [BC010934] |
| 89 | A_32_P179998 | DMRTC1 | ATATGCCAGAGTTTTATTCGTCTTGTGATTGCTGACATACCTGTGCACTCATGTGTATA | SEQ ID NO: 1670 | Homo sapiens DMRT-like family C1 (DMRTC1), mRNA [NM_033053] |
| 90 | A_32_P182458 | A_32_P182458 | ACCTAGCACAGTGGAGTGAAGTGAAACAGTTTAAATAGGACTGTTGCTTGAGTATATATGGAAA | SEQ ID NO: 1671 | |
| 91 | A_32_P185398 | THC2750143 | AAATATCCTGATACTTTAGCATATCTGCAATTATAAGAATTAAATATCAAAATTATACCAT | SEQ ID NO: 1672 | ALU1_HUMAN (P39188) Alu subfamily J sequence contamination warning entry, partial (11%) [THC2750143] |
| 92 | A_32_P194372 | AK129547 | AGACCACAGAAACATAGACCCATAGCTGATATTTGGACGCAAGCATAGGTTAAAACTAGGGGAGG | SEQ ID NO: 1673 | Homo sapiens cDNA FLJ26036 fis, clone PRS00145. [AK129547] |
| 93 | A_32_P196297 | THC2652466 | CCTTTCAGAAGACTGTAAGCCTTACCCAAGCATTAATTTTGCTGCATAGGCGGCTGTT | SEQ ID NO: 1674 | Q9BHM3_PARTE (Q9BHM3) Cyclophilin-RNA interacting protein, partial (4%) [THC2652466] |
| 94 | A_32_P208039 | AL049390 | TTTCATGTTTGAGCATTCAGATTGGGCTTTATTTCTCAAGGACATGTGGCAAACGTCACAA | SEQ ID NO: 1675 | Homo sapiens mRNA: cDNA DKFZp586D1318 (from clone DKFZp586D1318) [AL049390] |
| 95 | A_32_P208200 | THC2659414 | GACATTAAAATGAGTGGAGAAGAAACCTGAAAGCGCCGCAGAGAATAAGCTAAAATTTC | SEQ ID NO: 1676 | |
| 96 | A_32_P20912 | AK025669 | ACAACTACCTGTAGCTGGGGAGGAACATCTTGACATGCCCCATAAACTCCATTTTGGCAAA | SEQ ID NO: 1677 | Homo sapiens cDNA: FLJ22016 fis, clone HEP07422. [AK025669] |

Fig. 5-6

| No. | Probe ID No. | Symbols of genes | Sequence | SEQ ID NO: | Descriptions of genes (letters and numbers within [ ] indicates GenBank accession No.) |
|---|---|---|---|---|---|
| 97 | A_32_P209582 | THC2663167 | CAATGTAAAGCCAGAATATCAACGTCCTTTTGTCAAGATTTTCAAAGGTATTTGGCTGAT | SEQ ID NO: 1678 | ALU1_HUMAN (P39188) Alu subfamily J sequence contamination warning entry, partial (5%) [THC2663167] |
| 98 | A_32_P211048 | A_32_P211048 | GTTCAGAAAACACCTAGTAGTTAGGTTATTCAGTTGATTGATATTGGAATGAATGAGAAATGAGCAG | SEQ ID NO: 1679 | |
| 99 | A_32_P213509 | THC2663555 | GATTTGTTCCAGTGTTGGAGCCCTTTTAATGAAAATTCTCAACACCTACACTGGAAAA | SEQ ID NO: 1680 | |
| 100 | A_32_P214054 | THC2755661 | GGCTTATCTCCTTTGTTTTAACAGTTGGGGCTTTGGGTCCATAGCAATGATTGGAAAT | SEQ ID NO: 1681 | |
| 101 | A_32_P216122 | AK130891 | TTGTTCCTCTATATGTTTGGGAGGGATTCATGAAGAATTGAGTACACATATATAGGGTC | SEQ ID NO: 1682 | Homo sapiens cDNA FLJ27381 fis, clone UBA07680. [AK130891] |
| 102 | A_32_P225301 | THC2727302 | GCCTCAATCACATTTGTGATGGCCAACAAAATTTACCTAAGCATTTTGCTAACCTGAAGAA | SEQ ID NO: 1683 | ALU6_HUMAN (P39193) Alu subfamily SP sequence contamination warning entry, partial (9%) [THC2727302] |
| 103 | A_32_P227110 | THC2512148 | TAAAAGAAATCCTTTTGATTCAGCCACTGTGTATTGATAATGGCTTATTATTACAATCA | SEQ ID NO: 1684 | |
| 104 | A_32_P232851 | THC2645586 | GTTTGAAAAGGATATCCTTCACATTCGTTTCCAGAAAATTGAGGTCAGTGACTTATTTC | SEQ ID NO: 1685 | Q9P3E1_NEUGR (Q9P3E1) Related to rna-binding protein fus/tls, partial (5%) [THC2645586] |
| 105 | A_32_P34926 | AL833696 | GTGGCCAGAGAGTCAACTGCCAACCCTCCCAGTCGAGATCGGGGGTCTTGTGATAA | SEQ ID NO: 1686 | Homo sapiens mRNA; cDNA DKFZp667D139 (from clone DKFZ567D139). [AL833696] |
| 106 | A_32_P40673 | A_32_P40673 | CATCACACTTGATATTAGGACAGCGTACCTACTTGTTTATTAGTAAAGTGTCACAGGGTGATATGTA | SEQ ID NO: 1687 | |
| 107 | A_32_P41099 | THC2668419 | AGGGGCAGAAATATTTGGGTTCGTCCGTTCTATTAGTAAAGTGTCTTTGGACTATTGTCTC | SEQ ID NO: 1688 | |
| 108 | A_32_P42976 | THC2713078 | CTTATCCTTTCCTTTTGTTGGTGTGCAACCTGCCAACATTGTGGGCTCATTCTTTCTGGGTA | SEQ ID NO: 1689 | |
| 109 | A_32_P43878 | DB111455 | ATGTGAGAAAGGTTCTTAAGGTTTAATGACCAAGTTCCATGTGAGCTCTTACTTGGGA | SEQ ID NO: 1690 | DB111455 THYMU2 Homo sapiens cDNA clone THYMU2015028 5', mRNA sequence [DB111455] |
| 110 | A_32_P46404 | AK092468 | CTGTATGCCAAACCTCTTTTGCATAAATACTATGGATTCAGCCAAGAGAAAACACT | SEQ ID NO: 1691 | Homo sapiens cDNA FLJ35149 fis, clone PLACE6010485. [AK092468] |
| 111 | A_32_P5542 | AF131782 | GAGGCTCTTACGATCTAGGTAAGTCAAGTAAAGTCAAGTGGGAGGAAATGTCTTATAAATAAACAACAG | SEQ ID NO: 1692 | Homo sapiens clone 24941 mRNA sequence. [AF131782] |
| 112 | A_32_P55427 | THC2701763 | CACTTTTTATCCTATCTGTAAAACAACAAATCAGAGAGTAGATTCCATAGCTGG | SEQ ID NO: 1693 | Q9F8N7_CARHY (Q9F8N7) DTDP-glucose 4,6-dehydratase (Fragment), partial (11%) [THC2701763] |
| 113 | A_32_P55438 | A_32_P55438 | GTTGCCTTCGTCAAACCTGGTGAGGTTTGTAGTATCTTTAGTCTCACTACAGTGCAGCAG | SEQ ID NO: 1694 | |
| 114 | A_32_P61708 | A_32_P61708 | AGGAGGCAAGTGAATTGTTCTCTACAACCGAGACATACTACTATACCTTCAAGGAGACGAT | SEQ ID NO: 1695 | |
| 115 | A_32_P64570 | ANKRD15 | GCACCTTGTTCACTCCCACAGAAAATGGTGTCTGGTTCTCACTGAGACGTTTTAAGATTT | SEQ ID NO: 1696 | Homo sapiens ankyrin repeat domain 15 (ANKRD15), transcript variant 2, mRNA [NM_153186] |
| 116 | A_32_P65067 | THC2618074 | CCCCCAAAGTGAATTTAAACTTGAGTTATTATGCCGTTCTCATAGGAACAGGAAAACT | SEQ ID NO: 1697 | |

Fig. 5-7

| No. | Probe ID No. | Symbols of genes | Sequence | SEQ ID NO: | Descriptions of genes (letters and numbers within [ ] indicates GenBank accession No.) |
|---|---|---|---|---|---|
| 117 | A_32_P67209 | BU726029 | GTCCACTTATATTTATTCTGCACCTACCTGCACGTGACACTCTGCTATTCTTCAGAGAAG | SEQ ID NO: 1698 | UI-E-CI0-aac-g-02-0-UI.s1 UI-E-CI0 Homo sapiens cDNA clone UI-E-CI0-aac-g-02-0-UI 3', mRNA sequence [BU726029] |
| 118 | A_32_P70875 | CD236706 | GTTTGTTTGAGAAGTTCCTAATGCAGTAGGAGAACAAAGTGACAAGTTTTGTTATTTAGTG | SEQ ID NO: 1699 | FNDPXF03 FNP Homo sapiens cDNA, mRNA sequence [CD236706] |
| 119 | A_32_P71171 | A_32_P71171 | TCTAGAATAGTAATAGGAAAACAAGAATCCAGCCTGGTGATGGCTGGAGGGAGTGGATTGAA | SEQ ID NO: 1700 | |
| 120 | A_32_P79103 | BM932034 | GTGTACAGAATGAAAATAGACATTTTAGGAAGGTTGAGTCAGAGGTGGGAGTGGGGCATA | SEQ ID NO: 1701 | UI-E-EJ1-aji-k-24-0-UI.r1 UI-E-EJ1 Homo sapiens cDNA clone UI-E-EJ1-aji-k-24-0-UI 5', mRNA sequence [BM932034] |
| 121 | A_32_P88987 | AK022346 | ATGGGAAGTTACTACCCAGGCTTACCAAAAGGTCAGGTTTATATAAAGTGGCGTTCCTTT | SEQ ID NO: 1702 | Homo sapiens cDNA FLJ12284 fis, clone MAMMA1001757. [AK022346] |
| 122 | A_32_P89087 | AL134462 | TTCATGGAGGCTTCGTAGTGAAGGGAGACGGACTAAACAGTAAAGGGACAAATAGGATTACT | SEQ ID NO: 1703 | DKFZp547J085_r1 547 (synonym: hfbr1) Homo sapiens cDNA clone DKFZp547J085 5', mRNA sequence [AL134462] |
| 123 | A_32_P91328 | THC2841595 | GTTAGGCGAATAATGTCATTGAAGTCTTTAACTCTAGCGTGACTGTAAGGGCAGGGTTCA | SEQ ID NO: 1704 | |
| 124 | A_32_P97305 | THC2681839 | AATATGCACACAAAACTAAAGAAGAAGGATGTCACTTGACACACAGCTTCCTGCCCCCT | SEQ ID NO: 1705 | |
| 125 | A_32_P98940 | THC2745859 | AAGAGTATTCCCAAGATAGCAAAGGTGTGTTGTTTTTAGGCAGGTGTATTTCAGGCTAGTTA | SEQ ID NO: 1706 | |
| 126 | A_23_P102235 | SNRPG | ACAACAGAACAATATTGGAATGGTCGGTAATACCAGGAAGAATAGTATCATCATGTTAGAAGC | SEQ ID NO: 1707 | Homo sapiens small nuclear ribonucleoprotein polypeptide G (SNRPG), mRNA [NM_003096] |
| 127 | A_23_P104054 | C1orf9 | TAAATTTCTTTCCTGTCTGTCTGCACAATTAGCTATTCAGAGCAGAAGGGCCTGATTTTATAGA | SEQ ID NO: 1708 | Homo sapiens chromosome 1 open reading frame 9 (C1orf9), transcript variant 2, mRNA [NM_016227] |
| 128 | A_23_P106131 | KTN1 | ATGTTTTCACCCTTTCTAGTTTGTCAGAAACACTGAACAGAGTTTTGTCTTTTCAACTCC | SEQ ID NO: 1709 | Homo sapiens kinectin 1 (kinesin receptor) (KTN1), transcript variant 1, mRNA [NM_182926] |
| 129 | A_23_P108751 | FHL2 | TTTACAGAGTCGTGTAACCCTCCCGTTGCGTCAAGTCTAAACCAAGATTATGTGACTTGCAT | SEQ ID NO: 1710 | Homo sapiens four and a half LIM domains 2 (FHL2), transcript variant 2, mRNA [NM_201555] |
| 130 | A_23_P110362 | MAP2K1IP1 | ACTCAGACAAGTTGTGGAAGTTTCTTAATCTGACAGTGGTTTCAGTGTGTACCTTATCTT | SEQ ID NO: 1711 | Homo sapiens mitogen-activated protein kinase kinase 1 interacting protein 1 (MAP2K1IP1), mRNA [NM_021970] |
| 131 | A_23_P110611 | ZH2C2 | GTCTTGAAAAGGAGACTTTCAGTGTTGTTGGACTTCTTCAAACCAGGTTCTTGAATACTTAA | SEQ ID NO: 1712 | Homo sapiens zinc finger, H2C2 domain containing (ZH2C2), mRNA [NM_017676] |
| 132 | A_23_P110811 | COX7C | AGCCTCTGGAAGTGGATCAAAACTAGAACTCATATGCCATACTAGATATGTTTGTCAATAA | SEQ ID NO: 1713 | Homo sapiens cytochrome c oxidase subunit VIIc (COX7C), nuclear gene encoding mitochondrial protein, mRNA [NM_001867] |
| 133 | A_23_P111583 | CD36 | CTTTGGCTTAATGAGACTGGGACCATTGGTGATGAGAAGGCAAACATGCCTCAGAAGTGAA | SEQ ID NO: 1714 | Homo sapiens CD36 molecule (thrombospondin receptor) (CD36), transcript variant 2, mRNA [NM_001001547] |
| 134 | A_23_P114662 | CRYZ | AAGATGGTAGTTCAAAATAAGACTGCTCAGTTTCCAAGGGTTTTCAAGGCTACTTACCTT | SEQ ID NO: 1715 | Homo sapiens crystallin, zeta (quinone reductase) (CRYZ), mRNA [NM_001889] |

Fig. 5-8

| No. | Probe ID No. | Symbols of genes | Sequence | SEQ ID NO: | Descriptions of genes (letters and numbers within [ ] indicates GenBank accession No.) |
|---|---|---|---|---|---|
| 135 | A_23_P11652 | USP1 | TTGGGCATGGACTAATTGTATGTGTTTAACTCATATTCTGCACGATCTGTATAGTAC | SEQ ID NO: 1716 | Homo sapiens ubiquitin specific peptidase 1 (USP1), transcript variant 1, mRNA [NM_003368] |
| 136 | A_23_P11685 | PLA2G4A | GAAATGGCAAGCAGTTCTGATGCTGAGGCAGTTTGCAATCCCATGACACTGGATTTAAA | SEQ ID NO: 1717 | Homo sapiens phospholipase A2, group IVA (cytosolic, calcium-dependent) (PLA2G4A), mRNA [NM_024420] |
| 137 | A_23_P117721 | RPS17 | AATTATGTTCCTGAGGTCTCAGGCTTGGATGCAGGAGATTATTGAAGTAGAATCCTGACACT | SEQ ID NO: 1718 | Homo sapiens ribosomal protein S17 (RPS17), mRNA [NM_001021] |
| 138 | A_23_P117852 | KIAA0101 | TACTGCTGCCATTTTTATTGGTGTTTGATTATTGGAATGGTGCCATATTGTCACTCCTTC | SEQ ID NO: 1719 | Homo sapiens KIAA0101 (KIAA0101), transcript variant 1, mRNA [NM_014736] |
| 139 | A_23_P118516 | FAM18B | TATTTCTGTAGATTGTTTTCAGGAGAGAAAGTTTTGCTTGTGTATGGTAAGAGTGGAGCACTTTG | SEQ ID NO: 1720 | Homo sapiens family with sequence similarity 18, member B (FAM18B), mRNA [NM_016078] |
| 140 | A_23_P120048 | BA22B | TATTTTCGTCTGAAGGTAATGATAAGGTACACATCTGTACAGTAATTATCCTCTACCAAG | SEQ ID NO: 1721 | Homo sapiens bromodomain adjacent to zinc finger domain, 2B (BA22B), mRNA [NM_013450] |
| 141 | A_23_P120316 | MTHFD2 | AGGATTATTCCTTGGCTATTAGTACTCATTTTATGTATGTTACCCTTCAGTAAGTTCTCCG | SEQ ID NO: 1722 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 142 | A_23_P1206 | RPS24 | TTTGGATTCAGAACTCATTTGGTGGTGGCAAGACAGAACTGGGCTTTGGCATGATTTATGAT | SEQ ID NO: 1723 | Homo sapiens ribosomal protein S24 (RPS24), transcript variant 2, mRNA [NM_001026] |
| 143 | A_23_P120902 | LGALS2 | CTGAGCTACGTGAGCGTAAGGGCACGGGTTCAACGATGTCCTCTTTCAAGTTAAAAGAATAA | SEQ ID NO: 1724 | Homo sapiens lectin, galactoside-binding, soluble, 2 (LGALS2), mRNA [NM_006498] |
| 144 | A_23_P121386 | IFT57 | TGGAACACACACTACTCCAATCAAAGCTGAAGGAGAAGTGCAAACATGACTAGGAACATGC | SEQ ID NO: 1725 | Homo sapiens intraflagellar transport 57 homolog (Chlamydomonas) (IFT57), mRNA [NM_018010] |
| 145 | A_23_P121622 | SULT1B1 | GAAATAGAGATTGTCTGTAGTTGATTGAAACCAAGGGCAGTTATGAATTGATTTGGGCAAT | SEQ ID NO: 1726 | Homo sapiens mRNA for ST1B2, complete cds. [D89479] |
| 146 | A_23_P121825 | FLJ13611 | GATGTGTTACTGTTACAAAACTTTCTCTGTCCATGTAATCACACTTAGTTATGAGCAAAG | SEQ ID NO: 1727 | Homo sapiens hypothetical protein FLJ13611 (FLJ13611), mRNA [NM_024841] |
| 147 | A_23_P122174 | XRCC4 | AAACCAAAGTGATCTCTCTGGGTTGGCTTCAGCTGCTGTAAGTAAAGATGATTCCATTAT | SEQ ID NO: 1728 | Homo sapiens X-ray repair complementing defective repair in Chinese hamster cells 4 (XRCC4), transcript variant 3, mRNA [NM_022550] |
| 148 | A_23_P123315 | BC067244 | CTTCCAAATCACTGGTTTGGGAGGGGGTGGATACATCCTCATTTTCTGTACAGATGCAT | SEQ ID NO: 1729 | Homo sapiens cDNA clone IMAGE:4807381, partial cds. [BC067244] |
| 149 | A_23_P123343 | NUDCD1 | TTGGCCTCTTTTGTACTTGGAAAAGTATTCAGTGCTACGCTGGAGGTCGTGGACAGTTATACTG | SEQ ID NO: 1730 | Homo sapiens NudC domain containing 1 (NUDCD1), mRNA [NM_032869] |
| 150 | A_23_P123608 | JAK2 | GGATAAGATGGCTGGATGAAAGAAAATGACCTTCATTCTGAGACCAAAGTAGATTTACAGA | SEQ ID NO: 1731 | Homo sapiens Janus kinase 2 (a protein tyrosine kinase) (JAK2), mRNA [NM_004972] |
| 151 | A_23_P127279 | FAM35A | TGCTAGATTCCAGGCATTGTACTAAGTATGTGGGAACCACAGAGAAGACATTCCCTCAGAA | SEQ ID NO: 1732 | Homo sapiens family with sequence similarity 35, member A (FAM35A), mRNA [NM_019054] |
| 152 | A_23_P127579 | PTS | GTGGTTTATAAAGGAGAATAGGCTATTGGGGTTAGCATTGCACAAAGCCCAGTTTCTTTCT | SEQ ID NO: 1733 | Homo sapiens 6-pyruvoyltetrahydropterin synthase (PTS), mRNA [NM_000317] |
| 153 | A_23_P128192 | PFDN5 | CACGTCCATTGCTCAGGTCAAAGTGGTACAGAGCCAAGTATGTGGAAGGCAAGGACTGTCT | SEQ ID NO: 1734 | Homo sapiens prefoldin subunit 5 (PFDN5), transcript variant 1, mRNA [NM_002624] |

Fig. 5-9

| No. | Probe ID No. | Symbols of genes | Sequence | SEQ ID NO: | Descriptions of genes (letters and numbers within [ ] indicates GenBank accession No.) |
|---|---|---|---|---|---|
| 154 | A_23_P128384 | VPS29 | CAGGCTAATTGGAGAATGATGTGAAAAGTAGAACGAATGGAATAGAAAG AAAGGTTAAAGCCAG | SEQ ID NO: 1735 | Homo sapiens vacuolar protein sorting 29 homolog (S. cerevisiae) (VPS29), transcript variant 2, mRNA [NM_057180] |
| 155 | A_23_P128470 | CLEC12A | CCAACCAAATTTATGTCGTGAGGCTATATAGCAAAAGAACAAGAAGCACA AATGTAAGGCTTGTC | SEQ ID NO: 1736 | Homo sapiens C-type lectin domain family 12, member A (CLEC12A), transcript variant 1, mRNA [NM_138337] |
| 156 | A_23_P128930 | PSMC6 | GAACAAGGCAAGATTAGACATACTGAAAATCGATGCAGGTCGCATT ACAAAGGCATGGTGAA | SEQ ID NO: 1737 | Homo sapiens protease (prosome, macropain) 26S subunit, ATPase, 6 (PSMC6), mRNA [NM_002806] |
| 157 | A_23_P130444 | ZNF701 | CTCCTTGCAGAATATCATAACGTTCATTTTTGAGGTAATAGTTAC AAATGCGGTGAGCAC | SEQ ID NO: 1738 | Homo sapiens zinc finger protein 701 (ZNF701), mRNA [NM_018260] |
| 158 | A_23_P132863 | ENST00000306024 | AGGCTAAATGGTATTTTCATTTTTCAAGGCTGTCCAATAAATATG ACCAACAAGATGCAG | SEQ ID NO: 1739 | U6 snRNA-associated Sm-like protein LSm3. [Source:Uniprot/SWISSPROT;Acc:P62310] [ENST00000306024] |
| 159 | A_23_P132935 | SPCS3 | GAATGTCAGTTTGACCCTGTCTTGGAACGTCGTACCAAATGCTGG AATTCTAGTCTTGT | SEQ ID NO: 1740 | Homo sapiens signal peptidase complex subunit 3 homolog (S. cerevisiae) (SPCS3), mRNA [NM_021928] |
| 160 | A_23_P133293 | MCTP1 | AGGAAGCCAGTAAGTACAGTTATGAAAAATACTAGGAAAACTATAT CCATATGCTTTGG | SEQ ID NO: 1741 | Homo sapiens cDNA: FLJ22344 fis, clone HRC06080. [AK025997] |
| 161 | A_23_P133445 | GZMA | GAATGAATATGGTTTTGTGCTGAAGGCCTCCGAAGGTGGAAAAAACT CGTGCAATGGAGAGATT | SEQ ID NO: 1742 | Homo sapiens granzyme A (granzyme 1, cytotoxic T-lymphocyte-associated serine esterase 3) (GZMA), mRNA [NM_006144] |
| 162 | A_23_P133848 | FAM8A1 | AGTTCGGCCGAATTGAGAAAATGAGTGTGTTTTAGATTCAAGTGACG GTAAAAGGATTTGTT | SEQ ID NO: 1743 | Homo sapiens family with sequence similarity 8, member A1 (FAM8A1), mRNA [NM_016255] |
| 163 | A_23_P134714 | HRSP12 | TAAATTACACCTGTGTGCAGCGTGTATTACTGAATATAGGAAAGAG ATACCCATTACATAG | SEQ ID NO: 1744 | Homo sapiens heat-responsive protein 12 (HRSP12), mRNA [NM_005836] |
| 164 | A_23_P134786 | PHF20L1 | AGTTGTATGTGCCCCAGTGCTACATACGGCAGGTATGCGTAAGTG TGTATGCTTGTTTA | SEQ ID NO: 1745 | Homo sapiens PHD finger protein 20-like 1 (PHF20L1), transcript variant 1, mRNA [NM_016018] |
| 165 | A_23_P134925 | BNIP3L | ATTTGGGACAAAAAGGCAGGCGTTCATTTTCATATGTTCCTTGATGA AAACTGGCTGAAGAT | SEQ ID NO: 1746 | Homo sapiens BCL2/adenovirus E1B 19kDa interacting protein 3-like (BNIP3L), mRNA [NM_004331] |
| 166 | A_23_P135123 | BC216229 | CTGGTCTGAACGGTCACGGGCTGTGAACAGGTGTTCCTTACTCA TAATTCATTATTCAA | SEQ ID NO: 1747 | BC216229 RST35803 Athersys RAGE Library Homo sapiens cDNA, mRNA sequence [BC216229] |
| 167 | A_23_P135494 | CLIC4 | CTCCTCAAGCCGTAAGTGTGAACAGGAATTGGAGTATTTCTTTAT AATTTCTTGAAACAGG | SEQ ID NO: 1748 | Homo sapiens chloride intracellular channel 4 (CLIC4), mRNA [NM_013943] |
| 168 | A_23_P135499 | CLIC4 | CTTCGCTTTTTGATGTAGATGCAGATATTCTATACAGTTCTGTT GTCTTTTACTAGGAC | SEQ ID NO: 1749 | Homo sapiens chloride intracellular channel 4 (CLIC4), mRNA [NM_013943] |
| 169 | A_23_P137366 | C1QB | CACGCAGAAGAACTCACTACTGGGCATTGGAGGGTGCCAACAGCAT GTTTCCGGGTTCCT | SEQ ID NO: 1750 | Homo sapiens complement component 1, q subcomponent, B chain (C1QB), mRNA [NM_000491] |
| 170 | A_23_P137434 | RNF11 | TGTAGTATCCATATGTGTTGGTTAAATTTCCTTATGAGCCCCATGAT GGAAAGACTTAAGA | SEQ ID NO: 1751 | Homo sapiens ring finger protein 11 (RNF11), mRNA [NM_014372] |
| 171 | A_23_P136308 | CD58 | AACCTGTATCCAAGCAGGGGTCATTCAAGACACAGATATGCACT TATACGCATACCATT | SEQ ID NO: 1752 | Homo sapiens CD58 molecule (CD58), mRNA [NM_001779] |
| 172 | A_23_P136541 | AKR1C3 | TTTTGAGTTCCAGTTGACTGACTGCAGAGGACATGAAAGCCATAGATGG CCTAGAGAGAAATCT | SEQ ID NO: 1753 | Homo sapiens aldo-keto reductase family 1, member C3 (3-alpha hydroxysteroid dehydrogenase, type II) (AKR1C3), mRNA [NM_003739] |

Fig. 5-10

| No. | Probe ID No. | Symbols of genes | Sequence | SEQ ID NO: | Descriptors of genes (letters and numbers within [ ] indicates GenBank accession No.) |
|---|---|---|---|---|---|
| 173 | A_23_P140301 | PSMA3 | TGAACTAGAACTCAGCTGGGTTGGTGAATTAACTAATGGAAGACATGAAATTGTTCCAAA | SEQ ID NO: 1754 | Homo sapiens proteasome (prosome, macropain) subunit, alpha type, 3 (PSMA3), transcript variant 1, mRNA [NM_002788] |
| 174 | A_23_P141549 | RPS7 | GTCAAACTAGATGGCAGCCGGGTCATAAAGGTTCATTTGGACAAAGCACAGGAACAAT | SEQ ID NO: 1755 | Homo sapiens ribosomal protein S7 (RPS7), mRNA [NM_001011] |
| 175 | A_23_P142560 | ZEB2 | CTTTTAATGTGTGTTTGTGCAAGTCGCCATCCTTGTTACAGTGTTAAGAGGGTAACATGGGT | SEQ ID NO: 1756 | Homo sapiens zinc finger E-box binding homeobox 2 (ZEB2), mRNA [NM_014795] |
| 176 | A_23_P143858 | RPL22L1 | ATTGGCTGCAGGTGGTTGCATCTGACAAGGAGGACTAGGAACTTCGTTACTTCCAGATTA | SEQ ID NO: 1757 | Homo sapiens ribosomal protein L22-like 1, mRNA (cDNA clone IMAGE:4865966), [BC049823] |
| 177 | A_23_P144145 | DCUN1D1 | TCTTTAGTGAATATCATCTGCATATCTGTGTAAGTTGAATTGTGTTTGTTACAGTCCCTG | SEQ ID NO: 1758 | Homo sapiens RP42 protein mRNA, complete cds. [AF292100] |
| 178 | A_23_P144151 | DCUN1D1 | TATGTCTGTTTTTCTTAAAAGTCATATGGGTTCGTGGCTAATGCGTTGGATTTTACAT | SEQ ID NO: 1759 | Homo sapiens RP42 protein mRNA, complete cds. [AF292100] |
| 179 | A_23_P144497 | RPS3A | CCAAATCCGAAGAAGATGATGGAAATGATGACCGAGAGGTGCAGACAAATGACTTGAA | SEQ ID NO: 1760 | Homo sapiens ribosomal protein S3A (RPS3A), mRNA [NM_001006] |
| 180 | A_23_P145114 | GCLC | AGAATGCCTGGTTTTCGTTTGGCAAATTGGCTTGTGTAAATCAGGTTGTAAAAGGCAGATA | SEQ ID NO: 1761 | Homo sapiens glutamate-cysteine ligase, catalytic subunit (GCLC), mRNA [NM_001498] |
| 181 | A_23_P145397 | CCNC | TAGTGGACCACTTGGAAATAAACCATTGGACAGATTTCAGTAATGCTGTCAGTGGAACAC | SEQ ID NO: 1762 | Homo sapiens cyclin C (CCNC), transcript variant 1, mRNA [NM_005190] |
| 182 | A_23_P14564 | GPR65 | AACAAGTTTAAATTGTGTTGCTGATCCAATTCGTGTACTGTTTTGTAACCGAAACAGGAAG | SEQ ID NO: 1763 | Homo sapiens G protein-coupled receptor 65 (GPR65), mRNA [NM_003608] |
| 183 | A_23_P145777 | NDUFA4 | ACGCTGCTTTAGAATGAAGGTGCTTCCAGAAGCCACATCGGCACAATTTTCCACTTAACCA | SEQ ID NO: 1764 | Homo sapiens NADH dehydrogenase (ubiquinone) 1 alpha subcomplex, 4, 9kDa (NDUFA4), nuclear gene encoding mitochondrial protein, mRNA [NM_002489] |
| 184 | A_23_P14708 | SUHW4 | TCTTTGTACCTCCATACAGAGTGTTAGCGCTGCCAGGCTGTAAGCTTAGCTTAATTAAAGTT | SEQ ID NO: 1765 | Homo sapiens suppressor of hairy wing homolog 4 (Drosophila) (SUHW4), transcript variant 1, mRNA [NM_017661] |
| 185 | A_23_P14734 | RPS27L | TACAAGATCACCACGGTTTTCAGGCATGGTCAGACAGTGGTTCTTTGTGTAGGTGTTCA | SEQ ID NO: 1766 | Homo sapiens ribosomal protein S27-like (RPS27L), mRNA [NM_015920] |
| 186 | A_23_P147404 | A_23_P147404 | TGGGGTGAACATGAAATTGATTACATTTGTTGGATGGTGAGCAGCGTCCCTCTCATGTG | SEQ ID NO: 1767 | |
| 187 | A_23_P148969 | LRRC40 | GCATGTATATCAATTTATATAGATAGGTAGATAGGTTTTTGGATGATTGAGGCATGCTTAT | SEQ ID NO: 1768 | Homo sapiens leucine rich repeat containing 40 (LRRC40), mRNA [NM_017768] |
| 188 | A_23_P149775 | ARHGAP12 | TGTATAATAAAACACAGGGTTTGGAAGGTTTTGTTACAGGGAGCATGGTCTGTTGAAGAT | SEQ ID NO: 1769 | Homo sapiens Rho GTPase activating protein 12 (ARHGAP12), mRNA [NM_018287] |
| 189 | A_23_P149892 | GALNACT-2 | CATGGTGGTTCAGAATAGAATGAGACATAGCATGGTTTTTGTTTTGCTTCAATTTTC | SEQ ID NO: 1770 | Homo sapiens chondroitin sulfate GalNAcT-2 (GALNACT-2), mRNA [NM_018590] |
| 190 | A_23_P151018 | LEMD3 | GCCCATGTTGTAACCTGTTGCAAGAGTGAAATGTAAAAATAGTTGTGGCATTTTAAAAGG | SEQ ID NO: 1771 | Homo sapiens LEM domain containing 3 (LEMD3), mRNA [NM_014319] |
| 191 | A_23_P151637 | RNASE2 | GTGGTAACCCAAATATGAGCGTGTCCTAGTAACAAAACTCGCAAAATTGTCACCACAGTG | SEQ ID NO: 1772 | Homo sapiens ribonuclease, RNase A family, 2 (liver, eosinophil-derived neurotoxin) (RNASE2), mRNA [NM_002934] |

Fig. 5-11

| No. | Probe ID No. | Symbols of genes | Sequence | SEQ ID NO: | Descriptions of genes (letters and numbers within [ ] indicates GenBank accession No.) |
|---|---|---|---|---|---|
| 192 | A_23_P152002 | BCL2A1 | TGTAACGATATTTGGATTTGAAGGTATTCTCATCAAGAAACTTCTAGCAGCAAATGC | SEQ ID NO: 1773 | Homo sapiens BCL2-related protein A1 (BCL2A1), mRNA [NM_004049] |
| 193 | A_23_P154330 | TXNDC9 | CTCAGTTGTTAAATTATCTGGGAAGGGTCTGAATTCTCTATTTTTGAGATTGACTTATG | SEQ ID NO: 1774 | Homo sapiens thioredoxin domain containing 9 (TXNDC9), mRNA [NM_005783] |
| 194 | A_23_P155765 | HMGB2 | TAAAAATGCAGGTTGTAGGTTTTGATGGGTACTCATACAGTTAGATTTTAGAGCTTC | SEQ ID NO: 1775 | Homo sapiens high-mobility group box 2 (HMGB2), mRNA [NM_002129] |
| 195 | A_23_P155815 | NCAPG | AAGTTAGGAAAGACGATGGAGGTGGAATCGTTTAAGATTATGTCCAGTTATTTGTTAA | SEQ ID NO: 1776 | Homo sapiens non-SMC condensin I complex, subunit G (NCAPG), mRNA [NM_022346] |
| 196 | A_23_P155355 | TMEM161B | AGGTTTGACGTGCCATATTTTGTTTTATTCTGTGATCGTAACTAGTTGGTTTTAATAGG | SEQ ID NO: 1777 | Homo sapiens transmembrane protein 161B (TMEM161B), mRNA [NM_153354] |
| 197 | A_23_P156842 | EEF1E1 | AAGAAAAAGCAATCGTTCAGCAGTCGTTAGAATACAGGGGTCACTCAAGTAGATGGGCACT | SEQ ID NO: 1778 | Homo sapiens eukaryotic translation elongation factor 1 epsilon 1 (EEF1E1), mRNA [NM_004280] |
| 198 | A_23_P157449 | POLR2K | GGTCTCTCTTGCTTCAAAATATGTTCTTGTACAGTACTCACCATTTTAGAATGTGGTTGAC | SEQ ID NO: 1779 | Homo sapiens polymerase (RNA) II (DNA directed) polypeptide K, 7.0kDa (POLR2K), mRNA [NM_005034] |
| 199 | A_23_P157452 | POLR2K | GGAATTGTGTTCACTTATACTTGGATTTGGTCTCTTCGGCATTTCTGATTGTTGTATAGCTT | SEQ ID NO: 1780 | Homo sapiens polymerase (RNA) II (DNA directed) polypeptide K, 7.0kDa (POLR2K), mRNA [NM_005034] |
| 200 | A_23_P157795 | CTNNAL1 | GGATAGTAAAAGTTGGAGAAGCTTTTGGGGTCAGATCTGTGGAACATCATGTGATGAAGCT | SEQ ID NO: 1781 | Homo sapiens catenin (cadherin-associated protein), alpha-like 1 (CTNNAL1), mRNA [NM_003798] |
| 201 | A_23_P159650 | COX7B | CAAATACGGTAATGCTGTATTAGCTAGTGAGCAGCCACTTTCTGTATTGTTACATGGACATA | SEQ ID NO: 1782 | Homo sapiens cytochrome c oxidase subunit VIIb (COX7B), nuclear gene encoding mitochondrial protein, mRNA [NM_001866] |
| 202 | A_23_P159839 | C1GALT1C1 | TCCAAATCAGATGCATGCATGATGATGTGAATTTTGGGTTAAAGGTTTTGGCTGCGGCATTGGGCATAT | SEQ ID NO: 1783 | Homo sapiens C1GALT1-specific chaperone 1 (C1GALT1C1), transcript variant 1, mRNA [NM_152692] |
| 203 | A_23_P160405 | KCTD3 | TTGTAGGACTGCAGTTGTGAATTTGGGTTAAAGGTTTGGCTGCTGTAAGAATGTGAAT | SEQ ID NO: 1784 | Homo sapiens potassium channel tetramerisation domain containing 3 (KCTD3), mRNA [NM_016121] |
| 204 | A_23_P160466 | SLC19A2 | CTTGGTATGTGGCCATATTTATAGAATGCAATGTGCAAGTTGGTAGTGTGATGGA | SEQ ID NO: 1785 | Homo sapiens solute carrier family 19 (thiamine transporter), member 2 (SLC19A2), mRNA [NM_006996] |
| 205 | A_23_P161091 | ZMYM1 | GAGGTATTTTCCTAAGTGGTATTGTACGGTGTATACTGTGTCTTCAGCTGTGTCTCTG | SEQ ID NO: 1786 | Homo sapiens zinc finger, MYM-type 1 (ZMYM1), mRNA [NM_024772] |
| 206 | A_23_P162596 | ACTR6 | TTAACGGCTTGCACTGGACAGTTTCCTTAGAAGGAGTAGTTTTGTGTGACTGTGACTAAAGT | SEQ ID NO: 1787 | Homo sapiens ARP6 actin-related protein 6 homolog (yeast) (ACTR6), mRNA [NM_022496] |
| 207 | A_23_P163113 | PRPF39 | TAGTAATAGGGGGAAAATGTCAATTAGTAGCTTACCACAGATACTGTTCCTACCCATTTA | SEQ ID NO: 1788 | Homo sapiens PRP39 pre-mRNA processing factor 39 homolog (S. cerevisiae) (PRPF39), mRNA [NM_017922] |
| 208 | A_23_P167828 | RWDD1 | GAGGATGCGTGGAAACAACGGTGGAGGGTAGATGAGTCTTTGTTCCAAGAAATGGATGCTTG | SEQ ID NO: 1789 | Homo sapiens RWD domain containing 1 (RWDD1), transcript variant 2, mRNA [NM_016104] |
| 209 | A_23_P16817 | CLK1 | ATGGAAAGGATTCTTGAGCCTCTACCAAAACATATGAGAGAAAACCAGGAAACGTAAA | SEQ ID NO: 1790 | Homo sapiens CDC-like kinase 1 (CLK1), transcript variant 1, mRNA [NM_004071] |
| 210 | A_23_P168656 | GTPBP10 | AATTTGTGGATTTCTGATACAATGTCTTCACTGGAGCCACCATCAAAGGATGCTGTTAGT | SEQ ID NO: 1791 | Homo sapiens GTP-binding protein 10 (putative) (GTPBP10), transcript variant 2, mRNA [NM_033107] |
| 211 | A_23_P168050 | MRPS28 | GAGCAACAACAGATACAACTGTACTAGAGGGCTAATGCAGGTTCTGTTGGAATTCCAGGAGA | SEQ ID NO: 1792 | Homo sapiens mitochondrial ribosomal protein S28 (MRPS28), nuclear gene encoding mitochondrial protein, mRNA [NM_014018] |

Fig. 5-12

| No. | Probe ID No. | Symbols of genes | Sequence | SEQ ID NO: | Descriptions of genes (letters and numbers within [ ] indicate GenBank accession No.) |
|---|---|---|---|---|---|
| 212 | A_23_P17021 | SCRN3 | GTCAAAGTTAGTTCTTAGTGATGATATGGTCAAGCTAATATTAGTTCTTAGTGATCAGTGG | SEQ ID NO: 1793 | Homo sapiens secernin 3 (SCRN3), mRNA [NM_024583] |
| 213 | A_23_P170233 | CSTA | AACTGGCTACTGAGTCATGATGCCTTGCTGATAAATATAACCATCAATAAAGAAGCATTCT | SEQ ID NO: 1794 | Homo sapiens cystatin A (stefin A) (CSTA), mRNA [NM_005213] |
| 214 | A_23_P18325 | PDCD10 | CCAACCGACTAATTCATCAAACGAAGTTAATAGTTCAGACCTTCAAAACTGTGGCCTGAA | SEQ ID NO: 1795 | Homo sapiens programmed cell death 10 (PDCD10), transcript variant 1, mRNA [NM_007217] |
| 215 | A_23_P18422 | MRPL3 | GAGTAGAAAACATATGGGACTATAGTGCAACCTATTTGGGTAAAGAAACCATTTGCTA | SEQ ID NO: 1796 | Homo sapiens mitochondrial ribosomal protein L3 (MRPL3), nuclear gene encoding mitochondrial protein, mRNA [NM_007208] |
| 216 | A_23_P18598 | PI4K2B | AGGCTTAAAACGAATGTCAGCAGTTGGGGTTAACTGGGTAATTTGTGGTCTAGGGCTTTT | SEQ ID NO: 1797 | Homo sapiens phosphatidylinositol 4-kinase type 2 beta (PI4K2B), mRNA [NM_018323] |
| 217 | A_23_P19291 | TUBB2A | ACTTCTCAGATCAATCAATCGGTGCATCCTTAGTGAACTTCGTTCGTTGTGTCCTCAAGCATGGTCTTTC | SEQ ID NO: 1798 | Homo sapiens tubulin, beta 2A (TUBB2A), mRNA [NM_001069] |
| 218 | A_23_P200030 | FPGT | TAAAAATTGGTAAACTAGAAGTAAGTTGTCCACAACCCTCAGTTATGATACTTATGTGCG | SEQ ID NO: 1799 | Homo sapiens fucose-1-phosphate guanylyltransferase (FPGT), mRNA [NM_003838] |
| 219 | A_23_P200298 | AGL | TAGATTTTTAACAGGTGTCATTTGACTAAACGTTTCGGTAGAATGCTTCATACTTGAGTG | SEQ ID NO: 1800 | Homo sapiens amylo-1, 6-glucosidase, 4-alpha-glucanotransferase (glycogen debranching enzyme, glycogen storage disease type III) (AGL), transcript variant 4, mRNA [NM_000028] |
| 220 | A_23_P200507 | CNIH4 | TGGTTGAAGTCAGGCTACACTACAGTGCACAGTTGAGGAGCCAGAGAGTTCTTAAATCAT | SEQ ID NO: 1801 | Homo sapiens cornichon homolog 4 (Drosophila) (CNIH4), mRNA [NM_014184] |
| 221 | A_23_P200955 | | AGACCATGATTGAACCTCACATTGATGTCAAGACTACCGATGGTTATTTGTTTCATCTAC | SEQ ID NO: 1802 | |
| 222 | A_23_P201619 | NEK7 | TGAAGGCCAAGAGGAAGTCACTGTTAAAGGACTCGTGCCATCTTACAACGTTGGATGAA | SEQ ID NO: 1803 | Serine/threonine-protein kinase Nek7 (EC 2.7.11.1) (NimA-related protein kinase 7). [Source:Uniprot/SWISSPROT:Acc:Q8TDX7] [ENST00000367385] |
| 223 | A_23_P201918 | ABCB10 | CATGGATGAGGGTAGAGCCCTTAAGAAGTAATTAAGTCAATATGTAAATCAAATGAAGTTTTC | SEQ ID NO: 1804 | Homo sapiens ATP-binding cassette, sub-family B (MDR/TAP), member 10 (ABCB10), nuclear gene encoding mitochondrial protein, mRNA [NM_012089] |
| 224 | A_23_P202587 | KIAA1598 | GTAATAATTGCAGTAGTTGTATGTATTCGTATGTATTTTGACGTGTGGTAAGGATAGGCTG | SEQ ID NO: 1805 | Homo sapiens KIAA1598 (KIAA1598), mRNA [NM_018330] |
| 225 | A_23_P203376 | MS4A6A | ACGGGCTGTAAATTACTAGATTAGGCAAAATAGTCTGAATTCCAGAAAACAA | SEQ ID NO: 1806 | Homo sapiens membrane-spanning 4-domains, subfamily A, member 6A (MS4A6A), transcript variant 1, mRNA [NM_152852] |
| 226 | A_23_P203498 | TRIM22 | GTACATAAGAATCTATCACTAAGTAATGTATCCTTCAGAATGTGTTGGTTTACCAGTGAC | SEQ ID NO: 1807 | Homo sapiens tripartite motif-containing 22 (TRIM22), mRNA [NM_006074] |
| 227 | A_23_P203645 | CREBZF | TCTGTTGGAGTATTTTGTTCCTTACGTCAATAGTTTCCTTGCATTATTGAAATTGTGGG | SEQ ID NO: 1808 | Homo sapiens CREB/ATF bZIP transcription factor (CREBZF), mRNA [NM_001039618] |
| 228 | A_23_P204187 | FLJ22028 | CTATAAGGTTGTACTGCTGGGAAAATACAATGCACAGGAGCTAGGGACCAGATCATGAATT | SEQ ID NO: 1809 | Homo sapiens hypothetical protein FLJ22028 (FLJ22028), mRNA [NM_024854] |
| 229 | A_23_P204269 | USP15 | GACCAGGATAAATGAGGTATGTTGATCATGGCTTTGCTTTATATCTTGATATTAAAGGTG | SEQ ID NO: 1810 | Homo sapiens ubiquitin specific peptidase 15 (USP15), mRNA [NM_006313] |

Fig. 5-13

| No | Probe ID No. | Symbols of genes | Sequence | SEQ ID NO: | Descriptions of genes (letters and numbers within [ ] indicates GenBank accession No.) |
|---|---|---|---|---|---|
| 230 | A_23_P205027 | ABHD13 | ATTTGTGTGAGAATGATAAAGAATGTTCCTTTTAGAAGTGTGTTATGTCTGTAGCTGTCTG | SEQ ID NO:1811 | Homo sapiens abhydrolase domain containing 13 (ABHD13), mRNA [NM_032859] |
| 231 | A_23_P205336 | C14orf129 | CAATTCATTGCCAGACTTCATTGGAATGCTTGTTGTTGATGATGTATGTTCATTCAGCT | SEQ ID NO:1812 | Homo sapiens chromosome 14 open reading frame 129 (C14orf129), mRNA [NM_016472] |
| 232 | A_23_P205646 | MAP4K5 | CTAATGTAGGAGGGGGAAGTATTAATTGCCATGCATGATATGTATTTTACTTATACTATGCC | SEQ ID NO:1813 | Homo sapiens mitogen-activated protein kinase kinase kinase kinase 5 (MAP4K5), transcript variant 2, mRNA [NM_198794] |
| 233 | A_23_P20606 | NIPSNAP3A | GTAAGTACCGACTTCAAAAAATAGTTCTGTTTACTTTGTGATGGTATTTGAGTGTGTGTC | SEQ ID NO:1814 | Homo sapiens nipsnap homolog 3A (C. elegans) (NIPSNAP3A), mRNA [NM_015469] |
| 234 | A_23_P206228 | VPS13C | GGGATCATTATGAGTAATTTCATAGGCAACTGTCTAGTGTTTGTGTTTTAAAACAGAA | SEQ ID NO:1815 | Homo sapiens vacuolar protein sorting 13 homolog C (S. cerevisiae) (VPS13C), transcript variant 1A, mRNA [NM_017684] |
| 235 | A_23_P207299 | LOC51136 | CCAAAACAGAATTTGAAATTAGAACTAGTGGTTTTAGAGAACTGAGGTATTCTTTCCTG | SEQ ID NO:1816 | Homo sapiens PTD016 protein (LOC51136), mRNA [NM_016125] |
| 236 | A_23_P209032 | ZNF302 | TGAGAAAATGTATACTGGGGAAAAGTTGTATGAAGGTGGTGAACATGGGAGACTTTTAG | SEQ ID NO:1817 | Homo sapiens zinc finger protein 302 (ZNF302), transcript variant 1, mRNA [NM_018443] |
| 237 | A_23_P209232 | CLIP4 | GCTTATGAAATGTCATTTAAAGTTCACTCTTGAGCATCAATAAAAAGGGAAGCTGTGTG | SEQ ID NO:1818 | Homo sapiens CAP-GLY domain containing linker protein family, member 4 (CLIP4), mRNA [NM_024692] |
| 238 | A_23_P209625 | CYP1B1 | CTGTGTTTATGAAGAAGAAGTAAGGTGGTTGGAGTTTACGTGGCTTATTTAATATGCT | SEQ ID NO:1819 | Homo sapiens cytochrome P450, family 1, subfamily B, polypeptide 1 (CYP1B1), mRNA [NM_000104] |
| 239 | A_23_P210001 | PAX8 | CAAGCTTGCTTGTTTCTTAACCCCCAGAGTTTGGCCTCTGAGTGAAATGTCTCTTTGCC | SEQ ID NO:1820 | Homo sapiens paired box gene 8 (PAX8), transcript variant PAX8A, mRNA [NM_003466] |
| 240 | A_23_P210274 | PREI3 | GGATCAGTATGCCGATAGGATTTACAGAATATTTCAGACATGCTATTTCATGATCGGCAG | SEQ ID NO:1821 | Homo sapiens preimplantation protein 3 (PREI3), transcript variant 1, mRNA [NM_015387] |
| 241 | A_23_P210829 | PCMTD2 | TCCTGCGACACCTTACCAGAATTCAGTATAATACACTACTTCTGTTTTCAAACAGATA | SEQ ID NO:1822 | Homo sapiens protein-L-isoaspartate (D-aspartate) O-methyltransferase domain containing 2 (PCMTD2), mRNA [NM_018257] |
| 242 | A_23_P211840 | UBE1C | GGCAGCCTAGAGGGAAAAAATAGAACACTTACTTACGATCGGTAACCTCTATTGAAGAA | SEQ ID NO:1823 | Homo sapiens ubiquitin-activating enzyme E1C (UBA3 homolog, yeast) (UBE1C), transcript variant 1, mRNA [NM_003968] |
| 243 | A_23_P212383 | SACM1L | GCCTCTGAGGGTCTGTTCTAGATTTCATATTGCAGTTGGAGGGTAACAGCTGGTTT | SEQ ID NO:1824 | Homo sapiens SAC1 suppressor of actin mutations 1-like (yeast) (SACM1L), mRNA [NM_014016] |
| 244 | A_23_P2129 | TMEM126B | CATATGCATGATTGGCTACAGTCGATTTGTCTACTGTTGTTACTGAACGTTTTTG | SEQ ID NO:1825 | Homo sapiens transmembrane protein 126B (TMEM126B), mRNA [NM_018480] |
| 245 | A_23_P213638 | PANK3 | TGTATATAGGCAGTGTTAAATCCTTAAATGCAATACGAGGCTCTGATTATTGAGCTTCCTC | SEQ ID NO:1826 | Homo sapiens pantothenate kinase 3 (PANK3), mRNA [NM_024594] |
| 246 | A_23_P213691 | HISPPD1 | GTATGTAAGTTTCTGTTTGTTGAAAATGTAGTTAATGTACTCACTGTGGAGGTCATAAGG | SEQ ID NO:1827 | Homo sapiens histidine acid phosphatase domain containing 1 (HISPPD1), mRNA [NM_015216] |
| 247 | A_23_P213718 | UQCRQ | TTCCGTGTCTGTGAAAAGAACCGTTTCTCTGGAAAGAAGGAGTGTGCATTGTAGTGTCTCAAAGA | SEQ ID NO:1828 | Homo sapiens ubiquinol-cytochrome c reductase, complex III subunit VII, 9.5kDa (UQCRQ), nuclear gene encoding mitochondrial protein, mRNA [NM_014402] |

Fig. 5-14

| No. | Probe ID No. | Symbols of genes | Sequence | SEQ ID NO: | Descriptions of genes (letters and numbers within [ ] indicates GenBank accession No.) |
|---|---|---|---|---|---|
| 248 | A_23_P214108 | TPMT | GGTTGATGCTTTTGAAGAACGACATAAAAGTTGGGGAATTGACTGTCTTTTTGAAAAGTT | SEQ ID NO: 1829 | Homo sapiens thiopurine S-methyltransferase (TPMT), mRNA [NM_000367] |
| 249 | A_23_P215051 | ECHDC1 | TTTTTCAGAGGTAAACTCTAGATTAC:GTGTCAACCAATACTATTTGGCGCATAGATGT | SEQ ID NO: 1830 | Homo sapiens enoyl Coenzyme A hydratase domain containing 1 (ECHDC1), mRNA [NM_018479] |
| 250 | A_23_P215751 | NDUFA5 | TAAAAGTGGAGTCACTAAATAGTTGGAGTACGTTTCTAATATAAGTGTAGGTGGGTATG | SEQ ID NO: 1831 | Homo sapiens NADH dehydrogenase (ubiquinone) 1 alpha subcomplex, 5, 13kDa (NDUFA5), nuclear gene encoding mitochondrial protein, mRNA [NM_005000] |
| 251 | A_23_P216708 | RFK | ACTCAGAAAAACATCTAAAGGTGTTGGAGAAGAGGAGCTCATATAAATAGTTGGATTGCG | SEQ ID NO: 1832 | Homo sapiens riboflavin kinase (RFK), mRNA [NM_018391] |
| 252 | A_23_P21734 | TAF9 | CATGGTTGTGATTTCTTCCCTGAACGCGTGGTTTCATATAGTTTTTGTGCTGAGAACAGAT | SEQ ID NO: 1833 | Homo sapiens TAF9 RNA polymerase II, TATA box binding protein (TBP)-associated factor, 32kDa (TAF9), transcript variant 3, mRNA [NM_001015891] |
| 253 | A_23_P217384 | AP1S2 | AAACGTGTTGGTGTCTCTCACAGTATTATGTGTAAAGTCATTGTTTAAAGCACGAATGTTG | SEQ ID NO: 1834 | Homo sapiens adaptor-related protein complex 1, sigma 2 subunit (AP1S2), mRNA [NM_003916] |
| 254 | A_23_P217564 | ACSL4 | GTTATAGGTCGTTTAGAAAACACATAATTAACACTTAAGGTTGGGTGCTGCTAATTGTTTG | SEQ ID NO: 1835 | Homo sapiens acyl-CoA synthetase long-chain family member 4 (ACSL4), transcript variant 1, mRNA [NM_004458] |
| 255 | A_23_P217797 | DDX3Y | CACTGATAGGAAGGTCGACATCCACAAAGTTTCTCTTGAGTTTGTTATGTGTTTTGCTG | SEQ ID NO: 1836 | Homo sapiens DEAD (Asp-Glu-Ala-Asp) box polypeptide 3, Y-linked (DDX3Y), mRNA [NM_004660] |
| 256 | A_23_P218928 | C4orf18 | CAGATGAGTTGCATTTGGTCTGCTGTGTAGATGTGTTTTCAGAGGCTAGGTACAGAGGAATGTTTG | SEQ ID NO: 1837 | Homo sapiens chromosome 4 open reading frame 18 (C4orf18), transcript variant 2, mRNA [NM_016613] |
| 257 | A_23_P219072 | SAMD9 | AACCTACGTCGAGATAGTAAAGGCCAGTTGAAAAACTAAAAGATCAGCTTCGAGAAGTC | SEQ ID NO: 1838 | Homo sapiens sterile alpha motif domain containing 9 (SAMD9), mRNA [NM_017654] |
| 258 | A_23_P219161 | OLFM1 | GGGCTAACTTAAAAGAGTTTTTTCAATGCTGCAGTGACTGAAGAAGCAGTCACTCCCAT | SEQ ID NO: 1839 | Homo sapiens olfactomedin 1 (OLFM1), transcript variant 2, mRNA [NM_006334] |
| 259 | A_23_P2433 | RP2 | TTATTTCGTTGCATTAATAGTAGTAGTGGTGTTTTTGGTGTTTATATTTATGTCTA | SEQ ID NO: 1840 | Homo sapiens retinitis pigmentosa 2 (X-linked recessive) (RP2), mRNA [NM_006915] |
| 260 | A_23_P2262 | SURB7 | ATGTGGCTGAGAAAAGAACTGTTTGAGTGCCATTAAGAATTCTGCATCAGAGTTAGATAC | SEQ ID NO: 1841 | Homo sapiens SRB7 suppressor of RNA polymerase B homolog (yeast) (SURB7), mRNA [NM_004264] |
| 261 | A_23_P22871 | SYBL1 | CAAACGGAATACGGTCAGGAGTCAACTCCAGGGGTTGGGCTTGATTCCGTTGAATAATA | SEQ ID NO: 1842 | Homo sapiens synaptobrevin-like 1 (SYBL1), mRNA [NM_005638] |
| 262 | A_23_P2366 | NUDT4 | CATCAGTCTGTGTTGGTTTATTTGTCATCAGATTACTTGTGGGTATACCTACCCCAAATTG | SEQ ID NO: 1843 | Homo sapiens nudix (nucleoside diphosphate linked moiety X)-type motif 4 (NUDT4), transcript variant 2, mRNA [NM_199040] |
| 263 | A_23_P23765 | ITGB3BP | AGTATACAGGCTTTGGAGGGGAGTAGAGAGCTTGAAAATCTCATTGGAATCTCCTGTGGA | SEQ ID NO: 1844 | Homo sapiens integrin beta 3 binding protein (beta3-endonexin) (ITGB3BP), mRNA [NM_014288] |
| 264 | A_23_P23860 | BLOC1S2 | GAGTAAACTGGAGGACTGTGGCTATTCCTGAACCTCTTTTGAGACAGAATGCGTCAGAAT | SEQ ID NO: 1845 | Homo sapiens biogenesis of lysosome-related organelles complex-1, subunit 2 (BLOC1S2), transcript variant 2, mRNA [NM_001001342] |
| 265 | A_23_P24365 | ANKRD49 | GGGCACTGCTTGTTATAGTCTCTCGAAGTTCACAGGAAATGTTGATTTTCTAAGGTCCTCAT | SEQ ID NO: 1846 | Homo sapiens ankyrin repeat domain 49 (ANKRD49), mRNA [NM_017704] |

Fig. 5-15

| No. | Probe ID No. | Symbols of genes | Sequence | SEQ ID NO: | Descriptions of genes (letters and numbers within [ ] indicates GenBank accession No.) |
|---|---|---|---|---|---|
| 266 | A_23_P250002 | HACE1 | TAAGCAGTCATTGTGTTTCCAAGTAATAATGTTTGAGAGACAGTGTAAGTTGAAAGTTTTGGTA | SEQ ID NO: 1847 | Homo sapiens HECT domain and ankyrin repeat containing, E3 ubiquitin protein ligase 1 (HACE1), mRNA [NM_020771] |
| 267 | A_23_P250800 | ST3GAL6 | ATGTCACGAAGTTGCACCTAGCTGTTGGTTTTAAATACAAGTTTTCTGAGGTCAABAGTCCTTT | SEQ ID NO: 1848 | Homo sapiens ST3 beta-galactoside alpha-2,3-sialyltransferase 6 (ST3GAL6), mRNA [NM_061001] |
| 268 | A_23_P250930 | CRBN | TGATGTATTGAGAATTCAGGTCCTTAAAATTGGCAGTGCTATCCAGCGACTTCGCTGTGA | SEQ ID NO: 1849 | Homo sapiens cereblon (CRBN), mRNA [NM_016302] |
| 269 | A_23_P250994 | ANAPC10 | GATTCATGTTCCCTTAACTGACAATCATAAGAAGCCAACTCGTACATTCATGATACAGAT | SEQ ID NO: 1850 | Homo sapiens anaphase promoting complex subunit 10 (ANAPC10), mRNA [NM_014885] |
| 270 | A_23_P251937 | CPEB4 | GTATGTCAGTTAATTGTACTACTTGGGTGAATTTCCATATAGTTTTTACTGTGTATGGGG | SEQ ID NO: 1851 | Homo sapiens cytoplasmic polyadenylation element binding protein 4 (CPEB4), mRNA [NM_030627] |
| 271 | A_23_P252145 | C1GALT1 | ATATGTCTATATATATGAGGAACTTGTGTTTTTTAAATGGTGGCCAGGTAGAGGAAGTAG | SEQ ID NO: 1852 | Homo sapiens core 1 synthase, glycoprotein-N-acetylgalactosamine 3-beta-galactosyltransferase, 1 (C1GALT1), mRNA [NM_020156] |
| 272 | A_23_P252201 | EAF2 | CAGGATTCCTGATATAGATGCCAGTCATAATAGATTCGAGACAACAGTGGCCTTCTGAT | SEQ ID NO: 1853 | Homo sapiens ELL associated factor 2 (EAF2), mRNA [NM_018456] |
| 273 | A_23_P252235 | CLEC4D | CATTTAACCACGGCAGGAGTATTCTGGCATAAGAATGAAGCCGGACAACTCTCAGGGAGAAA | SEQ ID NO: 1854 | Homo sapiens C-type lectin domain family 4, member D (CLEC4D), mRNA [NM_080387] |
| 274 | A_23_P252371 | RBBP8 | GGGAAGGAGCAGAGAGACATAGACGTTGAAACAGAAAGAAAGAATGAAGGACAGTTTT | SEQ ID NO: 1855 | Homo sapiens retinoblastoma binding protein 8 (RBBP8), transcript variant 1, mRNA [NM_002894] |
| 275 | A_23_P252403 | COMMD10 | CCGTGCATGGATACAAGATAAGAGATGTACCTTAGTAGAATACAGAGCTTTGGTAATTAC | SEQ ID NO: 1856 | Homo sapiens COMM domain containing 10 (COMMD10), mRNA [NM_016144] |
| 276 | A_23_P252412 | MRPL50 | GAAAAGTTTTGAGAGGGGCACTGTCAACTGGGTTTAAGACAGGAGGACATTGCAAGTTCA | SEQ ID NO: 1857 | Homo sapiens mitochondrial ribosomal protein L50 (MRPL50), nuclear gene encoding mitochondrial protein, mRNA [NM_019051] |
| 277 | A_23_P254472 | C6orf211 | TTCATTTCAAATAGCTTGTTTCATTTGGACGGCCTTTGTATTTGATTGACCTGTAGAACC | SEQ ID NO: 1858 | Homo sapiens chromosome 6 open reading frame 211 (C6orf211), mRNA [NM_024573] |
| 278 | A_23_P254702 | DEK | TTTTTTATTAACTGCTTTTGCCCATATAACATGCTGATATTTAGTGGAAAGGTAGGCAGC | SEQ ID NO: 1859 | Homo sapiens DEK oncogene (DNA binding) (DEK), mRNA [NM_003472] |
| 279 | A_23_P254503 | FNDC3A | ATACTTGCCATTTGAGCCTCACTGACGAAAATTAGTGCAGAGGAGAAAACAATTTTAATGT | SEQ ID NO: 1860 | Homo sapiens fibronectin type III domain containing 3A (FNDC3A), transcript variant 2, mRNA [NM_014923] |
| 280 | A_23_P255663 | MANEA | AAAGAGTCTGTACATGTTCAGAGTTTCAGTGGGCAATTTCTTGGCCATGGATGTAGAACC | SEQ ID NO: 1861 | Homo sapiens mannosidase, endo-alpha (MANEA), mRNA [NM_024641] |
| 281 | A_23_P255827 | FKSG2 | ACTACGGTAAGGATGGTCAGTATGACCCCATATATGATTTTTTAAGGAATGGTTTAGAAA | SEQ ID NO: 1862 | Homo sapiens apoptosis inhibitor (FKSG2), mRNA [NM_021631] |
| 282 | A_23_P25638 | C13orf7 | CTTGCATCCAGGGGAGTTTCTTTGTTGAGTAGTATGTTTCTTGTTTGCATGTCCTGTGTC | SEQ ID NO: 1863 | Homo sapiens chromosome 13 open reading frame 7 (C13orf7), mRNA [NM_024546] |
| 283 | A_23_P25735 | PSMA6 | TAGGAGAGAGAGACTAAACATTGTCGTTAGTTTACCAGAATGGATCCGTGATGCCACTACGTGT | SEQ ID NO: 1864 | Homo sapiens proteasome (prosome, macropain) subunit, alpha type, 6 (PSMA6), mRNA [NM_002791] |
| 284 | A_23_P257911 | USP16 | GTACTTTGTTTTAATATATCTGGGTGATGATGACAACAACATCAATAAAGTGACTTACC | SEQ ID NO: 1865 | Homo sapiens ubiquitin specific peptidase 16 (USP16), transcript variant 1, mRNA [NM_006447] |

Fig. 5-16

| No. | Probe ID No. | Symbols of genes | Sequence | SEQ ID NO: | Descriptions of genes (letters and numbers within [ ] indicates GenBank accession No.) |
|---|---|---|---|---|---|
| 285 | A_23_P258108 | LOC731224 | GTGAGCCCAGGTGTTGGTTGCTTGTTCAATATCCCAAGCCCAGAAAGATGAGTTCATCCTTAAA | SEQ ID NO: 1866 | PREDICTED: Homo sapiens similar to 60S ribosomal protein L9 (LOC731224), mRNA [XR_015767] |
| 286 | A_23_P258582 | GK5 | ATGTCGATTTTTGGACACAGATATGATAGAACTAGAAATTAAGTTGCATTCTGCAAGTGC | SEQ ID NO: 1867 | Homo sapiens glycerol kinase 5 (putative) (GK5), mRNA [NM_001039547] |
| 287 | A_23_P259054 | SNX14 | CATGAGACTTCTCTTTGATGGGTTACAGAGCAACGAGTAGTCAAGAAGCAGCTGAGTTATGT | SEQ ID NO: 1868 | Homo sapiens sorting nexin 14 (SNX14), transcript variant 1, mRNA [NM_153816] |
| 288 | A_23_P26021 | COPS2 | TGCTTTTTCATCAACTGGTTGTGTTTTGCTGCTGCATTTATCCGAAGAAAAACAAGGTT | SEQ ID NO: 1869 | Homo sapiens COP9 constitutive photomorphogenic homolog subunit 2 (Arabidopsis) (COPS2), mRNA [NM_004236] |
| 289 | A_23_P26713 | RPL23 | TGGCCCGGAATTGCATGCAATGCTGGCAGGCATTGCATGATTCTCGAGTATATTTGTAAA | SEQ ID NO: 1870 | Homo sapiens ribosomal protein L23 (RPL23), mRNA [NM_000978] |
| 290 | A_23_P2705 | P2RY5 | TCTGTATTGCTGTTTCAACTGTTGTTTTGACCCTATAGTTTACTAGTTTACATGGGACA | SEQ ID NO: 1871 | Homo sapiens purinergic receptor P2Y, G-protein coupled, 5 (P2RY5), mRNA [NM_005767] |
| 291 | A_23_P29005 | SAMSN1 | CTCTGGTTGCTATATGTCATCAGGAAATTGAGATAATGGGAAAGAGGATGTGAGTCTGA | SEQ ID NO: 1872 | Homo sapiens SAM domain, SH3 domain and nuclear localization signals 1 (SAMSN1), mRNA [NM_022136] |
| 292 | A_23_P302550 | RGS18 | GAGTCTAAGGCCGTACGGATTTGGGCATGTGCCACATGGTTCATATTGCAGAAAGTGTTA | SEQ ID NO: 1873 | Homo sapiens regulator of G-protein signalling 18 (RGS18), mRNA [NM_130782] |
| 293 | A_23_P30307 | CRSP9 | CAATTGTTACTGGACAGAATGAACATGAAAGAGAAAAATTCAGGTGATAGGAGATCAGAT | SEQ ID NO: 1874 | Homo sapiens cofactor required for Sp1 transcriptional activation, subunit 9, 33kDa (CRSP9), mRNA [NM_004270] |
| 294 | A_23_P305140 | C10orf32 | AAATGGGACTCTATATGTTGTTAGTTCAGGTCTGTTCATTGACTAAGAGATTGAGAGAAATC | SEQ ID NO: 1875 | Homo sapiens chromosome 10 open reading frame 32 (C10orf32), mRNA [NM_144591] |
| 295 | A_23_P307840 | CAPZA2 | CTACAAGATTGGCAAAGATGCAGAATGCAGTAATGAGAACATCATGAGCGGGATCATT | SEQ ID NO: 1876 | Homo sapiens capping protein (actin filament) muscle Z-line, alpha 2 (CAPZA2), mRNA [NM_006136] |
| 296 | A_23_P308800 | GLS | CGGAAGAAGAGATAAGATACTGCGGAATAGGCCGTCAAACTTAAAAAAGAAAAAACTTTGC | SEQ ID NO: 1877 | Homo sapiens glutaminase C mRNA, complete cds. [AF158555] |
| 297 | A_23_P30955 | KIAA0776 | TTTTTTCATTGTCAAAATGCTTCTTTGTTGCCAGAGTAAAGAACAGTTTTTATGTT | SEQ ID NO: 1878 | Homo sapiens KIAA0776 (KIAA0776), mRNA [NM_015323] |
| 298 | A_23_P31097 | OSTM1 | ACTGAAAATGTGCTGGGGTTTGTCTGTCGTCACTGTTTATGCTGCTGAACTTAGGCACT | SEQ ID NO: 1879 | Homo sapiens osteopetrosis associated transmembrane protein 1 (OSTM1), mRNA [NM_014028] |
| 299 | A_23_P312246 | CCDC82 | GGCTTTATAACGACGATGACTGTCAAGTGAATGAGCTGTTGATATCCTGTCAGTTTAGTGAA | SEQ ID NO: 1880 | Homo sapiens coiled-coil domain containing 82 (CCDC82), mRNA [NM_024725] |
| 300 | A_23_P314191 | ZDHHC17 | TGGATACTTTTAGGCAAATAGGAAGCTTAATTCTCAGCACTGAACATGAATTACTTCCTGG | SEQ ID NO: 1881 | Homo sapiens zinc finger, DHHC-type containing 17 (ZDHHC17), mRNA [NM_015336] |
| 301 | A_23_P314591 | NFYB | GGAGGGATTTACTAACCAGTTACCAGCTGCGTTAATAACCACAGACGGTCAACAACAAAA | SEQ ID NO: 1882 | Homo sapiens nuclear transcription factor Y, beta (NFYB), mRNA [NM_006166] |
| 302 | A_23_P31571 | UQCRB | AAGGCATAAGAAGACTTCCTGAAGACACGTTATAATGAAGAGGATGTTTCGGATTAAGAGGG | SEQ ID NO: 1883 | Homo sapiens ubiquinol-cytochrome c reductase binding protein (UQCRB), mRNA [NM_006294] |
| 303 | A_23_P31702 | PXMP3 | CTTCTCTGGCATGGTTTTGCTGAATTTCTGATTTCTGTCTTACCACTTATCAATGTCCAG | SEQ ID NO: 1884 | Homo sapiens peroxisomal membrane protein 3, 35kDa (Zellweger syndrome) (PXMP3), transcript variant 1, mRNA [NM_000318] |
| 304 | A_23_P317347 | ESCO1 | GCTAATTTTAAAAGGCCTGAACTATACTTTGAAGAAACCCTATAGAAAAGGAAAGCTC | SEQ ID NO: 1885 | Homo sapiens establishment of cohesion 1 homolog 1 (S. cerevisiae) (ESCO1), mRNA [NM_052911] |

Fig. 5-17

| No. | Probe ID No. | Symbols of genes | Sequence | SEQ ID NO: | Descriptions of genes (letters and numbers within [ ] indicates GenBank accession No.) |
|---|---|---|---|---|---|
| 305 | A_23_P319133 | DNAJC10 | TCTAGGAAAGGGATCTTCTAGTTTCTGTGTTGTTTAGACTCAAAG AATCACAAATTTGTC | SEQ ID NO: 1886 | Homo sapiens DnaJ (Hsp40) homolog, subfamily C, member 10 (DNAJC10), mRNA [NM_018981] |
| 306 | A_23_P3204 | MAPK6 | AACGTGGTCACTGTGTATAGGAATTTGTATTTTGGAGGTGCTTGA TCTATCTAGAAAGAA | SEQ ID NO: 1887 | Homo sapiens mitogen-activated protein kinase 6 (MAPK6), mRNA [NM_002748] |
| 307 | A_23_P324633 | C9orf72 | TTTGTGGAATTTAGTCCCTGGGATTGAGTCTGTAGAAAATGTCTAAT AGTTCTGTATAGTCC | SEQ ID NO: 1888 | Homo sapiens chromosome 9 open reading frame 72 (C9orf72), transcript variant 1, mRNA [NM_018325] |
| 308 | A_23_P327022 | MDFIC | TTATGATTTGTTAATGTAAATGTTTGTTGAAGTATATGGCTAT CATGACTAAGTGCTA | SEQ ID NO: 1889 | Homo sapiens MyoD family inhibitor domain containing (MDFIC), mRNA [NM_199072] |
| 309 | A_23_P33045 | RPL26 | TACAAAGGTCAGCAAATTGGCAAAGTAGTCCAGGTTTACAGGAAAG AAATATGTTATCTAC | SEQ ID NO: 1890 | Homo sapiens ribosomal protein L26 (RPL26), mRNA [NM_000987] |
| 310 | A_23_P332439 | NUPL1 | ATTGAAAATCTTGAATGTATTGAATCTGTCAAGGTACAGACGGGTG CCTTTGTCAAATGTTC | SEQ ID NO: 1891 | Homo sapiens KIAA0410 mRNA, partial cds. [AB007870] |
| 311 | A_23_P339480 | HAT1 | AACATGAACATGGTGGAAGAGAGTTTCAGGAACTAGTAGGAAGATT ACCGGCGTGTTATTG | SEQ ID NO: 1892 | Homo sapiens histone acetyltransferase 1 (HAT1), mRNA [NM_003642] |
| 312 | A_23_P341448 | ZDHHC20 | TGTGAGTTAATGTTGAATGCTTGCTTGTCTTTGGCTGGCCTAA CCTACATTGACATGT | SEQ ID NO: 1893 | Homo sapiens cDNA FLJ25952 fis, clone SYNO0911. [AK098818] |
| 313 | A_23_P34307 | PIGK | ATTCATTTGCAGAGTCTTCTATTGTTGGACCAGTTACATTGTACCA AATGTTTCGTTTGG | SEQ ID NO: 1894 | Homo sapiens phosphatidylinositol glycan anchor biosynthesis, class K (PIGK), mRNA [NM_005482] |
| 314 | A_23_P345591 | PSMA2 | GCCTGGAAACGTACAGCAATGGGAAAGAAGTACTATGTGAATGGGAAG ACTTTGCTTGAAGAA | SEQ ID NO: 1895 | Homo sapiens proteasome (prosome, macropain) subunit, alpha type, 2 (PSMA2), mRNA [NM_002787] |
| 315 | A_23_P347059 | MOBKL1A | CTAGAAGGGGAAAAATCATCTAAGTTATGAAATCCAACATAGGCG CTATATTACAAACTG | SEQ ID NO: 1896 | Homo sapiens MOB1, Mps One Binder kinase activator-like 1A (yeast) (MOBKL1A), mRNA [NM_173468] |
| 316 | A_23_P347198 | SP3 | GACCACGTCAAATTTAAAGGCTACGTTATTGTACGTTTAAAGTGT ATTATAACAGTGTGG | SEQ ID NO: 1897 | Homo sapiens Sp3 transcription factor (SP3), transcript variant 1, mRNA [NM_003111] |
| 317 | A_23_P349083 | FCHO2 | GTGAAATGGTTAAACTTCTGCACTTGTTAGTTACCAGCAGTCTTC ATACCAAGTATTGGG | SEQ ID NO: 1898 | Homo sapiens FCH domain only 2 (FCHO2), mRNA [NM_138782] |
| 318 | A_23_P351457 | CMAH | GCTTAAATTTGTGGATCACTAGATAGGCAGATTCAAAAATATTT AGTTGTTCCATCCAC | SEQ ID NO: 1899 | Homo sapiens cytidine monophosphate-N-acetylneuraminic acid hydroxylase (CMP-N-acetylneuraminate monooxygenase) (CMAH) on chromosome 6 (NR_002174] |
| 319 | A_23_P351903 | TMEM167 | AAACTGGATTGTTGGGTATATTTTGGAAGTGTGCCAGAATTGGTG AACGGAAGAGTCCTT | SEQ ID NO: 1900 | Homo sapiens transmembrane protein 167 (TMEM167), mRNA [NM_174909] |
| 320 | A_23_P353704 | RP5-1022P6.2 | TGTCTCTGACTACCTATTACACACGTGTTGCTTGTTGGGTTTGTTT TGTATGTGCGTGTGT | SEQ ID NO: 1901 | Homo sapiens hypothetical protein KIAA1434 (KIAA1434), mRNA [NM_019593] |
| 321 | A_23_P354894 | ZNF567 | ACCTAAGAGTTACGAGTTCCGGTAGCCTATAACATCAAAAGTAGT TTTTGACATGTTTCA | SEQ ID NO: 1902 | Homo sapiens zinc finger protein 567 (ZNF567), mRNA [NM_152603] |
| 322 | A_23_P355067 | TMCO1 | AACTCAAGAACTCTTTATTTTCTATCATTCTTTCTACACACAC ACATCAGAGCTGGCAA | SEQ ID NO: 1903 | Homo sapiens transmembrane and coiled-coil domains 1 (TMCO1), mRNA [NM_019026] |
| 323 | A_23_P355244 | SAMD9 | TCACTGGAGGAAGAATTTTCCGTTGCTCTGCATAAAATTTAACT CCATAACTTATAAGC | SEQ ID NO: 1904 | Homo sapiens sterile alpha motif domain containing 9 (SAMD9), mRNA [NM_017654] |
| 324 | A_23_P356122 | ZNF451 | TTTTACCTGCTTAGACTTTTATGTGACTTGTAGTGGTCTCTGTT AAAGGGAATGGTGTC | SEQ ID NO: 1905 | Homo sapiens zinc finger protein 451 (ZNF451), transcript variant 2, mRNA [NM_015555] |

Fig. 5-18

| No. | Probe ID.No. | Symbols of genes | Sequence | SEQ ID NO: | Descriptions of genes (letters and numbers within [ ] indicates GenBank accession No.) |
|---|---|---|---|---|---|
| 325 | A_23_P358470 | CCDC111 | ATGACCCTGTATGTAAAGCAGAAAACTTCAAATCTGACTGTTTCCATTACCTGGTGAAG | SEQ ID NO: 1906 | Homo sapiens coiled-coil domain containing 111 (CCDC111), mRNA [NM_152683] |
| 326 | A_23_P358628 | DPY19L1 | ATATAAATTAGGCTTTTTCAAGAAGGATCGTTTTGTAGGAGTGTTTATAATGTAACGCCC | SEQ ID NO: 1907 | Homo sapiens DPY-19-like protein 1 (DPY19L1) mRNA, complete cds. [DQ287932] |
| 327 | A_23_P361448 | SESN3 | AAGGAGAAGAAAGAAAGTCTTTTGTGGTCTCTGGAGATAGTTTCATTGATTCCTCAT | SEQ ID NO: 1908 | Homo sapiens sestrin 3 (SESN3), mRNA [NM_144665] |
| 328 | A_23_P364107 | C14orf106 | AGGAGACAGTGTTGTGTATTTTGAACTGGAGTACATGTATTTTCTTTGTAAAGTAGGTCC | SEQ ID NO: 1909 | Homo sapiens chromosome 14 open reading frame 106 (C14orf106), mRNA [NM_018363] |
| 329 | A_23_P36776 | PUS7L | GGGCTTCAGTTTCAACATCGTAAAATGGGATGTTAACATTGCCTACCTCATAGGATTA | SEQ ID NO: 1910 | Homo sapiens pseudouridylate synthase 7 homolog (S. cerevisiae)-like (PUS7L), mRNA [NM_031292] |
| 330 | A_23_P3681 | NETO2 | AGACCTTAGGAAATGTGGACATAAGCTCTTCTTTGTTTGGTTTTTGTTACTGTATTTAGTTTGTG | SEQ ID NO: 1911 | Homo sapiens neuropilin (NRP) and tolloid (TLL)-like 2 (NETO2), mRNA [NM_018092] |
| 331 | A_23_P368681 | GIMAP2 | ATGACCAAGTGAAGGAACTAATGGACTGTGTATTGAAGATCTGTTGATGGAGAAAAATGGTG | SEQ ID NO: 1912 | Homo sapiens GTPase, IMAP family member 2 (GIMAP2), mRNA [NM_015660] |
| 332 | A_23_P371266 | DNM3 | ACTGTCTTCTTGGCAGTTTCAGGATTCCTTAATGCTGATACATATGGACTCTTAGAATGGAA | SEQ ID NO: 1913 | Homo sapiens dynamin 3 (DNM3), mRNA [NM_015569] |
| 333 | A_23_P37275 | CGRRF1 | GAGCAAGATAAAGACAAAACCGAAGACTCTTGAAGACTATCAACACTGAAAAGTACACT | SEQ ID NO: 1914 | Homo sapiens cell growth regulator with ring finger domain 1 (CGRRF1), mRNA [NM_006568] |
| 334 | A_23_P37441 | B2M | TTGTCTTCAGCAAGGACTGGTCTTCTTCTTGTATCTCTTGTACTACACTGAATTCAGCGCACT | SEQ ID NO: 1915 | Homo sapiens beta-2-microglobulin (B2M), mRNA [NM_004048] |
| 335 | A_23_P37636 | FAM96A | CTTGAACCTGACTGACTGATAGCTGTTTTAAGAGCCACTGCGGCCTGTAATTGTTTGATATATTTG | SEQ ID NO: 1916 | Homo sapiens family with sequence similarity 96, member A (FAM96A), transcript variant 1, mRNA [NM_032231] |
| 336 | A_23_P380848 | TXNL5 | CTGGTGGAAATGTGTTCTCTGAAGATTAAGATTTAGGATGGCAATCATGTCTTGATGT | SEQ ID NO: 1917 | Homo sapiens thioredoxin-like 5 (TXNL5), mRNA [NM_032731] |
| 337 | A_23_P38275 | THC2504576 | TCTCGGCCAAATGAAGTTTAATCCCTTGTGACTTCCGACCGAAGCAAGAATGGCAATGA | SEQ ID NO: 1918 | RL26_BOVIN (P61257) 60S ribosomal protein L26, complete [THC2504576] |
| 338 | A_23_P384056 | CCDC14 | TAGCTGAGTATCATCTCCGTTCATGTAAGCAGCACGTTTTAACTCTTAGGAAGCTGAATG | SEQ ID NO: 1919 | Homo sapiens coiled-coil domain containing 14 (CCDC14), mRNA [NM_022757] |
| 339 | A_23_P390734 | FGFR1OP2 | CCACCAGATACAGAAATGTCCTTTAAGATCAGTTGAAACCTAAATTTTCTTATGTGTGG | SEQ ID NO: 1920 | Homo sapiens FGFR1 oncogene partner 2 (FGFR1OP2), mRNA [NM_015633] |
| 340 | A_23_P394276 | RWDD4A | TTGTCAGGGCTTAATTATGGCGTTGTAATCAGAGAATGATGCTAGTTACATGCCAATGA | SEQ ID NO: 1921 | Homo sapiens RWD domain containing 4A (RWDD4A), mRNA [NM_152682] |
| 341 | A_23_P394605 | SEC24A | GATTTATTTCTTCTAATCAAAGATGGATAACAGTGTATTATCTAGGGAACCACCAAATGTG | SEQ ID NO: 1922 | Homo sapiens SEC24 related gene family, member A (S. cerevisiae) (SEC24A), mRNA [NM_021982] |
| 342 | A_23_P397899 | FZD5 | GGGAGCTTACAATCCTAAGGTTGGCGTTGTAATGAAGTTCCACTTGGTTCAGGTTTCTT | SEQ ID NO: 1923 | Homo sapiens frizzled homolog 5 (Drosophila) (FZD5), mRNA [NM_003468] |
| 343 | A_23_P410017 | TBCEL | ATACAGTTCATGTAAAGGGAAGGCTTCTCATTTAATTCAGGGGATGTGGGTATTTTAGG | SEQ ID NO: 1924 | Homo sapiens leucine rich repeat containing 35, mRNA (cDNA clone IMAGE:3913004). [BC020501] |
| 344 | A_23_P41114 | CSTA | AAACAAATTGAGACTTATGGAAAATTGGAAGCTGTGCAGTATAAACTCAAGTTGTTGCTG | SEQ ID NO: 1925 | Homo sapiens cystatin A (stefin A) (CSTA), mRNA [NM_005213] |
| 345 | A_23_P413796 | CCDC5 | GCATGGATGCTTCTCTGTCTCATCAGTCGTTAGTAGCAGTATCAGAGAAAGTGGCAAGAT | SEQ ID NO: 1926 | Homo sapiens coiled-coil domain containing 5 (spindle associated) (CCDC5), mRNA [NM_138443] |

Fig. 5-19

| No. | Probe ID No. | Symbols of genes | Sequence | SEQ ID NO: | Descriptions of genes (letters and numbers within [ ] indicates GenBank accession No.) |
|---|---|---|---|---|---|
| 346 | A_23_P41512 | C4orf15 | TAAGGCTGTTAGTCTTGAAGATTGAAAATTACTGAAAACTGAATCTTTATTACGTGTCCT | SEQ ID NO: 1927 | Homo sapiens chromosome 4 open reading frame 15 (C4orf15), mRNA [NM_024511] |
| 347 | A_23_P41645 | ELL2 | TGTCTTTTCAAAGTGCTGCCAGTTGAAAAGGGGAAGGATTATGTTTACAAATCTGTTTTGA | SEQ ID NO: 1928 | Homo sapiens elongation factor, RNA polymerase II, 2 (ELL2), mRNA [NM_012081] |
| 348 | A_23_P41664 | ENST00000334994 | TGGCTTGGAGCAGATTCGACTTCATAAAGACAAATTGTTCCTGAAAATGAGGCACAAGGTCAT | SEQ ID NO: 1929 | Syntaurin [Source:Uniprot/SPTREMBL:Acc:Q72207] [ENST00000334994] |
| 349 | A_23_P421563 | LSM3 | CATAAGAGAAACTGCATACATTTGATATTAAGAAATAATTCGGGGGATTCTTCCACTC | SEQ ID NO: 1930 | Homo sapiens LSM3 homolog, U6 small nuclear RNA associated (S. cerevisiae) (LSM3), mRNA [NM_014463] |
| 350 | A_23_P422794 | NSMCE2 | CATTGTTCGGATCATGATTGAGTGCAGGCAAAAAGCGGAAGAAAAAGGCCTATTGCCCTCAAAT | SEQ ID NO: 1931 | Homo sapiens non-SMC element 2, MMS21 homolog (S. cerevisiae) (NSMCE2), mRNA [NM_173685] |
| 351 | A_23_P42718 | NFE2L3 | CAGGCAATCGTTTTAAGAGTAAGTTGGTTACTTCAAAAAGAGCAAAGACTGGGATCAAA | SEQ ID NO: 1932 | Homo sapiens nuclear factor (erythroid-derived 2)-like 3 (NFE2L3), mRNA [NM_004289] |
| 352 | A_23_P428468 | ENST00000369677 | AAACCTACGGTCAGTCTGAAAAAACTGAAGTACATTGAAATGATCCAGATATGTCTGTT | SEQ ID NO: 1933 | Zinc finger protein 292 [Source:Uniprot/SWISSPROT:Acc:060281] [ENST00000369677] |
| 353 | A_23_P429491 | FLJ25416 | GCTTGGTCACCTGGAATTGTTTCATAAAAAGTCAGCTGAACCCAATTCCTGAACTTTTAA | SEQ ID NO: 1934 | Homo sapiens hypothetical protein FLJ25416 (FLJ25416), mRNA [NM_145018] |
| 354 | A_23_P42975 | PRKAR2B | GCCACATTTTTAGAACAGTGTTTAAGACATTTTTTGCAAAAGCTTCTTGTAGGAAAAGAGAGC | SEQ ID NO: 1935 | Homo sapiens protein kinase, cAMP-dependent, regulatory, type II, beta (PRKAR2B), mRNA [NM_002736] |
| 355 | A_23_P43049 | DCTN6 | AAATAGATTTGAAGTCATCCCGTGAGAATACGGTGATCTATGCTGCAGAGTGCTTCGGTCG | SEQ ID NO: 1936 | Homo sapiens dynactin 6 (DCTN6), mRNA [NM_006571] |
| 356 | A_23_P43150 | ZHX1 | TTTGTAAAGACTGGTGGTCGTGTTCATTCATATATGGGAAGACCCTTTCTTGTGACGATAGG | SEQ ID NO: 1937 | Homo sapiens zinc fingers and homeoboxes 1 (ZHX1), transcript variant 1, mRNA [NM_010179261] |
| 357 | A_23_P43157 | MYBL1 | ATACATATTTGGGTTGGTTGGTACTGGTTGAATCCTTCAGTTAAGCTGCTTTGTTGCTTTTTGCA | SEQ ID NO: 1938 | Homo sapiens v-myb myeloblastosis viral oncogene homolog (avian)-like 1 (MYBL1), mRNA [NM_001080416] |
| 358 | A_23_P43175 | SEPT10 | AAATGCACATAATTCATATATTCAGGTGGTATTTCAGTGCATTCAGTGCCTTACTGGTATTCTCA | SEQ ID NO: 1939 | Homo sapiens septin 10 (SEPT10), transcript variant 1, mRNA [NM_144710] |
| 359 | A_23_P433111 | C5orf35 | GTTCCAATGACAGAGGAGGAGTAATGTCTGTTATCACGAATTTGATGTGCCTGCAGTTTCC | SEQ ID NO: 1940 | Homo sapiens chromosome 5 open reading frame 35 (C5orf35), mRNA [NM_153706] |
| 360 | A_23_P434809 | S100A8 | AAAGCCATGAAGAAAGCACAGAAGAGTAGCTGAGTTACTGGGGCCCAGAGGCTGGGCCCCT | SEQ ID NO: 1941 | Homo sapiens S100 calcium binding protein A8 (S100A8), mRNA [NM_002964] |
| 361 | A_23_P44257 | COMMD8 | AACATTTTACTTCTCGGCTTCGTGTATGTTTGGGAAACATTGCTCTGATAAAAATAGCTGTC | SEQ ID NO: 1942 | Homo sapiens COMM domain containing 8 (COMMD8), mRNA [NM_017845] |
| 362 | A_23_P44974 | MRPL13 | ATGAGGTAAAACAACTGCTACAGTTCAGACACCGTGTTTTATGTGCCGAATCACTGTGGGGA | SEQ ID NO: 1943 | Homo sapiens mitochondrial ribosomal protein L13 (MRPL13), nuclear gene encoding mitochondrial protein, mRNA [NM_014078] |
| 363 | A_23_P45180 | GYPA | ACCTGCTAAGTTGTACAATTTCAGAATGCAATTTCATTATAATGAGTTCCAGTGACTC | SEQ ID NO: 1944 | Homo sapiens glycophorin A (MNS blood group) (GYPA), mRNA [NM_002099] |

Fig. 5-20

| No. | Probe ID No. | Symbols of genes | Sequence | SEQ ID NO: | Descriptions of genes (letters and numbers within [ ] indicates GenBank accession No.) |
|---|---|---|---|---|---|
| 364 | A_23_P45248 | SH2D1A | TTCTAAAGGCATTGTAGTCGTGTAATGGAAGGCATGTAGCATGTCGG TCAAAGCTGAAATGG | SEQ ID NO: 1945 | Homo sapiens SH2 domain protein 1A, Duncan's disease (lymphoproliferative syndrome) (SH2D1A), mRNA [NM_002351] |
| 365 | A_23_P45934 | SRP9 | TATACGGATTGTGATGGGAACTTGTGTGTTAAAGTAACAGATGAT TAGTTTGTTTGGTG | SEQ ID NO: 1946 | Homo sapiens signal recognition particle 9kDa (SRP9), mRNA [NM_003133] |
| 366 | A_23_P46396 | PTBP2 | AACCAGGTGGGACCAAAGTTTATGTGCCTTAGTCTTAATTACC TTGCATTGTAATATT | SEQ ID NO: 1947 | Homo sapiens polypyrimidine tract binding protein 2 (PTBP2), mRNA [NM_021190] |
| 367 | A_23_P48166 | TWF1 | TGGAGGACGACCATAGCTGAAGCTGTTATTTTCAGTCAGGAAGACT ACCGTGTCATGAAGGT | SEQ ID NO: 1948 | Homo sapiens twinfilin, actin-binding protein, homolog 1 (Drosophila) (TWF1), mRNA [NM_002822] |
| 368 | A_23_P48180 | ZNF92 | GAATATTAAGTGCCTACTTGAGGTAGATGTTCAGACTAACATTGTT TTGCAGTATAGTGAG | SEQ ID NO: 1949 | Homo sapiens zinc finger protein 92 (ZNF92), transcript variant 1, mRNA [NM_007139] |
| 369 | A_23_P51276 | TUBB2A | GTGGACGAGGAGATGCTGGAACGGTGCAGAACAAGAACAGCAGCTAC TTCGTGAGTGGATC | SEQ ID NO: 1950 | Homo sapiens tubulin, beta 2A (TUBB2A), mRNA [NM_001069] |
| 370 | A_23_P502425 | MRPL47 | GTTTCCACATCTTGCTGAAGGCCAAAAGTCAAGTCTGTCTAAGA TGTCTGAACTATTAA | SEQ ID NO: 1951 | Homo sapiens mitochondrial ribosomal protein L47 (MRPL47), nuclear gene encoding mitochondrial protein, transcript variant 1, mRNA [NM_020409] |
| 371 | A_23_P502797 | WDFY1 | GTAACAGTTTACTGGTTGTTCCATTGCTGAATATGCAGGCTAATT TGTACAGATAGGGAT | SEQ ID NO: 1952 | Homo sapiens WD repeat and FYVE domain containing 1 (WDFY1), mRNA [NM_020830] |
| 372 | A_23_P50907 | ITGAV | AAAGAGTGATTAAGTGAGGTTATTTTACCGGTAAATGGTCGATTCT GGATTGTATTTCAGG | SEQ ID NO: 1953 | Homo sapiens integrin, alpha V (vitronectin receptor, alpha polypeptide, antigen CD51) (ITGAV), mRNA [NM_002210] |
| 373 | A_23_P51009 | NDUFB3 | CCGGAATGAAGCTTGCAGATACATGGGATGGCTTTGCAAAGAGTGT TTCCTTTTCTGATGT | SEQ ID NO: 1954 | Homo sapiens NADH dehydrogenase (ubiquinone) 1 beta subcomplex, 3, 12kDa (NDUFB3), mRNA [NM_002491] |
| 374 | A_23_P51317 | CCDC76 | CCCTTGTTTATAAGTTTATGTCAAGTAAGGTAAGGTAGTTTGTTTTAAGTT AGTTACCCATGTCCC | SEQ ID NO: 1955 | Homo sapiens coiled-coil domain containing 76 (CCDC76), mRNA [NM_019083] |
| 375 | A_23_P51487 | GBP3 | AATCCTAAAGGATAAGTAAGTTAGTCTTTCCTGATTCTTAAAGGTGAT ACTTGAAATCCTGCC | SEQ ID NO: 1956 | Homo sapiens guanylate binding protein 3 (GBP3), mRNA [NM_018284] |
| 376 | A_23_P53668 | NFYB | TGGGCTGATATTCCAGGTATTCCATCTGTGGATGAAAGTAACAATGTT TAACATATATTGGG | SEQ ID NO: 1957 | Homo sapiens nuclear transcription factor Y, beta (NFYB), mRNA [NM_006166] |
| 377 | A_23_P53957 | C14orf112 | TTATACTTCCAGCTATTCCGATCGTGTGGATGAAAGTAACAATGTT GGGCACGTATATTT | SEQ ID NO: 1958 | Homo sapiens chromosome 14 open reading frame 112 (C14orf112), mRNA [NM_016468] |
| 378 | A_23_P56050 | TNNT1 | TCCGAGCGTAAGAAGCCTCGGACATTGACTAGATGGGAGGAGGAA CAGGTCCGGGGAGAAA | SEQ ID NO: 1959 | Homo sapiens troponin T type 1 (skeletal, slow), mRNA (cDNA clone MGC:104241 IMAGE:4247379), complete cds, [BC107798] |
| 379 | A_23_P5611 | RIF1 | ATGTATTCTTGGCTGCTAGTGCGTGGTTTTCAGGAAATTTAATTA TCTTACTGAGATGTG | SEQ ID NO: 1960 | Homo sapiens RAP1 interacting factor homolog (yeast) (RIF1), mRNA [NM_018151] |
| 380 | A_23_P56380 | ZC3H15 | GTCCACCCAAGTAAGAAAGTGTATCGTCCTTCCATCGTTTTGGTTT TCATTTGGGCATGTG | SEQ ID NO: 1961 | Homo sapiens zinc finger CCCH-type containing 15 (ZC3H15), mRNA [NM_018471] |
| 381 | A_23_P56734 | HNMT | CCTTTTGTCCACGATGGATATATATCTGACTGCTTTATTGATGGTAA TCAAAATGGAGACCT | SEQ ID NO: 1962 | Homo sapiens histamine N-methyltransferase (HNMT), transcript variant 1, mRNA [NM_006895] |
| 382 | A_23_P56759 | KRCC1 | GATATCCGTGTTCATACCACTTTCTTATGTGAATAAGGTTGTTTA AGTTGTAACAAAGGC | SEQ ID NO: 1963 | Homo sapiens lysine-rich coiled-coil 1 (KRCC1), mRNA [NM_016618] |

Fig. 5-21

| No. | Probe ID No. | Symbols of genes | Sequence | SEQ ID NO: | Descriptions of genes (letters and numbers within [ ] indicates GenBank accession No.) |
|---|---|---|---|---|---|
| 383 | A_23_P57277 | C21orf7 | CCAGCTTCTAGCTTGAGGAAGGATATTTTAAATGAGATCATTAACGTGAAAGTATTAC | SEQ ID NO: 1964 | Homo sapiens chromosome 21 open reading frame 7 (C21orf7), mRNA [NM_020152] |
| 384 | A_23_P58390 | C4orf32 | TAATACTAACTATTTAGTATAGTGTCAGTAGTGTACATCTGTGCAGACTGGTGTTAATAGGG | SEQ ID NO: 1965 | Homo sapiens chromosome 4 open reading frame 32 (C4orf32), mRNA [NM_152400] |
| 385 | A_23_P58396 | PDGFC | CATGGATATTTTTATGTACAGAAGTATGTCTCTTAACCAGTTCACTTATTGTAGTCTGGC | SEQ ID NO: 1966 | Homo sapiens platelet derived growth factor C (PDGFC), mRNA [NM_016205] |
| 386 | A_23_P58877 | GOPC | AAGGTTCATGTGATTCATGTCTGTAAGATGCACAGTATTTGACATCCTGATTATGTAATCC | SEQ ID NO: 1967 | Homo sapiens golgi associated PDZ and coiled-coil motif containing (GOPC), transcript variant 1, mRNA [NM_020399] |
| 387 | A_23_P58912 | SLC35A1 | ATGATCAGTGCGGTTATGTGGAAAACAAGAAACAAAACAAAGAAAGCTATCTGAGTGAACTGC | SEQ ID NO: 1968 | Homo sapiens solute carrier family 35 (CMP-sialic acid transporter), member A1 (SLC35A1), mRNA [NM_006416] |
| 388 | A_23_P59637 | DOCK4 | TTTGGCAGTGAGGAGTGAGTGTGAATTTATCTTGAATTTATCATGTGTGTGTATTTCTGAAGCAG | SEQ ID NO: 1969 | Homo sapiens dedicator of cytokinesis 4 (DOCK4), mRNA [NM_014705] |
| 389 | A_23_P59921 | SUB1 | CAGAATTGGGAAAATGAGGTTAGTGTTCGGCATTTTAAAGGCAAAGTGCTAATTGAT | SEQ ID NO: 1970 | Homo sapiens SUB1 homolog (S. cerevisiae) (SUB1), mRNA [NM_006713] |
| 390 | A_23_P60248 | TXN | GGACAAAAGGTGGGTGAATTTCTGGAGCCAATAAGGAAAAGGTTGAAGCCAGCATTAAT | SEQ ID NO: 1971 | Homo sapiens thioredoxin (TXN), mRNA [NM_003329] |
| 391 | A_23_P61674 | CLK4 | GAAAGGCATGCAGTTTGTCCATTGTGAGAGTTTGTTTAATAAACCACATACACACTTTA | SEQ ID NO: 1972 | Homo sapiens CDC-like kinase 4 (CLK4), mRNA [NM_020666] |
| 392 | A_23_P63655 | ATP5C1 | AGAGAGCTGAAACAGGCTCGGAATATATGGGATCTTAGCTCTGTATGAAAAAGCT | SEQ ID NO: 1973 | Homo sapiens ATP synthase, H+ transporting, mitochondrial F1 complex, gamma polypeptide 1 (ATP5C1), nuclear gene encoding mitochondrial protein, transcript variant 2, mRNA [NM_005174] |
| 393 | A_23_P63868 | IFIT5 | AAGATAGATCAGAAAATGCAGAATTCCTGACTGCTCTCTGTGAGCTCCGACTTTCCATT | SEQ ID NO: 1974 | Homo sapiens interferon-induced protein with tetratricopeptide repeats 5 (IFIT5), mRNA [NM_012420] |
| 394 | A_23_P63886 | FAS | ATGTCTATCCACAGAGGCTAACGCCACTCTATGAATCAATAGAAGAAGCTATGACGTTTTGC | SEQ ID NO: 1975 | Homo sapiens Fas (TNF receptor superfamily, member 6) (FAS), transcript variant 1, mRNA [NM_000043] |
| 395 | A_23_P65230 | TMTC4 | AGAAGGCAACACATCTGTGTAAGCTGCTTTTTAGTGTGTTTATCTGAAGGCGGTTTTTCCA | SEQ ID NO: 1976 | Homo sapiens transmembrane and tetratricopeptide repeat containing 4 (TMTC4), transcript variant 1, mRNA [NM_032813] |
| 396 | A_23_P65768 | C15orf15 | TCCTGCATTGCCATCTACATAATAATACAGATATTACGGATGTGTTAGATTGCATCTCAGTGTT | SEQ ID NO: 1977 | Homo sapiens chromosome 15 open reading frame 15 (C15orf15), mRNA [NM_016304] |
| 397 | A_23_P66260 | ZNF267 | TGTGATGAATGTGGTAAAGCGTTCAGGTATAGGCATACGTCACTACACATGGGAGAAGT | SEQ ID NO: 1978 | Homo sapiens zinc finger protein 267 (ZNF267), transcript variant 498723, mRNA [NM_003414] |
| 398 | A_23_P68472 | DPM1 | CTATTGGCAGAGGTTCGAATATCATTTGTGGATCGTGTTTATGGTGAATCCAAGTTGGGAG | SEQ ID NO: 1979 | Homo sapiens dolichyl-phosphate mannosyltransferase polypeptide 1, catalytic subunit (DPM1), mRNA [NM_003859] |
| 399 | A_23_P69109 | PLSCR1 | GTTAGCTCTTACACTCTATCCTTCCTAGAAAATGGTAATTGAGATTACTCAGATATTAA | SEQ ID NO: 1980 | Homo sapiens phospholipid scramblase 1 (PLSCR1), mRNA [NM_021105] |
| 400 | A_23_P69685 | ZCD2 | ATTTGTCTTACTAAGAGGAGGTTATTGTGAGGTGTTGGCGTTGTAAAACGTTTCCTGCCT | SEQ ID NO: 1981 | Homo sapiens zinc finger, CDGSH-type domain 2 (ZCD2), mRNA [NM_001008388] |

Fig. 5-22

| No. | Probe ID No. | Symbols of genes | Sequence | SEQ ID NO: | Descriptions of genes (letters and numbers within [ ] indicates GenBank accession No.) |
|---|---|---|---|---|---|
| 401 | A_23_P69908 | GLRX | GTGATAAAAGTTAGAGCCCCCTAGACAGCGAAGAGTCTATCTGTGAAAGAGCCCTACACTT | SEQ ID NO: 1982 | Homo sapiens glutaredoxin (thioltransferase) (GLRX), mRNA [NM_002064] |
| 402 | A_23_P70290 | TMEM30A | ATCTTGTGCCTGCAACTGTAAACCAGATGTAAGTGCTTAATGAGACTGTTTTCATTCTTG | SEQ ID NO: 1983 | Homo sapiens transmembrane protein 30A (TMEM30A), mRNA [NM_018247] |
| 403 | A_23_P70318 | ENPP4 | TGTTTTTTGGGTGTCTCCTTCTTGTGCGCATATCTGATAAGGCTTATGGATTATTGCATTT | SEQ ID NO: 1984 | Homo sapiens ectonucleotide pyrophosphatase/phosphodiesterase 4 (putative function) (ENPP4), mRNA [NM_014936] |
| 404 | A_23_P70328 | CENPQ | CAATGGCTTACAGATTTGTGTGTGGTCATCTGGAAGTTGAAAAATCCTCAAATGCCTTCAG | SEQ ID NO: 1985 | Homo sapiens centromere protein Q (CENPQ), mRNA [NM_018132] |
| 405 | A_23_P7066 | RPL9 | GGTCTCTTGTTGAAATCCGAAATTTCTTGGGTGAAAAATATCCGCAGGGTTCCAATGA | SEQ ID NO: 1986 | Homo sapiens ribosomal protein L9 (RPL9), transcript variant 1, mRNA [NM_000661] |
| 406 | A_23_P70938 | STARD3NL | GCATTATGTGTATGGCCTGAAGTGTTGGACTTGCAAAAGGGGGAAGAAAGGAATTGGGAAT | SEQ ID NO: 1987 | Homo sapiens STARD3 N-terminal like (STARD3NL), mRNA [NM_032016] |
| 407 | A_23_P71433 | UBE2W | CATGAGCCCTACTGCCTAAAGACTATTTCATTTATTTATGTTGGAAACCCGGGTAAACAT | SEQ ID NO: 1988 | Homo sapiens ubiquitin-conjugating enzyme E2W (putative) (UBE2W), transcript variant 1, mRNA [NM_001001481] |
| 408 | A_23_P72117 | SMPDL3A | TTTTGTGGGAATTTTAGATAAATCTTTGTTAATTACTGAGTGAGTCGGCAAGTAGACTTCCGTC | SEQ ID NO: 1989 | Homo sapiens sphingomyelin phosphodiesterase, acid-like 3A (SMPDL3A), mRNA [NM_006714] |
| 409 | A_23_P7221 | RPL34 | CGAAGGAGCAGAAAAATCGTTGTGAAAGTGTTGAAAGGCACAAGGAGAGAGTCAGAAAGCTAA | SEQ ID NO: 1990 | Homo sapiens ribosomal protein L34 (RPL34), transcript variant 2, mRNA [NM_033625] |
| 410 | A_23_P7229 | RPL34 | CGAAACCCGTGGTAATAGAATTGTTTACCTTTATACCAAGAAGGTTGGGAAAAGGCACAAAA | SEQ ID NO: 1991 | Homo sapiens ribosomal protein L34 (RPL34), transcript variant 2, mRNA [NM_033625] |
| 411 | A_23_P72568 | SNX4 | AAGCCTCAGTAATGAGGCTAAATTTAGTCTGCTTGGCTGTCTGTCACATGGCATTCAGGGCT | SEQ ID NO: 1992 | Homo sapiens sorting nexin 4 (SNX4), mRNA [NM_003794] |
| 412 | A_23_P7262 | MARCH1 | GATTATTGTGTCTTTGCATATTCATGTAAACTCATGTGTGAATGACATTGCAGTGAGC | SEQ ID NO: 1993 | Homo sapiens cDNA FLJ20668 fis, clone KAIA585. [AK000675] |
| 413 | A_23_P7282 | ELMOD2 | TTCAAGTAGCTTTCTCTGGGGGAAAAAAAGTACCACTTGGACACTTAAAGGAATTGGGATTT | SEQ ID NO: 1994 | ELMO domain-containing protein 2. [Source:Uniprot/SWISSPROT;Acc:Q8IZB1] [ENST00000323570] |
| 414 | A_23_P73577 | DYNLT3 | TGTTTCTTTATGCTGGCTTTTGTGCCCTGGAAGATCATAATAGTGACCAAAATATAC | SEQ ID NO: 1995 | Dynein light chain Tctex-type 3 (T-complex-associated testis-expressed 1-like) (Protein 91/23). [Source:Uniprot/SWISSPROT;Acc:P51808] [ENST00000378578] |
| 415 | A_23_P74001 | S100A12 | TGAAGGCTTTTACCGAGCAGCAATGCCTGAATGAGGGTGTCTTTTCTTTCCGCTCACCAAAACC | SEQ ID NO: 1996 | Homo sapiens S100 calcium binding protein A12 (S100A12), mRNA [NM_005621] |
| 416 | A_23_P74799 | SLC25A24 | GATTCTGTATCTTTTGAAAAAAGCCGAGAGTTGAAGATAGTATATTTCTGGCTAGTACTG | SEQ ID NO: 1997 | Homo sapiens solute carrier family 25 (mitochondrial carrier; phosphate carrier), member 24 (SLC25A24), transcript variant 2, mRNA [NM_213651] |
| 417 | A_23_P75028 | REEP3 | AGAAACGACCACAAGTGTATTTTAGTCATCTACACGTCAAATATCCCAAGACAGATTAT | SEQ ID NO: 1998 | Homo sapiens receptor accessory protein 3 (REEP3), mRNA [NM_001001330] |
| 418 | A_23_P7643 | ZFYVE16 | TCTGCCTCAGGCATTATCTCAAATGATCTTGATAGTGGTCTGATACCTGTGATCCATGGTGG | SEQ ID NO: 1999 | Homo sapiens zinc finger, FYVE domain containing 16 (ZFYVE16), mRNA [NM_014733] |

Fig. 5-23

| No. | Probe ID No. | Symbols of genes | Sequence | SEQ ID NO: | Descriptions of genes (letters and numbers within [ ] indicates GenBank accession No.) |
|---|---|---|---|---|---|
| 419 | A_23_P75789 | MS4A4A | CACCAAAAGATCAACAGACAAATGCTCAGAGAAATCTATGCTGACTGTGACACAAGAGCCT | SEQ ID NO: 2000 | Homo sapiens membrane-spanning 4-domains, subfamily A, member 4 (MS4A4A), transcript variant 1, mRNA [NM_024021] |
| 420 | A_23_P76159 | EEA1 | TATTGTGTTTACTAGTTGTGATCATGTAGTTAGTTGTGCCTTAGTTTGTGAGAAAGGTTAGGCTC | SEQ ID NO: 2001 | Homo sapiens early endosome antigen 1 (EEA1), mRNA [NM_003566] |
| 421 | A_23_P76480 | BF213738 | AAATGGAACACAGGACGAATGGGTAGAGCTAGATTTACCAAATCGTTTGGCATGACAGG | SEQ ID NO: 2002 | BF213738 601847628F1 NIH_MGC_55 Homo sapiens cDNA clone IMAGE:4078519 5', mRNA sequence [BF213738] |
| 422 | A_23_P76851 | TXNDC1 | ATTTGTGTAATGTGTCGCCTTCTTCTAGGCTCTGTTGGTGTGTGAATCCATTAGATTTACA | SEQ ID NO: 2003 | Homo sapiens thioredoxin domain containing 1 (TXNDC1), mRNA [NM_030755] |
| 423 | A_23_P78092 | EVI2A | GCTGAATCAGACACTTGGAAAAGAACAAAAGAGCTCACAGGACCCAACCTAGTATGCAA | SEQ ID NO: 2004 | Homo sapiens ecotropic viral integration site 2A (EVI2A), transcript variant 1, mRNA [NM_001003927] |
| 424 | A_23_P79199 | DBI | TGGCTCACCATACGGCTCTAAGAGATTAGGGGCTAAAACGATTACTGACTTTCGTTGAGTA | SEQ ID NO: 2005 | Homo sapiens diazepam binding inhibitor (GABA receptor modulator, acyl-Coenzyme A binding protein) (DBI), transcript variant 1, mRNA [NM_020548] |
| 425 | A_23_P81212 | MRPS18C | ATGGGGTTTATGCCAGTTACATACAAGGATCCTGCATATCTCAAGGACCCTAAAGTTTGT | SEQ ID NO: 2006 | Homo sapiens mitochondrial ribosomal protein S18C (MRPS18C), nuclear gene encoding mitochondrial protein, mRNA [NM_016067] |
| 426 | A_23_P83278 | CHMP5 | CATTGCTCTTTTATTTTTTCCATTAAGAGACTCATTGGTTGGAGAAATGCTTGTTCGTAC | SEQ ID NO: 2007 | Homo sapiens chromatin modifying protein 5 (CHMP5), mRNA [NM_016410] |
| 427 | A_23_P84070 | LARP7 | TGATTTCCTAGAAGGGGATACAGAATGCCATGGCTAGATAAAAACCTTAAGACTCCTGAGGATGCTCA | SEQ ID NO: 2008 | Homo sapiens La ribonucleoprotein domain family, member 7 (LARP7), transcript variant 1, mRNA [NM_016648] |
| 428 | A_23_P8640 | GPR30 | AACAGCTGGGGACAACTGCCGTGATGATGTAAAAAACCTTCCCATAAAATGTAAGAAAAGC | SEQ ID NO: 2009 | Homo sapiens G protein-coupled receptor 30 (GPR30), transcript variant 2, mRNA [NM_001505] |
| 429 | A_23_P86653 | SRGN | AGGAGTTGGGTCAACATGGATTAGAAGAGAGGATTTTATGTTATAAGAGAGGATTTTCCAC | SEQ ID NO: 2010 | Homo sapiens serglycin (SRGN), mRNA [NM_002727] |
| 430 | A_23_P87879 | CD69 | TGTCGCAATATGTGATGTGGCAAATGTCTATTAGGAAATATTCTGTAATGTTCAGACGTAG | SEQ ID NO: 2011 | Homo sapiens CD69 molecule (CD69), mRNA [NM_001781] |
| 431 | A_23_P89145 | ZNF83 | GTATAATGAATGTAGCAGAGACCTTTAGTTTTTGTTCAAGGCTAATAACCGTTAGCTAGA | SEQ ID NO: 2012 | Homo sapiens zinc finger protein 83 (ZNF83), mRNA [NM_018300] |
| 432 | A_23_P9056 | RB1CC1 | TTCATTTTCTCAAAGGGCATACCGTTGTGCATTGTGGCTTATGATGAGCCATATTAATTGC | SEQ ID NO: 2013 | Homo sapiens RB1-inducible coiled-coil 1 (RB1CC1), mRNA [NM_014781] |
| 433 | A_23_P91346 | BC008567 | GGGCTTAGGAGTGAGATTTCTGTCTACAGACAAATGATCATGCTCATGAATTTTGACATTT | SEQ ID NO: 2014 | Homo sapiens cDNA clone MGC:17708 IMAGE:3868595, complete cds. [BC008667] |
| 434 | A_23_P92410 | CASP3 | TGCACCAAGTCTCACTGGCTCTGTCAGTATGACATTTCAGGGAGATTTCTTGTTGCTCAAA | SEQ ID NO: 2015 | Homo sapiens caspase 3, apoptosis-related cysteine peptidase (CASP3), transcript variant alpha, mRNA [NM_004346] |
| 435 | A_23_P92842 | SAR1B | TAATCTGACATCACCCCAGGGCATTTGTAAAGAGCAACTTTCCAGCAGTACATTTGAAG | SEQ ID NO: 2016 | Homo sapiens SAR1 gene homolog B (S. cerevisiae) (SAR1B), transcript variant 2, mRNA [NM_016103] |
| 436 | A_23_P933 | RWDD3 | GGAATCTTTTAGTAAAATAGGACGTGTTTTTGTTGTTTTGCATTGGAATTGGGGAGTGG | SEQ ID NO: 2017 | Homo sapiens RWD domain containing 3 (RWDD3), mRNA [NM_015485] |

Fig. 5-24

| No. | Probe ID No. | Symbols of genes | Sequence | SEQ ID NO: | Descriptions of genes (letters and numbers within [ ] indicates GenBank accession No.) |
|---|---|---|---|---|---|
| 437 | A_23_P94230 | LY96 | TGAAGCTATTTCTGGGAGCCAGAAGAAATGCTGTTTGCTTGGA GTTTGTCATCCTACA | SEQ ID NO: 2018 | Homo sapiens lymphocyte antigen 96 (LY96), mRNA [NM_015364] |
| 438 | A_23_P94501 | ANXA1 | GGCTCTTTGTGGAGGAAACTAAACATTCCCTTGATGGTCTCAAGC TATGATCAGAAGACT | SEQ ID NO: 2019 | Homo sapiens annexin A1 (ANXA1), mRNA [NM_000700] |
| 439 | A_23_P94533 | CTSL1 | AAGACATGGATCATGGTGTCGTCGGTGGTGGGTAGGATTTGAAA GCACAGATCAGATA | SEQ ID NO: 2020 | Homo sapiens cathepsin L1 (CTSL1), transcript variant 1, mRNA [NM_001912] |
| 440 | A_23_P95594 | NAT1 | TCCTTGCAGAGAAAGCTTGTGCCAAACATGGTGATAGATTTTTT ACTATTTAGAATAAG | SEQ ID NO: 2021 | Homo sapiens N-acetyltransferase 1 (arylamine N-acetyltransferase) (NAT1), mRNA [NM_000662] |
| 441 | A_23_P9574 | ECT2 | TAATAGTTAACTGACTACTATAGATTGTTTGTATGCCATGTATGTGC CACTTCTGAGAGTAG | SEQ ID NO: 2022 | Homo sapiens epithelial cell transforming sequence 2 oncogene (ECT2), mRNA [NM_018098] |
| 442 | A_23_P96658 | CYorf15B | ATGCCCTAAAGTAAATACCAGCAGTCATATTTTATCAGATGTAAA TCTGGATGTAAGGTC | SEQ ID NO: 2023 | lipopolysaccharide-specific response 5-like protein [Source:RefSeq_peptide;Acc:NP_115965] [ENST00000392832] |
| 443 | A_23_P98382 | TIMM8B | TTGTTACTAAGCAGATTAAGGGTCAGTGGGGGAAGGCTATCAAC CCATTGTCAGATCAG | SEQ ID NO: 2024 | Homo sapiens translocase of inner mitochondrial membrane 8 homolog B (yeast) (TIMM8B), mRNA [NM_012459] |
| 444 | A_23_P98446 | SC5DL | TGTGAACACCAGGACTTTAATCTTATGCTTAAAATGCCAGAATGTT GTTCGGGGACAACT | SEQ ID NO: 2025 | Homo sapiens sterol-C5-desaturase (ERG3 delta-5-desaturase homolog, S. cerevisiae)-like (SC5DL), transcript variant 2, mRNA [NM_001024956] |
| 445 | A_23_P99980 | HMGB1 | GGATTCTTTCCATTTGGATTTGTTTATGTAATTTCAGGAGGAATA GTGAACATCTGAGTC | SEQ ID NO: 2026 | Homo sapiens high-mobility group box 1 (HMGB1), mRNA [NM_002128] |
| 446 | A_23_P99985 | HMGB1 | TGGGCCAGCTTTTCAAACAAGATGCCACATTCAAAATAAGGGTAT ATTTTGGTATATTAC | SEQ ID NO: 2027 | Homo sapiens high-mobility group box 1 (HMGB1), mRNA [NM_002128] |
| 447 | A_24_P105648 | BX111927 | TTATGAGATGCTTCAGTTCAAATAACAGTGCAGTAATTCACCTAT ATCTAAAAGACTGCC | SEQ ID NO: 2028 | BX111927 Soares multiple sclerosis 2NbHMSP Homo sapiens cDNA clone IMAGp998G05619, mRNA sequence [BX111927] |
| 448 | A_24_P105794 | RPL31 | CAGAGCCGTCTACAAAAGGTTTTACAGTTGAAATATGAAATGTG ATGTGGGTATGGAAA | SEQ ID NO: 2029 | Homo sapiens ribosomal protein L31, mRNA (cDNA clone MGC:88191 IMAGE:4714258), complete cds. [BC070210] |
| 449 | A_24_P105913 | THC2605573 | CTGTGCTCTAGGAAATGCACCAATACCAAAGGTCAATGTGGAAAT ATGGGCATGTTTGCC | SEQ ID NO: 2030 | AY151386 NAP1 [Homo sapiens] {exp=-1; wgp=0; cg=0}, partial (35%) [THC2605573] |
| 450 | A_24_P107257 | LIN7C | TATTAGTGTGGGACTGTGACTGAGGTCTTAAAGACTGAAAGAGTT GGGGTTCATTTTCTG | SEQ ID NO: 2031 | Homo sapiens lin-7 homolog C (C. elegans) (LIN7C), mRNA [NM_018362] |
| 451 | A_24_P11045 | THC2785765 | CCACCAGAAAGCTACAACCTGATTTCATGACAAATACGGTAGCAA GACAAGTCGGAATAG | SEQ ID NO: 2032 | COX7B HUMAN (P24311) Cytochrome c oxidase polypeptide VIIb, mitochondrial precursor, partial (78%) [THC2785765] |
| 452 | A_24_P114249 | GALNT3 | ATTTCAAATGGAGAATACTTGACTCATTTAAAGCTAAATTTTGTT ACTGATTCAATTATA | SEQ ID NO: 2033 | Homo sapiens UDP-N-acetyl-alpha-D-galactosamine:polypeptide N-acetylgalactosaminyltransferase 3 (GalNAc-T3) (GALNT3), mRNA [NM_004482] |
| 453 | A_24_P115774 | BIRC2 | GATACCATTTTGGTTAAAGGAAATGCTGCGGCCAACATCTCAAA AACTGTCTAAAAGAA | SEQ ID NO: 2034 | Homo sapiens baculoviral IAP repeat-containing 2 (BIRC2), mRNA [NM_001166] |

Fig. 5-25

| No. | Probe ID No. | Symbols of genes | Sequence | SEQ ID NO: | Descriptions of genes (letters and numbers within [ ] indicates GenBank accession No.) |
|---|---|---|---|---|---|
| 454 | A_24_P116766 | ZNF207 | TTTCTGAGAGCCAGGTATACGAGTGAAAATTAGCTTCTGAGTAAAT TTCTAATTTATGCCC | SEQ ID NO: 2035 | Homo sapiens mRNA; cDNA DKFZp761N202 (from clone DKFZp761N202), [AL834501] |
| 455 | A_24_P118855 | ENST00000329784 | GCTATGGTGGGCAGAGTAAGCCGATTTTCCAGAAAAAGGCTAAAA CTACAAAGAATACTG | SEQ ID NO: 2036 | PREDICTED: Homo sapiens similar to large subunit ribosomal protein L36a (LOC284230), mRNA [XM_208185] |
| 456 | A_24_P124992 | PSMA4 | AAAGGTCGCTTTGGTGTTGCATTGGTGTACATTGGGTGGATAAG CACTATGGCTTTCAG | SEQ ID NO: 2037 | Homo sapiens proteasome (prosome, macropain) subunit, alpha type, 4 (PSMA4), mRNA [NM_002789] |
| 457 | A_24_P126741 | ENST00000308178 | AGCCTCCAACCACACTAACAAGATTCAAGATTACTTGGAACACGCT CACAGGAGCGAGAAT | SEQ ID NO: 2038 | |
| 458 | A_24_P126890 | RPL9 | GGTGTTGCTTGTCAGTATGTCAAAGCCAGAGAACATGAATTAATC CTTGAAGGAAATGAC | SEQ ID NO: 2039 | Homo sapiens ribosomal protein L9 (RPL9), transcript variant 1, mRNA [NM_000661] |
| 459 | A_24_P127181 | LOC442237 | AACTGAAATCTTTCCAGAAAATCCAAGTCCAGCTAGTAGAATTGG AGAAAAAGTTCAGTG | SEQ ID NO: 2040 | PREDICTED: Homo sapiens similar to 40S ribosomal protein S7 (S8) (LOC442237), mRNA [XR_018963] |
| 460 | A_24_P127621 | A_24_P127621 | TCGAAGCAAGTACCACAAAAGGCATTCAAATGCACTTTCCACAT TCTCAGAAATATTAG | SEQ ID NO: 2041 | |
| 461 | A_24_P132787 | RAB18 | TAAAACGTCACATCTACTTGATTTACACTTCCTAGTGTACATT ACATGTGGTTGAAGG | SEQ ID NO: 2042 | Homo sapiens RAB18, member RAS oncogene family (RAB18), mRNA [NM_021252] |
| 462 | A_24_P133991 | ANKRD12 | TTTGGAATGGAGTATATGCCTGAAAAGGTTTTGGATTCAGAAAGA AAAAGGATGGTTAGT | SEQ ID NO: 2043 | Homo sapiens ankyrin repeat domain 12 (ANKRD12), mRNA [NM_015208] |
| 463 | A_24_P134392 | STCH | TGAGTAACTTATTTTGTATCAGGAATGTGTTTTCGGTACTGTGTTTTC AGTCAAACGACTGAC | SEQ ID NO: 2044 | Homo sapiens stress 70 protein chaperone, microsome-associated, 60kDa (STCH), mRNA [NM_006948] |
| 464 | A_24_P135242 | A_24_P135242 | GATGGCAAGACAAAAGGCTGGGAACTAGTTTGTACCTGCAGAACCGAA ACTGGGCATTGTCAT | SEQ ID NO: 2045 | |
| 465 | A_24_P135551 | LOC130866 | TAACAGCATAGCTGTCGCTGTGGGCATTCACGCAAAGGTGGTTAT CACTGAGACTAAAAGT | SEQ ID NO: 2046 | PREDICTED: Homo sapiens similar to gene 20 protein (SIG-20) (LOC130866), mRNA [XR_019454] |
| 466 | A_24_P139208 | USP25 | GAATATAGACAAGGTGATTATTTCGGTCTTGAGACTCCAAAGTACTT GAATAAGGGCTATTG | SEQ ID NO: 2047 | Homo sapiens ubiquitin specific peptidase 25 (USP25), mRNA [NM_013396] |
| 467 | A_24_P141214 | STOM | GGGTGACATTTGTAACATTTCGTCTTTGAGACTCGTGAGTTCAACGT AGAGAAGTCTAAGCA | SEQ ID NO: 2048 | Homo sapiens stomatin (STOM), transcript variant 2, mRNA [NM_198194] |
| 468 | A_24_P144383 | A_24_P144383 | GTGGCGTTGAGCCCAAAAGATCTAAGAGAATGGTGGCCTAAAAGATG CAAGCATTTGAACT | SEQ ID NO: 2049 | |
| 469 | A_24_P144688 | LOC401975 | TGTTCGATGTCAAGACTAATGATGGGCTAGTTCTTCTTTAATCTGTCTG TGTTGGTTTTACTGA | SEQ ID NO: 2050 | PREDICTED: Homo sapiens similar to ribosomal protein S3a (LOC401975), mRNA [XR_017247] |
| 470 | A_24_P148151 | TSNAX | AAAGTTGAGTTATATAGTTGTACATAGCAATGGAAATGCTTTTAGT AGTGATTATTTAGCA | SEQ ID NO: 2051 | Homo sapiens translin-associated factor X (TSNAX), mRNA [NM_005999] |
| 471 | A_24_P152753 | LOC285260 | TGTCTGATACCGGAATCGGTGCGATTATCCAGAGAAGGATGAAGA TTCACCGAAAATAAGCT | SEQ ID NO: 2052 | PREDICTED: Homo sapiens similar to ribosomal protein L31 (LOC285260), mRNA [XR_019376] |
| 472 | A_24_P152775 | LOC442195 | ACACAAACAAGGTGTGAGGAGATCCCGATTATCCTCAGCAAGA AGCTCCACAACAGGA | SEQ ID NO: 2053 | PREDICTED: Homo sapiens hypothetical LOC442195 (LOC442195), mRNA [XR_019264] |
| 473 | A_24_P153324 | LOC390413 | GAAGCTTAAGCAAGGTTTCAATTAACACTGCTGGGGATTGTAGAACC ATATATTGCAGGGTA | SEQ ID NO: 2054 | PREDICTED: Homo sapiens similar to 60S ribosomal protein L7 (LOC390413), mRNA [XR_018341] |

Fig. 5-26

| No. | Probe ID No. | Symbols of genes | Sequence | SEQ ID NO: | Descriptions of genes (letters and numbers within [ ] indicate GenBank accession No.) |
|---|---|---|---|---|---|
| 474 | A_24_P153511 | OSBPL8 | CCTTGTGCCATATACACAGAAAATTTGTGGAAGGGAGTTTTAACTTTCTGAAGAATATC | SEQ ID NO: 2055 | Homo sapiens oxysterol binding protein-like 8 (OSBPL8), transcript variant 1, mRNA [NM_020841] |
| 475 | A_24_P15755 | AK098635 | TCCAAGTCTGGCTAGTACGTGAATTGGAGAAAAAGTTTGGGAAGCATGTGTCTTATTG | SEQ ID NO: 2056 | Homo sapiens cDNA FLJ25739 fis, clone TST05834. [AK098605] |
| 476 | A_24_P161914 | LOC130728 | CTATACTGTTGGAAACACTTCAAAGAGAAATAACTTCCTGCGGCCATTCAAATTATCTC | SEQ ID NO: 2057 | PREDICTED: Homo sapiens similar to 60S ribosomal protein L7 (LOC130728), mRNA [XR_019248] |
| 477 | A_24_P165595 | ARL5A | GAAGTAACTTGACCCAGAAACACCTTTATGTTTGCTTAGGGTATATTTTTTTCAGTGTCTG | SEQ ID NO: 2058 | Homo sapiens ADP-ribosylation factor-like 5A (ARL5A), transcript variant 1, mRNA [NM_012097] |
| 478 | A_24_P165864 | P2RY14 | TTTTTCTGGAAAACAGACGGATTTTACTTCTTCTGGAGAATGGCATACGGTTACTGACTTAT | SEQ ID NO: 2059 | Homo sapiens purinergic receptor P2Y, G-protein coupled, 14 (P2RY14), transcript variant 2, mRNA [NM_014879] |
| 479 | A_24_P167063 | ZNF518 | AAAGAAAGCGATACATAGAATGCTTCAAGCTATCTTGCTATGCACATTATACTTGTTACTG | SEQ ID NO: 2060 | Homo sapiens zinc finger protein 518 (ZNF518), mRNA [NM_014803] |
| 480 | A_24_P169378 | RPS7 | AACTGAAATCTTCCAGAATTCCAAATCCGGCTAGTAAGTGAATTGGAGAAAAAGTTCA | SEQ ID NO: 2061 | Homo sapiens ribosomal protein S7 (RPS7), mRNA [NM_001011] |
| 481 | A_24_P171873 | FBXO4 | GATTCCACAGATTCAAAAAGTGTGTCAGAATGGTGTAGATGGGTTCATCTATGTTGCAAATGC | SEQ ID NO: 2062 | Homo sapiens F-box protein 4 (FBXO4), transcript variant 1, mRNA [NM_012176] |
| 482 | A_24_P172481 | TRIM22 | TGGCCCTTTAAAAGATTGAAAGAAAGAAACTTGTCAACTCATATCCACGTTATCTAGCAA | SEQ ID NO: 2063 | Homo sapiens tripartite motif-containing 22 (TRIM22), mRNA [NM_006074] |
| 483 | A_24_P175059 | ATG5 | TTGCACAAGAGGCTGGTCTGAATATGATGTTCACATTAAGAGTGTTATTCGTCGGTTC | SEQ ID NO: 2064 | Homo sapiens ATG5 autophagy related 5 homolog (S. cerevisiae) (ATG5), mRNA [NM_004849] |
| 484 | A_24_P175176 | PHTF2 | AGATTGAAGTTAACTTAAGTAGTTGGGAGTTGATTTATTAAGTACAGTATACCTCTCACAG | SEQ ID NO: 2065 | Homo sapiens putative homeodomain transcription factor 2 (PHTF2), mRNA [NM_020432] |
| 485 | A_24_P175187 | SAMD9 | GAACGAGGGATACGTAATGAAAATGTAATTTTGCCCTAATAAAATTATGGATAATGGGCAG | SEQ ID NO: 2066 | Homo sapiens sterile alpha motif domain containing 9 (SAMD9), mRNA [NM_017654] |
| 486 | A_24_P175188 | SAMD9 | TGCCAAGTGTACTGGCAGATTAACATACAACCTATGTTTCTTGAACAAAAAGCAGCGATA | SEQ ID NO: 2067 | Homo sapiens sterile alpha motif domain containing 9 (SAMD9), mRNA [NM_017654] |
| 487 | A_24_P175519 | TXN | AAGTAGAATGTGGATGAGTGTCAGGATGTGTTCTTCAAGAGTGTGAAGTCAAATGCAGGCAA | SEQ ID NO: 2068 | Homo sapiens thioredoxin (TXN), mRNA [NM_003329] |
| 488 | A_24_P175989 | VPS29 | GAGAGGAGACTTGGATGAGAATCTGAATTGATTATCCAGAACAGAGAAAGTTGTGACTGTTGGACA | SEQ ID NO: 2069 | Homo sapiens vacuolar protein sorting 29 homolog (S. cerevisiae) (VPS29), transcript variant 2, mRNA [NM_057180] |
| 489 | A_24_P178802 | ZNF600 | ATAAGATAATTCACACGGAGCAGGAGAAGCATACAAATGTAAGGTTTGTGACGAAGGCTTTTG | SEQ ID NO: 2070 | Homo sapiens zinc finger protein 600 (ZNF600), mRNA [NM_198457] |
| 490 | A_24_P179351 | TPT1 | GAACAGAGACCAGAGAAAGAGTAAAACCTTTATGACAGGGGCTGCAGAACAAATCAAGCAC | SEQ ID NO: 2071 | Homo sapiens tumor protein, translationally-controlled 1 (TPT1), mRNA [NM_003295] |
| 491 | A_24_P183424 | TMEM30A | CAATGTGTATGCACATTCTCTTAGTTAAGGACACCAATTGTTTGGTTGTTTCCTAAG | SEQ ID NO: 2072 | Homo sapiens transmembrane protein 30A (TMEM30A), mRNA [NM_018847] |
| 492 | A_24_P181120 | PFDN5 | CACGGCATGAAACAGGGCGGTCATGGAAATGATGAGTCAGAAGATTCAGCAGCTCACAGCC | SEQ ID NO: 2073 | Homo sapiens prefoldin subunit 5 (PFDN5), transcript variant 1, mRNA [NM_002624] |
| 493 | A_24_P183864 | IMPA1 | TCAGCCTTATCCCTTGGCACGTAAACAGAGTACTAGACTATTGTAGGTTCGTTTGAGCT | SEQ ID NO: 2074 | Homo sapiens inositol(myo)-1(or 4)-monophosphatase 1 (IMPA1), mRNA [NM_005536] |

Fig. 5-27

| No. | Probe ID No. | Symbols of genes | Sequence | SEQ ID NO: | Descriptions of genes (letters and numbers within [ ] indicates GenBank accession No.) |
|---|---|---|---|---|---|
| 494 | A_24_P186944 | LOC389404 | AGGAACCCTGCGGAGGGACTTCAATGACATCGTAGAACTCAGTCTTCTTGGAAAAGAAAAA | SEQ ID NO: 2075 | PREDICTED: Homo sapiens similar to 60S ribosomal protein L9 (LOC389404), mRNA [XR_018133] |
| 495 | A_24_P188800 | MARCH1 | GTCACGGCAAAAGATTTTCAGAAAATGTTCGGATATAATTAGCTCTGTTAAATACCCACAG | SEQ ID NO: 2076 | Homo sapiens membrane-associated ring finger (C3HC4) 1 (MARCH1), mRNA [NM_017923] |
| 496 | A_24_P188878 | RPL34 | TGTTTACGTTTATACGAAGAAGGTTGGGAAGCACGAAAATCGCATGTGGTGTGTGCCC | SEQ ID NO: 2077 | Homo sapiens ribosomal protein L34 (RPL34), transcript variant 2, mRNA [NM_033625] |
| 497 | A_24_P190804 | AP1S2 | GGTGGAAGATCTAAGGAGTCTTCATGTACTTCATTAAAAATAACATGGATTCCATACTG | SEQ ID NO: 2078 | Homo sapiens adaptor-related protein complex 1, sigma 2 subunit (AP1S2), mRNA [NM_003916] |
| 498 | A_24_P191417 | NAB1 | AAGTTCGTTAAGTACTCTTATGTTTCTAGTGTTTCAAGCTTAGTGATAAGGTGGAAGCAC | SEQ ID NO: 2079 | Homo sapiens NGFI-A binding protein 1 (EGR1 binding protein 1) (NAB1), mRNA [NM_005966] |
| 499 | A_24_P191833 | SFRS12 | AAGGACTTAGGAGTATATGGGAGGTTATTGGTTTTTATGTTTTAAGGATACGTTACTTGAG | SEQ ID NO: 2080 | Homo sapiens splicing factor, arginine/serine-rich 12 (SFRS12), transcript variant 2, mRNA [NM_139168] |
| 500 | A_24_P194313 | C21orf66 | ATTTAAATTAACCCTCTCAGTTAATGTGTCCCTGTAAACGATGTGTGCAGTGTAAATTGT | SEQ ID NO: 2081 | Homo sapiens chromosome 21 open reading frame 66 (C21orf66), transcript variant 1, mRNA [NM_016631] |
| 501 | A_24_P199600 | RNF2 | AAACTGCTTAGATTTTGTTGATGAGATTAGATTAGTAGTTGCATTAAATAACTAAATTCC | SEQ ID NO: 2082 | Homo sapiens ring finger protein 2 (RNF2), mRNA [NM_007212] |
| 502 | A_24_P20120 | KIAA1212 | TTGGACAATGAAAATGCCTTAAAAGGAATGCATATGGATAAAGTTGCACTTATAACACCC | SEQ ID NO: 2083 | Homo sapiens KIAA1212 (KIAA1212), mRNA [NM_018084] |
| 503 | A_24_P201353 | C10orf32 | TCCATCTTTTTAAATGACATTACGATGAGTGTTGTCAAACGTAAATATCTTTGTTTGA | SEQ ID NO: 2084 | Homo sapiens chromosome 10 open reading frame 32 (C10orf32), mRNA [NM_144591] |
| 504 | A_24_P201702 | CLEC2B | ATTGGAATTCAGTAAATAGTAAATACGAACTGTCCACTCAACATGCCGACCTAACTAAATTGACA | SEQ ID NO: 2085 | Homo sapiens C-type lectin domain family 2, member B (CLEC2B), mRNA [NM_005127] |
| 505 | A_24_P203103 | SH2D1A | AAGGCTAAGCTTCACTGTAAATAACTGGGAATTCTGGATTGTGTATGGGTGTTGGT | SEQ ID NO: 2086 | Homo sapiens SH2 domain protein 1A, Duncan's disease (lymphoproliferative syndrome) (SH2D1A), mRNA [NM_002351] |
| 506 | A_24_P203827 | LOC730647 | CTTGCTTTCGATGACACTTCCCCTCAAGACCAACACGTTTCTGTTGATATCGAAAAAA | SEQ ID NO: 2087 | PREDICTED: Homo sapiens similar to Histidine triad nucleotide-binding protein 1 (Adenosine 5-monophosphoramidase) (Protein Kinase C inhibitor 1) (Protein kinase C-interacting protein 1) (PKCI-1) (LOC730647), mRNA [XM_001126674] |
| 507 | A_24_P203909 | RPL34 | GAGGGGTTCATGGTGTAAGACTTAAAGTTCTTATGAAATTGTCCAAAACAAAGAAACATG | SEQ ID NO: 2088 | Homo sapiens ribosomal protein L34 (RPL34), transcript variant 2, mRNA [NM_033625] |
| 508 | A_24_P208045 | EDEM3 | TTTAGAGGGGGGTAGAATTAGTAGATATTCCAGCGGTCGTTTTATGCAGAAGGTTCA | SEQ ID NO: 2089 | Homo sapiens ER degradation enhancer, mannosidase alpha-like 3 (EDEM3), mRNA [NM_025191] |
| 509 | A_24_P20996 | BC043173 | CTGGAAAATGTTGATATATGTATATGAATGTGTCTTTATGCTGAAGGGCTCGTGATTGG | SEQ ID NO: 2090 | Homo sapiens cDNA clone IMAGE:5287121. [BC043173] |
| 510 | A_24_P212864 | LOC646161 | ACAGAAGTACAACGTGCGAATCCATGATCCGAAAGAATGATGAAGTTAGGCTTGTACCAGG | SEQ ID NO: 2091 | PREDICTED: Homo sapiens similar to 60S ribosomal protein L26 (LOC646161), mRNA [XR_018048] |
| 511 | A_24_P213354 | LOC731048 | CACGTGCTTAAAAACAGAGAGTAATGCTGAACTTAAGGGTGATTCTCTGGTCATTGAG | SEQ ID NO: 2092 | PREDICTED: Homo sapiens similar to 60S ribosomal protein L17 (L23) (LOC731048), mRNA [XR_015710] |
| 512 | A_24_P213375 | A_24_P213375 | AAATGTGTTCCATGATGAAAATGGACAACAATGATTGTTCATCTGTTCTGTGTGGTT | SEQ ID NO: 2093 | |

Fig. 5-28

| No. | Probe ID No. | Symbols of genes | Sequence | SEQ ID NO: | Descriptions of genes (letters and numbers within [ ] indicates GenBank accession No.) |
|---|---|---|---|---|---|
| 513 | A_24_P213783 | RPL31 | CTTTGGTTACCTATGTACCTGTTACCACTTTCAAAAATCTACAGACAGTCAATGTGGATG | SEQ ID NO: 2094 | Homo sapiens ribosomal protein L31 (RPL31), mRNA [NM_000993] |
| 514 | A_24_P221375 | A_24_P221375 | TACTTTGGTTACCCATGTACCTACCCACTTTCAAAAATCTACAGAGAGTGAATGTGGAGCA | SEQ ID NO: 2095 | |
| 515 | A_24_P222655 | C1QA | GGGTGACCAGGTCTGGGTTGAAAAGACCCCAAAAAGGGTGCATTTACCAGGGCTGA | SEQ ID NO: 2096 | Homo sapiens complement component 1, q subcomponent, A chain (C1QA), mRNA [NM_015991] |
| 516 | A_24_P222911 | SFRS7 | CAGAAATGTCAATGAGAGTAAGTGGTTTGTAAATCTCAGGTATATTAGGAACACTCC | SEQ ID NO: 2097 | Homo sapiens splicing factor, arginine/serine-rich 7, 35kDa (SFRS7), mRNA [NM_001031684] |
| 517 | A_24_P225308 | ARID4B | GTTGAAAATGGTTTCAAGTTATCAAATTTGTACAAGGACTGTAAAGATTTGTTGACAGCA | SEQ ID NO: 2098 | Homo sapiens AT rich interactive domain 4B (RBP1-like) (ARID4B), transcript variant 1, mRNA [NM_016374] |
| 518 | A_24_P225468 | ANP32E | TCATCTTACTGTGCAATCAAAATTAGAGTACTTTGGTTTGAAAAGAACACTTAGAGCGTC | SEQ ID NO: 2099 | Homo sapiens acidic (leucine-rich) nuclear phosphoprotein 32 family, member E (ANP32E), mRNA [NM_030920] |
| 519 | A_24_P225719 | PREI3 | GACTATTTCTTAGTGAATATTTATACTAAGGTAGTGACTGAGATTTGGTGATCTGGCTG | SEQ ID NO: 2100 | Homo sapiens preimplantation protein 3 (PREI3), transcript variant 1, mRNA [NM_015387] |
| 520 | A_24_P229066 | ENST00000078131 | AAGAAGGTCCACAACAAGACAGCAGGTTATGTCACCCATCTGATGAAGCAGAGTTCAGAGA | SEQ ID NO: 2101 | OTTHUMP00000016594. [Source:Uniprot/SPTREMBL:Acc:Q9NU98] [ENST00000078131] |
| 521 | A_24_P232856 | RPL9 | GAACCGTCCGGAGGGACTTCAATCACGATGCAATGTAGAACTCAGCCTTCTTGAAAGAAA | SEQ ID NO: 2102 | Homo sapiens ribosomal protein L9 (RPL9), transcript variant 1, mRNA [NM_000661] |
| 522 | A_24_P235429 | ABCA1 | CCAAAGAGGCATGTGTCATGTAATACTGAACCACTTTGATATTGAGACATTAATTTGTAC | SEQ ID NO: 2103 | Homo sapiens ATP-binding cassette, sub-family A (ABC1), member 1 (ABCA1), mRNA [NM_005502] |
| 523 | A_24_P236008 | SCYL2 | ATAGACTATGTACTTGTCTGTCGTTTTTGTTTTATTTTGGAATGCTTATAAGCTCG | SEQ ID NO: 2104 | Homo sapiens mRNA for KIAA1360 protein, partial cds. [AB037781] |
| 524 | A_24_P237511 | EIF1AY | GTTTCAGTTACTTAGATGTGTCTCATAAGGTTCTGATACAATTTAAGACAGAAATCTGC | SEQ ID NO: 2105 | Homo sapiens eukaryotic translation initiation factor 1A, Y-linked (EIF1AY), mRNA [NM_004681] |
| 525 | A_24_P242299 | ZRANB2 | GACTTTTGAAAGTCTACCTTCTAAATTGCCCGACGATCTAGATTCTACATGTTACGAT | SEQ ID NO: 2106 | Homo sapiens zinc finger, RAN-binding domain containing 2 (ZRANB2), transcript variant 2, mRNA [NM_005455] |
| 526 | A_24_P25326 | ZMYM6 | AGGACTATTTAAATCAGTGTGTCGTGTAACTCAGTGTTTGGATAAATGCAAAGCAAGTTACCC | SEQ ID NO: 2107 | Homo sapiens zinc finger, MYM-type 6 (ZMYM6), mRNA [NM_007167] |
| 527 | A_24_P255252 | A_24_P255252 | TGGACTACTGGAAGGATGGTGTGTGACTGCATATGTGTATTTCTTTGAGATGATTTAGAAA | SEQ ID NO: 2108 | |
| 528 | A_24_P263524 | TXNDC9 | TGACTTCACCACAGAAACTTAGAATGGGGCTCAGTTGTTCTGACATTGTTAATTACAG | SEQ ID NO: 2109 | Homo sapiens thioredoxin domain containing 9 (TXNDC9), mRNA [NM_005783] |
| 529 | A_24_P264549 | A_24_P264549 | ATTCATAGTACATAGCACATACAGAACATGATCAAAGGTGTTACACTGGACTTGCATTAGAATATG | SEQ ID NO: 2110 | |
| 530 | A_24_P265856 | SENP7 | TTGTGTGTTGGGGGGTACTTTTAAAGGTGACTATTGTTTTGTACATCTAATTTTGGGA | SEQ ID NO: 2111 | Homo sapiens SUMO1/sentrin specific peptidase 7 (SENP7), transcript variant 1, mRNA [NM_020654] |
| 531 | A_24_P268786 | MYNN | TGCAGGAGGATCATACTTTGAGTGAACAGGATTCCATAGAAAAAAGTCCTTTATCAGAAAC | SEQ ID NO: 2112 | Homo sapiens myoneurin (MYNN), mRNA [NM_018657] |

Fig. 5-29

| No. | Probe ID No. | Symbols of genes | Sequence | SEQ ID NO: | Descriptions of genes (letters and numbers within [ ] indicates GenBank accession No.) |
|---|---|---|---|---|---|
| 532 | A_24_P268917 | RAB33B | CCCAGAATCTAATGTAGTTCGTATTAATAACAATGCATTATTGAAAGTATATTGCAAAT | SEQ ID NO: 2113 | Homo sapiens RAB33B, member RAS oncogene family (RAB33B), mRNA [NM_031296] |
| 533 | A_24_P276583 | TMCO1 | CCTTCATTTTCCTGTATATTCTCTGTACTATGTCCATTCGACAGAACATTCAGAAGATTC | SEQ ID NO: 2114 | Homo sapiens transmembrane and coiled-coil domains 1 (TMCO1), mRNA [NM_019026] |
| 534 | A_24_P278008 | DCTN6 | CTATGAAAGGAAGCTCAACTCGAGTAAAGAACTAAGAACAGTGTATAACGTGAAGATAAC | SEQ ID NO: 2115 | Homo sapiens dynactin 6 (DCTN6), mRNA [NM_006571] |
| 535 | A_24_P278460 | MLSTD2 | ACCCATGGAAGAATATAGCTTAGGATTACAAGGAAGCAAGTCCTTACTTACACTGTCTGTCTG | SEQ ID NO: 2116 | Homo sapiens male sterility domain containing 2 (MLSTD2), mRNA [NM_032228] |
| 536 | A_24_P280897 | LOC388532 | AGCACTCTGAGAGCTGGGATAGCTTCCTGAAATACATGAAGGAAAATGACAGAAAAAGA | SEQ ID NO: 2117 | PREDICTED: Homo sapiens similar to ribosomal protein L21 (LOC388532), mRNA [XM_001127035] |
| 537 | A_24_P281304 | A_24_P281304 | GAGGAGAAGGCACCGGATATATGGTGTCTAAGCGTTTTAGAAAACAAGTTTTTCCTTTGGC | SEQ ID NO: 2118 | |
| 538 | A_24_P285179 | THC2649313 | AGTGGGAATTTTGAAATGCCATGTCCTATATATTCTGGCATATTGTTGGCACATTTGCA | SEQ ID NO: 2119 | |
| 539 | A_24_P286054 | ZFYVE16 | GTGTATGTATTCTGCCATGTAAGTAATTGAACAGAGTCTTAAAATAACCAAATGGTAGAGGG | SEQ ID NO: 2120 | Zinc finger FYVE domain-containing protein 16 (Endofin) (Endosome-associated FYVE domain protein). [Source:Uniprot/SWISSPROT:Acc:Q7Z3T8] [ENST00000380248] |
| 540 | A_24_P287756 | NUDT21 | CCCGATACTTACTTCACTTGTTATACATGACTGATTATTTGGGTTAAACTGCAGTCATTTC | SEQ ID NO: 2121 | Homo sapiens nudix (nucleoside diphosphate linked moiety X)-type motif 21 (NUDT21), mRNA [NM_007006] |
| 541 | A_24_P29001 | LSM3 | CCGTCCACTGAGAGTTGGCTGAAGAGTGTTGTCCTGTATGGAAAACGGGAGAGCTTT | SEQ ID NO: 2122 | Homo sapiens LSM3 homolog, U6 small nuclear RNA associated (S. cerevisiae) (LSM3), mRNA [NM_014463] |
| 542 | A_24_P290257 | A_24_P290257 | CCAATTCATTCAACATAGAACAAGGCAATTATACCATCCAGTCATTGAAGCACACGAAGA | SEQ ID NO: 2123 | |
| 543 | A_24_P295543 | BLOC1S2 | GTTTATTTCTATGTGAGTCACATTGACATCGGATCAGTTTGGGAAATGTGAAAACA | SEQ ID NO: 2124 | Homo sapiens biogenesis of lysosome-related organelles complex-1, subunit 2 (BLOC1S2), transcript variant 2, mRNA [NM_001013421] |
| 544 | A_24_P298238 | A_24_P298238 | ATCGTTGAAGGAAATGACATTGAGCGTTGTTCAATTCAGCAAGCCGATAACAGTTAAAAAC | SEQ ID NO: 2125 | |
| 545 | A_24_P298604 | LOC731599 | GATGGAAATCATGACCAGAGGTGCGGCAAATGACTTGAAAGAATTGGTCAATAAAATGAT | SEQ ID NO: 2126 | PREDICTED: Homo sapiens hypothetical protein LOC731599 (LOC731599), mRNA [XR_015536] |
| 546 | A_24_P30194 | IFIT5 | AATGTGGCTTCTCTAATGTAGTTTCTTTGATTACCGACTACAAGATTATGTACCATCACA | SEQ ID NO: 2127 | Homo sapiens interferon-induced protein with tetratricopeptide repeats 5 (IFIT5), mRNA [NM_012420] |
| 547 | A_24_P303118 | RPL34 | CGAGGAGGAGAAAATCGTTGTGAAAGTGTTGAAGGCACAAAGGACACAGAGTCAGAAAGCTAA | SEQ ID NO: 2128 | Homo sapiens ribosomal protein L34 (RPL34), transcript variant 2, mRNA [NM_033625] |
| 548 | A_24_P303127 | C5orf29 | CCCAAATGCCTAGAACATCACATAAGGCACTAAATGCCTCATGTTTACTGACGGGAATT | SEQ ID NO: 2129 | Homo sapiens chromosome 5 open reading frame 29 (C5orf29), mRNA [NM_152687] |
| 549 | A_24_P305570 | RIN2 | TATGCAGTGAGTTTGGCAAAATCTATTCATTCGTGTGATTTGCTTGTAGAAACAATTTTG | SEQ ID NO: 2130 | Homo sapiens Ras and Rab interactor 2 (RIN2), mRNA [NM_018993] |
| 550 | A_24_P306469 | LOC257039 | AGAGAAACAGAGAACAATTATGTTCCGGAGATCTCAGTCCTCGGATCAGGAGAACCGTTGAA | SEQ ID NO: 2131 | PREDICTED: Homo sapiens similar to 40S ribosomal protein S17 (LOC257039), mRNA [XM_172230] |

Fig. 5-30

| No. | Probe ID No. | Symbols of genes | Sequence | SEQ ID NO: | Descriptions of genes (letters and numbers within [ ] indicates GenBank accession No.) |
|---|---|---|---|---|---|
| 551 | A_24_P306527 | ENST00000308869 | ACCGGATCCGTGCGTGGTTGGTTATCCAGAAAATGTAATGAGGATGAAGATTCACGAAATAAGT | SEQ ID NO: 2132 | PREDICTED: Homo sapiens similar to ribosomal protein L3l (LOC729005), mRNA [XM_001133428] |
| 552 | A_24_P306726 | TPT1 | GACCAGAAACAGTAAAACCTTTTATGACAGGGCTGCAAAACAAATCAAGGACATGCTTG | SEQ ID NO: 2133 | Homo sapiens tumor protein, translationally-controlled 1 (TPT1), mRNA [NM_003295] |
| 553 | A_24_P310894 | CAPZA1 | TGTATTATTTGTCCTTCATACTATCCATCCATACCACACTATCTTCTGTATCAAGGTAGTC | SEQ ID NO: 2134 | Homo sapiens capping protein (actin filament) muscle Z-line, alpha 1 (CAPZA1), mRNA [NM_006135] |
| 554 | A_24_P312417 | ZBTB26 | AGAGGAGGAAGATTTTTAAAACCTTTATCATTCAGGCATTTGTATTTTATGGATCCCAGAGG | SEQ ID NO: 2135 | Zinc finger and BTB domain-containing protein 26 (Zinc finger protein 481) (Zinc finger protein Bioref). [Source:Uniprot/SWISSPROT:Acc:Q9HCK0] [ENST00000373656] |
| 555 | A_24_P315326 | LOC341412 | AAGCTCTATACTTTGGTTACCAATGTACCCGTTACCGCTTTCAAAAATCTACAAGGGCAATG | SEQ ID NO: 2136 | AGENCOURT_10640955 NIH_MGC_126 Homo sapiens cDNA clone IMAGE:6723668 5', mRNA sequence [CA455253] |
| 556 | A_24_P316074 | LOC730902 | TATCAATGGTCGTGAGCCCAAAGGTCAAAGGTCAGCGTTGCAGCTTCCTCCCTTGGTCAAATCTT | SEQ ID NO: 2137 | PREDICTED: Homo sapiens similar to 60S ribosomal protein L7 (LOC730902), mRNA [XR_015600] |
| 557 | A_24_P320328 | SUB1 | CAGAAAAACCTGTAAAGAAAACAGAGGTGAGACTTGAGAGAGCCCTGTCATCCTCTA | SEQ ID NO: 2138 | Homo sapiens SUB1 homolog (S. cerevisiae) (SUB1), mRNA [NM_006713] |
| 558 | A_24_P321511 | GOLT1B | TTAGAGCAAGAATAGTATCTGCTAATGTGTAAGGGACATCGTATTAAGTCCTTGTAGAC | SEQ ID NO: 2139 | Homo sapiens golgi transport 1 homolog B (S. cerevisiae) (GOLT1B), mRNA [NM_016072] |
| 559 | A_24_P324224 | A_24_P324224 | AAAGCTGTCTGGGCGCAAAGGAATAATTGCAAATACAAGTAATGGCTATTTCGTCGGTTGTCCAGAAAA | SEQ ID NO: 2140 | |
| 560 | A_24_P324506 | A_24_P324506 | GGAATATAAGGCAGGTAATTGCAAATACAAGTAATGGCTATTTCGTGTGGACATGCTGTGT | SEQ ID NO: 2141 | |
| 561 | A_24_P32790 | YOD1 | CTAGGGATCTAATTAAGGACATTAAAGTACCAATTCGTGAGCTACTAACCATCAGCTCTTC | SEQ ID NO: 2142 | Homo sapiens YOD1 OTU deubiquinating enzyme 1 homolog (S. cerevisiae) (YOD1), mRNA [NM_018566] |
| 562 | A_24_P33213 | A_24_P33213 | GACCATATATTACATGGGGGTACCCAAATCTGAAGTCAGTAAATGAACTTACTACAAGG | SEQ ID NO: 2143 | |
| 563 | A_24_P333112 | A_24_P333112 | GGTCATCAGAATCAGAAGTCAATGTGTGAGCCCACAGCCAAAAGTATTGCAACTT | SEQ ID NO: 2144 | |
| 564 | A_24_P33607 | LOC652558 | TAAGAAAATAATTGCTTGCTTGAGACGACAACGCTTTGATTGCTCGATCTCTTGGTAATATGG | SEQ ID NO: 2145 | PREDICTED: Homo sapiens similar to 60S ribosomal protein L7 (LOC652558), mRNA [XR_019386] |
| 565 | A_24_P339869 | ZNF295 | TCATATGCCTTAGCAGTAAGTCATTTTTCCATTTTACTTACTTAGGAATAAGGCTTTTTCGAA | SEQ ID NO: 2146 | Homo sapiens zinc finger protein 295 (ZNF295), mRNA [NM_020727] |
| 566 | A_24_P349636 | LOC388401 | AGTTGCTTGCACAGATAACACTTTGATTGCTCGATCTCTTGGTAATATAGCATCAACTG | SEQ ID NO: 2147 | PREDICTED: Homo sapiens similar to 60S ribosomal protein L7 (LOC388401), mRNA [XR_018879] |
| 567 | A_24_P351435 | CRBN | GAAAGTGAAAGCAATTGGAAGACAAAAGGTCAAAGTCGTTGAGCTAAGAGACAGTCAGA | SEQ ID NO: 2148 | Homo sapiens cereblon (CRBN), mRNA [NM_016302] |
| 568 | A_24_P352445 | MRPL42 | TTTTTAGTCATCACAATGACAAAAGGGGTGGTTTTCTTTCACCCAAGAAATGTGGTTTCC | SEQ ID NO: 2149 | Homo sapiens mitochondrial ribosomal protein L42 (MRPL42), nuclear gene encoding mitochondrial protein, transcript variant 3, mRNA [NM_172178] |
| 569 | A_24_P354412 | AK091335 | TGTAGACTGAAGGAGTCTTTGAAAAACACCCAGCATTAAATCTCACTCTGCCGCTGTCT | SEQ ID NO: 2150 | Homo sapiens cDNA FLJ34016 fis, clone FCBBF2002541. [AK091335] |
| 570 | A_24_P354954 | CCDC126 | AATGGAACTGTTGAGGACTTTAGCCAGGTCTATATAATAAAGGTACTTTGTGTCTGCATT | SEQ ID NO: 2151 | Homo sapiens coiled-coil domain containing 126 (CCDC126), mRNA [NM_138771] |

Fig. 5-31

| No. | Probe ID No. | Symbols of genes | Sequence | SEQ ID NO: | Descriptions of genes (letters and numbers within [ ] indicate GenBank accession No.) |
|---|---|---|---|---|---|
| 571 | A_24_P357518 | RPL21 | GGGCACATATATGCTAATCTATAAGAAGGTGATATTGCAGACATCAAGGGAAGGGGTAC | SEQ ID NO: 2152 | Homo sapiens ribosomal protein L21 (RPL21), mRNA [NM_000982] |
| 572 | A_24_P358205 | A_24_P358205 | TGTTCAAAAAGAATGCCCAAGTGTTACCATGGCTAAATGAAAGAGTCTGCAGTGTTC | SEQ ID NO: 2153 | |
| 573 | A_24_P362646 | TXNDC9 | CTCCACATCAGGTGTAAAATACTAGAACAGACATCTGGCAATATTGTCCAAGAAACACCT | SEQ ID NO: 2154 | Homo sapiens thioredoxin domain containing 9 (TXNDC9), mRNA [NM_005783] |
| 574 | A_24_P364025 | UBE2D1 | ATGTGATGGGTGTAGTCATTAGGAAAAGGATTTAAATCACTTGAGTATTTTGTCATGGTTC | SEQ ID NO: 2155 | Homo sapiens ubiquitin-conjugating enzyme E2D 1 (UBC4/5 homolog, yeast) (UBE2D1), mRNA [NM_003338] |
| 575 | A_24_P364807 | AYTL1 | TGTAAGTCTTGTTTCTAGGTAATGCTTCTCTCTGAACAAACTGCTCAAGGGTCTGTGTAA | SEQ ID NO: 2156 | Homo sapiens mRNA; cDNA DKFZp686H22112 (from clone DKFZp686H22112). [BX641069] |
| 576 | A_24_P366165 | LOC391126 | ACTTCCAACCAAATCAAAAATAGCAAAAATAGGCATTTGAATGCACGTTCCCACATTCAGAGG | SEQ ID NO: 2157 | PREDICTED: Homo sapiens similar to 60S ribosomal protein L26 (Silica-induced gene 20 protein) (SIG-20) (LOC391126), mRNA [XR_019504] |
| 577 | A_24_P366546 | RPL31P10 | CGGCTGTGTCAGAAAACGTAATGAGGATGAAGATTCAAATAAGCTCTATACTTTGGTTACC | SEQ ID NO: 2158 | PREDICTED: Homo sapiens similar to ribosomal protein L31 (LOC390283), mRNA [XR_018695] |
| 578 | A_24_P367139 | A_24_P367139 | ACACCATGAAAGTCGCTCAGGCCATGAAGGGTATACATAAAAGCCAAGAAGTATGTGAAAG | SEQ ID NO: 2159 | |
| 579 | A_24_P367191 | LOC652890 | AGTTAAGATCCTGAGGACTGTAGAGCCATATATTGCCTGCTGTGGGTACCCAAATCTGAAGTC | SEQ ID NO: 2160 | PREDICTED: Homo sapiens similar to 60S ribosomal protein L7 (LOC652890), mRNA [XR_019544] |
| 580 | A_24_P367199 | A_24_P367199 | TCTTATGCTCAGCACCAACAGTCTGCCAAATCCAAGAAGAAGGTGTAATCATGACCTGAGA | SEQ ID NO: 2161 | |
| 581 | A_24_P367369 | A_24_P367369 | ATTTAAAGGTTTCGATGTAGATTCTCTGGTGGATGAGGATATCCAAGTGAAGAAGACATCTAA | SEQ ID NO: 2162 | |
| 582 | A_24_P368575 | SLC4A7 | TTTTTAATGAGATTTTGCACACTGATTAGTTTTTGTGTTGTGGCTTTGTTTGGTTTAT | SEQ ID NO: 2163 | Homo sapiens solute carrier family 4, sodium bicarbonate cotransporter, member 7 (SLC4A7), mRNA [NM_003615] |
| 583 | A_24_P370096 | ZNF230 | GAAAGCTTATATTTGTGAGAAATGTGGGAGGGCCTTCATTCACGATTTAAACTTCAGAA | SEQ ID NO: 2164 | Homo sapiens zinc finger protein 230 (ZNF230), mRNA [NM_006300] |
| 584 | A_24_P371053 | ORMDL1 | GAATGAAAGAGTACAGACCAAGTTAAACATCAATTGGTGTCAGTAAACTGACTTTGG | SEQ ID NO: 2165 | Homo sapiens ORM1-like 1 (S. cerevisiae) (ORMDL1), mRNA [NM_016467] |
| 585 | A_24_P371303 | C3orf63 | GTCAGTGTCAAGAAAATGAGAATTAGTTCTTATCTGGTTATACTGAAAGCTGGATAGAG | SEQ ID NO: 2166 | Homo sapiens chromosome 3 open reading frame 63 (C3orf63), mRNA [NM_015224] |
| 586 | A_24_P371399 | C3orf58 | TAAAATAGTTGCATTCGGTTAATTTTTACACATTAGTGCATTGCGTATACAAGTCGGCGC | SEQ ID NO: 2167 | Homo sapiens chromosome 3 open reading frame 58 (C3orf58), mRNA [NM_173552] |
| 587 | A_24_P374319 | RAP2C | ATTGTGTGTTGATGTTCAAATAAAGTGGTATGTGACATTCATGTGATTTATGGGTCAAGCATG | SEQ ID NO: 2168 | Homo sapiens RAP2C, member of RAS oncogene family (RAP2C), mRNA [NM_021183] |
| 588 | A_24_P375599 | LOC731681 | TGTATGCTGACTTCCCGCACATCAAGTCGTTATCCAGAATGGGGTCTGTTGAAATCCGAA | SEQ ID NO: 2169 | PREDICTED: Homo sapiens similar to 60S ribosomal protein L9 (LOC731681), mRNA [XR_019944] |
| 589 | A_24_P375849 | ENST00000359659 | AAGAAAGCTCTGCAACAAGATAGGAGGCTATGTCACACATCTGATGAAGCGGATTCAGAGA | SEQ ID NO: 2170 | Q8BT90_MOUSE (Q8BT90) 10, 11 days embryo whole body cDNA, RIKEN full-length enriched library, clone:2810021H19 product:ribosomal protein S17, full insert sequence. (Fragment), partial (98%) [THC2559910] |

Fig. 5-32

| No. | Probe ID No. | Symbols of genes | Sequence | SEQ ID NO: | Descriptions of genes [letters and numbers within [ ] indicates GenBank accession No.] |
|---|---|---|---|---|---|
| 590 | A_24_P375932 | A_24_P375932 | ATGGTTAAAAATGGAGAGAGCAATGCAGAAGTTAAGGGTTTAGATGTAGAATTGTCTAGTC | SEQ ID NO: 2171 | |
| 591 | A_24_P379379 | CAPZA1 | ACCAGTTTCAGCCTAAAACTCTGGAATGGTCGTTGGAGATCAGAGTGGAAGTTCACCA | SEQ ID NO: 2172 | Homo sapiens capping protein (actin filament) muscle Z-line, alpha 1 (CAPZA1), mRNA [NM_006135] |
| 592 | A_24_P381625 | PSMC6 | ATGAAAGCAGTCAGAAAAGTGGCTGATTCTAAGAACCTGGAGTCTAAATTGGACTACAAA | SEQ ID NO: 2173 | Homo sapiens proteasome (prosome, macropain) 26S subunit, ATPase, 6 (PSMC6), mRNA [NM_002806] |
| 593 | A_24_P383569 | LOC391130 | ATGGATCTGGTGGAGTGGGATTCAGAGGGGGTAAGATACCAGTAAGAGGTATCCATCAAG | SEQ ID NO: 2174 | PREDICTED: Homo sapiens similar to 40S ribosomal protein S17 (LOC391130), mRNA [XR_019508] |
| 594 | A_24_P383998 | RPS3A | TGGTTTTTACTAAAAAACGCAACAATCAGATACAGAGAGACCTCTATGCCCAGCACCAACG | SEQ ID NO: 2175 | Homo sapiens ribosomal protein S3A (RPS3A), mRNA [NM_001006] |
| 595 | A_24_P384411 | A_24_P384411 | ATGGCAAAATCAATAAGAGTGAAGGTTTGACAGATAATGCTTGACAGTCGATGTCTTG | SEQ ID NO: 2176 | |
| 596 | A_24_P384639 | LOC730452 | CAAGAAAAGCTGGCAACTTTCTATGTACCGACAGAACCCAAATTGGCATTTGCATCAGGA | SEQ ID NO: 2177 | PREDICTED: Homo sapiens similar to 60S ribosomal protein L7 (LOC730452), mRNA [XM_001125895] |
| 597 | A_24_P387869 | PKN2 | TTGTCAGAGATCATTTATATTACCTCCAAATTGTTTATTACCCAAGATCCTTTGGGAG | SEQ ID NO: 2178 | Homo sapiens protein kinase N2 (PKN2), mRNA [NM_006256] |
| 598 | A_24_P392231 | LOC641784 | CCATCAATATTCAGAAGTGCATCCATGATGGGCAAGAAGCGTGCCCCTCGGGAACTCA | SEQ ID NO: 2179 | xr55h07.x1 NCI_CGAP_Ov26 Homo sapiens cDNA clone IMAGE:2764093 3' similar to gb:X69181 60S RIBOSOMAL PROTEIN L31 (HUMAN);, mRNA sequence [AW302767] |
| 599 | A_24_P392900 | A_24_P392900 | GTCTGTTCTGTGTTGGTTTCTAAAAACAATGTAACAATCGGAAAAACCTTTTATGGTC | SEQ ID NO: 2180 | |
| 600 | A_24_P39378 | CCPG1 | TACTTTTTGTCGCTGGAACGAACTGATCAGTTGATCAATAAGTTTTTCCTAAAGCGTGT | SEQ ID NO: 2181 | Homo sapiens cell cycle progression 1 (CCPG1), transcript variant 1, mRNA [NM_004748] |
| 601 | A_24_P393811 | TMCC1 | AGATGACACCAGAGTGTTCCTTCATTTCTGTATATGTCTGTACTATGTGATTGGAG | SEQ ID NO: 2182 | Homo sapiens transmembrane and coiled-coil domains 1 (TMCC1), mRNA [NM_019026] |
| 602 | A_24_P399942 | ATP11C | TGACGATGTTACCTACTAAACTGAAAACATTCATTCCATATCTACTACAGACAGAG | SEQ ID NO: 2183 | Homo sapiens ATPase, Class VI, type 11C (ATP11C), transcript variant 1, mRNA [NM_173694] |
| 603 | A_24_P40417 | FMR1 | TTGTGAGTTTGTTTTCTTTCATTTGAATTTCATTTACAGTTACTTTCCTTGGCATACAACAAG | SEQ ID NO: 2184 | Homo sapiens fragile X mental retardation 1 (FMR1), mRNA [NM_002024] |
| 604 | A_24_P405002 | PDIK1L | TGGTGCTAAGGGATACTTTGTCATTATGATGAACTAAGTGTTAAGTGTCAGATAAATAGC | SEQ ID NO: 2185 | Homo sapiens PDLIM1 interacting kinase 1 like (PDIK1L), mRNA [NM_152835] |
| 605 | A_24_P405298 | PPP1CB | GTATTAGGTTAGGTCACAAAGGTTTTATCTGAGGTGATTTAAATAACTTCCTGATTGGAG | SEQ ID NO: 2186 | Homo sapiens protein phosphatase 1, catalytic subunit, beta isoform (PPP1CB), transcript variant 1, mRNA [NM_002709] |
| 606 | A_24_P405430 | TIA1 | GGATTTTCTCTGTGTTAAATCACAAAATGATAGTCCCAATACGTTTCTTTATAGGAGG | SEQ ID NO: 2187 | Homo sapiens cDNA FLJ36425 fis, clone THYMU2011482. [AK093744] |
| 607 | A_24_P406034 | SLC35A1 | ATGTACAGTATTTTGTCCTAGCAGGATAAAGACCTAGCTGTCTTTCTTACAAGAGCAGAA | SEQ ID NO: 2188 | Homo sapiens solute carrier family 35 (CMP-sialic acid transporter), member A1 (SLC35A1), mRNA [NM_006416] |
| 608 | A_24_P409681 | A_24_P409681 | ACATGAGGCTCCCCTGCCGCTGGAGATGATTCTTGAAAAGGAACAGATTGTTCATAAAC | SEQ ID NO: 2189 | |

Fig. 5-33

| No. | Probe ID No. | Symbols of genes | Sequence | SEQ ID NO: | Descriptions of genes (letters and numbers within [ ] indicates GenBank accession No.) |
|---|---|---|---|---|---|
| 609 | A_24_P414256 | CCDC72 | TCTTTGGTTGCTTGTTCTGACCCTAAAGTTTGTATCACCTGAAATTAAACGAACTCATTTGA | SEQ ID NO: 2190 | Homo sapiens HSPC330 mRNA, partial cds. [AF161448] |
| 610 | A_24_P414556 | TTC33 | TACTGAACATTTGGTATATTGTTTTGAGTAATGACATGATCTTTGTTTTTGTGTAATTTGTGA | SEQ ID NO: 2191 | Homo sapiens tetratricopeptide repeat domain 33 (TTC33), mRNA [NM_012382] |
| 611 | A_24_P414952 | TMEM168 | TTTTCTACTGACGGTCAAGAGTCAGAGGATAGGAAAGAAGTATTCTCTTCTGGTATACATGTAATG | SEQ ID NO: 2192 | Homo sapiens transmembrane protein 168 (TMEM168), mRNA [NM_022484] |
| 612 | A_24_P41551 | LOC641790 | AAGGAGATGGGAACTCCTGATGTGGCATTGATATCAGGCACAACAAAGTAGTCTGGAAA | SEQ ID NO: 2193 | PREDICTED: Homo sapiens similar to ribosomal protein L31 (LOC641790), mRNA [XR_018025] |
| 613 | A_24_P417281 | TXNDC10 | ATGATGAGTGATTGCTTGGGAAGATAAATGTTAATGTTCCGAATAGTCAAGCTGTTTTGC | SEQ ID NO: 2194 | Homo sapiens thioredoxin domain containing 10 (TXNDC10), mRNA [NM_019022] |
| 614 | A_24_P418418 | RPS17 | GATGAACTTCAAAATGCCTCGGGGGACCTGTTTGAATTTTTTCTGCAGTGCTGTATTATT | SEQ ID NO: 2195 | Homo sapiens ribosomal protein S17 (RPS17), mRNA [NM_001021] |
| 615 | A_24_P418712 | A_24_P418712 | AGGCTCAACAAAGCTGTCTGGGCCAAAGAAATAAGGAATATCGATACCATATCGTGTTA | SEQ ID NO: 2196 | |
| 616 | A_24_P487736 | CXorf23 | TGCATACCTACTATCTGTGAAGAGCAAATGGATGGATTTTAAATGAAATTTTAGGCCC | SEQ ID NO: 2197 | Homo sapiens chromosome X open reading frame 23 (CXorf23), mRNA [NM_198279] |
| 617 | A_24_P50437 | BC065737 | TGCAGAATGATGAAGTTGCATTAGAAAATTCCTGATTACTGAAGATGTTCAAGGGCAAAA | SEQ ID NO: 2198 | Homo sapiens cDNA clone IMAGE:30404477, partial cds. [BC065737] |
| 618 | A_24_P50472 | LOC649839 | TAAAACTACAAAGAAGATGTGTGCTGGGCTTGAGTGCATTCAGCCCAACTGCAATCGAA | SEQ ID NO: 2199 | PREDICTED: Homo sapiens similar to large subunit ribosomal protein L36a (LOC649839), mRNA [XM_001129410] |
| 619 | A_24_P50554 | LOC391655 | TCAAGGGTTTAAGATGTAGATTCTCTGGTCATTGAGTATAACGGAGTAAACAAAGACCTA | SEQ ID NO: 2200 | PREDICTED: Homo sapiens similar to 60S ribosomal protein L17 (L23) (LOC391655), mRNA [XR_018405] |
| 620 | A_24_P50567 | A_24_P50567 | CCTTGCTAATTTGAAAAAGTACCAGAACAATGAATCAGATGCATGGTTGCTGTGACTA | SEQ ID NO: 2201 | |
| 621 | A_24_P538403 | ROCK1 | TTAGAGGTTTGTTGGACTTTCATAAATTGAGTACAACATGTTTGGATCAAACTACCTGCTAC | SEQ ID NO: 2202 | Homo sapiens Rho-associated, coiled-coil containing protein kinase 1 (ROCK1), mRNA [NM_005406] |
| 622 | A_24_P54178 | TMED5 | GCTCTGATATGCATTTGGATGATTAATGTTATGCTGTTCTTTCATGTGAATGTCAAGAGA | SEQ ID NO: 2203 | Homo sapiens transmembrane emp24 protein transport domain containing 5 (TMED5), mRNA [NM_016040] |
| 623 | A_24_P561223 | THC2697551 | TTATGCCAGTTACATACAAGAGATCCTGCCATATTTCAGGAGACCCTAAAGTTTATAACAT | SEQ ID NO: 2204 | ALU1_HUMAN (P39188) Alu subfamily J sequence contamination warning entry, partial (8%) [THC2697551] |
| 624 | A_24_P56240 | CPNE8 | TACAACTATGTGACTTAGTGCACAACACATTTGTGAAATAACCTACTCCTATATAGTGAG | SEQ ID NO: 2205 | Homo sapiens copine VIII (CPNE8), mRNA [NM_1536341] |
| 625 | A_24_P56252 | AF086032 | GTATCTAAAACTGAAGCAGTACTGTGCTATATTGATTTTATTGGTAGTATTGAGGCAGACC | SEQ ID NO: 2206 | Homo sapiens full length insert cDNA clone YM25609. [AF086032] |
| 626 | A_24_P57837 | THC2567891 | AGAAATCCGGAAGAGACGTCTTATGCTCAGTACGACCCAAATCCGGAAGAAGATGAGGAAA | SEQ ID NO: 2207 | Q6NXR8_HUMAN (Q6NXR8) Ribosomal protein S3a, partial (91%) [THC2567891] |
| 627 | A_24_P587938 | A_24_P587938 | CTTCAAAGAAGCAAAAGGTGGAGATGCTGGGCAACAGCGGAGGACGAGATTAACAGTCTTAT | SEQ ID NO: 2208 | |
| 628 | A_24_P606653 | LOC392030 | TGTGCGGTTGCCCAGAAAACGTAATGCCGGGTGAAGATTCACCAAATAAGGTCCATAGTTT | SEQ ID NO: 2209 | PREDICTED: Homo sapiens hypothetical LOC392030 (LOC392030), mRNA [XR_018063] |

Fig. 5-34

| No. | Probe ID No. | Symbols of genes | Sequence | SEQ ID NO: | Descriptions of genes (letters and numbers within [ ] indicates GenBank accession No.) |
|---|---|---|---|---|---|
| 629 | A_24_P62530 | RHOU | GGGTGAACTACAAGTGTAGGGCACCATTATAATTTATAAATACAG CATACTTCAAAAGTG | SEQ ID NO: 2210 | Homo sapiens ras homolog gene family, member U (RHOU), mRNA [NM_021205] |
| 630 | A_24_P62860 | STAM2 | GTCTATATGGTACTTGATCTACATATTAAGTGGAAAAATTAGCAGT ATTTGAAAGCTGAGT | SEQ ID NO: 2211 | Homo sapiens signal transducing adaptor molecule (SH3 domain and ITAM motif) 2 (STAM2), mRNA [NM_005843] |
| 631 | A_24_P630039 | AL049321 | AACAGAGACAATACAAAAGTTACATTTACATTTAAAACT GCAAGAAGACAGGGG | SEQ ID NO: 2212 | Homo sapiens mRNA; cDNA DKFZp564D156 (from clone DKFZp564D156). [AL049321] |
| 632 | A_24_P63347 | PF4V1 | CTACATATTTACCTTGAATGTACAATTAGCTGGCAATAAATAT TAGTAGCTCTTAAGC | SEQ ID NO: 2213 | Homo sapiens platelet factor 4 variant 1 (PF4V1), mRNA [NM_002620] |
| 633 | A_24_P62786 | THC2533996 | TGCTTGTTCGTATCTCAGCCCGAAGATGATTATCGTTGAGGAATG ACATTGAGCTTGTTT | SEQ ID NO: 2214 | HSU09954 ribosomal protein L9 [Homo sapiens] (exp=0; wgp=0; cg=0), partial (42%) [THC2533996] |
| 634 | A_24_P67100 | LOC646949 | AGTCATACCGCAGAAAAGATGGGGTGTTTCTTTATTTTGAAGATA ATGCAGGGGTCACAG | SEQ ID NO: 2215 | PREDICTED: Homo sapiens similar to ribosomal protein L23 (LOC646949), mRNA [XR_017241] |
| 635 | A_24_P675947 | ENST00000389400 | GTTCATGGCGAAGGTAGCAGTTCTCGAAAAAGCTACTGGAGAAGAG ACAGGTTCTAAAGTT | SEQ ID NO: 2216 | similar to 40S ribosomal protein S3a (V-fos transformation effector protein) (LOC391706), mRNA [Source:RefSeq_dna;Acc:XR_017186] [ENST00000389400] |
| 636 | A_24_P685729 | ENST00000389400 | TTGAAGCTTATGTTGATGTCAAGACTATCAGTGATTATTTGCTTT GTCTGTTTTGTGTGG | SEQ ID NO: 2217 | |
| 637 | A_24_P6975 | LOC342994 | GGAAAGACTTCGAGGGGGTTCGTGCTGTAAGACCTAAAGTTCTTATG AAAATGTCAAAAGA | SEQ ID NO: 2218 | PREDICTED: Homo sapiens similar to ribosomal protein L34 (LOC342994), mRNA [XM_938464] |
| 638 | A_24_P703614 | A_24_P703614 | AAGAACATACCCGAGTAATGGAGTCTGCACTGTAAGTGATCAGTAGC AGCTTTGTCTGTGTG | SEQ ID NO: 2219 | |
| 639 | A_24_P7181 | A_24_P7181 | TCATGGTCGGATTAACTCACAGTGATCTCTGGCTGCCACATGGA AATGATCTTTAGTGA | SEQ ID NO: 2220 | |
| 640 | A_24_P71938 | SMAD1 | TGTATTCACTTATGCTCTGCTGTACATTGAGTACTTTTATTCCAAAA CTAGTGGGTTTCTC | SEQ ID NO: 2221 | Homo sapiens SMAD family member 1 (SMAD1), transcript variant 1, mRNA [NM_005900] |
| 641 | A_24_P75158 | PTAR1 | CCATTAGATTTGTTCTTATGTGAAGCATGGTAGCACAGCCAGCTATAA AGTATGTATTTCTG | SEQ ID NO: 2222 | Homo sapiens mRNA; cDNA DKFZp313P0917 (from clone DKFZp313P0917). [AL832693] |
| 642 | A_24_P755505 | A_24_P755505 | ATACAGAAGACCTCTTATGCTCAGGACCAACAGAAAAGTAAAAT GCTGAAGAAGCCAA | SEQ ID NO: 2223 | |
| 643 | A_24_P76169 | ENST00000331306 | TTCTAAAATTCACTGCGACTTTCTCTAAGAAGTGTGGCAAGCATC AACCCGACAAAGTGA | SEQ ID NO: 2224 | PREDICTED: Homo sapiens similar to large subunit ribosomal protein L36a (LOC728202), mRNA [XM_001129191] |
| 644 | A_24_P76358 | LOC643981 | TTACTGAAGATGTTCAGGGCAAAAACTGCCTAACTTCCGGGCATGG ATCTTATTCGTGACA | SEQ ID NO: 2225 | PREDICTED: Homo sapiens similar to 40S ribosomal protein S3a (V-fos transformation effector protein) (LOC643981), mRNA [XR_018444] |
| 645 | A_24_P77681 | PAIP1 | AGCTGATCGAGATACCAAGAGAAATACCAAGAATACTTGAAAG AGAGGACTTTTTTCC | SEQ ID NO: 2226 | Homo sapiens poly(A) binding protein interacting protein 1 (PAIP1), transcript variant 1, mRNA [NM_006451] |
| 646 | A_24_P792734 | PSMC6 | AGAAACGTTAACGGAGTTACTGAATCAAATGGATTGATTGATACT CTGGATAGAGTTAAA | SEQ ID NO: 2227 | Homo sapiens proteasome (prosome, macropain) 26S subunit, ATPase, 6 (PSMC6), mRNA [NM_002806] |

Fig. 5-35

| No. | Probe ID No. | Symbols of genes | Sequence | SEQ ID NO: | Descriptions of genes (letters and numbers within [ ] indicates GenBank accession No.) |
|---|---|---|---|---|---|
| 647 | A_24_P813147 | TUBB8 | TACCTAACGGTGGCTGCCATTTTCAGGGGTCGCATGCCATCAGGGAGGTGGATGAACAA | SEQ ID NO: 2228 | Homo sapiens tubulin, beta 8 (TUBB8), mRNA [NM_177987] |
| 648 | A_24_P81965 | RAP2A | TTCTTTTGATGTTGCAACTTTTGGGTTCGTTCTTTAAACTGTGATAGTGATGGTAACTGATGC | SEQ ID NO: 2229 | Homo sapiens RAP2A, member of RAS oncogene family (RAP2A), mRNA [NM_021033] |
| 649 | A_24_P830667 | RPL21 | CTGTTCCTTTGGCGAACGTATATGCGAAATCTATAAGAAAGGTGATATTGTAGACATCAAGG | SEQ ID NO: 2230 | Homo sapiens ribosomal protein L21 (RPL21), mRNA [NM_000982] |
| 650 | A_24_P83968 | LOC730887 | ACAAAGCCCAGCAGGAACAACGTGGAACACAGAGAAAGTTTTTCTGGTGTCTCTAAGAAGC | SEQ ID NO: 2231 | PREDICTED: Homo sapiens similar to 40S ribosomal protein S7 (S8) (LOC730887), mRNA [XR_015607] |
| 651 | A_24_P84408 | A_24_P84408 | AAGGTACATCCAGCAGTGGTCATTGAGAAGTCATACCAGAGAAAAGATGGCGTGTTTCTT | SEQ ID NO: 2232 | |
| 652 | A_24_P84808 | LOC729449 | GAATTGCTTGGACAGATAACGCTTTGCGATCTCTTGGAAAATATGGCATCATCTGTATGG | SEQ ID NO: 2233 | PREDICTED: Homo sapiens similar to 60S ribosomal protein L7 (LOC729449), mRNA [XR_015548] |
| 653 | A_24_P857201 | AK022997 | CTGACATGTGATAAATATTTCAGTGACTTTTCAGATTTATTTCTTGTTAGCCGCTGTGTC | SEQ ID NO: 2234 | Homo sapiens cDNA FLJ12835 fis, clone NT2RP2004982. [AK022997] |
| 654 | A_24_P879895 | BC043357 | ACATACCTCAACTGCAACTGGTTTATGACACCTTGAATAAAAACAAAAGTGGCAG | SEQ ID NO: 2235 | Homo sapiens, clone IMAGE:3883659, mRNA. [BC043357] |
| 655 | A_24_P886040 | DCP2 | CATTTGGAACAAGGTTTCATTCTCGTTCTTAGATTTATGTGTTGTAGTTGAAACAGCAACTG | SEQ ID NO: 2236 | Homo sapiens DCP2 decapping enzyme homolog (S. cerevisiae) (DCP2), mRNA [NM_152624] |
| 656 | A_24_P880536 | CR627148 | AATTGCCTTCTTCTGTACCCCTAAGTATGGTGAAGCAGAATTGAATTCTACAAAAGTCTTTC | SEQ ID NO: 2237 | Homo sapiens mRNA; cDNA DKFZp779F2127 (from clone DKFZp779F2127). [CR627148] |
| 657 | A_24_P915806 | HNMT | GGAACAAGCTGCCAGGGCATAATAGGAAGAATACCAGAAATTGGCTGTTAACAAATAAATA | SEQ ID NO: 2238 | Homo sapiens histamine N-methyltransferase (HNMT), transcript variant 2, mRNA [NM_001024074] |
| 658 | A_24_P91852 | DYNLT3 | ATACATATAGAGAGGGAACCATAACTCATTGAATTTTGGAGAGGAATAAGCTTAGCGTT | SEQ ID NO: 2239 | Homo sapiens dynein, light chain, Tctex-type 3 (DYNLT3), mRNA [NM_006520] |
| 659 | A_24_P91916 | NXT2 | AAGCATGCTTCTTCTTGTAGTACTGATTGAAAAGTTACACGTTTATTCTAGTCATAGTGAGC | SEQ ID NO: 2240 | Homo sapiens nuclear transport factor 2-like export factor 2 (NXT2), mRNA [NM_018698] |
| 660 | A_24_P925505 | CD36 | CGTACCCTGTTTACCACAGTTGGTGTGTTTTATCTGTCGTAAGTACCAAATATGAATGGC | SEQ ID NO: 2241 | CD36=collagen type I/thrombospondin receptor [one exon] [human, mRNA Partial, 369 nt]. [S67044] |
| 661 | A_24_P931282 | THC2726401 | GGAAATATTTCCTGCTCAATGCATGAAATCATGTTGAAGTAATCTACTGGAGATTACAC | SEQ ID NO: 2242 | Q26195 PLAV1 (Q26195) Pval protein, partial (14%) [THC2726401] |
| 662 | A_24_P935986 | BCAT1 | ATGCTCTGAAGTTTTGTAGAAGCACAATTAAAGATCTAAAATGGCTTTGTTACACGGAGA | SEQ ID NO: 2243 | Homo sapiens branched chain aminotransferase 1, cytosolic (BCAT1), mRNA [NM_005504] |
| 663 | A_24_P937095 | SLC30A1 | TTTGATGTAGCTCTACCGATACTGTGGTAATGCTATTTGTTTTACTAACAAGCTCTG | SEQ ID NO: 2244 | Zinc transporter 1 (ZnT-1) (Solute carrier family 30 member 1). [Source:Uniprot/SWISSPROT;Acc:Q9Y6M5] [ENST00000367000] |
| 664 | A_24_P940426 | QKI | AAGCTGTTGAATGAGTCTTAAAAATTATACTAGTGTTAAGTGGACCAAGTTTGGTGAAGC | SEQ ID NO: 2245 | Homo sapiens quaking homolog, KH domain RNA binding (mouse) (QKI), transcript variant 4, mRNA [NM_206855] |
| 665 | A_24_P940776 | BDP1 | TCGAGGGGGAAATTGTCTATAAGTAGGCATTTATTTCATGATTGATATGTCAGAGAAATC | SEQ ID NO: 2246 | Homo sapiens B double prime 1, subunit of RNA polymerase III transcription initiation factor IIIB (BDP1), mRNA [NM_018429] |

Fig. 5-36

| No. | Probe ID No. | Symbols of genes | Sequence | SEQ ID NO: | Descriptions of genes (letters and numbers within [ ] indicates GenBank accession No.) |
|---|---|---|---|---|---|
| 666 | A_24_P941643 | PLCB1 | ATGATGTGCAGTTTTCTGCCTTTATGTATTTGCGTTGTTCTTTGTCGAATGTGTGAAATT | SEQ ID NO: 2247 | Homo sapiens phospholipase C, beta 1 (phosphoinositide-specific) (PLCB1), transcript variant 2, mRNA [NM_182734] |
| 667 | A_24_P941699 | PCGF5 | TGGTATATTCAACTACAGAGCTTTCTAAGGATAAGGAGTACTTCATGTCTAGTAATACAGTG | SEQ ID NO: 2248 | Homo sapiens polycomb group ring finger 5 (PCGF5), mRNA [NM_032373] |
| 668 | A_24_P98210 | TFEC | ACATGGGGCTTAGAAGTGCTTCTTGTCCAAGTAGTCTACCAATGAAAAGAGAAATTACAG | SEQ ID NO: 2249 | Homo sapiens transcription factor EC (TFEC), transcript variant 1, mRNA [NM_012252] |
| 669 | A_24_P99046 | STK38L | GCTATCTGTCTTTTGCTGATCTACAAATAAATGAATTGAGAATTTAGTCCATAGAGGTCC | SEQ ID NO: 2250 | Homo sapiens serine/threonine kinase 38 like (STK38L), mRNA [NM_015000] |
| 670 | A_32_P10100 | A_32_P10100 | TATGAGGAAATAGTATCATGATCATGTTAGAAGCCTTGGAATGAGTATAAATAATGGCTGGTC | SEQ ID NO: 2251 | |
| 671 | A_32_P105397 | THC2642694 | TAAAATGCTACTACAGTATTGTACGATGGAGGCTGAATGTATATTACAGTAATTCTCTGG | SEQ ID NO: 2252 | Q6TDT1_HUMAN (Q6TDT1) Protein transactivated by hepatitis B virus E antigen, partial (11%) [THC2642694] |
| 672 | A_32_P106732 | FANCM | AATCAAGCTGCTCAAGATGGGGTTTTCAAAGAGCGTCTCACATATTAAATGCAGTTCAAT | SEQ ID NO: 2253 | Homo sapiens Fanconi anemia, complementation group M (FANCM), mRNA [NM_020937] |
| 673 | A_32_P107372 | GBP1 | GGTACTGAGCAGAGTCGTTAGGTAAAAGTGTCTGGGAAATATTTGGGCATTGGTCTGGCCAA | SEQ ID NO: 2254 | Homo sapiens guanylate binding protein 1, interferon-inducible, 67kDa (GBP1), mRNA [NM_002053] |
| 674 | A_32_P107717 | BX100535 | TCTTGTCCACCCAAGATCTGCTCTCTGTTGTAAATCGTGTTCAGACCCTGGTCTAATTGGT | SEQ ID NO: 2255 | BX100535 Soares_testis_NHT Homo sapiens cDNA clone IMAGp998I094457, mRNA sequence [BX100535] |
| 675 | A_32_P109495 | THC2618720 | AAAGATATATCAGGCAACGAACAGTGGAGACTGCTCACCATGAATTTTTGGTTTGTTCATAAGA | SEQ ID NO: 2256 | |
| 676 | A_32_P109653 | THC2669092 | TGTGTTTGGTATTCGAAGTGGGGTCTTTTTCAGAATCTCTGCACTAGTCTGAGAATGCAA | SEQ ID NO: 2257 | |
| 677 | A_32_P113154 | LOC730861 | ACCACGAGTCCAAGAATCTGTTAAAGTTCAGACTTAAAACAGTACCAAATAAAAGTGC | SEQ ID NO: 2258 | PREDICTED: Homo sapiens similar to 40S ribosomal protein S3a (V-fos transformation effector protein) (LOC730861), mRNA [XR_015591] |
| 678 | A_32_P113584 | ZNF292 | GGGGCCTTTGGGTTTTATTGAATAGTTCATTTGACCTGTTAAGAGTTACTACCAATAAG | SEQ ID NO: 2259 | Zinc finger protein 292. [Source:Uniprot/SWISSPROT;Acc:O60281] [ENST00000339907] |
| 679 | A_32_P113742 | RPL21 | ATGTTCTCTAGGCCTTTTAGAAAAACATGGAGGAATGGGTACTGTTCAAAAAGGAATGCCC | SEQ ID NO: 2260 | Homo sapiens ribosomal protein L21, mRNA (cDNA clone IMAGE:6605832), complete cds. [BC104478] |
| 680 | A_32_P114215 | COMMD6 | AATTGCTATCATTCTAAAGTCATGGAGCTTCAGTTTCGGCAACAAACTAAATAAGGATGG | SEQ ID NO: 2261 | Homo sapiens COMM domain containing 6 (COMMD6), transcript variant 2, mRNA [NM_203495] |
| 681 | A_32_P1144 | AK091357 | GGGGACTTAATATTTTACATCTACTAGCCATGTCATAGGTTTTAAGTGCTTTTAATGGGG | SEQ ID NO: 2262 | Homo sapiens cDNA FLJ34038 fis, clone FCBBF2005645. [AK091357] |
| 682 | A_32_P11451 | NMD3 | CAGTTTAGGCAGGTAGCTGCTTTTGTCATAAATATCTTCGTACGACATCAAAAATGCTGC | SEQ ID NO: 2263 | Homo sapiens NMD3 homolog (S. cerevisiae) (NMD3), mRNA [NM_015938] |
| 683 | A_32_P115505 | ZNF294 | TGTGGTCAGAGAGTATATAGTTGAGAGTAAGTACTATGTGAGTTATAGATCTCTCGAA | SEQ ID NO: 2264 | Homo sapiens zinc finger protein 294 (ZNF294), mRNA [NM_015665] |

Fig. 5-37

| No. | Probe ID No. | Symbols of genes | Sequence | SEQ ID NO: | Descriptions of genes (letters and numbers within [ ] indicates GenBank accession No.) |
|---|---|---|---|---|---|
| 684 | A_32_P11931 | LOC441073 | GTGTGATGATCCCATGCCATCCGAAAAGGATGAGAAGTTCAGGTTGTACCGTGGACGACTATAAA | SEQ ID NO: 2265 | PREDICTED: Homo sapiens similar to 60S ribosomal protein L26 (Silica-induced gene 20 protein) (SIG-20) (LOC441073), mRNA [XR_016376] |
| 685 | A_32_P125549 | RPL31P4 | TCTACAGACAGTCAATGTCGATGAGAAGTAATCCCTGATCGTGCAGATACATCAAATAAAG | SEQ ID NO: 2266 | PREDICTED: Homo sapiens ribosomal protein L31 pseudogene 4 (RPL31P4), mRNA [XR_018222] |
| 686 | A_32_P125917 | THC2753798 | GCTTATAAAGTGTAAGTGGGAGAGGGCTAAATGTGTGAAGTACAAAGTTTCTTTTTCAGCAACAG | SEQ ID NO: 2267 | BF238843 601904455F1 NIH_MGC_54 Homo sapiens cDNA clone IMAGE:4132429 5', mRNA sequence [BF238843] |
| 687 | A_32_P128781 | A_32_P128781 | CATATATTGCATGGGGGTACCCAATCTGAAGTCAGTAAATGAACTAATCTACAAGAGTG | SEQ ID NO: 2268 | |
| 688 | A_32_P135818 | RPS3A | CTTGCTTCATCTGTTCTGTGTTGGTTTTAATAAAAACGGACAATCAGATATGGAAGAC | SEQ ID NO: 2269 | Homo sapiens ribosomal protein S3A (RPS3A), mRNA [NM_001006] |
| 689 | A_32_P136319 | RPL36A | AAGTGATCCAGTTGTAAGTGTCATCTTTATCATGAAGACAATAAAATCTTGAGTTTATG | SEQ ID NO: 2270 | Homo sapiens ribosomal protein L36a (RPL36A), mRNA [NM_021029] |
| 690 | A_32_P137266 | KIAA1799 | AAGTGGGACGCAAATCTAGAATGGTTTGTCAACATGTAATGCTTTGAATGAACGGACAAG | SEQ ID NO: 2271 | Homo sapiens KIAA1799 protein (KIAA1799), mRNA [NM_032437] |
| 691 | A_32_P143323 | CR613267 | AGAGAGCTCAAACGAATGGGGTTTATGCCAGTTACATACAAGGATCGTGCATATTTCAGGG | SEQ ID NO: 2272 | full-length cDNA clone CS0DL011YP14 of B cells (Ramos cell line) Cot 25-normalized of Homo sapiens (human) [CR613267] |
| 692 | A_32_P145153 | RPL31 | ATCGGTGTGCAGGTGTCCAGAAAAACTAATGAGGATGAAGATTCACCAAATAAGCATAT | SEQ ID NO: 2273 | Homo sapiens ribosomal protein L31 (RPL31), mRNA [NM_000993] |
| 693 | A_32_P145159 | A_32_P145159 | GATACATTGGGGTGTACATAAACGTTTGTGGAAAACTTAGTTGTGTGATTATTCTCTTTG | SEQ ID NO: 2274 | |
| 694 | A_32_P145477 | BX350256 | TGGCAAGCATCCTAAGAAGAACGGAAACCCAAGGGAACAGAGATGTCTACATAGGACTGTA | SEQ ID NO: 2275 | BX350256 BX350256 Homo sapiens PLACENTA COT 25-NORMALIZED Homo sapiens cDNA clone CS0DI081YM18 3-PRIME, mRNA sequence [BX350256] |
| 695 | A_32_P147747 | THC2575761 | TTGATACGTCTGATTCTGATGACAAACAGCGAATTGGGTTCTGCAGGTAGATAGAAGTTG | SEQ ID NO: 2276 | HUMRPL7Y ribosomal protein L7 [Homo sapiens] (exp=-1; wgp=0; cg=0) partial (40%) [THC2575761] |
| 696 | A_32_P148824 | C1orf27 | GAAAAAGAGATGTTATCCTCAGGAGAAAATTCAGTAAGAGACTACAAAGGATGATCTC | SEQ ID NO: 2277 | Homo sapiens chromosome 1 open reading frame 27 (C1orf27), mRNA [NM_017847] |
| 697 | A_32_P1515 | AA714637 | CTGAGCATAAGAGGGTCTTCCGTATCTGATTTTTTGGGTTTTTTAGTAAAACCAACAGAA | SEQ ID NO: 2278 | nw20g12.s1 NCI_CGAP_GCB0 Homo sapiens cDNA clone IMAGE:1241062 3' similar to gb:M84711 40S RIBOSOMAL PROTEIN S3A (HUMAN);, mRNA sequence [AA714637] |
| 698 | A_32_P153725 | KIAA1033 | TTTTGTAAAAGATGGCAAGTTTGTTACGTCACTTGAGTGGGGTTTTCCTTTTCCCCAAT | SEQ ID NO: 2279 | Homo sapiens KIAA1033 (KIAA1033), mRNA [NM_015275] |
| 699 | A_32_P156364 | RPL7 | TCAACAGGGTTATTAGAAAAATGAACCAAGGTGTCTACCATGATTATTTTCTAAGCTGG | SEQ ID NO: 2280 | Homo sapiens ribosomal protein L7 (RPL7), mRNA [NM_000971] |
| 700 | A_32_P155811 | CD2AP | AAAGGATGCTTCTCTCAAAAAGAAAATTAAAGGATTTATTGCCAGTCGTGTCAGTC | SEQ ID NO: 2281 | Homo sapiens CD2-associated protein (CD2AP), mRNA [NM_012120] |
| 701 | A_32_P158746 | RPL17 | TTTTGCTGACATGGCTAAAAAATGCAGAGACTAATGGTGAACTTAAGGGTTTAGATGTAG | SEQ ID NO: 2282 | Homo sapiens ribosomal protein L17 (RPL17), transcript variant 1, mRNA [NM_000985] |
| 702 | A_32_P158966 | KLRF1 | TACGTGATAGTATAAACCAATCTGACTTGATGTGATCATCCAGGATTTTTATTCGGTCG | SEQ ID NO: 2283 | Homo sapiens killer cell lectin-like receptor subfamily F, member 1 (KLRF1), mRNA [NM_016523] |

Fig. 5-38

| No | Probe ID No. | Symbols of genes | Sequence | SEQ ID NO: | Descriptions of genes (letters and numbers within [ ] indicates GenBank accession No.) |
|---|---|---|---|---|---|
| 703 | A_32_P159651 | PCAF | GAGTGGTGTCTAGATTTCTAATGAAGAATCATGATACAGTTTGGATTAAGTATGTTGGAC | SEQ ID NO: 2284 | Homo sapiens p300/CBP-associated factor (PCAF), mRNA [NM_003884] |
| 704 | A_32_P162250 | ARHGAP18 | AAGTCCTGAATAAGTCACTGGAAGAATATTCTTCTGGGTGAAAAAGCTTTTGTTGTG | SEQ ID NO: 2285 | Homo sapiens Rho GTPase activating protein 18 (ARHGAP18), mRNA [NM_033515] |
| 705 | A_32_P164203 | THC2883448 | TTGATGGTCATTGTACGGAGCTATTGTATGGATTACTGTGGAGTGCTGTTTACCACATGAT | SEQ ID NO: 2286 | Q7WZG3_PASP1 (Q7WZG3) Ferric uptake regulator, partial (9%) [THC2883448] |
| 706 | A_32_P165340 | SRP9 | ACATTGAAATATGTTTTGTATAAATTTGTCATGTTGAACAACATTTAGGATGGTAAGTT | SEQ ID NO: 2287 | Homo sapiens signal recognition particle 9kDa (SRP9), mRNA [NM_003133] |
| 707 | A_32_P167122 | RCOR3 | GTATCTGAGGGATGTGCTGTAATCTGATTAGACATGAATTAGAGCACACAGTAGAAAAACT | SEQ ID NO: 2288 | Homo sapiens REST corepressor 3 (RCOR3), mRNA [NM_018254] |
| 708 | A_32_P170444 | SUB1 | TAGGTATCTCTCCTGAAATTCTTTGCAGTTCATTTTTATGGCAGTTAATCCAGTGAAAC | SEQ ID NO: 2289 | Activated RNA polymerase II transcriptional coactivator p15 (SUB1 homolog) (Positive cofactor 4) (PC4) (p14). [Source:Uniprot/SWISSPROT;Acc:P53999] [ENST00000265073] |
| 709 | A_32_P170736 | AK098422 | ACGTCATAATTGTTGAGGGCAAGGTTCATTGTTGATAGTGGAAAGTGTCGGCTGTTGTGAT | SEQ ID NO: 2290 | Homo sapiens cDNA FLJ25556 fis, clone JTH02629. [AK098422] |
| 710 | A_32_P17163 | ENST00000368149 | TCCTTAGTGAGTTTAAATCTCAGGCTAGATTTTATTGTTTTCTGTGTGTGTATGAG | SEQ ID NO: 2291 | Rho GTPase-activating protein 18 (MacGAP). [Source:Uniprot/SWISSPROT;Acc:Q8N392] [ENST00000368149] |
| 711 | A_32_P173385 | ENST00000334683 | AAATGCAAGAGTGATGGTGAACTTAAGGGTCAGATGTAGATTCTCTGGTCATTGAGCA | SEQ ID NO: 2292 | PREDICTED: Homo sapiens similar to 60S ribosomal protein L17 (L23) (LOC650848), mRNA [XR_019013] |
| 712 | A_32_P17504 | THC2698682 | ATGTCTATGCTGTTTCAGTCTGCAAATATTCCCAGCTTTTCCCCTTGATGCCAAA | SEQ ID NO: 2293 | |
| 713 | A_32_P176819 | CMAH | GATTATATAGCTAGGTCTGATTCTGAAGATACAAGAATTGAATGGTGGAATTTGTCTCG | SEQ ID NO: 2294 | Homo sapiens cytidine monophosphate-N-acetylneuraminic acid hydroxylase (CMP-N-acetylneuraminate monooxygenase) (CMAH) on chromosome 6 [NR_002174] |
| 714 | A_32_P177685 | THC2632286 | TTTGACTGAGTATTTGTAGATGCTTAATGACTGAAATGAATTTGGAGGCACTGATGAAAG | SEQ ID NO: 2295 | AA665072 nu76b01.s1 NCI_CGAP_Alv1 Homo sapiens cDNA clone IMAGE:1216585, mRNA sequence [AA665072] |
| 715 | A_32_P179045 | YOD1 | TTGCCAGCATTTTGAAGTAATACAGTGCTGCTACCTGGAAGATGTCTAAGTTCATTT | SEQ ID NO: 2296 | Homo sapiens YOD1 OTU deubiquinating enzyme 1 homolog (S. cerevisiae) (YOD1), mRNA [NM_018566] |
| 716 | A_32_P179966 | ENST00000379426 | GTAATATACAGGGTGAAGCTCTTACTGATACACACAAGACAACTGTTAAAAGTGAATCC | SEQ ID NO: 2297 | Novel protein. [Source:Uniprot/SPTREMBL;Acc:Q5T4T1] [ENST00000379426] |
| 717 | A_32_P180435 | WBSCR19 | CTTTCAATCTTTGTATCTATCTATTATTACACGTGCTGCTGAAGGGAGCATGTTTTATCATG | SEQ ID NO: 2298 | Homo sapiens Williams Beuren syndrome chromosome region 19 (WBSCR19), mRNA [NM_175064] |
| 718 | A_32_P188961 | RPL17 | CATTGAGATGATCCTTACGGAAAAAGGAACAAGATTGTTCTAAACCAGAAGAGGAGGTTGC | SEQ ID NO: 2299 | Homo sapiens ribosomal protein L17 (RPL17), transcript variant 1, mRNA [NM_000985] |
| 719 | A_32_P190438 | hCG_26523 | GCCAGCAAGGTGGTTATCACTAGGCTAAAACTGGACAAGACGGGAAAAAGATCCTTGAA | SEQ ID NO: 2300 | PREDICTED: Homo sapiens similar to 60S ribosomal protein L26 (LOC646161), mRNA [XR_018048] |

Fig. 5-39

| No. | Probe ID No. | Symbols of genes | Sequence | SEQ ID NO: | Descriptions of genes (letters and numbers within [ ] indicates GenBank accession No.) |
|---|---|---|---|---|---|
| 720 | A_32_P192480 | ENST00000370857 | TAGTGCTGTAGTGCTTGTGTTTATGTTTAAAAGTGCACATTATGCAGCTCATTTTAGTATGC | SEQ ID NO: 2301 | Muscleblind-like X-linked protein (Muscleblind-like protein 3) (Cys3His CCG1-required protein) (Protein MCHCR). [Source:Uniprot/SWISSPROT;Acc:Q9NUK0] [ENST00000370857] |
| 721 | A_32_P193322 | RICTOR | ACCACATGAGTTCTTCTGTTTTTATTTAGTAATAACGGCTGCTACATATTTGGAGGTTCTGG | SEQ ID NO: 2302 | Homo sapiens rapamycin-insensitive companion of mTOR (RICTOR), mRNA [NM_152756] |
| 722 | A_32_P194421 | RPL21 | GAACGACAAAGAGAAGAAGAGGAGGGCACCCGGATATATGTTCTTTAGGCGTTTTAGAAAACA | SEQ ID NO: 2303 | Homo sapiens ribosomal protein L21 (RPL21), mRNA [NM_000982] |
| 723 | A_32_P195387 | DKFZP779L1068 | ATATAACCTTGGAATTCTATTCTAATTATGTTGTTCTGGGTGGTTGTAGTATCAGTTGGG | SEQ ID NO: 2304 | Homo sapiens cDNA clone IMAGE:5555490. [BC110326] |
| 724 | A_32_P196047 | DPY19L4 | ATATTAAGATAGTTGCAGGCAGTGTACCTCAGGTTGACTGTGTACATCTGAATAGTGAGT | SEQ ID NO: 2305 | Homo sapiens dpy-19-like 4 (C. elegans) (DPY19L4), mRNA [NM_181787] |
| 725 | A_32_P196483 | RPS3A | CGGGGCAAGAAGAAGTGGTTGATCGATTTCTTAAGAAAGATTGGTATGATGTGAAAGCA | SEQ ID NO: 2306 | Homo sapiens ribosomal protein S3A (RPS3A), mRNA [NM_001006] |
| 726 | A_32_P19752 | FAM76B | TTGTGCTTTTAGGCTGTTTTCCACTATTAATTAGCATTACCAGTAAGGGTCATTTTGAC | SEQ ID NO: 2307 | Homo sapiens family with sequence similarity 76, member B (FAM76B), mRNA [NM_144664] |
| 727 | A_32_P20240 | SP3 | CTTAGGCTCTTAATTGTAGTTTAAATTCCAGTACTAGCTGGCTACTGACCCCAAAAGTTTGT | SEQ ID NO: 2308 | Homo sapiens mRNA; cDNA DKFZp686N17231 (from clone DKFZp686N17231), mRNA [BX648577] |
| 728 | A_32_P202488 | RPL21 | AAGAAGGAGAGCCACCGGATATATGTTCTCTAGGCCTTTTAGAAAACATGGGAATGGGTAC | SEQ ID NO: 2309 | Homo sapiens ribosomal protein L21, mRNA (cDNA clone IMAGE:6605832), complete cds. [BC104478] |
| 729 | A_32_P203154 | RPL21 | CTTTGGCCACGTGTATGTGAATTCTATAAGAAAGGTGATATTGTAGAGTCAAGGGAATGG | SEQ ID NO: 2310 | Homo sapiens ribosomal protein L21 (RPL21), mRNA [NM_000982] |
| 730 | A_32_P203320 | ROCK1 | AACGGCCATCACTACTATCCAAAGATCAGGCTGATGGAAGGAGTAAGAAAATATCTCAAAATGAG | SEQ ID NO: 2311 | Homo sapiens Rho-associated, coiled-coil containing protein kinase 1, mRNA (cDNA clone IMAGE:5269982), complete cds. [BC041849] |
| 731 | A_32_P20367 | RPS7 | ATCCTTGAGGACTTGGTCTTCACAAGCAAATAATGTGGGAAGAAATGCGGCTGAAACTA | SEQ ID NO: 2312 | Homo sapiens ribosomal protein S7 (RPS7), mRNA [NM_001011] |
| 732 | A_32_P204330 | AK093982 | AAAGCCTGAGCTTTTTGCTCGTCTGTTGTAGCAGATATCGTAAAAACCTACCCAGAATTG | SEQ ID NO: 2313 | Homo sapiens cDNA FL36663 fis, clone UTERU2002826. [AK093982] |
| 733 | A_32_P205550 | RPL26L1 | AGGTAGTTCGAGGACACTACAAAGGTCAGCAAATTGGCAAGGTAATCCAGGTGTGACGAA | SEQ ID NO: 2314 | Homo sapiens ribosomal protein L26-like 1 (RPL26L1), mRNA [NM_016093] |
| 734 | A_32_P205553 | RPL26L1 | TCGGAATTGTCTGGAACATTTCATTTCCTGTTTTGTTACCTGTGGGCTCTGTAAATGTACT | SEQ ID NO: 2315 | Homo sapiens ribosomal protein L26-like 1 (RPL26L1), mRNA [NM_016093] |
| 735 | A_32_P207231 | AI630435 | TTCCTTCGCTTTTCTTTAAGGGTTTCTGGAACGACAGGAACCTGCTTGTTCTTGTCTTCT | SEQ ID NO: 2316 | AI630435 adi0b05.y1 Hembase; Erythroid Progenitor Cells (LCB:ad library) Homo sapiens cDNA clone adi0b05 random, mRNA sequence [AI630435] |
| 736 | A_32_P208178 | RPS3A | GGAAAAGACGTAGAAAAGGGTTGGAATTCTATTTATCGTCGATGATGCTCATTTACAGAAAACAGTGTGT | SEQ ID NO: 2317 | Homo sapiens ribosomal protein S3A (RPS3A), mRNA [NM_001006] |
| 737 | A_32_P21384 | RPL17 | ACGATGTCACTTTACAGAAAACAGTGTGTACGATTCCGACATTACAACGGTCGGAGTTGGCAG | SEQ ID NO: 2318 | Homo sapiens ribosomal protein L17 (RPL17), transcript variant 1, mRNA [NM_000985] |
| 738 | A_32_P219031 | RPL21 | AGAGGCACCGGATATATGTTCTCTAGGCCTTTTAGAAAACATGGAACGGGTACTGTTCA | SEQ ID NO: 2319 | Homo sapiens ribosomal protein L21, mRNA (cDNA clone IMAGE:6605832), complete cds. [BC104478] |

Fig. 5-40

| No. | Probe ID No. | Symbols of genes | Sequence | SEQ ID NO: | Descriptions of genes (letters and numbers within [ ] indicates GenBank accession No.) |
|---|---|---|---|---|---|
| 739 | A_32_P220127 | RPL34 | CAAAACTAGGGTGTCGTGAACCCCTGGTAATAGAATTGTTCACCT TTATACGAAGAAGGT | SEQ ID NO: 2320 | Homo sapiens ribosomal protein L34 (RPL34), transcript variant 2, mRNA [NM_033625] |
| 740 | A_32_P223319 | ESCO1 | ATGCCCTGATTAGTGGACTTCATTTTGATACTTGTGTATCGTTCA TAGTGCCGTCTACTT | SEQ ID NO: 2321 | Homo sapiens establishment of cohesion 1 homolog 1 (S. cerevisiae) (ESCO1), mRNA [NM_052911] |
| 741 | A_32_P224655 | CAPZA2 | AATGCTGTTTTCAGATTCTGAAATTAAATGAAAATACTTATTTCA GAAATATGTTTAATG | SEQ ID NO: 2322 | Homo sapiens capping protein (actin filament) muscle Z-line, alpha 2 (CAPZA2), mRNA [NM_006136] |
| 742 | A_32_P22539 | hCG_26523 | ACTACGAAGGTCAGCAAATTGGCAAAGTGGTCCAGGTTTACAGGA AGAATATGTTATCT | SEQ ID NO: 2323 | PREDICTED: Homo sapiens similar to 60S ribosomal protein L26 (Silica-induced gene 20 protein) (SIG-20) (LOC400055), mRNA [XM_374987] |
| 743 | A_32_P226786 | BC045174 | TTATTGGTGCATGTAAGGCATTATCCTGTCTTAATGAACCGATTA ATGCTGTTGATTGTT | SEQ ID NO: 2324 | Homo sapiens cDNA clone IMAGE:5273245. [BC045174] |
| 744 | A_32_P2333 | SUB1 | AGGAAGAAAAGGTATTTCTTTAAATCCAGAACAATGGAGCCAGGT GACGAACAGATTTC | SEQ ID NO: 2325 | Homo sapiens SUB1 homolog (S. cerevisiae) (SUB1), mRNA [NM_006713] |
| 745 | A_32_P26895 | KIAA1600 | AATTCTTGGTCCCTCCGGTGGAGAAAAGATGGCGTGTTGTTTATTTGA TAGCTAGTCTCTCTT | SEQ ID NO: 2326 | KIAA1600 (KIAA1600), mRNA [Source:RefSeq_dna;Acc:NM_020940] [ENST00000369248] |
| 746 | A_32_P30710 | RPL23 | ACGAAAGTCATACCGTAGAAAAAGATGGCGTGTTTGTTATTTGA AGATATGCAGGAGT | SEQ ID NO: 2327 | Homo sapiens ribosomal protein L23 (RPL23), mRNA [NM_000978] |
| 747 | A_32_P31182 | RPL7 | GTAGAAGAAGAAGAAGAGGTTCCGTCGTGCCAGAAAACCCTTAAG AAAAAGGAAGGAAT | SEQ ID NO: 2328 | Homo sapiens ribosomal protein L7 (RPL7), mRNA [NM_000971] |
| 748 | A_32_P335445 | HINT1 | GTGATACCCAAGAAACATATATCCAGATTTCTGTGGACAAGAT GATCATGAAAGTCTT | SEQ ID NO: 2329 | Homo sapiens histidine triad nucleotide binding protein 1 (HINT1), mRNA [NM_005340] |
| 749 | A_32_P36101 | ARL1 | CTATTCAAACACAGATGCAGTCATTTATGTAGTAGAACAGTTGTGA CCGAGACCGAATTGG | SEQ ID NO: 2330 | Homo sapiens ADP-ribosylation factor-like 1 (ARL1), mRNA [NM_001177] |
| 750 | A_32_P43217 | PSMA6 | TTGTTGTTAGTTTAGCAGATCCGTGATGCCAGTTACCTGTGTGTT TGGTAACAACAACA | SEQ ID NO: 2331 | Homo sapiens proteasome (prosome, macropain) subunit, alpha type, 6 (PSMA6), mRNA [NM_002791] |
| 751 | A_32_P4532 | LOC643932 | GATTCCAGAGAGCAGGCATTGGAAAAGACATAGAAAAAGGCTTGCCAATC TATGCTCTCCATGAT | SEQ ID NO: 2332 | PREDICTED: Homo sapiens similar to 40S ribosomal protein S3a (V-fos transformation effector protein) (LOC643932), mRNA [XR_017289] |
| 752 | A_32_P49164 | AV714556 | AAATGCAGAGTTTGTTATTTGCCAAAGAAGAATTCATCATGTTCCT TCCTTTCTTTTTCCC | SEQ ID NO: 2333 | AV714556 AV714556 DCB Homo sapiens cDNA clone DCBAD606 5', mRNA sequence [AV714556] |
| 753 | A_32_P49392 | A_32_P49392 | AATTCTGCCAAATCTGGAAGAACATGATGGAAATCATGACCCAAG AGGTGCAGACAAATG | SEQ ID NO: 2334 | |
| 754 | A_32_P54305 | LOC401397 | AGAATGTTAGGAAATCACCACTGTTCGGTTATATAATCACTGCCTC TGAATGCTTGAGGAG | SEQ ID NO: 2335 | Homo sapiens hypothetical LOC401397, mRNA (cDNA clone IMAGE:4244115), complete cds. [BC107860] |
| 755 | A_32_P58074 | RPS3A | GTTGGTTTACTAAAAAACGCAAAAATCAGATACGGAAGAGCTGT TATGCTCAGGACAA | SEQ ID NO: 2336 | Homo sapiens ribosomal protein S3A (RPS3A), mRNA [NM_001006] |
| 756 | A_32_P61857 | KIAA1468 | TCAGTGTACAGTTCGACTGGAATTTGACAGTTGTCTCTACAGTCA TGCAACTCGAAGTAG | SEQ ID NO: 2337 | Homo sapiens KIAA1468 (KIAA1468), mRNA [NM_020854] |
| 757 | A_32_P68686 | ARL1 | TTGGGTTAGGTGCGTTGAAGGACCGAAAATGGCAGATATTCAAAA CGTCAGGCAACCAAAG | SEQ ID NO: 2338 | Homo sapiens ADP-ribosylation factor-like 1 (ARL1), mRNA [NM_001177] |
| 758 | A_32_P7118 | PSMC6 | AGCAGACCTGAGAAATTTGTACTGAAGCAGGTATGTTGGCAAT TCGTGCTGATGATGA | SEQ ID NO: 2339 | Homo sapiens proteasome (prosome, macropain) 26S subunit, ATPase, 6 (PSMC6), mRNA [NM_002806] |

Fig. 5-41

| No. | Probe ID No. | Symbols of genes | Sequence | SEQ ID NO: | Descriptions of genes (letters and numbers within [ ] indicates GenBank accession No.) |
|---|---|---|---|---|---|
| 759 | A_32_P73222 | AA631847 | TTTCTTGTTTTGGACAATCTCATAAGAAGTTTAGGTCTTACAGC ACGAACGCGTGGAAG | SEQ ID NO: 2340 | np61b02.s1 NCI_CGAP_Br2 Homo sapiens cDNA clone IMAGE:1130763 3' similar to TR:G971838 G971838 60S RIBOSOMAL PROTEIN L34 ; mRNA sequence [AA631847] |
| 760 | A_32_P77102 | BC042469 | AAATGTGAAGTCTGGCTTGAAGAGGGTGTATAAGACACATAATT TACTGTGCATCAGTC | SEQ ID NO: 2341 | Homo sapiens, clone IMAGE:5198554, mRNA. [BC042469] |
| 761 | A_32_P81768 | TMEM167 | CCTCAGTACTGTGACTACAGTATTACATTCTGCAAATGTTATTCT GTTGTATGAAGATACG | SEQ ID NO: 2342 | Homo sapiens transmembrane protein 167 (TMEM167), mRNA [NM_174909] |
| 762 | A_32_P83784 | CENTD1 | ACAGGCCCATACTTCAGTCAGTCGAATCATAGTACAGTGATGTGG TGGTAGATGCTATGA | SEQ ID NO: 2343 | Homo sapiens centaurin, delta 1 (CENTD1), transcript variant 1, mRNA [NM_015230] |
| 763 | A_32_P86400 | LYSMD3 | AAATGTTGCTCAGGTAATCAGTATTTCTTCCACGTATGTGGATA TTGGACTGTTAGATC | SEQ ID NO: 2344 | Homo sapiens LysM, putative peptidoglycan-binding, domain containing 3 (LYSMD3), mRNA [NM_198273] |
| 764 | A_32_P86494 | A_32_P86494 | TGAGCCTTGCCTGCCACATTGAGATGCTTACTGAAAAGGAAC AGATTGTTCCTAAAC | SEQ ID NO: 2345 | |
| 765 | A_32_P8857 | A_32_P8857 | TAATGTCGGAAATGGTACACACTGTTTCTGTAAAGTGACATCTTTC AGATACTTGGTGGCT | SEQ ID NO: 2346 | |
| 766 | A_32_P93782 | RPL26 | AGGTGTACATGGACAGCTATAAAGGTCAGCAAATTGGCAAAGTAG TCCAGGTTTACAGA | SEQ ID NO: 2347 | Homo sapiens ribosomal protein L26 (RPL26), mRNA [NM_000987] |
| 767 | A_32_P9382 | RP11-11C5.2 | AACAAAGCAGGAAAATATATTGAGAAGGGATCGTGTTACAGAGG ACTTGTTTAAAGTGT | SEQ ID NO: 2348 | Homo sapiens similar to RIKEN cDNA 2410129H14 (LOC440145), mRNA [NM_001071775] |
| 768 | A_32_P96134 | DPY19L1 | ATAACTGCTTCATTTGCTGGGAACCATTACAAGTAGTATAAATTA GCTTTTTCCAGAAGG | SEQ ID NO: 2349 | Homo sapiens DPY-19-like protein 1 (DPY19L1) mRNA, complete cds. [DQ287932] |
| 769 | A_32_P96213 | TPT1 | GAAAGCACAGTAATCACTGCTGTGATGTTCTCATGAACCATCAC CTGCAGGAAACAAGT | SEQ ID NO: 2350 | Homo sapiens tumor protein, translationally-controlled 1 (TPT1), mRNA [NM_003295] |
| 770 | A_32_P96933 | AL571926 | GAGCCTGACAAATGTTCTCGGATGTAACAGTATGAACACCTATGAG CTGGGACTACTTCTG | SEQ ID NO: 2351 | AL571926 Homo sapiens PLACENTA COT 25-NORMALIZED Homo sapiens cDNA clone CS0D1029Y06 3-PRIME, mRNA sequence [AL571926] |
| 771 | A_32_P98313 | NDUFA4 | AGCCCGTGAACAAACTGGGTCCCAATGATGAATACAAGTTCTGCT CAGTGAATGTGGATT | SEQ ID NO: 2352 | Homo sapiens NADH dehydrogenase (ubiquinone) 1 alpha subcomplex, 4, 9kDa (NDUFA4), nuclear gene encoding mitochondrial protein, mRNA [NM_002489] |

Fig. 6-1

| No. | Probe ID No. | Symbols of genes | Sequence | SEQ ID NO. | [description] |
|---|---|---|---|---|---|
| 1 | A_23_P143247 | TSHZ2 | TTGCAAGAGCAGTAGGAATCTGTAATTCTTAAGTTACGGAACAGTCTCAA TGAATCACTATAATCA | SEQ ID NO: 1593 | Homo sapiens teashirt family zinc finger 2 (TSHZ2), mRNA [NM_173485] |
| 2 | A_23_P94938 | NOG | GCAGAGCTGCTGGGTGGATTTGAATAACATCCAGTAGGCCATAATTCC AATCCAAATTGTCGT | SEQ ID NO: 1601 | Homo sapiens noggin (NOG), mRNA [NM_005450] |
| 3 | A_23_P653158 | ANKRD15 | TTTACCGTTTCACTTTCATTTGTGGTTTATGTATTAAATT | SEQ ID NO: 1611 | Homo sapiens ankyrin repeat domain 15 (ANKRD15), transcript variant 1, mRNA [NM_153186] |
| 4 | A_23_P4399 | CNTNAP2 | CTTAGCCATTCTAAAATAACAGAGAATTGGGAGGGG | SEQ ID NO: 1614 | Homo sapiens contactin associated protein-like 2 (CNTNAP2), mRNA [NM_014141] |
| 5 | A_24_P909963 | IMAGE | CCAATGAATACATATG GCCCATTCAAGATAGCAGAGAAAAATTGCTCTTAAAT | SEQ ID NO: 1644 | Homo sapiens cDNA clone IMAGE:5284679 [BC040600] |
| 6 | A_24_P111934 | THC2643957 | AAGTATAGGTAAAAC | SEQ ID NO: 1651 | |
| 7 | A_32_P208682 | THC2663497 | CAATGTTAAGCCAATATCAAGTCCTTTTTGAAGAATTTGAA AAGGTATTTGGTGAT | SEQ ID NO: 1626 | ALU1_HUMAN (P39188) Alu subfamily J sequence contamination warning entry, partial (5%) [THC663167] |
| 8 | A_32_P213569 | THC2665836 | GATTTTTCAATGTTGACCCTTTTAATGAAAATTCTCAAC ACGTAAGTGGAAAA | SEQ ID NO: 1680 | |
| 9 | A_32_P227110 | THC2612340 | TAAGCAATTGGATCTTTGATTTGCCATCTGTATTAATGAC TTATTATTATAACTCA | SEQ ID NO: 1684 | |
| 10 | A_23_P26930 | PSMC6 | GAAGAAGAAATTTAAGACTAGACACTACAAATGAACGAAGCTCCAT TACAAAGCATGGTAAA | SEQ ID NO: 1737 | Homo sapiens proteasome (prosome, macropain) 26S subunit, ATPase, 6 (PSMC6), mRNA [NM_002806] |
| 11 | A_23_P134925 | BNIP3L | ATTGTTATTTCAGTGTATATTAGATATTGATATTCAAGT AAAGTCATTGGTCCCAA | SEQ ID NO: 1746 | Homo sapiens BCL2/adenovirus E1B 19kDa interacting protein 3-like (BNIP3L), mRNA [NM_004331] |
| 12 | A_23_P137380 | C1QB | TGTAGTATCCATATGTGGTTAAATTTGTTATGCGCCCATCA TTTTTCCGGTTTGC | SEQ ID NO: 1750 | Homo sapiens complement component 1, q subcomponent, B chain (C1QB), mRNA [NM_000491] |
| 13 | A_23_P107404 | RNF11 | TGTAGTATTCAATATGTGGTTAAATTTGTTATGCGCCCGATGA TCAAAACATTTAAAA | SEQ ID NO: 1751 | Homo sapiens ring finger protein 11 (RNF11), mRNA [NM_014372] |
| 14 | A_23_P143368 | RPL22L1 | ATTTATTTCTAGATTA GATTATTTTGAGATTA | SEQ ID NO: 1757 | Homo sapiens cDNA clone IMAGE:4552860 [BC040479] |
| 15 | A_23_P144487 | RPS3A | CGAAATCCAAAGAACAATTGAAATCATGAGCGAAGAAGTTGA AGAAAACATGATTGAA | SEQ ID NO: 1763 | Homo sapiens ribosomal protein S3A (RPS3A), mRNA [NM_001006] |
| 16 | A_23_P14706 | SH3HW4 | TCTTTGTTAGGTGATACAAATGTTTAGCGTGCCAGGGGTGTAGACT TAGGTAATTAAACT | SEQ ID NO: 1766 | Homo sapiens suppressor of hairy wing homolog 4 (Drosophila) (SUHW4), transcript variant 1, mRNA [NM_019105] |
| 17 | A_23_P14734 | RPS27L | TACAAATCAGCAGCTTTTTCATTTGAAGGTATGTCATGCAAGAAACTTG TAGTTAATTAAACT | SEQ ID NO: 1769 | Homo sapiens ribosomal protein S27-like (RPS27L), mRNA [NM_015920] |
| 18 | A_23_P163662 | BCL2A1 | CTCGCATTTCTTTTA GTACCAAGCAAATTGC TACGACAAGCAAAATTCC | SEQ ID NO: 1775 | Homo sapiens BCL2-related protein A1 (BCL2A1), mRNA [NM_004049] |
| 19 | A_23_P168842 | EEF1E1 | AAGGATAAATGAAAATTTCAGAGGTAGGTCAGCAAGCAAGAAACTGG CAAGTTAATGGCACT | SEQ ID NO: 1778 | Homo sapiens eukaryotic translation elongation factor 1 epsilon 1 (EEF1E1), mRNA [NM_004280] |

Fig. 6-2

| No. | Probe ID No. | Symbols of genes | Sequence | SEQ ID NO: | Descriptions of genes (letters and numbers within [ ] indicates GenBank accession No.) |
|---|---|---|---|---|---|
| 20 | A_23_P157449 | POLR2K | GGTCTCTGTTGCTTCAAATATGTTCTTGTACAGTAGTCACCAT TTTAGATGTTGGTTGAC | SEQ ID NO: 1779 | Homo sapiens polymerase (RNA) II (DNA directed) polypeptide K, 7.0kDa (POLR2K), mRNA [NM_005034] |
| 21 | A_23_P157452 | POLR2K | GGGAATGTCTTCAGTTATACTTGGATTTGCTCGTCTCTCCGATTCT GATTGTTGTATAGGTT | SEQ ID NO: 1780 | Homo sapiens polymerase (RNA) II (DNA directed) polypeptide K, 7.0kDa (POLR2K), mRNA [NM_005034] |
| 22 | A_23_P159650 | COX7B | CAAATACGGTAATGCTGTATTAGCTAGTGGAGGCAGTTCTGTA TTGTTACATGGACATA | SEQ ID NO: 1782 | Homo sapiens cytochrome c oxidase subunit VIIb (COX7B), nuclear gene encoding mitochondrial protein, mRNA [NM_001866] |
| 23 | A_23_P162596 | ACTR6 | TTAACGGCTTCACTGGACAGTTTCTTAAGAAGGTAGTTTTGTG TGAGTGTGACTAAAGT | SEQ ID NO: 1787 | Homo sapiens ARP6 actin-related protein 6 homolog (yeast) (ACTR6), mRNA [NM_022496] |
| 24 | A_23_P170233 | CSTA | AAGTGGCTACTGAGTGATGATCCTTGCTGATAAATATAACCATC AATAAAGAAGCATTCT | SEQ ID NO: 1794 | Homo sapiens cystatin A (stefin A) (CSTA), mRNA [NM_005213] |
| 25 | A_23_P18325 | PDCD10 | CCAACCGACTAATTCATCAAAACGAACTTAATACTTCAGACGTTG AAAAGTGTGGCCTGAA | SEQ ID NO: 1795 | Homo sapiens programmed cell death 10 (PDCD10), transcript variant 1, mRNA [NM_007217] |
| 26 | A_23_P19291 | TUBB2A | ACTTCTGAGATCAATGGTGCATCGTAGTGAACTTCTGTTGTCC TCAAGCATGTCTCTGAT | SEQ ID NO: 1798 | Homo sapiens tubulin, beta 2A (TUBB2A), mRNA [NM_001069] |
| 27 | A_23_P200955 | A_23_P200955 | AGACCATGATTGAACCTCAGATTGATGTCAAGATACGGATGGT TATTTGTTTGATCTAC | SEQ ID NO: 1802 | |
| 28 | A_23_P215751 | NDUFA5 | TAAAAGTGGAGTGACTAAATATTTGGAGTAGGTTTCTAATATA AGTGTAGGTGGGTATC | SEQ ID NO: 1831 | Homo sapiens NADH dehydrogenase (ubiquinone) 1 alpha subcomplex, 5, 13kDa (NDUFA5), nuclear gene encoding mitochondrial protein, mRNA [NM_005000] |
| 29 | A_23_P217797 | DDX3Y | CACTGATAGGAAGGTCAGATCCACAAAGTTCTGTCTGAGTTTT GTTATGTTGTTTGGTG | SEQ ID NO: 1836 | Homo sapiens DEAD (Asp-Glu-Ala-Asp) box polypeptide 3, Y-linked (DDX3Y), mRNA [NM_004660] |
| 30 | A_23_P218928 | C4orf18 | CAGAGTAGTTCATTTGCTCTGTGTAGATGTTGTTTCAGAGCTAGG TACAGAGGAATGTTTG | SEQ ID NO: 1837 | Homo sapiens chromosome 4 open reading frame 18 (C4orf18), transcript variant 2, mRNA [NM_016613] |
| 31 | A_23_P252201 | EAF2 | CAGGATTCGTGATAATAGATGGCAGTGATCATAATAGATTCGAGACA ACAGTGGCCTTCTGAT | SEQ ID NO: 1853 | Homo sapiens ELL associated factor 2 (EAF2), mRNA [NM_018456] |
| 32 | A_23_P25235 | CLEC4D | GATTTAACCACCACGAGAGTATTCTGGCATAAGAATGAAACCGAC AACTCTCAGGGAGAA | SEQ ID NO: 1854 | Homo sapiens C-type lectin domain family 4, member D (CLEC4D), mRNA [NM_080387] |
| 33 | A_23_P26021 | COPS2 | TGCTTTTTGATCAACTGGTTGTGTTTGTCTGCTGCATTTATC CCAAGAAAAACAGGTT | SEQ ID NO: 1869 | Homo sapiens COP9 constitutive photomorphogenic homolog subunit 2 (Arabidopsis) (COPS2), mRNA [NM_004236] |
| 34 | A_23_P2705 | P2RY5 | TCTGTATGCTGTTTCCAACTGTGTTGTTTGACCCTATAGTTTAC TACTTTACATCGGACA | SEQ ID NO: 1871 | Homo sapiens purinergic receptor P2Y, G-protein coupled, 5 (P2RY5), mRNA [NM_005767] |
| 35 | A_23_P302550 | RGS18 | GAGTCTAAGGACGCTAGGGATTTGGGGATCTGCCACATTGGTTCA TATTCAGAAAGTGTTA | SEQ ID NO: 1873 | Homo sapiens regulator of G-protein signalling 18 (RGS18), mRNA [NM_130782] |
| 36 | A_23_P307940 | CAPZA2 | CTACAAGATTGGCAAAGAGATGCAGAATGGATAAGAATGAAACATT GGCTGACCGGATCAT | SEQ ID NO: 1876 | Homo sapiens capping protein (actin filament) muscle Z-line, alpha 2 (CAPZA2), mRNA [NM_006136] |
| 37 | A_23_P312246 | CCDC82 | GGGCTTTATAACAGATGACTGTGAAGTGAATGACCTGTTGATATC GTGTCAGTTTAGTCAA | SEQ ID NO: 1880 | Homo sapiens coiled-coil domain containing 82 (CCDC82), mRNA [NM_024725] |
| 38 | A_23_P33045 | RPL26 | TACAAAGGTCAGCAAAATTGGCAAAGTAGTCCAGGTTACAGGAG GAAATATGTTATCTAC | SEQ ID NO: 1890 | Homo sapiens ribosomal protein L26 (RPL26), mRNA [NM_000987] |

Fig. 6-3

| No. | Probe ID No. | Symbols of genes | Sequence | SEQ ID NO: | Descriptions of genes (letters and numbers within [ ] indicates GenBank accession No.) |
|---|---|---|---|---|---|
| 39 | A_23_P339480 | HAT1 | AACATGAACAGCTGGAAGAGAGTTTTCAAGAAGTAGTGGAAGATTACGGGCGTGTTATTG | SEQ ID NO: 1892 | Homo sapiens histone acetyltransferase 1 (HAT1), transcript variant 1, mRNA [NM_003642] |
| 40 | A_23_P347059 | MOBKL1A | CTAGAAGGGAAAAATCATCTAAGTTATGAAATCCAACAATAGCCGCTATATTAGAAACTG | SEQ ID NO: 1896 | Homo sapiens MOB1, Mps One Binder kinase activator-like 1A (yeast) (MOBKL1A), mRNA [NM_173468] |
| 41 | A_23_P41114 | CSTA | AAACAAATGAGACTTATGGAAAATTGGAAGCTGTGTGAGTATAAAACTCAAGTTGTTGCTG | SEQ ID NO: 1925 | Homo sapiens cystatin A (stefin A) (CSTA), mRNA [NM_005213] |
| 42 | A_23_P44257 | COMMD8 | AACATTTTACTTCTGCGCTTCGTCTGTATGTTTGGGAAACAATTGGTCTGATAAAAATAGGTGTC | SEQ ID NO: 1942 | Homo sapiens COMM domain containing 8 (COMMD8), mRNA [NM_017845] |
| 43 | A_23_P501276 | TUBB2A | GTGGACGAGCAGATGTCAACGTGCAGAACAAGAAGAGACAGCTACTTGGTGGAGTGGATC | SEQ ID NO: 1950 | Homo sapiens tubulin, beta 2A (TUBB2A), mRNA [NM_001069] |
| 44 | A_23_P50907 | ITGAV | AAAGAGTGATTAAGTGAGGTTATTACCCCTAAATGGTCATTCTGCATTGTATTTCAGG | SEQ ID NO: 1953 | Homo sapiens integrin, alpha V (vitronectin receptor, alpha polypeptide, antigen CD51) (ITGAV), mRNA [NM_002210] |
| 45 | A_23_P56734 | HNMT | CGTTTTGTCCACCATGGAATATATCGTGACTGCTGTTTATTGGTAATGAAATGGAGACCT | SEQ ID NO: 1962 | Homo sapiens histamine N-methyltransferase (HNMT), transcript variant 1, mRNA [NM_006895] |
| 46 | A_23_P59921 | SUB1 | CAGATTGGGAAATGACGTAGTTGTTCGGGATTTTAAAGGCAAAGTGGCTAATTGAT | SEQ ID NO: 1970 | Homo sapiens SUB1 homolog (S. cerevisiae) (SUB1), mRNA [NM_006713] |
| 47 | A_23_P65768 | C15orf15 | TCCTGCATTGGCATCTACATATATCAGATATATGGGATGTTAGATTGCATGTCAGTGTT | SEQ ID NO: 1977 | Homo sapiens chromosome 15 open reading frame 15 (C15orf15), mRNA [NM_016304] |
| 48 | A_23_P66260 | ZNF267 | TGTATGAATGTGGTAAAGCCTTCAGGTATAGGTCATACGTCACTACACATCGGAGAAGT | SEQ ID NO: 1978 | Homo sapiens zinc finger protein 267 (ZNF267), transcript variant 498723, mRNA [NM_003414] |
| 49 | A_23_P70328 | CENPQ | CAATGGCTTACAGTTTCTGTCTGGTCATCTGGAACTTGAAAATCCTCAAATGCCTTCAC | SEQ ID NO: 1985 | Homo sapiens centromere protein Q (CENPQ), mRNA [NM_018132] |
| 50 | A_23_P7221 | RPL34 | CGAGGACGAGAAAATCGGTTGATGAAAGTGTTGAAGGCACAAGCACAGAGTCAGAAAGCTAA | SEQ ID NO: 1990 | Homo sapiens ribosomal protein L34 (RPL34), transcript variant 2, mRNA [NM_033625] |
| 51 | A_23_P7229 | RPL34 | CGAACCCTGGTTAATAGAATTGTTTACCTTTATACGAAGAAGGTTGGGAAAGCACGAAGA | SEQ ID NO: 1991 | Homo sapiens ribosomal protein L34 (RPL34), transcript variant 2, mRNA [NM_033625] |
| 52 | A_23_P75769 | MS4A4A | CACCAAAGATCAAGCAGCAGACAAATGCTCCAGAAATCTATGGTGACTGTGACACAGAGACCT | SEQ ID NO: 2000 | Homo sapiens membrane-spanning 4-domains, subfamily A, member 4 (MS4A4A), transcript variant 1, mRNA [NM_024021] |
| 53 | A_23_P78092 | EVI2A | GCTGAATCAGAGCACTTGGAAAABAACAAAACAGGTCACAGGACGCAACCTAGTGATGCAA | SEQ ID NO: 2004 | Homo sapiens ecotropic viral integration site 2A (EVI2A), transcript variant 1, mRNA [NM_001003927] |
| 54 | A_23_P83278 | CHMP5 | CATTGCTTCTTTATTTTTCCATTAAGAGAGTCATTGCTTGGGAAATGCTTCGTAC | SEQ ID NO: 2007 | Homo sapiens chromatin modifying protein 5 (CHMP5), mRNA [NM_016410] |
| 55 | A_23_P87879 | CD69 | TGTGCAATATGTGATGTGGGAAGCCCAAGAAATATCTGTATTAGGAAATATTCTGTAATCTTCAGACCTAG | SEQ ID NO: 2011 | Homo sapiens CD69 molecule (CD69), mRNA [NM_001781] |
| 56 | A_23_P94230 | LY96 | TGAAGCTATTTCTGGGAGGAAACCCAGAAATGCTCTTTGGTTGGAGTTTGTCATCCTACA | SEQ ID NO: 2018 | Homo sapiens lymphocyte antigen 96 (LY96), mRNA [NM_015364] |
| 57 | A_23_P94501 | ANXA1 | GGCTGTTTGTTGGGAGGAAAGTAAACATTCCCTTGATGGTCTCAAGCTATGATCAGAAGACT | SEQ ID NO: 2019 | Homo sapiens annexin A1 (ANXA1), mRNA [NM_000700] |

Fig. 6-4

| No. | Probe ID No. | Symbols of genes | Sequence | SEQ ID NO: | Descriptors of genes (letters and numbers within [ ] indicates GenBank accession No.) |
|---|---|---|---|---|---|
| 58 | A_23_P96658 | CYorf15B | ATGCCCTAAAGTTAATACAGCAGTCATATTTTATCAGATGTAAATCTGGATGTAAGGTC | SEQ ID NO: 2023 | lipopolysaccharide-specific response 5-like protein [Source:RefSeq_peptide;Acc:NP_115965] [ENST00000382832] |
| 59 | A_24_P11045 | THC2785765 | CCACCAGAAACGTAGACGTGATTTTCATGACAAATACGGTAGGAACACAAGTCGGAATAG | SEQ ID NO: 2032 | COX7B_HUMAN (P24311) Cytochrome c oxidase polypeptide VIIb, mitochondrial precursor partial (78%) [THC2785765] |
| 60 | A_24_P135551 | LOC130865 | TAACAGGATAGGTGTCCGTGTGGGCATTGACCGAAAGGTGGTTATCACTAGACTAAAACT | SEQ ID NO: 2046 | PREDICTED: Homo sapiens similar to 60S ribosomal protein L26 (Silica-induced gene 20 protein) (SIG-20) (LOC130865), mRNA [XR_019454] |
| 61 | A_24_P144636 | LOC401975 | TGTCGATGTCAAGACTAATGATGGCTACTTCTTTAATCTGTTCTGTGTTGGTTTTACTGA | SEQ ID NO: 2050 | PREDICTED: Homo sapiens similar to ribosomal protein S3a (LOC401975), mRNA [XR_017247] |
| 62 | A_24_P153324 | LOC390413 | GAAGGTTAAGAAGGTTCAATTAACATGCTGGGGATTGTAGAACCATATATTGCAGGGTA | SEQ ID NO: 2054 | PREDICTED: Homo sapiens similar to 60S ribosomal protein L7 (LOC390413), mRNA [XR_018341] |
| 63 | A_24_P188878 | RPL34 | TGTTACGTTTATACCAAGAAGGTTGGGAAAGCAGCAAAATCTGCATGTGGTGTGTGCCC | SEQ ID NO: 2077 | Homo sapiens ribosomal protein L34, mRNA [NM_033625] transcript variant 2, mRNA [NM_033625] |
| 64 | A_24_P201702 | CLEC2B | ATTGGAATTCAAGTAAATAGAACTGTTCACTGCAAACATGCCGAACCTAACTATAATTGACA | SEQ ID NO: 2085 | Homo sapiens C-type lectin domain family 2, member B (CLEC2B), mRNA [NM_005127] |
| 65 | A_24_P203909 | RPL34 | GAGGGGTTCGTGCTGTAAGACTTAAAGTGTTATGAAATTGTCCAAAACAAAGAAACATG | SEQ ID NO: 2088 | Homo sapiens ribosomal protein L34 (RPL34), transcript variant 2, mRNA [NM_033625] |
| 66 | A_24_P221375 | A_24_P221375 | TACTTTGGTTACCCATGTACCTACGGAGTTTGAAAAATCTACAGAGAGTCAATGTCGGAGGA | SEQ ID NO: 2095 | |
| 67 | A_24_P237511 | EIF1AY | GTTTCAGTTACTTAGATGCTCTACATAAGGTTCTGATACAATTTGAAGAGAAATCTGC | SEQ ID NO: 2105 | Homo sapiens eukaryotic translation initiation factor 1A, Y-linked (EIF1AY), mRNA [NM_004681] |
| 68 | A_24_P288604 | LOC731599 | GATGGAAATCATGACGAGAGGTGCGGCAAATGACTTGAAAGAATTGGTCAATAAAATGAT | SEQ ID NO: 2126 | Homo sapiens hypothetical protein LOC731599 (LOC731599), mRNA [XR_015536] |
| 69 | A_24_P303118 | RPL34 | CGAGGACCAGAAAATCGTTGTGAAGATGTTGAAGGCACAAGCACAGAGTCAGAAAGCTAA | SEQ ID NO: 2128 | Homo sapiens ribosomal protein L34 (RPL34), transcript variant 2, mRNA [NM_033625] |
| 70 | A_24_P306527 | ENST00000308989 | ACCGCATCCGGTGCGTGGTTATGCAGAGAAATGTAATGAGGATGAAGATTGACGAAATAAGT | SEQ ID NO: 2132 | PREDICTED: Homo sapiens similar to ribosomal protein L31 (LOC729005), mRNA [XM_001133428] |
| 71 | A_24_P320328 | SUB1 | CAGAAAAAGCTGTAAAGAACAAAAGAGAGGTGAGACTTCGAGAGCCCTGTCATCTTCTA | SEQ ID NO: 2138 | Homo sapiens SUB1 homolog (S. cerevisiae) (SUB1), mRNA [NM_006713] |
| 72 | A_24_P324224 | A_24_P324224 | AAAGCTGTCTGGGCCAAAGGAATAAGGAATTCCTATAGGCATGTGCCGGTTGTCCAGAAAA | SEQ ID NO: 2140 | |
| 73 | A_24_P33213 | A_24_P33213 | GACGATATATTACATGGGGGTACCCAAATCTGAAGTCAGTAAATGAACTTATCTACAAGG | SEQ ID NO: 2143 | |
| 74 | A_24_P333112 | A_24_P333112 | GGTCATCAGAATCAGAGGTATCAATCAATGTGTGAAGCCACAAGGACCAAAAGGTATTGCAACT | SEQ ID NO: 2144 | |
| 75 | A_24_P33607 | LOC652558 | TAAGAAAATAATTGCTTTGGACAGAGAACACGCTTTGATTGCTCGATCTCTTGGTAATATGG | SEQ ID NO: 2145 | PREDICTED: Homo sapiens similar to 60S ribosomal protein L7 (LOC652558), mRNA [XR_019386] |
| 76 | A_24_P349636 | LOC388401 | AGTTGCTTCGACAGATAACACAGTTTGATTGGTGGATCTCTTGGTAAATATAGGATCAAGTG | SEQ ID NO: 2147 | PREDICTED: Homo sapiens similar to 60S ribosomal protein L7 (LOC388401), mRNA [XR_016679] |

Fig. 6-5

| No. | Probe ID No. | Symbols of genes | Sequence | SEQ ID NO: | Descriptions of genes (letters and numbers within [ ] indicates GenBank accession No.) |
|---|---|---|---|---|---|
| 77 | A_24_P366546 | RPL31P10 | CGGGTGTCGAGAAAACGTAATGAGGATGAAGATTCAAATAAGCTCTATACTTTGGTTAGG | SEQ ID NO: 2158 | PREDICTED: Homo sapiens similar to ribosomal protein L31 (LOC390283), mRNA [XR_018695] |
| 78 | A_24_P367191 | LOC652890 | AGTTAACATGCTGAGGACTGTAGAGCCATATATTGCCTGTGGGTACCGAAATCTGAAGTC | SEQ ID NO: 2160 | PREDICTED: Homo sapiens similar to 60S ribosomal protein L7 (LOC652890), mRNA [XR_019544] |
| 79 | A_24_P367199 | A_24_P367199 | TCTTATGCTCGAGCGACGACAGTCTGCCAAATCGAGAAGAAGGTGTAATCATGACCTGAGA | SEQ ID NO: 2161 | |
| 80 | A_24_P381625 | PSMC6 | ATGAAAGCAGTCAGAAAAGTGGCTGATTGTAAGAAGCTGGAGTGTAAATTGGAGTACAAA | SEQ ID NO: 2173 | Homo sapiens proteasome (prosome, macropain) 26S subunit, ATPase, 6 (PSMC6), mRNA [NM_002806] |
| 81 | A_24_P383999 | RPS3A | TGGTTTTACTAAAAACGGAACAATGAGATACAGAAGAGCCTCTATGCCCAGCACCAAGG | SEQ ID NO: 2175 | Homo sapiens ribosomal protein S3A (RPS3A), mRNA [NM_001006] |
| 82 | A_24_P384411 | A_24_P384411 | ATGGCAAAATCAATAAGAGTGAAGGTTTGACAGATAATGCTTTGACACGCTCGATCTGTG | SEQ ID NO: 2176 | |
| 83 | A_24_P392900 | A_24_P392900 | GTCTGTTCTGTGTTGGTTTTCCTAAAAACAATGTAACAATCCGAAAAACGTTTTATGTC | SEQ ID NO: 2180 | |
| 84 | A_24_P414556 | TTC33 | TACTCAACATTTGGTATATTGTTTGAGTAATGAATGGATGTTTGCTTTTTGTGTAATTTGTGA | SEQ ID NO: 2191 | Homo sapiens tetratricopeptide repeat domain 33 (TTC33), mRNA [NM_012382] |
| 85 | A_24_P41551 | LOC641790 | AAGGAGAATGGGAACTCCTGATGTGCCATTGATATGAGGCACAACAAAGTAGTCGGAAA | SEQ ID NO: 2193 | PREDICTED: Homo sapiens similar to ribosomal protein L31 (LOC641790), mRNA [XR_018025] |
| 86 | A_24_P50437 | BC065737 | TGCAGAATGATGAAGTTGGCATTAGAAAAATTCCTGATTAGTGAAGATGTTCAGGGCAAAA | SEQ ID NO: 2198 | Homo sapiens cDNA clone IMAGE:30404477, partial cds. [BC065737] |
| 87 | A_24_P57837 | THC2567891 | ACAAATCCGGAAGACGTCTTATCTCAGTACGAGCCAAATCCGGAAGAAGATGAGAA | SEQ ID NO: 2207 | Q6NXR8_HUMAN (Q6NXR8) Ribosomal protein S3a, partial (91%) [THC2567891] |
| 88 | A_24_P606663 | LOC392030 | TGTGCGGTTGCCGAGAAAAACGTAATGCTGGGTGAAGATTCACCAAATAAGCTCATAGTTT | SEQ ID NO: 2209 | PREDICTED: Homo sapiens hypothetical LOC392030 (LOC392030), mRNA [XR_018063] |
| 89 | A_24_P63347 | PF4V1 | CTACATATTTACCTTGAATGTAGAATTAGCTGCCAATAAATATTAGTAGCTGTTAAGC | SEQ ID NO: 2213 | Homo sapiens platelet factor 4 variant 1 (PF4V1), mRNA [NM_002620] |
| 90 | A_24_P685729 | A_24_P685729 | TTGAAGCTTATGTTGATGTCAAGACTATCAGTGATTATTGCTTGTCTGTTTTGTGTGG | SEQ ID NO: 2217 | |
| 91 | A_24_P6975 | LOC342994 | GGAAGAGTTCGAGGGGTTCGTGCTGTAAGACGTAAAGTTCTTATGAAATTGTCAAAAGA | SEQ ID NO: 2218 | PREDICTED: Homo sapiens similar to ribosomal protein L34 (LOC342994), mRNA [XM_938484] |
| 92 | A_24_P755605 | A_24_P755605 | ATACAGAAGAGCCTCTTATGCTCAGCACCAAGCAACAAGAGAAAAGTAAAAATGCTGAAGAAGCCCAA | SEQ ID NO: 2223 | |
| 93 | A_24_P792734 | PSMC6 | AGAAACGTTAACGGAGTTAACGTAGTCAAATCAAATGGAATTGATACTCTGCATAGAGTTAAA | SEQ ID NO: 2227 | Homo sapiens proteasome (prosome, macropain) 26S subunit, ATPase, 6 (PSMC6), mRNA [NM_002806] |
| 94 | A_24_P84808 | LOC729449 | GAATTGCTTTGACAGATAACGGCTTTGGATCTCGTTGGAAAATATGGCATCATCTGTATGG | SEQ ID NO: 2233 | PREDICTED: Homo sapiens similar to 60S ribosomal protein L7 (LOC729449), mRNA [XR_015548] |
| 95 | A_24_P941643 | PLCB1 | ATGATGTGCAGTTTTGTGCCTTTAATGTATTTGGCTTGTCTGTTCTTTGTCGAATGTGAAATT | SEQ ID NO: 2247 | Homo sapiens phospholipase C, beta 1 (phosphoinositide-specific) (PLCB1), transcript variant 2, mRNA [NM_182734] |
| 96 | A_32_P107717 | BX100535 | TCTTGTGCACCCAAGATCTGCTCTCTGTTGTTAAATCGTGTTCAGACCTGGTCTAATTGGT | SEQ ID NO: 2255 | BX100535 Soares_testis_NHT Homo sapiens cDNA clone IMAGp998I094457, mRNA sequence [BX100535] |

Fig. 6-6

| No. | Probe ID No. | Symbols of genes | Sequence | SEQ ID NO: | Descriptions of genes (letters and numbers within [ ] indicates GenBank accession No.) |
|---|---|---|---|---|---|
| 97 | A_32_P109653 | THC2669092 | TGTGGTTTGGTATTCGAAGTGGGGTGTTTTTGAGAATGTCTGCACTATGTGTGAGATGCAA | SEQ ID NO: 2257 | |
| 98 | A_32_P113154 | LOC730861 | ACCACCAGTCCAAGAGAATCTGTTAAAGTTCAGACTTAAAACAGTACCAAATAAAAAGTCC | SEQ ID NO: 2258 | PREDICTED: Homo sapiens similar to 40S ribosomal protein S3a (v-fos transformation effector protein) (LOC730861), mRNA [XR_015591] |
| 99 | A_32_P114215 | COMMD6 | AATTGCTATCATCTGTAAAGTCATGGACTTGACTTTCGGCAACAAAAGTAATAAGGATGG | SEQ ID NO: 2261 | Homo sapiens COMM domain containing 6 (COMMD6), transcript variant 2, mRNA [NM_203495] |
| 100 | A_32_P125549 | RPL31P4 | TCTACAGACAGTCAATGTGGATGGAGAACTAATCCCTGATCGTCAGATACATCAAATAAAG | SEQ ID NO: 2266 | PREDICTED: Homo sapiens ribosomal protein L31 pseudogene 4 (RPL31P4), mRNA [XR_018222] |
| 101 | A_32_P128781 | A_32_P128781 | CATATATTGGATGGGGGGTACCCCAATCTGAAGTCAGTAAATGAACTAATCTACAAGAGTG | SEQ ID NO: 2268 | |
| 102 | A_32_P135818 | RPS3A | CTTGGTTCATCTGTCTGTGTTGGTTTTAATAAAACGGCAACAATCAGATATGGAAGAC | SEQ ID NO: 2269 | Homo sapiens ribosomal protein S3A (RPS3A), mRNA [NM_001006] |
| 103 | A_32_P145153 | RPL31 | ATCCGTGTGCAGGTGTCCAGAAAAACGTAATGAGGATGAAGATTCACGAAATAAGGCATAT | SEQ ID NO: 2273 | Homo sapiens ribosomal protein L31 (RPL31), mRNA [NM_000993] |
| 104 | A_32_P155364 | RPL7 | TCAAGCAGGCTTATTAGAAAAATGAACCAAGGTGTCTACCATGATTATTTTCTAAGCTGG | SEQ ID NO: 2280 | Homo sapiens ribosomal protein L7 (RPL7), mRNA [NM_000971] |
| 105 | A_32_P164203 | THC2683448 | TTGATGGTCATTGTACGAAGCTATTGTATGGATTACTGTGGACTGCTGTTTACGGAATGAT | SEQ ID NO: 2286 | Q7WZG3_PASP1 (Q7WZG3) Ferric uptake regulator, partial (8%) [THC2683448] |
| 106 | A_32_P178945 | YOD1 | TTGCAAGCATTTTTTGAAGTAATACACTGGTGGTACCTGGAAGATGTCTAAGTTGATTTT | SEQ ID NO: 2296 | Homo sapiens YOD1 OTU deubiquinating enzyme 1 homolog (S. cerevisiae) (YOD1), mRNA [NM_018566] |
| 107 | A_32_P196483 | RPS3A | GGGGCAAAGAAGAAGAAATGGTTGATCCATTTTCTAAGGAAGAATGGTATGATGTGAAGCA | SEQ ID NO: 2306 | Homo sapiens ribosomal protein S3A (RPS3A), mRNA [NM_001006] |
| 108 | A_32_P208178 | RPS3A | GGAAAAGACGTAGAAAAGGCTTGCCAATCTATTTATCCTCTCCATGATGTCTCGTTAGA | SEQ ID NO: 2317 | Homo sapiens ribosomal protein S3A (RPS3A), mRNA [NM_001006] |
| 109 | A_32_P220127 | RPL34 | CAAAACTAGGCTGTGCTGAACCCGTGGTAATAGAATTGTTGACCTTTATACCAAGAAGGT | SEQ ID NO: 2320 | Homo sapiens ribosomal protein L34 (RPL34), transcript variant 2, mRNA [NM_033625] |
| 110 | A_32_P224686 | CAPZA2 | AATTCTGTTTTGAGATTCTGAAATTAAATGAAAATAGTTATTTCAGAAATGCATTTAATG | SEQ ID NO: 2322 | Homo sapiens capping protein (actin filament) muscle Z-line, alpha 2 (CAPZA2), mRNA [NM_006136] |
| 111 | A_32_P2333 | SUB1 | AGGAAGAAAAGGTATTTCTTTAAATCCAGAACAACAGATACGGAAGACCAGGTGACAGAACAGATTTC | SEQ ID NO: 2325 | Homo sapiens SUB1 homolog (S. cerevisiae) (SUB1), mRNA [NM_006713] |
| 112 | A_32_P4532 | LOC643932 | GATTCCAGACAGCATTGGAAAAGACATAGAAAAAGGCTTGCCAATCTATGGTGTCCATGAT | SEQ ID NO: 2332 | PREDICTED: Homo sapiens similar to 40S ribosomal protein S3a (v-fos transformation effector protein) (LOC643932), mRNA [XR_017289] |
| 113 | A_32_P49392 | A_32_P49392 | AATTCTGCCAAATGTGGAAGAAGATGATGGAAATGATGACCAAGAGGTGCAGACAAATG | SEQ ID NO: 2334 | |
| 114 | A_32_P58074 | RPS3A | GTTGTTTACTAAAAAACGCAAAATCAGAATACGGAAGACCTCTTATGCTCAGACCAA | SEQ ID NO: 2336 | Homo sapiens ribosomal protein S3A (RPS3A), mRNA [NM_001006] |
| 115 | A_32_P7118 | PSMC6 | AGGAGACCTGAGAAATGTTTGTACTGAAGCAGGTATGTTGGAATTCGTGCTGATCATGA | SEQ ID NO: 2339 | Homo sapiens proteasome (prosome, macropain) 26S subunit, ATPase, 6 (PSMC6), mRNA [NM_002806] |

Fig. 6-7

| No | Probe ID No. | Symbols of genes | Sequence | SEQ ID NO: | Descriptions of genes (letters and numbers within [ ] indicates GenBank accession No.) |
|---|---|---|---|---|---|
| 116 | A_32_P73222 | AA631847 | TTTCTTTGTTTTGGACAATCTCATAAGAAGTTTAGGTGTTACAG CACGAACGCCTCGAAG | SEQ ID NO: 2340 | np61b02.s1 NCI_CGAP_CGAP_Br2 Homo sapiens cDNA clone IMAGE:1130763 3' similar to TR:G971838 G971838 60S RIBOSOMAL PROTEIN L34 ;. mRNA sequence [AA631847] |

Fig. 7-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P105803 | FGF9 | GAAAAGGACTGCAGCGTGATGACGTGGAAAAAGACACGGTTTT CATTCTGATCAGTT | SEQ ID NO: 2353 | Homo sapiens fibroblast growth factor 9 (glia-activating factor) (FGF9), mRNA [NM_002010] |
| 2 | A_23_P123172 | OR2A9P | CAGGCCTCAGTTGTCACGTTGGACTCGTTGATGCCAATTATTGCCTC AATCCAGAAAAGTTT | SEQ ID NO: 2354 | Homo sapiens olfactory receptor, family 2, subfamily A, member 9 pseudogene (OR2A9P) on chromosome 7 [NR_002157] |
| 3 | A_23_P153676 | TLE2 | CGTCCTCAGTCCTGAGTGTGACATCCAGAAATAACAAATACA TTGTGACAGGCTCGG | SEQ ID NO: 2355 | Homo sapiens transducin-like enhancer of split 2 (E(sp1) homolog, Drosophila) (TLE2), mRNA [NM_003260] |
| 4 | A_23_P157299 | AEBP1 | ACAGTAGAGACCTACACAGTGAACTTTGGGGAGTTCTGAGATCAG GGTCCTACGAAGACC | SEQ ID NO: 2356 | Homo sapiens AE binding protein 1 (AEBP1), mRNA [NM_001129] |
| 5 | A_23_P159907 | MAGED4 | GGAGGCTGTGGATGATGCTTCAAGAGAATGGATGTGGATTGGC CGAGGAACATGCCAG | SEQ ID NO: 2357 | Homo sapiens melanoma antigen family D, 4 (MAGED4), transcript variant 1, mRNA [NM_030801] |
| 6 | A_23_P166280 | THC2614148 | CTCAGGGAGTCTCAGGTTGGAGCGTTATCTCCCAGAATCCTG GAACCTGCTCCTTCT | SEQ ID NO: 2358 | Q59G86_HUMAN (Q59G86) Androgen-regulated short-chain dehydrogenase/reductase 1 variant (Fragment), partial (7%) [THC2614148] |
| 7 | A_23_P166371 | VPREB3 | TGCCCCTCGATATCTCCTCTACTACCGCTCGGAGGAGGATCACCA CCCGGGCCTGGCTGACAT | SEQ ID NO: 2359 | Homo sapiens pre-B lymphocyte gene 3 (VPREB3), mRNA [NM_013378] |
| 8 | A_23_P200015 | AK5 | AATCGAGAGGGAACACCAGAGGACGTTTTTCTTCAACTGTCACA GCTATTGACTCTATT | SEQ ID NO: 2360 | Homo sapiens adenylate kinase 5 (AK5), transcript variant 1, mRNA [NM_174858] |
| 9 | A_23_P202520 | ABLIM1 | TCACTGCACTCCTTCTGTCATAATACTCTGCATCACTCTCTCATACTGA CAACTTCGTGAATAA | SEQ ID NO: 2361 | Homo sapiens actin binding LIM protein 1 (ABLIM1), transcript variant 3, mRNA [NM_001003408] |
| 10 | A_23_P202881 | FEZ1 | TGCTGACAAACATTCTCTTTGCCATGAAGGAGGATAATGAGAAGG TGCCTACTTTGCTAA | SEQ ID NO: 2362 | Homo sapiens fasciculation and elongation protein zeta 1 (zygin I) (FEZ1), transcript variant 1, mRNA [NM_005103] |
| 11 | A_23_P209055 | CD22 | GCCCTCAGGGACAAGAAATGTGGACTATGTGATCCTCAAACATTG ACACTGGATGGGCTG | SEQ ID NO: 2363 | Homo sapiens CD22 molecule (CD22), mRNA [NM_001771] |
| 12 | A_23_P21495 | FCGBP | TCAGTCACCAGGAACGGAACGAAGATTTCCTGAAGAAGACCTGGTC CCTCTGAGGTTGCG | SEQ ID NO: 2364 | Homo sapiens Fc fragment of IgG binding protein (FCGBP), mRNA [NM_003890] |
| 13 | A_23_P256212 | DKFZp761P0423 | GAACTGAATGCAGGCTGGACACTGGCCTCAATACCTTGTTTAGGA TTTCTTGACCCTTT | SEQ ID NO: 2365 | Tyrosine-protein kinase SgK223 (EC 2.7.10.2) (Sugen kinase 223). [Source:Uniprot/SWISSPROT;Acc:Q86YV5] [ENST00000330777] |
| 14 | A_23_P25060 | FLJ13769 | CAGAGTCTTGGAGGATTCTGAGGTAGAGAGTAGGATAATCTCAT TTGTGTTTTATTCT | SEQ ID NO: 2366 | Homo sapiens cDNA FLJ13769 fis, clone PLACE4000222. [AK023831] |
| 15 | A_23_P255896 | ENST00000335459 | GCAAGGGGCTCTACGGAGACTACCTCTTCAATGCTATTGCCGGAA ACTAGGGAGCAAGA | SEQ ID NO: 2367 | Homo sapiens hypothetical protein LOC129293, mRNA (cDNA clone IMAGE:5762496), partial cds. [BC051789] |
| 16 | A_23_P30634 | BACH2 | CCCTCTGTACCTCTGATAAGTGGTCAACGACTGTAACAGGTTACA TGAGGTGTTTTCTA | SEQ ID NO: 2368 | Homo sapiens BTB and CNC homology 1, basic leucine zipper transcription factor 2 (BACH2), mRNA [NM_021813] |
| 17 | A_23_P315378 | ATG16L1 | GTGTGTTTCCAGTTTATACTCTTTGTCCAAAACTCAGTTTCAAAA TATTTGAATGGGAC | SEQ ID NO: 2369 | Homo sapiens cDNA FLJ10035 fis, clone HEMBA1000919. [AK000897] |

Fig. 7-2

| No. | Probe ID No. | Symbols of genes | Sequence | SEQ ID NO: | Descriptions of genes (letters and numbers within [ ] indicates GenBank accession No.) |
|---|---|---|---|---|---|
| 18 | A_23_P316472 | DNHD1 | TAAGCTGCAGAGCAGGAACATGGTGATGGCATCTGGCTTTACCCACCAAGCTCACCGCCAA | SEQ ID NO: 2370 | Homo sapiens dynein heavy chain domain 1 (DNHD1), mRNA [NM_144666] |
| 19 | A_23_P329212 | ETS1 | GTCAACCGCAGGCTATCCAGAATCGGGACTATACCGTAGGATTACTTCATTAGCTATGGTATT | SEQ ID NO: 2371 | Homo sapiens v-ets erythroblastosis virus E26 oncogene homolog 1 (avian) (ETS1), mRNA [NM_005238] |
| 20 | A_23_P329375 | POU6F1 | GTTCCTTTGGCGGGAAAATTGGACTAAAACAGAACCTTTTCTTAATGCATGTTGGAAGGA | SEQ ID NO: 2372 | Homo sapiens POU domain, class 6, transcription factor 1 (POU6F1), mRNA [NM_002702] |
| 21 | A_23_P341938 | NOG | GCCAGCGGTTGCGGCTGGATTCCATCCAGTACCCCATCATTTCCGAGTGCAAGTGCTCGT | SEQ ID NO: 2373 | Homo sapiens noggin (NOG), mRNA [NM_005450] |
| 22 | A_23_P343398 | CCR7 | AAGAGAGCAACATTTACCCACACAGAGATAAAGTTTCCGTTGAGGAAACGAACAGGTTT | SEQ ID NO: 2374 | Homo sapiens chemokine (C-C motif) receptor 7 (CCR7), mRNA [NM_001838] |
| 23 | A_23_P344531 | SYNPO | TCCTGCTGCTGTGAAGATGAAGAAGGTGCTCTTACTCAGTAATGATGAGTGACTATATT | SEQ ID NO: 2375 | Synaptopodin. [Source:Uniprot/SWISSPROT;Acc:Q8N3V7] [ENST00000307662] |
| 24 | A_23_P344884 | KIAA1394 | ACCCAAATTCTAGGATAGGCTGTGAAGCGCTGGAAAACTTGGTGCATCCAACCTGCCTC | SEQ ID NO: 2376 | Homo sapiens KIAA1394 protein, mRNA (cDNA clone IMAGE:4310128), complete cds. [BC036557] |
| 25 | A_23_P356581 | ROBO3 | GGGCTAGCTGAAGCCCATTGGTCTTCCAGGATTGTTCAATTGGCATTTGGCTGAGAAGGCAAGGAGCTAG | SEQ ID NO: 2377 | Homo sapiens roundabout, axon guidance receptor, homolog 3 (Drosophila) (ROBO3), mRNA [NM_022370] |
| 26 | A_23_P357104 | ANXA6 | CTGCTCAACATCCGGAGCATCCGGAGGGAATTCATTGAGAAATATGACAAGTCTCTCCACAAGCCATT | SEQ ID NO: 2378 | Homo sapiens annexin A6 (ANXA6), transcript variant 1, mRNA [NM_001155] |
| 27 | A_23_P357717 | TCL1A | TTTCCCGGGTTTATAGATGGTCAGGCACCTGGGTGTTAGAAAGTTGTATGTGGCATGAAT | SEQ ID NO: 2379 | Homo sapiens T-cell leukemia/lymphoma 1A (TCL1A), mRNA [NM_021966] |
| 28 | A_23_P359870 | C8orf16 | TCGAGGTATAATTTCACTTAACATTGTCGAGTTGGCAGTTGGCATTTTGGTTTAGTCGAATGGT | SEQ ID NO: 2380 | Homo sapiens mRNA for hypothetical protein (C8ORF16) [AJ312026] |
| 29 | A_23_P368996 | LRRC56 | CAAACCAACATTTCCAGCTCTGAGGTGTACAGAAATGGGAGTTTACTTGTAGGCACGTT | SEQ ID NO: 2381 | Homo sapiens leucine rich repeat containing 56 (LRRC56), mRNA [NM_198075] |
| 30 | A_23_P39067 | SPIB | CCTGTCGAAGGTTCCGCTCTTGTCAGATCTGAGATTTCCTAGTTATGTCTGGGGGCCTCTG | SEQ ID NO: 2382 | Homo sapiens Sp-B transcription factor (Spi-1/PU.1 related) (SPIB), mRNA [NM_003121] |
| 31 | A_23_P39356 | FFAR1 | GACCGGTTACTTGGGAAGGGAGTCCTGGGCTGAAGACAGTGTGTGCGGCAAGAAGGCAGG | SEQ ID NO: 2383 | Homo sapiens huntingtin interacting protein 1 related (HIP1R), mRNA [NM_003959] |
| 32 | A_23_P398294 | HIP1R | GTTAGGATTTCCTCCTGAAGTGTTCTTGTTGGCAATAAAATGCACTTTGACTGTTTGTTGT | SEQ ID NO: 2384 | Homo sapiens huntingtin interacting protein 1 related (HIP1R), mRNA [NM_003959] |
| 33 | A_23_P407601 | C8orf6 | GTCTCTCTAGGTTAGTGTAGCGAGGAGATCTATTCTCAGATAAGACTTCCGTGTCGGCTGAA | SEQ ID NO: 2385 | Homo sapiens mRNA for hypothetical protein (C8orf6 gene). [AJ307469] |
| 34 | A_23_P40989 | USP13 | TGAGATGGAGAATAATGCCAATGCAAACATTATTCTGAGGCCAAGCCGAAGGACCTAG | SEQ ID NO: 2386 | Homo sapiens ubiquitin specific peptidase 13 (isopeptidase T-3) (USP13), mRNA [NM_003940] |
| 35 | A_23_P420873 | NR1D1 | CCCTTGTACAGAATCGAACTCTGGACTTCTGTCTCTTACGAGACGAAAAAGCA | SEQ ID NO: 2387 | Homo sapiens nuclear receptor subfamily 1, group D, member 1 (NR1D1), mRNA [NM_021724] |
| 36 | A_23_P46585 | SALL2 | CTAGTAAAATGTCAAGAACAGAGAGGGAGATATTAGTGTCTTTCCCTCTATCATTAAAGGT | SEQ ID NO: 2388 | Homo sapiens sal-like 2 (Drosophila) (SALL2), mRNA [NM_005407] |
| 37 | A_23_P49643 | GRAP | CATCTGCCAGGAAGGTTGAGGACTCCCAGGTTTCACCCACTGGAGGCTCAACCTAAGGAA | SEQ ID NO: 2389 | Homo sapiens GRB2-related adaptor protein (GRAP), mRNA [NM_006613] |

Fig. 7-3

| No. | Probe ID No. | Symbols of genes | Sequence | SEQ ID NO: | Descriptions of genes (letters and numbers within [ ] indicate GenBank accession No.) |
|---|---|---|---|---|---|
| 38 | A_23_P57236 | GGTL3 | CGAAGGACGAACAACTTGATGATCGCTGTGTTAAGGACCCTCGGAGCCCAGATGAGCTGGA | SEQ ID NO: 2390 | Homo sapiens gamma-glutamyltransferase-like 3 (GGTL3), mRNA [NM_178026] |
| 39 | A_23_P83388 | EPPK1 | GTTTTTGGTCGTCGTTTCTGGGTCGTCGTTGTATGTCATGATGGTTTAGTTTGTCCGGGAA | SEQ ID NO: 2391 | Homo sapiens epiplakin 1 (EPPK1), mRNA [NM_031308] |
| 40 | A_23_P65269 | TTN | CTGACAACCTGATCATGATCATGGACGTACAGAAACAAGATGGTGGACTTTATACCGTCACT | SEQ ID NO: 2392 | Homo sapiens titin (TTN), transcript variant N2-A, mRNA [NM_133378] |
| 41 | A_23_P88222 | PLD4 | TGAAAGTCTCATCGGTGCCGGTGGGGAGCCATTCCAACATCCCATTCAGCAGGGTGAACC | SEQ ID NO: 2393 | Homo sapiens phospholipase D family, member 4 (PLD4), mRNA [NM_138790] |
| 42 | A_24_P102512 | CABIN1 | CTCCTGTGGGTGATATTTCTGGGGGAGGAGATAAATCCAAGAAAGGGTAAAACGGAAGAAGA | SEQ ID NO: 2394 | Homo sapiens calcineurin binding protein 1 (CABIN1), mRNA [NM_012295] |
| 43 | A_24_P134816 | BCL9L | TGCTCCTACGGAGGAGAGCTCCCTATCGCGCCTTTGGTCAGAGGTGAAGCCATATAGGACT | SEQ ID NO: 2395 | Homo sapiens B-cell CLL/lymphoma 9-like (BCL9L), mRNA [NM_182557] |
| 44 | A_24_P229164 | HIP1R | CGTGAGCGTCAACTCTTCAGAAAATAGTGTTTTTAATATTCCTGTTCAGAAAATAGTGTT | SEQ ID NO: 2396 | Homo sapiens huntingtin interacting protein 1 related (HIP1R), mRNA [NM_003959] |
| 45 | A_24_P298360 | LTBP3 | CTGCTGTTGGGGAAGGGCCAAGAGATGAGGACAGTCAGAGAGGATCAGAGACGAGTGT | SEQ ID NO: 2397 | Homo sapiens latent transforming growth factor beta binding protein 3 (LTBP3), mRNA [NM_021070] |
| 46 | A_24_P302506 | AMIGO1 | AATTGGAGAATTGAATAATCAGGACATATGTAAGCGCGACTAGAACCCTGTGTTGAAAACTAC | SEQ ID NO: 2398 | Amphoterin-induced protein 1 precursor (AMIGO-1) (Alivin-2). [Source:Uniprot/SWISSPROT;Acc:Q86WK6] [ENST00000369864] |
| 47 | A_24_P312325 | C8orf15 | CTTGTTCAATGTGACTACTTAGTTGCCTGTCCAATATGAAGTAGAAAGCAGATTTCTG | SEQ ID NO: 2399 | Homo sapiens chromosome 8 open reading frame 15 (C8orf15), mRNA [NM_001033662] |
| 48 | A_24_P324638 | IGHD | AGATGGTGCAGTGGTTAGAGCTGAGGCTTATCGGACAGAGAACCGTGGCGCCTTGGTCAA | SEQ ID NO: 2400 | Homo sapiens mRNA for FLJ00382 protein. [AK090461] |
| 49 | A_24_P354715 | NT5E | TCGCCTCCAAATCTGAAGACTGAAGACGTCAGTGTAAATCATTGTTAAGCCCAGATATGAGAACTTC | SEQ ID NO: 2401 | Homo sapiens 5'-nucleotidase, ecto (CD73) (NT5E), mRNA [NM_002526] |
| 50 | A_24_P37020 | THC2680931 | TGGTTCTACGTCGAACTAAAGAGGAAGAGAGGAGGTGAAGGTGACGCCATGTTAGGCTATGAGA | SEQ ID NO: 2402 | AF235005 suppression of tumorigenicity 16 protein [Homo sapiens] (exp=-1; wgp=0; cg=0), partial (13%) [THC2680931] |
| 51 | A_24_P385012 | BC030084 | TCCGGCGTCATGTGTTGGGTGAAATACTGTTTATGCTTAGTACTAAAATTAAAAGTTAC | SEQ ID NO: 2403 | Homo sapiens cDNA clone IMAGE:4791887. [BC030084] |
| 52 | A_24_P413126 | TMEPAI | AAGAAAGTGCTTGTTGTGTATCAGTAATCATTAGTGGGAATGATGACATTCTGAAAAGCT | SEQ ID NO: 2404 | Homo sapiens transmembrane, prostate androgen induced RNA (TMEPAI), transcript variant 1, mRNA [NM_020182] |
| 53 | A_24_P419028 | MOP-1 | ACCCCCTCACTTTTCAGACCTATAGTTGTCGTTTGATTGTCCAGTTAAAACTACAA | SEQ ID NO: 2405 | Homo sapiens mRNA for MOP-1, complete cds. [AB014711] |
| 54 | A_24_P525144 | A_24_P525144 | GATGATGACAACCTCTATTGGGGATTGGCACCTTGTCGAACCTTCCTATCAAATATTCTT | SEQ ID NO: 2406 | |
| 55 | A_24_P62505 | GLT25D2 | AGGATTTTAGACTAGGACTGTTCTACTGTGAAGAAAAGTTCTCTCTCCTTAGCCCGGTTT | SEQ ID NO: 2407 | Homo sapiens glycosyltransferase 25 domain containing 2 (GLT25D2), mRNA [NM_015101] |
| 56 | A_24_P662177 | THC2666469 | GGGACAGGTAGGATTTCAATGGGCATGTTAGATAACATGCTCTCAGGGACAAGAATGTACA | SEQ ID NO: 2408 | |
| 57 | A_24_P8257 | BC009036 | CTCCGGTACATGAAAGTAAGCCTGAAGAGTCAGGTCGTCGTCGTCGTCTCGATTTTTCTGAAGATTTT | SEQ ID NO: 2409 | Homo sapiens cDNA clone IMAGE:4155841, partial cds. [BC009036] |

Fig. 7-4

| No. | Probe ID No. | Symbols of genes | Sequence | SEQ ID NO: | Descriptions of genes (letters and numbers w/b[s ] indicate GenBank accession No.) |
|---|---|---|---|---|---|
| 58 | A_24_P910490 | BX099367 | AGGCCCAGAGTTGAGAGACCACCTTGGGCTACACAGTGACAGCCTGTCTGTAGAAAAACTA | SEQ ID NO: 2410 | BX099367 Soares_fetal_liver_spleen_1NFLS_S1 Homo sapiens cDNA clone IMAGp998G05977, mRNA sequence [BX099367] |
| 59 | A_24_P922909 | AF272377 | AAGAAAAAGCAGCCTCCACCACCACAGAAATCAGGTGTAGAGCGGAAGCTGGAGTGGTGGCCT | SEQ ID NO: 2411 | Homo sapiens clone 1370-48 MLL protein mRNA, partial cds. [AF272377] |
| 60 | A_24_P924462 | PRKCZ | GCATGAGAGTGAAAGATGATATTTTAATTCTATCATTGAGGCATAGTCTTTCGAACACACC | SEQ ID NO: 2412 | Homo sapiens mRNA, chromosome 1 specific transcript KIAA0505. [AB007974] |
| 61 | A_24_P930963 | LOC650392 | GCCCCATTTCAAGTATAAGCAGGGGAAAATGGTGCTTGAAATAAGCATGCCACAAAGG | SEQ ID NO: 2413 | Homo sapiens cDNA clone IMAGE:5264670. [BC036550] |
| 62 | A_24_P933482 | ZDHHC21 | GCGAGCCAGGGGCGAGAATGAAGAACTTTCACTTACTGCAGGATTTTCAAGCTGAGC | SEQ ID NO: 2414 | Homo sapiens zinc finger, DHHC-type containing 21 (ZDHHC21), mRNA [NM_178566] |
| 63 | A_24_P940348 | FAM129C | AGACAAGCTTTTACCGACTTCCTCTCTTGCCAGCAAAGTCATCTGGTAAGTGGATATTG | SEQ ID NO: 2415 | Homo sapiens family with sequence similarity 129, member C (FAM129C), mRNA [NM_173544] |
| 64 | A_24_P943263 | RASA4 | TCCTCGATAGTCTATCTTTTGTATATCTTTGAACTTTTCAAGAATAAAAAAGTTAAAAAG | SEQ ID NO: 2416 | Homo sapiens RAS p21 protein activator 4 (RASA4), transcript variant 1, mRNA [NM_006989] |
| 65 | A_24_P945396 | SF3B3 | ATCCAGTTTGTGGATCCAATTGAGAAAACATTTCATGAGACAACTACTTGTGGCATGCAT | SEQ ID NO: 2417 | Homo sapiens KIAA0017 mRNA, complete cds. [D13642] |
| 66 | A_32_P111394 | THC2643957 | GAATACAGTGTTCCTTTTCGTTTGCTTTAGGCTTTTGAATGAAAGTGAGATGTCTACATCAATTATAAGG | SEQ ID NO: 2418 | |
| 67 | A_32_P125589 | THC2643941 | GGCTGTATCCCCTTGCTTTAGGCTTTTCCTTAATTAGAGGTAGTCTGGGAAACATGAGCTCAGATAG | SEQ ID NO: 2419 | |
| 68 | A_32_P131294 | BM854107 | AGTTAGGCAAAAAGACTTTGTTGTTCCTTAATTAGAGGTAGTCTGGGAAATGCTAGGACTTGTGC | SEQ ID NO: 2420 | K-EST0136406 S22SNU16n1 Homo sapiens cDNA clone S22SNU16n1-145-F11 5', mRNA sequence [BM854107] |
| 69 | A_32_P133767 | C12orf42 | AAGGGCCTCAGATGTAGTGGTTCCACAGAACCATTGTTAGGGTTTTGTGAAGCATTTT | SEQ ID NO: 2421 | Homo sapiens chromosome 12 open reading frame 42 (C12orf42), mRNA [NM_198521] |
| 70 | A_32_P145764 | BC043547 | GGTCCCGTCCCTCTGTGTAACCAATAACGAATGCCATATAAATGGAAAGTATAAAGAA | SEQ ID NO: 2422 | Homo sapiens, clone IMAGE:5171873, mRNA. [BC043547] |
| 71 | A_32_P146659 | LOC401431 | AGGTGTGATGCAGTAGCTTTACTATTGGTGCAAATGATGTTTTTCCTTGAAAGTCTA | SEQ ID NO: 2423 | Homo sapiens hypothetical gene LOC401431 (LOC401431), mRNA 001008745] |
| 72 | A_32_P146844 | THC2639619 | CCTGTGTGGCGTGATTCGAGACTGAGAGTTGAAGTTTTGTGTGCATCATCATGTGCCATTAA | SEQ ID NO: 2424 | |
| 73 | A_32_P15829 | AW389914 | TGATCTCCAAGGTTCTGACCTCTGAGAGTGACGTTAAGTGCAGAGAGCCACACAGTACA | SEQ ID NO: 2425 | AW389914 RC4-ST0173-191099-032-f06 ST0173 Homo sapiens cDNA, mRNA sequence [AW389914] |
| 74 | A_32_P154378 | THC2703271 | GAAAGAACGTAGAAAAGCATTGGAATGAAGGAAAGCCACCTGGTTTAGAGTTTAATTTG | SEQ ID NO: 2426 | |
| 75 | A_32_P164573 | THC2611661 | AGCTGTTTTCTATTAACACTGAAGTACTCTGACAGCTTGGAAATTTTCAAGTGCAAAATC | SEQ ID NO: 2427 | RR12_SPINX (P42344) Chloroplast 30S ribosomal protein S12, partial (11%) [THC2611661] |
| 76 | A_32_P168222 | THC2673977 | GATAGGGTCTGAGGGACAGAAAAGCAGCATAGTCCAATTTAGTTTCTCAAAACACATAG | SEQ ID NO: 2428 | ALU1_HUMAN (P39188) Alu subfamily J sequence contamination warning entry, partial (14%) [THC2673977] |
| 77 | A_32_P170397 | ENST00000309874 | CTGTTTGGCACGACTGATTCAGGGCCCTGGTGAAATGAGAACCCTGTGCGTGGGAACAA | SEQ ID NO: 2429 | Homo sapiens cDNA FLJ33063 fis, clone TRACH2000047. [AK057625] |

Fig. 7-5

| No. | Probe ID No. | Symbols of genes | Sequence | SEQ ID NO: | Descriptions of genes (letters and numbers within [ ] indicates GenBank accession No.) |
|---|---|---|---|---|---|
| 78 | A_32_P179998 | DMRTC1 | ATATGCCAAGAGTTTTATTCGTCTTGTTGATTGGTGAGATACCTGT GGACTCATGTGTATA | SEQ ID NO: 2430 | Homo sapiens DMRT-like family C1 (DMRTC1), mRNA [NM_033053] |
| 79 | A_32_P184039 | A_32_P184039 | ATCATTGTTAGTCTTGGCCCAAAAATAGTTGTTGTATGTATCATGCG TAATAACTGACCAGC | SEQ ID NO: 2431 | |
| 80 | A_32_P190682 | THC2739159 | TCAATAGGTTTTTATTTGCTCCGGTTTACCTAGATGAGAAAATTGAG ACCCAGAATCCATGC | SEQ ID NO: 2432 | ALU8_HUMAN (P39195) Alu subfamily SX sequence contamination warning entry, partial (8%) [THC2739159] |
| 81 | A_32_P196287 | THC2652466 | CCTTTCACAAAGACTGTAAGGCTTACGCAAGCATTAATTTTGCTG CATAGGCGGCCTGTT | SEQ ID NO: 2433 | Q9BHM3_PARTE (Q9BHM3) Cyclophilin-RNA interacting protein, partial (4%) [THC2652466] |
| 82 | A_32_P209582 | THC2663167 | CAATGTAAAGCCAGAATATCAACGTCGTTTTTGTCAAGATTTTCAA ACCTATTTGGCTGAT | SEQ ID NO: 2434 | ALU7_HUMAN (P39188) Alu subfamily J sequence contamination warning entry, partial (5%) [THC2663167] |
| 83 | A_32_P32254 | COL6A1 | ATATGCATGTGTTCGACGTTTATCAAAAGGCCGCCTTCTATGTT CATGTTAGTTTTTGCT | SEQ ID NO: 2435 | Homo sapiens collagen, type VI, alpha 1 (COL6A1), mRNA [NM_001848] |
| 84 | A_32_P3342 | THC2676548 | TATAGCATTTTCTGAAGATCATGTTGTACTCTCTTCTTCGTCTAGA TGATTTTGGTCAAGAG | SEQ ID NO: 2436 | ALU7_HUMAN (P39194) Alu subfamily SQ sequence contamination warning entry, partial (19%) [THC2676548] |
| 85 | A_32_P356316 | HLA-DOA | TGGAAAGGTTTTCTCCATCTCTGTCCTAAGGCTTGATAAAGTC ATTAAAATTGTGTTC | SEQ ID NO: 2437 | Homo sapiens major histocompatibility complex, class II, DO alpha (HLA-DOA), mRNA [NM_002119] |
| 86 | A_32_P40673 | A_32_P40673 | CATCACACTTGATATTAGGACAGGCTACCTACTTGTTGAGTGTC ACAGCCTGATATGTA | SEQ ID NO: 2438 | |
| 87 | A_32_P62371 | THC2674900 | GTGTTGCCTGAAAGTATTTCTCAGTCTTTCAGTGAAAACAGTGGAA CTGACTGATCTGGTC | SEQ ID NO: 2439 | |
| 88 | A_32_P71171 | A_32_P71171 | TCTAGATAGTAATAGGAAACCAAGAATCCAAGCCTGGTGATGGCTC GAGGGAGTGATTGAA | SEQ ID NO: 2440 | |
| 89 | A_32_P79103 | BM932034 | GTGCTACAGATGAAAATAGCCATTTTAGGAAGGTTGAGTCAGAGAC TGCGAGTGGGGCATA | SEQ ID NO: 2441 | UI-E-EJ1-aji-k-24-0-UI.r1 UI-E-EJ1 Homo sapiens cDNA clone UI-E-EJ1-aji-k-24-0-UI 5', mRNA sequence [BM932034] |
| 90 | A_32_P82111 | LRFN2 | ATGCCGGACTGAGCGCCTGAGTGTTTGGAAAGGGAGACTCCGCCT TTCTAATCACAAATG | SEQ ID NO: 2442 | Homo sapiens leucine rich repeat and fibronectin type III domain containing 2 (LRFN2), mRNA [NM_020737] |
| 91 | A_32_P88987 | AK022346 | ATGGGAAGTTACTACCCAGGCTTACCAAAAGGTCAGGTTTATATA AAGTGGGGTCCTTT | SEQ ID NO: 2443 | Homo sapiens cDNA FLJ12284 fis, clone MAMMA1001757. [AK022346] |
| 92 | A_32_P90346 | THC2682291 | TACAGGGATTAGATCCGAGGCGACATTACGCATACGTCAGAAT GGTCTGTCGGGAACA | SEQ ID NO: 2444 | |
| 93 | A_32_P90468 | A_32_P90468 | AAGCCAGGAATAATTTTTCTATGTCATGCTAGCTAACTCCTGGAAG TTATCATGAGACCCT | SEQ ID NO: 2445 | |
| 94 | A_32_P91328 | THC2641695 | GTTAGGGGAATAATGTCATTGAAGTCTTTAACTCTAGCGTGACTC TAAGGCCAGGGTTCA | SEQ ID NO: 2446 | |
| 95 | A_32_P91743 | THC2724606 | TTCAAAGGATTCTCCAAGCATCAGTGATTCTCAAAGATTAAGAG CCACTAATTTAAGCC | SEQ ID NO: 2447 | Q96HL9_HUMAN (Q96HL9) CHP protein, partial (39%) [THC2724906] |
| 96 | A_32_P98840 | THC2745859 | AAAGTATTCCAAGATAGCAAAGGTGTTGTTTTTAGCAGGTG TATTTCAGCTAGTTA | SEQ ID NO: 2448 | |

Fig. 7-6

| No. | Probe ID No. | Symbols of genes | Sequence | SEQ ID NO: | Descriptions of genes (letters and numbers within [ ] indicate GenBank accession No.) |
|---|---|---|---|---|---|
| 97 | A_23_P102060 | SSFA2 | GTATCATCCAAATAATGGGGCCTATGACTTGAATGAATAGAAATG AATAAGCTGGTGTTT | SEQ ID NO: 2449 | Homo sapiens sperm specific antigen 2 (SSFA2), mRNA [NM_006751] |
| 98 | A_23_P102160 | FAM82A | GGGTATGTGTCCTTAGATTTGAAGGTAAAGCCATGTTTCTGCAGAA TGGATTCCACTAGTA | SEQ ID NO: 2450 | Homo sapiens unknown mRNA. [AF435956] |
| 99 | A_23_P102235 | SNRPG | ACAACAGAACAATATGGAATGGTAATACGAGGAAATAGTAT CATCATGTTAGAAGC | SEQ ID NO: 2451 | Homo sapiens small nuclear ribonucleoprotein polypeptide G (SNRPG), mRNA [NM_003096] |
| 100 | A_23_P102391 | SLC40A1 | CTCATGTTATCATCATTAGTGATCTGTGTTGTAGAACATGAGGGT GTAAGGCTTCAGCCT | SEQ ID NO: 2452 | Homo sapiens solute carrier family 40 (iron-regulated transporter), member 1 (SLC40A1), mRNA [NM_014585] |
| 101 | A_23_P104054 | C1orf9 | TAAATTTCTTCGTGTCGTGGACAATTAGCTATTCAGAGGAAGAGG GCCTGATTTTATAGA | SEQ ID NO: 2453 | Homo sapiens chromosome 1 open reading frame 9 (C1orf9), transcript variant 2, mRNA [NM_016227] |
| 102 | A_23_P104471 | DUSP13 | GATTTCCGTGACCAATTCAGAGATTCTTTATGCAAAAGTGAGTT CAGTCCATCTCTATA | SEQ ID NO: 2454 | Homo sapiens dual specificity phosphatase 13 (DUSP13), transcript variant 1, mRNA [NM_001007271] |
| 103 | A_23_P107847 | LILRA5 | CCAGTGACCTCCTGGAGATTCCGGTCTCAGGAGGAGGTGATAACC TGAGTCCGTCAGAAA | SEQ ID NO: 2455 | Homo sapiens leukocyte immunoglobulin-like receptor, subfamily A (with TM domain), member 5 (LILRA5), transcript variant 2, mRNA [NM_181985] |
| 104 | A_23_P108394 | THC2783023 | ATTCAGAAACTTGCTTGTGTGATACATAGTAAGTCTCTTCATTT ATTAGTGCTTGTGTG | SEQ ID NO: 2456 | Q81UM9_HUMAN (Q81UM9) ACSL3 protein, complete [THC2467888] |
| 105 | A_23_P110362 | MAP2K1IP1 | ACTGAGACAAGTTGTGGAAGTTTCTTAATCTGACAGTGGTTTCAG TGTGTACGTTATCTT | SEQ ID NO: 2457 | Homo sapiens mitogen-activated protein kinase kinase 1 interacting protein 1 (MAP2K1IP1), mRNA [NM_021970] |
| 106 | A_23_P110611 | ZH2C2 | CTGTTGAAAAGGAGAGTTCAGTCTGTCGTTGGACTCTCAAACCAGG TTCTGAATACTTAA | SEQ ID NO: 2458 | Homo sapiens zinc finger, H2C2 domain containing (ZH2C2), mRNA [NM_017676] |
| 107 | A_23_P111321 | ARG1 | TGAATCAGGAGAGACAAAGCTACGACACATGTGGAAAGGTACTATGTG TCCATGTCATTCAAA | SEQ ID NO: 2459 | Homo sapiens arginase, liver (ARG1), mRNA [NM_000045] |
| 108 | A_23_P111583 | CD36 | GTTTGGCTTTAATGAGACTGGGACCATTGGTGATGAGAAGGCAAAC ATGTTCAGAAGTCAA | SEQ ID NO: 2460 | Homo sapiens CD36 molecule (thrombospondin receptor) (CD36), transcript variant 2, mRNA [NM_001001547] |
| 109 | A_23_P11201 | GPR34 | AGTAGGAGTGAAAGCGACTTCAGAATTTAAACCAGGATACTCCGTG CATGATACATCGTGTG | SEQ ID NO: 2461 | Homo sapiens G protein-coupled receptor 34 (GPR34), transcript variant 1, mRNA [NM_005300] |
| 110 | A_23_P112251 | LOC552891 | AGAATTGTTAAGTTCAGAAGTGTTTTACTTCGACGATGTGCGTTT GATTAATTGGGAC | SEQ ID NO: 2462 | Homo sapiens hypothetical protein LOC552891 (LOC552891), mRNA [NM_004125] |
| 111 | A_23_P113972 | EXOC1 | CGTGGCAGGCAGCATAACGGAGCGAGGAAGTAAGTTACCAACTTGC ATTAACAAACAAGA | SEQ ID NO: 2463 | Homo sapiens exocyst complex component 1 (EXOC1), transcript variant 1, mRNA [NM_018261] |
| 112 | A_23_P114947 | RGS2 | TAGATCTGGGATTATGTGGGCGTTAGGTAGCTGGTTGTACATCGTTT CCCTAAATCGATCGA | SEQ ID NO: 2464 | Homo sapiens regulator of G-protein signalling 2, 24kDa (RGS2), mRNA [NM_002923] |
| 113 | A_23_P11685 | PLA2G4A | GAAATGGCAGCAGTTTCTGATGCTGCAGGCAGTTTGCAATCCGATG ACAACTGGATTTAAA | SEQ ID NO: 2465 | Homo sapiens phospholipase A2, group IVA (cytosolic, calcium-dependent) (PLA2G4A), mRNA [NM_024420] |
| 114 | A_23_P118061 | CKLF | GCACAAGCCCCTGAACCATATATTGTTATCACTGGATTTGAAGTC ACCGTTATCTTATTT | SEQ ID NO: 2466 | Homo sapiens chemokine-like factor (CKLF), transcript variant 4, mRNA [NM_181641] |

Fig. 7-7

| No. | Probe ID No. | Symbols of genes | Sequence | SEQ ID NO: | Descriptions of genes [colons and numbers within [ ] indicates GenBank accession No.] |
|---|---|---|---|---|---|
| 115 | A_23_P118246 | GINS2 | TGTGTGATGGTGCAAGGAATGGATTGAGTGTTGGAGAAAC AAGTTTGTGATTAGT | SEQ ID NO: 2467 | Homo sapiens GINS complex subunit 2 (Psf2 homolog) (GINS2), mRNA [NM_016095] |
| 116 | A_23_P119516 | FAM18B | TATTTCTGTAGAATGTTTCAGGAGAAAGTTTTGCTTCTATGGTA AGAGTGAGCACTTTG | SEQ ID NO: 2468 | Homo sapiens family with sequence similarity 18, member B (FAM18B), mRNA [NM_016079] |
| 117 | A_23_P119222 | RETN | CAATAAGCAGCATTGGCCTGGAGTGCCAGAGGTGCACCTCCAGGG GGGACCTGGCTACTT | SEQ ID NO: 2469 | Homo sapiens resistin (RETN), mRNA [NM_020415] |
| 118 | A_23_P120048 | BAZ2B | TATTTCTGTGAAGGTAATGATAGGTATACAGTCTGTACAGTAA TTATCCTCTACCAAC | SEQ ID NO: 2470 | Homo sapiens bromodomain adjacent to zinc finger domain, 2B (BAZ2B), mRNA [NM_013450] |
| 119 | A_23_P120316 | MTHFD2 | AGGATTATTCCTTGCTATTAGTACTACTGATTTATGTATGTTACCCT TCAGTAAGTTCTCCC | SEQ ID NO: 2471 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 120 | A_23_P120345 | PELI1 | CTTGCCACCCTTTTTTCAAAGGGACCACAAGTATAGACAGTGCA CTACATCAAATCTTT | SEQ ID NO: 2472 | Homo sapiens pellino homolog 1 (Drosophila) (PELI1), mRNA [NM_020651] |
| 121 | A_23_P121253 | TNFSF10 | GGAACAATCGATCTCTCAGCTAGTGTATCAGCTAGTAGCCTCCA GGTTTCCTTAAGGGA | SEQ ID NO: 2473 | Homo sapiens tumor necrosis factor (ligand) superfamily, member 10 (TNFSF10), mRNA [NM_003810] |
| 122 | A_23_P121622 | SULT1B1 | GAAATAGAGATTGTCTGTAGTTGATTGAAACGAGGGGCACTTATGA ATTGATTTGGGCAAT | SEQ ID NO: 2474 | Homo sapiens chromosome 5 open reading frame for ST1B2, complete cds. [D89479] |
| 123 | A_23_P121716 | ANXA3 | TGGACATTCGAACAGAGTTCAAGAACGATTATGGCTATTCCGTAT ATTGAGCAATTAAAT | SEQ ID NO: 2475 | Homo sapiens annexin A3 (ANXA3), mRNA [NM_005139] |
| 124 | A_23_P121825 | FLJ13611 | CATGTGTTACTGTTACAAAACTTCTCTCTGTCCATGTAATCAACT TAGTATATGAGCAAAG | SEQ ID NO: 2476 | Homo sapiens hypothetical protein FLJ13611 (FLJ13611), mRNA [NM_024941] |
| 125 | A_23_P122007 | C5orf30 | ATCAGATTTCTCGTTGGGCTGGAACAGTTGGGTGTGTATATTT TAAAGTAAATTGCAC | SEQ ID NO: 2477 | Homo sapiens chromosome 5 open reading frame 30 (C5orf30), mRNA [NM_033217] |
| 126 | A_23_P122174 | XRCC4 | AAACAAAGTGATCTCTCTGGGTTGGCTTCAGCTGCTGTAAGTAA AGATGATTCCATTAT | SEQ ID NO: 2478 | Homo sapiens X-ray repair complementing defective repair in Chinese hamster cells 4 (XRCC4), transcript variant 3, mRNA [NM_022550] |
| 127 | A_23_P122724 | VNN2 | AAAGAGCCTAGGCTGGGTGTTTGGGTCAGAATGAAGATCAAACTCCA GCTCCAGCGTCATTT | SEQ ID NO: 2479 | Homo sapiens vanin 2 (VNN2), transcript variant 1, mRNA [NM_004665] |
| 128 | A_23_P123608 | JAK2 | GGATAACATGGCTGGAATGAAAGAAATGACCTTCATTCTGAGACCA AAGTAGATTTACAGA | SEQ ID NO: 2480 | Homo sapiens Janus kinase 2 (a protein tyrosine kinase) (JAK2), mRNA [NM_004972] |
| 129 | A_23_P123727 | ZCCHC6 | TTGAAGAGGGGAAATTATACTTATTGTTGTTACTGAATGCTCGT GTGAAAAGCATATCAG | SEQ ID NO: 2481 | Homo sapiens zinc finger, CCHC domain containing 6 (ZCCHC6), mRNA [NM_024617] |
| 130 | A_23_P128384 | VPS29 | CAGCTAATTCGAGATGATGTGAAAGTAGAACGAATCGAATACAAA AAACCTTAAAGGCAG | SEQ ID NO: 2482 | Homo sapiens vacuolar protein sorting 29 homolog (S. cerevisiae) (VPS29), transcript variant 2, mRNA [NM_057180] |
| 131 | A_23_P128447 | LRRK2 | GCAGAAAGAGATAGCAATCTTGCTTGGACCGTTTGGGACATCGAATCT TCCACATGAAGTGCA | SEQ ID NO: 2483 | Homo sapiens leucine-rich repeat kinase 2 (LRRK2), mRNA [NM_198578] |
| 132 | A_23_P128930 | PSMC6 | GAACAAGCAAGATTAGACATACTGAAAATGCAGGTCCCATT ACAAAGCATGGTGAA | SEQ ID NO: 2484 | Homo sapiens proteasome (prosome, macropain) 26S subunit, ATPase, 6 (PSMC6), mRNA [NM_002806] |

Fig. 7-8

| No. | Probe ID No. | Symbols of genes | Sequence | SEQ ID NO: | Descriptions of genes (letters and numbers within [ ] indicates GenBank accession No.) |
|---|---|---|---|---|---|
| 133 | A_23_P129940 | C14orf138 | TTGGTATTGAGGCGAGGCTGAAATCTGCCAAAAACAGCCAACATG ATTTGACTGGACCTT | SEQ ID NO: 2485 | Homo sapiens chromosome 14 open reading frame 138 (C14orf138), transcript variant 1, mRNA [NM_024558] |
| 134 | A_23_P129935 | TMEM49 | CACAGGGAGAAAAACTGGTTGTCCTGGATGTTTGAAAAGTTGGTCG TTGTCATGGTGTGTT | SEQ ID NO: 2486 | Homo sapiens transmembrane protein 49 (TMEM49), mRNA [NM_030938] |
| 135 | A_23_P132910 | FLJ20273 | CACGGGATTTTTTGTTGATGGCTGAATTCTTGTGGATTGATAAGAG GATCATGCCCTTAGC | SEQ ID NO: 2487 | Homo sapiens RNA-binding protein (FLJ20273), mRNA [NM_019027] |
| 136 | A_23_P133470 | PJA2 | GTTTGTTTCCTTTTAAGTACTGTTGATCAGTTGTGACAGTTAGTG GTTAAACTTACGTTG | SEQ ID NO: 2488 | Homo sapiens praja 2, RING-H2 motif containing (PJA2), mRNA [NM_014819] |
| 137 | A_23_P133848 | FAM8A1 | ACTTCGCCGAATTACAAAATGAGTGTGTTTTAGAATTGAAGTGACG GTAAAGGATTTGTT | SEQ ID NO: 2489 | Homo sapiens family with sequence similarity 8, member A1 (FAM8A1), mRNA [NM_016255] |
| 138 | A_23_P133691 | RRAGD | CTGCTCTGTGTATATGATGGTTATTGACATCTCTTGTATTTA TGGTGTCAAAGAAGA | SEQ ID NO: 2490 | Homo sapiens Ras-related GTP binding D (RRAGD), mRNA [NM_021244] |
| 139 | A_23_P134786 | PHF20L1 | AGTTGTATGTCCCGCAGTGCTACATACGCAGGTATGCGTAAGTG TGTATGCTTGTTTTA | SEQ ID NO: 2491 | Homo sapiens PHD finger protein 20-like 1 (PHF20L1), transcript variant 1, mRNA [NM_016018] |
| 140 | A_23_P134910 | GGH | GCAAGGTCAATTGCACAGCAGAATGTTCCAGAATTTTCCTACTGAG TTGTTGCTCTCATTA | SEQ ID NO: 2492 | Homo sapiens gamma-glutamyl hydrolase (conjugase, folylpolygammaglutamyl hydrolase) (GGH), mRNA [NM_003878] |
| 141 | A_23_P135494 | CLIC4 | GTCCTCAAGCGTAATGTTGAACAGAATGGAGGTATTTCTTTAT AATTCTTGAACAGG | SEQ ID NO: 2493 | Homo sapiens chloride intracellular channel 4 (CLIC4), mRNA [NM_013943] |
| 142 | A_23_P135499 | CLIC4 | CTTCCCTTTTTTGATGTAGAATGCAGATATTCTATACAGTTGTGTT GTCTTTTTACTAGGAC | SEQ ID NO: 2494 | Homo sapiens chloride intracellular channel 4 (CLIC4), mRNA [NM_013943] |
| 143 | A_23_P136964 | RPGR | GACGAGAACCCACACTGAGTCAGAATCATCAGAAATATCCACGAACA AATACAGAGAGAA | SEQ ID NO: 2495 | Homo sapiens retinitis pigmentosa GTPase regulator (RPGR), transcript variant A, mRNA [NM_000328] |
| 144 | A_23_P137201 | TMBIM4 | TGCACATCCGGAATGGCCTTTCTGAGAAGAAAGTCTACAGCATTCTT CTCTGCAGGTCTCT | SEQ ID NO: 2496 | Homo sapiens transmembrane BAX inhibitor motif containing 4 (TMBIM4), mRNA [NM_016056] |
| 145 | A_23_P137016 | SAT1 | GAAATAATAGAATGAGAGACGCATTCGAAAGCTTTATTACCAGTGG CGTTGTTGCATGTT | SEQ ID NO: 2497 | Homo sapiens spermidine/spermine N1-acetyltransferase 1 (SAT1), mRNA [NM_002970] |
| 146 | A_23_P138262 | PADI4 | AAGAACATTCTCTCAACAAGAGACATTGAGAGAACATAATTCATTT GTGGAGAGATGATC | SEQ ID NO: 2498 | Homo sapiens peptidyl arginine deiminase, type IV (PADI4), mRNA [NM_012387] |
| 147 | A_23_P133308 | CD58 | AAGCTGTATCCCAAGCAGCAGCGGTCATTCAAGCAGATATGCACT TATACGCATACCAT | SEQ ID NO: 2499 | Homo sapiens CD58 molecule (CD58), mRNA [NM_001779] |
| 148 | A_23_P140089 | FBXL3 | TAAGCCCAGTGGAATAGATTAATTCTTAAGCGGCTCTTTTCAGT AGTGTGACTTTTAGA | SEQ ID NO: 2500 | Homo sapiens F-box and leucine-rich repeat protein 3 (FBXL3), mRNA [NM_012158] |
| 149 | A_23_P14105 | RCBTB2 | TGACTTTCATGTCACTCACTATAAAATAGGTCTCTTAACCTGGCA CCAGTATAACTATAA | SEQ ID NO: 2501 | Homo sapiens regulator of chromosome condensation (RCC1) and BTB (POZ) domain containing protein 2 (RCBTB2), mRNA [NM_001268] |
| 150 | A_23_P143958 | RPL22L1 | ATTGGCTTGGATGGTTGCATCTGACAAGGAGAGACCTACGAACCTC GTTACTTCCAGATTA | SEQ ID NO: 2502 | Homo sapiens ribosomal protein L22-like 1, mRNA (cDNA clone IMAGE:4865966), [BC049823] |
| 151 | A_23_P144145 | DCUN1D1 | TCTTTAAGTAAATTGAATATCATCTGGGATATGTCTGTAAGTTCAATTGAATGT TTCTTACAGTCCGTa | SEQ ID NO: 2503 | Homo sapiens RP2 protein mRNA, complete cds. [AF292100] |

Fig. 7-9

| No. | Probe ID No. | Symbols of genes | Sequence | SEQ ID NO: | Descriptions of genes (letters and numbers within [ ] indicates GenBank accession No.) |
|---|---|---|---|---|---|
| 152 | A_23_P144384 | GALNT7 | TACTGTAGGGTGCTTTGGAAATAATTCCCATATCCTTGCTTGTAAGTTGGTAATATCAC | SEQ ID NO: 2504 | Homo sapiens UDP-N-acetyl-alpha-D-galactosamine:polypeptide N-acetylgalactosaminyltransferase 7 (GalNAc-T7) (GALNT7), mRNA [NM_017423] |
| 153 | A_23_P144684 | ANKRD32 | AAACTTCTACAAAACGTCTAGTATGGGCTTCGTGACTTTTTTCCAGGGTGTAGAATTTGACTC | SEQ ID NO: 2505 | Homo sapiens ankyrin repeat domain 32 (ANKRD32), mRNA [NM_032290] |
| 154 | A_23_P14564 | GPR65 | AAGAAGTTTAAATTGTGTTGCTGATCAAATTCGTGTACGTGTTTGTAACCGAAACAGGAAG | SEQ ID NO: 2506 | Homo sapiens G protein-coupled receptor 65 (GPR65), mRNA [NM_003608] |
| 155 | A_23_P14708 | SUHW4 | TCTTTGTACCTCCATACAAGTGTTAGCCTGCCAGGCTGTAAGCTTACCTTAATTAAACTT | SEQ ID NO: 2507 | Homo sapiens suppressor of hairy wing homolog 4 (Drosophila) (SUHW4), transcript variant 1, mRNA [NM_017661] |
| 156 | A_23_P14734 | RPS27L | TACAAGATCACCACGGTTTCAGGCATGCTCGAGACAGTGGTTCTTTGTGTAGGTTGTTCA | SEQ ID NO: 2508 | Homo sapiens ribosomal protein S27-like (RPS27L), mRNA [NM_015920] |
| 157 | A_23_P148584 | DOCK11 | TTGCACCACTCATGTGTTTGGTTGTACTTTTTTTAGGTAAATCTATATGCTGAAAAGTAGAGC | SEQ ID NO: 2509 | Homo sapiens dedicator of cytokinesis 11 (DOCK11), mRNA [NM_144688] |
| 158 | A_23_P149775 | ARHGAP12 | TGTATATAAAACACAGGGTTTGGAAGGTTTGTTACAGGGAGGATGGCTGTGTTGAAGAT | SEQ ID NO: 2510 | Homo sapiens Rho GTPase activating protein 12 (ARHGAP12), mRNA [NM_018287] |
| 159 | A_23_P149892 | GALNACT-2 | CATGGTGGTTCAGAATAGATGAGGCATAGGATGGTTGTTGTTTTGTTTGTTTTTGCTTTCAATTTTC | SEQ ID NO: 2511 | Homo sapiens chondroitin sulfate GalNAcT-2 (GALNACT-2), mRNA [NM_018590] |
| 160 | A_23_P150128 | SAPS3 | TTACCTTGTTAACAAGCATCACGCAATGAACATTTCAGAGCAATCTGCATATTTAACGAC | SEQ ID NO: 2512 | Homo sapiens SAPS domain family, member 3 (SAPS3), mRNA [NM_018312] |
| 161 | A_23_P151018 | LEMD3 | CCCCATCCTGTAACCTGTTGCAAGAGTGAATGTAAAAAATAGTTGTGGCATTTTAAAAGG | SEQ ID NO: 2513 | Homo sapiens LEM domain containing 3 (LEMD3), mRNA [NM_014319] |
| 162 | A_23_P151637 | RNASE2 | GTGGTAACCCAAATATGACCTGTCCTAGTAACAAAACTCGGCAAAAATTGTCACCACAGTG | SEQ ID NO: 2514 | Homo sapiens ribonuclease, RNase A family, 2 (liver, eosinophil-derived neurotoxin) (RNASE2), mRNA [NM_002934] |
| 163 | A_23_P152092 | BCL2A1 | GTAACCATATTTGCATTTGAAGGTATTCTCATCAAGAGAACTTCTACGACAGCAAATTGC | SEQ ID NO: 2515 | Homo sapiens BCL2-related protein A1 (BCL2A1), mRNA [NM_004049] |
| 164 | A_23_P154235 | NMI | CCATGTTCGTGAATCTCTTGTTTGTTCAAATGGTGCTGGCATGTTTCAACTACAATAAGTG | SEQ ID NO: 2516 | Homo sapiens N-myc (and STAT) interactor (NMI), mRNA [NM_004688] |
| 165 | A_23_P154330 | TXNDC9 | CTCAGTTCTTAAATTATCTGGGAAGGGTGTGGATTCTGTATTTCAGAATTGACTTTATC | SEQ ID NO: 2517 | Homo sapiens thioredoxin domain containing 9 (TXNDC9), mRNA [NM_005783] |
| 166 | A_23_P154367 | STK17B | TACCGAATCCCCATGAACTTGTTTCAGATTTGCTCTGTTAGCACTTTTTCTTTGACTCA | SEQ ID NO: 2518 | Homo sapiens serine/threonine kinase 17b (STK17B), mRNA [NM_004226] |
| 167 | A_23_P155765 | HMGB2 | TAAAAATGCAGGGTTGTAGGTTTTGATGGGCTACTACAGAGTTAGTTATTTGCTTTAA | SEQ ID NO: 2519 | Homo sapiens high-mobility group box 2 (HMGB2), mRNA [NM_002129] |
| 168 | A_23_P155815 | NCAPG | AAGTTAGGAAGAGACGAATGGGAGGTGGAATCCTTAAGATATGTCGAGTTATTTGCTTTAA | SEQ ID NO: 2520 | Homo sapiens non-SMC condensin I complex, subunit G (NCAPG), mRNA [NM_022346] |
| 169 | A_23_P156609 | A_23_P156609 | TTCACGTGTTTAGTAGCTGCGGGTTTCAAGTTAAATGGTCTTATTACGGCTTGGCTTCAT | SEQ ID NO: 2521 | |
| 170 | A_23_P156842 | EEF1E1 | AAGAAAAAGGAATCGTTCAGCAGTGGTTAGAATACAGAGGTCACTCAAGTAGAATCGGCACT | SEQ ID NO: 2522 | Homo sapiens eukaryotic translation elongation factor 1 epsilon 1 (EEF1E1), mRNA [NM_004280] |

Fig. 7-10

| No. | Probe ID No. | Symbols of genes | Sequence | SEQ ID NO: | Descriptions of genes (letters and numbers within [ ] indicates GenBank accession No.) |
|---|---|---|---|---|---|
| 171 | A_23_P157449 | POLR2K | GGTCTCTGTGTTGGCTCAAAATATCCTTCTTGATACAGTACTCACCATTTTAGATGTGGTTGAC | SEQ ID NO: 2523 | Homo sapiens polymerase (RNA) II (DNA directed) polypeptide K, 7.0kDa (POLR2K), mRNA [NM_005034] |
| 172 | A_23_P157452 | POLR2K | GGAATGTCTTCACTTATACTTGGATTTTGCTCTGTCTTCCCATTTCTGATTGTTGTATAGCTT | SEQ ID NO: 2524 | Homo sapiens polymerase (RNA) II (DNA directed) polypeptide K, 7.0kDa (POLR2K), mRNA [NM_005034] |
| 173 | A_23_P159650 | COX7B | CAAATACGGTAATGCTGTATTAGCTAGTGGAGCCACTTTCTGTATTGTTACATGGACATA | SEQ ID NO: 2525 | Homo sapiens cytochrome c oxidase subunit VIIb (COX7B), nuclear gene encoding mitochondrial protein, mRNA [NM_001866] |
| 174 | A_23_P159839 | C1GALT1C1 | TGCAAATCAGATGCATGTGATGATGTATGGGGTATACCGCGCTTAGGGCATTTGGGCATAT | SEQ ID NO: 2526 | Homo sapiens C1GALT1-specific chaperone 1 (C1GALT1C1), transcript variant 1, mRNA [NM_152692] |
| 175 | A_23_P160406 | KCTD3 | TTGTAGGACTGCAGTTCTGAATTTTGGGTTAAAGGTTTTGGCTGCTGTAAGAATGTGAAT | SEQ ID NO: 2527 | Homo sapiens potassium channel tetramerisation domain containing 3 (KCTD3), mRNA [NM_016121] |
| 176 | A_23_P160466 | SLC19A2 | CTTGGTATGTGGCCATATTTATAGAATGCTGAACTGAATGTCAAGTTACTGTATGCA | SEQ ID NO: 2528 | Homo sapiens solute carrier family 19 (thiamine transporter), member 2 (SLC19A2), mRNA [NM_006996] |
| 177 | A_23_P162300 | IRAK3 | TTGTCTCATGACCAAATGCACGCGCTCAATTAGAGCCATTCAAAATTCCTTAAGACATGGG | SEQ ID NO: 2529 | Homo sapiens interleukin-1 receptor-associated kinase 3 (IRAK3), mRNA [NM_007199] |
| 178 | A_23_P162586 | ACTR6 | TTAACGGCTTCACTGGACAGTTTTCCTTAGAAGGTAGTTTTGTGTGACTGTGACTAAACT | SEQ ID NO: 2530 | Homo sapiens ARP6 actin-related protein 6 homolog (yeast) (ACTR6), mRNA [NM_022496] |
| 179 | A_23_P163216 | ATP8B4 | ATCAGTGTATTTTCCATAAAGTGATTCGGGCATATTTGTGTCGAAAACCTCAGTTGTGTCA | SEQ ID NO: 2531 | Homo sapiens ATPase, Class I, type 8B, member 4 (ATP8B4), mRNA [NM_024837] |
| 180 | A_23_P165624 | TNFAIP6 | AAATGGTACGAAGATAACCAAAATCTGGTACTGGACAATATCAAGTATGGTGATCA | SEQ ID NO: 2532 | Homo sapiens tumor necrosis factor, alpha-induced protein 6 (TNFAIP6), mRNA [NM_007115] |
| 181 | A_23_P167005 | GPR160 | AGGCACAGAAATGCTTATTCTGGTCACTGTCCTTTGTATGTGAGCATTCAAGTTAGTGGC | SEQ ID NO: 2533 | Homo sapiens G protein-coupled receptor 160 (GPR160), mRNA [NM_014373] |
| 182 | A_23_P167983 | HIST1H2AC | GCATTATGCAAATGCATTATATTTATGTAACCTGTCACTGTTGGTAGGCACTTGAGTT | SEQ ID NO: 2534 | Histone H2A type 1-C [Source:Uniprot/SWISSPROT;Acc:Q93077] [ENST00000314083] |
| 183 | A_23_P16817 | CLK1 | ATGGAAAGGATTCTTGGACCTCTACCAAAACATATGTACACAGAAAACCAGGAAAGGTAAA | SEQ ID NO: 2535 | Homo sapiens CDC-like kinase 1 (CLK1), transcript variant 1, mRNA [NM_004071] |
| 184 | A_23_P168656 | GTPBP10 | AATTTGTGGATTTCTGATACAATGTCTCTACTGAGCCAGCATCAAAGCATGCTGTTAGT | SEQ ID NO: 2536 | Homo sapiens GTP-binding protein 10 (putative) (GTPBP10), transcript variant 2, mRNA [NM_033107] |
| 185 | A_23_P168882 | TP53INP1 | GGGAGGTTAGATGTGTGTTTCAGGCTTGGAGTGTATGAGTGGTTTGCTTGTATTTTCCT | SEQ ID NO: 2537 | Homo sapiens tumor protein p53 inducible nuclear protein 1 (TP53INP1), mRNA [NM_033285] |
| 186 | A_23_P168974 | SDCBP | GGAAACGAACAAGTTCATCTTGAGAATTTATACAGACTGGTCGAGAAGAAGCATCCTCAG | SEQ ID NO: 2538 | Homo sapiens cDNA FLJ46804 fis, clone TRACH3032570, highly similar to Homo sapiens syndecan binding protein (syntenin) (SDCBP), mRNA [AK128645] |
| 187 | A_23_P16915 | QPCT | CATATTCATTTTAAGAAGAGGGTGTTCAGTTCGCATCTGATACCGTCTCCTTTCCCT | SEQ ID NO: 2539 | Homo sapiens glutaminyl-peptide cyclotransferase (glutaminyl cyclase) (QPCT), mRNA [NM_012413] |
| 188 | A_23_P169278 | AGTPBP1 | AAACCTGAGTATCATTGGATCGAATTTTATCTCCCTATAGTTATATCCTGGACTCAAGTGG | SEQ ID NO: 2540 | Homo sapiens ATP/GTP binding protein 1 (AGTPBP1), mRNA [NM_015239] |

Fig. 7-11

| No. | Probe ID No. | Symbols of genes | Sequence | SEQ ID NO: | Descriptions of genes (letters and numbers within [ ] indicates GenBank accession No.) |
|---|---|---|---|---|---|
| 189 | A_23_P169576 | EXOC6 | ATGCTGAATCTCCGCTTTGGCTTTTCAGGATTTAGGCCTGTAAGAAACTATGCCTGATTC | SEQ ID NO: 2541 | Homo sapiens exocyst complex component 6 (EXOC6), transcript variant 2, mRNA [NM_001013848] |
| 190 | A_23_P17021 | SCRN3 | GTCAAAGTTAGTTCTTAGTGATCATATGGTCAGGTAATATTAGTTCTTAGTGATCAGTGG | SEQ ID NO: 2542 | Homo sapiens secernin 3 (SCRN3), mRNA [NM_024583] |
| 191 | A_23_P170233 | CSTA | AACTGGCTACTGAGTCATGATCCTTGCTGATAATATAACCATCAATAAAGAAGCATTCT | SEQ ID NO: 2543 | Homo sapiens cystatin A (stefin A) (CSTA), mRNA [NM_005213] |
| 192 | A_23_P18325 | PDCD10 | CCAAGCGACTAATTCATCAAACGAACTTAATACTTCAGACCTTCAAAACGTGGCCTGAA | SEQ ID NO: 2544 | Homo sapiens programmed cell death 10 (PDCD10), transcript variant 1, mRNA [NM_007217] |
| 193 | A_23_P18372 | B3GNT5 | AAAATGTCAACAAAGGGAAAATAAACTATCAGGTTGGATGGTCACTTGAATAGAGATGGT | SEQ ID NO: 2545 | Homo sapiens UDP-GlcNAc:betaGal beta-1,3-N-acetylglucosaminyltransferase 5 (B3GNT5), mRNA [NM_032047] |
| 194 | A_23_P19543 | SRPK1 | CTGTCAAATTGGCACGATCTCACTCAGCTAAAGGATTCTATTTGCTGTCAGTAAAATAAAGC | SEQ ID NO: 2546 | Homo sapiens SFRS protein kinase 1 (SRPK1), mRNA [NM_003137] |
| 195 | A_23_P200030 | FPGT | TAAAAATTGGTAAACTAGAAGTAACTGTCCACAACCCTCAGTTATGATACTTATGTGCG | SEQ ID NO: 2547 | Homo sapiens fucose-1-phosphate guanylyltransferase (FPGT), mRNA [NM_003838] |
| 196 | A_23_P200493 | LBR | GAGCGCTTTATCAATACAGTGCTGCAATTTCTGGATATCAGGTACACTTGTTTTAAGT | SEQ ID NO: 2548 | Homo sapiens lamin B receptor (LBR), transcript variant 1, mRNA [NM_002296] |
| 197 | A_23_P200507 | CNIH4 | TGGTTGAAGTCAGCGTACTACGAGTGAGGAGCAGACAGTTGTTCTTAAATCAT | SEQ ID NO: 2549 | Homo sapiens cornichon homolog 4 (Drosophila) (CNIH4), mRNA [NM_014184] |
| 198 | A_23_P201619 | NEK7 | TGAAGGCCAAGAGGAAGTCACTGTTAAAGGACTCTGTGCCATCTTACAACCTTGGATGAA | SEQ ID NO: 2550 | Serine/threonine-protein kinase Nek7 (EC 2.7.11.1) (NimA-related protein kinase 7). [Source:Uniprot/SWISSPROT;Acc:Q8TDX7] [ENST00000367385] |
| 199 | A_23_P201758 | CD46 | CTCATGAAGTGCAACTGTGGCTTAGCTAATATGCAATGTGGCTTGAATGTAGGTAGGATC | SEQ ID NO: 2551 | Homo sapiens CD46 molecule, complement regulatory protein (CD46), transcript variant a, mRNA [NM_002389] |
| 200 | A_23_P201951 | ARID4B | ATGTTACAGGGTTTGAATTAGGCTAAAAGGTCTAAAAAGGTCTTGCAGATGGCTTTCATGGCCCTTCAAA | SEQ ID NO: 2552 | Homo sapiens AT rich interactive domain 4B (RBP1-like) (ARID4B), transcript variant 1, mRNA [NM_016374] |
| 201 | A_23_P20225 | RRM2B | TGGTTCCTTGTTAAAAAAGTTAAAGAATTTGAAAAGAAGAATCTCATATTCCGGAGCATTAGGA | SEQ ID NO: 2553 | Homo sapiens ribonucleotide reductase M2 B (TP53 inducible) (RRM2B), mRNA [NM_015713] |
| 202 | A_23_P202637 | SAPS3 | TGATTATTCCTACAAGTGAAACAGTAGACTATTTGGAGTGTATATGGCTGTGTTTTGGG | SEQ ID NO: 2554 | Homo sapiens SAPS domain family, member 3 (SAPS3), mRNA [NM_018312] |
| 203 | A_23_P202978 | CASP1 | CTGTTCCTGTGATGTGGAGGGAAATTTTCCGGCAAGGTCGGATTTTCATTTGAGCAGCCAGA | SEQ ID NO: 2555 | Homo sapiens caspase 1, apoptosis-related cysteine peptidase (interleukin 1, beta, convertase) (CASP1), transcript variant alpha, mRNA [NM_033292] |
| 204 | A_23_P203376 | MS4A6A | ACGGGGCTGTAAATTACCATTTACTAGAATTAGCCAAATAGTCTGAATTTCAGAAAACAA | SEQ ID NO: 2556 | Homo sapiens membrane-spanning 4-domains, subfamily A, member 6A (MS4A6A), transcript variant 1, mRNA [NM_152852] |
| 205 | A_23_P203498 | TRIM22 | GTAGATAAGAATCTATCACTAAGTAATGTATCGTTCAGAATGTGTTGGTTTACCAGTGAC | SEQ ID NO: 2557 | Homo sapiens tripartite motif-containing 22 (TRIM22), mRNA [NM_006074] |

Fig. 7-12

| No. | Probe ID No. | Symbols of genes | Sequence | SEQ ID NO: | Descriptions of genes (letters and numbers within [ ] indicates GenBank accession No.) |
|---|---|---|---|---|---|
| 206 | A_23_P204269 | USP15 | GACCAAGGAATAAATGAGGTATGTTGATCATGGCTTTGCTTTAATATCTTGATATTAAAGCTG | SEQ ID NO: 2558 | Homo sapiens ubiquitin specific peptidase 15 (USP15), mRNA [NM_006313] |
| 207 | A_23_P204564 | PPP1R12A | GTATAAGATGTTAGATTCTGTAATCTTCACATTCATTTTAGCAGGTACTGAGTGATGCTG | SEQ ID NO: 2559 | Homo sapiens protein phosphatase 1, regulatory (inhibitor) subunit 12A (PPP1R12A), mRNA [NM_002480] |
| 208 | A_23_P205027 | ABHD13 | ATTTGTGCAGAATGATAAAGAATGTTCGTTTTAGAAGTGTGTTATGTCTGTACCTGCTG | SEQ ID NO: 2560 | Homo sapiens abhydrolase domain containing 13 (ABHD13), mRNA [NM_032859] |
| 209 | A_23_P205336 | C14orf129 | CAATTCATTGCCAGACTTCATTGGAATGCTTGTTTGATGATGTATGTTCATTCTCAGCT | SEQ ID NO: 2561 | Homo sapiens chromosome 14 open reading frame 129 (C14orf129), mRNA [NM_016472] |
| 210 | A_23_P20606 | NIPSNAP3A | GTAAGTACCACTCAAAAAATAGTTCTGTTACTTCTGCATGGTATTTCAGTGTGTGTC | SEQ ID NO: 2562 | Homo sapiens nipsnap homolog 3A (C. elegans) (NIPSNAP3A), mRNA [NM_015469] |
| 211 | A_23_P206396 | CKLF | ATTATGAACTGCAGTGGTAAGAACAGTATTCATGGTCATCGTATCTGTGTTGGCAGTGATA | SEQ ID NO: 2563 | Homo sapiens chemokine-like factor (CKLF), transcript variant 1, mRNA [NM_016951] |
| 212 | A_23_P207299 | LOC51136 | GCAAAACAGCAATTTGAAATTAGAACGTAGTGGTTTTAGAGAACTCAGGTATTCTTTCCTG | SEQ ID NO: 2564 | Homo sapiens PTD016 protein (LOC51136), mRNA [NM_016125] |
| 213 | A_23_P207666 | USP6 | TCCATTACCCTTTCTCCTCATAGGTAGTAGTAATTACCAATCGTAACTAAGCAATTGTGTGT | SEQ ID NO: 2565 | Homo sapiens ubiquitin specific peptidase 6 (Tre-2 oncogene) (USP6), mRNA [NM_004505] |
| 214 | A_23_P207999 | PMAIP1 | TTAGAGAATCGTTCGTAGTGTTTTGCCGAAGATTACCGCTCTGGCCTAGTGTGAAGGGAGAT | SEQ ID NO: 2566 | Homo sapiens phorbol-12-myristate-13-acetate-induced protein 1 (PMAIP1), mRNA [NM_021127] |
| 215 | A_23_P208119 | PSTPIP2 | AATTAGGTTTTCAACATGGGAACATGAAATCCACTTCTGGATTTGGAGCATCCACTCGA | SEQ ID NO: 2567 | Homo sapiens proline-serine-threonine phosphatase interacting protein 2 (PSTPIP2), mRNA [NM_024430] |
| 216 | A_23_P209116 | CYP4F3 | GTTGAAATTTGGGTGGAATAAATTCTGGATTTCTATTCCATGTTGGACCAATACC | SEQ ID NO: 2568 | Homo sapiens mRNA for leukotriene B4 omega-hydroxylase, complete cds. [AB002454] |
| 217 | A_23_P209625 | CYP1B1 | CTGTGTTTATATGGAAGAAAGTAAGGTGCTTGGAGTTTACCTGGCTTATTAATATGCTT | SEQ ID NO: 2569 | Homo sapiens cytochrome P450, family 1, subfamily B, polypeptide 1 (CYP1B1), mRNA [NM_000104] |
| 218 | A_23_P210274 | PRE3 | GGATCAGTATGCCGTAGGATTACAGAAGATATTTCACATGCTTATTTCATCATCGGCAC | SEQ ID NO: 2570 | Homo sapiens preimplantation protein 3 (PRE3), transcript variant 1, mRNA [NM_015337] |
| 219 | A_23_P211047 | BACH1 | ATGTTAGATGCAGTAGACGATAGACAGGTTGCATGTGGACACTCAGTCACATTAAGCACTTG | SEQ ID NO: 2571 | Homo sapiens BTB and CNC homology 1, basic leucine zipper transcription factor 1 (BACH1), transcript variant 1, mRNA [NM_206866] |
| 220 | A_23_P211840 | UBE1C | GCCACCCTAGAGGGAAAAAATAGAAACACTTTACTTACGAGTCGGTAACGCTCATTGAAGAA | SEQ ID NO: 2572 | Homo sapiens ubiquitin-activating enzyme E1C (UBA3 homolog, yeast) (UBE1C), transcript variant 1, mRNA [NM_003968] |
| 221 | A_23_P211899 | THC2522899 | AACAAAGCATTTCGTTAAAATGTTTGGTAGGTTAAGCTGTGCTGTTCTACTGATGGTTG | SEQ ID NO: 2573 | GPR27_HUMAN (Q9NS67) Probable G-protein coupled receptor 27 (Super conserved receptor expressed in brain 1), complete [THC2522889] |
| 222 | A_23_P212061 | MME | TTTATTACTGCCAGAAGAACAACTATCCTGACTCTAATATCATTCACTAGGTTTGCCTG | SEQ ID NO: 2574 | Homo sapiens membrane metallo-endopeptidase (MME), transcript variant 2b, mRNA [NM_007289] |
| 223 | A_23_P212728 | TBC1D23 | TGTACCGTGTTAACAGGCAGTCATTTTGATTTAGTTATGGAAATCAAGTGAATAAAAGGC | SEQ ID NO: 2575 | Homo sapiens TBC1 domain family, member 23, mRNA (cDNA clone MGC:8800 IMAGE:3847561), complete cds. [BC020955] |

Fig. 7-13

| No. | Probe ID No. | Symbols of genes | Sequence | SEQ ID NO: | Descriptions of genes (letters and numbers within [ ] indicate GenBank accession No.) |
|---|---|---|---|---|---|
| 224 | A_23_P213247 | FBXL5 | ATGGAGGTGATTGGTTCTTCTTTACACATTAACACTGTACCAAGCTTTGGAGATCTTTTCC | SEQ ID NO: 2576 | Homo sapiens F-box and leucine-rich repeat protein 5 (FBXL5), transcript variant 2, mRNA [NM_033535] |
| 225 | A_23_P213661 | HISPPD1 | GTATGTAAGTTTTCTGTTTGTGAAAATGTAGTTAGTTACTGACTGTGGAGGTCATAAGG | SEQ ID NO: 2577 | Homo sapiens histidine acid phosphatase domain containing 1 (HISPPD1), mRNA [NM_015216] |
| 226 | A_23_P215751 | NDUFA5 | TAAAAGTGGAGTCACTAAATAGTTTCGAGTAGTTTCTAATATAAGTGTAGGTGGGTATC | SEQ ID NO: 2578 | Homo sapiens NADH dehydrogenase (ubiquinone) 1 alpha subcomplex, 5, 13kDa (NDUFA5), nuclear gene encoding mitochondrial protein, mRNA [NM_005000] |
| 227 | A_23_P216325 | ASAH1 | ATGAAGTCGATGCTAAGCAAGGGTAGATGGTATGTGGTACAAAGAAATTATGACGGTTGGA | SEQ ID NO: 2579 | Homo sapiens N-acylsphingosine amidohydrolase (acid ceramidase) 1 (ASAH1), transcript variant 2, mRNA [NM_004315] |
| 228 | A_23_P217384 | AP1S2 | AAACGTGTTGCTCTCTTCAGAGTATTATGTGTAAAGTCATTGTTTAAAGCACGAATGTTC | SEQ ID NO: 2580 | Homo sapiens adaptor-related protein complex 1, sigma 2 subunit (AP1S2), mRNA [NM_003916] |
| 229 | A_23_P217564 | ACSL4 | GTTATAGGTGCTTAGAAACACATAATTAACACTTAAGGTTGGGTGCTGCTAATTCTTTG | SEQ ID NO: 2581 | Homo sapiens acyl-CoA synthetase long-chain family member 4 (ACSL4), transcript variant 1, mRNA [NM_004458] |
| 230 | A_23_P217737 | ENST00000341514 | CACAAGCATGAGTTCGTTGTTCTTCAGTTAAAAGAGTTGTTCACAGTGTTGATAAGCAA | SEQ ID NO: 2582 | Copper-transporting ATPase 1 (EC 3.6.3.4) (Copper pump 1) (Menkes disease-associated protein). [Source:Uniprot/SWISSPROT:Acc:Q04656] [ENST00000341514] |
| 231 | A_23_P218928 | C4orf18 | CAGATGAGTTCATTTGCTTCTGTAGATGTGTTTCAGAGGCTAGGTACAAGAGGAATGTTTG | SEQ ID NO: 2583 | Homo sapiens chromosome 4 open reading frame 18 (C4orf18), transcript variant 2, mRNA [NM_016613] |
| 232 | A_23_P219072 | SAMD9 | AAGCTACCTCCAGATTAGTAAAGCCAGTTGAAAAACTAAAAGATCAGGTTCGAGAAGTCT | SEQ ID NO: 2584 | Homo sapiens sterile alpha motif domain containing 9 (SAMD9), mRNA [NM_017654] |
| 233 | A_23_P22433 | RP2 | TTATTTCTCTTGCATTAATAGTACTGCTGTTTTTGTTTTGCTTCTTTATATTTATGTCTA | SEQ ID NO: 2585 | Homo sapiens retinitis pigmentosa 2 (X-linked recessive) (RP2), mRNA [NM_006915] |
| 234 | A_23_P23048 | S100A9 | GAGCTGGTGCGAAAAGATCTGGAAAATTTCTGAAGAAGGAGAATAAGAATGAAAAGGTC | SEQ ID NO: 2586 | Homo sapiens S100 calcium binding protein A9 (S100A9), mRNA [NM_002965] |
| 235 | A_23_P23705 | SPATA6 | CATCTTTGCTAAGTGTCTCATTATCTTCATCCCCTAGGAGGAAAAGAGTGGTCCATGTTG | SEQ ID NO: 2587 | Spermatogenesis-associated protein 6 precursor. [Source:Uniprot/SWISSPROT:Acc:Q8NHH7] [ENST00000371847] |
| 236 | A_23_P23960 | BLOC1S2 | GAGTAAACTGGAGAGTGTGGGTATTCCTGAACCTTCTTGAGACAGAATCCCTCAGAAT | SEQ ID NO: 2588 | Homo sapiens biogenesis of lysosome-related organelles complex-1, subunit 2 (BLOC1S2), transcript variant 2, mRNA [NM_001001342] |
| 237 | A_23_P24004 | IFIT2 | AGCTGACCGAGCATCAGCCACACTCTGGGTTGGAAAATGTTTGCCTGTTGGAATTAATTT | SEQ ID NO: 2589 | Homo sapiens interferon-induced protein with tetratricopeptide repeats 2 (IFIT2), mRNA [NM_015471] |
| 238 | A_23_P24260 | ENST00000371207 | AAGGCACAATCTATTTTTCCAAGGTTTAATTTAGTGAGAGGGGCAGCATTAGTGTGGAGTG | SEQ ID NO: 2590 | Ectonucleoside triphosphate diphosphohydrolase 1 (EC 3.6.1.5) (NTPDase 1) (Ecto-ATP diphosphohydrolase) (ATPDase) (Lymphoid cell activation antigen) (Ecto-apyrase) (CD39 antigen). [Source:Uniprot/SWISSPROT:Acc:P49961] [ENST00000371207] |

Fig. 7-14

| No. | Probe ID No. | Symbols of genes | Sequence | SEQ ID NO: | Descriptions of genes (letters and numbers within [ ] indicates GenBank accession No.) |
|---|---|---|---|---|---|
| 239 | A_23_P24365 | ANKRD49 | GGGCACTGCTTGTATAGTCTCTCAAGTTCAGCAGGAAATGTTGATTTTCTAAGGTCCTCAT | SEQ ID NO: 2591 | Homo sapiens ankyrin repeat domain 49 (ANKRD49), mRNA [NM_017704] |
| 240 | A_23_P250002 | HACE1 | TAAGCAGTCATTGTTGTTGCCAGTAATGTTTGAGAGACATGTAAGATTGAAAGTTTTGCTA | SEQ ID NO: 2592 | Homo sapiens HECT domain and ankyrin repeat containing, E3 ubiquitin protein ligase 1 (HACE1), mRNA [NM_020771] |
| 241 | A_23_P250800 | ST3GAL6 | ATGTCACGAAGTTCAGCTAGCTGCTTGGTTTTAAATACAACTTTCTGACCTCAAGAGTCCTTT | SEQ ID NO: 2593 | Homo sapiens ST3 beta-galactoside alpha-2,3-sialyltransferase 6 (ST3GAL6), mRNA [NM_006100] |
| 242 | A_23_P251002 | NBN | CCTGATGGATCTGACAAGATGGACGTGAGAGGATGAAAATCTGTCTGATTAGTTTTGACTG | SEQ ID NO: 2594 | |
| 243 | A_23_P251480 | NBN | TTGGAAGAAACGTGAACTCAAGGAAGAAGTCACTATGGTCAGCTAAAGAAATATGTAAGA | SEQ ID NO: 2595 | Homo sapiens nibrin (NBN), transcript variant 1, mRNA [NM_002485] |
| 244 | A_23_P251825 | IFRD1 | CTATGAGACACCTTTAAGGAGGTTCTTGGATCGAGGGATGCAGTACCCAGTTGCAGTCAAAT | SEQ ID NO: 2596 | Homo sapiens interferon-related developmental regulator 1 (IFRD1), transcript variant 2, mRNA [NM_001007245] |
| 245 | A_23_P251937 | CPEB4 | GTATGTCAGTTAATTGTACTACTTGGCTGAATTCCATATAGTTTTACTGTGTATGGGG | SEQ ID NO: 2597 | Homo sapiens cytoplasmic polyadenylation element binding protein 4 (CPEB4), mRNA [NM_030627] |
| 246 | A_23_P252145 | C1GALT1 | ATATGTCTATATATAGAGGAAGTGTGTTTTTTAAATGGTGGCCAGGTAGAGGAACTAG | SEQ ID NO: 2598 | Homo sapiens core 1 synthase, glycoprotein-N-acetylgalactosamine 3-beta-galactosyltransferase, 1 (C1GALT1), mRNA [NM_020156] |
| 247 | A_23_P252201 | EAF2 | CAGGATTCCTGATATAGATGGCAGTCATAATAGATTCGAGACAACAGTGGGCCTTGCTGAT | SEQ ID NO: 2599 | Homo sapiens ELL associated factor 2 (EAF2), mRNA [NM_018456] |
| 248 | A_23_P25235 | CLEC4D | CATTTAACCACGCAGAGTATTCTGGCATAAGAATGAACCCGACAAGTCTCAGGGAGAAA | SEQ ID NO: 2600 | Homo sapiens C-type lectin domain family 4, member D (CLEC4D), mRNA [NM_080387] |
| 249 | A_23_P252371 | RBBP8 | GGCAAGGAGCAGAAGACATAGGACGTTGAAACAGAAACAAGAAGGATGAAAGGACAGTTTTTT | SEQ ID NO: 2601 | Homo sapiens retinoblastoma binding protein 8 (RBBP8), transcript variant 1, mRNA [NM_002894] |
| 250 | A_23_P253012 | GRAMD1C | GAATTCCAACGAACCACTACCGTAGGGGTAACAGTGAACCTACCTGGGTTTGTTTTGTTTTG | SEQ ID NO: 2602 | Homo sapiens GRAM domain containing 1C (GRAMD1C), mRNA [NM_017577] |
| 251 | A_23_P253602 | BMX | TTATGCTGCTCCTGATATAACACTTTCCAGCCTATAGCAAGAAGCACATTTTCAGACTGCA | SEQ ID NO: 2603 | Homo sapiens BMX non-receptor tyrosine kinase (BMX), mRNA [NM_001721] |
| 252 | A_23_P254472 | C6orf211 | TTCATTTCAATAGCTTGTTTCATTTGCACCGCCCTTTGTATTTTGATTGACCTGTAGAATGG | SEQ ID NO: 2604 | Homo sapiens chromosome 6 open reading frame 211 (C6orf211), mRNA [NM_024573] |
| 253 | A_23_P254702 | DEK | TTTTTATTAACTGCTTTTGCCCATATAACATGCTGATATTACTGGAAACCTAGCCAGC | SEQ ID NO: 2605 | Homo sapiens DEK oncogene (DNA binding) (DEK), mRNA [NM_003472] |
| 254 | A_23_P255503 | FNDC3A | ATACTTGCATTGAGCCTCACTGACAAAATTAGTGCAGGAGAAAAGCATTTTAATGT | SEQ ID NO: 2606 | Homo sapiens fibronectin type III domain containing 3A (FNDC3A), transcript variant 2, mRNA [NM_014923] |
| 255 | A_23_P255444 | DAPP1 | AGAAGAATGAGATAGTGATGTCCACAGTTCATTGGCAGAGAATCTAACATTTTAATGT | SEQ ID NO: 2607 | Homo sapiens dual adaptor of phosphotyrosine and 3-phosphoinositides (DAPP1), mRNA [NM_014395] |
| 256 | A_23_P256231 | FBXO30 | GCCCTTTTAAAGTTTTGCTGAAGAATGTGTCTGTGGTTAGGATAGCACAAGCATTAACTTT | SEQ ID NO: 2608 | Homo sapiens F-box protein 30 (FBXO30), mRNA [NM_032145] |
| 257 | A_23_P256342 | SNX13 | ATTAGGCAGGTGAATGATCCTTGAAACATCTCTTCAGGTCTGGAGAAAGAGACAGAATG | SEQ ID NO: 2609 | Homo sapiens sorting nexin 13 (SNX13), mRNA [NM_015132] |

Fig. 7-15

| No. | Probe ID No. | Symbols of genes | Sequence | SEQ ID NO: | Descriptions of genes (letters and numbers within [ ] indicates GenBank accession No.) |
|---|---|---|---|---|---|
| 258 | A_23_P255432 | PPP2R5A | TTGGTCAAGTATTTCTCACATCTTTTGTTATCAGAGATACCATTCCAATCTCTAACTTGG | SEQ ID NO: 2610 | Homo sapiens protein phosphatase 2, regulatory subunit B', alpha isoform (PPP2R5A), mRNA [NM_006243] |
| 259 | A_23_P25735 | PSMA6 | TAGGAGAGAGAGACTAAACATTGTCGTTAGTTTACCAGATCCGTGATGCCACTTACCTGT | SEQ ID NO: 2611 | Homo sapiens proteasome (prosome, macropain) subunit, alpha type, 6 (PSMA6), mRNA [NM_002791] |
| 260 | A_23_P255054 | SNX14 | CATCAGACTTCTGTTTGATGGCTTACAGCAACCAGTACTCAACAAGCAGCTGACTTATGT | SEQ ID NO: 2612 | Homo sapiens sorting nexin 14 (SNX14), transcript variant 1, mRNA [NM_153816] |
| 261 | A_23_P26021 | COPS2 | TGGTTTTTGATCAACTGGTTTGTGTTTTGCTGCTGACATTTATCCCAAGAAAACAGCTT | SEQ ID NO: 2613 | Homo sapiens COP9 constitutive photomorphogenic homolog subunit 2 (Arabidopsis) (COPS2), mRNA [NM_004236] |
| 262 | A_23_P2705 | P2RY5 | TCTGTATTGGTGTGTTTCCAACTGTTGTTTTGACCGTATAGTTTACTACTTACATCGGACA | SEQ ID NO: 2614 | Homo sapiens purinergic receptor P2Y, G-protein coupled, 5 (P2RY5), mRNA [NM_005767] |
| 263 | A_23_P28169 | ARL6IP6 | GGAAAGCAAATAATGCCTACTACTCGGACTTTATAGAAGCTACTTTAAATCAGAATAT | SEQ ID NO: 2615 | Homo sapiens ADP-ribosylation-like factor 6 interacting protein 6 (ARL6IP6), mRNA [NM_152522] |
| 264 | A_23_P28485 | GCA | TGGTGGTGTTTGAGGGTTGGCTAGAAATGAAAGCCATGGATTTTGTGGCATGTTTGTAATA | SEQ ID NO: 2616 | Homo sapiens grancalcin, EF-hand calcium binding protein (GCA), mRNA [NM_012198] |
| 265 | A_23_P29005 | SAMSN1 | CTCTGGTTGCTATATCTCATCAGGAGAATTCAGATAATGGGAAAGAGGATCTGGAGTGTGA | SEQ ID NO: 2617 | Homo sapiens SAM domain, SH3 domain and nuclear localization signals 1 (SAMSN1), mRNA [NM_022136] |
| 266 | A_23_P30069 | FLJ31033 | AGATTTGTTTAAGTCGCTACACTTCTTATTCTAAATGATCAAGAGTACACTTGGTGG | SEQ ID NO: 2618 | Homo sapiens cDNA FLJ13681 fis, clone PLACE2000014, weakly similar to HYPOTHETICAL HELICASE C28H8.3 IN CHROMOSOME III. [AK023743] |
| 267 | A_23_P30175 | ERBB2IP | TAGTTGAGGCTAGTCTGGAACGTTCATTAGAGCAATATTGGTTATTGCACTTCATTTT | SEQ ID NO: 2619 | Homo sapiens erbb2 interacting protein (ERBB2IP), transcript variant 2, mRNA [NM_018695] |
| 268 | A_23_P302470 | SULT1B1 | TGTCTAAGTCAGAAATCTGAAGAAATAAGAGATTGTGTGTAGTTGATTGAAACGAGGGCA | SEQ ID NO: 2620 | Homo sapiens sulfotransferase family, cytosolic, 1B, member 1 (SULT1B1), mRNA [NM_014465] |
| 269 | A_23_P302550 | RGS18 | GAGTCTAAGGCCCTAGGGATTTGGGCATCTGCCACATTGGTTCATATTCAGAAAGTGTTA | SEQ ID NO: 2621 | Homo sapiens regulator of G-protein signalling 18 (RGS18), mRNA [NM_130782] |
| 270 | A_23_P30307 | CRSP9 | CAATTGTACTGGACAGAAGAATGAAGAACTCAAAGAGAAAATTCAGGTCATAGGAGAGATACGAT | SEQ ID NO: 2622 | Homo sapiens cofactor required for Sp1 transcriptional activation, subunit 9, 33kDa (CRSP9), mRNA [NM_004270] |
| 271 | A_23_P303210 | IKIP | TTTAGGTTCCAACTGTGTTAGACATGAGTTTCCTAGATCCATGGTCTCTAGATGGTTTAC | SEQ ID NO: 2623 | Homo sapiens IKK interacting protein (IKIP), transcript variant 1, mRNA [NM_153687] |
| 272 | A_23_P303260 | STX7 | GTCTGATGTTTACGGGGGAGAGTGTAGTTACTAAAAATGTTTACATAATTCAGAAGAAG | SEQ ID NO: 2624 | Homo sapiens syntaxin 7 (STX7), mRNA [NM_003569] |
| 273 | A_23_P305060 | PBEF1 | TGCCTGTGCTCTAATATGCACCTCAAGCATTTTAAGGAGATAATGTTTTTAGAGAGAATT | SEQ ID NO: 2625 | Homo sapiens pre-B-cell colony enhancing factor 1 (PBEF1), mRNA [NM_005746] |
| 274 | A_23_P305723 | MIER1 | TGATGTATTTTCAAATAGAGTTCAGGATCTGCAATTCAGTTCAACACAAGTTTGTTGGAGC | SEQ ID NO: 2626 | Homo sapiens mesoderm induction early response 1 homolog (Xenopus laevis) (MIER1), transcript variant 1, mRNA [NM_020948] |
| 275 | A_23_P305759 | ABHD3 | AGTTGGTAGACTGGAAGTCAGTAGGAAATTCCAGTATGTGTCTAAATTCTGTGATGATGTT | SEQ ID NO: 2627 | Homo sapiens abhydrolase domain containing 3 (ABHD3), mRNA [NM_138340] |
| 276 | A_23_P307940 | CAPZA2 | CTACAAGATTGGCAAAGAGATGCAGAAGATGCATAAGAATGAACATTGCATGACCGGATCATT | SEQ ID NO: 2628 | Homo sapiens capping protein (actin filament) muscle Z-line, alpha 2 (CAPZA2), mRNA [NM_006136] |

Fig. 7-16

| No. | Probe ID No. | Symbols of genes | Sequence | SEQ ID NO: | Descriptions of genes (letters and numbers within [ ] indicates GenBank accession No.) |
|---|---|---|---|---|---|
| 277 | A_23_P308800 | GLS | CGGAAGAAGAGATAAGAATACTGCAATAGGCCCTCAAACTTAAAAAAGAAAAAACTTTGC | SEQ ID NO: 2628 | Homo sapiens glutaminase C mRNA, complete cds. [AF158555] |
| 278 | A_23_P30995 | CYB5R4 | TGGAATTGTGGACAGTGCGATTGCCATTTACAGAACAAGGAGTAAGGTTGCTGCATGATGTCAAC | SEQ ID NO: 2629 | Homo sapiens cytochrome b5 reductase 4 (CYB5R4), mRNA [NM_016230] |
| 279 | A_23_P31097 | OSTM1 | ACTGAAAATGTGCTGGGGTTTGTTCTGCTGTCACTGTTTATGCTGCTGGAAGCTTAGCACT | SEQ ID NO: 2630 | Homo sapiens osteopetrosis associated transmembrane protein 1 (OSTM1), mRNA [NM_014028] |
| 280 | A_23_P312246 | CCDC82 | GGCTTTATAACGAGATGAGTGTCAAGTGAATGAGGTGTTGATATCCTGTCAGTTTAGTCAA | SEQ ID NO: 2631 | Homo sapiens coiled-coil domain containing 82 (CCDC82), mRNA [NM_024725] |
| 281 | A_23_P312932 | KRTAP8-1 | GGCTATGGCTTCGGCTATGGCTACAACGGGCTGTGGGGCTTTGGGGTACAGGAGATACTCG | SEQ ID NO: 2632 | Homo sapiens keratin associated protein 8-1 (KRTAP8-1), mRNA [NM_175857] |
| 282 | A_23_P314191 | ZDHHC17 | TGGATAGTTTTAGGAAATAGGAAGTTAATTCTCAGGACTGAAGATGAATTACTTCGTTGG | SEQ ID NO: 2633 | Homo sapiens zinc finger, DHHC-type containing 17 (ZDHHC17), mRNA [NM_015336] |
| 283 | A_23_P314691 | NFYB | GGAGGCATTTACTAACCAGTTACCAGCTGGCTTAATAACGACAGACGGGTCAACAACAAAA | SEQ ID NO: 2634 | Homo sapiens nuclear transcription factor Y, beta (NFYB), mRNA [NM_006166] |
| 284 | A_23_P317001 | BNIP2 | TTTGAAGCCGGTAGTTTGTTTGACCTAGTTAGATTGTGGTGTTTATTCAAGTTTGAAATCA | SEQ ID NO: 2635 | Homo sapiens BCL2/adenovirus E1B 19kDa interacting protein 2 (BNIP2), mRNA [NM_004330] |
| 285 | A_23_P317347 | ESCO1 | GCTAATTTTTAAAAGGCCTGAACTAATAGTTTGAAGAAAACCCCTATAGAAAAGGAAAGCTC | SEQ ID NO: 2636 | Homo sapiens establishment of cohesion 1 homolog 1 (S. cerevisiae) (ESCO1), mRNA [NM_052911] |
| 286 | A_23_P317465 | RAB8B | CCTTGAATATAGAGGGACCTAGACAGGATATGCTAAAATAATTTCAAATGTTAGCAC | SEQ ID NO: 2637 | Homo sapiens RAB8B, member RAS oncogene family (RAB8B), mRNA [NM_016530] |
| 287 | A_23_P321354 | TMEM71 | AACCACGTTGTCAACCAAGTTTTAATCTCTTGGGGCTCGTAATTACCTTCAGTTAA | SEQ ID NO: 2638 | Homo sapiens transmembrane protein 71 (TMEM71), mRNA 144649] |
| 288 | A_23_P324633 | C9orf72 | TGTGTGGATTTAGTCCCTGGGATTCAGTCGTGTAGAAATGTCTAATAGTCTGTATAGTCC | SEQ ID NO: 2639 | Homo sapiens chromosome 9 open reading frame 72 (C9orf72), transcript variant 1, mRNA [NM_018325] |
| 289 | A_23_P325501 | MORC3 | CATGCCATAAAATACTATGCTTATTGGTCCCATGTTTTGTTGTGCAATTTTAAAGAGATGGC | SEQ ID NO: 2640 | Homo sapiens MORC family CW-type zinc finger 3 (MORC3), mRNA [NM_015358] |
| 290 | A_23_P329198 | OBFC2A | ACATGTCATAAGTGGTACCCACTTCGCCTTTTTACTGTAGGGTGGATAACTGTTAGGATT | SEQ ID NO: 2641 | Homo sapiens oligonucleotide/oligosaccharide-binding fold containing 2A (OBFC2A), mRNA [NM_001031716] |
| 291 | A_23_P330531 | C19orf59 | CTGTCTCCCTGTTTGTGTAAACATAGTAGTATACTGCGGCCGTGTTTCTGTGTCACCGA | SEQ ID NO: 2642 | Homo sapiens chromosome 19 open reading frame 59 (C19orf59), mRNA [NM_174918] |
| 292 | A_23_P332439 | NUPL1 | ATTGAAATCTTGAATGTATTGAATCTGTCAAGGTACAGAGGCGGTGCCTTGTAAATGTC | SEQ ID NO: 2643 | Homo sapiens KIAA0410 mRNA, partial cds. [AB007870] |
| 293 | A_23_P339480 | HAT1 | AACATGAACAGCTCGGAAGGAGAGAGTTTCAGGAAACTAGTTGGAAGATTACCGGCGTGTTATTG | SEQ ID NO: 2644 | Homo sapiens histone acetyltransferase 1 (HAT1), transcript variant 1, mRNA [NM_003642] |
| 294 | A_23_P339554 | MLSTD2 | CAATAACTCGTCTTCAGAAAGCTATAGTGTTTCTTGAATATTGACAAGTAATTCTTGGG | SEQ ID NO: 2645 | Homo sapiens male sterility domain containing 2 (MLSTD2), mRNA [NM_032228] |
| 295 | A_23_P34307 | PIGK | ATTCATTTGACAGTTCTCTATTGTTGGACCACTTACATTGTAAATGTTTCCTTTGG | SEQ ID NO: 2646 | Homo sapiens phosphatidylinositol glycan anchor biosynthesis, class K (PIGK), mRNA [NM_005482] |
| 296 | A_23_P346006 | CCPG1 | TATGGTCGGCACTAATGGAAGACAAATGGGCAAATCTTGAAATAGAATTGGGGCAATTACGT | SEQ ID NO: 2647 | Homo sapiens cell cycle progression 1 (CCPG1), transcript variant 2, mRNA [NM_020739]. |

Fig. 7-17

| No. | Probe ID No. | Symbols of genes | Sequence | SEQ ID NO: | Descriptions of genes (letters and numbers within [ ] indicates GenBank accession No.) |
|---|---|---|---|---|---|
| 297 | A_23_P347059 | MOBKL1A | CTAGAAGGGAAAAATCATCTAAGTTATGAAATCGAACATAGGCG CTATATTACAAACTG | SEQ ID NO: 2849 | Homo sapiens MOB1, Mps One Binder kinase activator-like 1A (yeast) (MOBKL1A), mRNA [NM_173468] |
| 298 | A_23_P34710 | EGLN1 | TGATTGTCAAATGTACAGCCACAGGCCTTTTAATTTGGAGGCCCC TGTTGTCATTCAAAT | SEQ ID NO: 2850 | Egl nine homolog 1 (EC 1.14.11.-) (Hypoxia-inducible factor prolyl hydroxylase 2) (HIF-prolyl hydroxylase 2) (HIF-PH2) (HPH-2) (Prolyl hydroxylase domain-containing protein 2) (PHD2) (SM-20). [Source:Uniprot/SWISSPROT;Acc:Q9GZT9] [ENST00000357180] |
| 299 | A_23_P347198 | SP3 | GACCACCTGAAATTTAAAGGGTACCTTATTGTACGTTTAAAGTGT ATTATAACAGTGTGG | SEQ ID NO: 2851 | Homo sapiens Sp3 transcription factor (SP3), transcript variant 1, mRNA [NM_003111] |
| 300 | A_23_P349083 | FCHO2 | GTGAAATGGTAAACTTCTGGCAGTTCTTCTTAGTTACCACAGTCTTC ATACCAAGTATTGGG | SEQ ID NO: 2852 | Homo sapiens FCH domain only 2 (FCHO2), mRNA [NM_138782] |
| 301 | A_23_P350187 | ENST00000265149 | TTGCTAATATATAGGAATATCAGGTTGACTATATAGGCATACTTGAA AATGCTTCTGAGTGG | SEQ ID NO: 2853 | Homo sapiens mRNA for KIAA1546 protein, partial cds. [AB046766] |
| 302 | A_23_P353704 | RP5-1022P6.2 | TGTCTCTCACTACCTATTACACACTGTTGGCTTTGTGGGTTTGTTT TGTATGTGGGTGTGT | SEQ ID NO: 2854 | Homo sapiens hypothetical protein KIAA1434 (KIAA1434), mRNA [NM_019593] |
| 303 | A_23_P354074 | LYST | GTGGATGTTGTAGGAAACATTTCGTAAATTATCACAAGCTCGT TACCTTTATATAAGC | SEQ ID NO: 2855 | Homo sapiens lysosomal trafficking regulator (LYST), transcript variant 1, mRNA [NM_000081] |
| 304 | A_23_P355067 | TMCO1 | AACTGAAGAACTCTGTTTATTTGTATCATCATTCTTCTAGACACACAC ACATCGAGACTGGCAA | SEQ ID NO: 2856 | Homo sapiens transmembrane and coiled-coil domains 1 (TMCO1), mRNA [NM_019026] |
| 305 | A_23_P355244 | SAMD9 | TCACTGGAGGAAGATTTTCCCTTGCTCTGCATAAATTTAACT CCATAACTTATAAGC | SEQ ID NO: 2857 | Homo sapiens sterile alpha motif domain containing 9 (SAMD9), mRNA [NM_017654] |
| 306 | A_23_P356125 | KIAA1468 | GCACTGCTTTATTACTGCTGCTGTATATTTGTTGATTTGGAGTTA CAACTGTGGTGATAG | SEQ ID NO: 2858 | Homo sapiens KIAA1468 (KIAA1468), mRNA [NM_020854] |
| 307 | A_23_P364107 | C14orf106 | AGGAGACAGTGTTTGTATTTCAAGTGAGTACAGTGTTTCTT TGTAAAGTAGCTTCC | SEQ ID NO: 2859 | Homo sapiens chromosome 14 open reading frame 106 (C14orf106), mRNA [NM_018353] |
| 308 | A_23_P371266 | DNM3 | ACTGTCTTCTTGGCAGTTCAAGCATTTCAGGAGATTTCTTAATGCTGATATATGG ACTCTTAGAATGGAA | SEQ ID NO: 2860 | Homo sapiens dynamin 3 (DNM3), mRNA [NM_015569] |
| 309 | A_23_P37275 | CGRRF1 | GAGGAAGATAAAGACAAAGCGGAAGACTCTTTGAAGACATGGTAAC ACTGAAAAGTACACT | SEQ ID NO: 2861 | Homo sapiens cell growth regulator with ring finger domain 1 (CGRRF1), mRNA [NM_006568] |
| 310 | A_23_P37441 | B2M | TTGCTTTCAGCAAGGACTGGTCTTTCTATCTCTTGTACTACACT GAATTCACGCGGACT | SEQ ID NO: 2862 | Homo sapiens beta-2-microglobulin (B2M), mRNA [NM_004048] |
| 311 | A_23_P378722 | SAT1 | CCATGTACTATTTTACCTATGACCCGGTGGGATTGGGCAAGTTATTGT ATCTGAGGACTGT | SEQ ID NO: 2863 | Homo sapiens spermidine/spermine N1-acetyltransferase 1 (SAT1), mRNA [NM_002970] |
| 312 | A_23_P383764 | CR592K3P | TCCATCTCTGACTTGTTGGAAATTTGGTGAATTATCCAGTCAGAT TCCCGAGTTAGGACC | SEQ ID NO: 2864 | Homo sapiens clone IMAGE:110749 mRNA sequence. [AF143328] |
| 313 | A_23_P38723 | SMCHD1 | ACAAGTACGTGGGCATGGAATTTGCATTTCGATTCAGATGGGACTG GAAACAACCATTCAA | SEQ ID NO: 2865 | Homo sapiens cDNA FLJ44350 fis, clone TRACH3006228. [AK126324] |
| 314 | A_23_P388900 | SLC22A15 | AGGGTAGGCTGGCATCCAGTTGCTTATTCAGATGTGTCACTAAA TTTTCCTTCTAGATG | SEQ ID NO: 2866 | Homo sapiens solute carrier family 22 (organic cation transporter), member 15 (SLC22A15), mRNA [NM_018420] |

Fig. 7-18

| No. | Probe ID No. | Symbols of genes | Sequence | SEQ ID NO: | Descriptions of genes (letters and numbers within [ ] indicate GenBank accession No.) |
|---|---|---|---|---|---|
| 315 | A_23_P390734 | FGFR1OP2 | CCACCAGATACAGAGAAATGTGCTTTAACAATCAGTTGAAACCTAAAT TTTGTTATGTTGTGG | SEQ ID NO: 2667 | Homo sapiens FGFR1 oncogene partner 2 (FGFR1OP2), mRNA [NM_015633] |
| 316 | A_23_P394545 | KIAA1033 | AGCATTTGAATACTATTAATATTCGGCATATTGCTAATTCAATTC GAACACATGGCACGG | SEQ ID NO: 2668 | Homo sapiens KIAA1033 (KIAA1033), mRNA [NM_015275] |
| 317 | A_23_P394605 | SEC24A | GATTTATTTCTTCTAATCAAGATGCATAACAGCTATTATGTAGG GGACCACCAAATGTG | SEQ ID NO: 2669 | Homo sapiens SEC24 related gene family, member A (S. cerevisiae) (SEC24A), mRNA [NM_021982] |
| 318 | A_23_P396353 | NIN | ATCTTGCAGGTCTAGTATTTAATAATGCACTATTACCCAGGGGA GATATTGAGAAAC | SEQ ID NO: 2670 | Homo sapiens ninein (GSK3B interacting protein) (NIN), transcript variant 2, mRNA [NM_020921] |
| 319 | A_23_P398073 | PPM1B | GGTTCAGTAACTTTTCATTTTATAACATTGGGACGGATACAAGAGT GATTGTCACATAAGG | SEQ ID NO: 2671 | Homo sapiens protein phosphatase 1B (formerly 2C), magnesium-dependent, beta isoform (PPM1B), transcript variant 2, mRNA [NM_177968] |
| 320 | A_23_P398449 | VNN3 | ACATATCAATTGTGACCCCAGAAGAATGGAATCTATGGTTGGATGTT CACCAGGGAAGAGCAT | SEQ ID NO: 2672 | Homo sapiens vanin 3 (VNN3), transcript variant 2, mRNA [NM_078625] |
| 321 | A_23_P40108 | COL9A3 | TCAAAAGGCCCTAGCTAATAAACCTGTAAGCCAGGCATTTGAGAG AAGGTAGGGTGTGTA | SEQ ID NO: 2673 | Homo sapiens collagen, type IX, alpha 3 (COL9A3), mRNA [NM_001853] |
| 322 | A_23_P405873 | C9orf72 | GAGAATGGAAGATCAGAGGTCAGAGTATTATTCCAATGCTTACTGG AGAAGTGATTCCTGT | SEQ ID NO: 2674 | Homo sapiens chromosome 9 open reading frame 72 (C9orf72), transcript variant 2, mRNA [NM_145005] |
| 323 | A_23_P406986 | MOSPD2 | TTACTATTCTGAAGGGTAGTGTGTTGGTTTTCATCTTCAAGAAG TTGATTCCAAAAGTG | SEQ ID NO: 2675 | Homo sapiens motile sperm domain containing 2 (MOSPD2), mRNA [NM_152581] |
| 324 | A_23_P4096 | CA4 | TAATATCCCAAACCTGAGATGAGCACTAGCATGGCAGAGAGCAG GCTGTTGGACCTGCT | SEQ ID NO: 2676 | Homo sapiens carbonic anhydrase IV (CA4), mRNA [NM_000717] |
| 325 | A_23_P41114 | CSTA | AAACAAATGAGACTTATGCAGAAAATTGGAAGCTGTGCAGTATAAA CTCAAGTTGTTGCTG | SEQ ID NO: 2677 | Homo sapiens cystatin A (stefin A) (CSTA), mRNA [NM_005213] |
| 326 | A_23_P412980 | SNX13 | CCCGATCTCAAGCAACAAGAATGGGGTTGGTTTCTTCCATTTCAAACT AATCAGCATGTCCA | SEQ ID NO: 2678 | Homo sapiens sorting nexin 13 (SNX13), mRNA [NM_015132] |
| 327 | A_23_P41645 | ELL2 | TGTCTTTTCAAAGTGCTGCCAGTTGAAAGGGAAGCATTATGTTT ACAAATCTCTTTTGA | SEQ ID NO: 2679 | Homo sapiens elongation factor, RNA polymerase II, 2 (ELL2), mRNA [NM_012081] |
| 328 | A_23_P41664 | ENST00000334994 | TGGCTTGGAAGCAGATTCGACTTCATAAACAAATTGTTCCTGAAAA TGAGGCACAGGTCAT | SEQ ID NO: 2680 | Synleurin (GGL01891) [Source:Uniprot/SPTREMBL;Acc:Q72207] [ENST00000334994] |
| 329 | A_23_P420431 | XKR3 | CAGAGGTGGGGCCATAGAATCGTACACGTACACGCTTCAGTTTTTT AGAAAATGTGATAAT | SEQ ID NO: 2681 | Homo sapiens XK, Kell blood group complex subunit-related family, member 3 (XKR3), mRNA [NM_175878] |
| 330 | A_23_P422083 | TMEM55A | AAATTTATGGAATCAGGTCTGCTGCACTGCCATCTTTGGAGTTTTG AAAAGAAATTGCTT | SEQ ID NO: 2682 | Homo sapiens transmembrane protein 55A (TMEM55A), mRNA [NM_018710] |
| 331 | A_23_P424080 | YIPF4 | AAAGGATTGTGTTTTTAAGATTGTGTGGATATTCACCTAAAACT TGTGCCAAAAGCAGC | SEQ ID NO: 2683 | Homo sapiens Yip1 domain family, member 4 (YIPF4), mRNA [NM_032312] |
| 332 | A_23_P427217 | JMJD1C | TCCAGAACATCTTGTAGAGTGCATTTCATTTAACAGAGGAACTGAG ACTTTGAAGGAAGA | SEQ ID NO: 2684 | Homo sapiens jumonji domain containing 1C (JMJD1C), transcript variant 2, mRNA [NM_004241] |
| 333 | A_23_P429491 | FLJ25416 | GCTTGGTCACCCGAATTGTTTTCATAAAAGTCACCTGAACCGAA TTGCTGAACTTTTAA | SEQ ID NO: 2685 | Homo sapiens hypothetical protein FLJ25416 (FLJ25416), mRNA [NM_145018] |
| 334 | A_23_P429689 | FAM44A | ACCAATACTCTTTCGCATATTCTCTTTTTCAGTGAAGAGAAATGCA TTCAAGATTAGGTCC | SEQ ID NO: 2686 | Homo sapiens family with sequence similarity 44, member A (FAM44A), mRNA [NM_148894] |

Fig. 7-19

| No | Probe ID No. | Symbols of genes | Sequence | SEQ ID NO: | Descriptions of genes (letters and numbers within [ ] indicates GenBank accession No.) |
|---|---|---|---|---|---|
| 335 | A_23_P42969 | FGL2 | TTCAGGCTGGTGGTTTGATGCATGCTTTCTGCAAAGTTAAATGGCAAATATTATCACCA | SEQ ID NO: 2687 | Homo sapiens fibrinogen-like 2 (FGL2), mRNA [NM_006682] |
| 336 | A_23_P42975 | PRKAR2B | GCCACATTTTTAGAACACTGTTTAAGCAATTTTTGGAAAACCTTGTTGTAGGAAAAGAGAGC | SEQ ID NO: 2688 | Homo sapiens protein kinase, cAMP-dependent, regulatory, type II, beta (PRKAR2B), mRNA [NM_002736] |
| 337 | A_23_P430161 | EXOC8 | AAGTACAGGATTTTCTTCAGGTAAAATCTGTGTTCCAATTACAGTTGTAGGTCAAGGA | SEQ ID NO: 2689 | Homo sapiens exocyst complex component 8 (EXOC8), mRNA [NM_175876] |
| 338 | A_23_P431630 | USP32 | CCCATACCCTTTCTTCCTCATAGATAGTAATTACCAATGTAAGTAAGTATTGTGTCTG | SEQ ID NO: 2690 | Homo sapiens ubiquitin specific peptidase 32 (USP32), mRNA [NM_032582] |
| 339 | A_23_P434609 | S100A8 | AAAGGGATGAAGAAAGCCACAAAGAGATAGCTGAGTTACTGGGCCAGAGGCTGGGCCCCT | SEQ ID NO: 2691 | Homo sapiens S100 calcium binding protein A8 (S100A8), mRNA [NM_002964] |
| 340 | A_23_P44257 | COMMD8 | AACATTTACTTCTGCGCTTCTCATGTGTTGGGAAACATTGGTGTGATAAAAATAGGTGTC | SEQ ID NO: 2692 | Homo sapiens COMM domain containing 8 (COMMD8), mRNA [NM_017845] |
| 341 | A_23_P44768 | TBK1 | TCTACTCTGAGTGGGGGGTAAATAAGTTATTTTGTCTGACGGCCTAGTGGAAATATTTTA | SEQ ID NO: 2693 | Homo sapiens TANK-binding kinase 1 (TBK1), mRNA [NM_013254] |
| 342 | A_23_P46141 | CTSS | TCTGTTGGTGTGTAGATGCGGTCATCCTGTTCTTCCTCTACAGAAGTGGTGTCTACTAT | SEQ ID NO: 2694 | Homo sapiens cathepsin S (CTSS), mRNA [NM_004079] |
| 343 | A_23_P46396 | PTBP2 | AACCAAGGTGGGACCCAAAGTTTATGTGCTTTAGTCTTAATTTACCTTCCATTGTAATATT | SEQ ID NO: 2695 | Homo sapiens polypyrimidine tract binding protein 2 (PTBP2), mRNA [NM_021190] |
| 344 | A_23_P48166 | TWF1 | TGGAACCAGACCATAGCTGAAGCTGTTATTTCAGTCAGGAAGAAGCTACCTTGCATGAAGGT | SEQ ID NO: 2696 | Homo sapiens twinfilin, actin-binding protein, homolog 1 (Drosophila) (TWF1), mRNA [NM_002822] |
| 345 | A_23_P48897 | CCPG1 | AAGTCAGAAGGTCATACATATAATTCTAATGTCCAACTATGTCCATTCCATGTACCA | SEQ ID NO: 2697 | Homo sapiens cell cycle progression restoration protein (CPR8) mRNA, complete cds. [AF011794] |
| 346 | A_23_P50108 | NDC80 | AAAGTGGGAAATAACTTCGAACGTCTGTTAGAGATGGTCGTACACATGTTGGGTCTGTA | SEQ ID NO: 2698 | Homo sapiens NDC80 homolog, kinetochore complex component (S. cerevisiae) (NDC80), mRNA [NM_006101] |
| 347 | A_23_P502797 | WDFY1 | GTAACAGTTTACTGGTTGTTCCATTCCTGAATATGCAGGGTAATTTGTACAGATAGGGAT | SEQ ID NO: 2699 | Homo sapiens WD repeat and FYVE domain containing 1 (WDFY1), mRNA [NM_020830] |
| 348 | A_23_P50907 | ITGAV | AAAGAGTGATTAAGTGAGGTTATTTACCCGCTAAATGGTCCATTCTGCCATTGTATTTCAGG | SEQ ID NO: 2700 | Homo sapiens integrin, alpha V (vitronectin receptor, alpha polypeptide, antigen CD51) (ITGAV), mRNA [NM_002210] |
| 349 | A_23_P50974 | HECW2 | GAGAAAGATGAACCCATACATGATCAGGTCCACGGTAATTTTTAGGGACTCAGGAGAATC | SEQ ID NO: 2701 | Homo sapiens HECT, C2 and WW domain containing E3 ubiquitin protein ligase 2 (HECW2), mRNA [NM_020760] |
| 350 | A_23_P51009 | NDUFB3 | CCGCAATGAAGCTTGGAGATACATGGGTGGCTTGCAAAGAGAGTGTTTGCTTTTCTGATGT | SEQ ID NO: 2702 | Homo sapiens NADH dehydrogenase (ubiquinone) 1 beta subcomplex, 3, 12kDa (NDUFB3), mRNA [NM_002491] |
| 351 | A_23_P51996 | STXBP3 | ATTCAGTGATTAATAGAAATGGAGTGATTTGACAGTGTGTACTGTTTTGCCACATACTTG | SEQ ID NO: 2703 | Homo sapiens syntaxin binding protein 3 (STXBP3), mRNA [NM_007269] |
| 352 | A_23_P53467 | IKIP | GTTAGAACCATTAGTAAATGATTTAACACTACGCATTGGGAGATTGGTTACCGAGTAC | SEQ ID NO: 2704 | Homo sapiens IKK interacting protein (IKIP), transcript variant 2, mRNA [NM_201612] |
| 353 | A_23_P53668 | NFYB | TGGGTCATATTGTGCATACCATTTGTAACCTGCTTTTTCACTTAACAATATATGGG | SEQ ID NO: 2705 | Homo sapiens nuclear transcription factor Y, beta (NFYB), mRNA [NM_006166] |

Fig. 7-20

| No. | Probe ID No. | Symbols of genes | Sequence | SEQ ID NO: | Descriptions of genes (letters and numbers within [ ] indicates GenBank accession No.) |
|---|---|---|---|---|---|
| 354 | A_23_P53891 | KLF5 | CGTTGAATTGATGATGCAGTTTTCATATATCGAGATGTTCGGTCGTGACAGTACTGTTGGT | SEQ ID NO: 2706 | Homo sapiens Kruppel-like factor 5 (intestinal) (KLF5), mRNA [NM_001730] |
| 355 | A_23_P5611 | RIF1 | ATGTATTCTTGGGTCGGTATGGGTGGTTTTCAGGAAATTAATTATCTTACTGAGTGTG | SEQ ID NO: 2707 | Homo sapiens RAP1 interacting factor homolog (yeast) (RIF1), mRNA [NM_018151] |
| 356 | A_23_P56734 | HNMT | CCTTTGTCCACCATGGATATCTGACTGCTTATTGATGGTAATGAAAATGGAGAACCT | SEQ ID NO: 2708 | Homo sapiens histamine N-methyltransferase (HNMT), transcript variant 1, mRNA [NM_006895] |
| 357 | A_23_P56759 | KRCC1 | GATATCGGTGTTCATACCAGTTTTCTTATGTGAATAGGTCTTTAACTCTAACAAAGGC | SEQ ID NO: 2709 | Homo sapiens lysine-rich coiled-coil 1 (KRCC1), mRNA [NM_016618] |
| 358 | A_23_P57658 | HRASLS | TTGGGAGGAGGAAAAGAAAACCTGGGGTGAATACTTATTTTCAGTGCATCATTACTGTTCC | SEQ ID NO: 2710 | Homo sapiens HRAS-like suppressor (HRASLS), mRNA [NM_020386] |
| 359 | A_23_P57856 | BCL6 | CTGGTTAAAGGCTCAGATTTTGTATCTGCAGGCAGGACGAAACGGATCTGAGAATCTTTATTGA | SEQ ID NO: 2711 | Homo sapiens B-cell CLL/lymphoma 6 (zinc finger protein 51) (BCL6), transcript variant 2, mRNA [NM_138931] |
| 360 | A_23_P58390 | C4orf32 | TAATACTAACTATTTAGTATACTGTCAGTACTGTGTACATCTGGACACTGGTGTTAATAGGG | SEQ ID NO: 2712 | Homo sapiens chromosome 4 open reading frame 32 (C4orf32), mRNA [NM_152400] |
| 361 | A_23_P58912 | SLC35A1 | ATGATCAGTGCGGGTTATGTGGAAACAACGAACAAACAACGAAGCTATCTGAGTGAACTGC | SEQ ID NO: 2713 | Homo sapiens solute carrier family 35 (CMP-sialic acid transporter), member A1 (SLC35A1), mRNA [NM_006416] |
| 362 | A_23_P59637 | DOCK4 | TTTGGCAGTGAGGAGGGTTCAATTTATCTTGAATTTATCATCATGTGTGTATTTCTGAAGCAG | SEQ ID NO: 2714 | Homo sapiens dedicator of cytokinesis 4 (DOCK4), mRNA [NM_014705] |
| 363 | A_23_P58921 | SUB1 | CAGATTGGGAAATGAGGTACGTTAGTGTTCGGCATTTTAAAGGCAAAGTGCTAATTGAT | SEQ ID NO: 2715 | Homo sapiens SUB1 homolog (S. cerevisiae) (SUB1), mRNA [NM_006713] |
| 364 | A_23_P63896 | ZNF354A | AAACGAAAAGGTCATCGAACAGACATCCTTGAGAGAGAGTGTAATAAATGTATGACATGT | SEQ ID NO: 2716 | Homo sapiens zinc finger protein 354A (ZNF354A), mRNA [NM_005649] |
| 365 | A_23_P61674 | CLK4 | GAAAAGGCATGCAGTTTTGTCCATTGTGACAGTTTGTTTAATAAAACCAGATACACACTTTA | SEQ ID NO: 2717 | Homo sapiens CDC-like kinase 4 (CLK4), mRNA [NM_020666] |
| 366 | A_23_P62227 | CXorf21 | AGGAACACTTTATCCATTTATTCTGAGAATGATGCAGGAAGGGGTTAGTGAAGGGGAATTAA | SEQ ID NO: 2718 | Homo sapiens chromosome X open reading frame 21 (CXorf21), mRNA [NM_025159] |
| 367 | A_23_P63343 | UTS2 | AGAATCTGGAAAGCATACAAGAAGAATGAGAGACTCCTGATTGCTTCTCGAAATACTGTGTC | SEQ ID NO: 2719 | Homo sapiens urotensin 2 (UTS2), transcript variant 1, mRNA [NM_021995] |
| 368 | A_23_P63655 | ATP5C1 | AGAGAGCTGAAACGAGCTCGAATATATGGATCTTAGCTCTGTATGAAAAAGCT | SEQ ID NO: 2720 | Homo sapiens ATP synthase, H+ transporting, mitochondrial F1 complex, gamma polypeptide 1 (ATP5C1), nuclear gene encoding mitochondrial protein, transcript variant 2, mRNA [NM_005174] |
| 369 | A_23_P63896 | FAS | ATGTCTATCCACAGGGTCAACCCCACTCTATGAATCAATAGAAGAAGCTATGACCTTTGC | SEQ ID NO: 2721 | Homo sapiens Fas (TNF receptor superfamily, member 6) (FAS), transcript variant 1, mRNA [NM_000043] |
| 370 | A_23_P65262 | RP11-298P3.3 | AGCCAAGAGTTAAGCAAGCACTGACTACCGTTCCCTTGAGCTACCATTATCACAAAGGGTTT | SEQ ID NO: 2722 | Human BRCA2 region, mRNA sequence CG016. [U50529] |
| 371 | A_23_P65768 | C15orf15 | TCCTGGATTGCCATCTACATAATAATCGAGATATTACGGATGTTAGATTGCATCGAGTGTT | SEQ ID NO: 2723 | Homo sapiens chromosome 15 open reading frame 15 (C15orf15), mRNA [NM_016304] |
| 372 | A_23_P66260 | ZNF267 | TGTGATGAATGTGGTAAGGCTTCAGCTATAGGTCATACCTCACTACACATGGAGAAGT | SEQ ID NO: 2724 | Homo sapiens zinc finger protein 267 (ZNF267), transcript variant 498723, mRNA [NM_003414] |

Fig. 7-21

| No. | Probe ID No. | Symbols of genes | Sequence | SEQ ID NO: | Descriptions of genes (letters and numbers within [ ] indicates GenBank accession No.) |
|---|---|---|---|---|---|
| 373 | A_23_P68472 | DPM1 | CTATTGGGAGGTTCCAATATCATTTGTGATGGTGTTTATGGTG AATCCAAGTTGGGAG | SEQ ID NO: 2725 | Homo sapiens dolichyl-phosphate mannosyltransferase polypeptide 1, catalytic subunit (DPM1), mRNA [NM_003859] |
| 374 | A_23_P69109 | PLSCR1 | GTTAGCTCTTAGACTGTCTATCCTTCCTAGAGAAATGGTAATTGAGA TTACTGAGATATTAA | SEQ ID NO: 2726 | Homo sapiens phospholipid scramblase 1 (PLSCR1), mRNA [NM_021105] |
| 375 | A_23_P6914 | OSBPL11 | GGTCTTCCAATCAGTGTGTGTAACATACCTGTTGTTTATCAGGCA TTGTAGGTGGGTGTG | SEQ ID NO: 2727 | Homo sapiens oxysterol binding protein-like 11 (OSBPL11), mRNA [NM_022776] |
| 376 | A_23_P69908 | GLRX | CTGATAAAACTTAGAGCCCCTACACCAAGAGTGTATGTGTGAAA GAGCTCCTACAGTT | SEQ ID NO: 2728 | Homo sapiens glutaredoxin (thioltransferase) (GLRX), mRNA [NM_002064] |
| 377 | A_23_P70290 | TMEM30A | ATCTTCTCCTCCAACTGTGTAAAGCACATGTAAGTGCTTAATGGAGA CTGTTTTCATTCTG | SEQ ID NO: 2729 | Homo sapiens transmembrane protein 30A (TMEM30A), mRNA [NM_018247] |
| 378 | A_23_P70297 | ANKRD6 | CCTTGTTTGTGGAGTCAAGTGTTGATATACTTGAGGGATGATTATG TGTCTTCTAATTAAT | SEQ ID NO: 2730 | Homo sapiens mRNA for KIAA0957 protein, partial cds. [AB023174] |
| 379 | A_23_P70326 | CENPQ | CAATGGCTTACAGTTTCTGTCTCGTCATCTGGAAACTTGAAAAATC CTCAAATGCTTCAC | SEQ ID NO: 2731 | Homo sapiens centromere protein Q (CENPQ), mRNA [NM_018132] |
| 380 | A_23_P70938 | STARD3NL | GCATTATGTGTATGGGCCTGAAGTGTTGGAGCTTGCAAAAGGGGAAG AAAGGAATTGGAAT | SEQ ID NO: 2732 | Homo sapiens STARD3 N-terminal like (STARD3NL), mRNA [NM_032016] |
| 381 | A_23_P71430 | UBE2W | AAATTGTTGAAAGGTCCAAGTCTCAGTACCATGTGAGTAATGAT AGTACAACTAAGTTG | SEQ ID NO: 2733 | Homo sapiens ubiquitin-conjugating enzyme E2W (putative) (UBE2W), transcript variant 1, mRNA [NM_001001481] |
| 382 | A_23_P71433 | UBE2W | CATGAGCGCTACTGGCTAAACACTATTCATTATTATGTTTGG AAACGCCCGTAAAGAT | SEQ ID NO: 2734 | Homo sapiens ubiquitin-conjugating enzyme E2W (putative) (UBE2W), transcript variant 1, mRNA [NM_001001481] |
| 383 | A_23_P72503 | KLHL2 | TTTTTGATATTTAACAATGCTTAAACACTTAAATGCCAGTTGTGA GGAATGGACCTGGTG | SEQ ID NO: 2735 | Homo sapiens kelch-like 2, Mayven (Drosophila) (KLHL2), mRNA [NM_007246] |
| 384 | A_23_P7262 | MARCH1 | GATTATTGTGTTCTTTGGATATTCATATGTAAAACTGATGTGTGAAT GACATTGCAGTGAGC | SEQ ID NO: 2736 | Homo sapiens cDNA FLJ20608 fis, clone KAIA585. [AK000675] |
| 385 | A_23_P7282 | ELMOD2 | TTCAAGTAGGTTTCTCTGGGGAAAAGTACCACTTGGACACTTA AAGGAATTGGGATTT | SEQ ID NO: 2737 | ELMO domain-containing protein 2. [Source:Uniprot/SWISSPROT:Acc:Q8IZ81] [ENST00000323570] |
| 386 | A_23_P74001 | S100A12 | TGAAGGCTTTTTACCGAGCAATGATGTCCTCAATGAGGGTCTTTTGTT TCCCTCACCAAAACC | SEQ ID NO: 2738 | Homo sapiens S100 calcium binding protein A12 (S100A12), mRNA [NM_005621] |
| 387 | A_23_P75028 | REEP3 | AGAAACAGCACACAAGTGTATTTTAGTCATCTACACGTCAAATAT CCCAAGACAGATAT | SEQ ID NO: 2739 | Homo sapiens receptor accessory protein 3 (REEP3), mRNA [NM_001013390] |
| 388 | A_23_P7543 | ZFYVE16 | TCTGCCTCAGCATTATGTAACCTAAATGATCTTGATAGTGCTGATACC TGTGATCCATGGTGG | SEQ ID NO: 2740 | Homo sapiens zinc finger, FYVE domain containing 16 (ZFYVE16), mRNA [NM_014733] |
| 389 | A_23_P75769 | MS4A4A | CACCAAAAGATCAACAGACAAAATGCTCCAGAAATGTATGCTGACT GTGACAAGAGCCT | SEQ ID NO: 2741 | Homo sapiens membrane-spanning 4-domains, subfamily A, member 4 (MS4A4A), transcript variant 1, mRNA [NM_024021] |
| 390 | A_23_P76480 | BF213738 | AAATCGAACAGGACAATGGGTAGAGTTTACCAAATC GTTTGGATCGAGAGG | SEQ ID NO: 2742 | BF213738 601847628F1 NIH_MGC_55 Homo sapiens cDNA clone IMAGE:4078519 5', mRNA sequence [BF213738] |

Fig. 7-22

| No. | Probe ID No. | Symbols of genes | Sequence | SEQ ID NO: | Descriptors of genes (letters and numbers within [ ] indicates GenBank accession No.) |
|---|---|---|---|---|---|
| 391 | A_23_P76799 | BAZ1A | TACAACATGAATGAATCCAATCTTATAACCTTGAAGTGCTGTACCAGTGCTGGCTGCAGGT | SEQ ID NO: 2743 | Homo sapiens bromodomain adjacent to zinc finger domain, 1A (BAZ1A), transcript variant 1, mRNA [NM_013448] |
| 392 | A_23_P76951 | TXNDC1 | ATTTCTGTAATGTCCCCTTCTTCTAGGCTGCTGTTGCTGTGTGAATCCATTAAGATTTACA | SEQ ID NO: 2744 | Homo sapiens thioredoxin domain containing 1 (TXNDC1), mRNA [NM_030755] |
| 393 | A_23_P77286 | C15orf29 | TGGTTTAGAGTTAATGCTGATCTGTGTATTTTAAATTCCAAGACTTTGTGTCAGCTACCTGC | SEQ ID NO: 2745 | Homo sapiens chromosome 15 open reading frame 29 (C15orf29), mRNA [NM_024713] |
| 394 | A_23_P78092 | EVI2A | GCTGAATCAGAGACTTGAAAAGAACAAAGAGCTCAGAGGACCCAACCTAGTGATGCAA | SEQ ID NO: 2746 | Homo sapiens ecotropic viral integration site 2A (EVI2A), transcript variant 1, mRNA [NM_001003927] |
| 395 | A_23_P81248 | TAF7 | TGCTAGTTGCATATGTTTTCCTATGCAATAGTTGTTTGTTTTCCCAGTTATTCAAAGGCAGCTT | SEQ ID NO: 2747 | Homo sapiens TAF7 RNA polymerase II, TATA box binding protein (TBP)-associated factor, 55kDa (TAF7), mRNA [NM_005642] |
| 396 | A_23_P82047 | BU507302 | TCTGTTTCGTTAATGTCAGCTGGCTGAACATTGAGCAGTTTATAAATTGCTTAATTTGTG | SEQ ID NO: 2748 | AGENCOURT_10309688 NIH_MGC_71 Homo sapiens cDNA clone IMAGE:6501220 5'. mRNA sequence [BU507302] |
| 397 | A_23_P8281 | IFNGR1 | CTTTACATCCAGATAGGTTACCAGTAACGGAAGAGTATCCAGTACTCCTGGTTCCTAGGT | SEQ ID NO: 2749 | Homo sapiens interferon gamma receptor 1 (IFNGR1), mRNA [NM_000416] |
| 398 | A_23_P83073 | HIATL1 | AAACAACTCAAGACTGTGGTGGCAACATAGAGATTGTAGGGTGCTTCTAAGAAAGTTAT | SEQ ID NO: 2750 | Homo sapiens hippocampus abundant transcript-like 1 (HIATL1), mRNA [NM_032558] |
| 399 | A_23_P83094 | TLE4 | ACCTCCCTCTGAAAAACAACACAAGAATGGACTCTCTCCTAGGATGAGGACTTGCTTCTT | SEQ ID NO: 2751 | Homo sapiens transducin-like enhancer of split 4 (E(sp1) homolog, Drosophila) (TLE4), mRNA [NM_007005] |
| 400 | A_23_P83175 | PTPLAD2 | CATGCTCTTTTGTGTGGTGATCACCAGTCAAGAGGAAGTCCAAGAGAAATATGTGTGTGT | SEQ ID NO: 2752 | Homo sapiens protein tyrosine phosphatase-like A domain containing 2 (PTPLAD2), mRNA [NM_001010915] |
| 401 | A_23_P83278 | CHMP5 | CATTGCTCTTTATTTTTCCATTAAGAGACTCATTGCTTGCGGAAATGCTTCGTTCGTATG | SEQ ID NO: 2753 | Homo sapiens chromatin modifying protein 5 (CHMP5), mRNA [NM_016410] |
| 402 | A_23_P84070 | LARP7 | TGATTTGCTAGAAGGGATACAGAGAATGCCATGCTAGATTTAAGACTCCTGAGGATGCTCA | SEQ ID NO: 2754 | Homo sapiens La ribonucleoprotein domain family, member 7 (LARP7), transcript variant 1, mRNA [NM_016648] |
| 403 | A_23_P8513 | SNX10 | TTTAAGAGCGAATCTCATCCCTTCAGCAATTGATTTGAGTTCACACTATTCTGTTT | SEQ ID NO: 2755 | Homo sapiens sorting nexin 10 (SNX10), mRNA [NM_013322] |
| 404 | A_23_P86853 | SRGN | AGGACTTGGGTCAACATGAATTAGGAAGAGGATTTTATGTTATAAAAGAGGATTTTCCCAC | SEQ ID NO: 2756 | Homo sapiens serglycin (SRGN), mRNA [NM_002727] |
| 405 | A_23_P87879 | CD69 | TGTGAAATATGGTGAGTGTGGGAAATGTCTCATTAGGAAATATCTGTAATCTTCAGACCTAG | SEQ ID NO: 2757 | Homo sapiens CD69 molecule (CD69), mRNA [NM_001781] |
| 406 | A_23_P89755 | RNF138 | TGTGACCGTGATATAGTGAGAAAGATTGTACGAACCACTGTTTCACTACTTTTTAGTTAA | SEQ ID NO: 2758 | Homo sapiens ring finger protein 138 (RNF138), transcript variant 1, mRNA [NM_016271] |
| 407 | A_23_P9056 | RB1CC1 | TTGATTTTCTCAAGGGCATACCTTGTGCATTGGCTTATGATGAGCCATATTAATTGC | SEQ ID NO: 2759 | Homo sapiens RB1-inducible coiled-coil 1 (RB1CC1), mRNA [NM_014781] |
| 408 | A_23_P91346 | BC008667 | GGGCTTAGGAGTGAGATTTCTGGTCTACAGAAATGATGATGCTGAATGAATTTTGACATTT | SEQ ID NO: 2760 | Homo sapiens cDNA clone MGC:17708 IMAGE:3368595, complete cds. [BC008667] |

Fig. 7-23

| No. | Probe ID No. | Symbols of genes | Sequence | SEQ ID NO: | Descriptions of genes (letters and numbers within [ ] indicates GenBank accession No.) |
|---|---|---|---|---|---|
| 409 | A_23_P92410 | CASP3 | TGCACCAAGTCTCACTGGCTGGTCAGTATGACATTTCACGGGAGAATTTCTTGTTGTCGAA | SEQ ID NO: 2761 | Homo sapiens caspase 3, apoptosis-related cysteine peptidase (CASP3), transcript variant alpha, mRNA [NM_004346] |
| 410 | A_23_P94216 | LONRF1 | GGGTCATTTATTGCCCAAGTTTAGAAGAGTAGGATACAAGTTTTTGCAAATTGAATTTG | SEQ ID NO: 2762 | Homo sapiens LON peptidase N-terminal domain and ring finger 1 (LONRF1), mRNA [NM_152271] |
| 411 | A_23_P94230 | LY96 | TGAAGTCATTTCTGGGAGCCAGAAGAAATGCTCTTTGCTTGGAGTTTGTCATCCTACA | SEQ ID NO: 2763 | Homo sapiens lymphocyte antigen 96 (LY96), mRNA [NM_015364] |
| 412 | A_23_P94501 | ANXA1 | GGCTCTTTGTGGAGGAAAGTAAACATTCCCTTGATGGTCTGAAGCTATGATCGAAGACT | SEQ ID NO: 2764 | Homo sapiens annexin A1 (ANXA1), mRNA [NM_000700] |
| 413 | A_23_P95130 | SLC37A3 | TTGAGGGATACCTAATTTGCATTCGGTTAGGGGATATTTTCAACCTCTTGCTTTATACT | SEQ ID NO: 2765 | Homo sapiens solute carrier family 37 (glycerol-3-phosphate transporter), member 3 (SLC37A3), transcript variant 1, mRNA [NM_207113] |
| 414 | A_23_P95594 | NAT1 | TCCTTGGAGAGAAAGTTGTGCCCAAACATGGTCATGATAGATTTTTACTATTTAGAATAAG | SEQ ID NO: 2766 | Homo sapiens N-acetyltransferase 1 (arylamine N-acetyltransferase) (NAT1), mRNA [NM_000662] |
| 415 | A_23_P9574 | ECT2 | TAATAGTTACTGACTATAGATTGTTTCTATGCCATGTATGTGCCACTTCTGAGAGTAG | SEQ ID NO: 2767 | Homo sapiens epithelial cell transforming sequence 2 oncogene (ECT2), mRNA [NM_018098] |
| 416 | A_23_P98085 | PTEN | ACAGCAACAATGACTTAACCATATAAATGTGGAGGCTATCAAGAAAGAATGGGCTTGAAA | SEQ ID NO: 2768 | Homo sapiens phosphatase and tensin homolog (mutated in multiple advanced cancers 1) (PTEN), mRNA [NM_000314] |
| 417 | A_23_P98382 | TIMM8B | TTGTTACTAAGCAGATTTAAGGGTCAGTGGGGGAAGGCTATCAACCCATTGTCGATCAG | SEQ ID NO: 2769 | Homo sapiens translocase of inner mitochondrial membrane 8 homolog B (yeast) (TIMM8B), mRNA [NM_012459] |
| 418 | A_23_P98930 | C12orf35 | GCCATGTCTTGAGGGAGGACCGTTCCTCAGTTAAGGACTTGTTTATTTAAATGGGACTGTAA | SEQ ID NO: 2770 | Homo sapiens chromosome 12 open reading frame 35 (C12orf35), mRNA [NM_018169] |
| 419 | A_23_P99163 | DRAM | GGTCACGATGGAGTTTCATGCTTCATTTCACATCTCTCTGCACAATTAGATGGGAGCT | SEQ ID NO: 2771 | Homo sapiens damage-regulated autophagy modulator (DRAM), mRNA [NM_018370] |
| 420 | A_23_P99405 | ZMYM2 | GCTGGGTATACCATGTAAATATCGTGAGTGAAAGTTGCCATTATTGTATGTAGTGGT | SEQ ID NO: 2772 | Homo sapiens zinc finger, MYM-type 2 (ZMYM2), mRNA [NM_003453] |
| 421 | A_23_P99442 | FLT3 | CGTGTGGGTTTAGTCTTGTTTGTTTCAAAAGGGACTTTGTAAAATGAAATCGTCGTCACAA | SEQ ID NO: 2773 | Homo sapiens fms-related tyrosine kinase 3 (FLT3), mRNA [NM_004119] |
| 422 | A_23_P99853 | KIAA1370 | CTTTTGTACTGTTGAAACCACTTGTTGTAATTTCAGGAGGAATATAAAAGCCCCAGTTAG | SEQ ID NO: 2774 | Homo sapiens KIAA1370 (KIAA1370), mRNA [NM_019600] |
| 423 | A_23_P99880 | HMGB1 | GGATTCTTCCATTTGCATTTGTAATTTCAGGAGGAATACTGAACATCTGAGTC | SEQ ID NO: 2775 | Homo sapiens high-mobility group box 1 (HMGB1), mRNA [NM_002128] |
| 424 | A_23_P99985 | HMGB1 | TGGGGCAAGCTTTTCAAACAAAGATGCGACATTCAAAATAGGGTATATTTTCCTATTAC | SEQ ID NO: 2776 | Homo sapiens high-mobility group box 1 (HMGB1), mRNA [NM_002128] |
| 425 | A_23_P100387 | GK | TAAAAGGTCTGTTTGTTTGGAATCAATGATAGCTTATTGACTGTTCTGAATTGTGCTG | SEQ ID NO: 2777 | Homo sapiens glycerol kinase (GK), transcript variant 1, mRNA [NM_203391] |
| 426 | A_23_P105848 | BX111927 | TTATGAGATGCTTCAGTTCAAATAACAGTGCAGTAATTCACGTATATCTAAAAGACTGCC | SEQ ID NO: 2778 | BX111927 Soares_multiple_sclerosis_2NbHMSP Homo sapiens cDNA clone IMAGp998G05619, mRNA sequence [BX111927] |
| 427 | A_24_P105913 | THC2606573 | CTGTGCTCTAGGAAATGACCAATACCAAAGGTCAATGTGGAAATATGGGCATGTTTGCC | SEQ ID NO: 2779 | AY151386 NAP1 [Homo sapiens] (exp=0; wgp=0; cg=0), partial (35%) [THC2606573] |

Fig. 7-24

| No. | Probe ID No. | Symbols of genes | Sequence | SEQ ID NO: | Descriptions of genes (letters and numbers within [ ] indicate GenBank accession No.) |
|---|---|---|---|---|---|
| 428 | A_24_P107257 | LIN7C | TATTAGTAGTGGGACTGTGACTGAGGTCTTAAAGACTGAAAGAGTT GGGGTTCATTTCTG | SEQ ID NO: 2780 | Homo sapiens lin-7 homolog C (C. elegans) (LIN7C), mRNA [NM_018362] |
| 429 | A_24_P11045 | THC2785765 | CCACCAGAAACGTACACCTGATTTTCATGACAAATACGGTAGCAA CACAAGTCGGAATAG | SEQ ID NO: 2781 | COX7B_HUMAN (P24311) Cytochrome c oxidase polypeptide VIIb, mitochondrial precursor partial (78%) [THC2785765] |
| 430 | A_24_P114249 | GALNT3 | ATTTCAAATCGAGAATACTTGACTCATTTAAAGCTAAATTTTGTT ACTGATTCAATTATA | SEQ ID NO: 2782 | Homo sapiens UDP-N-acetyl-alpha-D-galactosamine:polypeptide N-acetylgalactosaminyltransferase 3 (GalNAc-T3) (GALNT3), mRNA [NM_004482] |
| 431 | A_24_P115774 | BIRC2 | GATACGATTTTGGTTAAAGGAAATGCTGCGGCAACATGTTCAAA AACTGTCTAAAAGAA | SEQ ID NO: 2783 | Homo sapiens baculoviral IAP repeat-containing 2 (BIRC2), mRNA [NM_001166] |
| 432 | A_24_P116786 | ZNF207 | TTTGTGAGACAGCAGTATACCAGTGAAATTAGCTTCTGAGTAAAT TTGTAATTTATGCC | SEQ ID NO: 2784 | Homo sapiens mRNA; cDNA DKFZp761N202 (from clone DKFZp761N202), [AL834501] |
| 433 | A_24_P123521 | CLK4 | CCGCACACTGAAAACACAGAGATATCAAGTCGTTGACTTGGAAGT GCAACGTATGATGAT | SEQ ID NO: 2785 | Homo sapiens CDC-like kinase 4 (CLK4), mRNA [NM_020666] |
| 434 | A_24_P124325 | IKZF5 | GCTACAACTTCTTGAACTTCAAGTTAAGGCTAGACATTTACTTTG AAAAATTGCACTGG | SEQ ID NO: 2786 | Homo sapiens mRNA; cDNA DKFZp781B0249 (from clone DKFZp781B0249), [CR749800] |
| 435 | A_24_P124992 | PSMA4 | AAACGTCCTTTGTGTTTCATTGCTGTCGTAGATTGGCTGGGATAAG CACTATGGGTTCAG | SEQ ID NO: 2787 | Homo sapiens proteasome (prosome, macropain) subunit, alpha type, 4 (PSMA4), mRNA [NM_002789] |
| 436 | A_24_P126060 | DDX3X | TGTTGAACGGAGCTTGTCTCTAGGAAGGGGATGGGACTAGATATGTAA AATTTATTTGGGACC | SEQ ID NO: 2788 | Homo sapiens DEAD (Asp-Glu-Ala-Asp) box polypeptide 3, X-linked (DDX3X), mRNA [NM_001356] |
| 437 | A_24_P126741 | ENST00000309178 | AGGCCTCCAACCACACAGTAACAAGATTCAAGATGTTTAGAATAAGTCGTCTGGCTTA CACAGAGGCGAGAAT | SEQ ID NO: 2789 | |
| 438 | A_24_P129232 | SERINC1 | CAAGGTCAGAAGATGATGATGTTTAGAATAAAGTCGTCTGGCTTA TAGTATACTACACAG | SEQ ID NO: 2790 | Homo sapiens serine incorporator 1 (SERINC1), mRNA [NM_020755] |
| 439 | A_24_P132787 | RAB18 | TAAAAACGTCACATTCTACTTGATTTACACGTTCCTAGTCTACATT ACATGTCGTTGAAGG | SEQ ID NO: 2791 | Homo sapiens RAB18, member RAS oncogene family (RAB18), mRNA [NM_021252] |
| 440 | A_24_P133991 | ANKRD12 | TTTGGAATGGAGTATATGCCTGAAAAGGTTTTTGGATTCAGAAGA AAAAGGATGGTTAGT | SEQ ID NO: 2792 | Homo sapiens ankyrin repeat domain 12 (ANKRD12), mRNA [NM_015208] |
| 441 | A_24_P137897 | IFRD1 | AACCAAAGCTAGAAGCAAATGTCGAGATAAGAGAGAGATGTTGG AGAATTCTTCTAGAT | SEQ ID NO: 2793 | Homo sapiens interferon-related developmental regulator 1 (IFRD1), transcript variant 2, mRNA [NM_001007245] |
| 442 | A_24_P139208 | USP25 | CAATATACAGCAAGGTGATTATTTCAAGAGAATCCAAAGTACTT GAATAAGGCTATTG | SEQ ID NO: 2794 | Homo sapiens ubiquitin specific peptidase 25 (USP25), mRNA [NM_013396] |
| 443 | A_24_P146151 | TSNAX | AAAGTTGAGTTATATACTTGTACATAGAATGGAAATGCTTTTAGT AGTGATTATTTAGCA | SEQ ID NO: 2795 | Homo sapiens translin-associated factor X (TSNAX), mRNA [NM_005999] |
| 444 | A_24_P150874 | BX647930 | GTATATTTTGTAATAACCGCGTAGATACTGTACCTAACAAAACAT GACTCGTATTAGGTC | SEQ ID NO: 2796 | Homo sapiens mRNA; cDNA DKFZp686l20201 (from clone DKFZp686l20201), [BX647930] |
| 445 | A_24_P153511 | OSBPL8 | CCTTGTGCATATACAACACAAAAATTTTGTGGAAGGCAGTTTTAAC TTTCTCAAGAATATC | SEQ ID NO: 2797 | Homo sapiens oxysterol binding protein-like 8 (OSBPL8), transcript variant 1, mRNA [NM_020841] |
| 446 | A_24_P157415 | ATP11B | CTGTACTGTAAGCAGCCTGTAAAGTTAGCGATATAAATGAAGG GTATATCATATATC | SEQ ID NO: 2798 | Homo sapiens ATPase, Class VI, type 11B (ATP11B), mRNA [NM_014616] |

Fig. 7-25

| No. | Probe ID No. | Symbols of genes | Sequence | SEQ ID NO: | Descriptions of genes (letters and numbers within [ ] indicates GenBank accession No.) |
|---|---|---|---|---|---|
| 447 | A_24_P165816 | AK023645 | AAGATTGAATGGCTAGGAGTAATTCTGTTCTGGTATAGGGAACTTAACTTCACTGTGGAA | SEQ ID NO: 2799 | Homo sapiens cDNA FLJ13583 fis, clone PLACE1008050. [AK023645] |
| 448 | A_24_P166094 | ARFIP1 | TCATTCCTTCCTGTATATTTGTACTCAGAGAGCCTTATTTTATTCTTCCAGGAGAATTAC | SEQ ID NO: 2800 | Homo sapiens ADP-ribosylation factor interacting protein 1 (arfaptin 1) (ARFIP1), transcript variant 1, mRNA [NM_001025595] |
| 449 | A_24_P166794 | BC047111 | AGCTTACAGTGTTCAGGTTGTGATTATTTCAAAATGGAGTGACTGTGAACATCACT | SEQ ID NO: 2801 | Homo sapiens cDNA clone IMAGE:5314178. [BC047111] |
| 450 | A_24_P167063 | ZNF518 | AAAGAAAGCCATACATAGAATGCTTCAAGGTATCTTGGCTATGCACATTATAGTTGTACTG | SEQ ID NO: 2802 | Homo sapiens zinc finger protein 518 (ZNF518), mRNA [NM_014803] |
| 451 | A_24_P172481 | TRIM22 | TGCCCCTTAAAGATTGAAGAGAAGAAAGTTCAACTCATATCCACGTTATCTAGCAA | SEQ ID NO: 2803 | Homo sapiens tripartite motif-containing 22 (TRIM22), mRNA [NM_006074] |
| 452 | A_24_P175059 | ATG5 | TTGACAAGAGGGCTGGTCTGAATGATTGTTCACATTAAGAGTGTTTATTCGTCGGTTC | SEQ ID NO: 2804 | Homo sapiens ATG5 autophagy related 5 homolog (S. cerevisiae) (ATG5), mRNA [NM_004849] |
| 453 | A_24_P175176 | PHTF2 | AGATTGAGGTTAACTTAGAGTTGGGAGTTGATTTATTAAGTAGAGTATACGTCTCAACAG | SEQ ID NO: 2805 | Homo sapiens putative homeodomain transcription factor 2 (PHTF2), mRNA [NM_020432] |
| 454 | A_24_P175187 | SAMD9 | CAACCAGGGATACGTAATCAAACAGTAATCAAAATGTAATTTTCCGCTAATAAAATTATGGAATGGAAGCAG | SEQ ID NO: 2806 | Homo sapiens sterile alpha motif domain containing 9 (SAMD9), mRNA [NM_017654] |
| 455 | A_24_P175188 | SAMD9 | TGCCAATGTACTGGCACATTCTCTTTAGTTACAACAACCTATGTTTTTGAACAAAAACAACCAGGGATA | SEQ ID NO: 2807 | Homo sapiens sterile alpha motif domain containing 9 (SAMD9), mRNA [NM_017654] |
| 456 | A_24_P180424 | TMEM30A | CAATGTGTATGGACAATTCTCTTTAGTTACAAGAAGGTAGTAGCAGTTGGTTTCCTAAG | SEQ ID NO: 2808 | Homo sapiens transmembrane protein 30A (TMEM30A), mRNA [NM_018247] |
| 457 | A_24_P18105 | ASPH | GCTCTGTTGAAAATAACCTTGTCAGAAAAGAAGGTAGTAGCAGCATGATTTTGAAAGG | SEQ ID NO: 2809 | Homo sapiens aspartate beta-hydroxylase (ASPH), transcript variant 3, mRNA [NM_032466] |
| 458 | A_24_P183864 | IMPA1 | TCAGCTTATCCCTTGGCACGTAAACAGACTACTATTGTAGGTTCGTTTGAGCT | SEQ ID NO: 2810 | Homo sapiens inositol(myo)-1(or 4)-monophosphatase 1 (IMPA1), mRNA [NM_005536] |
| 459 | A_24_P190804 | AP1S2 | GGTGGAAGATCTAAGGAGTCTTCATGTACTTCATTAAAAATAACATGGATTCCAATACTG | SEQ ID NO: 2811 | Homo sapiens adaptor-related protein complex 1, sigma 2 subunit (AP1S2), mRNA [NM_003916] |
| 460 | A_24_P191417 | NAB1 | AAGTTTCCTTAACTATCTATGTTTCTAGTCTTTCAAGCTTAGTGATAAGGTGGAAGCAC | SEQ ID NO: 2812 | Homo sapiens NGFI-A binding protein 1 (EGR1 binding protein 1) (NAB1), mRNA [NM_005966] |
| 461 | A_24_P196351 | PLXNC1 | ACCTCAAAGAAGAAAATACGAAAACTAGATGACAGATGAGAATAAAGGTGAGAGGTCTGG | SEQ ID NO: 2813 | Homo sapiens mRNA for plexin C1 variant protein. [AB208934] |
| 462 | A_24_P20120 | KIAA1212 | TTGGACAATGAAAATGGCTAAAAGGAATGCATATGGATAAAGTTGCACTTATAACAGCC | SEQ ID NO: 2814 | Homo sapiens KIAA1212 (KIAA1212), mRNA [NM_018084] |
| 463 | A_24_P201702 | CLEC2B | ATTGGAATTCAAGTAAATAAATAGAATTTAGTAAATATTCCAGCCGGTCGTTTTAGTATAATTGACA | SEQ ID NO: 2815 | Homo sapiens C-type lectin domain family 2, member B (CLEC2B), mRNA [NM_005127] |
| 464 | A_24_P208045 | EDEM3 | TTTAGAGGGGGTAGAATTTAGTAAATATTCCAGCGGGTCGTTTTATGACAAGGCTTCA | SEQ ID NO: 2816 | Homo sapiens ER degradation enhancer, mannosidase alpha-like 3 (EDEM3), mRNA [NM_025191] |
| 465 | A_24_P208567 | IL18R1 | GGGAGGCTTCTTGATGATCTCAAAAATAATAGCTATTCAAGAAAATCACCAAGTGACTGT | SEQ ID NO: 2817 | Homo sapiens interleukin 18 receptor 1 (IL18R1), mRNA [NM_003855] |
| 466 | A_24_P20996 | BC043173 | CTGAAAATGTTCATATATGTATATGAATGTCTTTATGCTGAAGGGCTCGATTGG | SEQ ID NO: 2818 | Homo sapiens cDNA clone IMAGE:5287121. [BC043173] |

Fig. 7-26

| No. | Probe ID No. | Symbols of genes | Sequence | SEQ ID NO: | Descriptions of genes (letters and numbers within [ ] indicates GenBank accession No.) |
|---|---|---|---|---|---|
| 467 | A_24_P216654 | SOAT1 | CGCAGTAATGTTCTGGCACAAACAGTATTGTAATTGTAATGGAATCATAAGCTGCTAACTAG | SEQ ID NO: 2819 | Homo sapiens sterol O-acyltransferase (acyl-Coenzyme A: cholesterol acyltransferase) 1 (SOAT1), transcript variant 688113, mRNA [NM_003101] |
| 468 | A_24_P223124 | FNDC3B | CTCACTGTTGGACATACATCCAAGCTTTCAACTGTAGGAGAAAAAGAAAATCATGTTT | SEQ ID NO: 2820 | Homo sapiens fibronectin type III domain containing 3B (FNDC3B), mRNA [NM_022763] |
| 469 | A_24_P225308 | ARID4B | GTTGAAAATGGTTTCCAAGTTATTCAAATTGTACAGGACTGTAAAGATTGTTGACAGGA | SEQ ID NO: 2821 | Homo sapiens AT rich interactive domain 4B (RBP1-like) (ARID4B), transcript variant 1, mRNA [NM_016374] |
| 470 | A_24_P225719 | PREI3 | GACTATTTCTTAGTGAATATTGAATATTTATAGTAAGGTAGTCACTGAGATTTGGTGATCTGGCTG | SEQ ID NO: 2822 | Homo sapiens preimplantation protein 3 (PREI3), transcript variant 1, mRNA [NM_015387] |
| 471 | A_24_P235429 | ABCA1 | CCAAGAGCCATGTGTCATGTAATACTGAACCACTTTGATATTGAGACATTAATTTGTAC | SEQ ID NO: 2823 | Homo sapiens ATP-binding cassette, sub-family A (ABC1), member 1 (ABCA1), mRNA [NM_005502] |
| 472 | A_24_P235988 | CLEC7A | TTTTTTCCAGTAATTACCTGTAAAATGGTATTATTGGAATAGAAACTATATTCCTCATGT | SEQ ID NO: 2824 | Homo sapiens C-type lectin domain family 7, member A (CLEC7A), transcript variant 1, mRNA [NM_197947] |
| 473 | A_24_P238008 | SCYL2 | ATAGACTATGTAGTTGTCTGTGGTTTTGTTTTATTTGGAATGCTTATAAAGCCTCC | SEQ ID NO: 2825 | Homo sapiens mRNA for KIAA1360 protein, partial cds. [AB037781] |
| 474 | A_24_P236799 | RAB31 | ATTAAAGAGCTCGAACTGTATTCAGACGCAGTTGGTATCGTAGCTTACTGTTTTAAGATC | SEQ ID NO: 2826 | Homo sapiens RAB31, member RAS oncogene family (RAB31), mRNA [NM_006868] |
| 475 | A_24_P242299 | ZRANB2 | GACTTTTTGAAAGTCTACCTTCTAAATTGCCGCGACGATGTAGATTCTACATGTTACGAT | SEQ ID NO: 2827 | Homo sapiens zinc finger, RAN-binding domain containing 2 (ZRANB2), transcript variant 2, mRNA [NM_005455] |
| 476 | A_24_P248606 | ACSL3 | GTATTTGATGATGAATAGCATTCTCACTAAGACACATGAGAATTTAACTTTAATAACCCGGCTGAG | SEQ ID NO: 2828 | Homo sapiens acyl-CoA synthetase long-chain family member 3 (ACSL3), transcript variant 1, mRNA [NM_004457] |
| 477 | A_24_P250922 | PTGS2 | TGAGATATTTAAGGTTGAATGTTGTCCTTAGGATAGGGCCTATGTGCTAGCCCACAAAGA | SEQ ID NO: 2829 | Homo sapiens prostaglandin-endoperoxide synthase 2 (prostaglandin G/H synthase and cyclooxygenase) (PTGS2), mRNA [NM_000963] |
| 478 | A_24_P251221 | PPP2R5A | TGAATTCTTCTTTGAATTGTGTTGGACATAGATATGGTAGTCTGCTCTGTATATTTTCCC | SEQ ID NO: 2830 | Homo sapiens protein phosphatase 2, regulatory subunit B', alpha isoform (PPP2R5A), mRNA [NM_006243] |
| 479 | A_24_P25326 | ZMYM6 | AGCACTATTTAAATACAGTGTCTGTAACTCAGTTTTGGATAAATGCAAAGACAAGTTACCC | SEQ ID NO: 2831 | Homo sapiens zinc finger, MYM-type 6 (ZMYM6), mRNA [NM_007167] |
| 480 | A_24_P257151 | CLK1 | TATGCAAAGTCTGTGAATTTTTGGACAGTAATAAGTTGACTGACACAGACTAAAGCCTG | SEQ ID NO: 2832 | Homo sapiens CDC-like kinase 1 (CLK1), transcript variant 1, mRNA [NM_004071] |
| 481 | A_24_P263144 | BMX | CAGCTCCAGAGGTGTTTCATTACTTCAAATACAGCAGCAAGTCAGACGTATGGGCATTTG | SEQ ID NO: 2833 | Homo sapiens BMX non-receptor tyrosine kinase (BMX), mRNA [NM_001721] |
| 482 | A_24_P263524 | TXNDC9 | TGACTTCACCACAGAAAGCTTAGAAATGGGAGGCTCAGTGTTCTGACATTCTTAATTACAG | SEQ ID NO: 2834 | Homo sapiens thioredoxin domain containing 9 (TXNDC9), mRNA [NM_005783] |
| 483 | A_24_P265856 | SENP7 | TTGTGTGTGTTGGGGGGTAGTTTTAAAGGTGACTATTGTTAGATGTAATTTTGGGA | SEQ ID NO: 2835 | Homo sapiens SUMO1/sentrin specific peptidase 7 (SENP7), transcript variant 1, mRNA [NM_020654] |

Fig. 7-27

| No. | Probe ID No. | Symbols of genes | Sequence | SEQ ID NO: | Descriptions of genes (letters and numbers within [ ] indicates GenBank accession No.) |
|---|---|---|---|---|---|
| 484 | A_24_P268786 | MYNN | TGCAGAGGATCATACATTTGAGTGAACAGGATTCCATACAAAAAAG TCCTTTATCAGAAAC | SEQ ID NO: 2836 | Homo sapiens myoneurin (MYNN), mRNA [NM_018657] |
| 485 | A_24_P269917 | RAB33B | CCCAGAATCTAATGTAGTTCGCTATTAATAAGAATGCATTATTGA AAGTATATTGCAAAT | SEQ ID NO: 2837 | Homo sapiens RAB33B, member RAS oncogene family (RAB33B), mRNA [NM_031296] |
| 486 | A_24_P274615 | ARRDC3 | AGCAAAACAAAGTGCAATATTAAATGTTTGGTTTATAGATATTAT TCTATGGGTGTTTGT | SEQ ID NO: 2838 | Homo sapiens arrestin domain containing 3 (ARRDC3), mRNA [NM_020801] |
| 487 | A_24_P278583 | TMCO1 | CCTTCATTTTCCTGTATATTCTCGTACTATGTCGATTCGACAGA ACATTCAGAAGATTC | SEQ ID NO: 2839 | Homo sapiens transmembrane and coiled-coil domains 1 (TMCO1), mRNA [NM_019026] |
| 488 | A_24_P278460 | MLSTD2 | AGCCATGGAAACAATATGCTTAGGATTAGAGGAAGCAGTCCTTACT TACACTTCTTGTCTG | SEQ ID NO: 2840 | Homo sapiens male sterility domain containing 2 (MLSTD2), mRNA [NM_032228] |
| 489 | A_24_P285501 | ZNF650 | CATGGTATAATGTATTCAGACTTTGATTACTACTTATTTAAAATG GAATGTTTTATGGTT | SEQ ID NO: 2841 | Homo sapiens zinc finger protein 650 (ZNF650), mRNA [NM_170707] |
| 490 | A_24_P286054 | ZFYVE16 | GTGTATGTATTCTGCCATGTAAGTAATTGAACAGTCTTAAAATAA CCAAATGGTAGAGGG | SEQ ID NO: 2842 | Zinc finger FYVE domain-containing protein 16 (Endofin) (Endosome-associated FYVE domain protein). [Source:Uniprot/SWISSPROT:Acc:Q7Z3T8] [ENST00000380248] |
| 491 | A_24_P28657 | AHCTF1 | AACAGACGGCCTGTTGTCTACAGAGTACAACTGTGTGGAATTAAGCA ATGGTACTTGATGTA | SEQ ID NO: 2843 | Homo sapiens AT hook containing transcription factor 1 (AHCTF1), mRNA [NM_015446] |
| 492 | A_24_P287756 | NUDT21 | CCCATACTTACTTCACTTGTTATACATCACTGATTATTTGCGTTA AACTGGAGTCATTTC | SEQ ID NO: 2844 | Homo sapiens nudix (nucleoside diphosphate linked moiety X)-type motif 21 (NUDT21), mRNA [NM_007006] |
| 493 | A_24_P290257 | A_24_P290257 | CGAATTCATTCAACGATAGAACAAGCCAATTATACCATCGAGTCAT TGAAGGACAGCAAGA | SEQ ID NO: 2845 | |
| 494 | A_24_P29277 | COL4A3BP | TTAAAGTACCTTGGGAGTGTGTAGAGTAAGTCTCTATAATAGCTTT ATGATCCTGATGATG | SEQ ID NO: 2846 | Goodpasture antigen-binding protein (EC 2.7.11.9) (GPBP) (Collagen type IV alpha-3-binding protein) (StAR-related lipid transfer protein 11) (StARD11) (START domain-containing protein 11). [Source:Uniprot/SWISSPROT:Acc:Q9Y5P4] [ENST00000380494] |
| 495 | A_24_P295543 | BLOC1S2 | GTTTATTTCTATGTGAGTCACATTGACATGCGATCAGTTTGGGA AATGTGATGAAAACA | SEQ ID NO: 2847 | Homo sapiens biogenesis of lysosome-related organelles complex-1, subunit 2 (BLOC1S2), transcript variant 2, mRNA [NM_001001342] |
| 496 | A_24_P2995 | PUM2 | TTTTTGAATAGGCTACTCCCAAGTAAGAGCAAATCTGTATGATAA CATTTTTGCTGTGG | SEQ ID NO: 2848 | Homo sapiens pumilio homolog 2 (Drosophila) (PUM2), mRNA [NM_015317] |
| 497 | A_24_P30194 | IFIT5 | AATGTGGCTTGTCTAATGTAGTTCTTTGATTACCGACTACAACGA TTATGACCATCACA | SEQ ID NO: 2849 | Homo sapiens interferon-induced protein with tetratricopeptide repeats 5 (IFIT5), mRNA [NM_012420] |
| 498 | A_24_P303454 | TIAM2 | GCGAGAATTCAGTGTCCAGAGATTTAACATCGTTGTCAGTGAGGA GTGTTTTTATGAAAC | SEQ ID NO: 2850 | Homo sapiens T-cell lymphoma invasion and metastasis 2 (TIAM2), transcript variant 1, mRNA [NM_012454] |
| 499 | A_24_P303647 | FLJ31818 | ACTGTATGGGTACTCCTAAGAATTATTTCATTTTGGATATAAAGA AGTTATGAGGCCTCG | SEQ ID NO: 2851 | Homo sapiens hypothetical protein FLJ31818 (FLJ31818), mRNA [NM_152556] |

Fig. 7-28

| No. | Probe ID No. | Symbols of genes | Sequence | SEQ ID NO: | Descriptions of genes (letters and numbers within [ ] indicates GenBank accession No.) |
|---|---|---|---|---|---|
| 500 | A_24_P303852 | GNAQ | GCTTTTGGTAGACAGAAAAACAGAAAAGGTATTCGTTGGTAGAACATTTTTAAGTTCAGG | SEQ ID NO: 2852 | Guanine nucleotide-binding protein G(q) subunit alpha (Guanine nucleotide-binding protein alpha-q) [Source:Uniprot/SWISSPROT:Acc:P50148] [ENST00000376611] |
| 501 | A_24_P307395 | A_24_P307395 | CTCGTCTGTTTATGTGGACATGATTCAACTCCAACTTAAATTGCAGGGGTGTGTTCCAT | SEQ ID NO: 2853 | |
| 502 | A_24_P310894 | CAPZA1 | TGTATTATTGTCGTTCATACTATCCATCCATACCACACTGTTCTGTATCAGGTAGTC | SEQ ID NO: 2854 | Homo sapiens capping protein (actin filament) muscle Z-line, alpha 1 (CAPZA1), mRNA [NM_006135] |
| 503 | A_24_P312417 | ZBTB26 | AGAGGAGGAAGATTTTTAAAAACCTTTATCATTCAGGATTTGTATTTATGGATCCCAGG | SEQ ID NO: 2855 | Zinc finger and BTB domain-containing protein 26 (Zinc finger protein 481) (Zinc finger protein Bioref). [Source:Uniprot/SWISSPROT:Acc:Q9HCK0] [ENST00000373856] |
| 504 | A_24_P317604 | SLC37A3 | CCCGGTGTTGTTTGGCCTATTGAGGTTTAGGGTTTTTAACCTTAAGTGTTGTTTGGAC | SEQ ID NO: 2856 | Homo sapiens solute carrier family 37 (glycerol-3-phosphate transporter), member 3 (SLC37A3), transcript variant 1, mRNA [NM_207113] |
| 505 | A_24_P320328 | SUB1 | CAGAAAAACGTGTAAAGAAACAGAAAAGACAGGTGAGACTCGAGAGCCCTGTCTGTCTGTA | SEQ ID NO: 2857 | Homo sapiens SUB1 homolog (S. cerevisiae) (SUB1), mRNA [NM_006713] |
| 506 | A_24_P322353 | PSTPIP2 | AGAATCTTTCGCTTGCTAGACCCAGAATTTTTAAATGCATCCGTCTTACACTTTCAGAAA | SEQ ID NO: 2858 | Homo sapiens proline-serine-threonine phosphatase interacting protein 2 (PSTPIP2), mRNA [NM_024430] |
| 507 | A_24_P324506 | A_24_P324506 | GCAATATAAGGAGGTAATTGCAAATACAAGTATGGCTATTTCGTGTGGACATGCTGTGT | SEQ ID NO: 2859 | |
| 508 | A_24_P324577 | KIAA1466 | AAGAATTTAAGTAGGCGGCCCTGAAGTTAGGAGTTAAAGAAGGATATTAACTGCCAGTCGCA | SEQ ID NO: 2860 | Homo sapiens mRNA for KIAA1466 protein, partial cds. [AB040899] |
| 509 | A_24_P324551 | KIAA1466 | ATAATAGCTCATAGAATGAATTGCTGTACCAACCAAGGCTAAAAGAATTTAAGTAGCGG | SEQ ID NO: 2861 | Homo sapiens mRNA for KIAA1466 protein, partial cds. [AB040899] |
| 510 | A_24_P324886 | DOCK4 | ATTTTCGCTTTCGTTTGTTGGGAAGCTCATTTTAGTTTAACCATGTTGTTTTGTTGGTAGG | SEQ ID NO: 2862 | Homo sapiens dedicator of cytokinesis 4 (DOCK4), mRNA [NM_014705] |
| 511 | A_24_P325176 | KIAA1109 | TTGATCCAGTAGGTGTTGATTATATTCTTGAAAAATTGGGCTTTGATCATGCTAGGACTA | SEQ ID NO: 2863 | Homo sapiens KIAA1109, mRNA (cDNA clone IMAGE:3924668), complete cds. [BC108274] |
| 512 | A_24_P330397 | STRN3 | ATGGTGTAACTAACTAAAGATTTGTTTGTGTAATGCATGATTAAGACAATAAAGTATTTTTC | SEQ ID NO: 2864 | Homo sapiens striatin, calmodulin binding protein 3 (STRN3), mRNA [NM_014574] |
| 513 | A_24_P33213 | A_24_P33213 | GACCATATATTACATGGGGATACCGAAATCTGAAGTCACTAAATGAACTTATCTACAAGG | SEQ ID NO: 2865 | |
| 514 | A_24_P333112 | A_24_P333112 | GGTCATCAGAATCAGAGTATCAATGTGTGAGCCCAGAGGACCAAAAGGTATTGCAACTT | SEQ ID NO: 2866 | |
| 515 | A_24_P336728 | LPGAT1 | AGAGCAAAAGTTTTTAAGTGTATTCAGTTGGCAAAGTATGCACACATATCTTGAATGGC | SEQ ID NO: 2867 | Homo sapiens lysophosphatidylglycerol acyltransferase 1 (LPGAT1), mRNA [NM_014873] |
| 516 | A_24_P351906 | STEAP4 | ATATCCCGTTGATTTGACTTGCATTGTGGAATAAGCAAAGAAGGGTTGATAAAGTTCT | SEQ ID NO: 2868 | Homo sapiens STEAP family member 4 (STEAP4), mRNA [NM_024636] |
| 517 | A_24_P354412 | AK091335 | TGTAGACTGAAGGAGTCTTCAAAACACGCCAGCAATAAATCTCACTCTGGGGTGCTTCT | SEQ ID NO: 2869 | Homo sapiens cDNA FLJ34016 fis, clone FCBBF2002541. [AK091335] |
| 518 | A_24_P354954 | CCDC126 | AATGGAACTCTTTGAGGACTTTAGGCAGGTGTATATAATAAAGGTACTTTTGTGCTGCATT | SEQ ID NO: 2870 | Homo sapiens coiled-coil domain containing 126 (CCDC126), mRNA [NM_138771] |

Fig. 7-29

| No. | Probe ID No. | Symbols of genes | Sequence | SEQ ID NO: | Descriptions of genes (letters and numbers w/hile [ ] indicates GenBank accession No.) |
|---|---|---|---|---|---|
| 519 | A_24_P355816 | DRAM | ATAATATAGAATGGGATTACTGCTGGTTTACCAGTTAGTTTGATAATAAACAAATAGTCT | SEQ ID NO: 2871 | Homo sapiens damage-regulated autophagy modulator (DRAM), mRNA [NM_018370] |
| 520 | A_24_P357576 | KIAA1370 | TGCTGCATATGAAGCTCAAATCTTACACTGAATCACCAACAAACCCTCAGTTTCACGAAG | SEQ ID NO: 2872 | Homo sapiens KIAA1370 (KIAA1370), mRNA [NM_019600] |
| 521 | A_24_P362646 | TXNDC9 | CTCGAGATTCAGGTGTAAAATACTAGAGAGACATCGGAATATTGTCAAGAAACACGT | SEQ ID NO: 2873 | Homo sapiens thioredoxin domain containing 9 (TXNDC9), mRNA [NM_005783] |
| 522 | A_24_P364025 | UBE2D1 | ATGTGATGGGTGTAGTCATTAGCAAAGCATTAAATACTCAGTATTTTGTCATGGTTC | SEQ ID NO: 2874 | Homo sapiens ubiquitin-conjugating enzyme E2D 1 (UBC4/5 homolog, yeast) (UBE2D1), mRNA [NM_003338] |
| 523 | A_24_P364066 | BC030112 | AATGTCTATTACGGTTTGGGATAGTATTTCTGTCTAGTTCTCAGTGATTTAAATGTGAGG | SEQ ID NO: 2875 | Homo sapiens cDNA clone IMAGE:4799578. [BC030112] |
| 524 | A_24_P364807 | AYTL1 | TGTAACTGTTGTTCTAGGTAATCGTTCTCTCTCAAGAAACTCTGAAGCGTCTGTGTAA | SEQ ID NO: 2876 | Homo sapiens mRNA; cDNA DKFZp686H22112 (from clone DKFZp686H22112). [BX641069] |
| 525 | A_24_P370096 | ZNF230 | GAAACCTTATATTGTGAGAAATGTGGAGGGCCTTCATTCAAGATTTAAAGGTCAGAA | SEQ ID NO: 2877 | Homo sapiens zinc finger protein 230 (ZNF230), mRNA [NM_006301] |
| 526 | A_24_P370172 | LILRA5 | AGCCACAGGTGGATGCTCAGATGCTATATGGCTCTCGCAGGCATATCCTGCAGGTATGGTCA | SEQ ID NO: 2878 | Homo sapiens leukocyte immunoglobulin-like receptor, subfamily A (with TM domain), member 5 (LILRA5), transcript variant 3, mRNA [NM_181879] |
| 527 | A_24_P371053 | ORMDL1 | GAATGAAAAGAGTTACAGACCAACTTAAACATCAATTCGTCTGTCAGTAAACTGACTTTTGG | SEQ ID NO: 2879 | Homo sapiens ORM1-like 1 (S. cerevisiae) (ORMDL1), mRNA [NM_016467] |
| 528 | A_24_P372625 | RNF141 | CTATGTACTGAACTTTAGAGGGTTGAGATGTGAGAATAATAATCATCTGTGTTATTCTTAGTACCCACTG | SEQ ID NO: 2880 | Homo sapiens ring finger protein 141 (RNF141), mRNA [NM_016422] |
| 529 | A_24_P374319 | RAP2C | AATTGTGTGATGTTCAAATAAAGTCGTATCATCACATTCATGTGATTTATGGTCAGCATG | SEQ ID NO: 2881 | Homo sapiens RAP2C, member of RAS oncogene family (RAP2C), mRNA [NM_021183] |
| 530 | A_24_P379379 | CAPZA1 | ACCAGTTCAGCGTAAAAAGTTCGGAATGGTCGTTGGAGATAGAGTGGAAGTTCACCA | SEQ ID NO: 2882 | Homo sapiens capping protein (actin filament) muscle Z-line, alpha 1 (CAPZA1), mRNA [NM_006135] |
| 531 | A_24_P380679 | FLJ38575 | GAACCTGCATTAGTTCCAGGAATGAAAGTAAGACAGAGAGATATGACATAAGAACAGT | SEQ ID NO: 2883 | Homo sapiens hypothetical protein FLJ39575 (FLJ39575), mRNA [NM_182597] |
| 532 | A_24_P381625 | PSMC6 | ATGAAAGGAGTCAGAAAAGTGGCTGATCTAAGAAGCTGGAGGTCTAAAATTGGACTAGAA | SEQ ID NO: 2884 | Homo sapiens proteasome (prosome, macropain) 26S subunit, ATPase, 6 (PSMC6), mRNA [NM_002806] |
| 533 | A_24_P387869 | PKN2 | TTGTCGAGATGATCATTTATATTAGCTTCCAAATTGTTTGTCAGAATTAAGATGCTTTGGGAG | SEQ ID NO: 2885 | Homo sapiens protein kinase N2 (PKN2), mRNA [NM_006256] |
| 534 | A_24_P39378 | CCPG1 | TACTTTTTGTGGCTGGAACGAAGTTGATCAGTTCATGAATAAGTTTTTCCTAAACGGTGT | SEQ ID NO: 2886 | Homo sapiens cell cycle progression 1 (CCPG1), transcript variant 1, mRNA [NM_004748] |
| 535 | A_24_P393811 | TMCO1 | AGATGACACGACAGACAGAGACTGTTCGTTCATTTCTGTATATTCCTCTGTACTATGCGATTCG | SEQ ID NO: 2887 | Homo sapiens transmembrane and coiled-coil domains 1 (TMCO1), mRNA [NM_019026] |
| 536 | A_24_P396231 | BC040653 | GGATGTATCGATTTAGAGAAACCAATTAATACCTGCAAAATAAAGCATAGGTGGTAGTTG | SEQ ID NO: 2888 | Homo sapiens cDNA clone IMAGE:4797120. [BC040653] |
| 537 | A_24_P396702 | CD302 | GGATTCTTGTAGTGAGGAGTGTATGGTCTCTTTTGTTCAGAATTAAAACTGATAACCAA | SEQ ID NO: 2889 | Homo sapiens CD302 molecule (CD302), mRNA [NM_014880] |
| 538 | A_24_P398940 | CASC4 | CACTTGGTTGGTTGTATTGTAGGTATTAGTATACAGGAACATTCTTCAATTAGGAGTC | SEQ ID NO: 2890 | Homo sapiens cancer susceptibility candidate 4 (CASC4), transcript variant 1, mRNA [NM_138423] |

Fig. 7-30

| No. | Probe ID No. | Symbols of genes | Sequence | SEQ ID NO: | Descriptions of genes (letters and numbers within [ ] indicate GenBank accession No.) |
|---|---|---|---|---|---|
| 539 | A_24_P399942 | ATP11C | TGAGGATGTTACCTACTACTAAACTGAAAACATTCATTCCATATCTACTTAACATACACCAG | SEQ ID NO: 2891 | Homo sapiens ATPase, Class VI, type 11C (ATP11C), transcript variant 1, mRNA [NM_173694] |
| 540 | A_24_P40417 | FMR1 | TTGTGAGTTTGTTCTTTGAATTTTGAATTTTTACAGTTACTTTGCTTGCATACAAACAAG | SEQ ID NO: 2892 | Homo sapiens fragile X mental retardation 1 (FMR1), mRNA [NM_002024] |
| 541 | A_24_P405298 | PPP1CB | GTATTAGGTTAGGTCAGAAAGGTTTATCTGAGGTGATTAAATAACTTCCTGATTGGAG | SEQ ID NO: 2893 | Homo sapiens protein phosphatase 1, catalytic subunit, beta isoform (PPP1CB), transcript variant 1, mRNA [NM_002709] |
| 542 | A_24_P405430 | TIA1 | GGATTTTCTCTGTTGTTAAATCACAAAAATGATAGTCCCAATCGTTTCTTTATAGGAGG | SEQ ID NO: 2894 | Homo sapiens cDNA FLJ36425 fis, clone THYMU2011482. [AK093744] |
| 543 | A_24_P406034 | SLC35A1 | ATGTACAGTATTTTGTCCTAGCAGCATAAAGACCTAGCTCTTTTCTTACAAGAGGCAGAA | SEQ ID NO: 2895 | Homo sapiens solute carrier family 35 (CMP-sialic acid transporter), member A1 (SLC35A1), mRNA [NM_006416] |
| 544 | A_24_P406060 | IBRDC2 | CTTATCCAGGTTGCAAATGTACATGTTCATTTGAATGTAAATCACCATTCTCTGGAACC | SEQ ID NO: 2896 | Homo sapiens IBR domain containing 2 (IBRDC2), mRNA [NM_182757] |
| 545 | A_24_P407311 | ERO1L | TAACATGTTGAAATGTCACATTAGTAGTAAAGTGGGGTTTATTATATAATGGTTAAGAA | SEQ ID NO: 2897 | Homo sapiens ERO1-like (S. cerevisiae) (ERO1L), mRNA [NM_014584] |
| 546 | A_24_P413699 | PFKFB2 | TCAAATGGTTCTTTTATACTCTGGATGATACAGGACTCTGTTACCTAAGATGTGATAAGC | SEQ ID NO: 2898 | Homo sapiens 6-phosphofructo-2-kinase/fructose-2,6-biphosphatase 2 (PFKFB2), transcript variant 2, mRNA [NM_001018053] |
| 547 | A_24_P414556 | TTC33 | TACTCAAGATTGTATATTTGTTTTGAGTAATGATGTTTGTTTTTGTGTAATTTTGTGA | SEQ ID NO: 2899 | Homo sapiens tetratricopeptide repeat domain 33 (TTC33), mRNA [NM_012382] |
| 548 | A_24_P417281 | TXNDC10 | ATGATGAGTGATTCTTGGGAAGAATAAATGTTAATGTTCCGAATAGTCAAGCTTGTTTGC | SEQ ID NO: 2900 | Homo sapiens thioredoxin domain containing 10 (TXNDC10), mRNA [NM_019022] |
| 549 | A_24_P419211 | MTMR6 | AGAAACAAAACATAAAAACCCGAAAACTAAATCGACTTGGAATTAGCAATATCACCCAAGTGG | SEQ ID NO: 2901 | Homo sapiens myotubularin related protein 6 (MTMR6), mRNA [NM_004685] |
| 550 | A_24_P450172 | AK095151 | ATGCACTGAATAAAGCTACTTAAACCAGAGTAATTTTGGGATATTAATCCTAGGGCTAC | SEQ ID NO: 2902 | Homo sapiens cDNA FLJ37832 fis, clone BRSSN2009630. [AK095151] |
| 551 | A_24_P45620 | UTS2 | AGAAAGTTCAGGATTTCTCTGGACAAGAATGGCTAACATTTTACTGAGTCATCTTTTGGCG | SEQ ID NO: 2903 | Homo sapiens urotensin 2 (UTS2), transcript variant 1, mRNA [NM_021995] |
| 552 | A_24_P487736 | CXorf23 | TGCATACCTACTATGTCGTAAGAGACAAATGGAATGGAATTTTTAAATGAAATTTTTAAGGCCC | SEQ ID NO: 2904 | Homo sapiens chromosome X open reading frame 23 (CXorf23), mRNA [NM_198279] |
| 553 | A_24_P514678 | DB728175 | ATCAACAGTGTGTCAATTAAGGAATTGCTCATATTCTCGTGAATAAAGAGCAAAGTCG | SEQ ID NO: 2905 | DB728175 RIKEN full-length enriched human cDNA library, hypothalamus Homo sapiens cDNA clone HQ33001B22 3', mRNA sequence [DB728175] |
| 554 | A_24_P532232 | CREB5 | TCGTGAACACATTTATTGTTACCAATGGAGAATGAGTCATTAAGACTGTTGTTCAACTAGGT | SEQ ID NO: 2906 | Homo sapiens cAMP responsive element binding protein 5 (CREB5), transcript variant 1, mRNA [NM_182898] |
| 555 | A_24_P538403 | ROCK1 | TTAGAGGTTTGTTGGACTTTCATAAATTGAGTACAGATCTCTTTGGATCAAACTACCTGCTAC | SEQ ID NO: 2907 | Homo sapiens Rho-associated, coiled-coil containing protein kinase 1 (ROCK1), mRNA [NM_005406] |
| 556 | A_24_P54178 | TMED5 | GCTCTGATAATGCATTTGGATGATTAATGTTATGCTGTTGTTCATGTGAATGTCAAGACA | SEQ ID NO: 2908 | Homo sapiens transmembrane emp24 protein transport domain containing 5 (TMED5), mRNA [NM_016040] |

Fig. 7-31

| No. | Probe ID No. | Symbols of genes | Sequence | SEQ ID NO: | Descriptions of genes (letters and numbers within [ ] indicate GenBank accession No.) |
|---|---|---|---|---|---|
| 557 | A_24_P551028 | LOC339745 | TCCAGTTGAAGAAATATTGAGTGCCTATGATATGGAAGACTAACT CCTTACTACGGAATGA | SEQ ID NO: 2909 | Homo sapiens hypothetical protein LOC339745 (LOC339745), mRNA [NM_001001684] |
| 558 | A_24_P56240 | CPNE8 | TACAACTATGTGACTTAGTGCACAACACATTGTGAAATAACCTA GTCCTATATACTGAC | SEQ ID NO: 2910 | Homo sapiens copine VIII (CPNE8), mRNA [NM_153634] |
| 559 | A_24_P56252 | AF086032 | GTATCTAAAGTGAACAGCTGTGCTATATTGATTTTATTGGT AGTATTGAGCAGAGC | SEQ ID NO: 2911 | Homo sapiens full length insert cDNA clone YW25609. [AF086032] |
| 560 | A_24_P592591 | A_24_P592591 | GAATTTGTTACACGTGGAGGAAGGGAGACGTTGAGGAATATGGT CAGGATGTTCCAT | SEQ ID NO: 2912 | |
| 561 | A_24_P592591 | THC2815064 | CAGTGGTGTAACTCATCAATACATGGTGTCATTTTATTCTCTATATTTC AGGTAAGTGAAAGGG | SEQ ID NO: 2913 | BX491310 DKFZp686K2197_r1 686 (synonym: hlcc3) Homo sapiens cDNA clone DKFZp686K2197 5', mRNA sequence [BX491310] |
| 562 | A_24_P62860 | STAM2 | GTCTATATGGTAGTTGATCTAGATTTAAGTGGAAAAATTAGGAGT ATTTGAAAGCTCAGT | SEQ ID NO: 2914 | Homo sapiens signal transducing adaptor molecule (SH3 domain and ITAM motif) 2 (STAM2), mRNA [NM_005843] |
| 563 | A_24_P630039 | AL049321 | AACATGAGACAATACAAAGTTACATTTTTGGACCATATATAAAAGT GGAAGAAGACAGGCG | SEQ ID NO: 2915 | Homo sapiens mRNA; cDNA DKFZp564D156 (from clone DKFZp564D156). [AL049321] |
| 564 | A_24_P68027 | APOBEC3B | GCTGCCCGGCATCTATGATTACGACCCCTATATAAGGAGGCGCTG CAAATGCTGCGGAT | SEQ ID NO: 2916 | Homo sapiens apolipoprotein B mRNA editing enzyme, catalytic polypeptide-like 3B (APOBEC3B), mRNA [NM_004900] |
| 565 | A_24_P66125 | STAG2 | TAATCATTCCATGGCCTTAATATGGTTGCAATACAAGAATATCTTC AGATGGGTGAATACC | SEQ ID NO: 2917 | Homo sapiens stromal antigen 2 (STAG2), transcript variant 4, mRNA [NM_006603] |
| 566 | A_24_P675947 | ENST00000389400 | CTTCATGGGCGAAGGTAGCAGTTCTGGAAAGCTACTGAGAAGAG ACAGAGTTCTAAAGTT | SEQ ID NO: 2918 | similar to 40S ribosomal protein S3a (V-fos transformation effector protein) (LOC391706), mRNA [Source:RefSeq_dna;Acc:XR_017186] [ENST00000389400] |
| 567 | A_24_P681266 | A_24_P681266 | TAAGCAGAAAAGCACGAGATGATATATCGTTCCTGAGTTGGTGA TTCAAGTCGGCTTTCC | SEQ ID NO: 2919 | |
| 568 | A_24_P688133 | AK124299 | TAGCATATCTGCAGGAAAAATATCTTGTTGTTGATATGCCCCA ATAGTGATTGATTTC | SEQ ID NO: 2920 | Homo sapiens cDNA FLJ42306 fis, clone TRACH2001646. [AK124299] |
| 569 | A_24_P703614 | A_24_P703614 | AAGAACATTACCGGATGGAGTCTGCACTGTAAGTCATCAGTAGG AGCTTTGTGTGTGTG | SEQ ID NO: 2921 | |
| 570 | A_24_P71468 | QPCT | GTGTGGAAAGATCTATCCTATAGATCATCCTATTCTTATGTGTCT TTGGTTATCGATCA | SEQ ID NO: 2922 | Homo sapiens glutaminyl-peptide cyclotransferase (glutaminyl cyclase) (QPCT), mRNA [NM_012413] |
| 571 | A_24_P71938 | SMAD1 | TGTATTCATATGGTCGTACATTGAGTAGTACTTTTATTCCAAAA GTAGTGGGTTTCTG | SEQ ID NO: 2923 | Homo sapiens SMAD family member 1 (SMAD1), transcript variant 1, mRNA [NM_005900] |
| 572 | A_24_P725898 | THC2706471 | GTCTGAGGACACTTAGTGCTCGTACATTGAACAAGAAGCCATCATTGGTCTT TTGTCCAGAATTTGC | SEQ ID NO: 2924 | |
| 573 | A_24_P75158 | PTAR1 | CCATTAGATTTGTTGTTATGTGACGATGTACGAAGCCAGCTATAA AGTATTGTATTCTG | SEQ ID NO: 2925 | Homo sapiens mRNA; cDNA DKFZp313P0917 (from clone DKFZp313P0917). [AL832683] |
| 574 | A_24_P781846 | AK024092 | ACTTTTTATAGATACAAATGTATCGTGGTAGTAGTAGAAGGACTTT GTTACTTTGGCGTGG | SEQ ID NO: 2926 | Homo sapiens cDNA FLJ14030 fis, clone HEMBA1004086. [AK024092] |
| 575 | A_24_P781829 | THC2543120 | TTTTCCGTTTTGCTAAATGCTAGGTATTGCTTAGGTGTGTTTCT GATGTCATGGATTCT | SEQ ID NO: 2927 | |

Fig. 7-32

| No. | Probe ID No. | Symbols of genes | Sequence | SEQ ID NO: | Descriptions of genes (letters and numbers within [ ] indicates GenBank accession No.) |
|---|---|---|---|---|---|
| 576 | A_24_P792734 | PSMC6 | AGAACGTTAACGGAGTTACTGAATCAAATGGATGATTTGATACTCTGATAGAGTTAAA | SEQ ID NO: 2928 | Homo sapiens proteasome (prosome, macropain) 26S subunit, ATPase, 6 (PSMC6), mRNA [NM_002806] |
| 577 | A_24_P80915 | BCLAF1 | AACTTGTGTCAATGAATGGTAATGAGACCAAACTTGTACATTTAATTAAGGGTACCAGTC | SEQ ID NO: 2929 | Homo sapiens BCL2-associated transcription factor 1 (BCLAF1), transcript variant 1, mRNA [NM_014739] |
| 578 | A_24_P82630 | SMCHD1 | TGTTTAATATGTAACACGTAAGAAGAATTGAAATTTCTCTAAGATTAATACTAGTCT | SEQ ID NO: 2930 | Homo sapiens mRNA for KIAA0650 protein, partial cds. [AB014550] |
| 579 | A_24_P859859 | THC2553238 | TTAACCAGACGTCTGCACCCTTTTCTGATATACTGAGGACACTCGGTCTCTAGCAAT | SEQ ID NO: 2931 | 1305349A cystic fibrosis antigen. [Homo sapiens] (exp=-1; wgp=0; cg=0) partial (65%) [THC2553238] |
| 580 | A_24_P87201 | AK022997 | CTGACATGTGATAAATATTTGAGTGACTTTCAGATTATTCTTGTTAGCGCTGTGTC | SEQ ID NO: 2932 | Homo sapiens cDNA FLJ12935 fis, clone NT2RP2004982. [AK022997] |
| 581 | A_24_P886040 | DCP2 | CATTTGGAACAGGTTTCATTCTGTTCTAGATTTATGTGTTGTAGTTGAACAGGAACTG | SEQ ID NO: 2933 | Homo sapiens DCP2 decapping enzyme homolog (S. cerevisiae) (DCP2), mRNA [NM_152624] |
| 582 | A_24_P890536 | CR627148 | AATTGCCTTCTTGTAACCTAAGTATGGTGAAGCAGAATTGAAATCTAGAAAAGTCTTTC | SEQ ID NO: 2934 | Homo sapiens mRNA; cDNA DKFZp779F2127 (from clone DKFZp779F2127) [CR627148] |
| 583 | A_24_P915269 | SRGN | GCATCATATTCGGAAATATCTTCCTAGGGTTTATCTACCATTTAGTGTTGTTTAGTGAGAC | SEQ ID NO: 2935 | Homo sapiens serglycin, mRNA (cDNA clone IMAGE:4668573), complete cds. [BC022313] |
| 584 | A_24_P91916 | NXT2 | AACGATGTTTCCTTGTAGTACTGATTGAAACTTACACAGTTTATTCTAGTCATAGTGAGC | SEQ ID NO: 2936 | Homo sapiens nuclear transport factor 2-like export factor 2 (NXT2), mRNA [NM_018698] |
| 585 | A_24_P921386 | CALD1 | TTCGTTGTTTACTGGTTTGACTATAATTCTCTGTTATGTTTAGGAGGTAAAACTGGAAGC | SEQ ID NO: 2937 | Homo sapiens caldesmon 1 (CALD1), transcript variant 1, mRNA [NM_033138] |
| 586 | A_24_P924697 | AK055915 | GGCCAGAATAACCCAAAATTATTCAGACGACGGTTAACTATTATTGGTACTGGCTAAGCAATAC | SEQ ID NO: 2938 | Homo sapiens cDNA FLJ31353 fis, clone MESAN2000264. [AK055915] |
| 587 | A_24_P925505 | CD36 | CGTACCCTGTTACTACCACAGTTGGTCTGTTTATCGTGTAAGTACCAAATATGAATGGC | SEQ ID NO: 2939 | CD36-collagen type 1/thrombospondin receptor (one exon) [human, mRNA Partial, 369 nt] [S67044] |
| 588 | A_24_P935986 | BCAT1 | ATGCTGTGAAGGTTTTGTAGAAGCACAATTAAACATGTAAAATGGCTTTGTTGGTGAAGC | SEQ ID NO: 2940 | Homo sapiens branched chain aminotransferase 1, cytosolic (BCAT1), mRNA [NM_005504] |
| 589 | A_24_P936319 | BC030115 | GAAAGATACGAATGCATTCTATGGTACAACTACTGTCAATAACATCTGATGTTACATGCAG | SEQ ID NO: 2941 | Homo sapiens cDNA clone IMAGE:4801326. [BC030115] |
| 590 | A_24_P937095 | SLC30A1 | TTTGATGTAGGTCGTCACCGATACTATGTGGTAATGGTATTTTGTTTACTAACAAGCTCTG | SEQ ID NO: 2942 | Zinc transporter 1 (ZnT-1) (Solute carrier family 30 member 1). [Source:Uniprot/SWISSPROT:Acc:Q9Y6M5] [ENST00000367000] |
| 591 | A_24_P940426 | QKI | AAGTGTTGAATGAGTCTTAAAAATTATACTACTGTTAAGTGGACCAAGTTTGGTGAAGC | SEQ ID NO: 2943 | Homo sapiens quaking homolog, KH domain RNA binding (mouse) (QKI), transcript variant 4, mRNA [NM_206855] |
| 592 | A_24_P940725 | C6orf111 | AATTATGATTAGTGAGTGGTCTAACAGTTTAAGGGATTGATAACTTACAAGTAGAGTGGG | SEQ ID NO: 2944 | Splicing factor, arginine/serine-rich 130 (Serine-arginine-rich splicing regulatory protein 130) (SRrp130) (SR-rich protein) (SR-related protein). [Source:Uniprot/SWISSPROT:Acc:Q8TF01] [ENST00000369239] |

Fig. 7-33

| No. | Probe ID No. | Symbols of genes | Sequence | SEQ ID NO: | Descriptions of genes (letters and numbers within [ ] indicates GenBank accession No.) |
|---|---|---|---|---|---|
| 593 | A_24_P941643 | PLCB1 | ATGATGTGCAGTTTGTGCCTTTATGTATTTGGCTTGTCTTTGT CGAATGTGTGAAATT | SEQ ID NO: 2945 | Homo sapiens phospholipase C, beta 1 (phosphoinositide-specific) (PLCB1), transcript variant 2, mRNA [NM_182734] |
| 594 | A_24_P942002 | CENTB2 | TGGATTCTCATGGTAGGATTTCTGAGATCTTAATCTAAGCTGCAA AGTTGTCTACTTTTT | SEQ ID NO: 2946 | Homo sapiens centaurin, beta 2 (CENTB2), mRNA [NM_012287] |
| 595 | A_24_P942469 | SPAG9 | AAACAGATGTGTCATAATATTAACTGTCGTAAAGAACACATGTGTCT TGCAAATGCCATGGA | SEQ ID NO: 2947 | Homo sapiens cDNA FLJ26141 fis, clone TST03911. [AK129662] |
| 596 | A_24_P942773 | SLMAP | AAAGTACAATAGAATTCTGGAGTACAGATTAAACTATTTGCACT AACACACGTGACGTG | SEQ ID NO: 2948 | Homo sapiens sarcolemma associated protein (SLMAP), mRNA [NM_007159] |
| 597 | A_24_P943957 | PIP5K3 | TTGGCTCTTATTAGGTATTGTAAATAGTAGGGTTATATCGATATG AGCTTTTGTGATGGC | SEQ ID NO: 2949 | Homo sapiens phosphatidylinositol-3-phosphate/phosphatidylinositol 5-kinase, type III (PIP5K3), transcript variant 2, mRNA [NM_015040] |
| 598 | A_24_P97526 | CMTM6 | GTGGATCTCTAGTTGGTCACTTGGTCACTTAATCTGTTCTTTCTTGTTGAGAAAGA TAGTATGTTCACTGG | SEQ ID NO: 2950 | Homo sapiens CKLF-like MARVEL transmembrane domain containing 6 (CMTM6), mRNA [NM_017801] |
| 599 | A_24_P98109 | SNX10 | AACAGTGGGACAGAGGGTACTACAAAAGCAACCTTTTCTTCATTTTCAG TAAGAGTTTAAAAGC | SEQ ID NO: 2951 | Homo sapiens sorting nexin 10 (SNX10), mRNA [NM_013322] |
| 600 | A_24_P99046 | STK38L | GCTATCTGTCTTTTGTGATGTACAAATAAATGAATTGAGAATTT AGTGCAATAGAGGTCC | SEQ ID NO: 2952 | Homo sapiens serine/threonine kinase 38 like (STK38L), mRNA [NM_015000] |
| 601 | A_32_P100109 | REPS2 | GTGTGGAGAATTGGATCAACTGACTTGTGTATTTTGTTTTAAGT CACGTTGTCGAGAA | SEQ ID NO: 2953 | Homo sapiens RALBP1 associated Eps domain containing 2 (REPS2), transcript variant 1, mRNA [NM_004726] |
| 602 | A_32_P101313 | PTPLAD2 | AAAGTGTGAATAACTGATAGTCATTGGTGTATCATTGATGTATCA CTCAATTTTTGGTAA | SEQ ID NO: 2954 | Homo sapiens protein tyrosine phosphatase-like A domain containing 2 (PTPLAD2), mRNA [NM_001010915] |
| 603 | A_32_P108254 | FAM20A | TCGTGCGTTGCCTTGCTCGGTTTTCCGAAAAGCACTGGCTTCA TCAAGGCACCCACCG | SEQ ID NO: 2955 | Homo sapiens family with sequence similarity 20, member A (FAM20A), mRNA [NM_017565] |
| 604 | A_32_P112452 | BI026064 | CGTGAGGAGGTGTTGATGATCGTCTGTATGTTGCCTTCCAGCTGCG ACATTTTGCAAGTCA | SEQ ID NO: 2956 | BI026064 GNO-MTC374-060201-774-h11 MTC374 Homo sapiens cDNA, mRNA sequence [BI026064] |
| 605 | A_32_P113584 | ZNF292 | GGGCCTTTTGGGTTTATTGAATAGTTCATTTCAGCTGTTTAAGA CTTACTACGAATAAG | SEQ ID NO: 2957 | Zinc finger protein 292. [Source:Uniprot/SWISSPROT:Acc:Q602281] [ENST00000339907] |
| 606 | A_32_P11451 | NMD3 | CAGTTTAGGGCAGTAGGCGTTGTCATAAATATCTTCCTACCA CATCAAAAATGCTGC | SEQ ID NO: 2958 | Homo sapiens NMD3 homolog (S. cerevisiae) (NMD3), mRNA [NM_015938] |
| 607 | A_32_P115220 | C9orf66 | TTCTCAAAAAATGTTTTCGTCACACACCTGGCGTGAATGCTTTTCT CCGGAGAAACACTGA | SEQ ID NO: 2959 | Homo sapiens chromosome 9 open reading frame 66 (C9orf66), mRNA [NM_152669] |
| 608 | A_32_P115565 | ZNF294 | TGTGGTCAGAGGATTATAGTTGAGAGTGAAGTACTATGTGTGAGT TATAGATCTCTGAA | SEQ ID NO: 2960 | Homo sapiens zinc finger protein 294 (ZNF294), mRNA [NM_015665] |
| 609 | A_32_P117313 | DKFZP779L1068 | ATGACTGTAAGATCTGAGAGTATGTTCTTACTACTGCATTCTGTAAT TGCAGTAGTGTAGTC | SEQ ID NO: 2961 | Homo sapiens cDNA clone IMAGE:5555490. [BC103326] |
| 610 | A_32_P118325 | BU567832 | ATTAATTCTGACTAAATGGCATTAAAGGAGGTCTGAGGAATTTGC ATGTCACATTCTGGA | SEQ ID NO: 2962 | AGENCOURT_10399047 NIH_MGC_82 Homo sapiens cDNA clone IMAGE:6614537 5', mRNA sequence [BU567832] |

Fig. 7-34

| No. | Probe ID No. | Symbols of genes | Sequence | SEQ ID NO: | Descriptions of genes (letters and numbers within [ ] indicates GenBank accession No.) |
|---|---|---|---|---|---|
| 611 | A_32_P123204 | AI381562 | AACTGCTAGAAATGGTCTCGTTTAAGGAGTGTCTGCTAATAATGTGATCACTTTTGACTT | SEQ ID NO: 2963 | AI381562 te76g06.x1 Soares_NFL_T_GBC_S1 Homo sapiens cDNA clone IMAGE:2092666 3', mRNA sequence [AI381562] |
| 612 | A_32_P124580 | THC2610143 | ATTAGCTGGGACTAAAACGGAGACATGTTTGTTTGTGAATTCTACCTAAATGTCTCTCTA | SEQ ID NO: 2964 | AA490192  za43f10.r1 Soares_NhHMPu_S1 Homo sapiens cDNA clone IMAGE:823723 5', mRNA sequence [AA490192] |
| 613 | A_32_P125917 | THC2753798 | GCTTATAAAGTGTAAGTGGAGACGCCTAAATTGTGAGTACAAAGTTTCTTTTCAGAACAG | SEQ ID NO: 2965 | BF238843 601904455F1 NIH_MGC_64 Homo sapiens cDNA clone IMAGE:4132429 5', mRNA sequence [BF238843] |
| 614 | A_32_P126023 | THC2559360 | AGTCTTCTAGATTCTCGCTAGGACAAACTGATATGAGGTAGAGATGGTGAAAGATGTTTCAGC | SEQ ID NO: 2966 | ALU6_HUMAN (P39188) Alu subfamily SC sequence contamination warning entry, partial (9%) [THC2559380] |
| 615 | A_32_P128980 | BC062780 | AGATGGGAGACAGAGGAGGTAGTGACAGGAGTAGAAGGCACTGTAGAGCTTTCATATCAT | SEQ ID NO: 2967 | Homo sapiens cDNA clone IMAGE:4700531, partial cds. [BC062780] |
| 616 | A_32_P128894 | MEGF9 | TTTAGACAAGATTTGTAGGACAGCCTGAAATTATATGACTGTTCTCTAGGGCCAATATTCCC | SEQ ID NO: 2968 | Homo sapiens multiple EGF-like-domains 9 (MEGF9), mRNA [NM_001080497] |
| 617 | A_32_P131401 | AI276257 | TCAGAAAAACAGAGTAAGGCACCACTCTGGGAAATTAAGGTAGCTTCGAGTAAGAAGT | SEQ ID NO: 2969 | AI276257 qi65f01.x1 Soares_NhHMPu_S1 Homo sapiens cDNA clone IMAGE:1877209 3', mRNA sequence [AI276257] |
| 618 | A_32_P148824 | C1orf27 | GAAAAACAGAGATGTTATCCTGAGCACAAATTCAGTAAAGAGACTACAAAAGGATGATCTTG | SEQ ID NO: 2970 | Homo sapiens chromosome 1 open reading frame 27 (C1orf27), mRNA [NM_017847] |
| 619 | A_32_P149404 | LOC728371 | GTAAAGCTGTGGAATTCTGTTGATGATGGATGGATGGATGGTGAAGCCCTGCGGGATGAT | SEQ ID NO: 2971 | PREDICTED: Homo sapiens similar to ankyrin repeat domain 20A (LOC728371), mRNA [XR_015273] |
| 620 | A_32_P153725 | KIAA1033 | TTTTGTAAAAGAGATGGCAAGTTTGTTACCTCACTTGAGTGGGGTTTTCCTTTTGCCCCAAT | SEQ ID NO: 2972 | Homo sapiens KIAA1033 (KIAA1033), mRNA [NM_015275] |
| 621 | A_32_P162183 | C2 | GGTTGACTTGACTCATGCTTGTTCACTTTGACATGGAATTGCCAGTTATGAAATTAAT | SEQ ID NO: 2973 | Homo sapiens complement component 2 (C2), mRNA [NM_000063] |
| 622 | A_32_P162250 | ARHGAP18 | AAGTCCTGAATAAGTCTAGTGGAAGAATTATTGTTCTGTGGGTGAAAAAGCTTTTGTTGTG | SEQ ID NO: 2974 | Homo sapiens Rho GTPase activating protein 18 (ARHGAP18), mRNA [NM_033515] |
| 623 | A_32_P164203 | THC2683448 | TTGATGGTCATTGTACGAGCTATTGTATGGATTACTGTGGAGTGCTGTTTACCACATGAT | SEQ ID NO: 2975 | Q7WZG3_PASP1 (Q7WZG3) Ferric uptake regulator, partial (8%) [THC2633448] |
| 624 | A_32_P166272 | THC2650457 | ATACATTTAATTCCTCACGTTTATATTGGGAGAGTTGGGTACAGACTGTCGATTACTGC | SEQ ID NO: 2976 | ALU6_HUMAN (P39188) Alu subfamily SP sequence contamination warning entry, partial (12%) [THC2650457] |
| 625 | A_32_P167122 | RCOR3 | GTATCTGAGGATGGTCTGTAATCTGATTTAGATGATTAGATGCATTAGAGACACAGTAGAAAAAGT | SEQ ID NO: 2977 | Homo sapiens REST corepressor 3 (RCOR3), mRNA [NM_018254] |
| 626 | A_32_P170444 | SUB1 | TAGGTATCTCTCCTGAAATTCTTGGAGTTCATTGTTTTATGGCAGTTAATCCAAGTGAAAG | SEQ ID NO: 2978 | Activated RNA polymerase II transcriptional coactivator p15 (SUB1 homolog) (Positive cofactor 4) (PC4) (p14). [Source:Uniprot/SWISSPROT;Acc:P53999] [ENST00000265073] |
| 627 | A_32_P171313 | GNB4 | GATTTAAGTGTTGTTAGATCTTTGTTACAGAGTGATTCATTGCTCTATTTGTTACAGTGGG | SEQ ID NO: 2979 | Homo sapiens guanine nucleotide binding protein (G protein), beta polypeptide 4 (GNB4), mRNA [NM_021629] |

Fig. 7-35

| No. | Probe ID No. | Symbols of genes | Sequence | SEQ ID NO: | Descriptions of genes (letters and numbers within [ ] indicates GenBank accession No.) |
|---|---|---|---|---|---|
| 628 | A_32_P17163 | ENST00000368149 | TGCTTAGTGAGTTTTAAATCTGAGGTAGATTTTTATTTGTTTTCTGTGTGTGATGAG | SEQ ID NO: 2980 | Rho GTPase-activating protein 18 (MacGAP). [Source:Uniprot/SWISSPROT:Acc:Q8N392] [ENST00000368149] |
| 629 | A_32_P172678 | THC2661509 | ACTTAATCAATGTGTCAAAGATTTCTAGGCATTCTCCATCTCATGGATTCGTTCGTTCC | SEQ ID NO: 2981 | |
| 630 | A_32_P17504 | THC2698682 | ATGTCTATGCTGTTTCACTATGCTGCAAGATGGTTGGTGAAATAATTCCGAGGGTTTCCCGTTGATGCGGAAA | SEQ ID NO: 2982 | |
| 631 | A_32_P177640 | WBSCR19 | AATCTTGTATGCTATTATTACACAGGTGTTGGTGAAGGGAGGATGGTTTTTATCTGTGATAC | SEQ ID NO: 2983 | Homo sapiens Williams Beuren syndrome chromosome region 19 (WBSCR19), mRNA [NM_175064] |
| 632 | A_32_P177685 | THC2632266 | TTTGACTGAGTATTTGTAGATGCTTAATGACTGAAATGAATTTGGAGGGACTGATGAAAG | SEQ ID NO: 2984 | AA665072 nu76a01.s1 NCI_CGAP_Alv1 Homo sapiens cDNA clone IMAGE:1216595, mRNA sequence [AA665072] |
| 633 | A_32_P178966 | ENST00000379426 | GTAATATACAGGGTGAACTCTTTACTGATAGACAAGAGACAACGTGTTAAAAAGTGAATCC | SEQ ID NO: 2985 | Novel protein. [Source:Uniprot/SPTREMBL:Acc:Q5T4T1] [ENST00000379426] |
| 634 | A_32_P180435 | WBSCR19 | CTTTGAATCTTTGTATCTATTATTACAGGTGCTGCTGAAGGGAGCATGTTTTATGTATG | SEQ ID NO: 2986 | Homo sapiens Williams Beuren syndrome chromosome region 19 (WBSCR19), mRNA [NM_175064] |
| 635 | A_32_P184417 | A_32_P184417 | AAGGTCTGTTGGTGTGGTAGGCATTCAGTTATTCCTAATAGTTTATTTAGGTACTATAC | SEQ ID NO: 2987 | |
| 636 | A_32_P184916 | GNB4 | CAATGTGAGAGTGTTACATTTGGAGAGAAGTGTGAAATCTAACCAATCGCTAGCAGCATAT | SEQ ID NO: 2988 | Homo sapiens guanine nucleotide binding protein (G protein), beta polypeptide 4 (GNB4), mRNA [NM_021629] |
| 637 | A_32_P193322 | RICTOR | ACCACATGAGTTTCTTCTTTTTATTTAGTAATACGGCTGGTACAT | SEQ ID NO: 2989 | Homo sapiens rapamycin-insensitive companion of mTOR (RICTOR), mRNA [NM_152756] |
| 638 | A_32_P194032 | LONRF1 | GTTAGATCACGATGGTGCAACATGGTTTTATATTGATGCTGGGGTAGAAACTTTTGTATT | SEQ ID NO: 2990 | Homo sapiens LON peptidase N-terminal domain and ring finger 1 (LONRF1), mRNA [NM_152271] |
| 639 | A_32_P195367 | DKFZP779L1068 | ATATAACCTTGGAATTCTATTCTAATTATGTGTCTGGCTGCTTGTAGTATGCAGTTCGG | SEQ ID NO: 2991 | Homo sapiens cDNA clone IMAGE:5555490. [BC110326] |
| 640 | A_32_P19752 | FAM76B | TTGTGCTTTAGCCTGTTTTCCACTATTAATTAGGCATTTACCAGTAAGGGTCATTTTGAC | SEQ ID NO: 2992 | Homo sapiens family with sequence similarity 76, member B (FAM76B), mRNA [NM_146664] |
| 641 | A_32_P20240 | SP3 | CTTAGGCTGTTAATTGTAGTTTAAATTGCAGTAGTGCCTACTCAGACCCAAAAGTTTTGT | SEQ ID NO: 2993 | Homo sapiens mRNA; cDNA DKFZp686N17231 (from clone DKFZp686N17231). [BX648857] |
| 642 | A_32_P203320 | ROCK1 | AACGGCCATGACTCACTATCGAAGATCAAGCTCATGGAAGGAGTAAAGAAAATATCTCAAAATGAG | SEQ ID NO: 2994 | Homo sapiens Rho-associated, coiled-coil containing protein kinase 1, mRNA (cDNA clone IMAGE:5269982), complete cds. [BC041849] |
| 643 | A_32_P203749 | AF086547 | CACGTGTCTATTCTGTAGACTATCTCGTTAGATTTGTAGATGCATTTTTTGCGGACTT | SEQ ID NO: 2995 | Homo sapiens full length insert cDNA clone ZE12B03. [AF086547] |
| 644 | A_32_P205653 | RPL26L1 | TTGGAATGTCTGGAACATTTCATTTCGTGTTTTGTTGTTAGGTGTGGCTCGTAAATCTACT | SEQ ID NO: 2996 | Homo sapiens ribosomal protein L26-like 1 (RPL26L1), mRNA [NM_016093] |
| 645 | A_32_P210798 | BF513730 | AAACACCTACCTAATCTGACTGCTAAATTTCTAGGTCTTGTTTTAAATAATGCTCAGG | SEQ ID NO: 2997 | BF513730 UI-H-BW1-amy-e-05-0-UI.s1 NCI_CGAP_Sub7 Homo sapiens cDNA clone IMAGE:3071696 3', mRNA sequence [BF513730] |

Fig. 7-36

| No. | Probe ID No. | Symbols of genes | Sequence | SEQ ID NO: | Descriptors of genes (letters and numbers within [ ] indicates GenBank accession No.) |
|---|---|---|---|---|---|
| 646 | A_32_P221552 | BE173582 | ATTTAACTGAGGTAGAGGAGATGTTCTAAATTCGGGGTTTCATAGAATCCCGTGAATCT | SEQ ID NO: 2998 | BE173582 RC2-HT0560-290200-014-F06 HT0560 Homo sapiens cDNA, mRNA sequence [BE173582] |
| 647 | A_32_P224666 | CAPZA2 | AATGCTGTTTGAGATTCTGAAATTAAATGAAAATACTTATTTCAGAAATGCATTTAATG | SEQ ID NO: 2999 | Homo sapiens capping protein (actin filament) muscle Z-line, alpha 2 (CAPZA2), mRNA [NM_006136] |
| 648 | A_32_P226678 | BX114764 | CTCTACATCCTTACGTAGGTAAATTCAGGGATGGGCGCCAGTATTTTGGAGGGGTCCAAATTA | SEQ ID NO: 3000 | BX114764 NCI_CGAP_GCB1 Homo sapiens cDNA clone IMAGp998H182012, mRNA sequence [BX114764] |
| 649 | A_32_P226786 | BC045174 | TTATTGGTGCATGTAAGCCATTATCCTGTCTTAATGAACCGATTAATGCTGTTGATGTT | SEQ ID NO: 3001 | Homo sapiens cDNA clone IMAGE:5273245. [BC045174] |
| 650 | A_32_P228438 | THC2637028 | CTGTCCTATTCCACCCCTAGTAGATGAATAGATAATGCGTTGAACTATTCCTATCACCACAGGT | SEQ ID NO: 3002 | Q8N4F7_HUMAN (Q8N4F7) Ring finger protein 175, partial (12%) [THC2637028] |
| 651 | A_32_P2333 | SUB1 | AGGAAGAAAAGGTATTTCTTTAAATCCAGAACAATGGAGCCAAGGTGACGAACAGATTTC | SEQ ID NO: 3003 | Homo sapiens SUB1 homolog (S. cerevisiae) (SUB1), mRNA [NM_006713] |
| 652 | A_32_P233314 | EXOC8 | AGGATTGGGATTTGGGACATGGACATGTACTATAAAGTCAGTCGTATGTACAGTCAGTCT | SEQ ID NO: 3004 | Homo sapiens exocyst complex component 8 (EXOC8), mRNA [NM_175876] |
| 653 | A_32_P26895 | KIAA1600 | AATTCTTGGTCCTCCGTGGGAGAAACTCTCAGATGGTCATTGTGTACGTACTGTCTCTT | SEQ ID NO: 3005 | KIAA1600 (KIAA1600), mRNA [Source:RefSeq_dna;Acc:NM_020940] [ENST00000369248] |
| 654 | A_32_P31123 | THC2680780 | GATTAGGGAAAGTTCGTCGGGTGCATTAGAATGTCAAGTTCAAGTTTGGTGGCTCATTGTAGGACTG | SEQ ID NO: 3006 | |
| 655 | A_32_P32315 | A_32_P32315 | AAAGTGGGAAGATACGGATTCCAAGTCCTGGATTGTCGTCGTTTGGAAAAAGGTCAGTCCTCA | SEQ ID NO: 3007 | |
| 656 | A_32_P3742 | RFX3 | CCTGTCGAAAATTGGCAGGAGCTAAATAATAGTTTGTGGGGGATTTGTATTGTGTAGTGTA | SEQ ID NO: 3008 | Transcription factor RFX3. [Source:Uniprot/SWISSPROT;Acc:P48380] [ENST00000382004] |
| 657 | A_32_P38745 | THC2656841 | AAAGTTGGTATTGGTACCAGATCCGTGCATGCCACTTACGTCTGTGTTTCCTCTCTAATTGGT | SEQ ID NO: 3009 | |
| 658 | A_32_P43217 | PSMA6 | TTGTTTGTTAGTTTACCAGATGCTTACCAAGTTCAATGCCACTTACGACTGTCGAACTCACAGTGTCAAAAATGGAAGAAAAACTACAG | SEQ ID NO: 3010 | Homo sapiens proteasome (prosome, macropain) subunit, alpha type, 6 (PSMA6), mRNA [NM_002791] [NM_004833] |
| 659 | A_32_P44394 | AIM2 | GAAGGAGATAAGGTTCGACTACATTCTCCAACTGCTGTCAAAAAATGGAGAAAAAACTACAG | SEQ ID NO: 3011 | Homo sapiens absent in melanoma 2 (AIM2), mRNA [NM_004833] |
| 660 | A_32_P49164 | AV714556 | AAATGCAGAGCTTGTTATTTGCCAAAGAAGAGATTCATCATGTTCCTTCCTTTGTTTTCCG | SEQ ID NO: 3012 | AV714556 AV714556 DCB Homo sapiens cDNA clone DCBAOD906_5, mRNA sequence [AV714556] |
| 661 | A_32_P6107 | A_32_P6107 | ATGTAATGAATGTCAGAAAGCCTTTGGTGATAGGTCAGCTCTAAAGTACACAGAGAAT | SEQ ID NO: 3013 | |
| 662 | A_32_P61145 | AK096154 | GATAGGATCTTAACAGTAAGCTCTTTATAATTCAACAATGTGATCTTTACTCCTACCC | SEQ ID NO: 3014 | Homo sapiens cDNA FLJ38835 fis, clone MESAN2002424. [AK096154] |
| 663 | A_32_P61857 | KIAA1468 | TCAGTGTACAGTTCCACTGGAATTTGACAGTTGTCTCTACAGTCATGCAACTCGAAGTAG | SEQ ID NO: 3015 | Homo sapiens KIAA1468 (KIAA1468), mRNA [NM_020854] |
| 664 | A_32_P62342 | GLT8D3 | TGTGATGTGTAACTGATGTAACCATTGACAATGTCAATGTGTGCCCTTTATACATTTCATCTCTG | SEQ ID NO: 3016 | Homo sapiens glycosyltransferase 8 domain containing 3, mRNA (cDNA clone MGC:21651 IMAGE:4508300), complete cds. [BC039145] |

Fig. 7-37

| No. | Probe ID No. | Symbols of genes | Sequence | SEQ ID NO: | Descriptions of genes (letters and numbers within [ ] indicates GenBank accession No.) |
|---|---|---|---|---|---|
| 665 | A_32_P63113 | THC2706386 | AGAAAAAGAACAGAAGTCTGGGGTCCACACATAGTGTTTCCAGATGACTGTATTTT | SEQ ID NO: 3017 | Q9T6M0_GLOPA (Q9T6M0) NADH-ubiquinone oxidoreductase subunit 1, partial (6%) [THC2706386] |
| 666 | A_32_P66881 | TLR4 | TTACTGAGTGTTCAGAGTGTGTTTGGTTTGAGCAGGTCTAGGGTGATTGAACATCCCTG | SEQ ID NO: 3018 | Homo sapiens toll-like receptor 4 (TLR4), mRNA [NM_138554] |
| 667 | A_32_P7118 | PSMC6 | AGCAGACCTGAGAAATGTTTGTACTGAAGCAGGTATGTTGGCAATTCGTGCTGATCATGA | SEQ ID NO: 3019 | Homo sapiens proteasome (prosome, macropain) 26S subunit, ATPase, 6 (PSMC6), mRNA [NM_002806] |
| 668 | A_32_P73222 | AA631847 | TTTCTTTGTTTGGACAATCTCATAAGAACTTAAGGTCTTACAAGCACGAACCCCTCGAAG | SEQ ID NO: 3020 | np61b02.s1 NCI_CGAP_Br2 Homo sapiens cDNA clone IMAGE:1130763 3' similar to TR:Q9T1838 Q9T1838 60S RIBOSOMAL PROTEIN L34 ;, mRNA sequence [AA631847] |
| 669 | A_32_P75115 | BF373107 | AGAAGTGAAAAACTGAAGAATGTGGAGTGTTTACTGTCCGGTTACTGACAGACGTGCT | SEQ ID NO: 3021 | BF373107 CM2-FT0123-280700-305-C12 FT0123 Homo sapiens cDNA, mRNA sequence [BF373107] |
| 670 | A_32_P79396 | PBEF1 | AGGGCCGATTATCTTTACATAGGACGACAGGCCAGGAATTTGTTACACTGGAAGAAGGAA | SEQ ID NO: 3022 | Homo sapiens pre-B-cell colony enhancing factor 1 (PBEF1), mRNA [NM_005746] |
| 671 | A_32_P81768 | TMEM167 | CCTCAGGTACTGTCACTACAATATTACATTCTGCAAATGTTATTCTGTTGTATCAGATACG | SEQ ID NO: 3023 | Homo sapiens transmembrane protein 167 (TMEM167), mRNA [NM_174909] |
| 672 | A_32_P83000 | FLJ31222 | ACCATCTGCTGGGACGGAGACCTCTCTTGATCTCACTCCCAGAAAAGACTGAA | SEQ ID NO: 3024 | Homo sapiens cDNA FLJ31222 fis, clone KIDNE2004294. [AK055784] |
| 673 | A_32_P83256 | AK023663 | CAAATAGTCCTTCAAAGCATCTTCAGAATCAAGATTGTCATCTAGATTGCACCCGAAGTT | SEQ ID NO: 3025 | Homo sapiens cDNA FLJ13601 fis, clone PLACE1010069. [AK023663] |
| 674 | A_32_P86400 | LYSMD3 | AAATGTTGCTCAGGTAATCAGTATTTTCTTCGACGTATGTCATATTGCACTGTTAGATC | SEQ ID NO: 3026 | Homo sapiens LysM, putative peptidoglycan-binding, domain containing 3 (LYSMD3), mRNA [NM_198273] |
| 675 | A_32_P877 | BM999343 | TAAAATGCTTGCAGAACTGCACTGTCATTCTCAGAGATTTCCATGGGAAGCCATGCCTA | SEQ ID NO: 3027 | BM999343 UI-H-DPO-avf-i-24-0-UI.s1 NCI_CGAP_Fs1 Homo sapiens cDNA clone IMAGE:5878751 3', mRNA sequence [BM999343] |
| 676 | A_32_P97046 | BU076193 | ATTTATATAGACGATGGGGCAGGCTAATGACATCATAACATTAACTTTTCCAAAGAAGT | SEQ ID NO: 3028 | im55f06.x1 HR85 islet Homo sapiens cDNA clone IMAGE:6038939 3', mRNA sequence [BU076193] |
| 677 | A_32_P98435 | PCMTD1 | ACACTTTGCCATGGTCAAAGAATGAAGGAGAATATGGAAAAGCCAATCTTCAAATATATC | SEQ ID NO: 3029 | Homo sapiens clone 122482 unknown mRNA. [AF293366] |

Fig. 8-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P341938 | NOG | GCCAGGGGTGCGGCTGGATTCGCATCCAGTACCCATCATTTCCGAGTGCAATGCTCGT | SEQ ID NO: 2373 | Homo sapiens noggin (NOG), mRNA [NM_005450] |
| 2 | A_24_P413126 | TMEPAI | AAGAAAGTGCTTGTTGTGTATCAGTAATCATTAGTGGCAATGATGACATTCTGAAAAGCT | SEQ ID NO: 2404 | Homo sapiens transmembrane, prostate androgen induced RNA (TMEPAI), transcript variant 1, mRNA [NM_020182] |
| 3 | A_32_P111394 | THC2643957 | GAATACAGGTGTTCCTTTCATCCCATATTTGAGTGAACCTAAGACACATCAATTATAAGG | SEQ ID NO: 2418 | |
| 4 | A_32_P125589 | THC2649341 | CGGTCTATCCCTTGCTTTAGCCTTTTGAATGAAAGTGAGATGTCTCATCAGCTCAGATAG | SEQ ID NO: 2419 | |
| 5 | A_32_P164378 | THC2703271 | GAAAGAACATGAAAAGCATTGGAATGAAGGAAAGCCAGCTGGTTTAGACTTTAATTTG | SEQ ID NO: 2426 | |
| 6 | A_32_P178998 | DMRTC1 | ATATGCAGGAGTTTTATTGGTGTTGATTGCTGCTGAGATACCTGTGCAGTCAGTGTGTATA | SEQ ID NO: 2430 | Homo sapiens DMRT-like family C1 (DMRTC1), mRNA [NM_033053] |
| 7 | A_23_P111321 | ARG1 | TGGAATCAGGAGGACAAAGGTACCACACATGTGGAAAGGTAGTATGTGTCCATGTCATTCAAA | SEQ ID NO: 2459 | Homo sapiens arginase, liver (ARG1), mRNA [NM_000045] |
| 8 | A_23_P11201 | GPR34 | AGTAGGAGTGAAAAGCACTTGAGAATTTAAACCAGGATACTCCCTGCATGATACATCTGTG | SEQ ID NO: 2461 | Homo sapiens G protein-coupled receptor 34 (GPR34), transcript variant 1, mRNA [NM_005300] |
| 9 | A_23_P19222 | RETN | CAATAAGGACGTTGGCCTGGACTGCCAGAGGGTCACCTCCAGGGGGGACCTGGCTACTT | SEQ ID NO: 2469 | Homo sapiens resistin (RETN), mRNA [NM_020415] |
| 10 | A_23_P121716 | ANXA3 | TGGACATTCGAACAGAGTTGAAGAAAGCATTATGGGCTATTCCCTATATTCAGGAATTAAAT | SEQ ID NO: 2475 | Homo sapiens annexin A3 (ANXA3), mRNA [NM_005139] |
| 11 | A_23_P14708 | SUHW4 | TCTTTGTTACCTCCATACAAGTGTTAGCCTGCCAGGCTGTAAGCTTACGTTAATTAAGCT | SEQ ID NO: 2507 | Homo sapiens suppressor of hairy wing homolog 4 (Drosophila) (SUHW4), transcript variant 1, mRNA [NM_017661] |
| 12 | A_23_P151637 | RNASE2 | GTGGTAACCGCAAATATGACCTGTCCTAGTAACAAAAGTCGCAAAAATTGTCACCACAGTG | SEQ ID NO: 2514 | Homo sapiens ribonuclease, RNase A family, 2 (liver, eosinophil-derived neurotoxin) (RNASE2), mRNA [NM_002934] |
| 13 | A_23_P152002 | BCL2A1 | TGTAACGTATATTTGCATTTGAAGGTATTCCATCAAGAAACTTCTACGACAGGCAAATTGC | SEQ ID NO: 2516 | Homo sapiens BCL2-related protein A1 (BCL2A1), mRNA [NM_004049] |
| 14 | A_23_P159650 | COX7B | CAAAATACGGCTAATGCTGTGTATTAGCTAGTGGAGCCACTTTCTGTATTGTTACAGATGGACATA | SEQ ID NO: 2525 | Homo sapiens cytochrome c oxidase subunit VIIb (COX7B), nuclear gene encoding mitochondrial protein, mRNA [NM_001866] |
| 15 | A_23_P170233 | CSTA | AACTGGCTACTGAGTCATGATCGTTGCTGATAAATATAACCATCAATAAGAAGCATTCT | SEQ ID NO: 2543 | Homo sapiens cystatin A (stefin A) (CSTA), mRNA [NM_005213] |
| 16 | A_23_P25235 | CLEC4D | CATTTAACCCACGAGAGTATTCTGGCATAAGAATGAACCCGACAACTGTCAGGGGAGAAA | SEQ ID NO: 2600 | Homo sapiens C-type lectin domain family 4, member D (CLEC4D), mRNA [NM_080387] |
| 17 | A_23_P263012 | GRAMD1C | GAATTCCAAGAAGGATACGTAGGGGGTAACAGTGAACCTACCTGGGTTTGTTTTGTTTTG | SEQ ID NO: 2602 | Homo sapiens GRAM domain containing 1C (GRAMD1C), mRNA [NM_017577] |
| 18 | A_23_P302550 | RGS18 | GAGTCGTAAGGCCCTAGGCGATTTGGGCATCTGCCACATTGGTTCATATTGGAGAAAGTGTTA | SEQ ID NO: 2621 | Homo sapiens regulator of G-protein signalling 18 (RGS18), mRNA [NM_130782] |

Fig. 8-2

| No. | Probe ID No. | Symbols of genes | Sequence | SEQ ID NO: | Descriptions of genes (letters and numbers within [ ] indicates GenBank accession No.) |
|---|---|---|---|---|---|
| 19 | A_23_P307940 | CAPZA2 | CTACAAGATTGGCAAAGAGATGCATAAGATGAACATT GCATGACCGGATCATT | SEQ ID NO: 2628 | Homo sapiens capping protein (actin filament) muscle Z-line, alpha 2 (CAPZA2), mRNA [NM_006136] |
| 20 | A_23_P314191 | ZDHHC17 | TGGATACTTTAGCAAATAGGAACTTAATTCTCAGGACTGAACA TGAATTACTTCCTTGG | SEQ ID NO: 2634 | Homo sapiens zinc finger, DHHC-type containing 17 (ZDHHC17), mRNA [NM_015336] |
| 21 | A_23_P324633 | C9orf72 | TTTGTGGATTTAGTCCCTGGGATTCAGTCTGTAGAAATGTCTAA TAGTTCTCTATAGTCC | SEQ ID NO: 2640 | Homo sapiens chromosome 9 open reading frame 72 (C9orf72), transcript variant 1, mRNA [NM_018325] |
| 22 | A_23_P347198 | SP3 | GACGAGCTCAAATTTAAAGGGCTACGTTATTGTGACGTTTAAAGTG TATTATAACAGTGTGG | SEQ ID NO: 2651 | Homo sapiens Sp3 transcription factor (SP3), transcript variant 1, mRNA [NM_003111] |
| 23 | A_23_P349083 | FCHO2 | GTGAAATGTTAAACTGTGCACTTCTTAGTTACCACAGTCTT CATACCAAGTATTGGG | SEQ ID NO: 2652 | Homo sapiens FCH domain only 2 (FCHO2), mRNA [NM_138782] |
| 24 | A_23_P405873 | C9orf72 | GAGAATGGAAGATCAGGGTCAGAGTATTATTCCAATGCTTACTG GAGAAGTGATTCCTGT | SEQ ID NO: 2674 | Homo sapiens chromosome 9 open reading frame 72 (C9orf72), transcript variant 2, mRNA [NM_145005] |
| 25 | A_23_P41114 | CSTA | AAACAAATGAGACTTATGGAAGCTGTGCAGTATAAA ACTCAAGTTGTTGCTG | SEQ ID NO: 2677 | Homo sapiens cystatin A (stefin A) (CSTA), mRNA [NM_005213] |
| 26 | A_23_P41664 | ENST00000334994 | TGGCTTGGAGGCAGATTCGACTTCATAAACAAATGTTCGTGAAAA ATGAGGCACAGGTCAT | SEQ ID NO: 2680 | Synleurin (CGL01891) [Source:Uniprot/SPTREMBL;Acc:Q72207] ENST00000334994 |
| 27 | A_23_P420431 | XKR3 | CAGAGGTGGGCCATAGAATCCTACAGTACAGCTTCAGTTTTT TAGAAAATGTGATAAT | SEQ ID NO: 2681 | Homo sapiens XK, Kell blood group complex subunit-related family, member 3 (XKR3), mRNA [NM_175878] |
| 28 | A_23_P434809 | S100A8 | AAAAGCCATGAAGAAAGCCACAAAGAGTAGCTGAGGTTACTGGGACC CAGAGGGCTGGGCCCT | SEQ ID NO: 2691 | Homo sapiens S100 calcium binding protein A8 (S100A8), mRNA [NM_002964] |
| 29 | A_23_P44257 | COMMD8 | AACATTTTAGTTCTGCGCTTCTATGTTTGGGAAAACATTGCTCTG ATAAAAATAGCTGTC | SEQ ID NO: 2692 | Homo sapiens COMM domain containing 8 (COMMD8), mRNA [NM_017845] |
| 30 | A_23_P50907 | ITGAV | AAAGAGTGATTAAGTGAGGTTATTTACCCCTAAATGGTCCATTC TGGATTGTATTTGAGG | SEQ ID NO: 2700 | Homo sapiens integrin, alpha V (vitronectin receptor, alpha polypeptide, antigen CD51) (ITGAV), mRNA [NM_002210] |
| 31 | A_23_P59637 | DOCK4 | TTTGGCAGTGAGCAGTTAAGTGAGGTTATCTTGAATTTATGATGTGTG TGTATTTCTGAAGCAG | SEQ ID NO: 2714 | Homo sapiens dedicator of cytokinesis 4 (DOCK4), mRNA [NM_014705] |
| 32 | A_23_P59921 | SUB1 | CAGATTGGGAAAATGAGGTACGTTAGTGTTCGCGATTTTAAAGG CAAAGTGGTAATTCAT | SEQ ID NO: 2715 | Homo sapiens SUB1 homolog (S. cerevisiae) (SUB1), mRNA [NM_006713] |
| 33 | A_23_P63343 | UTS2 | AGAATCTGGAAACCATACACAAGAAAACGTGAGACTTCCTGATTGTT CTGGAAATACTGTGTC | SEQ ID NO: 2719 | Homo sapiens urotensin 2 (UTS2), transcript variant 1, mRNA [NM_021995] |
| 34 | A_23_P63768 | C15orf15 | TCCTGGATTGCCATCTACATTAGATAATATCACGATATTACGGATGTTAG ATTGCATCTCCAGTGTT | SEQ ID NO: 2723 | Homo sapiens chromosome 15 open reading frame 15 (C15orf15), mRNA [NM_016304] |
| 35 | A_23_P66260 | ZNF267 | TGTGATGAATGTGGTAAAGCCTCAGCTATGAAGGTCATACCCTCAC TACAACATGGAGAAGT | SEQ ID NO: 2724 | Homo sapiens zinc finger protein 267 (ZNF267), transcript variant 498723, mRNA [NM_003414] |
| 36 | A_23_P74001 | S100A12 | TGAAGGTTTTACCCAGCAATGTCCTCAATGAGGGTCTTTTCT TTCCGTCACGAAAACC | SEQ ID NO: 2738 | Homo sapiens S100 calcium binding protein A12 (S100A12), mRNA [NM_005621] |
| 37 | A_23_P7543 | ZFYVE16 | TGTGGCTCGAGCATTATGTAAATGATCTTGATAGTGCTGTGATAC CTGTGATCCATGGTGG | SEQ ID NO: 2740 | Homo sapiens zinc finger, FYVE domain containing 16 (ZFYVE16), mRNA [NM_014733] |
| 38 | A_23_P78092 | EVI2A | GCTGAATCAGACACTTGGAAAAGACAAAGACTCACAGGACC CAACGTAGTGATGGAA | SEQ ID NO: 2746 | Homo sapiens ecotropic viral integration site 2A (EVI2A), transcript variant 1, mRNA [NM_001003927] |

Fig. 8-3

| No. | Probe ID No. | Symbols of genes | Sequence | SEQ ID NO: | Descriptions of genes (letters and numbers within [ ] indicates GenBank accession No.) |
|---|---|---|---|---|---|
| 39 | A_23_P82047 | BU507302 | TCTGTTTGGTTAATGTCAAGCTGCCTGAAGATTGAGCAGTTTATAAATTGGTTAATTTGTG | SEQ ID NO: 2748 | AGENCOURT_IC309688 NIH_MGC_71 Homo sapiens cDNA clone IMAGE:6501220 5', mRNA sequence [BU507302] |
| 40 | A_23_P94230 | LY96 | TGAAGCTATTTCTGGGAGCCCAAGAAGAAATGTCTTTTGCTTGGAGTTTGTGATCGTACA | SEQ ID NO: 2763 | Homo sapiens lymphocyte antigen 96 (LY96), mRNA [NM_015364] |
| 41 | A_24_P105648 | BX111927 | TTATGAGATGCTCAGTTGAGTTCAAATAACAGTGCAGTAATTCACCTATATGTAAAAGACTGCC | SEQ ID NO: 2778 | BX111927 Soares_multiple_sclerosis_2NbHMSP Homo sapiens cDNA clone IMAGp998G05619, mRNA sequence [BX111927] |
| 42 | A_24_P11045 | THC2785765 | CCACCAGAAACGTACACCTGATTTTCATGACAAATACGGTAGCAACAGAAGTCGGGAATAG | SEQ ID NO: 2781 | COX7B_HUMAN (P24311) Cytochrome c oxidase polypeptide VIIb, mitochondrial precursor partial (78%) [THC2785765] |
| 43 | A_24_P201702 | CLEC2B | ATTGGAATTCAAGTAATAACAACTGTTCCACTCAACATGCCGACCTAACTATAATTGACA | SEQ ID NO: 2815 | Homo sapiens C-type lectin domain family 2, member B (CLEC2B), mRNA [NM_005127] |
| 44 | A_24_P20996 | BC043173 | CTGGAAAATGTTCATATATATGTATATGAATGTGTCTTTATGGTGAAGGGCTCTGATTGG | SEQ ID NO: 2818 | Homo sapiens cDNA clone IMAGE:5287121. [BC043173] |
| 45 | A_24_P235429 | ABCA1 | GCAAAGAGCCATGTGTCATGTAATACTGAACCACTTGATATTGAGACATTAATTTGTAC | SEQ ID NO: 2823 | Homo sapiens ATP-binding cassette, sub-family A (ABC1), member 1 (ABCA1), mRNA [NM_005502] |
| 46 | A_24_P286054 | ZFYVE16 | GTGTATGTATTCTGCCATGTAAGTAATTGAACAGTCTAAAATAACCAAATGGTAGAAGGG | SEQ ID NO: 2842 | Zinc finger FYVE domain-containing protein 16 (Endofin) (Endosome-associated FYVE domain protein). [Source:Uniprot/SWISSPROT;Acc:Q7Z3T8] [ENST00000380248] |
| 47 | A_24_P320328 | SUB1 | CAGAAAACCTGTAAAGAACAAAAGACAGGTGAGACTTCGAGAGGCCTGTCTATCTTGTA | SEQ ID NO: 2857 | Homo sapiens SUB1 homolog (S. cerevisiae) (SUB1), mRNA [NM_006713] |
| 48 | A_24_P324581 | KIAA1466 | ATAATAGCTCATAGAATGAATTGCTGTACCAACCAAGGCTAAAAGAAATTTAAGTAGCCC | SEQ ID NO: 2861 | Homo sapiens mRNA for KIAA1466 protein, partial cds. [AB040899] |
| 49 | A_24_P387869 | PKN2 | TTGTCCAGAGATCATTTATATTTACGTTCGAAATTGTTTATTACCCAAGATCGTTTGGGAG | SEQ ID NO: 2885 | Homo sapiens protein kinase N2 (PKN2), mRNA [NM_006256] |
| 50 | A_24_P413669 | PFKFB2 | TCAAATGGTTCTTTTATACTGTGGATGATACAGGACTCTGTTACCTAAGATGTGATAAGC | SEQ ID NO: 2898 | Homo sapiens 6-phosphofructo-2-kinase/fructose-2,6-biphosphatase 2 (PFKFB2), transcript variant 2, mRNA [NM_001018053] |
| 51 | A_24_P450172 | AK095151 | TATGCCAGTGAATAAAGGTAGTTCTCTGGACAAGATGCTAACACATTTTACTATTAATCCTAGGGTAC | SEQ ID NO: 2902 | Homo sapiens cDNA FLJ37832 fis, clone BRSSN2009630. [AK095151] |
| 52 | A_24_P45620 | UTS2 | AGAAAGTTTCAGGATTTCTCTGGACAAGATGCTAACACATTTTACTGAGTCATCTTTTGGCC | SEQ ID NO: 2903 | Homo sapiens urotensin 2 (UTS2), transcript variant 1, mRNA [NM_021995] |
| 53 | A_24_P667201 | AK022997 | CTGACATGTGATAAATATTCAGTGAGTTTCAGATTTATTTCTTGTTAGGCGCTGTGTC | SEQ ID NO: 2932 | Homo sapiens cDNA FLJ12935 fis, clone N12RP2004992. [AK022997] |
| 54 | A_24_P890536 | CR627148 | AATTGCTTCTTGTAACCCTAAGTATGGTGAAGCAGAGAATTGAATTCTACAAAAGTCTTTC | SEQ ID NO: 2934 | Homo sapiens mRNA; cDNA DKFZp779F2127 (from clone DKFZp779F2127). [CR627148] |
| 55 | A_32_P153725 | KIAA1033 | TTTTGTAAAAGATGGCAAGTTTGTTACCTCAGTTGAGTCGGGTTTCGTTTTCCGCGAAT | SEQ ID NO: 2972 | Homo sapiens KIAA1033 (KIAA1033), mRNA [NM_015275] |
| 56 | A_32_P164203 | THC2683448 | TTGATGGTCATTGTACGAGCTATTGTATGGATTACGTCAGTTTACCACATGAT | SEQ ID NO: 2975 | Q7WZG3_PASPI (Q7WZG3) Ferric uptake regulator, partial (8%) [THC2683448] |

Fig. 8-4

| No. | Probe ID No. | Symbols of genes | Sequence | SEQ ID NO: | Descriptions of genes (letters and numbers within [ ] indicates GenBank accession No.) |
|---|---|---|---|---|---|
| 57 | A_32_P17504 | THC2693682 | ATGTGTATGCTGTGTTTGAGTATGCTGGAAATATTGCCAGGCTTTT CCCGTTGATGCCAAA | SEQ ID NO: 2982 | |
| 58 | A_32_P178966 | ENST00000379426 | GTAATATACAGAGGGTGAAGTCTTTACTGATACACAAGAGACAAACT GTTAAAAAGTGAATCC | SEQ ID NO: 2985 | Novel protein. [Source:Uniprot/SPTREMBL;Acc:Q5T4T1] [ENST00000379426] |
| 59 | A_32_P224666 | CAPZA2 | AATGCTGTTTGAGATTCTGAAATTAAATGAAAATAGTTATTTC AGAAATGCATTTAATG | SEQ ID NO: 2999 | Homo sapiens capping protein (actin filament) muscle Z-line, alpha 2 (CAPZA2), mRNA [NM_006136] |
| 60 | A_32_P226786 | BC045174 | TTATTGGTGCATGTAAGCCATTATCCGTGTCTTAATGAACGGATT AATGGTTGATTGTT | SEQ ID NO: 3001 | Homo sapiens cDNA clone IMAGE:5273245. [BC045174] |
| 61 | A_32_P2333 | SUB1 | AGGAAGAAAACGTATTCTTTAAATCCAGAACAATGGAGCCAGC TGACAGAACGATTTC | SEQ ID NO: 3003 | Homo sapiens SUB1 homolog (S. cerevisiae) (SUB1), mRNA [NM_006713] |

Fig. 21-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P341938 | NOG | GCCAGCGCCTGGGCCTGGAATTCCGATCGAGTAGCCCATCGATTTCC GAGTGCAAGTGCTGGT | SEQ ID NO: 3030 | Homo sapiens noggin (NOG), mRNA [NM_005450] |
| 2 | A_23_P359174 | BC069659 | CCAAGGGGTGCATACTAGGGTAAAGAAAAATTTGTGATAAGGAAC AGTGGTTTGGGATTTT | SEQ ID NO: 3031 | Homo sapiens cDNA clone IMAGE:7262526, with apparent retained intron. [BC069659] |
| 3 | A_24_P15797 | NUDT22 | CGCGGCGTCACATTCTCATTGGGGTGGATGCAAGACCACGGTCC ACCTGTCAGGAAAAAA | SEQ ID NO: 3032 | Homo sapiens cDNA FLJ34477 fis, clone HLUNG2003833. [AK091796] |
| 4 | A_24_P930391 | AK022351 | AAGTGGGTTTAATTTCTTTTCATGAAAGGAAAGATTAGCTTTC ATGCAAACACTTGGTC | SEQ ID NO: 3033 | Homo sapiens cDNA FLJ12289 fis, clone MAMMA1001788. [AK022351] |
| 5 | A_24_P931364 | AK022062 | TCCCATCGTGGAGTATGGTTTGGAAGTCATTGCTTTGTAGTAAG GCATTATTTCCTGGT | SEQ ID NO: 3034 | Homo sapiens cDNA FLJ12000 fis, clone HEMBB1001531. [AK022062] |
| 6 | A_32_P111394 | THC2643957 | GAATACAGTGTTCCTTTCATCCCATATTTGACTGAACGTAAGA CACATCAATTATAAGG | SEQ ID NO: 3035 | |
| 7 | A_32_P125589 | THC2649341 | CGCTCTATCCGTTGCTTTAGCCTTTTGAATGAAAGTGAGATGTC TCATCAGCTCAGATAG | SEQ ID NO: 3036 | |
| 8 | A_32_P142802 | THC2699446 | CGGCCGCAAGCACATCCGAAGAAAAGGGGTCAGGTATTCTAGGCG TACGGGGACTGATAAA | SEQ ID NO: 3037 | |
| 9 | A_32_P19561 | THC2728305 | AAGAAGGGACAGTTACAACAGTAATTGGGAAAAGCTTCTGAAGGA CAGATGTGCATTTCTC | SEQ ID NO: 3038 | |
| 10 | A_32_P209682 | THC2663167 | CAATGTAAAGCCAGAATATCAAGGTCGTTTGTCAAGATTTTGA AACGTATTTGGCTGGT | SEQ ID NO: 3039 | ALU1_HUMAN (P39188) Alu subfamily J sequence contamination warning entry, partial (5%) [THC2663167] |
| 11 | A_32_P226941 | THC2689491 | ACACCTACTACAGGCTCAGAACTACTATAGTTGAGTAAGCTTGGG ATGTGGAGTAGGCCCA | SEQ ID NO: 3040 | |
| 12 | A_32_P33304 | ANK3 | TGTTGGAATACCGGGGGGTGATCTGTCTTTTATAAACTCACCTGA TTTAAAGGAAAGATGA | SEQ ID NO: 3041 | Homo sapiens cDNA FLJ44903 fis, clone BRAMY3005184, highly similar to Mus musculus ankyrin 3, epithelial (Ank3). [AK126851] |
| 13 | A_32_P71171 | A_32_P71171 | TCTAGATAGTAATAGGAAAACCAAGAATCAAGCCTGGTGATGGCT GGAGGGAGTGATTGAA | SEQ ID NO: 3042 | |
| 14 | A_32_P98940 | T-HC2745859 | AAGAGTATTCCAAGATAGGCAAAGGTGTTGTTTTTAGCAGGT GTATTTCAGCTAGTTA | SEQ ID NO: 3043 | |
| 15 | A_23_P41664 | ENST00000334994 | TGGCTTGGAAGCAGATTCGAGTTGATAAACAAATTGTTCCTGAAA ATGAGGCACAGGTCAT | SEQ ID NO: 3044 | Synleurin (QGLQ1891). [Source:Uniprot/SPTREMBL;Acc:Q7Z2O7] ENST00000334994 |
| 16 | A_23_P65768 | C15orf15 | TCCTGCATTGCCATCTACATAATATCAGATATTACGGATGTTAG ATTGCATCGTCAGTGTT | SEQ ID NO: 3045 | Homo sapiens chromosome 15 open reading frame 15 (C15orf15), mRNA [NM_016304] |
| 17 | A_23_P70007 | HMMR | ACTATTTCTTCAGAGTTGTTGTCATATACTGGTTGTCATCTGCATG TGTACTCAGCATTTGA | SEQ ID NO: 3046 | Homo sapiens hyaluronan-mediated motility receptor (RHAMM) (HMMR), transcript variant 1, mRNA [NM_012484] |
| 18 | A_23_P70326 | CENPQ | GAATGGCTTACAGTTTCTGTCTGGTCATCTGAACTTGAAAAAT CCTGAAATGGCTTCAC | SEQ ID NO: 3047 | Homo sapiens centromere protein Q (CENPQ), mRNA [NM_018131] |

Fig. 21-2

| No. | Probe ID No. | Symbols of genes | Sequence | SEQ ID NO: | Descriptions of genes (letters and numbers within [ ] indicates GenBank accession No.) |
|---|---|---|---|---|---|
| 19 | A_23_P78092 | EVI2A | GCTGAATCAGAGACACTTGGAAAGAAGAACAAACAAGGTCACAGGACC CAACGTAGTGATGCAA | SEQ ID NO: 3048 | Homo sapiens ecotropic viral integration site 2A (EVI2A), transcript variant 1, mRNA [NM_001003927] |
| 20 | A_24_P11045 | THC2785765 | CCACCAGAAACGTACAGACCTGATTTTCATGACAAATACGGTAGGCA ACACAAGTCGGAAATAG | SEQ ID NO: 3049 | COX7B_HUMAN (P24311) Cytochrome c oxidase polypeptide VIIb, mitochondrial precursor partial (78%) [THC2785765] |
| 21 | A_24_P126741 | ENST00000309178 | AGGGTCGAACGACGAGTAAGAAGAGTTCAAGATTACTTGCAAGAGC TCACAGGAGCGGAGAAT | SEQ ID NO: 3050 | |
| 22 | A_24_P169378 | RPS7 | AACTGAAATCTTTCCAGAAATCCAAATCGGGCTAGTAAGTGAA TTGGAGAAAAGTTCA | SEQ ID NO: 3051 | Homo sapiens ribosomal protein S7 (RPS7), mRNA [NM_001011] |
| 23 | A_24_P201702 | CLEC2B | ATTGGAATCAAGTAAATACAACTGTTCCACTCAACATGCGGAG CTAACTATAATTGACA | SEQ ID NO: 3052 | Homo sapiens C-type lectin domain family 2, member B (CLEC2B), mRNA [NM_005127] |
| 24 | A_24_P276583 | TMCO1 | CCTTCATTTCCGTGTATATTCTCGTACTATGTCGATTCGGACAG AAGATTCAGAAGAATTC | SEQ ID NO: 3053 | Homo sapiens transmembrane and coiled-coil domains 1 (TMCO1), mRNA [NM_019026] |
| 25 | A_24_P333112 | A_24_P333112 | GGTCATGAGAATCAGAGAGGTATCAATGTGTGAGCCAACAGGACCA AAAGGTATTCGAACTT | SEQ ID NO: 3054 | |

Fig. 24-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P100263 | CMIP | CCCCCGCGGAATTCTTTTAGGTTCGTAATTGGAACCTTTGACCT GATCTAAAGTGGACTT | SEQ ID NO: 3055 | Homo sapiens c-Maf-inducing protein (CMIP), transcript variant C-mip, mRNA [NM_198390] |
| 2 | A_23_P103561 | NAV1 | TCGTCCCGCAAGAGATCTGCCTGGAGCCCAGAAAAACAAGACATGT GGTTTAAAAAATGTTT | SEQ ID NO: 3056 | Homo sapiens neuron navigator 1 (NAV1), mRNA [NM_020443] |
| 3 | A_23_P106122 | RP5-860F19.3 | CAAGCCGCCCCCCAGGTGGCGTCAGTTGCTCTCGCTAAGGTTT GGAGAAACAGAACAA | SEQ ID NO: 3057 | Homo sapiens KIAA1442 protein, mRNA (cDNA clone IMAGE:5502800), complete cds. [BC054347] |
| 4 | A_23_P115161 | DARC | TCCCCCTCAACTGAGAAGTCAAGTCAGCTGGACTTCGAAGATGT ATGAATTGTTCCTAT | SEQ ID NO: 3058 | Homo sapiens Duffy blood group, chemokine receptor (DARC), mRNA [NM_002036] |
| 5 | A_23_P117694 | CORO2B | ATTAGTAGGATCTACTAGATGCATTATACTGCATACGTGGTTT TCCCATGGCCGGCCCTA | SEQ ID NO: 3059 | Homo sapiens coronin, actin binding protein, 2B (CORO2B), mRNA [NM_006091] |
| 6 | A_23_P119143 | ICAM5 | GACGCCCCACAGCTCACACGGGGGCTTATTTATTGGTTTATT ATTTACTTATTCATTT | SEQ ID NO: 3060 | Homo sapiens intercellular adhesion molecule 5, telencephalin (ICAM5), mRNA [NM_003259] |
| 7 | A_23_P142187 | HIF3A | ACCCCCAGCTTTCTTTCTACAGAGATGGTGCTAGTCTTGGTCTCC CACAGGAAAAGGCCTC | SEQ ID NO: 3061 | Homo sapiens hypoxia inducible factor 3, alpha subunit (HIF3A), transcript variant 2, mRNA [NM_022462] |
| 8 | A_23_P144796 | PDLIM4 | TGGTCCCAGGCCTGCTTCTTAAGGTCCCTCGTCGGCCAGGTGTAA ATATGTTTCACCCTGT | SEQ ID NO: 3062 | Homo sapiens PDZ and LIM domain 4 (PDLIM4), mRNA [NM_003687] |
| 9 | A_23_P145681 | ACTL6B | CCCCCCAAACTGGAAGAGAAGAAGGAGAAGCTACCCCAGGTCTCCA AGTCGTGGGCATAAGTA | SEQ ID NO: 3063 | Homo sapiens actin-like 6B (ACTL6B), mRNA [NM_016188] |
| 10 | A_23_P150407 | CREB3L1 | TGGCTGCTGGGTGGCC ATATGTTTCACCCTGT TTATATTTATGAAGTTAGTGCGGGCT | SEQ ID NO: 3064 | Homo sapiens cAMP responsive element binding protein 3-like 1 (CREB3L1), mRNA [NM_052854] |
| 11 | A_23_P164258 | PIPOX | TGAATCCCCACATAAAGACCAGATGATTGAGTCGTACGTCTTCC TTGGGCGGCTCCGTT | SEQ ID NO: 3065 | Homo sapiens pipecolic acid oxidase (PIPOX), mRNA [NM_016518] |
| 12 | A_23_P164927 | SYNGR4 | CAAAGTCCCCCGGGCTGCTATGATGGCCTGAGAACTAAATATCC TTATCAAATCAATAA | SEQ ID NO: 3066 | Homo sapiens synaptogyrin 4 (SYNGR4), mRNA [NM_012451] |
| 13 | A_23_P18119 | IMPG2 | CGTGATCATAGGACATCACTATTGCCTCCGGTGGTTGGAGTCTTG TCATGTTTTCTGCTAT | SEQ ID NO: 3067 | Homo sapiens interphotoreceptor matrix proteoglycan 2 (IMPG2), mRNA [NM_016247] |
| 14 | A_23_P204144 | KRT85 | CTCGGCTGGGCCTTTTCATGCTAGGGAGAGTGCATCCTAGTTGTC GTCCTGGCAGCTGTT | SEQ ID NO: 3068 | Homo sapiens keratin 85 (KRT85), mRNA [NM_002283] |
| 15 | A_23_P204998 | FARP1 | TCCTCCTGCAACTGCAAGTGGGTTTGAAACTGCGCATTCTCTAGTAGTA TATATGTGCCTGTGT | SEQ ID NO: 3069 | Homo sapiens FERM, RhoGEF (ARHGEF) and pleckstrin domain protein 1 (chondrocyte-derived) (FARP1), transcript variant 1, mRNA [NM_005766] |
| 16 | A_23_P208482 | CLEC4M | CCAACCCACACATCTTCTTGTCCGTATACATGTCTTCGCATTTGG CTGTTTCTGAGTTGTA | SEQ ID NO: 3070 | Homo sapiens C-type lectin domain family 4, member M (CLEC4M), transcript variant 4, mRNA [NM_214677] |
| 17 | A_23_P209389 | CASP8 | GCCCAGCCACCAACCACCTGGGCTAATTTTTTAAAAATATTTTAGTA GAGACAGGGTTTCACT | SEQ ID NO: 3071 | Homo sapiens caspase 8, apoptosis-related cysteine peptidase (CASP8), transcript variant C, mRNA [NM_033356] |
| 18 | A_23_P21495 | FCGBP | TCAGTCATCCACCAGGAACGAAGAATTCCTGAAGAAGACCTGGT CCGTGTGGAGGTTGCG | SEQ ID NO: 3072 | Homo sapiens Fc fragment of IgG binding protein (FCGBP), mRNA [NM_003890] |
| 19 | A_23_P268381 | SPSB4 | CCAACCCACTGCCGCCACCCTTAATGTGAATTGACTGATGAATG AAGAGGGTTTCTAATA | SEQ ID NO: 3073 | Homo sapiens splA/ryanodine receptor domain and SOCS box containing 4 (SPSB4), mRNA [NM_080862] |

Fig. 24-2

| No. | Probe ID No. | Symbols of genes | Sequence | SEQ ID NO: | Descriptions of genes (aliases and numbers within [ ] indicates GenBank accession No.) |
|---|---|---|---|---|---|
| 20 | A_23_P29079 | PFKL | CGACCAGCGCTACGTCTTCGAGGAGGACCGTTTCGAAGATCCGACGACT TAAAGGTCAAGCTGGA | SEQ ID NO: 3074 | Homo sapiens phosphofructokinase, liver (PFKL), transcript variant 1, mRNA [NM_001002021] |
| 21 | A_23_P326212 | ETS1 | GTCAACGCAGCCTATCCAGAAGATCCGGCTATACGCTCGGATTACTT CATTAGGTATGGTATT | SEQ ID NO: 3075 | Homo sapiens v-ets erythroblastosis virus E26 oncogene homolog 1 (avian) (ETS1), mRNA [NM_005238] |
| 22 | A_23_P341938 | NOG | GGCAACGGCTGGGGCTGGATTCCCATCCAGTAGCCCATCATTTCG GAGTGCAAGTGCTCGT | SEQ ID NO: 3076 | Homo sapiens noggin (NOG), mRNA [NM_005450] |
| 23 | A_23_P344531 | SYNPO | TCCTGCTGCTGTGAAGATGAGAAGGTGCTCTTACTCAGTTAATG ATGAGTGACTATATTT | SEQ ID NO: 3077 | Synaptopodin. [Source:Uniprot/SWISSPROT:Acc:Q8N3Y7] [ENST00000307662] |
| 24 | A_23_P34554 | CACNA1E | CCCCCCTCCGATGCATGCTCTTCTCTGCACATGGAGAAAACCAAG ACAGAATTGGGAAGCC | SEQ ID NO: 3078 | Homo sapiens calcium channel, voltage-dependent, R type, alpha 1E subunit (CACNA1E), mRNA [NM_000721] |
| 25 | A_23_P358370 | FOXE1 | CCCCGGGCTACGACCAAGGGCTACGAACCAGCAGGCTTCACCCG GGACCCGTCGGGCCAA | SEQ ID NO: 3079 | H. sapiens HFKH4 mRNA for fork head like protein. [X94553] |
| 26 | A_23_P372144 | C19orf29 | CCCCGGCTCATCTGGAAATAGTTCGGTTGTTCTCTAAAAGA CTTGTAGGTGGGAAAA | SEQ ID NO: 3080 | Homo sapiens chromosome 19 open reading frame 29 (C19orf29), transcript variant 2, mRNA [NM_021231] |
| 27 | A_23_P38265 | LYPD3 | TCCCGTAGTCCCGGCATCTTTGGGGAATCGGTTCCCGATATGTC TTCCTTACTAGAGTGT | SEQ ID NO: 3081 | Homo sapiens LY6/PLAUR domain containing 3 (LYPD3), mRNA [NM_014400] |
| 28 | A_23_P398774 | PLD1 | AGTCTTCCTGGGAATCAATTTTGATTTGGGTGTTGATCTG ATACAGTCTCCCAA | SEQ ID NO: 3082 | Homo sapiens cDNA FLJ34578 fis, clone KIDNE2008404, highly similar to PHOSPHOLIPASE D1 (EC 3.1.4.4). [AK091897] |
| 29 | A_23_P40334 | NPBWR2 | CCTCCCCACGATGGGTGCGAAGGTGTCTCAGGAGACAATGGCACTG GGCACAATGCCACCTT | SEQ ID NO: 3083 | Homo sapiens neuropeptides B/W receptor 2 (NPBWR2), mRNA [NM_005286] |
| 30 | A_23_P407801 | C6orf6 | GTCTCCTAGGTTAGTGTAGGACGAGATTCTATTCTCAGATAAGAC TTCGGTGTGGGCTGAA | SEQ ID NO: 3084 | Homo sapiens mRNA for hypothetical protein (C8orf6 gene). [AJ307469] |
| 31 | A_23_P49310 | ERN2 | CCCACCCCTCTCTTTTTGGAGGACAGCCAAGCAACTCCAGTTCTTC CAGGACGTCAGTGAGT | SEQ ID NO: 3085 | Homo sapiens endoplasmic reticulum to nucleus signalling 2 (ERN2), mRNA [NM_033266] |
| 32 | A_23_P50349 | TRIP10 | CGGAGTTTGATGAGGATTTCGAAGGAGGAGGAAGCGACATCCCCATA GGTCACTGTGTGGCCA | SEQ ID NO: 3086 | Homo sapiens thyroid hormone receptor interactor 10 (TRIP10), mRNA [NM_004240] |
| 33 | A_23_P74668 | C1orf158 | GGTACGTGTCGGCCCTCAAAACCCACAGGTTCCTTCTTTCTTTCCA TCCAACAATTAAAGAT | SEQ ID NO: 3087 | Homo sapiens chromosome 1 open reading frame 158 (C1orf158), mRNA [NM_152290] |
| 34 | A_23_P75867 | OR10A4 | AGTCCTATGTACTTCTTCCTCGAGAAACTTGTCCTTCCTGGAGAT AGGTTTCAAGTTGGTC | SEQ ID NO: 3088 | Homo sapiens olfactory receptor, family 10, subfamily A, member 4 (OR10A4), mRNA [NM_207186] |
| 35 | A_23_P84399 | CNTNAP2 | CTTGAGACATCCTTAAAATATCACCACAAGTTGGGGGAGGGCAG GCAATGGAATATAATG | SEQ ID NO: 3089 | Homo sapiens contactin associated protein-like 2 (CNTNAP2), mRNA [NM_014141] |
| 36 | A_23_P87310 | LMO1 | CCCTCCTGGGGCCAGGCGGGCCTGTACAGATCTGTCTTCTGTAT ATACATGGGAAGATTT | SEQ ID NO: 3090 | Homo sapiens LIM domain only 1 (rhombotin 1) (LMO1), mRNA [NM_002315] |
| 37 | A_24_P102895 | WDTC1 | CTTCCCAGCCCTGTCTTCTAGGTTGGTAATGAAGTATATTTATT GGTGAAGGAAACAGCT | SEQ ID NO: 3091 | Homo sapiens WD and tetratricopeptide repeats 1 (WDTC1), mRNA [NM_015023] |
| 38 | A_24_P108517 | CRB3 | TGGCAACCTGCGTCCGGAAGCCATCACTGCTCTATCATCGTGTCT TCTCCCTCTTGGGTGC | SEQ ID NO: 3092 | Homo sapiens crumbs homolog 3 (Drosophila) (CRB3), transcript variant 3, mRNA [NM_174881] |

Fig. 24-3

| No. | Probe ID No. | Symbols of genes | Sequence | SEQ ID NO: | Descriptions of genes (letters and numbers within [ ] indicates GenBank accession No.) |
|---|---|---|---|---|---|
| 39 | A_24_P117368 | AK055306 | GTGCCTGGGTCGCATTCAAACTCGAGCAGGGGGGGTTGGATCAG GCAGGTTTATTCGAAA | SEQ ID NO: 3093 | Homo sapiens cDNA FLJ30744 fis, clone FEBRA2000378. [AK055306] |
| 40 | A_24_P129107 | NKD2 | CCCCCACCCGCACCCTACGGCCACAAGCGGTACCGCGCAAAAGGG CAGGGAGGGCCACTCG | SEQ ID NO: 3094 | Homo sapiens naked cuticle homolog 2 (Drosophila) (NKD2), mRNA [NM_033120] |
| 41 | A_24_P150428 | FAM124A | CGTCCGTGGCCTCGTCAGCTGAAACACACAGTGGTTTCAAACACA GGTGCCCCAGGGGACA | SEQ ID NO: 3095 | Homo sapiens family with sequence similarity 124A (FAM124A), mRNA [NM_145019] |
| 42 | A_24_P15182 | LOC646960 | GCCAGGACCCTGCCGGAACCGGCCTGCGGCCATCGCGGGCTGG GGGCGGCTCTTCGGAAG | SEQ ID NO: 3096 | PREDICTED: Homo sapiens similar to transmembrane protease, serine 9 (LOC646960), mRNA [XM_929928] |
| 43 | A_24_P15797 | NUDT22 | CCGGCGCTCACATTCATTGGCGTGGATGCCAAGACACAGTCC ACCTGTCAGGAAAAAA | SEQ ID NO: 3097 | Homo sapiens cDNA FLJ34477 fis, clone HLUNG2003833. [AK091796] |
| 44 | A_24_P161144 | MGC46336 | CCTCCGTCGACAGAGACCCGGCTCAGGACGCGCTTTCTGTATGGC AGATCTTTCTCAGAAG | SEQ ID NO: 3098 | Homo sapiens hypothetical protein MGC46336, mRNA (cDNA clone MGC:46336 IMAGE:5589928), complete cds. [BC036762] |
| 45 | A_24_P161681 | LOC729956 | TCTCGGATCGTGCCCGGTCCTACGAGGGCTGCGGTGAAATCCGAG CTGAACCGCTACTCTT | SEQ ID NO: 3099 | PREDICTED: Homo sapiens hypothetical protein LOC729956 (LOC729956), mRNA [XM_001131873] |
| 46 | A_24_P166434 | PSORS1C2 | CCTACCCGGCCCCAGTCGTCCCTGGAGAGACCTGCCTGAAACTGG AGTGTGGCCCCTGAA | SEQ ID NO: 3100 | Homo sapiens psoriasis susceptibility 1 candidate 2 (PSORS1C2), mRNA [NM_014069] |
| 47 | A_24_P178877 | LOC339809 | TGCGCCCACCCCGCCAGCATGGCTTGGAAGAGTGAAAGGCATAGAG GGATTCTTTTGCTGCA | SEQ ID NO: 3101 | Homo sapiens mRNA for KIAA2012 protein. [AB095932] |
| 48 | A_24_P20795 | IRX4 | CCCTTCCGCACTCGCGCGCCCTGGACAGGACCACCACTCCCCG GTAAGCAGTCTGTCAGAA | SEQ ID NO: 3102 | Homo sapiens iroquois homeobox protein 4 (IRX4), mRNA [NM_016358] |
| 49 | A_24_P209339 | MLXIPL | CCAGCCCGCTTCCCATAGAGCTTCTACCCTTGGGGTATTGGGAG CCTGGCTTTGGGCCTT | SEQ ID NO: 3103 | Homo sapiens MLX interacting protein-like (MLXIPL), transcript variant 4, mRNA [NM_032954] |
| 50 | A_24_P218074 | ZNF467 | GGATGCCCCGGCGGCCAAAGCGCCTGGCCAGCGCGCTGGCGGAC CAGGCTGCGGGCCAGG | SEQ ID NO: 3104 | Homo sapiens zinc finger protein 467 (ZNF467), mRNA [NM_207336] |
| 51 | A_24_P252223 | C6orf85 | ACACCCTCGTTCCGCTACCTAGCCTCGTCCAGGCTTTCAATAA AAGTTATGCAGAAATG | SEQ ID NO: 3105 | Homo sapiens chromosome 6 open reading frame 85 (C6orf85), mRNA [NM_021945] |
| 52 | A_24_P254133 | APC2 | TGTGCCCAGGGCCATGGTCGTCGGCAGCCACCACCGAGTCCGGCCG CGGAGAAAGCCGCGGC | SEQ ID NO: 3106 | Homo sapiens adenomatosis polyposis coli 2 (APC2), mRNA [NM_005883] |
| 53 | A_24_P272845 | DOCK3 | GCCGGCATTCATGACTGTCGTCGTCTCCAGTGCCTCACATGCGTCAGTGAA GCAGGAAACAACTGGTGA | SEQ ID NO: 3107 | Homo sapiens dedicator of cytokinesis 3 (DOCK3), mRNA [NM_004947] |
| 54 | A_24_P280497 | KIAA1545 | CATCCCCGGCTCCCGGCAGAGGAAGCGCGGGCCCTGGAGAGACGGTGAAGGTC AAGGAGGAGGCGCGG | SEQ ID NO: 3108 | Homo sapiens XTP9 (XTP9) mRNA, complete cds. [AF490258] |
| 55 | A_24_P306034 | ANKDD1A | CTCTCTCCCGGTTGTACTCATCAATTCTGCCAGTAAAATTCTC CTCTATGACCTGAAA | SEQ ID NO: 3109 | Homo sapiens cDNA FLJ25870 fis, clone CBR02141. [AK098736] |
| 56 | A_24_P315066 | ZMIZ2 | CACGCGGACCTCCTACGAACAACATGACGACCTGGTTTCTCTG TTTGAGACAACTGAT | SEQ ID NO: 3110 | Homo sapiens zinc finger, MIZ-type containing 2 (ZMIZ2), transcript variant 1, mRNA [NM_031449] |
| 57 | A_24_P316454 | BC022826 | AGAACACAGAGGGCGGGCCCCACCGAATCAAGGTCATTGGTCTT CAAGATAAAGTGCCTA | SEQ ID NO: 3111 | Homo sapiens cDNA clone IMAGE:5441030, partial cds. [BC022826] |
| 58 | A_24_P331711 | THEM5 | TATCACGGCTCGTCCCACACCACCCTGGCTTCATCATGAGTGC AGTGTCATGTCAGCGG | SEQ ID NO: 3112 | Homo sapiens thioesterase superfamily member 5 (THEM5), mRNA [NM_182578] |
| 59 | A_24_P345637 | MSX1 | ACCGCGCGGCCAAGGCAAAGAGACTACAAGAGGCAGAATGGGAG AAGGTCGAAGATGGCGCG | SEQ ID NO: 3113 | Homo sapiens msh homeobox 1 (MSX1), mRNA [NM_002448] |

Fig. 24-4

| No. | Probe ID No. | Symbols of genes | Sequence | SEQ ID NO: | Descriptions of genes (letters and numbers within [ ] indicate GenBank accession No.) |
|---|---|---|---|---|---|
| 60 | A_24_P348885 | CYB561D1 | CCTCCCTGCTCTCAAACTCTCCAGTGTGGTGTGAAACTCAGAAGAAACGGTTACTGGGGCT | SEQ ID NO: 3114 | Homo sapiens cytochrome b-561 domain containing 1 (CYB561D1), mRNA [NM_182580] |
| 61 | A_24_P349274 | OR4X2 | GGAGGGCTTGATGCATTCCTTTGCACAAATCCTTCTCCATCTTCCACCTGCTCTTCTGTGG | SEQ ID NO: 3115 | Homo sapiens olfactory receptor, family 4, subfamily X, member 2 (OR4X2), mRNA [NM_001004727] |
| 62 | A_24_P366122 | ACBD4 | TACCGCCCCTCCTATGAAGAGATGCTGGGATTCCTACAGTTACTACAAGCAGGGCACCATG | SEQ ID NO: 3116 | Homo sapiens acyl-Coenzyme A binding domain containing 4 (ACBD4), mRNA [NM_024722] |
| 63 | A_24_P385012 | BC030084 | TCCCCCCTCATGTGTTGGGTCAAATACTGCTTTATCCTTTAGTACTAAAATTAAAAGTTAC | SEQ ID NO: 3117 | Homo sapiens cDNA clone IMAGE:4791887. [BC030084] |
| 64 | A_24_P39484 | AK025430 | CGGAGCTCGGGCACCGGTCACGGAGTCGCGGGCGGCGGCGGCGACCGGACACGGGCCAAATGCCGGG | SEQ ID NO: 3118 | Homo sapiens cDNA: FLJ21777 fis, clone HEP00173. [AK025430] |
| 65 | A_24_P401270 | LOC649294 | TCCTCTCCTCCAGCTCTCCCCACATGAAATAATTCTGATAACGACACATGGAGTTTG | SEQ ID NO: 3119 | Homo sapiens cDNA FLJ33940 fis, clone CTONG2018069. [AK091259] |
| 66 | A_24_P401294 | FLJ35934 | CCCAGCCCCTTCTCGCGCGTCTCCAACTGCCTTTCACCTAGAAGCGCTCAGCAGCGTGCGCC | SEQ ID NO: 3120 | Homo sapiens cDNA FLJ35934 fis, clone TEST12011315. [AK093253] |
| 67 | A_24_P405892 | SYNPO | CCTCCCCAGCCAAGCCCAGGCTCCGTTGGACCTGGTGCCAACCTGCCCAAGGGGGCTCCCC | SEQ ID NO: 3121 | Homo sapiens synaptopodin (SYNPO), mRNA [NM_007286] |
| 68 | A_24_P419028 | MCP-1 | ACCCCCTCACTTTTCAGACCTATAGTTGTCCTTTTGATTCTCCAGTTAAAACTACAA | SEQ ID NO: 3122 | Homo sapiens mRNA for MCP-1, complete cds. [AB014711] |
| 69 | A_24_P478362 | NP511100 | ATCGACCCCGGCCCGGAAGAGAACCACTGCGATGCGGGGGCTCAACGCCAGGCAGGCAATCCTAG | SEQ ID NO: 3123 | GB_AB065467.1 [BAC35726.1 seven transmembrane helix receptor [Homo sapiens]. [NP511100] |
| 70 | A_24_P542291 | LOC339352 | CACTTCCGCGGCCTCCGACTACTTCTCAGAGAGAGGAGGCGCCGGGAACCTGCAAGCGC | SEQ ID NO: 3124 | PREDICTED: Homo sapiens similar to ATP binding domain 3 (LOC339352), mRNA [XR_017668] |
| 71 | A_24_P662177 | THC2666469 | GGGGAGGTAGGATTTGAATTGCATGTTACATAACCATCGTCTAAAGGGACAGAATGTACA | SEQ ID NO: 3125 | |
| 72 | A_24_P689119 | A_24_P689119 | CCGCCTCCCCACAACACCCAAAGACACCAGAACCCAGGTCCTCCACTGCATCCCGGACGCCTC | SEQ ID NO: 3126 | |
| 73 | A_24_P752279 | A_24_P752279 | GCCCCACCCTCTCGAGACAGGCACCAGGCTGTGGTGACCGGCTCTCAGCAGTCCTCCT | SEQ ID NO: 3127 | |
| 74 | A_24_P778928 | A_24_P778928 | TCCAGGCCGGCGCACCTGCCATCGGCAAGAGCCGGCTCAGACAAAGACCCCGC | SEQ ID NO: 3128 | |
| 75 | A_24_P828125 | A_24_P828125 | CAGTCCCACCCGCACCAGCAGCAGCAAAGTCAGCGCCAGGATTGACACCCAGCAGTGGGGGC | SEQ ID NO: 3129 | |
| 76 | A_24_P848662 | CR594528 | CTGCGCTGCCGCGACGCACGACGCCATCGTCAAGAAATGAGGACTGAGGACTGCGCAGCAGGCGGC | SEQ ID NO: 3130 | full-length cDNA clone CS0DM002YC17 of Fetal liver of Homo sapiens (human). [CR594528] |
| 77 | A_24_P916317 | FOXC1 | CAGAAGCCCGGACAAGAAGATCAGCGCTGAATGGGATTTACCAGTTCATCATGGAGCGGC | SEQ ID NO: 3131 | Homo sapiens FOXC4a mRNA, partial cds. [AF343007] |
| 78 | A_24_P929524 | THC2534212 | TCCTGGACCTATTATGGCCTCCATCTCTTCCTGGGGAAGGTCGAGGTTGGCTGGCTCTCA | SEQ ID NO: 3132 | 060448_HUMAN (060448) Neuronal thread protein AD7c-NTP, partial (15%) [THC2534212] |
| 79 | A_24_P930963 | LOC650392 | GCCCCATTTGAAGTATAACCAGGAGGGGAAAATGGTCCTTGAAATAAGGACATGCCAGAAGG | SEQ ID NO: 3133 | Homo sapiens cDNA clone IMAGE:5264670. [BC036550] |
| 80 | A_32_P101073 | A_32_P101073 | GCCCGGCCCGACGTGCGCGACACCTGGTACGACGGGGACGTCACCGAGGTGGAGGAGCCC | SEQ ID NO: 3134 | |

Fig. 24-5

| No. | Probe ID No. | Symbols of genes | Sequence | SEQ ID NO: | Descriptions of genes (letters and numbers within [ ] indicates GenBank accession No.) |
|---|---|---|---|---|---|
| 81 | A_32_P125589 | THC2649341 | CGCTCTATCCCTTGCTTTAGGCTTTTGAATGAAAGTGAGATGTCTCATCAGCTCAGATAG | SEQ ID NO: 3135 | |
| 82 | A_32_P132356 | THC2635710 | GTGTTTTTCCCCCTCCAGAATCTAAGACGCGATAGGGTTTCTCCAAATAAACGGGCAAT | SEQ ID NO: 3136 | |
| 83 | A_32_P136622 | BC020341 | CCCAGCCCGAAGAGGTGCTCGACCTTCAGATACTGGGCAGCCCTCTGCACGCTCCAGCCG | SEQ ID NO: 3137 | Homo sapiens cDNA clone IMAGE:4177218, [BC020341] |
| 84 | A_32_P142802 | THC2699446 | CCGCCGCAACCACATCCGAAGAAAGGGGTCAGGTATTCTAGGCGTACGGGGACTGATAAA | SEQ ID NO: 3138 | |
| 85 | A_32_P145784 | BC043547 | GGTCCCGTCCCTCTCTGTAACCAATAACCAATGCCATATAATGGAAAAGTATAAGCAA | SEQ ID NO: 3139 | Homo sapiens, clone IMAGE:5171873, mRNA. [BC043547] |
| 86 | A_32_P156776 | THC2503530 | CCCCCCTTTTTTCCTTAAGCATAATTGTCTTAGGTTTGCCTAGTTTGATTTTAAGAA | SEQ ID NO: 3140 | AA360388 EST169518 T-cell lymphoma Homo sapiens cDNA 5' end similar to EST containing Alu repeat, mRNA sequence [AA360388] |
| 87 | A_32_P16662 | THC2567600 | TGGGTGGTCTGGGCTAAATGATCAAGTGAAACAGAAAGCCAGGAAGGATCTGTGCTAATT | SEQ ID NO: 3141 | F10881 HSC3LC012 normalized infant brain cDNA Homo sapiens cDNA clone c-3lc01 3', mRNA sequence [F10881] |
| 88 | A_32_P172002 | A_32_P172002 | GGGACCGAGGTCTCTCTCTCTCTCTTTCATTCATTTATTCAAAACTATGCATCCAGGGC | SEQ ID NO: 3142 | |
| 89 | A_32_P199506 | BU191598 | GATCCTCTGAGGTTTTGCAGGAAGACCCCGGCCTAATCTCTGAAGGTCGGAGGTCACAG | SEQ ID NO: 3143 | AGENCOURT_8099541 NIH_MGC_102 Homo sapiens cDNA clone IMAGE:6254414 5', mRNA sequence [BU191598] |
| 90 | A_32_P213509 | THC2663555 | GATTGTTCAGTGTTGGAGGGGTTTTTAATGAAAATTCAACACCTACACTGGAAAA | SEQ ID NO: 3144 | |
| 91 | A_32_P29130 | BG058000 | CCCAGCCAACGGTGTTTGTTAAGGAACTAAAACATTACATCTGGTGAACAGCAAAGATTTCA | SEQ ID NO: 3145 | BG058000 7f78d09.x1 Lupski_dorsal_root_ganglion Homo sapiens cDNA clone IMAGE:3303208 3', mRNA sequence [BG058000] |
| 92 | A_32_P34325 | RIMBP2 | ACGGAGAGCGTGCACCCCAATCAAAGCCATTAGCAGCAAGTTCTGGAGTCCCCGAAACCAAAG | SEQ ID NO: 3146 | Homo sapiens RIMS binding protein 2 (RIMBP2), mRNA [NM_015347] |
| 93 | A_32_P37943 | A_32_P37943 | CCGCCGCGGACCCCCGTCTGGCAGTCCCCAGCCGCGTGGGGCTCGGCTGTGGGGCGGGGTC | SEQ ID NO: 3147 | |
| 94 | A_32_P4466 | FLJ32214 | AACCCCCCTGTGGCAAACCTCTACACTTGGATTAATAACATCCAACATAGCGGAATG | SEQ ID NO: 3148 | Homo sapiens FLJ32214 protein, mRNA (cDNA clone IMAGE:40024597), complete cds. [BC104018] |
| 95 | A_32_P74615 | SP5 | GCCCCCGCATCCCAGCTTGGGGCTGACGCCGGAGAGAGAGCCACCTGCAGCCGTCGTTCGG | SEQ ID NO: 3149 | Homo sapiens Sp5 transcription factor (SP5), mRNA [NM_001003845] |
| 96 | A_32_P76566 | THC2608192 | CTTCCCGTGTGCGGCGCGCCGCTGTACTGTCTTCACACTCGCCATCACGTTGCACACGGTGC | SEQ ID NO: 3150 | Q7XQ69_ORYSA (Q7XQ69) Expressed protein, partial (6%) [THC2689192] |
| 97 | A_32_P79103 | BM932034 | GTGCTACAGAATGAAAATAGCATTTTAGGAAGGTTGAGTCAGAGGTGCGAGTGGGGCATA | SEQ ID NO: 3151 | UI-E-EJ1-aji-k-24-0-UI.r1 UI-E-EJ1 Homo sapiens cDNA clone UI-E-EJ1-aji-k-24-0-UI 5', mRNA sequence [BM932034] |
| 98 | A_32_P82111 | LRFN2 | ATGGGGACTGAGCCGCTGAGTGTTTGGAAAGGCAGAGGACTCCGCCTTTCTAATCACAAATG | SEQ ID NO: 3152 | Homo sapiens leucine rich repeat and fibronectin type III domain containing 2 (LRFN2), mRNA [NM_020737] |

Fig. 24-6

| No. | Probe ID No. | Symbols of genes | Sequence | SEQ ID NO: | Descriptions of genes (letters and numbers within [ ] indicates GenBank accession No.) |
|---|---|---|---|---|---|
| 99 | A_23_P102235 | SNRPG | ACAACAGAACAATATTGGAATGTGGTAATACGAGGGAAATAGTATCATCATGTTAGAAGC | SEQ ID NO: 3153 | Homo sapiens small nuclear ribonucleoprotein polypeptide G (SNRPG), mRNA [NM_003096] |
| 100 | A_23_P108394 | THC2783023 | ATTCAGAAAGTTGCTGTGTGTGATAGATAGTAAGTCTGTTGATTTATTAGTTGGTTGTGTG | SEQ ID NO: 3154 | Q8IUM9_HUMAN (Q8IUM9) ACSL3 protein, complete [THC2467888] |
| 101 | A_23_P110362 | MAP2K1IP1 | ACTGAGACAAGTTGTGGAAGTTCTTAATCTGACAGTGGTTCAGTGTGTACCTTATCTT | SEQ ID NO: 3155 | Homo sapiens mitogen-activated protein kinase kinase 1 interacting protein 1 (MAP2K1IP1), mRNA [NM_021970] |
| 102 | A_23_P110611 | ZH2C2 | CTCTTGAAAAGCAGAACTTTCAGTCTGTCTGTTGGACTTCTTCAAAACCAGGTTCTGAATACTTAA | SEQ ID NO: 3156 | Homo sapiens zinc finger, H2C2 domain containing (ZH2C2), mRNA [NM_017676] |
| 103 | A_23_P111321 | ARG1 | TGGAATCACGAGACAAAGCTACCACAGTGTGGAAAGGTAGTATGTGTCGATGTCATTCAAA | SEQ ID NO: 3157 | Homo sapiens arginase, liver (ARG1), mRNA [NM_000045] |
| 104 | A_23_P11201 | GPR34 | AGTAGGAGTGAAAGCACTTCAGAATTTAAACCAGGATAGTCCCTGCATGATGATCATCTGTG | SEQ ID NO: 3158 | Homo sapiens G protein-coupled receptor 34 (GPR34), transcript variant 1, mRNA [NM_005300] |
| 105 | A_23_P112251 | LOC552891 | AGAATTCTTAACTTCACAAGTTGTTTTAGTTCGACGATGTGCCTTTGATTTAATTGGGAC | SEQ ID NO: 3159 | Homo sapiens hypothetical protein LOC552891 (LOC552891), mRNA [NM_004125] |
| 106 | A_23_P117852 | KIAA0101 | TACTGCTGCATTTTTATTGGTGTTTGATTATGGAATGGTGCCATATGTCACTCGTTG | SEQ ID NO: 3160 | Homo sapiens KIAA0101 (KIAA0101), transcript variant 1, mRNA [NM_014736] |
| 107 | A_23_P120048 | BAZ2B | TATTTTCGTCTGAAGGTAATGATAGCTATACAGTCTGTACAGTAATTATCCTGTACGAAC | SEQ ID NO: 3161 | Homo sapiens bromodomain adjacent to zinc finger domain, 2B (BAZ2B), mRNA [NM_013450] |
| 108 | A_23_P120316 | MTHFD2 | AGGATATATCGTTGCTATTAGTACTCATTTTATGTATGTTACCCTTCAGTAAGTTCTCCC | SEQ ID NO: 3162 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 109 | A_23_P121622 | SULT1B1 | GAAATAGAGATTGTCTGTAGTTGATTGAAACGAGGGCAGTTATGAATTGATTTGGGGAAT | SEQ ID NO: 3163 | Homo sapiens mRNA for ST1B2, complete cds. [D89479] |
| 110 | A_23_P121716 | ANXA3 | TGGACATTCGAACAGAGTTCAAGAAGCATTATGGCTATTCCCTATATTCAGGAATTAAAT | SEQ ID NO: 3164 | Homo sapiens annexin A3 (ANXA3), mRNA [NM_005139] |
| 111 | A_23_P128930 | PSMC6 | GAACAAGCAAGATTAGACATACTGAAAATCCATGCAGGTCCCATTACAAACCATGGTGAA | SEQ ID NO: 3165 | Homo sapiens proteasome (prosome, macropain) 26S subunit, ATPase, 6 (PSMC6), mRNA [NM_002806] |
| 112 | A_23_P134714 | HRSP12 | TAAATTACAGCGTGTGTGACCTGTGTATTACTGAATATAGGAAGAGATACGCATTAGATAG | SEQ ID NO: 3166 | Homo sapiens heat-responsive protein 12 (HRSP12), mRNA [NM_005836] |
| 113 | A_23_P137366 | C1QB | CACCGACACAGAACTCACTACTGGGCGATGGAGGTGCCAACAGCATCTTTTCCGGGTTCCT | SEQ ID NO: 3167 | Homo sapiens complement component 1, q subcomponent, B chain (C1QB), mRNA [NM_000491] |
| 114 | A_23_P141549 | RPS7 | GTGAAACTAGATCAGCAGGGCGGGTCATAAAGGTTCATTTGGACGAAGCAGGAACGAAT | SEQ ID NO: 3168 | Homo sapiens ribosomal protein S7 (RPS7), mRNA [NM_001011] |
| 115 | A_23_P143858 | RPL22L1 | ATTGGCTTCGAGTGGTTGCATCGTGGACAAGGAGACCTACGAAGTTCGTTACTTCCAGATTA | SEQ ID NO: 3169 | Homo sapiens ribosomal protein L22-like 1, mRNA (cDNA clone IMAGE:4865966), [BC049823] |
| 116 | A_23_P144497 | RPS3A | CCAAATCCGACGAAGAATGATGGAAATCATGACCCGAGAGTGCAGACAAATGACTTGAA | SEQ ID NO: 3170 | Homo sapiens ribosomal protein S3A (RPS3A), mRNA [NM_001006] |
| 117 | A_23_P14564 | GPR65 | AACAAGTTAAATTGTTGCTGATCGAATTCTGTAGTGTTTGTAACCGAAACAGGAAG | SEQ ID NO: 3171 | Homo sapiens G protein-coupled receptor 65 (GPR65), mRNA [NM_003608] |

Fig. 24-7

| No. | Probe ID No. | Symbols of genes | Sequence | SEQ ID NO: | Descriptions of genes (letters and numbers within [ ] indicates GenBank accession No.) |
|---|---|---|---|---|---|
| 118 | A_23_P14708 | SUHW4 | TCTTTGTACGTCCATACAAGTGTTAGGCTGCCAGGCTGTAAGCTTACCTTAATTAAACTT | SEQ ID NO: 3172 | Homo sapiens suppressor of hairy wing homolog 4 (Drosophila) (SUHW4), transcript variant 1, mRNA [NM_017661] |
| 119 | A_23_P14734 | RPS27L | TACAAGATCACCACGGTTTTCAGCCATGCTCAGACAGTGGTTCTTTGTGTAGGTTGTTCA | SEQ ID NO: 3173 | Homo sapiens ribosomal protein S27-like (RPS27L), mRNA [NM_015920] |
| 120 | A_23_P151637 | RNASE2 | GTGGTAACGCAAATATGACCTGTCCTAGTAACAAAACTCGGAAAAATTGTCACCACAGTG | SEQ ID NO: 3174 | Homo sapiens ribonuclease, RNase A family, 2 (liver, eosinophil-derived neurotoxin) (RNASE2), mRNA [NM_002934] |
| 121 | A_23_P152002 | BCL2A1 | TGTAACCATATTTGCATTTGAAGGTATTCTGATCAAGAAACTTCTACGACAGCAAATTGC | SEQ ID NO: 3175 | Homo sapiens BCL2-related protein A1 (BCL2A1), mRNA [NM_004049] |
| 122 | A_23_P153037 | ZNF624 | TGTCGTTAGATGCAGATGGAGGACAGGTATGGAAGAATATACACCAGGCTGTTAATATTGA | SEQ ID NO: 3176 | Homo sapiens zinc finger protein 624 (ZNF624), mRNA [NM_020787] |
| 123 | A_23_P155765 | HMGB2 | TAAAAATGCAGGTTGTAGGTTTTTGATGGGCTACTCATACAGTTAGATTTACAGGTTC | SEQ ID NO: 3177 | Homo sapiens high-mobility group box 2 (HMGB2), mRNA [NM_002129] |
| 124 | A_23_P155815 | NCAPG | AAGTTAGGAAAGACGAATGGAGGTGGAATCCTTTAAGATTATGTCCAGTTATTTGGTTTAA | SEQ ID NO: 3178 | Homo sapiens non-SMC condensin I complex, subunit G (NCAPG), mRNA [NM_022346] |
| 125 | A_23_P165842 | EEF1E1 | AAGAAAAAGGAATCGTTCAGCAGTGGTTAGAATACAGAGGGTCACTCAAGTGATGGGCACT | SEQ ID NO: 3179 | Homo sapiens eukaryotic translation elongation factor 1 epsilon 1 (EEF1E1), mRNA [NM_004280] |
| 126 | A_23_P157449 | POLR2K | GGTCTCTCTTGCTTCAAATATCTCTTGTACAGTACTCACCATTTTAGATGGTTGGAC | SEQ ID NO: 3180 | Homo sapiens polymerase (RNA) II (DNA directed) polypeptide K, 7.0kDa (POLR2K), mRNA [NM_005034] |
| 127 | A_23_P159950 | COX7B | CAAATACGGTAATGCTGTATTAGCTAGTGGAGCCACTTCTGTATTGTTACATGGACAATA | SEQ ID NO: 3181 | Homo sapiens cytochrome c oxidase subunit VIIb (COX7B), nuclear gene encoding mitochondrial protein, mRNA [NM_001866] |
| 128 | A_23_P160466 | SLC19A2 | CTTGGTATGTGGGCATATTTATAGAATGCTGAACTCAATGTGCAAGTGTACTGTATGCA | SEQ ID NO: 3182 | Homo sapiens solute carrier family 19 (thiamine transporter), member 2 (SLC19A2), mRNA [NM_006996] |
| 129 | A_23_P162596 | ACTR6 | TTAACGGCTCACTGGACAGAGTTTTCCTTAGAAGGTAGTTTTGTGTGACTGTGACTAAACT | SEQ ID NO: 3183 | Homo sapiens ARP6 actin-related protein 6 homolog (yeast) (ACTR6), mRNA [NM_022496] |
| 130 | A_23_P163225 | RNASE3 | AGCCACAGCCTCAGAGACTGGGAAACATGGTTCCAAAACTGTTCAGTCCCAAATTTGTCT | SEQ ID NO: 3184 | Homo sapiens ribonuclease, RNase A family, 3 (eosinophil cationic protein) (RNASE3), mRNA [NM_002935] |
| 131 | A_23_P167168 | IGJ | TTGGGTGATGTAAAACCAACTGCGTGCGACCACCAAAATAATTAAAATAGTCACATTGTTATC | SEQ ID NO: 3185 | Homo sapiens immunoglobulin J polypeptide, linker protein for immunoglobulin alpha and mu polypeptides (IGJ), mRNA [NM_144646] |
| 132 | A_23_P170233 | CSTA | AACTGGGTAGTGAGTCATGATCGTTGCTGCTGATAAATATAACCATCAATAAAGAAGCATTCT | SEQ ID NO: 3186 | Homo sapiens cystatin A (stefin A) (CSTA), mRNA [NM_005213] |
| 133 | A_23_P18325 | PDCD10 | CCAACCGACTAATTCATCAAACCAACTTAATACTTCAGACCTTCAAAACTGTGCCTGAA | SEQ ID NO: 3187 | Homo sapiens programmed cell death 10 (PDCD10), transcript variant 1, mRNA [NM_007217] |
| 134 | A_23_P18372 | B3GNT5 | AAATGTCAACAAAGGGAAAATAAACTATCAGCTTGGATGGTCACTTGAATAGAAGAATGGT | SEQ ID NO: 3188 | Homo sapiens UDP-GlcNAc:betaGal beta-1,3-N-acetylglucosaminyltransferase 5 (B3GNT5), mRNA [NM_032047] |
| 135 | A_23_P18291 | TUBB2A | AGTTCTCAGATCAATCAATGCATCCTTAGTGAACTTCTGTTGTGCTCAAGGCATGGTCTTTC | SEQ ID NO: 3189 | Homo sapiens tubulin, beta 2A (TUBB2A), mRNA [NM_001069] |

Fig. 24-8

| No. | Probe ID No. | Symbols of genes | Sequence | SEQ ID NO: | Descriptions of genes (letters and numbers within [ ] indicates GenBank accession No.) |
|---|---|---|---|---|---|
| 136 | A_23_P200030 | FPGT | TAAAAATTGGTAAACTAGAAGTAACTTGTCACAACCCTCAGTTATGATACTTATGTGCG | SEQ ID NO: 3190 | Homo sapiens fucose-1-phosphate guanylyltransferase (FPGT), mRNA [NM_003838] |
| 137 | A_23_P200228 | AGL | TAGATTTTAACAGGTGTCATTTGACTCATTGACTAAACGTTTCGGTAGAATGCTTCATACTTGAGTG | SEQ ID NO: 3191 | Homo sapiens amylo-1, 6-glucosidase, 4-alpha-glucanotransferase (glycogen debranching enzyme, glycogen storage disease type III) (AGL), transcript variant 4, mRNA [NM_000028] |
| 138 | A_23_P200955 | A_23_P200955 | AGAACATGATTGAACCTCACATTGATGTCAAGACTACCGATGGTTATTTGTTTCATCTAC | SEQ ID NO: 3192 | |
| 139 | A_23_P20225 | RRM2B | TGCTCCTTTGTAAAAAGTTAAAGATTTGAAAGAGAATCTCATATTGCCGAGGGCATTAGGA | SEQ ID NO: 3193 | Homo sapiens ribonucleotide reductase M2 B (TP53 inducible) (RRM2B), mRNA [NM_015713] |
| 140 | A_23_P204289 | USP15 | GACCAGGATAAATGAGGTATGTTGATGATGGCTTTGTTTATATCTTGATATTAAAGCTG | SEQ ID NO: 3194 | Homo sapiens ubiquitin specific peptidase 15 (USP15), mRNA [NM_006313] |
| 141 | A_23_P205336 | C14orf129 | CAATTCATTGCCAGACTTCATTGGAATGCTTTCGTTGTTGATGATGTATGTTCATTCTCAGCT | SEQ ID NO: 3195 | Homo sapiens chromosome 14 open reading frame 129 (C14orf129), mRNA [NM_016472] |
| 142 | A_23_P207299 | LOC51136 | CCAAACACGAATTTGAAATTAGAAGTAGTGGTTTTAGAGAAGTCAGGTATTCGTTCCTG | SEQ ID NO: 3196 | Homo sapiens PTD016 protein (LOC51136), mRNA [NM_016125] |
| 143 | A_23_P210274 | PREI3 | GGATACAGTATGCCGTAGGATTTACAGAATATTTTCACATGGCTATTTCATCATCGGCAG | SEQ ID NO: 3197 | Homo sapiens preimplantation protein 3 (PREI3), transcript variant 1, mRNA [NM_015387] |
| 144 | A_23_P2129 | TMEM126B | CATATGCATCATTGGCTACACTGGCATTCTTTTGTCTACTGTTGTTACTGACAAGCTTTTG | SEQ ID NO: 3198 | Homo sapiens transmembrane protein 126B (TMEM126B), mRNA [NM_018480] |
| 145 | A_23_P213561 | HISPPD1 | GTATGTAAGTTTTCTGTTTGTGAAAATGTAGTAATGTAGTCACGTGTGGGAGGTCATAAGG | SEQ ID NO: 3199 | Homo sapiens histidine acid phosphatase domain containing 1 (HISPPD1), mRNA [NM_015216] |
| 146 | A_23_P215751 | NDUFA5 | TAAAAGTGGAGTCAGTCAGTAAATAGTTGCAGTACACGTTTCTAATATAAGTGTAGGTGGGTATC | SEQ ID NO: 3200 | Homo sapiens NADH dehydrogenase (ubiquinone) 1 alpha subcomplex, 5, 13kDa (NDUFA5), nuclear gene encoding mitochondrial protein, mRNA [NM_005000] |
| 147 | A_23_P217319 | FGF13 | TTGCATGGAAGAAAGTTGGGTTGTTGGCATAGAGATTGCATGATATGTAAGATTTTGTGCA | SEQ ID NO: 3201 | Homo sapiens fibroblast growth factor 13 (FGF13), transcript variant 1A, mRNA [NM_004114] |
| 148 | A_23_P218926 | C4orf18 | CAGATGAGTTCCTTCTCTGTAGATGTGTTTTCAGAGGTAGGTACAGAGGAATGTTTG | SEQ ID NO: 3202 | Homo sapiens chromosome 4 open reading frame 18 (C4orf18), transcript variant 2, mRNA [NM_016613] |
| 149 | A_23_P260002 | HACE1 | TAAGCAGTCATTGTGTTGTTTGGCAGTAATGTTGAGAGACATGTAAGTTGAAAGTTTGCTA | SEQ ID NO: 3203 | Homo sapiens HECT domain and ankyrin repeat containing, E3 ubiquitin protein ligase 1 (HACE1), mRNA [NM_020771] |
| 150 | A_23_P251937 | CPEB4 | GTATGTCAGTTAATTGTACTACTTGGCTGAATTTCGATATAGTTTTTACTGTGTATGGGG | SEQ ID NO: 3204 | Homo sapiens cytoplasmic polyadenylation element binding protein 4 (CPEB4), mRNA [NM_030627] |
| 151 | A_23_P252201 | EAF2 | CACGATTCCTGATATAGATGCCAGTCATCATAATAGATTTCGAGACAACAGTGGCGTCTGAT | SEQ ID NO: 3205 | Homo sapiens ELL associated factor 2 (EAF2), mRNA [NM_018456] |
| 152 | A_23_P25235 | CLEC4D | CATTTAACGCCACGACGAGTATTCTGGCATAAGAATGAACCCGACAACTCTCAGGGACAAA | SEQ ID NO: 3206 | Homo sapiens C-type lectin domain family 4, member D (CLEC4D), mRNA [NM_080387] |
| 153 | A_23_P252371 | RBBP8 | GGGAAGGAAGCAGAAGAGACATAGACGTTGAAACAGAAACAGAAGAAGATGAAGGACAAGTTTTTT | SEQ ID NO: 3207 | Homo sapiens retinoblastoma binding protein 8 (RBBP8), transcript variant 1, mRNA [NM_002894] |
| 154 | A_23_P26021 | COPS2 | TGCTTTTTTGATCAACTGCTTTGTGTTTGTGTGCTGCATTTATCCCAAGGAAAAACAGCTT | SEQ ID NO: 3208 | Homo sapiens COP9 constitutive photomorphogenic homolog subunit 2 (Arabidopsis) (COPS2), mRNA [NM_004236] |

Fig. 24-9

| No. | Probe ID No. | Symbols of genes | Sequence | SEQ ID NO: | Descriptions of genes (letters and numbers within [ ] indicates GenBank accession No.) |
|---|---|---|---|---|---|
| 155 | A_23_P2705 | P2RY5 | TCTGTATTGCTGTTTCGAACTGTTGTTTTGAGCCCTATAGTTTAC TACTTTACATCGGACA | SEQ ID NO: 3209 | Homo sapiens purinergic receptor P2Y, G-protein coupled, 5 (P2RY5), mRNA [NM_005767] |
| 156 | A_23_P302470 | SULT1B1 | TGTCTAAGTCACAAATCTGAAGAAATAAGAGATTGTCTGTGTAGTT GATTGAAACGAGGGCA | SEQ ID NO: 3210 | Homo sapiens sulfotransferase family, cytosolic, 1B, member 1 (SULT1B1), mRNA [NM_014465] |
| 157 | A_23_P302550 | RGS18 | GAGTGTAAGGCCTAGGAGATTTGGGCATCTGCACATTGGTTCA TATCAGAAAGTGTTA | SEQ ID NO: 3211 | Homo sapiens regulator of G-protein signalling 18 (RGS18), mRNA [NM_130782] |
| 158 | A_23_P30307 | CRSP9 | CAATTGTACTGCGACAGAATGAACATCAAAGAGAAAATTCAGGTC ATAGGAGAGATCAGAT | SEQ ID NO: 3212 | Homo sapiens cofactor required for Sp1 transcriptional activation, subunit 9, 33kDa (CRSP9), mRNA [NM_004270] |
| 159 | A_23_P305060 | PBEF1 | TGGCTGTGCTCTATATGCACCTCAAGATTTTAAGGAGATAAT GTTTTAGAGAGAATT | SEQ ID NO: 3213 | Homo sapiens pre-B-cell colony enhancing factor 1 (PBEF1), mRNA [NM_005746] |
| 160 | A_23_P307940 | CAPZA2 | CTACAAGATTGGCAAGAGATGCAGAATGCATAAGAATGAAGATT GCATGACGGGATCATT | SEQ ID NO: 3214 | Homo sapiens capping protein (actin filament) muscle Z-line, alpha 2 (CAPZA2), mRNA [NM_006136] |
| 161 | A_23_P308800 | GLS | CGGAAGAAGAGAATAAGAATACTGCGAATAGGCCCTCAAACTTAAA AAAGAAAAAAACTTGC | SEQ ID NO: 3215 | Homo sapiens glutaminase C mRNA, complete cds. [AF158555] |
| 162 | A_23_P30956 | KIAA0776 | TTTTTTCATTTGTCAAAATGGTTCTTTTGTTGCCAAGTAAAGA ACAGTTTTTATTGTT | SEQ ID NO: 3216 | Homo sapiens KIAA0776 (KIAA0776), mRNA [NM_015323] |
| 163 | A_23_P312246 | CCDC82 | GGCTTTATAACAGATGACGTGTCAAGTGACGTTGATGAGCTGTCTGATATC CTGTCACGTTTAGTCAA | SEQ ID NO: 3217 | Homo sapiens coiled-coil domain containing 82 (CCDC82), mRNA [NM_024725] |
| 164 | A_23_P314191 | ZDHHC17 | TGGATACTTTTAGCAAATAGGACAAAGTTAATTCTCAGCACTGAACA TGAATTAGTTCCTTGG | SEQ ID NO: 3218 | Homo sapiens zinc finger, DHHC-type containing 17 (ZDHHC17), mRNA [NM_015336] |
| 165 | A_23_P31671 | UQCRB | AAGGCATAAGAAGAGACTTCCTGAGAACCTTTATAATGACAGGATG TTTCAGCATTAAGAGGG | SEQ ID NO: 3219 | Homo sapiens ubiquinol-cytochrome c reductase binding protein (UQCRB), mRNA [NM_006294] |
| 166 | A_23_P327022 | MDFIC | TTATGATTTGTTAATGTAAAATGTTTGTTGAAGTATATGGCTA TCATGACTAAGTGCTA | SEQ ID NO: 3220 | Homo sapiens MyoD family inhibitor domain containing (MDFIC), mRNA [NM_199072] |
| 167 | A_23_P33045 | RPL26 | TACAAAGGTCAGCAAATTGGGAAAGTAGTCCAGGTTTACAGGAA GAAATATGTTATCTAC | SEQ ID NO: 3221 | Homo sapiens ribosomal protein L26 (RPL26), mRNA [NM_000987] |
| 168 | A_23_P332439 | NUPL1 | ATTGAAATCTGAATGTTGAATGTATGAACTGTGAAGTACAGAGCGGGT GCCTTTGTAAATGTTC | SEQ ID NO: 3222 | Homo sapiens KIAA0410 mRNA, partial cds. [AB007870] |
| 169 | A_23_P339480 | HAT1 | AACATGAACAGCTGGAAGAGAGTTTCAGGAACTAGTGGAAGAT TACCGGCGTGTTTATTG | SEQ ID NO: 3223 | Homo sapiens histone acetyltransferase 1 (HAT1), transcript variant 1, mRNA [NM_003642] |
| 170 | A_23_P347059 | MOBKL1A | CTAGAAGGGGAAAAATCATCTAAGTTATGAAATCGAAGACATAGGC GCTATATACAAAGTG | SEQ ID NO: 3224 | Homo sapiens MOB1, Mps One Binder kinase activator-like 1A (yeast) (MOBKL1A), mRNA [NM_173468] |
| 171 | A_23_P348992 | MYSM1 | CATGTATTTAAACCTATGAATTATAAAATAGTATTTAGATTCTA GGGTGAGTTAAATAGA | SEQ ID NO: 3225 | Homo sapiens mRNA for KIAA1915 protein, partial cds. [AB067502] |
| 172 | A_23_P349083 | FCHO2 | GTGAAATGGTTAAACTTGTGCACTTGTTAGTTACCACAGTGTT CATACCAAGTATTGGG | SEQ ID NO: 3226 | Homo sapiens FCH domain only 2 (FCHO2), mRNA [NM_138782] |
| 173 | A_23_P353704 | RP5-1022P6.2 | TGTCTCTCACTACGTATTACACAGTGTTGCTTTGTGGGTTTGTT TTGTATGTGCGTGTGT | SEQ ID NO: 3227 | Homo sapiens hypothetical protein KIAA1434 (KIAA1434), mRNA [NM_019593] |
| 174 | A_23_P355067 | TMCO1 | AACTCAAGAACTGTTTATTTTCTATCATTCTGTTTCTAGACACAGA CACATCAGAACTGGGAA | SEQ ID NO: 3228 | Homo sapiens transmembrane and coiled-coil domains 1 (TMCO1), mRNA [NM_019026] |

Fig. 24-10

| No. | Probe ID No. | Symbols of genes | Sequence | SEQ ID NO: | Descriptions of genes [letters and numbers within [ ] indicates GenBank accession No.) |
|---|---|---|---|---|---|
| 175 | A_23_P37736 | TNFRSF17 | GATCTCTTTAGGAGTGATGTATTTTCAGTTGCCGATACAGCTT TTTGTCGTCTAAGTGT | SEQ ID NO: 3229 | Homo sapiens tumor necrosis factor receptor superfamily, member 17 (TNFRSF17), mRNA [NM_001192] |
| 176 | A_23_P38275 | THC2504576 | TCTCGCCAAAATGAAGTTAATCCGTTTGTGACTTCCGACCGAA GCAAGAATCGGCAAAG | SEQ ID NO: 3230 | RL26_BOVIN (P61257) 60S ribosomal protein L26, complete [THC2504576] |
| 177 | A_23_P380734 | FGFR10P2 | CCAACAGATACAGAGAAATGTGCTTAAGATCAGTTGAAACCTAAA TTTCTTATGTGTGG | SEQ ID NO: 3231 | Homo sapiens FGFR1 oncogene partner 2 (FGFR10P2), mRNA [NM_015633] |
| 178 | A_23_P405873 | C9orf72 | GAGAATGGAAGATCAGGGTCAGAGATTATTCAATGCTTACTG GAGAAGTGATTCCTGT | SEQ ID NO: 3232 | Homo sapiens chromosome 9 open reading frame 72 (C9orf72), transcript variant 2, mRNA [NM_145005] |
| 179 | A_23_P41114 | CSTA | AAACAAATGAGACTTATGGAAAATTGGAAGCTGTGCAGTATAAA ACTCAAGTTGTTGCTG | SEQ ID NO: 3233 | Homo sapiens cystatin A (stefin A) (CSTA), mRNA [NM_005213] |
| 180 | A_23_P41645 | ELL2 | TGTCTTTTCAAAGTGCTGCCAGTTGAAAAGGGAAGCATTATGTT TACAAATCTGTTTTGA | SEQ ID NO: 3234 | Homo sapiens elongation factor, RNA polymerase II, 2 (ELL2), mRNA [NM_012081] |
| 181 | A_23_P41664 | ENST00000334994 | TGGCTTGGAGCAGATTCGACTTCATAAACAAATTGTTCCTGAAA ATGAGGCACAGGTCAT | SEQ ID NO: 3235 | Synleurin [Source:Uniprot/SPTREMBL;Acc:Q7Z207] [ENST00000334994] |
| 182 | A_23_P421563 | LSM3 | CATAAGAGAAGAACCTGGATACATTTTGATATTAAGAAATAATTCC GGGGATTCTTCCACTC | SEQ ID NO: 3236 | Homo sapiens LSM3 homolog, U6 small nuclear RNA associated (S. cerevisiae) (LSM3), mRNA [NM_014463] |
| 183 | A_23_P42975 | PRKAR2B | GCCACATTTTAGAAGACTGTTAACATTTTGCAAAAGCTTCT TGTAGGAAAAGAGAGC | SEQ ID NO: 3237 | Homo sapiens protein kinase, cAMP-dependent, regulatory, type II, beta (PRKAR2B), mRNA [NM_002736] |
| 184 | A_23_P494809 | S100A8 | AAAGGCATGAAAGAAACGCACAAAGAGAGTAGGCTGAGTTACTGGGCC CAGAAGCTGGGCCCCT | SEQ ID NO: 3238 | Homo sapiens S100 calcium binding protein A8 (S100A8), mRNA [NM_002964] |
| 185 | A_23_P4257 | COMMD8 | AACATTTTACTTCTGGGCTTCTATGTTTGGGAAACATTGCTCTG ATAAAAATAGCTGTC | SEQ ID NO: 3239 | Homo sapiens COMM domain containing 8 (COMMD8), mRNA [NM_017845] |
| 186 | A_23_P48166 | TWF1 | TGGACAGGACCATAGCTGAAGGTGTTATTTCAGTCAGGAAGAAC AAGCTGTCATGAAGGT | SEQ ID NO: 3240 | Homo sapiens twinfilin, actin-binding protein, homolog 1 (Drosophila) (TWF1), mRNA [NM_002822] |
| 187 | A_23_P48897 | CCPG1 | AAGTCAGAAGAGCTCATATATATAATTGTAATGTGCCACCTATG TCCATCCATCTACCA | SEQ ID NO: 3241 | Homo sapiens cell cycle progression restoration protein (CPR8) mRNA, complete cds. [AF011794] |
| 188 | A_23_P500956 | B3GNT2 | TCCTGGTGGTATCATAGTGTAATTTTAGTATTTGAAAATCAGTG TGATTCCTTAATGGCC | SEQ ID NO: 3242 | Homo sapiens UDP-GlcNAc:betaGal beta-1,3-N-acetylglucosaminyltransferase 2 (B3GNT2), mRNA [NM_006577] |
| 189 | A_23_P501080 | ZNF92 | GAATATTAAGTGCTAGTTGAGGTAGATCAGTCGAAGCTAAGATTCT TTTGCAGTATAGTGAG | SEQ ID NO: 3243 | Homo sapiens zinc finger protein 92 (ZNF92), transcript variant 1, mRNA [NM_007139] |
| 190 | A_23_P502425 | MRPL47 | GTTCCGCACATCTTGCTGAAGAGCCCAAAAGTCAAGTCTTGTCTAAG ATGTGTGAAGTATTAA | SEQ ID NO: 3244 | Homo sapiens mitochondrial ribosomal protein L47 (MRPL47), nuclear gene encoding mitochondrial protein, transcript variant 1, mRNA [NM_020409] |
| 191 | A_23_P50907 | ITGAV | AAAGAGTGATTAAGTAAGGTTATTACCGCTAAATGGTCCATTC TGCATTGTATTTCAGG | SEQ ID NO: 3245 | Homo sapiens integrin, alpha V (vitronectin receptor, alpha polypeptide, antigen CD51) (ITGAV), mRNA [NM_002210] |
| 192 | A_23_P51317 | CCDC76 | CCCTTGTTTATAAGTTTTTATGTCAAGTAAGGTAGTTTGTTTAAGT TAGTTACCCATGTCCC | SEQ ID NO: 3246 | Homo sapiens coiled-coil domain containing 76 (CCDC76), mRNA [NM_019083] |

Fig. 24-11

| No. | Probe ID No. | Symbols of genes | Sequence | SEQ ID NO: | Descriptions of genes (letters and numbers within [ ] indicates GenBank accession No.) |
|---|---|---|---|---|---|
| 193 | A_23_P52846 | THC2694735 | TTTATGCGTTTTCACTACAATAACAAGTAGAACACGTAGAACAGATGATTAGTCACAGCAG | SEQ ID NO: 3247 | AB003177 proteasome subunit p27 [Homo sapiens] (exp=-1; wgp=0; cg=0), partial (0%) [THC2694735] |
| 194 | A_23_P53668 | NFYB | TGGGCTCATATTGTGCATACCATTTGTAACCTGCTTTTTTCACTTAACAATATATTGGG | SEQ ID NO: 3248 | Homo sapiens nuclear transcription factor Y, beta (NFYB), mRNA [NM_006166] |
| 195 | A_23_P56759 | KRCC1 | GATATCCGTGTTCATACCACTTTCTTCTTATGTTGAATAGGTTCTTAACTCTAACAAAGGC | SEQ ID NO: 3249 | Homo sapiens lysine-rich coiled-coil 1 (KRCC1), mRNA [NM_016618] |
| 196 | A_23_P58266 | S100P | CCAAAAGTGTTTGTTGGGAATTATTCCCCTAGGCTGAGCCTGCTCATGTACGTCTGATTA | SEQ ID NO: 3250 | Homo sapiens S100 calcium binding protein P (S100P), mRNA [NM_005980] |
| 197 | A_23_P59637 | DOCK4 | TTGGCAGTGAGCAGTTGAATTTATCTGAATTTATCATGTGTGTATTTCTGAAGCAG | SEQ ID NO: 3251 | Homo sapiens dedicator of cytokinesis 4 (DOCK4), mRNA [NM_014705] |
| 198 | A_23_P59921 | SUB1 | CAGATTGGGAAAATGAGGTACGTTAGTGTTCGCGATTTTAAAGGCAAAGTGCTAATTGAT | SEQ ID NO: 3252 | Homo sapiens SUB1 homolog (S. cerevisiae) (SUB1), mRNA [NM_006713] |
| 199 | A_23_P60565 | ZNF354A | AAACAAAAGCTACTGGAAGAAATACATCCTTGAGAGAGATGTAATAAATGTAATGGATGTG | SEQ ID NO: 3253 | Homo sapiens zinc finger protein 354A (ZNF354A), mRNA [NM_036491] |
| 200 | A_23_P61674 | CLK4 | GAAAGGCATGCAGTTTGTCCAGTTGTGACAGTTGTTTAATAAACCACAATACACACTTTA | SEQ ID NO: 3254 | Homo sapiens CDC-like kinase 4 (CLK4), mRNA [NM_020666] |
| 201 | A_23_P63896 | FAS | ATGTGTATCCACAGGGCTAACCCACTCTATGAATCAATAGAAGAAGCTATGACCTTTTGC | SEQ ID NO: 3255 | Homo sapiens Fas (TNF receptor superfamily, member 6) (FAS), transcript variant 1, mRNA [NM_000043] |
| 202 | A_23_P65768 | C15orf15 | TCCTGCATTGCCATCTACATAATATCAGATATTACGGATGGTAGATTGGCATCTCAGTGTT | SEQ ID NO: 3256 | Homo sapiens chromosome 15 open reading frame 15 (C15orf15), mRNA [NM_016304] |
| 203 | A_23_P66260 | ZNF267 | TGTGATGAATGGTAAAGCCTTCAGCTATAGGTCATACCTCACTACACATGGAGAAGT | SEQ ID NO: 3257 | Homo sapiens zinc finger protein 267 (ZNF267), transcript variant 498723, mRNA [NM_003414] |
| 204 | A_23_P70007 | HMMR | ACTATTTCTTCAGAGTTTGTCATAGTCGTCTGTCATCTGCATGTCTACTCAGCATTTGA | SEQ ID NO: 3258 | Homo sapiens hyaluronan-mediated motility receptor (RHAMM) (HMMR), transcript variant 1, mRNA [NM_012484] |
| 205 | A_23_P70328 | CENPQ | CAATGGCTTAGAGTTCTGTCGTGTCTGGTCATCTGGAACTTGAAAAATCCTCAAATGCCTTCAC | SEQ ID NO: 3259 | Homo sapiens centromere protein Q (CENPQ), mRNA [NM_018132] |
| 206 | A_23_P71727 | CKS2 | GATAAAAGTTCTTCCAGTCAGTCAGTTTTCTCTTAAGTGCCTGTTTGAGTTTAGTGAAACAGT | SEQ ID NO: 3260 | Homo sapiens CDC28 protein kinase regulatory subunit 2 (CKS2), mRNA [NM_001827] |
| 207 | A_23_P7221 | RPL34 | CGAGGAGGCAGAAATCGTTGTGAAAGTGTTGAAGGCACAAGCACAGAGTCAGAAAGCTAA | SEQ ID NO: 3261 | Homo sapiens ribosomal protein L34 (RPL34), transcript variant 2, mRNA [NM_033625] |
| 208 | A_23_P7229 | RPL34 | CGAACCCCTGGTAATAGAATTGTTACCTTTATACCAAGAAGGTTGGGAAAGCACCAAAA | SEQ ID NO: 3262 | Homo sapiens ribosomal protein L34 (RPL34), transcript variant 2, mRNA [NM_033625] |
| 209 | A_23_P72603 | KLHL2 | TTTTTGATATTTAACAATGCTAAAACAGTTTAAATGCCACTCTGAGGAATGCACCTGGTG | SEQ ID NO: 3263 | Homo sapiens kelch-like 2, Mayven (Drosophila) (KLHL2), mRNA [NM_007246] |
| 210 | A_23_P73114 | PROS1 | CCAGAACAAATTTTAACAAAAGGACAACCACAGACAGGGATATAGTGAATATCGTATCATTG | SEQ ID NO: 3264 | Homo sapiens protein S (alpha) (PROS1), mRNA [NM_000313] |
| 211 | A_23_P74001 | S100A12 | TGAAGGCTTTTTACCCAGCAATGTCCTCAATGAGGGTGTTTTCTTTCCCTCACGAAAAGC | SEQ ID NO: 3265 | Homo sapiens S100 calcium binding protein A12 (S100A12), mRNA [NM_005621] |
| 212 | A_23_P75769 | MS4A4A | CACCAAAAGATCAACAGAGACAAATGCTCCAGAAATCTATGGTGACTGTGACAACAAGAGCT | SEQ ID NO: 3266 | Homo sapiens membrane-spanning 4-domains, subfamily A, member 4 (MS4A4A), transcript variant 1, mRNA [NM_024021] |

Fig. 24-12

| No. | Probe ID No. | Symbols of genes | Sequence | SEQ ID NO: | Descriptions of genes (letters and numbers within [ ] indicates GenBank accession No.) |
|---|---|---|---|---|---|
| 213 | A_23_P76480 | BF213738 | AAATCGAAGACGGACAATGGGTAGATGGAGCTACATTTACCAAAT CGTTTGGCATGACAGG | SEQ ID NO: 3267 | BF213738 601847626F1 NIH_MGC_55 Homo sapiens cDNA clone IMAGE:4078519 5', mRNA sequence [BF213738] |
| 214 | A_23_P78092 | EVI2A | GCTGAATCAGACACTTGGAAAAGAACAAAACAGCTCACAGGACC CAACCTAGTAGTGATGCAA | SEQ ID NO: 3268 | Homo sapiens ecotropic viral integration site 2A (EVI2A), transcript variant 1, mRNA [NM_001003927] |
| 215 | A_23_P82047 | BU507302 | TCTGTTTCGTTAATGTCAGGTGCCTGAACATTCAGCAGTTTATA AATTGCTTAATTGTG | SEQ ID NO: 3269 | AGENCOURT_10309688 NIH_MGC_71 Homo sapiens cDNA clone IMAGE:6501220 5', mRNA sequence [BU507302] |
| 216 | A_23_P83278 | CHMP5 | CATTGCTCTTTTATTTTTTCCATTAAGAGACTCATTGCTTGGGA AATGCTTCTTCGTAC | SEQ ID NO: 3270 | Homo sapiens chromatin modifying protein 5 (CHMP5), mRNA [NM_016410] |
| 217 | A_23_P87769 | C12orf48 | GTAAGAAATATCGTCAGTCGTCCTAATGCATATTGTGACTGTTT GCATATACTTCTGTT | SEQ ID NO: 3271 | Homo sapiens chromosome 12 open reading frame 48 (C12orf48), mRNA [NM_017915] |
| 218 | A_23_P87879 | CD69 | TGTCAATATGTGATGTGGCAAATCTCTATTAGGAAAATATTCTG TAATCTCAGACCTAG | SEQ ID NO: 3272 | Homo sapiens CD69 molecule (CD69), mRNA [NM_001781] |
| 219 | A_23_P94095 | ANKRD46 | GCTCTTGGTATTTTCTTGTATGTATCTAGTATGAGG CTTGCTCTTCATGTG | SEQ ID NO: 3273 | Homo sapiens ankyrin repeat domain 46 (ANKRD46), mRNA [NM_198401] |
| 220 | A_23_P94230 | LY96 | TGAAGGTATTTGTGGGAGCCAGAAGAAATGCTCTTTTGCTTGG AGTTGTCATCTACA | SEQ ID NO: 3274 | Homo sapiens lymphocyte antigen 96 (LY96), mRNA [NM_015364] |
| 221 | A_23_P94501 | ANXA1 | GGCTCTTTGTGAAGGAAACTAAACATTCCGTTGATGGTCTCAAG CTATGATCAGAAGACT | SEQ ID NO: 3275 | Homo sapiens annexin A1 (ANXA1), mRNA [NM_000700] |
| 222 | A_23_P95564 | NAT1 | TCGTTGGAGAAGAAGGTTGTGCCCAAACATGGTGATAGATTTTT TACTATTTAGAATAAG | SEQ ID NO: 3276 | Homo sapiens N-acetyltransferase 1 (arylamine N-acetyltransferase) (NAT1), mRNA [NM_000662] |
| 223 | A_23_P99980 | HMGB1 | GGAATCTTTTCCATTTGTTTATGTAATTCAGGAGGAAT ACTGAACATCTGAGTC | SEQ ID NO: 3277 | Homo sapiens high-mobility group box 1 (HMGB1), mRNA [NM_002128] |
| 224 | A_24_P100387 | GK | TAAAGGTTCTGTTTTTGTTTGGAATCAATGAGCTTATTGAC TGTTCTGATTGTGCTG | SEQ ID NO: 3278 | Homo sapiens glycerol kinase (GK), transcript variant 1 mRNA [NM_203391] |
| 225 | A_24_P100830 | AMN1 | TCTTGAAAGAATTTAGGTATTTGTTTCACGGAGAAATGAAGTGACT TATTAGCCATTCAGCG | SEQ ID NO: 3279 | Homo sapiens antagonist of mitotic exit network 1 homolog (S. cerevisiae) (AMN1), mRNA [NM_207337] |
| 226 | A_24_P105648 | BX111927 | TTATGAGATGCTTCAGTTCCAGGTGTACAAGAAGAAATATGTCATCTACA TATCTAAAAGAGTGCC | SEQ ID NO: 3280 | BX111927 Soares_multiple_sclerosis_2NbHMSP Homo sapiens cDNA clone IMAGp998G05619, mRNA sequence [BX111927] |
| 227 | A_24_P106306 | RPL26L1 | TGGCAAGGTAGTCCAGGTGTACAGAAGAAGAAATATGTCATCTACA TCGAGCGGGTGCAGCGG | SEQ ID NO: 3281 | Homo sapiens ribosomal protein L26-like 1 (RPL26L1), mRNA [NM_016093] |
| 228 | A_24_P11045 | THC2785765 | CCACCAGAAACGTACACGTGATTTTCATGACAAATACGGTAGCA ACACAGTCGGAATAG | SEQ ID NO: 3282 | COX7B_HUMAN (P24311) Cytochrome c oxidase polypeptide VIIb, mitochondrial precursor partial (78%) [THC2785765] |
| 229 | A_24_P114249 | GALNT3 | ATTTCAAATGCAGAATACTTGACTGCATTTAAAGCTAAATTTTGT TACTGATTCAATTATA | SEQ ID NO: 3283 | Homo sapiens UDP-N-acetyl-alpha-D-galactosamine:polypeptide N-acetylgalactosaminyltransferase 3 (GalNAc-T3) (GALNT3), mRNA [NM_004482] |
| 230 | A_24_P113382 | A_24_P113382 | CATACCATGTCTGTGTGTGGTTGTCCAGAAAATGAGGCTGAAGA TTCACCAAATAAGCTC | SEQ ID NO: 3284 | |
| 231 | A_24_P127621 | A_24_P127621 | TCGAAGCAAGTACCACCAAAAGGCATTGAATGCACTTGCACA TTCTGAAAATATTAG | SEQ ID NO: 3285 | |

Fig. 24-13

| No. | Probe ID No. | Symbols of genes | Sequence | SEQ ID NO: | Descriptions of genes (letters and numbers within [ ] indicates GenBank accession No.) |
|---|---|---|---|---|---|
| 232 | A_24_P133991 | ANKRD12 | TTTGGAATGGAGTATATGGCTGAAAAGGTTTTGGATTCAGAAAAG AAAAAGGATGGTTAGT | SEQ ID NO: 3286 | Homo sapiens ankyrin repeat domain 12 (ANKRD12), mRNA [NM_015208] |
| 233 | A_24_P134392 | STCH | TGAGTAACTTATTTTGTATCAGGAATGTTTTGGTTACTGTGTTTT CACTCAAACCACTGAC | SEQ ID NO: 3287 | Homo sapiens stress 70 protein chaperone, microsome-associated, 60kDa (STCH), mRNA [NM_006948] |
| 234 | A_24_P135242 | A_24_P135242 | GATGGCAAGAAAAGCTGGGAAGTAGTTTGTAGCTGCAGAACCCA AACTGGCATTTGTCAT | SEQ ID NO: 3288 | |
| 235 | A_24_P135551 | LOC130865 | TAACAGCATAGCTGTCCCTGTGGGGATTCAGCCAAAGGTGGTTA TCACTAGACTAAAACT | SEQ ID NO: 3289 | PREDICTED: Homo sapiens similar to 60S ribosomal protein L26 (Silica-induced gene 20 protein) (SIG-20) (LOC130865), mRNA [XR_019454] |
| 236 | A_24_P144666 | LOC401975 | TGTCGATGTGAAGAGTAATGATGGCTACTTCTTTAATCTGTTCT GTGTTGGTTTTAGTGA | SEQ ID NO: 3290 | PREDICTED: Homo sapiens similar to ribosomal protein S3a (LOC401975), mRNA [XR_017247] |
| 237 | A_24_P152753 | LOC285260 | TGTCTCATACCGAATCCGTGTGGGATTATCCAGAAAGATGAAGG ATTCACCAAATGAGCT | SEQ ID NO: 3291 | PREDICTED: Homo sapiens similar to ribosomal protein L31 (LOC285260), mRNA [XR_019376] |
| 238 | A_24_P163324 | LOC390413 | GAAGCTTAACACATGCTTCAATTAACATGCTGGGGATTGTAGAAC CATATATTGCAGGGTA | SEQ ID NO: 3292 | PREDICTED: Homo sapiens similar to 60S ribosomal protein L7 (LOC390413), mRNA [XR_018341] |
| 239 | A_24_P165864 | P2RY14 | TTTTTCTGGAAAACAGAGGGATTTTACTTCTGGAGACATGGCAT ACGGTTACTGAGTTAT | SEQ ID NO: 3293 | Homo sapiens purinergic receptor P2Y, G-protein coupled, 14 (P2RY14), transcript variant 2, mRNA [NM_014879] |
| 240 | A_24_P175176 | PHTF2 | AGATTAGGGTTAACTTAGAGTTGGGAGTTGGATTTATTAAGTACA GTATACCTGTCAACAG | SEQ ID NO: 3294 | Homo sapiens putative homeodomain transcription factor 2 (PHTF2), mRNA [NM_020432] |
| 241 | A_24_P188878 | RPL34 | TGTTTAGCTTTATCCAAGAAGAAGGTTGGGAAAGCACAAAATCTG CATGTGGTGTGTGCC | SEQ ID NO: 3295 | Homo sapiens ribosomal protein L34 (RPL34), transcript variant 2, mRNA [NM_033625] |
| 242 | A_24_P201702 | CLEC2B | ATTGGAATTCAAGTAAATACAACTGTTCGACTCAACATGCCGAC CTAACTATAATTGACA | SEQ ID NO: 3296 | Homo sapiens C-type lectin domain family 2, member B (CLEC2B), mRNA [NM_005127] |
| 243 | A_24_P203909 | RPL34 | GAGGGGTTCGTGCTGAGTAAGACTAAAGTTCTATATGAAATTGTCC AAAACAAACAACATG | SEQ ID NO: 3297 | Homo sapiens ribosomal protein L34 (RPL34), transcript variant 1, mRNA [NM_033625] |
| 244 | A_24_P20996 | BC043173 | CTGAAAATGTTGATATATATGCAAAAATGGCAGGACAATGATCTTCAT GAAGGGCTCTGATTGG | SEQ ID NO: 3298 | Homo sapiens cDNA clone IMAGE:5287121. [BC043173] |
| 245 | A_24_P213375 | A_24_P213375 | AAATGTGTTCCATGATCAAAAATGCAAAATGGCAGACAATGATCTTCAT CTGTTCTGTGTTGGTT | SEQ ID NO: 3299 | |
| 246 | A_24_P213783 | RPL31 | CTTTGGTTAGCTATGTACGTGTTACCACTTTCAAAAATGTACAG ACAGTCAATGTGGATG | SEQ ID NO: 3300 | Homo sapiens ribosomal protein L31 (RPL31), mRNA [NM_000993] |
| 247 | A_24_P221375 | A_24_P221375 | TACTTTGGTTACCCATGTACCACTTTCAAAAAATCTACAGA GAGTCAATGTGGAGGA | SEQ ID NO: 3301 | |
| 248 | A_24_P225308 | ARID4B | GTTGAAAATGTTTCAAGTATTCAAATTTGTACAGGACTGTAA AGATTTGTTGACAGACA | SEQ ID NO: 3302 | Homo sapiens AT rich interactive domain 4B (RBP1-like) (ARID4B), transcript variant 1, mRNA [NM_016374] |
| 249 | A_24_P225719 | PREI3 | GACTATTTTCTTAGTGAATATTTATACTAAGGTAGTGACTGAGA TTTGGTGATCTGGCTG | SEQ ID NO: 3303 | Homo sapiens preimplantation protein 3 (PREI3), transcript variant 1, mRNA [NM_015387] |
| 250 | A_24_P235429 | ABCA1 | CCAAAGAGCCATGTGTCATGAATGAATACTGAACCACTTTGATATTG AGACATTAATTTGTAC | SEQ ID NO: 3304 | Homo sapiens ATP-binding cassette, sub-family A (ABC1), member 1 (ABCA1), mRNA [NM_005502] |

Fig. 24-14

| No. | Probe ID No. | Symbols of genes | Sequence | SEQ ID NO: | Descriptions of genes (letters and numbers within [ ] indicates GenBank accession No.) |
|---|---|---|---|---|---|
| 251 | A_24_P235008 | SCYL2 | ATAGACTATGTACTTCGTCTGGTTTTTGTTTTATTTGGAATGGTTATAAGGGTCC | SEQ ID NO: 3305 | Homo sapiens mRNA for KIAA1360 protein, partial cds. [AB037781] |
| 252 | A_24_P243749 | PDK4 | ATTTGACATTTGTGTGTAATTTCATGGTGGCCTAGTGTTGTGGTGCTTCTGTAATGGTA | SEQ ID NO: 3306 | Homo sapiens pyruvate dehydrogenase kinase, isozyme 4 (PDK4), mRNA [NM_002612] |
| 253 | A_24_P24890 | A_24_P24890 | ATGAAGGAGATTTGGTCTTTGTATTGTTACGTTCCTCGTACTTTGTAGCTGTGGCTGTACT | SEQ ID NO: 3307 | |
| 254 | A_24_P264549 | A_24_P264549 | ATTCATAGTAGGCATACAGAGAACATGATCAAAGGTGTTACACTGGACTTCCATTACAATATG | SEQ ID NO: 3308 | |
| 255 | A_24_P268917 | RAB33B | CCCAGAATGCTAATGTAGTTCGGCTATTAATAACAATGCATTATTGAAAGTATATTGGAAAT | SEQ ID NO: 3309 | Homo sapiens RAB33B, member RAS oncogene family (RAB33B), mRNA [NM_031296] |
| 256 | A_24_P273583 | TMCO1 | CCTTCATTTTCCTGTATATTCTCTGTACTATGTCGATTCGACAGAACATTCAGAAGATTC | SEQ ID NO: 3310 | Homo sapiens transmembrane and coiled-coil domains 1 (TMCO1), mRNA [NM_019026] |
| 257 | A_24_P278460 | MLSTD2 | ACCCATGGAACAATATGCTTAGGATTACAGGAAGCAGTCCTTACTTACACTTCTTGTCTG | SEQ ID NO: 3311 | Homo sapiens male sterility domain containing 2 (MLSTD2), mRNA [NM_032228] |
| 258 | A_24_P286054 | ZFYVE16 | GTGTATGTATTCTGCCATGTAAGTAATTGAACAGTGTTAAAATAAGCAAATGGTAGAAGGG | SEQ ID NO: 3312 | Zinc finger FYVE domain-containing protein 16 (Endofin) (Endosome-associated FYVE domain protein). [Source:Uniprot/SWISSPROT:Acc:Q7Z3T8] [ENST00000360248] |
| 259 | A_24_P298238 | A_24_P298238 | ATCCTTGAAGGAAATGACATTGAGGTTGTTTCAATTCAGCAAGCCACAACAGTTAAAAAC | SEQ ID NO: 3313 | |
| 260 | A_24_P298604 | LOC731599 | GATGGAAATCATGAACCAGAGAGGTTGGGGCAAATGAGTTGAAAGAATTGGTCAATAAAATGAT | SEQ ID NO: 3314 | PREDICTED: Homo sapiens hypothetical protein LOC731599 (LOC731599), mRNA [XR_015536] |
| 261 | A_24_P303118 | RPL34 | CGAGGAGCAGAAAAATGGTTGTGTGAAAGTGTTGAAGGGACAAGCAGAGAGTCAGAAGGTAA | SEQ ID NO: 3315 | Homo sapiens ribosomal protein L34 (RPL34), transcript variant 2, mRNA [NM_033625] |
| 262 | A_24_P306527 | ENST00000308899 | ACGGCATCCGTCCGTGGTTATCCAGAAATGTAATGAGGATGAAGATTCACCAAATAAGT | SEQ ID NO: 3316 | PREDICTED: Homo sapiens similar to ribosomal protein L31 (LOC729005), mRNA [XM_001133428] |
| 263 | A_24_P315326 | LOC344412 | AAGCTCTATACTTTGGTTACCAAATGTACCGGTTACGGCTTTCAAAAATCACAGGGAATG | SEQ ID NO: 3317 | AGENCOURT_10640855 NIH_MGC_126 Homo sapiens cDNA clone IMAGE:6723568 5', mRNA sequence [CA455253] |
| 264 | A_24_P316074 | LOC730902 | TATCAAATGGTGTGAGCCCAAAAGTGAAGGTCAAAGGTGTTGCAGCTTCTTCCCTTCGTCAAATCTT | SEQ ID NO: 3318 | PREDICTED: Homo sapiens similar to 60S ribosomal protein L7 (LOC730902), mRNA [XR_015660] |
| 265 | A_24_P326328 | SUB1 | CAGAAAAACCTGTAAAGAAACAAGAACAGGTGAGAGACTTCGAGAGCCCGTGTCATGTCTA | SEQ ID NO: 3319 | Homo sapiens SUB1 homolog (S. cerevisiae) (SUB1), mRNA [NM_006713] |
| 266 | A_24_P324224 | A_24_P324224 | AAAGCTGTGTGGGCAAAGGAATAAGGAATTCGTATAGGCATGTGCGGTTGTCCAGAAAA | SEQ ID NO: 3320 | |
| 267 | A_24_P324581 | KIAA1466 | ATAATAGGTCATAGAATGAATTGGTGTACGGAACCAAGGGTAAAAGAATTTAAGTAGCCC | SEQ ID NO: 3321 | Homo sapiens mRNA for KIAA1466 protein, partial cds. [AB040899] |
| 268 | A_24_P33213 | A_24_P33213 | GACCATATATTACGTGGGGGTACGGAAATGTGAAGTCAGTAAATGAACTTAGAAGG | SEQ ID NO: 3322 | |
| 269 | A_24_P333052 | A_24_P333052 | TAGACATCAAGAAATGGATACTGTTCAAAAATGCCCACAAATGTTAACCATGGCAAA | SEQ ID NO: 3323 | |
| 270 | A_24_P333112 | A_24_P333112 | GGTCATCAGAATCAGAAGGTATCAATGTGTGAGCCCAGCAGGACGAAAAGGTATTGCAACTT | SEQ ID NO: 3324 | |

Fig. 24-15

| No. | Probe ID No. | Symbols of genes | Sequence | SEQ ID NO: | Descriptions of genes (letters and numbers within [ ] indicates GenBank accession No.) |
|---|---|---|---|---|---|
| 271 | A_24_P33807 | LOC652558 | TAAGAAAATAATTGGTTTGACAGACAAGCTTTGATTGCTCCATGTCTTGGTAAATATGG | SEQ ID NO: 3325 | PREDICTED: Homo sapiens similar to 60S ribosomal protein L7 (LOC652558), mRNA [XR_019386] |
| 272 | A_24_P344537 | ZNF625 | TCGAGCGGTTAAAATCCAGTGAAAGGCTCACAGTGGAGAAAAACCCTGTAGCTCCAACACT | SEQ ID NO: 3326 | Homo sapiens zinc finger protein 625 (ZNF625), mRNA [NM_145233] |
| 273 | A_24_P349636 | LOC388401 | AGTTGCTTGGACAGATAACACTTTGATTGCTCGATCTCTTGGTAAATATAGGATCAACTG | SEQ ID NO: 3327 | PREDICTED: Homo sapiens similar to 60S ribosomal protein L7 (LOC388401), mRNA [XR_016879] |
| 274 | A_24_P364025 | UBE2D1 | ATGTGATGGGTGTAGTCATTAAGAAAGCATTTAAATACACTTGAGTATTTTGTCATGGTTC | SEQ ID NO: 3328 | Homo sapiens ubiquitin-conjugating enzyme E2D 1 (UBC4/5 homolog, yeast) (UBE2D1), mRNA [NM_003338] |
| 275 | A_24_P364807 | AYTL1 | TGTAACTCTTGTTCTAGGTAATCGTTCTGTCTCAACAAACTTGTCAAGGGTGTGTGTAA | SEQ ID NO: 3329 | Homo sapiens mRNA; cDNA DKFZp686H22112 (from clone DKFZp686H22112). [BX641069] |
| 276 | A_24_P366165 | LOC391126 | ACTTCGAAGCAAATCAAAATAGGAAAAGGCATTTGAATGCACCTTCCCACATTCACAGG | SEQ ID NO: 3330 | PREDICTED: Homo sapiens similar to 60S ribosomal protein L26 (Silica-induced gene 20 protein) (SIG-20) (LOC391126), mRNA [XR_019504] |
| 277 | A_24_P366546 | RPL31P10 | CGGCTGTGCAGAAGAACGGTATGAGGATGAAGATCAAATAAGCTGTATACTTGGTTACC | SEQ ID NO: 3331 | PREDICTED: Homo sapiens similar to ribosomal protein L31 (LOC390283), mRNA [XR_018695] |
| 278 | A_24_P367191 | LOC652890 | AGTTAACATGCTCAGGACTGTAGAGGCCATATATTGCCTGTCTGTGGGTACCCAAATCTGAAGTC | SEQ ID NO: 3332 | PREDICTED: Homo sapiens similar to 60S ribosomal protein L7 (LOC652890), mRNA [XR_019544] |
| 279 | A_24_P367199 | A_24_P367199 | TCTTATGCTCAGCACCAACAGTCTGCCAAATCCAGAAGAAGGTGTAATCATGACCTGAGA | SEQ ID NO: 3333 | |
| 280 | A_24_P367369 | A_24_P367369 | ATTTAAAGGTTTCGATGTTAGAATTCTCTGGTCGGTCGAGGATATCCAAGTGAACAAAGCATCTAA | SEQ ID NO: 3334 | |
| 281 | A_24_P375932 | A_24_P375932 | ATGGTTAAAAATCGAGAGGAACAATGCAGAAACTTAAGGGTTTAGATGTAGATTGTCTGGTC | SEQ ID NO: 3335 | |
| 282 | A_24_P381825 | PSMC6 | ATGAAAGCAGTCAGAAAGTCGGTCGATTGCTAAGAAGGTGGAGTCTAAATTGGACTACAAA | SEQ ID NO: 3336 | Homo sapiens proteasome (prosome, macropain) 26S subunit, ATPase, 6 (PSMC6), mRNA [NM_002806] |
| 283 | A_24_P383999 | RPS3A | TGGTTTTTGTCGTAAAAGCGAACAATCAGATACAACAGAGAAGACGTCTTATGGCAGACCAACG | SEQ ID NO: 3337 | Homo sapiens ribosomal protein S3A (RPS3A), mRNA [NM_001006] |
| 284 | A_24_P384411 | A_24_P384411 | ATGGGAAAATCAATAAGAGTGAAGCTTTGACAGATAATGCTTTGACAGCTCGATCTCTTG | SEQ ID NO: 3338 | |
| 285 | A_24_P384539 | LOC730452 | GAAGAAAAGCTGGCAACTTTCTATGTACCCACGAAGCCAAATTGGCATTTGTCATCAGGA | SEQ ID NO: 3339 | PREDICTED: Homo sapiens similar to 60S ribosomal protein L7 (LOC730452), mRNA [XM_001125895] |
| 286 | A_24_P392622 | A_24_P392622 | CATGGAATTGTTCCTTTGGCACACAGTGATCTATAAGAAAGATGATATTGTAGACACCAAA | SEQ ID NO: 3340 | |
| 287 | A_24_P39378 | CCPG1 | TACTTTTGTCGCTGGAACGAACGTGATCAGTTCATCAATAAGTTTTGGTAAAGGGTGT | SEQ ID NO: 3341 | Homo sapiens cell cycle progression 1 (CCPG1), transcript variant 1, mRNA [NM_004748] |
| 288 | A_24_P403303 | PHF20L1 | AAAGCGAGTTATAAAGGTCTTAATTAGATCGAATTGGATCAGCAATAGACCTAAAGG | SEQ ID NO: 3342 | Homo sapiens PHD finger protein 20-like 1 (PHF20L1), transcript variant 3, mRNA [NM_198513] |
| 289 | A_24_P414556 | TTC33 | TACTCAACATTTGCTATATTGTTTTGAGTAATGGATGTTTGTTTTTTGTGTTAATTTGTGA | SEQ ID NO: 3343 | Homo sapiens tetratricopeptide repeat domain 33 (TTC33), mRNA [NM_012382] |
| 290 | A_24_P41551 | LOC641790 | AGGAGATGGGAACTCCTGATGTGGCATTGTGATATGAGGCACAACAAAGTGCTAGTCTGGAAA | SEQ ID NO: 3344 | PREDICTED: Homo sapiens similar to ribosomal protein L31 (LOC641790), mRNA [XR_018025] |

Fig. 24-16

| No. | Probe ID No. | Symbols of genes | Sequence | SEQ ID NO: | Descriptions of genes (letters and numbers within [ ] indicates GenBank accession No.) |
|---|---|---|---|---|---|
| 291 | A_24_P418712 | A_24_P418712 | AGGGTCAACAAAGCTGTCTGGGGCAAAGAATAAGGAATATCGATACCATATGTGTGTTA | SEQ ID NO: 3345 | |
| 292 | A_24_P4877 | ZCRB1 | GAAAAATTAATAGTATCATGTTAATACTATTATTGTCATCCCAAGAAAAAAGATATTTA | SEQ ID NO: 3346 | Homo sapiens zinc finger CCHC-type and RNA binding motif 1 (ZCRB1), mRNA [NM_033114] |
| 293 | A_24_P60437 | BC065737 | TGCAGAATGATGAAGTTGACATTTAGAAAATTCCTGATTAGTGAAGATGTTCAGGGCAAA | SEQ ID NO: 3347 | Homo sapiens cDNA clone IMAGE:30404477, partial cds. [BC065737] |
| 294 | A_24_P538403 | ROCK1 | TTAAGAGGTTTGTTGGACTTTCATAAATTGAGTAGAATGTTTGAATCAAAGTACCTGCTAC | SEQ ID NO: 3348 | Homo sapiens Rho-associated, coiled-coil containing protein kinase 1 (ROCK1), mRNA [NM_005406] |
| 295 | A_24_P54178 | TMED5 | GCTCTGTATATGCATTTGGATGATTAATGTTATGTGTTCTTTCATGTGAATGTCAAGACA | SEQ ID NO: 3349 | Homo sapiens transmembrane emp24 protein transport domain containing 5 (TMED5), mRNA [NM_016040] |
| 296 | A_24_P557232 | CB111670 | GTTTCTTCTTGGTCAAAAACACACTCAAGTCGTCTCCAAGTTCGAAGCATTCAGCAAACAA | SEQ ID NO: 3350 | K-EST0153390 L5HLK1 Homo sapiens cDNA clone L5HLK1-3-D02 5', mRNA sequence [CB111670] |
| 297 | A_24_P6252 | AF086032 | GTATCTAAAACTGAAACAGGCTACTGTGCTATATTGATTTTATTGGTAGTATTGAGCAGACC | SEQ ID NO: 3351 | Homo sapiens full length insert cDNA clone YW25G09. [AF086032] |
| 298 | A_24_P57837 | THC2567891 | AGAAATCCGGAAAGACCTCTTATGCTCAGTAGGACAAATCCGGAAGAAGATGATGGAAA | SEQ ID NO: 3352 | Q6NXR8_HUMAN (Q6NXR8) Ribosomal protein S3a, partial (91%), [THC2567891] |
| 299 | A_24_P587938 | A_24_P587938 | CTTCAAAGAAGCAAAAGGTGGAGATGCTGGGAACAGGAGGACCAGATTAACAGTCTTAT | SEQ ID NO: 3353 | |
| 300 | A_24_P606663 | LOC392030 | TGTGCGGTTGCCCAGAGCAAAAGCGTAATGCGGGTGAAGATTCACCAGATAAGCTCCATACTT | SEQ ID NO: 3354 | PREDICTED: Homo sapiens hypothetical LOC392030 (LOC392030), mRNA [XR_018063] |
| 301 | A_24_P62860 | STAM2 | GTCTATATGGTACGTACTTGATCTACATTTAACGTGGAAAATTAGGAGTATTTGAAAGGTCAGT | SEQ ID NO: 3355 | Homo sapiens signal transducing adaptor molecule (SH3 domain and ITAM motif) 2 (STAM2), mRNA [NM_005843] |
| 302 | A_24_P630039 | AL049321 | AAGATGAGACAATACAAAGTTACATTTTGGACAGATATTAAAACTGGAGAAGACAGGGG | SEQ ID NO: 3356 | Homo sapiens mRNA; cDNA DKFZp564D156 (from clone DKFZp564D156). [AL049321] |
| 303 | A_24_P63347 | PF4V1 | CTACATTTACCTTGAATGTTAGCATTAGCTTGGCAATAATATTAGTAGCTCTTAAGC | SEQ ID NO: 3357 | Homo sapiens platelet factor 4 variant 1 (PF4V1), mRNA [NM_002620] |
| 304 | A_24_P652786 | THC2533996 | TGGTTGTTCGTATCTCAGCCGGAACGATGATTATCCTTGAGGAATGACATTGAGCTGTTT | SEQ ID NO: 3358 | HSU09964 ribosomal protein L9 [Homo sapiens] (exp=-1; wgp=0; cg=0), partial (42%) [THC2533996] |
| 305 | A_24_P685729 | A_24_P685729 | TTGAAGCTTATGTTGATGTCAAGACTATCAGTGATTATTGCTTTGTCGTTTTGTGG | SEQ ID NO: 3359 | |
| 306 | A_24_P6975 | LOC342994 | GGAAGACTTCGAGGGGTTCGTCGTCGTAAGACCTAAAGTTGTTATGAAATTGTCAAAAGA | SEQ ID NO: 3360 | PREDICTED: Homo sapiens similar to ribosomal protein L34 (LOC342994), mRNA [XM_938484] |
| 307 | A_24_P75158 | PTAR1 | CCATTAGATTTGTTCTTATGTCAACGATGACCAAGCGAGCTATAAGTATTGTATTTCTG | SEQ ID NO: 3361 | Homo sapiens mRNA; cDNA DKFZp313P0917 (from clone DKFZp313P0917). [AL832683] |
| 308 | A_24_P755505 | A_24_P755505 | ATACAGAGACCTCTTATGCTCAGGACCAACAGAGAAAGTAAAATGCTGAAGAAGCCCAA | SEQ ID NO: 3362 | |
| 309 | A_24_P76358 | LOC643981 | TTACTGAAGATGTTCAGGGCAAAAACTGCCTAACTTCCGGCATGGATCTTATTCGTGACA | SEQ ID NO: 3363 | PREDICTED: Homo sapiens similar to 40S ribosomal protein S3a (V-fos transformation effector protein) (LOC643981), mRNA [XR_018444] |

Fig. 24-17

| No. | Probe ID No. | Symbols of genes | Sequence | SEQ ID NO: | Descriptions of genes (letters and numbers within [ ] indicates GenBank accession No.) |
|---|---|---|---|---|---|
| 310 | A_24_P792734 | PSMC3 | AGAACGTTAACGGAGTTACTGAATGAAATGGATGATTGATAC TGTGATAGAGTTAAA | SEQ ID NO: 3364 | Homo sapiens protasome (prosome, macropain) 26S subunit, ATPase, 6 (PSMC6), mRNA [NM_002806] |
| 311 | A_24_P82630 | SMCHD1 | TGTTTAATATGTAACACGTAAGAACAATGAAATTTTCTTCTAA GATTTAATACTATCT | SEQ ID NO: 3365 | Homo sapiens mRNA for KIAA0650 protein, partial cds. [AB014560] |
| 312 | A_24_P83968 | LOC730887 | ACAAAGCCCAGCAGAACAACGTGGAACAACAGAGAAACTTTTCT GGTGTGTCTAAGAAGC | SEQ ID NO: 3366 | PREDICTED: Homo sapiens similar to 40S ribosomal protein S7 (S8) (LOC730887), mRNA [XR_015607] |
| 313 | A_24_P84808 | LOC729449 | GAATTGGTTGACAGATAAGACGTCTTGCGATCTCTTGGAAAATAT GGGATCATCTGTATGG | SEQ ID NO: 3367 | PREDICTED: Homo sapiens similar to 60S ribosomal protein L7 (LOC729449), mRNA [XR_015548] |
| 314 | A_24_P850187 | A_24_P850187 | TAAATGAAGTAATCTACAAGGGTGGTTATGGCAAATCAATTG AGTTGCACTTTCCTAG | SEQ ID NO: 3368 | |
| 315 | A_24_P867201 | AK022997 | CTGACATGTGATAAATATTTCAGTGACTTTCAGATTTATTTCT TGTTAGCCGCTGTGTC | SEQ ID NO: 3369 | Homo sapiens cDNA FLJ12935 fis, clone NT2RP2004982. [AK022997] |
| 316 | A_24_P91852 | DYNLT3 | ATAGACATAGAGAGCGGAACACATAACTCATTGAATTTGGAGAG GAATAAGGTTAGGGTT | SEQ ID NO: 3370 | Homo sapiens dynein, light chain, tctex-type 3 (DYNLT3), mRNA [NM_006520] |
| 317 | A_24_P935985 | BCAT1 | ATGCTGTCGAAGGTTTTGTAGAAGCACAGATTAAACATCTAAAATG GCTTGTTACACCAGA | SEQ ID NO: 3371 | Homo sapiens branched chain aminotransferase 1, cytosolic (BCAT1), mRNA [NM_005504] |
| 318 | A_24_P940426 | QKI | AAGCTGTTGAATGAGTCTTAAAATTATACTACTGTGTAAGTGGA CCAAGTTTGGTGAAGC | SEQ ID NO: 3372 | Homo sapiens quaking homolog, KH domain RNA binding (mouse) (QKI), transcript variant 4, mRNA [NM_206855] |
| 319 | A_24_P99046 | STK38L | GCTATGTGTCTTTGCTGATCGATCACAAATAAATGAATGAGAATT TAGTCCATAGAGGTCC | SEQ ID NO: 3373 | Homo sapiens serine/threonine kinase 38 like (STK38L), mRNA [NM_015000] |
| 320 | A_32_P10100 | A_32_P10100 | TATGAGGAAATAGTATCATCATGTTAGAAGCCTTGGAATGACTA TAAATAATGGCTGGTC | SEQ ID NO: 3374 | |
| 321 | A_32_P105397 | THC2642694 | TAAAATGCTACTACAGTATTCTACGATGCAGCGTGAATGTATAT TACAGATAATTCTCTGG | SEQ ID NO: 3375 | Q6TDT1_HUMAN (Q6TDT1) Protein transactivated by hepatitis B virus E antigen, partial (11%) [THC2642694] |
| 322 | A_32_P107935 | DB527271 | GTTTTATGTGAAATAGAGTTTTCAGATTTATGTAGGATGGAAAG TTTTAATACGTCAGAG | SEQ ID NO: 3376 | DB527271 RIKEN full-length enriched human cDNA library, testis Homo sapiens cDNA clone H013095P12 3', mRNA sequence [DB527271] |
| 323 | A_32_P109036 | ZNF493 | AAAGAGGTCAATATCTGCTGCTCACATCTTACTAAACACCAGAGAGT TCATGCTTAATAAAAG | SEQ ID NO: 3377 | Homo sapiens zinc finger protein 493 (ZNF493), transcript variant 1, mRNA [NM_175910] |
| 324 | A_32_P113154 | LOC730861 | ACGACCAAGTTGCAAGAATCGTCTTAAAGTTCAGACTTAAAACAGT ACCAAATAAAAGTCC | SEQ ID NO: 3378 | PREDICTED: Homo sapiens similar to 40S ribosomal protein S3a (V-fos transformation effector protein) (LOC730861), mRNA [XR_015591] |
| 325 | A_32_P114215 | COMMD6 | AATTGCTATCATTCTAAAGTCATGGAGTTGACTTCAGCTTCCGCAACAA AACTAAGGATGG | SEQ ID NO: 3379 | Homo sapiens COMM domain containing 6 (COMMD6), transcript variant 2, mRNA [NM_203495] |
| 326 | A_32_P11451 | NMD3 | CAGTTTAGGGCAGTAGCTGGTTTTGTGATAAATATGTTCCTACC ACATCAAAATGCTGC | SEQ ID NO: 3380 | Homo sapiens NMD3 homolog (S. cerevisiae) (NMD3), mRNA [NM_015938] |
| 327 | A_32_P11931 | LOC441073 | GTGTGATCGATGCCATCCGAAAAGGATGATGAAGGTTCAGGTTGT ACGTGGACACTATAAA | SEQ ID NO: 3381 | PREDICTED: Homo sapiens similar to 60S ribosomal protein L26 (Silica-induced gene 20 protein) (SIG-20) (LOC441073), mRNA [XR_016376] |
| 328 | A_32_P125549 | RPL31P4 | TCTACAGACAGTCAATGTGATGGATGAGAACTAATCCCTGATGATGTCA GATAGATCAAATAAAG | SEQ ID NO: 3382 | PREDICTED: Homo sapiens ribosomal protein L31 pseudogene 4 (RPL31P4), mRNA [XR_018222] |

Fig. 24-18

| No. | Probe ID No. | Symbols of genes | Sequence | SEQ ID NO: | Descriptions of genes (letters and numbers within [ ] indicates GenBank accession No.) |
|---|---|---|---|---|---|
| 329 | A_32_P125917 | THC2753798 | GGCTATAAAGTGTAAGTGGAGACGGCTAAATTGTGAGTACAAAGTTTCTTTTTCACAACAG | SEQ ID NO: 3383 | BF238843 601904445F1 NIH_MGC_54 Homo sapiens cDNA clone IMAGE:4132429 5', mRNA sequence [BF238843] |
| 330 | A_32_P127454 | A_32_P127454 | GGACAGGTTCGATTCTATTCGGAACTTGGTTGCTGCTTACATATGTCCATGTAACAATACAGAA | SEQ ID NO: 3384 | |
| 331 | A_32_P128781 | A_32_P128781 | CATATATTGCATGGGGGTACCCAATCTGAAGTCAGTAATGAACTAATCTCACAAGAGTC | SEQ ID NO: 3385 | |
| 332 | A_32_P135818 | RPS3A | CTTGGTTCATCTGTTCTGTGTTGGTTTTAATAAAAAGGAACAATCAGATATGGAAGAG | SEQ ID NO: 3386 | Homo sapiens ribosomal protein S3A (RPS3A), mRNA [NM_001006] |
| 333 | A_32_P137266 | KIAA1799 | AAGTGGGACCCAAATCTACAATGGTTTGTCAACATGTAATGCCTTTGAATGAACGACAAG | SEQ ID NO: 3387 | Homo sapiens KIAA1799 protein (KIAA1799), mRNA [NM_032437] |
| 334 | A_32_P145153 | RPL31 | ATCGGTGTGCAGGTGTCCAGAAAACGTAATGAGGATGAAGAATTCACCAAATAAGCCATAT | SEQ ID NO: 3388 | Homo sapiens ribosomal protein L31 (RPL31), mRNA [NM_000993] |
| 335 | A_32_P153725 | KIAA1033 | TTTTGTAAAAGATGGCAAGTTGTTACCTACTGAGTGGGGTTTCCTTTTCCCGCAAT | SEQ ID NO: 3389 | Homo sapiens KIAA1033 (KIAA1033), mRNA [NM_015275] |
| 336 | A_32_P155364 | RPL7 | TGAACAGGCTTATTAGAAAAATGAACGAAGGTGTCTACGCATGATTATTTTTCTAAGCTGG | SEQ ID NO: 3390 | Homo sapiens ribosomal protein L7 (RPL7), mRNA [NM_000971] |
| 337 | A_32_P158746 | RPL17 | TTTTGCTGCACATGCTAAAAATGCAGAGAGTAATGGTGAACTTAAGGGTTTAGATGTAG | SEQ ID NO: 3391 | Homo sapiens ribosomal protein L17 (RPL17), transcript variant 1, mRNA [NM_000985] |
| 338 | A_32_P164203 | THC2683448 | TTGATGGTCATTGTAGGAGGCTATTGTATGAATTACTGTGGAGTGCTGTTTACCACATGAT | SEQ ID NO: 3392 | Q7WZG3_PASP1 (Q7WZG3) Ferric uptake regulator, partial (8%) [THC2683448] |
| 339 | A_32_P166340 | SRP9 | ACATTGAAATATGTTTTGTATAAATTTGTCATGTTGAACAAGATTTTAGGATGGTAAGTT | SEQ ID NO: 3393 | Homo sapiens signal recognition particle 9kDa (SRP9), mRNA [NM_003133] |
| 340 | A_32_P170444 | SUB1 | TAGGTATCTCTCCTGAAATTCTTTGCAGTTCATTTTTTATGGCAGTTAATCCAGTGAAAC | SEQ ID NO: 3394 | Activated RNA polymerase II transcriptional coactivator p15 (SUB1 homolog) (Positive cofactor 4) (PC4) (p14). [Source:Uniprot/SWISSPROT:Acc:P53999] [ENST00000265073] |
| 341 | A_32_P1712 | RNASE2 | TCCAGGTGCGTTTAATGTACTGTAACCTCACAACTCGAAGTCGACAGAATATTTCAAACT | SEQ ID NO: 3395 | Homo sapiens ribonuclease, RNase A family, 2 (liver, eosinophil-derived neurotoxin) (RNASE2), mRNA [NM_002934] |
| 342 | A_32_P176619 | CMAH | GATTATATATGGTAGGTCTGATTCTGAAGATAGAAGAATTCAATGGTGGAATTTTGTCTCG | SEQ ID NO: 3396 | Homo sapiens cytidine monophosphate-N-acetylneuraminic acid hydroxylase (CMP-N-acetylneuraminate monooxygenase) (CMAH) on chromosome 6 [NR_002174] |
| 343 | A_32_P178966 | ENST00000379426 | GTAATATAGAGGGTGAAGTCTTTAGTGATACAGACAAGACAACTGTTAAAAAGTGAATCC | SEQ ID NO: 3397 | Novel protein. [Source:Uniprot/SPTREMBL:Acc:Q6T4T1] [ENST00000379426] |
| 344 | A_32_P184394 | TFEC | AGTTGCTTATGGCATACAAGAGGCTAAAATTAATTCAGGTATATTTAATCTTAATAATTATTAT | SEQ ID NO: 3398 | Homo sapiens transcription factor EC (TFEC), transcript variant 1, mRNA [NM_012252] |
| 345 | A_32_P190488 | hCG_26523 | CCCAGCAAGGTGGTTATGACTAGGCTAAAACTGGACAAAGACCGCAAAAGATGCTTGAA | SEQ ID NO: 3399 | PREDICTED: Homo sapiens similar to 60S ribosomal protein L26 (LOC646161), mRNA [XR_018048] |
| 346 | A_32_P193322 | RICTOR | ACCACATGAGTTTCTTCTTTTTTATTTAGTAATAGGCTGGTAGATATTTGGAGGTTCTGG | SEQ ID NO: 3400 | Homo sapiens rapamycin-insensitive companion of mTOR (RICTOR), mRNA [NM_152756] |

Fig. 24-19

| No. | Probe ID No. | Symbols of genes | Sequence | SEQ ID NO: | Descriptions of genes (letters and numbers within [ ] indicates GenBank accession No.) |
|---|---|---|---|---|---|
| 347 | A_32_P198483 | RPS3A | GGGGCGAAGAAGAAAGTGGTTGATGGATTTCTAAGAAGAGATTGGTATGATGTGAAAGCA | SEQ ID NO: 3401 | Homo sapiens ribosomal protein S3A (RPS3A), mRNA [NM_001006] |
| 348 | A_32_P197752 | FAM76B | TTGTGCTTTTAGCCTGTTTCCAACTAATAATTAGGATTTACCAGTAAGGGTCATTTTGAC | SEQ ID NO: 3402 | Homo sapiens family with sequence similarity 76, member B (FAM76B), mRNA [NM_144664] |
| 349 | A_32_P208178 | RPS3A | GGAAAAGACGTAGAAAAGGCTTGGCAATGCTATTTATCGTGTCGATGATGTCTTCGTTAGA | SEQ ID NO: 3403 | Homo sapiens ribosomal protein S3A (RPS3A), mRNA [NM_001006] |
| 350 | A_32_P224666 | CAPZA2 | AATGCTGTTTTGAGATCTGAAATTAAATGAAAATACTTATTTCAGAAATGCATTTAATG | SEQ ID NO: 3404 | Homo sapiens capping protein (actin filament) muscle Z-line, alpha 2 (CAPZA2), mRNA [NM_006136] |
| 351 | A_32_P22539 | hCG_28523 | ACTACGAAGGTCAGCAAATTGGCAAATTGGTCCAAGGTTTACAGGAAGAAATATGTTATCT | SEQ ID NO: 3405 | PREDICTED: Homo sapiens similar to 60S ribosomal protein L26 (Silica-induced gene 20 protein) (SIG-20) (LOC400055), mRNA [XM_374987] |
| 352 | A_32_P226786 | EC045174 | TTATTGGTGCATGTAAGGCATTATCCTGTCTTAATGAACGGATTAATGCTGTTGATTGTT | SEQ ID NO: 3406 | Homo sapiens cDNA clone IMAGE:5273245. [BC045174] |
| 353 | A_32_P2333 | SUB1 | AGGAAGAAAAGTATTTCTTTAAATGCAGAACAATGGAGGCCAGCTGACAGAACAGATTTC | SEQ ID NO: 3407 | Homo sapiens SUB1 homolog (S. cerevisiae) (SUB1), mRNA [NM_006713] |
| 354 | A_32_P4532 | LOC643932 | GATTCGAGACAGCATTGGAAAAAGACATAGAAAAAGGCTTGCCAATCTATCCTCTCCATGAT | SEQ ID NO: 3408 | PREDICTED: Homo sapiens similar to 40S ribosomal protein S3a (V-fos transformation effector protein) (LOC643932), mRNA [XR_017289] |
| 355 | A_32_P49164 | AV714556 | AAATGGAGAGCTTTGTTATTTGCCAAAGAAGAATTCATCATGTTCCTTCCTTTGTTTTCCC | SEQ ID NO: 3409 | AV714556 AV714556 DCB Homo sapiens cDNA clone DCBADG06 5', mRNA sequence [AV714556] |
| 356 | A_32_P49392 | A_32_P49392 | AATGCTGCCAAATCTGGAAGAAGATGATGGAAATCATGAGCCAAGAGGTGCAGAAATG | SEQ ID NO: 3410 | |
| 357 | A_32_P58074 | RPS3A | GTTGGTTTTACTAAAAAACGGCAAAATCAGATACGGAAGAACCTCTTATGCTCAGCACGAA | SEQ ID NO: 3411 | Homo sapiens ribosomal protein S3A (RPS3A), mRNA [NM_001006] |
| 358 | A_32_P66934 | BX641014 | AATGGCAGTTGCCACCATTCGTCGTAAAATGGCAGTTGTGTGAAGTTTATTTGTTAGAAA | SEQ ID NO: 3412 | Homo sapiens mRNA; cDNA DKFZp686l19109 (from clone DKFZp686l19109) [BX641014] |
| 359 | A_32_P88586 | ARL1 | TTGGGTTACCTGCCTTGAAGGACGGAAAATGGCAGATATTCAAAACGTGAGCAACGAAAG | SEQ ID NO: 3413 | Homo sapiens ADP-ribosylation factor-like 1 (ARL1), mRNA [NM_001177] |
| 360 | A_32_P7118 | PSMC6 | AGCAGACCTGAGAAATGTTTGTACTGAAGCAGGTATATCGCAATTCGTGCTGATCATGA | SEQ ID NO: 3414 | Homo sapiens proteasome (prosome, macropain) 26S subunit, ATPase, 6 (PSMC6), mRNA [NM_002806] |
| 361 | A_32_P73222 | AA631847 | TTTCTTTGTTTTGGACAATCTCATAAGAACTTTAGGTCTTACAGCACGAACCCGTCGAAG | SEQ ID NO: 3415 | np61b02.s1 NCI_CGAP_Br2 Homo sapiens cDNA clone IMAGE:1130763 3' similar to TR:G971838 G971838 60S RIBOSOMAL PROTEIN L34 ;, mRNA sequence [AA631847] |
| 362 | A_32_P93782 | RPL26 | AGGTGTGTAGATGGACAGTATAAAGGTCAGCAAATTGGCAAAGTAGTCGAGGTTTACAGGA | SEQ ID NO: 3416 | Homo sapiens ribosomal protein L26 (RPL26), mRNA [NM_000987] |
| 363 | A_32_P9362 | RP11-11C5.2 | AACAAGACGAGAAATATAATTGAGAAGGATCGTGTTTACAGAGGACTTGTTTAAAGTGT | SEQ ID NO: 3417 | Homo sapiens similar to RIKEN cDNA 2410129H14 (LOC440145), mRNA [NM_001071775] |

DETECTION OF DIGESTIVE ORGAN CANCER, GASTRIC CANCER, COLORECTAL CANCER, PANCREATIC CANCER, AND BILIARY TRACT CANCER BY GENE EXPRESSION PROFILING

CROSS-REFERENCE TO RELATED APPLICATIONS

This application is a 371 of PCT/JP2010/063122, filed Aug. 3, 2010, which claims the benefit of Japanese Patent Application No. 2009-193702, filed Aug. 24, 2009, the contents of each of which are incorporated herein by reference.

TECHNICAL FIELD

The present invention relates to detection and diagnosis of digestive organ cancer, gastric cancer, colorectal cancer, pancreatic cancer, and biliary tract cancer via gene expression analysis using peripheral blood as a material.

BACKGROUND ART

Digestive organ cancer is the most common form of malignant tumor among the Japanese. According to a survey by the Ministry of Health, Labour and Welfare, 177,000 patients die annually. Early detection and treatment can result in complete healing. The earlier the stage of the lesions, the fewer clinical symptoms are presented. Hence, some digestive organ cancer cases are detected in an advanced state, resulting in a poor prognostic outcome.

Gastric cancer is the most common form of digestive system malignant tumor among the Japanese. According to a survey by the Ministry of Health, Labour and Welfare, 50,000 patients die annually. Also, colorectal cancer is the form of digestive system malignant tumor that ranks $3^{rd}$ highest number in terms of deaths due to site-specific cancer (including both males and females) among the Japanese. According to a survey by the Ministry of Health, Labour and Welfare, 41,000 patients die annually. Both gastric cancer and colorectal cancer can be cured by early detection and treatment. The earlier the stage of the lesions, the fewer clinical symptoms are presented. Hence, some cases are detected in an advanced state, resulting in a poor prognostic outcome. Opportunities for early detection include many incidental detections by endoscopic examination and/or imaging studies upon examination and many detections during investigation of symptoms that are not directly associated with cancer. Currently, no hemodiagnosis marker useful for early detection of digestive organ cancer exists. It is extremely important to establish a system capable of diagnosing the presence of digestive organ cancer at as early a stage as possible.

In particular, pancreatic cancer is a form of digestive system malignant tumor that ranks the $5^{th}$ highest in terms of the number of deaths due to site-specific cancer (including both males and females) among the Japanese. According to a survey by the Ministry of Health, Labour and Welfare, 23,000 patients die annually. Cancer detection is very difficult and early cancer detection is rare. 75% of cases diagnosed with pancreatic cancer are already inoperable cases. Pancreatic cancer is a digestive organ cancer resulting in extremely poor prognosis such that the patients die within 1 to 2 years after detection (According a survey by the Center for Cancer Control and Information Services, National Cancer Center, http colon, forward slash, forward slash, gangojo, dot jp public, forward slash, cancer, forward slash, data forward slash, pancreas dot html). Although an advanced diagnostic technique for pancreatic cancer has long been desired, no useful early diagnosis method has been established.

Furthermore, biliary tract cancer is a form of malignant tumor that ranks $6^{th}$ highest in terms of the number of deaths due to site-specific cancer (including both males and females) among the Japanese. According to a survey by the Ministry of Health, Labour and Welfare, 15,000 patients die annually. In most cases, early detection is difficult because of the lack of subjective symptoms.

Recent development in DNA microarray techniques and human genome sequencing have enabled extensive gene expression analysis of all genes. Accordingly, new types of cancer diagnosis, prognostic prediction, prediction of recurrence rate after treatment, and the like have become possible. The present inventors have analyzed the pathological conditions of various diseases and developed for the purpose of developing a diagnostic tool through application of gene expression analysis such as analysis of gene expression profiles in chronic hepatitis patients (see non-patent documents 1 to 3) and gene expression analysis of liver tissue in diabetes mellitus patients. However, these forms of analysis are problematic in terms of their excessive invasiveness, and hospitalization and tissue (organ tissue such as liver tissue) sampling are required. Thereafter, a method requiring less invasiveness has been reported, wherein a gene group capable of distinguishing type C cirrhosis from type C liver cancer and peripheral blood mononuclear cells are used (see patent document 1 and non-patent document 4). This method is advantageous for patients because blood is used in this method and thus it offers a low degree of invasiveness for patients. However, the method is problematic in that collection of peripheral blood mononuclear cells requires several separation processes, the method is complicated as an actual test method, and the method requires much time for the test results to be obtained.

PRIOR ART DOCUMENTS

Patent Document

Patent document 1 JP Patent Publication (Kokai) No. 2008-126 A

Non-Patent Documents

Non-patent document 1 MASAO HONDA et al., GASTROENTEROLOGY 2001; 120:955-966

Non-patent document 2 MASAO HONDA et al., Am J Gastroenterol 2005; 100: 2019-2030

Non-patent document 3 YUKIHIRO SHIROTA et al., HEPATOLOGY Vol. 33, No. 4, 2001, 832-840

Non-patent document 4 YOSHIO SAKAI et al., Cancer Research; 68 (24) 2008. 10267-10279

DISCLOSURE OF THE INVENTION

Problem to be Solved by the Invention

An object of the present invention is to provide:

a method for detecting digestive organ cancer, gastric cancer, colorectal cancer, pancreatic cancer, and biliary tract cancer by analyzing genes with expression levels that vary in association with digestive organ cancer, gastric cancer, colorectal cancer, pancreatic cancer, and biliary tract cancer, whereby invasiveness to patients is low and genes can be easily extracted from patients; and an in vitro diagnostic.

Means for Solving the Problem

The present inventors have initiated clinical trials to verify if digestive organ cancer, gastric cancer, colorectal cancer, pancreatic cancer, and biliary tract cancer can be diagnosed by gene expression analysis using peripheral blood, and thus found that such diagnosis is possible.

Peripheral blood can be collected in a manner that requires a relatively low degree of invasiveness, and thus its practicality and usefulness in clinical examination are extremely high. Peripheral blood is composed of cell components including, in addition to erythrocytes and blood platelets, leukocytes containing lymphocytes, monocytes, and granulocytes. These cell components are thought to vary their phenotypes and functions depending on lesions in an in vivo environment.

The present inventors have conducted gene expression analysis of peripheral blood from 24 digestive organ cancer patients and 8 normal healthy subjects. Specifically, they have found that digestive organ cancer cases can be distinguished from normal healthy subjects by clustering analysis conducted using data from analysis with about 23,000 probes on DNA microarrays. Through comparison of the gene expression of a group of digestive organ cancer cases with that of a group of normal healthy subjects, 868 probes corresponding to genes with expression levels that differ significantly between the groups were found. With the use of the probe set, hierarchical clustering was performed for the above digestive organ cancer case group and the above normal healthy subject group, so that 2 clusters were formed. Thus the present inventors have found that the digestive organ cancer cases can be distinguished from the normal healthy subjects. Also, a prediction model was applied to 40 cancer cases and 13 normal healthy subject cases (differing from the cancer cases and the normal healthy subjects used for extraction of 868 probes), so that cancer cases and normal healthy subjects were determined. As a result, 39 out of 40 previously diagnosed cancer cases were determined to be actually cancer cases, and the probability that such cases had been properly diagnosed was 97.5%. Moreover, 9 out of 13 previously diagnosed normal healthy subject cases were determined to be normal healthy subject cases, and the probability that such cases had been properly diagnosed was 69.2%. The percentage of cases correctly determined was 90.6% ($^{48}/_{53}$).

Furthermore, the present inventors have conducted gene expression analysis of peripheral blood from 39 digestive organ cancer patients and peripheral blood from 15 normal healthy subjects. Specifically, they have found that digestive organ cancer cases can be distinguished from normal healthy subjects by clustering analysis conducted using data from analysis with about 23,000 probes on DNA microarrays. Through comparison of the gene expression of a group of digestive organ cancer cases with that of a group of normal healthy subjects, 25 probes corresponding to genes with expression levels that differ significantly between the groups were found. With the use of the probe set, hierarchical clustering was performed for the above digestive organ cancer case group and the above normal healthy subject group, so that 2 clusters were formed. Thus the present inventors have found that the digestive organ cancer cases can be distinguished from the normal healthy subjects.

As a result of the use of the above probes, the percentage of cases correctly determined was 92.3%.

Also, the present inventors have conducted gene expression analysis of peripheral blood from 8 gastric cancer patients and 8 normal healthy subjects. Specifically, they have found that gastric cancer cases can be distinguished from normal healthy subjects by clustering analysis conducted using data from analysis with about 22,000 probes on DNA microarrays. Through comparison of the gene expression of a group of gastric cancer cases with that of a group of normal healthy subjects, 713 probes corresponding to genes with expression levels that differ significantly between the groups were found. With the use of the probe set, hierarchical clustering was performed for the above gastric cancer case group and the above normal healthy subject group, so that 2 clusters were formed. Thus the present inventors have found that the gastric cancer cases can be distinguished from the normal healthy subjects. Also, a prediction model was applied to 10 cancer cases and 13 normal healthy subject cases (differing from the cancer cases and the normal healthy subjects used for extraction of 713 probes), so that cancer cases and normal healthy subjects were determined. As a result, 7 out of 10 previously diagnosed cancer cases were determined to be actually cancer cases, and the probability that such cases had been properly diagnosed was 70%. Moreover, 13 out of 13 previously diagnosed normal healthy subject cases were determined to be normal healthy subject cases, and the probability that such cases had been properly diagnosed was 100%. The percentage of cases correctly determined was 87.0% ($^{20}/_{23}$).

The present inventors have conducted gene expression analysis of peripheral blood from 8 colorectal cancer patients and 8 normal healthy subjects. Specifically, they have found that colorectal cancer cases can be distinguished from normal healthy subjects by clustering analysis conducted using data from analysis with about 22,000 probes on DNA microarrays. Through comparison of the gene expression of a group of colorectal cancer cases with that of a group of normal healthy subjects, 771 probes corresponding to genes with expression levels that differ significantly between the groups were found. With the use of the probe set, hierarchical clustering was performed for the above colorectal cancer case group and the above normal healthy subject group, so that 2 clusters were formed. Thus, colorectal cancer cases were distinguished from the normal healthy subjects. Also, a prediction model was applied to 10 cancer cases and 13 normal healthy subject cases (differing from the cancer cases and the normal healthy subjects used for extraction of 771 probes), so that cancer cases and normal healthy subjects are determined. As a result, 9 out of 10 previously diagnosed cancer cases were determined to be actually cancer cases, and the probability that such cases had been properly diagnosed was 90%. Moreover, 13 out of 13 previously diagnosed normal healthy subject cases were determined to be normal healthy subject cases, and the probability that such cases had been properly diagnosed was 100%. The percentage of cases correctly determined was 95.7% ($^{22}/_{23}$).

The present inventors have conducted gene expression analysis of peripheral blood from 8 pancreatic cancer patients and 8 normal healthy subjects. Specifically, they have found that pancreatic cancer cases can be distinguished from normal healthy subjects by clustering analysis conducted using data from analysis with about 22,000 probes on DNA microarrays. Through comparison of the gene expression of a group of pancreatic cancer cases with that of a group of normal healthy subjects, 677 probes corresponding to genes with expression levels that differ significantly between the groups were found. With the use of the probe set, hierarchical clustering was performed for the above pancreatic cancer case group and the above normal healthy subject group, so that 2 clusters were formed. Thus the present inventors have found that pancreatic cancer cases can be distinguished from the normal healthy subjects. Also, a prediction model was applied to 20 cancer cases and 13 normal healthy subject cases (differing from the cancer cases and the normal healthy subjects used for extraction of 677 probes), so that cancer cases and normal healthy subjects were determined. As a result, 15 out of 20 previously diagnosed cancer cases were determined to be actually cancer cases, and the probability that such cases had been properly diagnosed was 75%. Moreover, 13 out of 13 previously diagnosed normal healthy subject cases were determined to be normal healthy subject cases, and the probability that such cases had been properly diagnosed was 100%. The percentage of cases correctly determined was 84.8% (28/33).

The present inventors have conducted gene expression analysis of peripheral blood from 8 biliary tract cancer patients and 8 normal healthy subjects. Specifically, they have found that biliary tract cancer cases can be distinguished from normal healthy subjects by clustering analysis conducted (to form 3 clusters) using data from analysis with about 22,000 probes on DNA microarrays. Through comparison of the gene expression of a group of biliary tract cancer cases with that of a group of normal healthy subjects, 363 probes corresponding to genes with expression levels that differ significantly between the groups were found. With the use of the probe set, hierarchical clustering was performed for the above biliary tract cancer case group and the above normal healthy subject group, so that 2 clusters were formed. Thus the present inventors have found that the biliary tract cancer cases can be distinguished from the normal healthy subjects. Also, a prediction model was applied to 8 cancer cases and 13 normal healthy subject cases (differing from the cancer cases and the normal healthy subjects used for extraction of 363 probes), so that cancer cases and normal healthy subjects were determined. As a result, 8 out of 8 previously diagnosed cancer cases were determined to be actually cancer cases, and the probability that such cases had been properly diagnosed was 100%. Moreover, 13 out of 13 previously diagnosed normal healthy subject cases were determined to be normal healthy subject cases, and the probability that such cases had been properly diagnosed was 100%. The percentage of cases correctly determined was 100% (21/21).

Based on these results, it was found that examination of changes in expression of the gene set in peripheral blood enables diagnosis of digestive organ cancer, gastric cancer, colorectal cancer, pancreatic cancer, and biliary tract cancer. Thus, the present invention was completed. The method of the present invention enables preparation of a new practical diagnostic kit for diagnosis of digestive organ cancer by applying a DNA microarray developmental technique, a real-time PCR method, and an ELISA method.

Currently, general tumor markers covered by health insurance are not always useful for all digestive organ cancer patients. However, the detection sensitivity of the gene expression analysis of the present invention is 90.6%, allowing digestive organ cancer to be specified with very high detection sensitivity through convenient blood collection. Specifically, the present invention is as follows.

[1] A reagent for detecting digestive organ cancer by measuring the expression of genes corresponding to probes consisting of nucleotide sequences shown in SEQ ID NO: 220, 506, 508, 523, 538, 554, 570, 589, 597, 602, 618, 654, 689, 701, 726, 744, 762, 763, 781, 795, and 849 in peripheral blood, wherein the reagent contains all probes consisting of the nucleotide sequences shown in SEQ ID NOs: 220, 506, 508, 523, 538, 554, 570, 589, 597, 602, 618, 654, 689, 701, 726, 744, 762, 763, 781, 795, and 849; or a reagent for detecting digestive organ cancer by measuring the expression of genes corresponding to probes consisting of the nucleotide sequences shown in SEQ ID NOs: 3030 to 3054 in peripheral blood, wherein the reagent contains all probes consisting of the nucleotide sequences shown in SEQ ID NOs: 3030 to 3054.

[2] The reagent for detecting digestive organ cancer according to [1], containing a DNA microarray in which the probes of [1] bind to a substrate.

[3] A method for detecting digestive organ cancer, comprising obtaining the gene expression profiles of all genes corresponding to probes consisting of the nucleotide sequences shown in SEQ ID NOs: 220, 506, 508, 523, 538, 554, 570, 589, 597, 602, 618, 654, 689, 701, 726, 744, 762, 763, 781, 795, and 849 in peripheral blood from a subject, or all genes corresponding to probes consisting of the nucleotide sequences shown in SEQ ID NOs: 3030 to 3054 in peripheral blood from a subject and then detecting digestive organ cancer based on the expression profiles.

[4] A reagent for detecting gastric cancer by measuring the expression of genes corresponding to probes consisting of the nucleotide sequences shown in SEQ ID NOs: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578 in peripheral blood, wherein the reagent contains all probes consisting of the nucleotide sequences shown in SEQ ID NO: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578.

[5] The reagent for detecting gastric cancer according to [4], containing a DNA microarray in which the probes of [4] bind to a substrate.

[6] A method for detecting gastric cancer, comprising obtaining the gene expression profiles of all genes corresponding to probes consisting of the nucleotide sequences shown in SEQ ID NOs: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578 in peripheral blood from a subject and then detecting gastric cancer based on the expression profiles.

[7] A reagent for detecting colorectal cancer by measuring the expression of genes corresponding to probes consisting of the nucleotide sequences shown in SEQ ID NOs: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340, wherein the reagent contains all probes consisting of the nucleotide sequences shown in SEQ ID NOs: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340.

[8] The reagent for detecting colorectal cancer according to [7], containing a DNA microarray in which the probes of [7] bind to a substrate.

[9] A method for detecting colorectal cancer, comprising obtaining the gene expression profiles of all genes corresponding to probes consisting of the nucleotide sequences shown in SEQ ID NOs: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340 in peripheral blood from a subject and then detecting colorectal cancer based on the gene expression profiles.

[10] A reagent for detecting pancreatic cancer by measuring the expression of genes corresponding to probes consisting of the nucleotide sequences shown in SEQ ID NOs: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003, wherein the reagent contains all probes consisting of the nucleotide sequences shown in SEQ ID NO: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003.

[11] The reagent for detecting pancreatic cancer according to [10], containing a DNA microarray in which the probes of [10] bind to a substrate.

[12] A method for detecting pancreatic cancer, comprising obtaining the gene expression profiles of all genes corresponding to probes consisting of the nucleotide sequences shown in SEQ ID NOs: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003 in peripheral blood from a subject and detecting pancreatic cancer based on the expression profiles.

[13] A reagent for detecting biliary tract cancer by measuring the expression of genes corresponding to probes consisting of the nucleotide sequences shown in SEQ ID NOs: 3055 to 3417, which contains all probes consisting of the nucleotide sequences shown in SEQ ID NOs: 3055 to 3417.

[14] The reagent for detecting biliary tract cancer according to [13], containing a DNA microarray in which the probes of [13] bind to a substrate.

[15] A method for detecting biliary tract cancer, comprising obtaining the gene expression profiles of all genes corresponding to probes consisting of the nucleotide sequences shown in SEQ ID NOs: 3055 to 3417 in peripheral blood from a subject, and then detecting biliary tract cancer based on the expression profiles.

This description includes the disclosure of the description and drawings of Japanese Patent Application No. 2009-193702, from which the present application claims priority.

Effects of the Invention

The expression levels of the genes corresponding to the probes of the present invention vary among digestive organ cancer, gastric cancer, colorectal cancer, pancreatic cancer, and biliary tract cancer. Through analysis of the expression profiles of these genes, digestive organ cancer, gastric cancer, colorectal cancer, pancreatic cancer, or biliary tract cancer can be detected. Furthermore, a risk of developing digestive organ cancer, gastric cancer, colorectal cancer, pancreatic cancer, or biliary tract cancer can be predicted, for example.

BRIEF DESCRIPTION OF THE DRAWINGS

FIG. 1-1 shows 868 probes of a $1^{st}$ probe group that can be used for detection of digestive organ cancer.

FIG. 1-2 shows 868 probes that can be used for detection of digestive organ cancer (continuation).

FIG. 1-3 shows 868 probes that can be used for detection of digestive organ cancer (continuation).

FIG. 1-4 shows 868 probes that can be used for detection of digestive organ cancer (continuation).

FIG. 1-5 shows 868 probes that can be used for detection of digestive organ cancer (continuation).

FIG. 1-6 shows 868 probes that can be used for detection of digestive organ cancer (continuation).

FIG. 1-7 shows 868 probes that can be used for detection of digestive organ cancer (continuation).

FIG. 1-8 shows 868 probes that can be used for detection of digestive organ cancer (continuation).

FIG. 1-9 shows 868 probes that can be used for detection of digestive organ cancer (continuation).

FIG. 1-10 shows 868 probes that can be used for detection of digestive organ cancer (continuation).

FIG. 1-11 shows 868 probes that can be used for detection of digestive organ cancer (continuation).

FIG. 1-12 shows 868 probes that can be used for detection of digestive organ cancer (continuation).

FIG. 1-13 shows 868 probes that can be used for detection of digestive organ cancer (continuation).

FIG. 1-14 shows 868 probes that can be used for detection of digestive organ cancer (continuation).

FIG. 1-15 shows 868 probes that can be used for detection of digestive organ cancer (continuation).

FIG. 1-16 shows 868 probes that can be used for detection of digestive organ cancer (continuation).

FIG. 1-17 shows 868 probes that can be used for detection of digestive organ cancer (continuation).

FIG. 1-18 shows 868 probes that can be used for detection of digestive organ cancer (continuation).

FIG. 1-19 shows 868 probes that can be used for detection of digestive organ cancer (continuation).

FIG. 1-20 shows 868 probes that can be used for detection of digestive organ cancer (continuation).

FIG. 1-21 shows 868 probes that can be used for detection of digestive organ cancer (continuation).

FIG. 1-22 shows 868 probes that can be used for detection of digestive organ cancer (continuation).

FIG. 1-23 shows 868 probes that can be used for detection of digestive organ cancer (continuation).

FIG. 1-24 shows 868 probes that can be used for detection of digestive organ cancer (continuation).

FIG. 1-25 shows 868 probes that can be used for detection of digestive organ cancer (continuation).

FIG. 1-26 shows 868 probes that can be used for detection of digestive organ cancer (continuation).

FIG. 1-27 shows 868 probes that can be used for detection of digestive organ cancer (continuation).

FIG. 1-28 shows 868 probes that can be used for detection of digestive organ cancer (continuation).

FIG. 1-29 shows 8.68 probes that can be used for detection of digestive organ cancer (continuation).

FIG. 1-30 shows 868 probes that can be used for detection of digestive organ cancer (continuation).

FIG. 1-31 shows 868 probes that can be used for detection of digestive organ cancer (continuation).

FIG. 1-32 shows 868 probes that can be used for detection of digestive organ cancer (continuation).

FIG. 1-33 shows 868 probes that can be used for detection of digestive organ cancer (continuation).

FIG. 1-34 shows 868 probes that can be used for detection of digestive organ cancer (continuation).

FIG. 1-35 shows 868 probes that can be used for detection of digestive organ cancer (continuation).

FIG. 1-36 shows 868 probes that can be used for detection of digestive organ cancer (continuation).

FIG. 1-37 shows 868 probes that can be used for detection of digestive organ cancer (continuation).

FIG. 1-38 shows 868 probes that can be used for detection of digestive organ cancer (continuation).

FIG. 1-39 shows 868 probes that can be used for detection of digestive organ cancer (continuation).

FIG. 1-40 shows 868 probes that can be used for detection of digestive organ cancer (continuation).

FIG. 1-41 shows 868 probes that can be used for detection of digestive organ cancer (continuation).

FIG. 1-42 shows 868 probes that can be used for detection of digestive organ cancer (continuation).

FIG. 1-43 shows 868 probes that can be used for detection of digestive organ cancer (continuation).

FIG. 1-44 shows 868 probes that can be used for detection of digestive organ cancer (continuation).

FIG. 1-45 shows 868 probes that can be used for detection of digestive organ cancer (continuation).

FIG. 1-46 shows 868 probes that can be used for detection of digestive organ cancer (continuation).

FIG. 1-47 shows 868 probes that can be used for detection of digestive organ cancer (continuation).

FIG. 1-48 shows 868 probes that can be used for detection of digestive organ cancer (continuation).

FIG. 2 shows 21 probes with expression levels that differed, significantly particularly between digestive organ cancer patients and normal healthy subjects, from among the 868 probes shown in FIG. 1.

FIG. 3-1 shows 713 probes that can be used for detection of gastric cancer.

FIG. 3-2 shows 713 probes that can be used for detection of gastric cancer (continuation).

FIG. 3-3 shows 713 probes that can be used for detection of gastric cancer (continuation).

FIG. 3-4 shows 713 probes that can be used for detection of gastric cancer (continuation).

FIG. 3-5 shows 713 probes that can be used for detection of gastric cancer (continuation).

FIG. 3-6 shows 713 probes that can be used for detection of gastric cancer (continuation).

FIG. 3-7 shows 713 probes that can be used for detection of gastric cancer (continuation).

FIG. 3-8 shows 713 probes that can be used for detection of gastric cancer (continuation).

FIG. 3-9 shows 713 probes that can be used for detection of gastric cancer (continuation).

FIG. 3-10 shows 713 probes that can be used for detection of gastric cancer (continuation).

FIG. 3-11 shows 713 probes that can be used for detection of gastric cancer (continuation).

FIG. 3-12 shows 713 probes that can be used for detection of gastric cancer (continuation).

FIG. 3-13 shows 713 probes that can be used for detection of gastric cancer (continuation).

FIG. 3-14 shows 713 probes that can be used for detection of gastric cancer (continuation).

FIG. 3-15 shows 713 probes that can be used for detection of gastric cancer (continuation).

FIG. 3-16 shows 713 probes that can be used for detection of gastric cancer (continuation).

FIG. 3-17 shows 713 probes that can be used for detection of gastric cancer (continuation).

FIG. 3-18 shows 713 probes that can be used for detection of gastric cancer (continuation).

FIG. 3-19 shows 713 probes that can be used for detection of gastric cancer (continuation).

FIG. 3-20 shows 713 probes that can be used for detection of gastric cancer (continuation).

FIG. 3-21 shows 713 probes that can be used for detection of gastric cancer (continuation).

FIG. 3-22 shows 713 probes that can be used for detection of gastric cancer (continuation).

FIG. 3-23 shows 713 probes that can be used for detection of gastric cancer (continuation).

FIG. 3-24 shows 713 probes that can be used for detection of gastric cancer (continuation).

FIG. 3-25 shows 713 probes that can be used for detection of gastric cancer (continuation).

FIG. 3-26 shows 713 probes that can be used for detection of gastric cancer (continuation).

FIG. 3-27 shows 713 probes that can be used for detection of gastric cancer (continuation).

FIG. 3-28 shows 713 probes that can be used for detection of gastric cancer (continuation).

FIG. 3-29 shows 713 probes that can be used for detection of gastric cancer (continuation).

FIG. 3-30 shows 713 probes that can be used for detection of gastric cancer (continuation).

FIG. 3-31 shows 713 probes that can be used for detection of gastric cancer (continuation).

FIG. 3-32 shows 713 probes that can be used for detection of gastric cancer (continuation).

FIG. 3-33 shows 713 probes that can be used for detection of gastric cancer (continuation).

FIG. 3-34 shows 713 probes that can be used for detection of gastric cancer (continuation).

FIG. 3-35 shows 713 probes that can be used for detection of gastric cancer (continuation).

FIG. 3-36 shows 713 probes that can be used for detection of gastric cancer (continuation).

FIG. 3-37 shows 713 probes that can be used for detection of gastric cancer (continuation).

FIG. 3-38 shows 713 probes that can be used for detection of gastric cancer (continuation).

FIG. 3-39 shows 713 probes that can be used for detection of gastric cancer (continuation).

FIG. 4-1 shows 107 probes with expression levels that differed significantly particularly between gastric cancer patients and normal healthy subjects, from among 713 probes shown in FIG. 3.

FIG. 4-2 shows 107 probes with expression levels that differed significantly particularly between gastric cancer patients and normal healthy subjects, from among the 713 probes shown in FIG. 3 (continuation).

FIG. 4-3 shows 107 probes with expression levels that differed significantly particularly between gastric cancer patients and normal healthy subjects, from among the 713 probes shown in FIG. 3 (continuation).

FIG. 4-4 shows 107 probes with expression levels that differed significantly particularly between gastric cancer patients and normal healthy subjects, from among the 713 probes shown in FIG. 3 (continuation).

FIG. 4-5 shows 107 probes with expression levels that differed significantly particularly between gastric cancer patients and normal healthy subjects, from among the 713 probes shown in FIG. 3 (continuation).

FIG. 4-6 shows 107 probes with expression levels that differed significantly particularly between gastric cancer patients and normal healthy subjects, from among the 713 probes shown in FIG. 3 (continuation).

FIG. 5-1 shows 771 probes that can be used for detection of colorectal cancer.

FIG. 5-2 shows 771 probes that can be used for detection of colorectal cancer (continuation).

FIG. 5-3 shows 771 probes that can be used for detection of colorectal cancer (continuation).

FIG. 5-4 shows 771 probes that can be used for detection of colorectal cancer (continuation).

FIG. 5-5 shows 771 probes that can be used for detection of colorectal cancer (continuation).

FIG. 5-6 shows 771 probes that can be used for detection of colorectal cancer (continuation).

FIG. 5-7 shows 771 probes that can be used for detection of colorectal cancer (continuation).

FIG. 5-8 shows 771 probes that can be used for detection of colorectal cancer (continuation).

FIG. 5-9 shows 771 probes that can be used for detection of colorectal cancer (continuation).

FIG. 5-10 shows 771 probes that can be used for detection of colorectal cancer (continuation).

FIG. 5-11 shows 771 probes that can be used for detection of colorectal cancer (continuation).

FIG. 5-12 shows 771 probes that can be used for detection of colorectal cancer (continuation).

FIG. 5-13 shows 771 probes that can be used for detection of colorectal cancer (continuation).

FIG. 5-14 shows 771 probes that can be used for detection of colorectal cancer (continuation).

FIG. 5-15 shows 771 probes that can be used for detection of colorectal cancer (continuation).

FIG. 5-16 shows 771 probes that can be used for detection of colorectal cancer (continuation).

FIG. 5-17 shows 771 probes that can be used for detection of colorectal cancer (continuation).

FIG. 5-18 shows 771 probes that can be used for detection of colorectal cancer (continuation).

FIG. 5-19 shows 771 probes that can be used for detection of colorectal cancer (continuation).

FIG. 5-20 shows 771 probes that can be used for detection of colorectal cancer (continuation).

FIG. 5-21 shows 771 probes that can be used for detection of colorectal cancer (continuation).

FIG. 5-22 shows 771 probes that can be used for detection of colorectal cancer (continuation).

FIG. 5-23 shows 771 probes that can be used for detection of colorectal cancer (continuation).

FIG. 5-24 shows 771 probes that can be used for detection of colorectal cancer (continuation).

FIG. 5-25 shows 771 probes that can be used for detection of colorectal cancer (continuation).

FIG. 5-26 shows 771 probes that can be used for detection of colorectal cancer (continuation).

FIG. 5-27 shows 771 probes that can be used for detection of colorectal cancer (continuation).

FIG. 5-28 shows 771 probes that can be used for detection of colorectal cancer (continuation).

FIG. 5-29 shows 771 probes that can be used for detection of colorectal cancer (continuation).

FIG. 5-30 shows 771 probes that can be used for detection of colorectal cancer (continuation).

FIG. 5-31 shows 771 probes that can be used for detection of colorectal cancer (continuation).

FIG. 5-32 shows 771 probes that can be used for detection of colorectal cancer (continuation).

FIG. 5-33 shows 771 probes that can be used for detection of colorectal cancer (continuation).

FIG. 5-34 shows 771 probes that can be used for detection of colorectal cancer (continuation).

FIG. 5-35 shows 771 probes that can be used for detection of colorectal cancer (continuation).

FIG. 5-36 shows 771 probes that can be used for detection of colorectal cancer (continuation).

FIG. 5-37 shows 771 probes that can be used for detection of colorectal cancer (continuation).

FIG. 5-38 shows 771 probes that can be used for detection of colorectal cancer (continuation).

FIG. 5-39 shows 771 probes that can be used for detection of colorectal cancer (continuation).

FIG. 5-40 shows 771 probes that can be used for detection of colorectal cancer (continuation).

FIG. 5-41 shows 771 probes that can be used for detection of colorectal cancer (continuation).

FIG. 6-1 shows 116 probes with expression levels that differed significantly particularly between colorectal cancer patients and normal healthy subjects, from among the 771 probes shown in FIG. 5.

FIG. 6-2 shows 116 probes with expression levels that differed significantly particularly between colorectal cancer patients and normal healthy subjects, from among the 771 probes shown in FIG. 5 (continuation).

FIG. 6-3 shows 116 probes with expression levels that differed significantly particularly between colorectal cancer patients and normal healthy subjects, from among the 771 probes shown in FIG. 5 (continuation).

FIG. 6-4 shows 116 probes with expression levels differed significantly particularly between colorectal cancer patients and normal healthy subjects, from among the 771 probes shown in FIG. 5 (continuation).

FIG. 6-5 shows 116 probes with expression levels differed significantly particularly between colorectal cancer patients and normal healthy subjects, from among the 771 probes shown in FIG. 5 (continuation).

FIG. 6-6 shows 116 probes with expression levels differed significantly particularly between colorectal cancer patients and normal healthy subjects, from among the 771 probes shown in FIG. 5 (continuation).

FIG. 6-7 shows 116 probes with expression levels differed significantly particularly between colorectal cancer patients and normal healthy subjects, from among the 771 probes shown in FIG. 5 (continuation).

FIG. 7-1 shows 677 probes that can be used for detection of pancreatic cancer.

FIG. 7-2 shows 677 probes that can be used for detection of pancreatic cancer (continuation).

FIG. 7-3 shows 677 probes that can be used for detection of pancreatic cancer (continuation).

FIG. 7-4 shows 677 probes that can be used for detection of pancreatic cancer (continuation).

FIG. 7-5 shows 677 probes that can be used for detection of pancreatic cancer (continuation).

FIG. 7-6 shows 677 probes that can be used for detection of pancreatic cancer (continuation).

FIG. 7-7 shows 677 probes that can be used for detection of pancreatic cancer (continuation).

FIG. 7-8 shows 677 probes that can be used for detection of pancreatic cancer (continuation).

Figure 9:
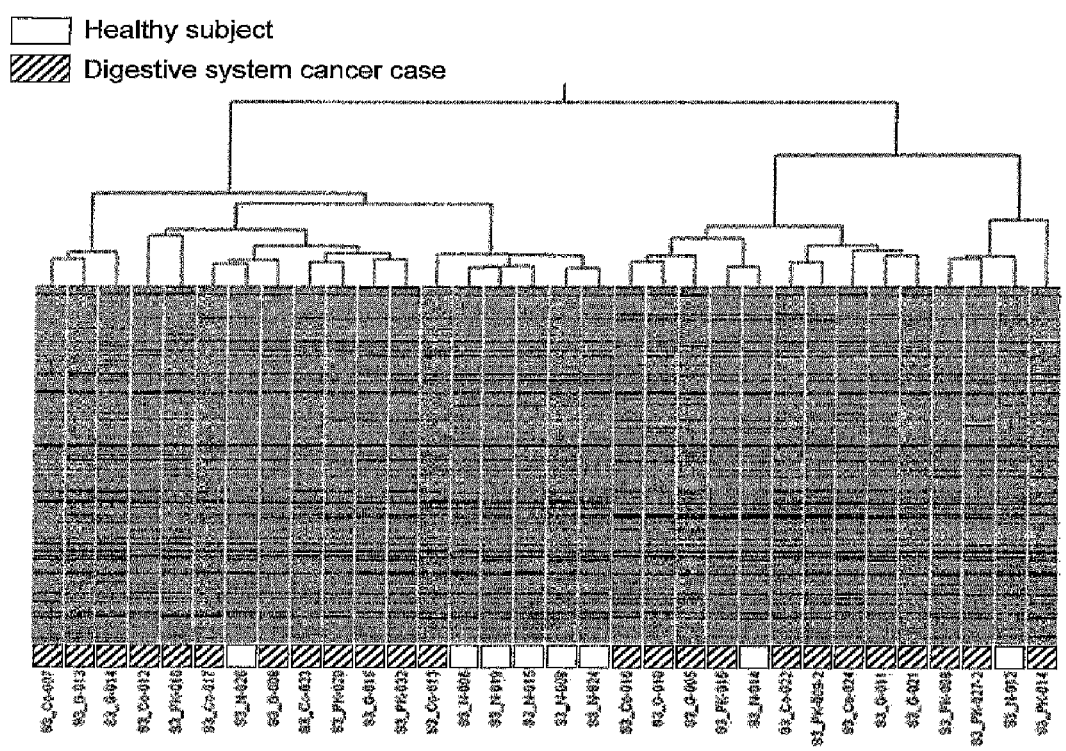

FIG. 7-9 shows 677 probes that can be used for detection of pancreatic cancer (continuation).

FIG. 7-10 shows 677 probes that can be used for detection of pancreatic cancer (continuation).

FIG. 7-11 shows 677 probes that can be used for detection of pancreatic cancer (continuation).

FIG. 7-12 shows 677 probes that can be used for detection of pancreatic cancer (continuation).

FIG. 7-13 shows 677 probes that can be used for detection of pancreatic cancer (continuation).

FIG. 7-14 shows 677 probes that can be used for detection of pancreatic cancer (continuation).

FIG. 7-15 shows 677 probes that can be used for detection of pancreatic cancer (continuation).

FIG. 7-16 shows 677 probes that can be used for detection of pancreatic cancer (continuation).

FIG. 7-17 shows 677 probes that can be used for detection of pancreatic cancer (continuation).

FIG. 7-18 shows 677 probes that can be used for detection of pancreatic cancer (continuation).

FIG. 7-19 shows 677 probes that can be used for detection of pancreatic cancer (continuation).

FIG. 7-20 shows 677 probes that can be used for detection of pancreatic cancer (continuation).

FIG. 7-21 shows 677 probes that can be used for detection of pancreatic cancer (continuation).

FIG. 7-22 shows 677 probes that can be used for detection of pancreatic cancer (continuation).

FIG. 7-23 shows 677 probes that can be used for detection of pancreatic cancer (continuation).

FIG. 7-24 shows 677 probes that can be used for detection of pancreatic cancer (continuation).

FIG. 7-25 shows 677 probes that can be used for detection of pancreatic cancer (continuation).

FIG. 7-26 shows 677 probes that can be used for detection of pancreatic cancer (continuation).

FIG. 7-27 shows 677 probes that can be used for detection of pancreatic cancer (continuation).

FIG. 7-28 shows 677 probes that can be used for detection of pancreatic cancer (continuation).

FIG. 7-29 shows 677 probes that can be used for detection of pancreatic cancer (continuation).

FIG. 7-30 shows 677 probes that can be used for detection of pancreatic cancer (continuation).

FIG. 7-31 shows 677 probes that can be used for detection of pancreatic cancer (continuation).

FIG. 7-32 shows 677 probes that can be used for detection of pancreatic cancer (continuation).

FIG. 7-33 shows 677 probes that can be used for detection of pancreatic cancer (continuation).

FIG. 7-34 shows 677 probes that can be used for detection of pancreatic cancer (continuation).

FIG. 7-35 shows 677 probes that can be used for detection of pancreatic cancer (continuation).

FIG. 7-36 shows 677 probes that can be used for detection of pancreatic cancer (continuation).

FIG. 7-37 shows 677 probes that can be used for detection of pancreatic cancer (continuation).

FIG. 8-1 shows 61 probes with expression levels that differed significantly particularly between pancreatic cancer patients and normal healthy subjects, from among the 677 probes shown in FIG. 7.

FIG. 8-2 shows 61 probes with expression levels that differed significantly particularly between pancreatic cancer patients and normal healthy subjects, from among the 677 probes shown in FIG. 7 (continuation).

FIG. 8-3 shows 61 probes with expression levels that differed significantly particularly between pancreatic cancer patients and normal healthy subjects, from among the 677 probes shown in FIG. 7 (continuation).

FIG. 8-4 shows 61 probes with expression levels that differed significantly particularly between pancreatic cancer patients and normal healthy subjects, from among the 677 probes shown in FIG. 7 (continuation).

FIG. 9 shows the results of hierarchical clustering using 23352 probes for digestive organ cancer cases and normal healthy subjects.

Figure 10:
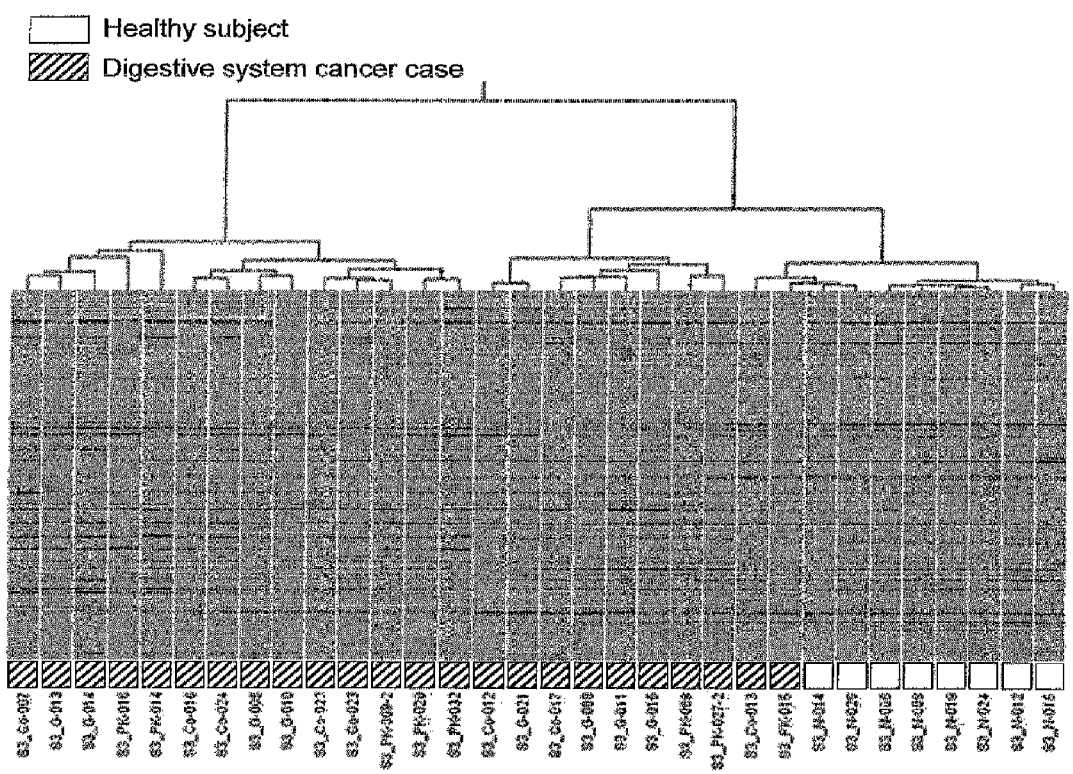

FIG. 10 shows the results of hierarchical clustering using 868 probes corresponding to genes with expression levels that were observed to be attenuated or enhanced in digestive organ cancer cases compared with normal healthy subjects.

Figure 11:
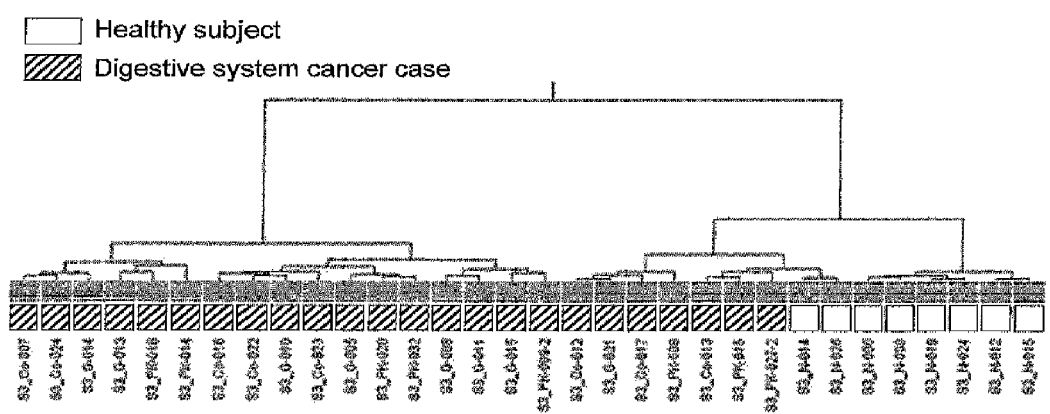

FIG. 11 shows the results of hierarchical clustering using 21 probes corresponding to genes with expression levels that were observed to be attenuated in digestive organ cancer cases at levels 0.4 times or less or enhanced in the same at levels 2.5 times or more than normal healthy subjects.

Figure 12:
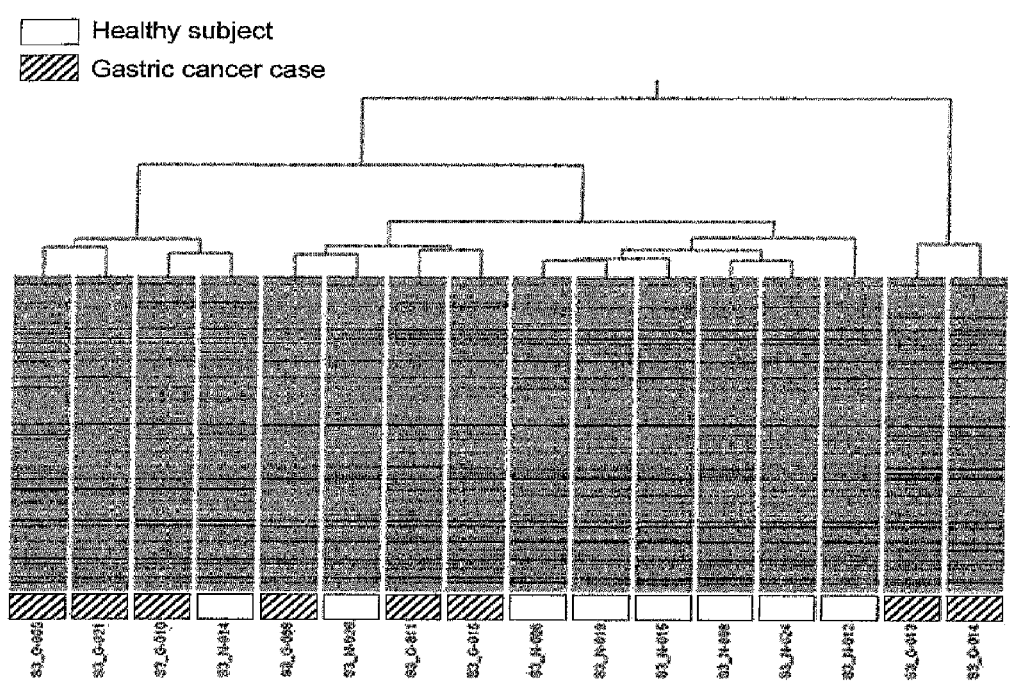

FIG. 12 shows the results of hierarchical clustering using 22155 probes for gastric cancer cases and normal healthy subjects.

Figure 13:
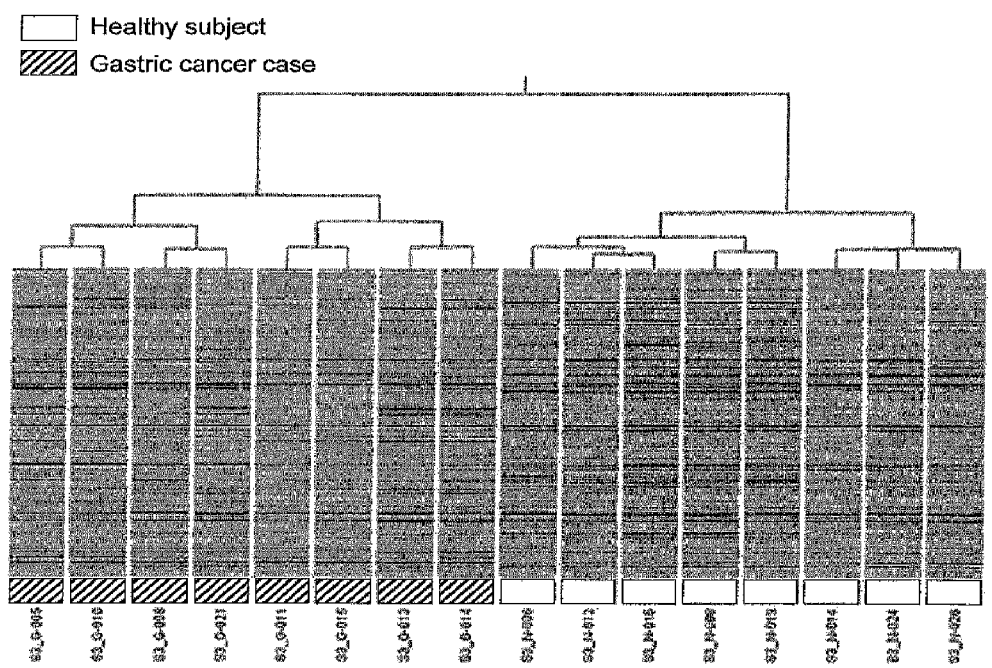

FIG. 13 shows the results of hierarchical clustering using 713 probes corresponding to genes with expression levels that were observed to be attenuated in gastric cancer cases at levels 0.5 times or less or enhanced in the same at levels 2.0 times or more than normal healthy subjects.

Figure 14:
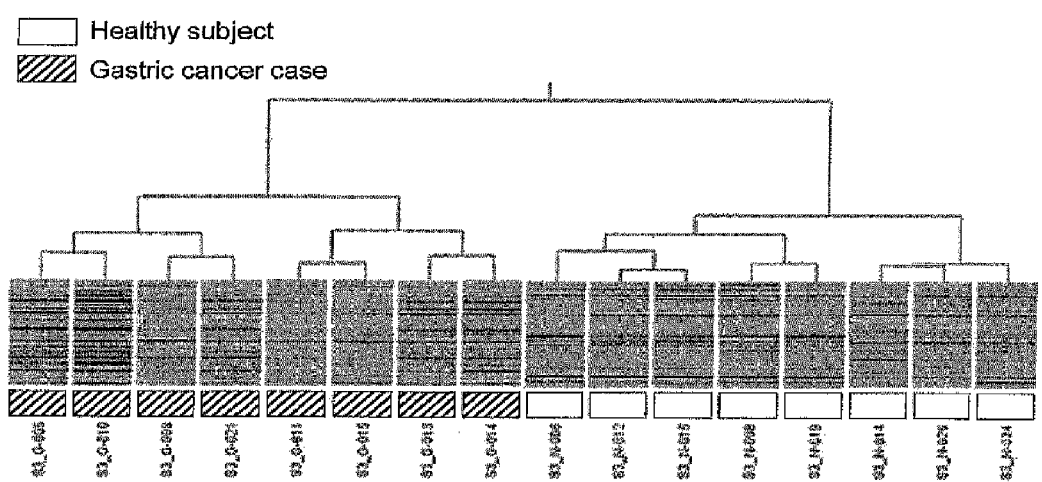

FIG. 14 shows the results of hierarchical clustering using 107 probes corresponding to genes with expression levels that were observed to be attenuated in gastric cancer cases at levels 0.33 times or less or enhanced in the same at levels 3 times or more than normal healthy subjects.

Figure 15:
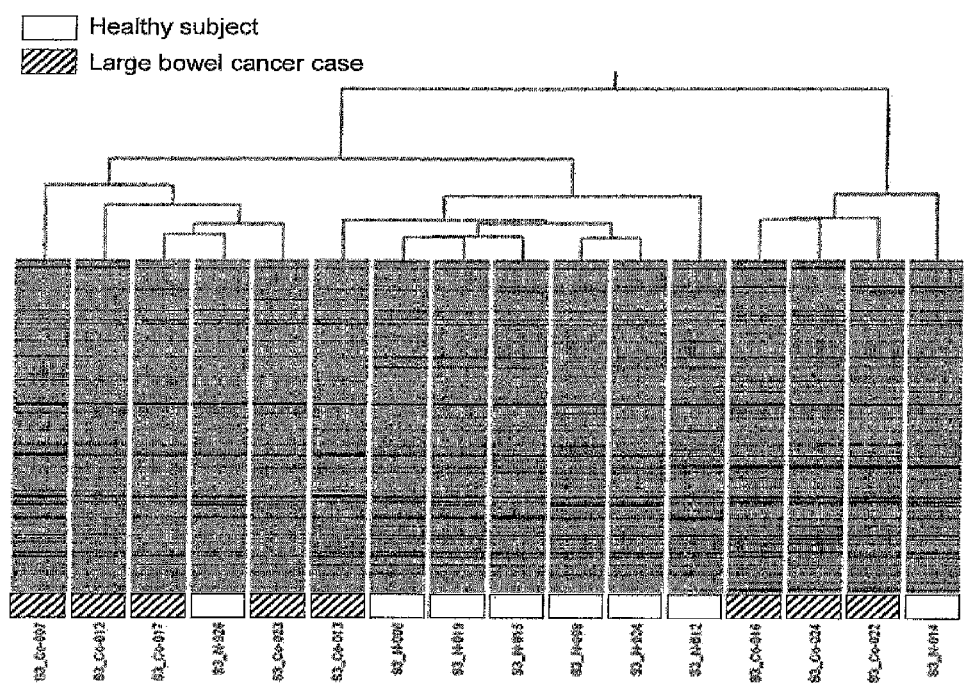

FIG. 15 shows the results of hierarchical clustering using 22181 probes for gastric cancer cases and normal healthy subjects.

Figure 16:
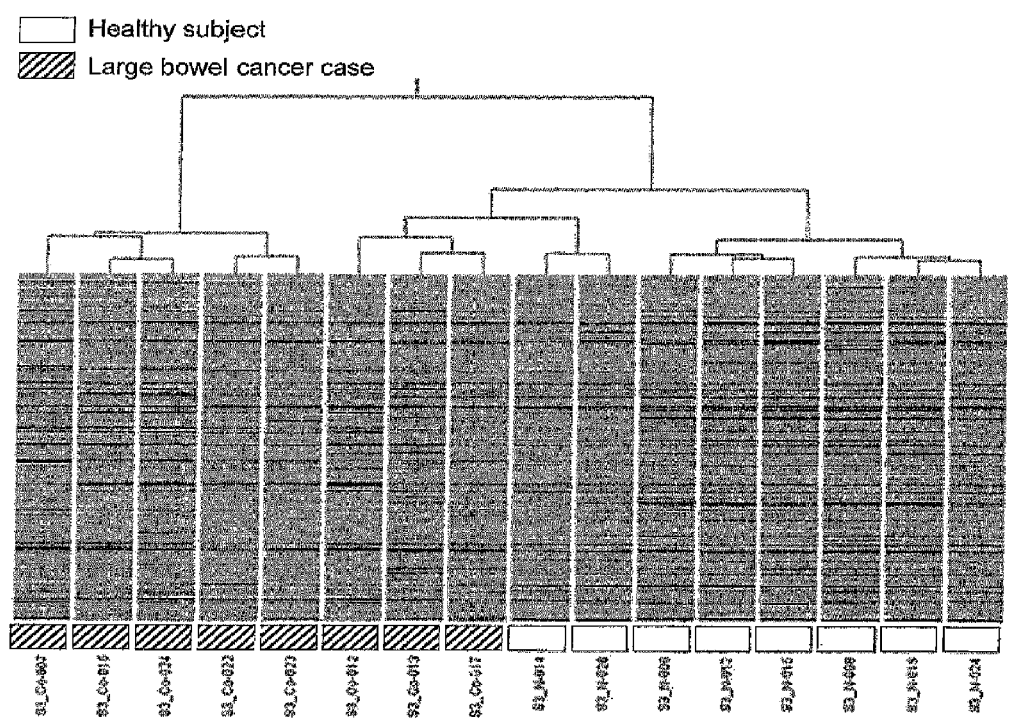

FIG. 16 shows the results of hierarchical clustering using 771 probes corresponding to genes with expression levels that were observed to be attenuated in colorectal cancer cases at levels 0.5 times or less or enhanced in the same at levels 2 times or more than normal healthy subjects.

Figure 17:
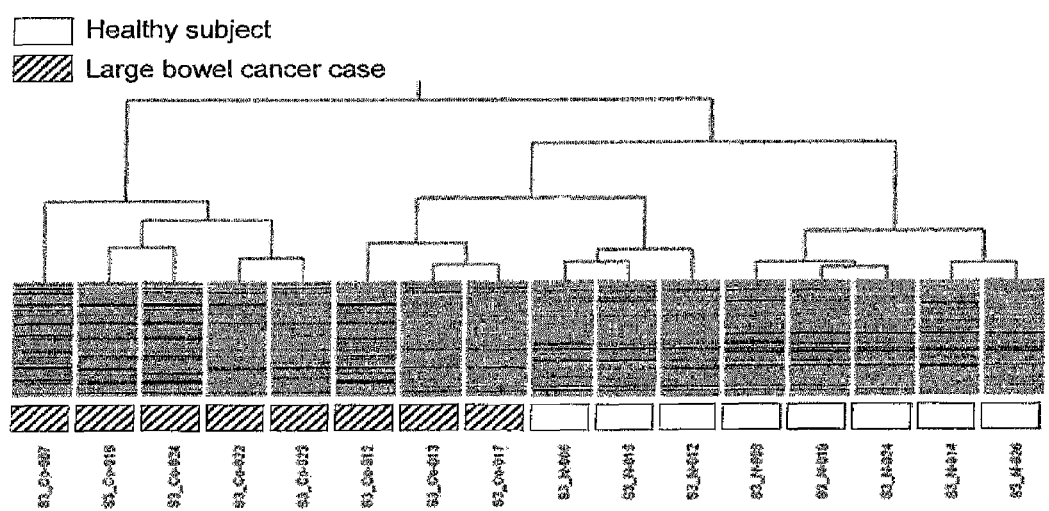

FIG. 17 shows the results of hierarchical clustering using 116 probes corresponding to genes with expression levels that were observed to be attenuated in colorectal cancer cases at levels 0.33 times or less or enhanced in the same at levels 3 times or more than normal healthy subjects.

Figure 18:
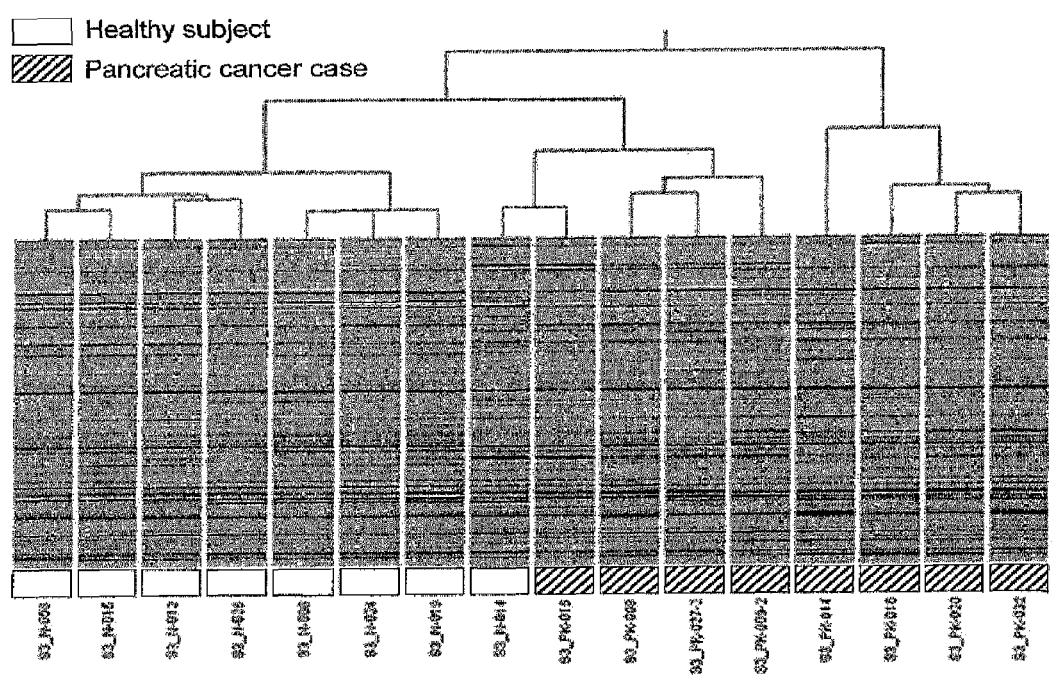

FIG. 18 shows the results of hierarchical clustering using 22149 probes for pancreatic cancer cases and normal healthy subjects.

Figure 19:
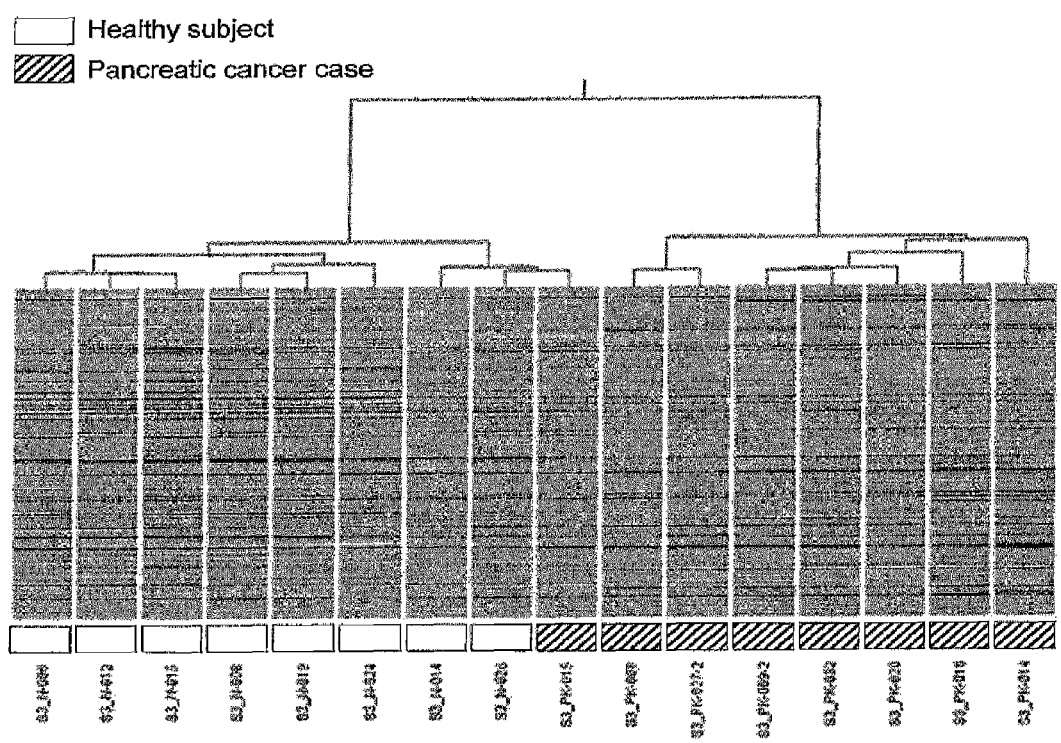

FIG. 19 shows the results of hierarchical clustering using 677 probes corresponding to genes with expression levels that were observed to be attenuated in pancreatic cancer cases at levels 0.5 times or less or enhanced in the same at levels 2 times or more than normal healthy subjects.

Figure 20:
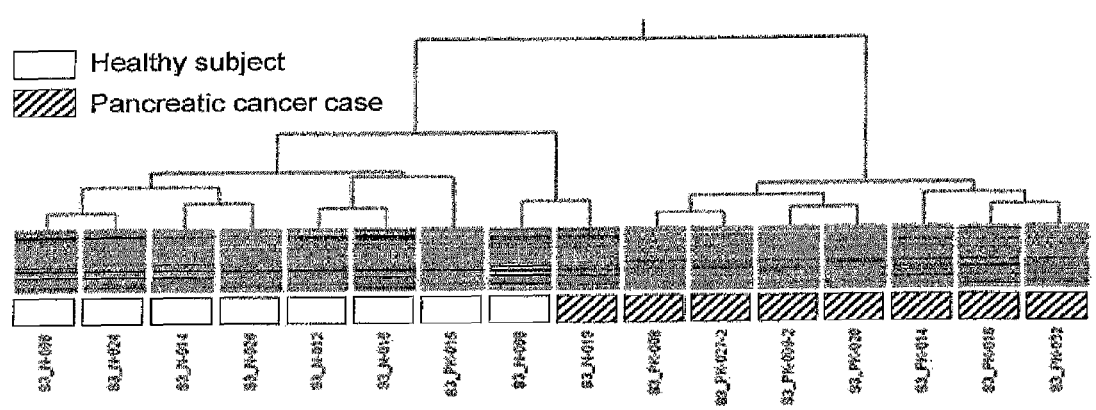

FIG. 20 shows the results of hierarchical clustering using 61 probes corresponding to genes with expression levels that were observed to be attenuated in pancreatic cancer cases at levels 0.33 times or less or enhanced in the same at levels 3 times or more than normal healthy subjects.

FIG. 21-1 shows 25 probes of a 2" probe group that can be used for detection of digestive organ cancer.

FIG. 21-2 shows 25 probes of a 2" probe group that can be used for detection of digestive organ cancer (continuation).

Figure 22:
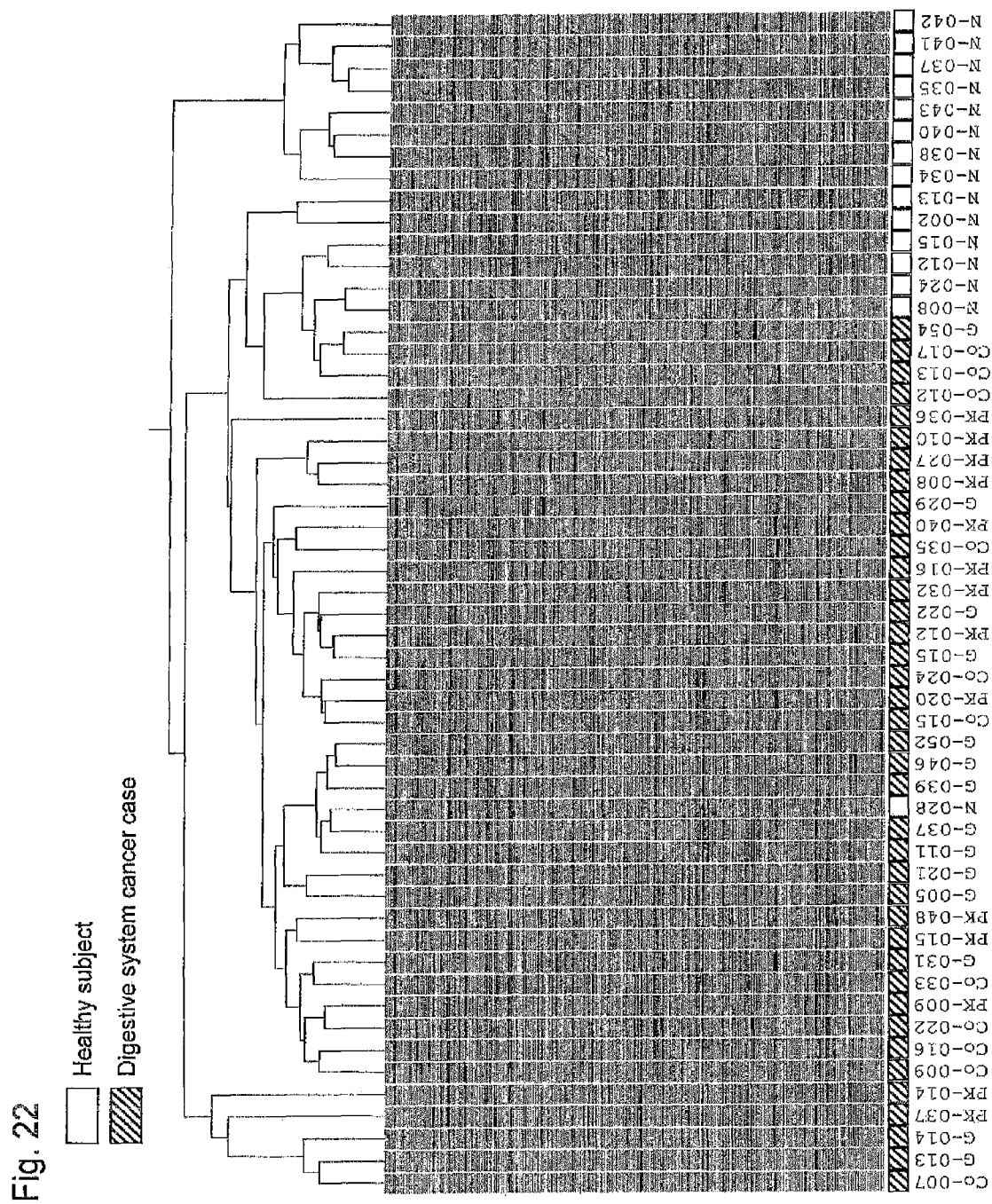

FIG. 22 shows the results of hierarchical clustering using 23278 probes for digestive organ cancer cases and normal healthy subjects.

Figure 23:
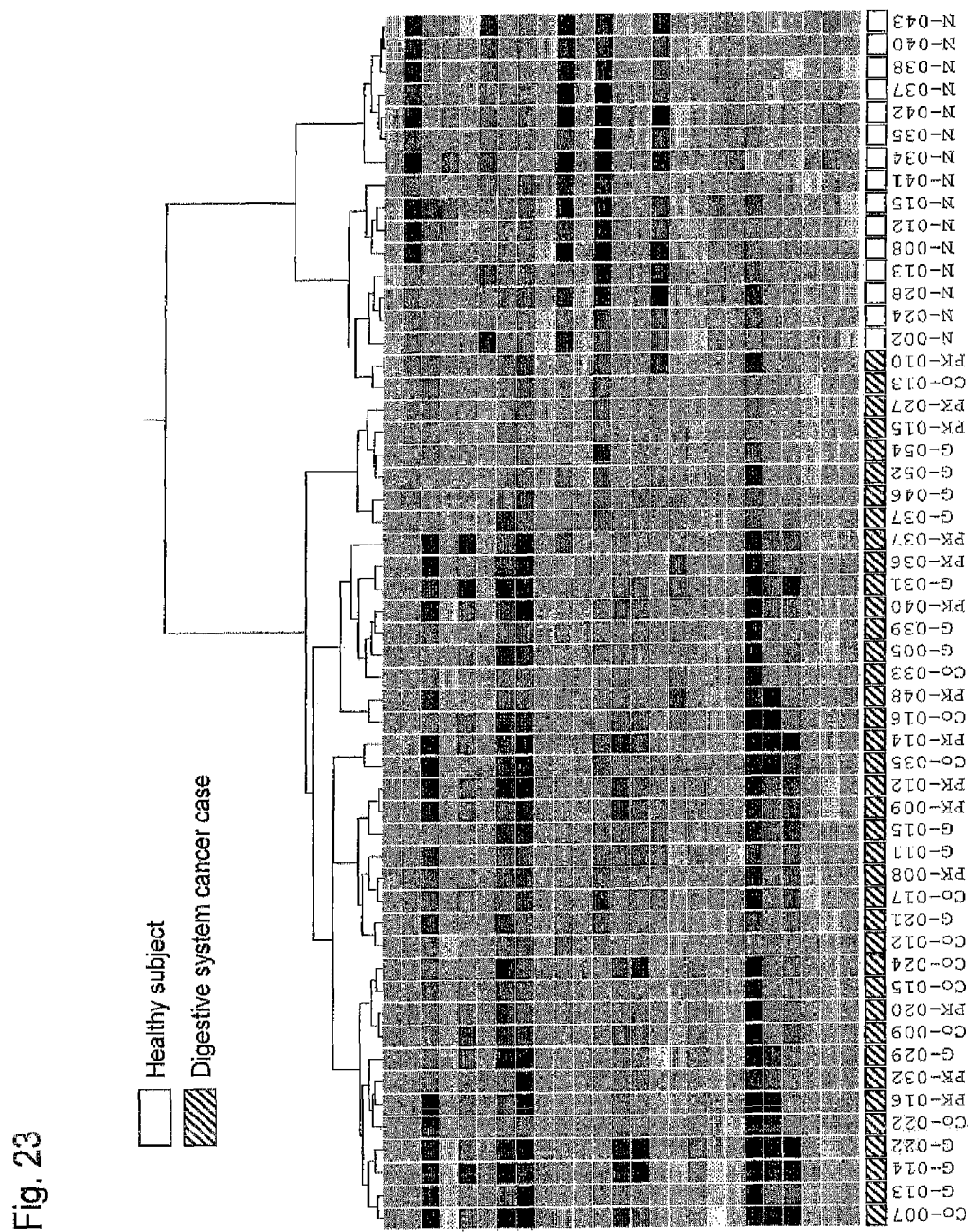

FIG. 23 shows the results of hierarchical clustering using 25 probes corresponding to genes with expression levels that were observed to be attenuated or enhanced in digestive organ cancer cases compared with normal healthy subjects.

FIG. 24-1 shows 363 probes that can be used for detection of biliary tract cancer.

FIG. 24-2 shows 363 probes that can be used for detection of biliary tract cancer (continuation).

FIG. 24-3 shows 363 probes that can be used for detection of biliary tract cancer (continuation).

FIG. 24-4 shows 363 probes that can be used for detection of biliary tract cancer (continuation).

FIG. 24-5 shows 363 probes that can be used for detection of biliary tract cancer (continuation).

FIG. 24-6 shows 363 probes that can be used for detection of biliary tract cancer (continuation).

FIG. 24-7 shows 363 probes that can be used for detection of biliary tract cancer (continuation).

FIG. 24-8 shows 363 probes that can be used for detection of biliary tract cancer (continuation).

FIG. 24-9 shows 363 probes that can be used for detection of biliary tract cancer (continuation).

FIG. 24-10 shows 363 probes that can be used for detection of biliary tract cancer (continuation).

FIG. 24-11 shows 363 probes that can be used for detection of biliary tract cancer (continuation).

FIG. 24-12 shows 363 probes that can be used for detection of biliary tract cancer (continuation).

FIG. 24-13 shows 363 probes that can be used for detection of biliary tract cancer (continuation).

FIG. 24-14 shows 363 probes that can be used for detection of biliary tract cancer (continuation).

FIG. 24-15 shows 363 probes that can be used for detection of biliary tract cancer (continuation).

FIG. 24-16 shows 363 probes that can be used for detection of biliary tract cancer (continuation).

FIG. 24-17 shows 363 probes that can be used for detection of biliary tract cancer (continuation).

FIG. 24-18 shows 363 probes that can be used for detection of biliary tract cancer (continuation).

FIG. 24-19 shows 363 probes that can be used for detection of biliary tract cancer (continuation).

Figure 25:
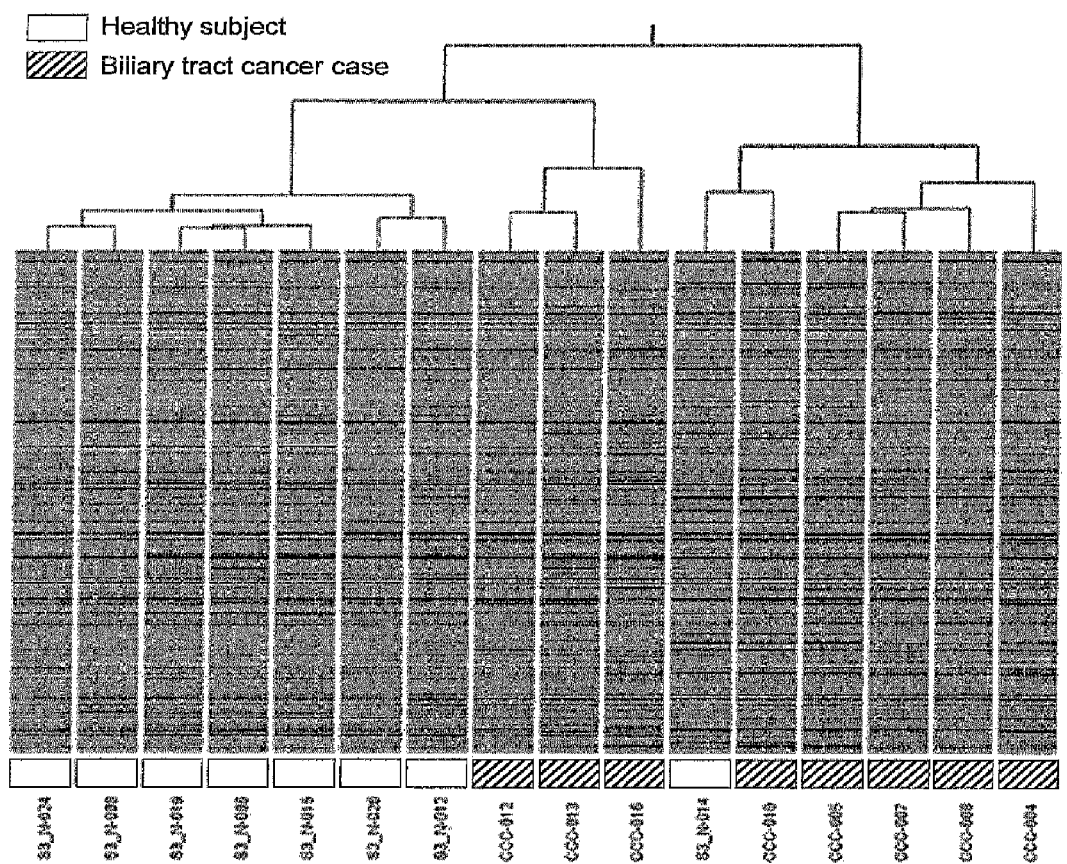

FIG. 25 shows the results of hierarchical clustering using 22066 probes for biliary tract cancer cases and normal healthy subjects.

Figure 26:
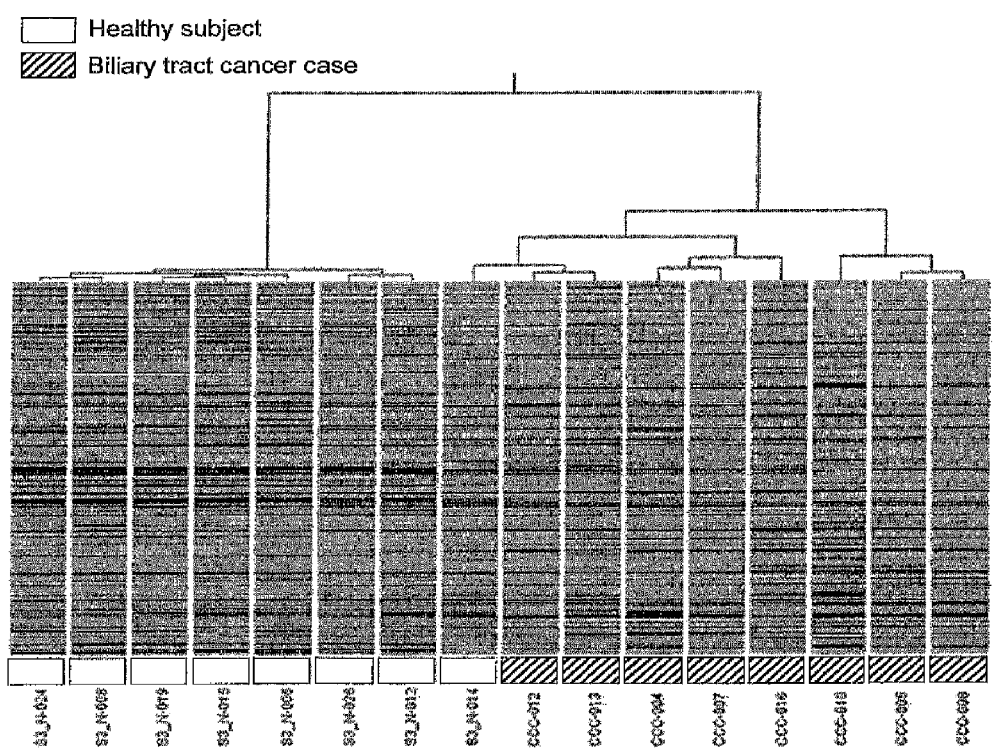

FIG. 26 shows the results of hierarchical clustering using 363 probes corresponding to genes with expression levels that were observed to be attenuated in biliary tract cancer cases at levels 0.33 times or less or enhanced in the same at levels 3 times or more than normal healthy subjects.

BEST MODES FOR CARRYING OUT THE INVENTION

In the present invention, examples of digestive organ cancer include gastric cancer, colorectal cancer, pancreatic cancer, and biliary tract cancer. All of these types of digestive organ cancer can be detected by the method for detecting digestive organ cancer of the present invention. Moreover, gastric cancer, colorectal cancer, pancreatic cancer, or biliary tract cancer can be specifically detected by the method for detecting gastric cancer, colorectal cancer, pancreatic cancer, or biliary tract cancer of the present invention.

The method of the present invention comprises measuring the expression in peripheral blood of:

a gene group with an expression level that varies in digestive organ cancer patients compared with normal healthy subjects;

a gene group with an expression level that varies in gastric cancer patients compared with normal healthy subjects;

a gene group with an expression level that varies in colorectal cancer patients compared with normal healthy subjects;

a gene group with an expression level that varies in pancreatic cancer patients compared with normal healthy subjects; or a gene group with an expression level that varies in biliary tract cancer patients compared with normal healthy subjects, so as to obtain the expression profile of each gene group, and then detecting digestive organ cancer, gastric cancer, colorectal cancer, pancreatic cancer, or biliary tract cancer. Here, examples of such variation in expression include attenuated expression and enhanced expression.

Gene expression in peripheral blood is measured by extracting and isolating mRNA from peripheral blood and then measuring mRNA. mRNA can be extracted and isolated from peripheral blood by a known method. Examples of mRNA that can be extracted and isolated from peripheral blood include mRNAs derived from, in addition to erythrocytes and blood platelets, leukocytes including lymphocytes, monocytes, and granulocytes in peripheral blood, for example.

In the method of the present invention, the expression levels of the above genes are measured.

In the present invention, the term "gene expression level" refers to a gene expression amount, expression intensity, or expression frequency. Such a gene expression level can be generally analyzed based on the production amount of a transcript corresponding to a gene, or the production amount of the translation product therefrom, activity, and the like. Also, the term "expression profiles" refers to information concerning the expression level of each gene. A gene expression level may be expressed with an absolute value or a relative value. In addition, expression profiles may also be referred to as expression patterns.

Expression levels may be measured by measuring gene transcripts (that is, mRNA) or measuring gene translation products (that is, proteins). Preferably, gene expression levels are measured by measuring gene transcripts. An example of a gene transcript is cDNA obtained from mRNA via reverse transcription.

A gene transcript can be measured by measuring the degree of gene expression using nucleotides containing the full-length nucleotide sequences or partial nucleotide sequences of the above genes, or sequences complementary thereto, specifically, nucleotides consisting of the nucleotide sequences consisting of the nucleotide sequences of the genes or partial sequences of the genes, or sequences complementary thereto, as probes or primers. These nucleotides are nucleotides capable of hybridizing to the genes, nucleotides capable of binding to the genes, or nucleotides for detection, which can be used for detection of the genes. The degree of gene expression can be measured by a method using a microarray (microchip), a Northern blot method, or a quantitative PCR method using a gene to be quantitatively determined or a fragment thereof as a target, for example. Examples of a quantitative PCR method include an agarose gel electrophoresis method, a fluorescent probe method, an RT-PCR method, a real-time PCR method, an ATAC-PCR method (Kato, K. et al., Nucl. Acids Res., 25, 4694-4696, 1997), a Taqman PCR method (SYBR (trademark) Green method) (Schmittgen T D, Methods 25, 383-385, 2001), Body Map method (Gene, 174, 151-158 (1996)), a serial analysis of gene expression (SAGE) method (U.S. Pat. Nos. 527,154 and 544,861, EP Publication No. 0761822), and a MAGE method (Micro-analysis of Gene Expression) (JP Patent Publication (Kokai) No. 2000-232888 A). All methods listed herein can be performed by known techniques. The amount of messenger RNA (mRNA) transcribed from the full-length sequence or a partial sequence of the above gene may be measured using these methods. Specifically, the amount of mRNA can be measured using nucleotide probes or primers hybridizing to the mRNA. The base length of a probe or a primer to be used for measurement ranges from 10 bp to 100 bp, preferably ranges from 20 bp to 80 bp, and further preferably ranges from 50 bp to 70 bp.

A DNA microarray (DNA chip) can be prepared by immobilizing nucleotides consisting of the nucleotide sequences of the above genes or partial sequences thereof, or nucleotides containing complementary sequences thereof on an appropriate substrate.

Examples of a substrate for immobilization include glass plates, quartz plates, silicon wafers. Examples of the size of such a substrate include 3.5 mm×5.5 mm, 18 mm×18 mm, and 22 mm×75 mm. The size thereof can be set variously depending on the number of spots for probes or the size of the spots on a substrate. Polynucleotides or fragments thereof can be immobilized by the following methods. Polynucleotides or fragments thereof can be electrostatically bound to a solid-phase support surface-treated with a polycation such as polylysine, polyethylene imine, or polyalkylamine with the use of the electric charge of nucleotides. Alternatively, nucleotides, into which a functional group such as an amino group, an aldehyde group, an SH group, or biotin has been introduced, are covalently bound to the surface of a solid phase to which a functional group such as an amino group, an aldehyde group, or an epoxy group has been introduced. Immobilization may be performed using an array system. A DNA microarray is prepared by immobilizing at least one of genes corresponding to the above 868 probes or a fragment thereof to a substrate, the DNA microarray is brought into contact with subject-derived mRNA or cDNA labeled with a fluorescent substance for hybridization, and then fluorescence intensity on the DNA microarray is measured, so that the type and the amount of the mRNA can be determined. As a result, a gene(s) with expression levels that vary in a subject, can be detected, so that the gene expression profile can be obtained. A fluorescent substance for labeling subject-derived mRNA is not limited and any commercially available fluorescent substance can be used. For example, Cy3 and Cy5 may be used. mRNA can be labeled by a known method.

In the present invention, the term "probe" refers to the sequence of a nucleotide arranged on a DNA microarray. One nucleotide sequence is designated for one probe ID No. There is a single gene that corresponds to a plurality of probes comprising different nucleotide sequences. The expression "a probe(s) corresponding) to a gene(s)" means that the sequence of the probe is complementary to a partial nucleotide sequence of the gene or a sequence complementary thereto, so that the gene can hybridize to the probe. The nucleotide sequence of a gene corresponding to a probe contains the nucleotide sequence of the probe or a nucleotide sequence complementary thereto as a partial sequence.

Examples of nucleotides to be used as probes or primers in the present invention include nucleotides containing the sequences of the above genes, nucleotides consisting of the sequences of fragments thereof, and nucleotides consisting of sequences complementary to these sequences. Further examples of nucleotides to be used in the present invention include nucleotides hybridizing under stringent conditions to nucleotides having the above nucleotide sequences and nucleotides consisting of the sequences of the fragments thereof. Specific examples of such a nucleotide include a nucleotide and the like containing the nucleotide sequence having the degree of homology with the above nucleotide sequences, about 80% or more, preferably about 90% or more, and more preferably about 95% or more on an overall average. Hybridization can be performed according to a method known in the art or a method according thereto, such as the methods described in Current Protocols in Molecular Biology (Current protocols in molecular biology (edited by Frederick M. Ausubel et al., 1987)). Also, when a commercially available library is used, hybridization can be performed according to the methods described in the attached instructions. Here, the term "stringent conditions" refers to conditions of about "1×SSC, 0.1% SDS, 37° C.," more stringent conditions refer to conditions of about "0.5×SSC, 0.1% SDS, and 42° C.," and even more stringent conditions refer to conditions of about "0.2×SSC, 0.1% SDS, 65° C." As such, higher stringency of hybridization conditions enables isolation of a nucleotide having high homology with the probe sequence. Here, the above combinations of SSC, SDS, and temperature are merely examples. Persons skilled in the art can realize stringency similar to the above by appropriately combining the above or other factors (e.g., probe concentration, probe length, and reaction time for hybridization) for determination of stringency for hybridization. Moreover, these genes may have variants. Hence, examples of genes to be used in the present invention include variants of the above genes. The nucleotide sequences of variants can be obtained by accessing a gene database. Examples of the nucleotides of the present invention include nucleotides containing the nucleotide sequences of the variants or nucleotides consisting of the sequences of the fragments thereof.

Also, as a nucleotide to be used in the present invention, either a nucleotide consisting of a sense strand of the above gene or a nucleotide consisting of the antisense strand of the same can be used.

FIG. 1 (FIG. 1-1 to FIG. 1-48) shows 868 probes of the 1$^{st}$ probe group that can be used for detection of digestive organ cancer. FIG. 1 shows probe ID numbers, symbols of genes corresponding to the probes, the nucleotide sequences (SEQ ID NOs: 1-868) of the probes, and descriptions of genes corresponding to the probes (gene names and GenBank accession numbers). The full-length sequences of these genes are known. Arbitrary partial sequences can be used as nucleotides for detection of the genes. FIG. 2 shows the nucleotide sequences (SEQ ID NOs: 220, 506, 508, 523, 538, 554, 570, 589, 597, 602, 618, 654, 689, 701, 726, 744, 762, 763, 781, 795, and 849) of 21 probes with expression levels that differ significantly particularly between digestive organ cancer patients and normal healthy subjects, from among the 868 probes shown in FIG. 1. In FIG. 1, genes corresponding to 555 probes (No. 1 to No. 555) (SEQ ID NOs: 1-555) exhibit attenuated expression in digestive organ cancer patients compared with normal healthy subjects. Genes corresponding to 313 probes (No. 556 to No. 868) (SEQ ID NOs: 556-868) exhibit enhanced expression in digestive organ cancer patients compared with normal healthy subjects. Also, in FIG. 2, genes corresponding to probes No. 1 to No. 6 (SEQ ID NOs: 220, 506, 508, 523, 538, and 554) exhibit attenuated expression in digestive organ cancer patients compared with normal healthy subjects. Genes corresponding to probes No. 7 to No. 21 (SEQ ID NOs: 570, 589, 597, 602, 618, 654, 689, 701, 726, 744, 762, 763, 781, 795, and 849) exhibit enhanced expression in digestive organ cancer patients compared with normal healthy subjects.

Furthermore, FIG. 21 (FIG. 21-1 and FIG. 21-2) shows 25 probes of the 2$_{nd}$ probe group that can be used for detection of digestive organ cancer. FIG. 21 shows probe ID numbers, symbols of genes corresponding to the probes, the nucleotide sequences (SEQ ID NOs: 3030-3054) of the probes, and descriptions of genes corresponding to the probes (gene names and GenBank accession numbers). The full-length sequences of these genes are known. Arbitrary partial sequences can be used as nucleotides for detection of the genes.

FIG. 3 (FIG. 3-1 to FIG. 3-39) shows 713 probes that can be used for detection of gastric cancer. FIG. 3 shows probe ID numbers, symbols of genes corresponding to the probes, the nucleotide sequences (SEQ ID NOs: 869-1581) of the probes, and descriptions of genes corresponding to the probes (gene names and GenBank accession numbers). The full-length sequences of these genes are known. Arbitrary partial sequences can be used as nucleotides for detection of the genes. FIG. 4 (FIG. 4-1 to FIG. 4-6) shows the nucleotide sequences (SEQ ID NO: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578) of 107 probes with expression levels that differ significantly particularly between gastric cancer patients and normal healthy subjects, from among the 713 probes shown in FIG. 3. In FIG. 3, genes corresponding to 84 probes (No. 1 to No. 84) (SEQ ID NOs: 869-952) exhibit attenuated expression in gastric cancer patients compared with normal healthy subjects. Genes corresponding to 629 probes (No. 85 to No. 713) (SEQ ID NOs: 953-1581) exhibit enhanced expression in gastric cancer patients compared with normal healthy subjects. Also, in FIG. 4, genes corresponding to probes No. 1 to No. 6 (SEQ ID NOs: 923, 927, 929, 932, 946, and 952) exhibit attenuated expression in gastric cancer patients compared with normal healthy subjects. Genes corresponding to probes No. 7 to No. 107 (SEQ ID NOs: 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578) exhibit enhanced expression in gastric cancer patients compared with normal healthy subjects.

FIG. 5 (FIG. 5-1 to FIG. 5-41) shows 771 probes that can be used for detection of colorectal cancer. FIG. 5 shows probe ID numbers, symbols of genes corresponding to the probes, the nucleotide sequences (SEQ ID NOs: 1582-2352) of the probes, and descriptions of genes corresponding to the probes (gene names and GenBank accession numbers). The full-length sequences of these genes are known. Arbitrary partial sequences can be used as nucleotides for detection of the genes. FIG. 6 (FIG. 6-1 to FIG. 6-6) shows 116 probes (SEQ ID NO: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340) with expression levels that differ significantly particularly between colorectal cancer patients and normal healthy subjects, from among 771 probes shown in FIG. 5. In FIG. 5, genes corresponding to 125 probes (No. 1 to No. 125) (SEQ ID NOs: 1582-1706) exhibit attenuated expression in colorectal cancer patients compared with normal healthy subjects. Genes corresponding to 646 probes (No. 126 to No. 771) (SEQ ID NOs: 1707-2352) exhibit enhanced expression in colorectal cancer patients compared with normal healthy subjects. Also, in FIG. 6, genes corresponding to probes No. 1 to No. 9 (SEQ ID NOs: 1583, 1601, 1611, 1614, 1644, 1651, 1678, 1680, and 1684) exhibit attenuated expression in colorectal cancer patients compared with normal healthy subjects. Genes corresponding to probes No. 10 to No. 116 (SEQ ID NOs: 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340) exhibit enhanced expression in colorectal cancer patients compared with normal healthy subjects.

FIG. 7 (FIG. 7-1 to FIG. 7-37) shows 677 probes that can be used for detection of pancreatic cancer. FIG. 7 shows probe ID numbers, symbols of genes corresponding to the probes, the nucleotide sequences (SEQ ID NOs: 2353-3029) of the probes, and descriptions of genes corresponding to the probes (gene names and GenBank accession numbers). The full-length sequences of these genes are known. Arbitrary partial sequences can be used as nucleotides for detection of the genes. FIG. 8 (FIG. 8-1 to FIG. 8-3) shows 61 probes (SEQ ID NOs: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003) with expression levels that differ significantly particularly between pancreatic cancer patients and normal healthy subjects, from among 677 probes. In FIG. 7, genes corresponding to 96 probes (No. 1 to No. 96) (SEQ ID NOs: 2353-2448) exhibit attenuated expression in pancreatic cancer patients compared with normal healthy subjects. Genes corresponding to 581 probes (No. 97 to No. 677) (SEQ ID NO: 2449 to 3029) exhibit enhanced expression in pancreatic cancer patients compared with normal healthy subjects. Also, in FIG. 8, genes corresponding to probes No. 1 to No. 6 (SEQ ID NOs: 2373, 2404, 2418, 2419, 2426, and 2430) exhibit attenuated expression in pancreatic cancer patients compared with normal healthy subjects. Genes corresponding to probes No. 7 to No. 61 (SEQ ID NOs: 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003) exhibit enhanced expression in pancreatic cancer patients compared with normal healthy subjects.

FIG. 24 (FIG. 24-1 to FIG. 24-19) shows 363 probes that can be used for detection of biliary tract cancer. FIG. 24 shows probe ID numbers, symbols of genes corresponding to the probes, the nucleotide sequences (SEQ ID NOs: 3055-3417) of the probes, and descriptions of genes corresponding to the probes (gene names and GenBank accession numbers). The full-length sequences of these genes are known. Arbitrary partial sequences can be used as nucleotides for detection of the genes. In FIG. 24, genes corresponding to 98 probes (No. 1 to No. 98) (SEQ ID NOs: 3055-3152) exhibit attenuated expression in biliary tract cancer patients compared with normal healthy subjects. Genes corresponding to 265 probes (No. 99 to No. 363) (SEQ ID NOs: 3153-3417) exhibit enhanced expression in biliary tract cancer patients compared with normal healthy subjects.

The method for detecting digestive organ cancer of the present invention comprises measuring the expression levels of genes (described in the rightmost column in FIG. 1) in peripheral blood of a subject using at least one of 868 probes shown in FIG. 1, wherein the genes correspond to the 868 probes. At this time, with the use of at least 1 to 867 probes from among the 868 probes shown in FIG. 1, specifically at least 1, 2, 3, 4, 5, 6, 7, 8, 9, 10, 50, 100, 150, 200, 250, 300, 350, 400, 450, 500, 550, 600, 650, 700, 750, 800, 850, 867, or 868 probes, the expression levels of the genes corresponding thereto are measured. Also, with the use of at least one of probes corresponding to genes that exhibit attenuated expression in a group of digestive organ cancer patients, the expression level of the gene corresponding thereto may be measured. Also, with the use of at least one of probes corresponding to genes that exhibit enhanced expression in a group of digestive organ cancer patients, the expression level of the gene corresponding to the probe may be measured. Furthermore, with the use of a combination of at least one of probes corresponding to genes that exhibit attenuated expression in a group of digestive organ cancer patients and at least one of probes corresponding to genes that exhibit enhanced expression in the group of digestive organ cancer patients, the expression levels of the genes corresponding to the probes may be measured. Specifically, with the use of at least one of 555 probes (No. 1 to No. 555) (SEQ ID NOs: 1-555) shown in FIG. 1, the expression level of at least one of the genes corresponding to the probes may be measured. At this time, with the use of at least 1 to 554 probes from among the 555 probes, specifically at least 1, 2, 3, 4, 5, 6, 7, 8, 9, 10, 50, 100, 150, 200, 250, 300, 350, 400, 450, 500, 550, 554, or 555 probes, the expression levels of the genes corresponding thereto may be measured. Also, with the use of at least one of 313 probes (No. 556 to No. 868) (SEQ ID NOs: 556-868) shown in FIG. 1, the expression level of the gene corresponding thereto may be measured. At this time, with the use of at least 1 to 312 probes from among the 313 probes, specifically at least 1, 2, 3, 4, 5, 6, 7, 8, 9, 10, 50, 100, 150, 200, 250, 300, 312, or 313 probes, the expression levels of the genes corresponding thereto may be measured. Furthermore, with the use of a combination of at least one of the 555 probes (No. 1 to No. 555) (SEQ ID NOs: 1-555) shown in FIG. 1 and at least one of the 313 probes (No. 556 to No. 868) (SEQ ID NOs: 556-868) shown in FIG. 1, the expression levels of the genes corresponding thereto may be measured.

Furthermore, with the use of at least one of 21 probes shown in FIG. 2 corresponding particularly to genes with expression levels that vary significantly from among genes corresponding to the above 868 probes, the expression levels of the genes (described in the rightmost column in FIG. 2) corresponding to the probes may be measured. At this time, with the use of the 21 probes, specifically 1, 2, 3, 4, 5, 6, 7, 8, 9, 10, 11, 12, 13, 14, 15, 16, 17, 18, 19, 20, or 21 probes, the expression levels of the genes corresponding to the probes may be measured. Also, with the use of at least one of probes No. 1 to No. 6 (from among the 21 probes shown in FIG. 2) corresponding to genes that exhibit attenuated expression in digestive organ cancer patients compared with normal healthy subjects, the expression levels of the genes may be measured. With the use of, from among the 21 probes shown in FIG. 2, at least one of probes No. 7 to No. 21 corresponding to genes that exhibit enhanced expression in digestive organ cancer patients compared with normal healthy subjects, the expression levels of the genes may be measured. Furthermore, with the use of a combination of at least one of the probes No. 1 to No. 6 and at least one of the probes No. 7 to No. 21, the expression levels of the genes may be measured. At this time, 1, 2, 3, 4, 5, or 6 probes of the probes No. 1 to No. 6 may be used and 1, 2, 3, 4, 5, 6, 7, 8, 9, 10, 11, 12, 13, 14, or 15 probes of the probes No. 7 to No. 21 may be used.

The method for detecting digestive organ cancer of the present invention comprises measuring the expression levels of genes (described in the rightmost column in FIG. 1A) in peripheral blood of a subject using at least one of 25 probes shown in FIG. 21, wherein the genes correspond to the 25 probes. At this time, with the use 1, 2, 3, 4, 5, 6, 7, 8, 9, 10, 11, 12, 13, 14, 15, 16, 17, 18, 19, 20, 21, 22, 23, 24, or 25 probes shown in FIG. 1A, the expression levels of the genes corresponding thereto may be measured. Also, with the use of at least one of probes corresponding to genes that exhibit attenuated expression in a group of digestive organ cancer patients, the expression level of the gene corresponding thereto may be measured. Also, with the use of at least one of probes corresponding to genes that exhibit enhanced expression in a group of digestive organ cancer patients, the expression level of the gene corresponding thereto may be measured. Furthermore, with the use of a combination of at least one of probes corresponding to genes that exhibit attenuated expression in a group of digestive organ cancer patients and at least one of probes corresponding to genes that exhibit enhanced expression in the group of digestive organ cancer patients, the expression levels of the genes corresponding to the probes may be measured. Specifically, with the use of at least one of 14 probes (No. 1 to No. 14) (SEQ ID NOs: 3030-3043) shown in FIG. 21, the expression level of at least one of the genes corresponding to the probes may be measured. At this time, with the use of 14 probes, specifically, 1, 2, 3, 4, 5, 6, 7, 8, 9, 10, 11, 12, 13, or 14 probes, the expression levels of the genes corresponding thereto may be measured. Also, with the use of at least one of 11 probes (No. 15 to No. 25) (SEQ ID NOs: 3044-3054) shown in FIG. 21, the expression level of the gene corresponding to the probe may be measured. At this time, with the use of 11 probes, specifically, 1, 2, 3, 4, 5, 6, 7, 8, 9, 10, or 11 probes, the expression levels of the genes corresponding thereto may be measured. Furthermore, with the use of a combination of at least one of 14 probes (No. 1 to No. 14) (SEQ ID NOs: 3030-3043) shown in FIG. 21 and at least one of 11 probes (No. 15 to No. 25) (SEQ ID NOs: 3044-3054) shown in FIG. 21, the expression levels of the genes corresponding thereto may be measured.

The method for detecting gastric cancer of the present invention comprises measuring the expression levels of genes in peripheral blood of a subject (described in the rightmost column in FIG. 3) using at least one of 713 probes shown in FIG. 3, wherein the genes correspond to the 713 probes. At this time, with the use of at least 1 to 712 probes from among the 713 probes shown in FIG. 3, specifically at least 1, 2, 3, 4, 5, 6, 7, 8, 9, 10, 50, 100, 150, 200, 250, 300, 350, 400, 450, 500, 550, 600, 650, 700, 712, or 713 probes, the expression levels of the genes corresponding thereto may be measured. Also, with the use of at least one of probes corresponding to genes that exhibit attenuated expression in a group of gastric cancer patients, the expression level of the gene corresponding thereto may be measured. Also, with the use of at least one of probes corresponding to genes that exhibit enhanced expression in a group of gastric cancer patients, the expression level of the gene corresponding to the probe may be measured. Furthermore, with the use of a combination of at least one of probes corresponding to genes that exhibit attenuated expression in a group of gastric cancer patients and at least one of probes corresponding to genes that exhibit enhanced expression in the group of gastric cancer patients, the expression levels of the genes corresponding to the probes may be measured. Specifically, with the use of at least one of 84 probes (No. 1 to No. 84) (SEQ ID NOs: 869-952) shown in FIG. 1, the expression level of at least one of the genes corresponding to the probes may be measured. At this time, with the use of at least 1 to 83 probes from among the 84 probes, specifically at least 1, 2, 3, 4, 5, 6, 7, 8, 9, 10, 20, 30, 40, 50, 60, 70, 80, 83, or 84 probes, the expression levels of the genes corresponding thereto may be measured. Also, with the use of at least one of 629 probes (No. 85 to No. 713) (SEQ ID NOs: 953-1581) shown in FIG. 3, the expression levels of the genes corresponding to the probes may be measured. At this time, with the use of at least 1 to 628 probes from among the 629 probes, specifically at least 1, 2, 3, 4, 5, 6, 7, 8, 9, 10, 50, 100, 150, 200, 250, 300, 350, 400, 450, 500, 550, 600, 628, or 629 probes, the expression levels of the genes corresponding thereto may be measured. Furthermore, with the use of a combination of at least one of the 84 probes (No. 1 to No. 84) (SEQ ID NOs: 869-952) shown in FIG. 3 and at least one of the 629 probes (No. 85 to No. 713) (SEQ ID NOs: 953-1581) shown in FIG. 3, the expression levels of the genes corresponding to the probes may be measured.

Furthermore, with the use of at least one of 107 probes shown in FIG. 4 corresponding particularly to genes with expression levels that vary significantly from among the genes corresponding to the above 713 probes, the expression levels of the genes (described in the rightmost column in FIG. 4) corresponding to the probes may be measured. At this time, with the use of the 107 probes, specifically at least 1, 2, 3, 4, 5, 6, 7, 8, 9, 10, 20, 30, 40, 50, 60, 70, 80, 90, 100, 106, or 107 probes, the expression levels of the genes corresponding to the probes may be measured. Also, with the use of at least one of probes No. 1 to No. 6 (from among the 107 probes shown in FIG. 4) corresponding to genes that exhibit attenuated expression in gastric cancer patients compared with normal healthy subjects, the expression levels of the genes may be measured. With the use of, from among the 107 probes shown in FIG. 4, at least one of probes No. 7 to No. 107 corresponding to genes that exhibit enhanced expression in gastric cancer patients compared with normal healthy subjects, the expression levels of the genes may be measured. Furthermore, with the use of a combination of at least one of the probes No. 1 to No. 6 and at least one of the probes No. 7 to No. 107, the expression levels of the genes may be measured. At this time, 1, 2, 3, 4, 5, or 6 probes of the probes No. 1 to No. 6 may be used and at least 1, 2, 3, 4, 5, 6, 7, 8, 9, 10, 20, 30, 40, 50, 60, 70, 80, 90, or 100, or 101 probes of the probes No. 7 to No. 107 may be used.

The method for detecting colorectal cancer of the present invention comprises measuring the expression levels of genes in peripheral blood of a subject (described in the rightmost column in FIG. 5) using at least one of 771 probes shown in FIG. 5, wherein the genes correspond to the 771 probes. At this time, with the use of at least 1 to 770 probes from among the 771 probes shown in FIG. 5, specifically at least 1, 2, 3, 4, 5, 6, 7, 8, 9, 10, 50, 100, 150, 200, 250, 300, 350, 400, 450, 500, 550, 600, 650, 700, 750, 770, or 771 probes, the expression levels of the genes corresponding thereto may be measured. Also, with the use of at least one of probes corresponding to genes that exhibit attenuated expression in a group of colorectal cancer patients, the expression level of the gene corresponding thereto may be measured. Also, with the use of at least one of probes corresponding to genes that exhibit enhanced expression in a group of colorectal cancer patients, the expression level of the gene corresponding to the probe may be measured. Furthermore, with the use of a combination of at least one of probes corresponding to genes that exhibit attenuated expression in a group of colorectal cancer patients and at least one of probes corresponding to genes that exhibit enhanced expression in the group of colorectal cancer patients, the expression levels of the genes corresponding to the probes may be measured. Specifically, with the use of at least one of 125 probes (No. 1 to No. 125) (SEQ ID NOs: 1582-1706) shown in FIG. 5, the expression level of at least one of the genes corresponding to the probes may be measured. At this time, with the use of at least 1 to 124 probes from among the 125 probes, specifically at least 1, 2, 3, 4, 5, 6, 7, 8, 9, 10, 20, 30, 40, 50, 60, 70, 80, 90, 100, 110, 120, 124, or 125 probes, the expression levels of the genes corresponding thereto may be measured. Also, with the use of at least one of 646 probes (No. 126 to No. 771) (SEQ ID NOs: 1707-2352) shown in FIG. 5, the expression levels of the genes corresponding thereto may be measured. At this time, with the use of at least 1 to 645 probes from among the 646 probes, specifically at least 1, 2, 3, 4, 5, 6, 7, 8, 9, 10, 50, 100, 150, 200, 250, 300, 350, 400, 450, 500, 550, 600, 645, or 646 probes, the expression levels of the genes corresponding thereto may be measured. Furthermore, with the use of a combination of at least one of the 125 probes (No. 1 to No. 125) (SEQ ID NOs: 1582-1706) shown in FIG. 5 and at least one of the 646 probes (No. 126 to No. 771) (SEQ ID NOs: 1707-2352) shown in FIG. 5, the expression levels of the genes corresponding thereto may be measured.

Furthermore, with the use of at least one of 116 probes shown in FIG. 6 corresponding particularly to genes with expression levels that vary significantly from among the genes corresponding to the above 771 probes, the expression levels of the genes (described in the rightmost column in FIG. 6) corresponding to the probes may be measured. At this time, with the use of the 116 probes, specifically 1, 2, 3, 4, 5, 6, 7, 8, 9, 10, 20, 30, 40, 50, 60, 70, 80, 90, 100, 110, or 115, or 116 probes, the expression levels of the genes corresponding to the probes may be measured. Also, with the use of at least one of probes No. 1 to No. 9 (from among the 116 probes shown in FIG. 6) corresponding to genes that exhibit attenuated expression in colorectal cancer patients compared with normal healthy subjects, the expression levels of the genes may be measured. With the use of, from among the 116 probes shown in FIG. 6, at least one of probes No. 10 to No. 116 corresponding to genes that exhibit enhanced expression in colorectal cancer patients compared with normal healthy subjects, the expression levels of the genes may be measured. Furthermore, with the use of a combination of at least one of the probes No. 1 to No. 9 and at least one of the probes No 10 to No. 116, the expression levels of the genes may be measured. At this time, 1, 2, 3, 4, 5, 6, 7, 8, or 9 probes of the probes No. 1 to No. 9 may be used and at least 1, 2, 3, 4, 5, 6, 7, 8, 9, 10, 20, 30, 40, 50, 60, 70, 80, 90, 100, or 109, or 110 probes of the probes No. 10 to No. 116 may be used.

The method for detecting pancreatic cancer of the present invention comprises measuring the expression levels of genes in peripheral blood of a subject (described in the rightmost column in FIG. 7) using at least one of 677 probes shown in FIG. 7, wherein the genes correspond to the 677 probes. At this time, with the use of at least 1 to 676 probes from among the 677 probes shown in FIG. 7, specifically at least 1, 2, 3, 4, 5, 6, 7, 8, 9, 10, 50, 100, 150, 200, 250, 300, 350, 400, 450, 500, 550, 600, 650, 676, or 677 probes, the expression levels of the genes corresponding thereto may be measured. Also, with the use of at least one of probes corresponding to genes that exhibit attenuated expression in a group of pancreatic cancer patients, the expression level of the gene corresponding thereto may be measured. Also, with the use of at least one of probes corresponding to genes that exhibit enhanced expression in a group of pancreatic cancer patients, the expression level of the gene corresponding to the probe may be measured. Furthermore, with the use of a combination of at least one of probes corresponding to genes that exhibit attenuated expression in a group of pancreatic cancer patients and at least one of probes corresponding to genes that exhibit enhanced expression in the group of pancreatic cancer patients, the expression levels of the genes corresponding to the probes may be measured. Specifically, with the use of at least one of 96 probes (No. 1 to No. 96) (SEQ ID NOs: 2353-2448) shown in FIG. 7, the expression level of at least one of the genes corresponding to the probes may be measured. At this time, with the use of at least 1 to 95 probes from among the 96 probes, specifically at least 1, 2, 3, 4, 5, 6, 7, 8, 9, 10, 20, 30, 40, 50, 60, 70, 80, 90, or 95, or 96 probes, the expression levels of the genes corresponding thereto may be measured. Also, with the use of at least one of 581 probes (No. 97 to No. 677) (SEQ ID NOs: 2449-3029) shown in FIG. 7, the expression levels of the genes corresponding thereto may be measured. At this time, with the use of at least 1 to 580 probes from among the 581 probes, specifically at least 1, 2, 3, 4, 5, 6, 7, 8, 9, 10, 50, 100, 150, 200, 250, 300, 350, 400, 450, 500, 550, or 580, or 581 probes, the expression levels of the genes corresponding thereto may be measured. Furthermore, with the use of a combination of at least one of the 96 probes (No. 1 to No. 96) (SEQ ID NOs: 2353-2448) shown in FIG. 7 and at least one of the 581 probes (No. 97 to No. 677) (SEQ ID NOs: 2449-3029) shown in FIG. 7, the expression levels of the genes corresponding thereto may be measured.

Furthermore, with the use of at least one of 61 probes shown in FIG. 8 corresponding particularly to genes with expression levels that vary significantly (from among the genes corresponding to the above 677 probes), the expression levels of the genes (described in the rightmost column in FIG. 8) corresponding to the probes may be measured. At this time, with the use of the 61 probes, specifically at least 1, 2, 3, 4, 5, 6, 7, 8, 9, 10, 20, 30, 40, 50, or 60, or 61 probes, the expression levels of the genes corresponding to the probes may be measured. Also, with the use of at least one of probes No. 1 to No. 6 (from among the 61 probes shown in FIG. 8) corresponding to genes that exhibit attenuated expression in pancreatic cancer patients compared with normal healthy subjects, the expression levels of the genes may be measured. With the use of, from among the 61 probes shown in FIG. 8, at least one of probes No. 7 to No. 61 corresponding to genes that exhibit enhanced expression in pancreatic cancer patients compared with normal healthy subjects, the expression levels of the genes may be measured. Furthermore, with the use of a combination of at least one of the probes No. 1 to No. 6 and at least one of the probes No. 7 to No. 61, the expression levels of the genes may be measured. At this time, 1, 2, 3, 4, 5, or 6 probes of the probes No. 1 to No. 6 may be used and 1, 2, 3, 4, 5, 6, 7, 8, 9, 10, 20, 30, 40, 50, or 54, or 55 probes of the probes No. 7 to No. 61 may be used.

The method for detecting biliary tract cancer of the present invention comprises measuring the expression levels of genes in peripheral blood of a subject (described in the rightmost column in FIG. 24) using at least one of 363 probes shown in FIG. 24 (FIG. 24-1 to FIG. 24-19), wherein the genes correspond to the 363 probes. At this time, with the use of at least 1 to 362 probes from among the 363 probes shown in FIG. 24, specifically at least 1, 2, 3, 4, 5, 6, 7, 8, 9, 10, 50, 100, 150, 200, 250, 300, 350, or 362, or 363 probes, the expression levels of the genes corresponding thereto may be measured. Also, with the use of at least one of probes corresponding to genes that exhibit attenuated expression in a group of biliary tract cancer patients, the expression level of the gene corresponding thereto may be measured. Also, with the use of at least one of probes corresponding to genes that exhibit enhanced expression in a group of biliary tract cancer patients, the expression level of the gene corresponding to the probe may be measured. Furthermore, with the use of a combination of at least one of probes corresponding to genes that exhibit attenuated expression in a group of biliary tract cancer patients and at least one of probes corresponding to genes that exhibit enhanced expression in the group of biliary tract cancer patients, the expression levels of the genes corresponding to the probes may be measured. Specifically, with the use of at least one of 98 probes (No. 1 to No. 98) (SEQ ID NOs: 3055-3152) shown in FIG. 24, the expression level of at least one of the genes corresponding to the probes may be measured. At this time, with the use of at least 1 to 97 probes from among the 98 probes, specifically at least 1, 2, 3, 4, 5, 6, 7, 8, 9, 10, 20, 30, 40, 50, 60, 70, 80, 90, or 97, or 98 probes, the expression levels of the genes corresponding thereto may be measured. Also, with the use of at least one of 265 probes (No. 99 to No. 363) (SEQ ID NOs: 3153-3417) shown in FIG. 24, the expression levels of the genes corresponding thereto may be measured. At this time, with the use of at least 1 to 264 probes from among the 265 probes, specifically at least 1, 2, 3, 4, 5, 6, 7, 8, 9, 10, 50, 100, 150, 200, 250, 264, or 265 probes, the expression levels of the genes corresponding thereto may be measured. Furthermore, with the use of a combination of at least one of the 98 probes (No. 1 to No. 98) (SEQ ID NOs: 3055-3152) shown in FIG. 24 and at least one of the 265 probes (No. 99 to No. 363) (SEQ ID NOs: 3153-3417) shown in FIG. 24, the expression levels of the genes corresponding thereto may be measured.

The method of the present invention enables identification of a patient with digestive organ cancer, gastric cancer, colorectal cancer, pancreatic cancer, or biliary tract cancer. Specifically, the presence of digestive organ cancer, gastric cancer, colorectal cancer, pancreatic cancer, or biliary tract cancer can be detected.

Subjects may exhibit unknown pathological conditions. When such a subject with unknown pathological conditions is used, whether the subject is normal or affected with digestive organ cancer, gastric cancer, colorectal cancer, pancreatic cancer, or biliary tract cancer can be determined and diagnosed.

In the present invention, the above determination of the pathological conditions of digestive organ cancer, gastric cancer, colorectal cancer, pancreatic cancer, or biliary tract cancer, prognostic prediction, and the like are broadly referred to as detection of digestive organ cancer, gastric cancer, colorectal cancer, pancreatic cancer, or biliary tract cancer.

Furthermore, the pathological conditions of a subject can be determined by obtaining the expression profiles of one or more genes corresponding to the above probes (specifically, 868 probes or 25 probes for digestive organ cancer, 713 probes for gastric cancer, 771 probes for colorectal cancer, 677 probes for pancreatic cancer, and 363 probes for biliary tract cancer) and then analyzing the expression profiles. If expression profiles obtained from a subject are analogous to expression profiles obtained from a digestive organ cancer, gastric cancer, colorectal cancer, pancreatic cancer, or biliary tract cancer patient, the subject can be determined as having digestive organ cancer, gastric cancer, colorectal cancer, pancreatic cancer, or biliary tract cancer. Also, expression profiles obtained from a subject are compared with expression profiles obtained from a normal subject and then evaluation and determination can be made based on a difference in expression profiles between the subject and the normal subject.

Gene expression profiling comprises recording the patterns of expression signals such as fluorescence intensities in the form of digital numerical values or color images. Gene expression profiles can be compared using pattern comparison software. Cox hazard analysis, discriminant analysis, and the like can be used herein. A discriminant analysis model is constructed in advance for evaluation and determination of pathological conditions, prediction of pathological conditions, or prognostic prediction, data concerning gene expression profiles obtained from a subject are input into the discriminant analysis model, and thus determination of pathological conditions, prediction of pathological conditions, or prognostic prediction can also be performed. For example, pathological conditions, prediction of pathological conditions, or prognostic prediction can be evaluated and determined by obtaining a discriminant via discriminant analysis, relating fluorescence intensities to pathological conditions, predicting pathological conditions, or conducting prognostic prediction, and then substituting the numerical value representing the expression signal of the subject into the discriminant.

The present invention encompasses an in vitro diagnostic or a kit for detecting digestive organ cancer, gastric cancer, colorectal cancer, pancreatic cancer, or biliary tract cancer, which contains: nucleotides consisting of the nucleotide sequences of genes with expression levels that vary in digestive organ cancer patients compared with normal healthy subjects, genes with expression levels that vary in gastric cancer patients compared with normal healthy subjects, genes with expression levels that vary in colorectal cancer patients compared with normal healthy subjects, genes with expression levels that vary in pancreatic cancer patients compared with normal healthy subjects, or genes with expression levels that vary in biliary tract cancer patients compared with normal healthy subjects for measurement of the expression levels of these genes, or nucleotides containing partial sequences thereof.

The reagent contains nucleotides consisting of the nucleotide sequences of the above genes or nucleotides containing partial sequences thereof as probes or primers. The reagent is also a substrate such as a micro array on which nucleotides consisting of the nucleotide sequences of the above genes or nucleotides containing partial sequences thereof have been immobilized.

For example, a reagent or a kit for detecting digestive organ cancer contains at least one of the above 868 or 25 probes that can be used for detection of digestive organ cancer and is capable of measuring the expression level of at least one of genes corresponding to the probes. Also, a reagent or a kit for detecting gastric cancer contains at least one of the above 713 probes that can be used for detection of gastric cancer and is capable of measuring the expression level of at least one of genes corresponding to the probes. Also, a reagent or a kit for detecting colorectal cancer contains at least one of the above 771 probes that can be used for detection of colorectal cancer and is capable of measuring the expression level of at least one of genes corresponding to the probes. Moreover, a reagent or a kit for detecting pancreatic cancer contains at least one of 677 probes that can be used for detection of pancreatic cancer, and is capable of measuring the expression level of at least one of genes corresponding to the probes. Furthermore, a reagent or a kit for detecting biliary tract cancer contains at least one of 363 probes that can be used for detection of biliary tract cancer and is capable of measuring the expression level of at least one of genes corresponding to the probes.

The present invention encompasses a system for detecting digestive organ cancer, gastric cancer, colorectal cancer, pancreatic cancer, or biliary tract cancer of a subject by the method for detecting digestive organ cancer, gastric cancer, colorectal cancer, pancreatic cancer, or biliary tract cancer of the present invention.

The system for detecting digestive organ cancer, gastric cancer, colorectal cancer, pancreatic cancer, or biliary tract cancer of the present invention comprises:
(a) a data input means for inputting data concerning the gene expression profiles of a subject (here, the "data concerning gene expression profiles to be input" refers to data representing the expression level of each gene, such as a numerical value for signals in each gene;
(b) a memory means for storing the thus constructed discriminant model;
(c) a data processing means for applying data input using the input means (a) to the discriminant model stored in the memory means (b), and then determining the pathological conditions of digestive organ cancer, gastric cancer, colorectal cancer, pancreatic cancer, or biliary tract cancer; and
(d) a data output means for outputting data concerning the determination of predicted pathological conditions of digestive organ cancer, gastric cancer, colorectal cancer, pancreatic cancer, or biliary tract cancer, prediction of the pathological conditions, and prognostic prediction.

The data input means (a) contains a key board or an external memory device storing data, for example. The memory means (b) contains a hard disk, for example. The data processing means receives a discriminant model from the memory means and processing the input data, sends the processing result to the data output means, and then displaying the processing result with the data output means. The data processing means contains a central processing unit (CPU) and the like for processing data. Also, the output means contains a monitor, a printer, and the like for displaying the results.

The system of the present invention can be constructed using a commercially available personal computer and the like.

EXAMPLES

The present invention will be specifically described using the following examples, but the present invention is not limited to these examples.

Materials and experimental methods employed in the examples are as follows.
Object
Blood samples collected from patients diagnosed by a doctor as having digestive organ cancer, gastric cancer, colorectal cancer, pancreatic cancer, or biliary tract cancer were designated as a digestive organ cancer case, a gastric cancer case, a colorectal cancer case, a pancreatic cancer case, and a biliary tract cancer case, respectively. Regarding a control group, blood samples provided with the consent of patients who had received health checkups for residents held by local governments and consented to provide their blood were used herein. Blood samples were examined through a search for the following test items, and patients who exhibited normal values were designated as normal healthy subjects.

Test items: systolic blood pressure, diastolic blood pressure, number of erythrocytes, number of leukocytes, hemoglobin value, hematocrit value, liver functions (GOT, GPT, γ-GTP), renal functions (creatinine value), lipid metabolism (LDL cholesterol value, HDL cholesterol value, total cholesterol value), protein in urine, urinary blood
Collection of Peripheral Blood:
Peripheral blood was collected from patients using PAXgene™ RNA blood collecting tube (Becton, Dickinson and Company, Japan, Medical Device Marketing Authorization No. (Iryo-kiki Seizo Hanbai Ninsho No.): 218AFBZX00014000).
RNA Extraction and Hybridization
RNA was extracted via a PAXgene™ RNA blood collecting tube according to protocols using a PAXgene Blood RNA Kit (QIAGEN GmbH, Hilden, Germany). RNA was amplified based on the thus extracted RNA using a QuickAmp Labeling Kit, 1 color (Agilent Technologies, Santa Clara, Calif.), and at the same time labeled with a Cy3 dye. The thus labeled RNA was mixed using a Gene Expression Hybridization Kit (Agilent Technologies, Santa Clara, Calif.), followed by hybridization to Whole Human Genome oligo DNA microarrays (Agilent Technologies, Santa Clara, Calif.). In addition, the process from RNA amplification to hybridization was performed according to experimental protocols disclosed by Agilent Technologies.
Image Analysis and Data Analysis of DNA Microarrays:
The fluorescence intensity of each spot on the oligo DNA microarrays was acquired using a DNA microarray scanner (Agilent Technologies, Santa Clara, Calif.). The thus acquired images were processed with Feature Extraction software (Agilent Technologies, Santa Clara, Calif.), so that the fluorescence intensity of each spot was quantitated. The fluorescence intensity of a probe at each spot was calculated by quantitation.

The numerical values of the fluorescence intensities of all probes on the microarrays were normalized using GeneSpring GX (Agilent Technologies, Santa Clara, Calif.). A quality check was performed for the fluorescence intensity of each probe based on the thus normalized numerical value representing the enhanced or attenuated expression of each probe. Only probes that had passed the quality check were subjected as analytical objects to hierarchical clustering. Also, similarly, with the use of GeneSpring GX, genes with expression levels that were observed to differ between the digestive organ cancer patient group and the normal healthy subject group, were examined using Welch t-test as a statistic analysis tool. Candidate probes were extracted using the Benjamini and Hochberg False Discovery Rate as a multiple test and $p<0.05$ as significant value. Furthermore, similarly, with the use of GeneSpring GX, predictive determination was performed to determine if a subject belonged to a cancer case group or a normal healthy subject group (differing from the cancer case group or the normal healthy subject group used for extraction of candidate probes) using a class prediction tool and support vector machines for calculation.

The following results were obtained from the examples.
1. Detection of Digestive Organ Cancer (1)
Hierarchical Clustering:
Hierarchical clustering was performed using a GeneSpring GX hierarchical clustering tool and 23352 probes that had passed a quality check. As shown in FIG. 9, 5 clusters were formed. In the $1^{st}$ cluster, 3 out of 3 cases (100%) were digestive organ cancer cases. In the $2^{nd}$ cluster, 8 out of 9 cases (88.9%) were digestive organ cancer cases. In the $3^{rd}$ cluster, 5 out of 6 cases (83.3%) and in the $4^{th}$ cluster, 9 out of 10 cases (90.0%) were digestive organ cancer cases. In the $5^{th}$ cluster, 3 out of 4 cases (75.0%) were digestive organ cancer cases. Hence, digestive organ cancer cases and normal healthy subjects were separately clustered.

Genes with expression levels that were observed to differ between a digestive organ cancer case group and a normal healthy subject group:
Similarly, with the use of a GeneSpring GX Statistic Analysis tool, probes capable of discriminating between a digestive organ cancer case group and a normal healthy subject group were examined using the Benjamini and Hochberg false discovery rate for a multiple test and $p<0.0005$. As a result, the expression of 868 probes was observed to differ between the two groups.

Also, normalized numerical values for fluorescence intensities of the 868 probes were compared using a Fold Change tool between the digestive organ cancer case group and the normal healthy subject group. The expression of 555 probes was observed to be attenuated regardless of multiplying factor, and the expression of 313 probes was observed to be enhanced regardless of multiplying factor, in the digestive organ cancer case group, compared with normal healthy subjects. Also, the expression of 6 probes was observed to be attenuated at levels 0.4 times or less that of the normal healthy subject group and the expression of 15 probes was observed to be enhanced at levels 2.5 times or more that of the normal healthy subject group.

Hierarchical Clustering with 868 Probes Corresponding to Genes with Expression Levels that were Observed to be Attenuated or Enhanced in Digestive Organ Cancer Cases Compared with Normal Healthy Subjects:

Hierarchical clustering was performed for subject cancer cases and normal healthy subjects using a total of 868 probes including the above 555 probes and 313 probes. As shown in FIG. 10, 3 clusters were formed. In the $1^{st}$ cluster, 14 out of 14 cases (100%) were digestive organ cancer cases. In the $2^{nd}$ cluster, 8 out of 8 cases (100%) were digestive organ cancer cases. In the $3^{rd}$ cluster, 8 out of 10 cases (80%) were normal healthy subject cases. Thus, digestive organ cancer cases and normal healthy subjects were separately clustered.

Predictive Determination Using 868 Probes Corresponding to Genes With Expression Levels that were Observed to be Attenuated or Enhanced in Digestive Organ Cancer Cases Compared with Normal Healthy Subjects:

Similarly with the use of a GeneSpring GX Class Prediction tool, a prediction model was prepared based on 868 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 39 out of 40 separately analyzed cancer cases were determined with the prediction model to be cancer cases and the probability that such cases had been properly diagnosed was 97.5%. Also, 9 out of 13 normal healthy subject cases were determined with prediction model to be normal healthy subjects, and the probability that such cases had been properly diagnosed was 69.2%. Altogether, 48 out of 53 such cases were correct answers. Thus, the percentage of cases determined correctly was 90.6% ($^{48}/_{53}$).

Hierarchical Clustering with 21 Probes Corresponding to Genes with Expression Levels that were Observed to be Attenuated at Levels 0.4 Times or Less the Normal Healthy Subject Group or Enhanced at Levels 2.5 Times or More the Normal Healthy Subject Group:

Hierarchical clustering was performed using a total of 21 probes including the above 6 probes and 15 probes for subject cancer cases and normal healthy subjects. As shown in FIG. 11, 3 clusters were formed. In the $1^{st}$ cluster, 17 out of 17 cases (100%) were digestive organ cancer cases. In the $2^{nd}$ cluster, 7 out of 9 cases (77.8%) were digestive organ cancer eases. In the $3^{rd}$ cluster, 6 out of 6 cases (100%) were normal healthy subject cases. Thus, digestive organ cancer cases and normal healthy subjects were separately clustered.

Predictive Determination Using 21 Probes Corresponding to Genes with Expression Levels that were Observed to be Attenuated at Levels 0.4 Times or Less the Normal Healthy Subject Group or Enhanced at Levels 2.5 Times or More the Normal Healthy Subject Group:

Similarly, with the use of a GeneSpring GX Class Prediction tool, a prediction model was prepared based on 21 probes observed to exhibit differences in expression, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 37 out of 40 separately analyzed cancer cases were determined with the prediction model to be cancer cases and the probability that such cases had been properly diagnosed was 92.5%. Also, 12 out of 13 normal healthy subjects were determined with the prediction model to be normal healthy subjects, and the probability that such cases had been properly diagnosed was 92.3%. Altogether, 49 out of 53 such cases were correct answers. Thus, the percentage of cases determined correctly was 92.5% ($^{49}/_{53}$).

1-2. Detection of Digestive Organ Cancer (2)

In a manner similar to that in the above detection of digestive organ cancer (1), 39 cancer cases and 15 normal healthy subject cases were examined using a GeneSpring GX hierarchical clustering tool and 23278 probes that had passed a quality check. As shown in FIG. 22, 5 clusters were formed. In the $1^{st}$ cluster, 5 out of 5 cases (100%) were digestive organ cancer cases. In the $2^{nd}$ cluster, 29 out of 30 cases (96.7%) were digestive organ cancer cases. In the $3^{rd}$ cluster, 1 out of 1 case (100%) and in the $4^{th}$ cluster, 6 out of 10 cases (60%) were digestive organ cancer cases. In the $5^{th}$ cluster, 8 out of 8 cases (100%) were normal healthy subject cases. Thus, the digestive organ cancer cases and the normal healthy subjects were separately clustered.

Furthermore, in a manner similar to that in the above detection of digestive organ cancer (1), probes capable of discriminating between a group of 39 digestive organ cancer cases and a group of 15 normal healthy subject cases were examined using a GeneSpring GX Statistic Analysis tool. Probes were extracted using Benjamini and Hochberg False Discovery Rate as a multiple test and p<0.000005. The normalized numerical values of fluorescence intensities of the thus extracted probes were compared between the group of digestive organ cancer cases and the group of normal healthy subjects using a Fold Change tool. Thus, the expression of 14 probes was observed to be attenuated at levels 0.33 times or less that of the normal healthy subject group and the expression of 11 probes was observed to be enhanced at levels 3 times or more that of the normal healthy subject group (FIG. 21, SEQ ID NOs: 3030-3054).

Hierarchical Clustering with 25 Probes Corresponding to Genes with Expression Levels that were Observed to be Attenuated or Enhanced in Digestive Organ Cancer Cases Compared with Normal Healthy Subjects:

Hierarchical clustering was performed using a total of 25 probes including the above 14 probes and 11 probes for subject cancer cases and normal healthy subjects. As shown in FIG. 23, 3 clusters were formed. In the $1^{St}$ cluster, 31 out of 31 cases (100%) were digestive organ cancer cases. In the $2^{nd}$ cluster, 6 out of 6 cases (100%) were digestive organ cancer cases. In the $3^{rd}$ cluster, 15 out of 17 cases (88.2%) were normal healthy subject cases. Thus, the digestive organ cancer cases and the normal healthy subjects were separately clustered.

Predictive Determination Using 25 Probes Corresponding to Genes with Expression Levels that were Observed to be Attenuated or Enhanced in Digestive Organ Cancer Cases Compared with Normal Healthy Subjects:

Similarly, with the use of a GeneSpring GX Class Prediction tool, a prediction model was prepared based on 25 probes observed to exhibit differences in expression, using Support Vector Machines. The prediction model was applied to cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 3.7 out of 37 separately analyzed cancer cases were determined with the prediction model to be cancer cases and the probability that such cases had been properly diagnosed was 100%. Also, 11 out of 15 normal healthy subjects were determined with the prediction model to be normal healthy subjects, and the probability that such cases had been properly diagnosed was 73.3%. Altogether, 48 out of 52 such cases were correct answers. Thus, the percentage of cases determined correctly was 92.3% (48/52).

2. Detection of Gastric Cancer

Hierarchical Clustering:

Hierarchical clustering was performed using a GeneSpring GX hierarchical clustering tool and 22155 probes that had passed a quality check. As shown in FIG. 12, 4 clusters were formed. In the $1^{st}$ cluster, 6 out of 6 cases (100%) were gastric cancer cases. In the $2^{nd}$ cluster, 3 out of 4 cases (75%) were normal healthy subject cases. In the $3^{rd}$ cluster, 3 out of 4 cases (75%) and in the $4^{th}$ cluster, 2 out of 2 cases (100%) were normal healthy subject cases. Hence, gastric cancer cases and normal healthy subjects were separately clustered.

Genes with Expression Levels that were Observed to Differ Between a Gastric Cancer Case Group and a Normal Healthy Subject Group:

Similarly, with the use of a GeneSpring GX Statistic Analysis tool, probes capable of discriminating between a gastric cancer case group and a normal healthy subject group were examined using the Benjamini and Hochberg false discovery rate for a multiple test and $p<0.05$. As a result, the expression of 3453 probes was observed to differ between the two groups.

Also, normalized numerical values for fluorescence intensities of the 3453 probes were compared using a Fold Change tool between the gastric cancer case group and the normal healthy subject group. The expression of 84 probes was observed to be attenuated in the gastric cancer case group at levels 0.5 times or less that of the normal healthy subject group and the expression of 629 probes was observed to be enhanced in the gastric cancer case group at levels 2 times or more that of the normal healthy subject group. Also, the expression of 6 probes was observed to be attenuated in the gastric cancer case group at levels 0.33 times or less that of the normal healthy subject group and the expression of 101 probes was observed to be enhanced in the gastric cancer case group at levels 3 times or more that of the normal healthy subject group.

Hierarchical Clustering with 713 Probes Corresponding to Genes with Expression Levels that were Observed to be Attenuated at Levels 0.5 Times or Less or Enhanced at Levels 2 Times or More that of the Normal Healthy Subject Group:

Hierarchical clustering was performed for subject cancer cases and normal healthy subjects using a total of 713 probes including the above 84 probes and 629 probes. As shown in FIG. 13, 2 clusters were formed, in which a cluster of cancer cases accounting for 100% and a cluster of normal healthy subject cases accounting for 100%.

Predictive Determination Using 713 Probes Corresponding to Genes with Expression Levels that were Observed to be Attenuated at Levels 0.5 Times or Less or Enhanced at Levels 2 Times or More that of the Normal Healthy Subject Group:

Similarly with the use of a GeneSpring GX Class Prediction tool, a prediction model was prepared based on 713 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 7 out of 10 separately analyzed cancer cases were determined with the prediction model to be cancer cases and the probability that such cases had been properly diagnosed was 70%. Also, 13 out of 13 normal healthy subject cases were determined with prediction model to be normal healthy subject cases, and the probability that such cases had been properly diagnosed was 100%. Altogether, 20 out of 23 such cases were correct answers. Thus, the percentage of cases determined correctly was 87.0% (20/23).

Hierarchical Clustering with 107 Probes Corresponding to Genes with Expression Levels that were Observed to be Attenuated at Levels 0.33 Times or Less or Enhanced at Levels 3 Times or More that of the Normal Healthy Subject Group:

Hierarchical clustering was performed for subject cancer cases and normal healthy subjects using a total of 107 probes including the above 6 probes and 101 probes. As shown in FIG. 14, 2 clusters were formed, in which a cluster of cancer cases accounting for 100% and a cluster of normal healthy subject cases accounting for 100%.

Predictive Determination Using 107 Probes Corresponding to Genes with Expression Levels that were Observed to be Attenuated at Levels 0.33 Times or Less or Enhanced at Levels 3 Times or More that of the Normal Healthy Subject Group:

Similarly with the use of a GeneSpring GX Class Prediction tool, a prediction model was prepared based on 107 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 8 out of 10 separately analyzed cancer cases were determined with the prediction model to be cancer cases and the probability that such cases had been properly diagnosed was 80%. Also, 13 out of 13 normal healthy subject cases were determined with prediction model to be normal healthy subject cases, and the probability that such cases had been properly diagnosed was 100%. Altogether, 21 out of 23 such cases were correct answers. Thus, the percentage of cases determined correctly was 91.3% (21/23).

3. Detection of Colorectal Cancer

Hierarchical Clustering:

Hierarchical clustering was performed using a GeneSpring GX hierarchical clustering tool and 22181 probes that had passed a quality check. As shown in FIG. 15, 3 clusters were formed. In the $1^{st}$ cluster, 4 out of 5 cases (80%) were colorectal cancer cases. In the $2^{nd}$ cluster, 6 out of 7 cases (85.7%) were normal healthy subject cases. In the $3^{rd}$ cluster, 3 out of 4 cases (75%) were colorectal cancer cases. Hence, colorectal cancer cases and normal healthy subjects were separately clustered.

Genes with Expression Levels that were Observed to Differ Between a Colorectal Cancer Case Group and a Normal Healthy Subject Group:

Similarly, with the use of a GeneSpring GX Statistic Analysis tool, probes capable of discriminating between a colorectal cancer case group and a normal healthy subject group were examined using the Benjamini and Hochberg false discovery rate for a multiple test and p<0.05. As a result, the expression of 5267 probes was observed to differ between the two groups.

Also, normalized numerical values for fluorescence intensities of the 5267 probes were compared using a Fold Change tool between the colorectal cancer case group and the normal healthy subject group. The expression of 125 probes was observed to be attenuated in the large bowel case group at levels 0.5 times or less that of the normal healthy subject group and the expression of 646 probes was observed to be enhanced in the colorectal cancer case group at levels 2 times or more that of the normal healthy subject group. Also, the expression of 9 probes was observed to be attenuated in the colorectal cancer case group at levels 0.33 times or less that of the normal healthy subject group and the expression of 107 probes was observed to be enhanced in the colorectal cancer case group at levels 3 times or more that of the normal healthy subject group.

Hierarchical Clustering with 771 Probes Corresponding to Genes with Expression Levels that were Observed to be Attenuated at Levels 0.5 Times or Less or Enhanced at Levels 2 Times or More that of the Normal Healthy Subject Group:

Hierarchical clustering was performed for subject cancer cases and normal healthy subjects using a total of 771 probes including the above 125 probes and 646 probes. As shown in FIG. 16, 3 clusters were formed. In the $1^{st}$ cluster, 5 out of 5 cases (100%) were colorectal cancer cases. In the $2^{nd}$ cluster, 3 out of 5 cases (60.0%) were colorectal cancer cases. In the $3^{rd}$ cluster, 7 out of 7 cases (100%) were normal healthy subject cases.

Predictive Determination Using 771 Probes Corresponding to Genes with Expression Levels that were Observed to be Attenuated at Levels 0.5 Times or Less or Enhanced at Levels 2 Times or More that of the Normal Healthy Subject Group:

Similarly with the use of a GeneSpring GX Class Prediction tool, a prediction model was prepared based on 771 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 9 out of 10 separately analyzed cancer cases were determined with the prediction model to be cancer cases and the probability that such cases had been properly diagnosed was 90%. Also, 13 out of 13 normal healthy subject cases were determined with prediction model to be normal healthy subject cases, and the probability that such cases had been properly diagnosed was 100%. Altogether, 22 out of 23 such cases were correct answers. Thus, the percentage of cases determined correctly was 95.7% ($^{22}/_{23}$).

Hierarchical Clustering with 116 Probes Corresponding to Genes with Expression Levels that were Observed to be Attenuated at Levels 0.33 Times or Less or Enhanced at Levels 3 Times or More that of the Normal Healthy Subject Group:

Hierarchical clustering was performed using a total of 116 probes including the above 9 probes and 107 probes for subject cancer cases and normal healthy subjects. As shown in FIG. 17, 3 clusters were formed. In the $1^{st}$ cluster, 5 out of 5 cases (100%) were colorectal cancer cases. In the $2^{nd}$ cluster, 3 out of 6 cases (50.0%) were colorectal cancer cases. In the $3^{rd}$ cluster, 5 out of 5 cases (100%) were normal healthy subject cases.

Predictive Determination Using 116 Probes Corresponding to Genes with Expression Levels that were Observed to be Attenuated at Levels 0.33 Times or Less or Enhanced at Levels 3 Times or More that of the Normal Healthy Subject Group:

Similarly with the use of a GeneSpring GX Class Prediction tool, a prediction model was prepared based on 116 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 9 out of 10 separately analyzed cancer cases were determined with the prediction model to be cancer cases and the probability that such cases had been properly diagnosed was 90%. Also, 13 out of 13 normal healthy subject cases were determined with prediction model to be normal healthy subject cases, and the probability that such cases had been properly diagnosed was 100%. Altogether, 22 out of 23 such cases were correct answers. Thus, the percentage of cases determined correctly was 95.7% ($^{22}/_{23}$).

4. Detection of Pancreatic Cancer

Hierarchical Clustering:

Hierarchical clustering was performed using a GeneSpring GX hierarchical clustering tool and 22149 probes that had passed a quality check. As shown in FIG. 18, 3 clusters were formed. In the $1^{st}$ cluster, 7 out of 7 cases (100%) were normal healthy subject cases. In the $2^{nd}$ cluster, 4 out of 5 cases (80%) were pancreatic cancer cases. In the $3^{rd}$ cluster, 4 out of 4 cases (100%) were pancreatic cancer cases. Hence, pancreatic cancer cases and normal healthy subjects were separately clustered.

Genes with Expression Levels that were Observed to Differ Between a Pancreatic Cancer Case Group and a Normal Healthy Subject Group:

Similarly, with the use of a GeneSpring GX Statistic Analysis tool, probes capable of discriminating between a pancreatic cancer case group and a normal healthy subject group were examined using the Benjamini and Hochberg false discovery rate for a multiple test and p<0.05. As a result, the expression of 3301 probes was observed to differ between the two groups.

Also, normalized numerical values for fluorescence intensities of the 3301 probes were compared using a Fold Change tool between the pancreatic cancer case group and the normal healthy subject group. The expression of 96 probes was observed to be attenuated in the pancreatic cancer case group at levels 0.5 times or less that of the normal healthy subject group and the expression of 581 probes was observed to be enhanced in the pancreatic cancer case group at levels 2 times or more that of the normal healthy subject group. Also, the expression of 6 probes was observed to be attenuated in the pancreatic cancer case group at levels 0.33 times or less that of the normal healthy subject group and the expression of 55 probes was observed to be enhanced in the pancreatic cancer case group at levels 3 times or more that of the normal healthy subject group.

Hierarchical Clustering with 677 Probes Corresponding to Genes with Expression Levels that were Observed to be Attenuated at Levels 0.5 Times or Less or Enhanced at Levels 2 Times or More that of the Normal Healthy Subject Group:

Hierarchical clustering was performed for subject cancer cases and normal healthy subjects using a total of 677 probes including the above 96 probes and 581 probes. As shown in FIG. 19, 2 clusters were formed. In the $1^{st}$ cluster, 8 out of 9 cases (88.9%) were normal healthy subject cases. In the $2^{nd}$ cluster, 7 out of 7 cases (100%) were pancreatic cancer cases.

Predictive Determination Using 677 Probes Corresponding to Genes with Expression Levels that were Observed to be Attenuated at Levels 0.5 Times or Less or Enhanced at Levels 2 Times or More that of the Normal Healthy Subjects:

Similarly with the use of a GeneSpring GX Class Prediction tool, a prediction model was prepared based on 677 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 15 out of 20 separately analyzed cancer cases were determined with the prediction model to be pancreatic cancer cases and the probability that such cases had been properly diagnosed was 75%. Also, 13 out of 13 normal healthy subject cases were determined with prediction model to be normal healthy subject cases, and the probability that such cases had been properly diagnosed was 100%. Altogether, 28 out of 33 such cases were correct answers. Thus, the percentage of cases determined correctly was 84.8% ($^{28}/_{33}$).

Hierarchical Clustering with 61 Probes Corresponding to Genes with Expression Levels that were Observed to be Attenuated at Levels 0.33 Times or Less or Enhanced at Levels 3 Times or More that of the Normal Healthy Subject Group:

Hierarchical clustering was performed for subject cancer cases and normal healthy subjects using a total of 61 probes including the above 6 probes and 5.5 probes. As shown in FIG. 20, 2 clusters were formed. In the $1^{st}$ cluster, 8 out of 9 cases (88.9%) were normal healthy subject cases. In the $2^{nd}$ cluster, 7 out of 7 cases (100%) were pancreatic cancer cases.

Predictive Determination Using 61 Probes Corresponding to Genes with Expression Levels that were Observed to be Attenuated at Levels 0.33 Times or Less or Enhanced at Levels 3 Times or More that of the Normal Healthy Subjects:

Similarly with the use of a GeneSpring GX Class Prediction tool, a prediction model was prepared based on 61 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 15 out of 20 separately analyzed cancer cases were determined with the prediction model to be pancreatic cancer cases and the probability that such cases had been properly diagnosed was 75%. Also, 9 out of 13 normal healthy subject cases were determined with prediction model to be normal healthy subject cases, and the probability that such cases had been properly diagnosed was 69.2%. Altogether, 24 out of 33 such cases were correct answers. Thus, the percentage of cases determined correctly was 72.7% ($^{24}/_{33}$).

5. Detection of Biliary Tract Cancer

Hierarchical Clustering

Hierarchical clustering was performed using a GeneSpring GX hierarchical clustering tool and 22066 probes that had passed a quality check. As shown in FIG. 25, 3 clusters were formed. In the $1^{st}$ cluster, 7 out of 7 cases (100%) were normal healthy subject cases. In the $2^{nd}$ cluster, 3 out of 3 cases (100%) were biliary tract cancer cases. In the $3^{rd}$ cluster, 5 out of 6 cases (83.3%) were biliary tract cancer cases. Hence, biliary tract cancer cases and normal healthy subjects were separately clustered.

Genes with Expression Levels that were Observed to Differ Between a Biliary Tract Cancer Case Group and a Normal Healthy Subject Group:

Similarly, with the use of a GeneSpring GX Statistic Analysis tool, probes capable of discriminating between a biliary tract cancer case group and a normal healthy subject group were examined using the Benjamini and Hochberg false discovery rate for a multiple test and p<0.05. As a result, the expression of 8090 probes was observed to differ between the two groups.

Also, normalized numerical values for fluorescence intensities of the 8090 probes were compared using a Fold Change tool between the biliary tract cancer case group and the normal healthy subject group. The expression of 98 probes was observed to be attenuated in the biliary tract cancer case group at levels 0.33 times or less that of the normal healthy subject group and the expression of 265 probes was observed to be enhanced in the biliary tract cancer case group at levels 3 times or more that of the normal healthy subject group.

Hierarchical Clustering with 363 Probes Corresponding to Genes with Expression Levels that were Observed to be Attenuated at Levels 0.33 Times or Less or Enhanced at Levels 3 Times or More that of the Normal Healthy Subject Group:

Hierarchical clustering was performed for subject cancer cases and normal healthy subjects using a total of 363 probes including the above 98 probes and 265 probes. As shown in FIG. 26, 2 clusters were formed. In the $1^{St}$ cluster, 7 out of 7 cases (100%) were normal healthy subject cases. In the $2^{nd}$ cluster, 8 out of 9 cases (88.9%) were biliary tract cancer cases.

Predictive Determination Using 363 Probes Corresponding to Genes With Expression Levels that were Observed to be Attenuated at Levels 0.33 Times or Less or Enhanced at Levels 3 Times or More that of the Normal Healthy Subjects:

Similarly with the use of a GeneSpring GX Class Prediction tool, a prediction model was prepared based on 363 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 8 out of 8 separately analyzed cancer cases were determined with the prediction model to be cancer cases and the probability that such cases had been properly diagnosed was 100%. Also, 13 out of 13 normal healthy subject cases were determined with prediction model to be normal healthy subject cases, and the probability that such cases had been properly diagnosed was 100%. Altogether, 21 out of 21 such cases were correct answers. Thus, the percentage of cases determined correctly was 100% (21/21).

All publications, patents, and patent applications cited in this description are herein incorporated by reference in their entirety.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08932990B2). An electronic copy of the "Sequence Listing" will also be available from the USPTO upon request and payment of the fee set forth in 37 CFR 1.19(b)(3).

The invention claimed is:

1. A reagent that comprises a set of all probes consisting of the nucleotide sequences of SEQ ID NOs: 220, 506, 508, 523, 538, 554, 570, 589, 597, 602, 618, 654, 689, 701, 726, 744, 762, 763, 781, 795, and 849; or
    that comprises a set of all probes consisting of the nucleotide sequences of SEQ ID NOs: 3030 to 3054,
    the reagent further comprising a DNA microarray wherein the probes are bound to a substrate.

2. A method for detecting any one of gastric cancer, colorectal cancer, pancreatic cancer and biliary tract cancer in a subject, comprising
    (i) obtaining a set of the gene expression profiles of all genes corresponding to probes consisting of the nucleotide sequences of SEQ ID NOs: 220, 506, 508, 523, 538, 554, 570, 589, 597, 602, 618, 654, 689, 701, 726, 744, 762, 763, 781, 795, and 849, in peripheral blood from the subject, or a set of all genes corresponding to probes consisting of the nucleotide sequences of SEQ ID NOs: 3030 to 3054, in peripheral blood from the subject, by measuring the expression of the genes using the reagent of claim 1;
    (ii) analyzing the expression profiles, and if the expression profiles obtained from the subject are analogous to expression profiles obtained from a gastric cancer, colorectal cancer, pancreatic cancer, and biliary tract cancer patient, the subject can be determined as having gastric cancer, colorectal cancer, pancreatic cancer, or biliary tract cancer, or comparing the expression profiles obtained from the subject with expression profiles obtained from a normal subject and making a determination based on a difference in expression profiles between the subject and the normal subject;
    (iii) detecting any one of gastric cancer, colorectal cancer, pancreatic cancer and biliary tract cancer based on the expression profiles; and
    (iv) identifying which subject has any one of gastric cancer, colorectal cancer, pancreatic cancer and biliary tract cancer.

3. The method of claim 2 for detecting gastric cancer in a subject.

4. The method of claim 2 for detecting colorectal cancer in a subject.

5. The method of claim 2 for detecting pancreatic cancer in a subject.

6. The method of claim 2 for detecting biliary tract cancer in a subject.

* * * * *